United States Patent
Molteni et al.

(10) Patent No.: US 9,023,839 B2
(45) Date of Patent: May 5, 2015

(54) COMPOUNDS AND COMPOSITIONS AS C-KIT KINASE INHIBITORS

(71) Applicants: Valentina Molteni, San Diego, CA (US); Hank Michael James Petrassi, San Diego, CA (US); Xiaolin Li, Alameda, CA (US); Xiaodong Liu, San Diego, CA (US); Jon Loren, San Diego, CA (US); Juliet Nabakka, San Diego, CA (US); Bao Nguyen, San Diego, CA (US); Vince Yeh, San Diego, CA (US)

(72) Inventors: Valentina Molteni, San Diego, CA (US); Hank Michael James Petrassi, San Diego, CA (US); Xiaolin Li, Alameda, CA (US); Xiaodong Liu, San Diego, CA (US); Jon Loren, San Diego, CA (US); Juliet Nabakka, San Diego, CA (US); Bao Nguyen, San Diego, CA (US); Vince Yeh, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 14/258,963

(22) Filed: Apr. 22, 2014

(65) Prior Publication Data
US 2014/0228347 A1    Aug. 14, 2014

Related U.S. Application Data

(63) Continuation of application No. 14/031,792, filed on Sep. 19, 2013, now Pat. No. 8,754,071, which is a continuation of application No. 13/598,213, filed on Aug. 29, 2012, now Pat. No. 8,569,283.

(60) Provisional application No. 61/530,038, filed on Sep. 1, 2011.

(51) Int. Cl.
| | | |
|---|---|---|
| *C07D 498/04* | (2006.01) | |
| *C07D 471/04* | (2006.01) | |
| *C07D 491/044* | (2006.01) | |
| *C07D 491/107* | (2006.01) | |
| *C07D 491/048* | (2006.01) | |

(52) U.S. Cl.
CPC .......... *C07D 491/107* (2013.01); *C07D 471/04* (2013.01); *C07D 491/048* (2013.01); *C07D 498/04* (2013.01); *C07D 491/044* (2013.01)

(58) Field of Classification Search
None
See application file for complete search history.

(56) References Cited

U.S. PATENT DOCUMENTS

| 8,569,283 | B2 | 10/2013 | Molteni et al. |
| 8,754,071 | B2 | 6/2014 | Molteni et al. |
| 2007/0072862 | A1 | 3/2007 | Dimauro et al. |
| 2013/0059846 | A1 | 3/2013 | Yeh et al. |
| 2013/0023751 | A1 | 12/2013 | Bruce et al. |

FOREIGN PATENT DOCUMENTS

| WO | 2006027795 | 3/2006 |
| WO | 2006071940 | 7/2006 |
| WO | 2008058037 | 5/2008 |
| WO | WO2008058037 | 5/2008 |
| WO | 2013033203 | 3/2013 |
| WO | 2013033620 | 3/2013 |

OTHER PUBLICATIONS

Morphy Richard, "Selectively Nonselective Kinase Inhibition: Striking the Right Balance," Journal of Medicinal Chemistry 53, No. 4 (Feb. 25, 2010).

Kim Okseon et al., "Design and Synthesis of Imidazopyridine Analogues as Inhibitors of Phosphoinositide 3-Kinase Signaling and Angiogenesis," Journal of Medicinal Chemistry 54, No. 7 (Apr. 14, 2011).

Database Registry, Chemical Abstracts Service, Columbus, Ohio, US, Mar. 14, 2010, XP002685990, Database accession No. 1209616-10-3, N-[3-[6-[(4-morpholinyl)-3-pyridazinyl]phenyl-2-methylimidazo[1,2-a]pyridine-3-carboxamide.

*Primary Examiner* — Timothy R Rozof
(74) *Attorney, Agent, or Firm* — The Genomics Institute of the Novartis Research Foundation; Daniel E. Raymond

(57) ABSTRACT

The invention provides compounds and pharmaceutical compositions thereof, which are useful as protein kinase inhibitors, as well as methods for using such compounds to treat, ameliorate or prevent a condition associated with abnormal or deregulated kinase activity. In some embodiments, the invention provides methods for using such compounds to treat, ameliorate or prevent diseases or disorders that involve abnormal activation of c-kit or c-kit and PDGFR (PDGFRα, PDGFRβ) kinases.

24 Claims, No Drawings

COMPOUNDS AND COMPOSITIONS AS C-KIT KINASE INHIBITORS

CROSS-REFERENCE TO RELATED APPLICATIONS

This application is a continuation of prior application Ser. No. 14/031,792, filed Sep. 19, 2013, which is a continuation of prior application Ser. No. 13/598,213, filed Aug. 29, 2012, now U.S. Pat. No. 8,569,283, which claims the benefit of priority under 35 U.S.C. §119(e) to U.S. Provisional Patent Application No. 61/530,038, filed Sep. 1, 2011, the disclosures of which are incorporated herein by reference in their entirety and for all purposes.

FIELD OF THE INVENTION

The invention relates to inhibitors of PDGFR and/or c-kit kinases, and methods of using such compounds.

BACKGROUND OF THE INVENTION

Protein kinases (PK) are a large set of structurally related phosphoryl transferases having highly conserved structures and catalytic functions. Protein kinases are enzymatic components of the signal transduction pathways which catalyze the transfer of the terminal phosphate from ATP to the hydroxy group of tyrosine, serine and/or threonine residues of proteins, and are therefore categorized into families by the substrates they phosphorylate: Protein Tyrosine Kinases (PTK), and Protein Serine/Threonine Kinases.

Protein kinases play a critical role in the control of cell growth and differentiation and are responsible for the control of a wide variety of cellular signal transduction processes, wherein protein kinases are key mediators of cellular signals leading to the production of growth factors and cytokines. The overexpression or inappropriate expression of normal or mutant protein kinases plays a significant role in the development of many diseases and disorders including, central nervous system disorders such as Alzheimer's, inflammatory disorders such as arthritis, bone diseases such as osteoporosis, metabolic disorders such as diabetes, blood vessel proliferative disorders such as angiogenesis, autoimmune diseases such as rheumatoid arthritis, ocular diseases, cardiovascular disease, atherosclerosis, cancer, thrombosis, psoriasis, restenosis, schizophrenia, pain sensation, transplant rejection and infectious diseases such as viral, and fungal infections.

SUMMARY OF THE INVENTION

Provided herein are compounds, and pharmaceutically acceptable salts, pharmaceutically acceptable solvates (e.g. hydrates), the N-oxide derivatives, protected derivatives, individual isomers and mixture of isomers thereof, which are inhibitors of c-kit kinase, or inhibitors of c-kit and PDGFR (PDGFRα and PDGFRβ) kinases.

In one aspect provided herein such compounds, and the pharmaceutically acceptable salts, pharmaceutically acceptable solvates (e.g. hydrates), the N-oxide derivatives, protected derivatives, individual isomers and mixture of isomers thereof, have a structure according to Formula (I) or Formula

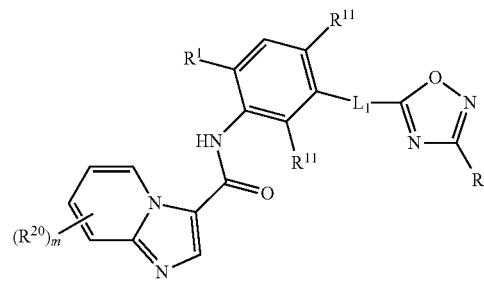

Formula (I)

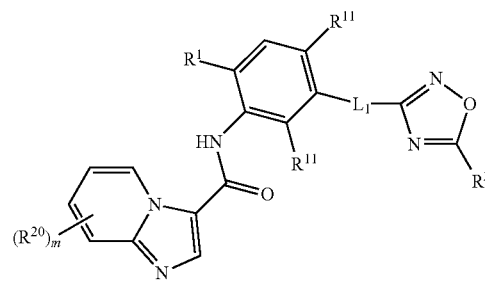

Formula (II)

wherein:
m is 1 and $R^{20}$ is selected from H, halo, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9{}_2)_nOR^4$, —$C(O)R^4$, —$(CR^9{}_2)_nC(=O)OR^4$, $R^{10}$, —$(CR^9{}_2)_nR^{10}$, —$((CR^9{}_2)_nO)_rR^4$, —$(CR^9{}_2)_nO(CR^9{}_2)_nR^7$, —$(CR^9{}_2)_nC(=O)R^4$, —$C(=O)N(R^4)_2$, —$OR^4$, and —$(CR^9{}_2)_nCN$;
or m is 4 and $R^{20}$ is deuterium;
$R^1$ is selected from $C_1$-$C_6$alkyl and halo;
each $R^1$ is independently selected from H, halo and $C_1$-$C_6$alkyl;
$L_1$ is a bond, —NH— or —C(O)NH—;
$L_2$ is —$(CR^9{}_2)_n$—, —$CHR^6$—, —$(CR^9{}_2)_nO$—, —NH—, —$(CR^9{}_2)_nC(=O)$—, —$C(=O)O(CR^9{}_2)_n$—, —$(CR^9{}_2)_n$ OC(=O)NR$^4$—, —$(CF^9{}_2)_nNR^4C(=O)(CR^9{}_2)_n$—, —$(CR^9{}_2)_nNR^4C(=O)$—, or —$(CR^9{}_2)_nNR^4C(=O)O$—;
$R^2$ is $R^3$ or $L_2R^3$;
$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —$C(=O)OR^4$, —$C(=O)R^4$, —$C(=O)R^7$, —$C(=O)OR^5$, —$(CR^9{}_2)_nOR^4$, —$O(CR^9{}_2)_nOR^4$, —$C(=O)O(CR^9{}_2)_nOR^4$, —$N(R^4)_2$, —$C(=O)NR^4{}_2$, —$NR^4C(=O)OR^4$, —$NR^4C(=O)(CR^9{}_2)_nOR^4$, —$NR^4(CR^9{}_2)_nOR^4$, —$NR^4S(=O)_2R^4$, —$N(C(=O)OR^4)_2$, $R^8$, —$(CR^9{}_2)_nR^8$, deuterated $C_1$-$C_6$alkoxy, —$S(=O)_2R^4$, —$S(=O)_2R^7$, —$S(=O)_2R^8$, —$S(=O)_2N(R^4)_2$, —$S(=O)_2NHC(=O)OR^4$, —$S(=O)_2(CR^9{}_2)_nC(=O)OR^4$, $S(=O)_2(CR^9{}_2)_nOR^4$, a spiro attached dioxolane, a spiro attached dioxolane which is substituted with $C_1$-$C_6$alkyl, a spiro attached dioxane, a spiro attached tetrahydrofuranyl, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, —$OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl;

each $R^6$ is independently selected from —$NR^4C(O)OR^4$, —$OR^4$ and —$(CR^9{}_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —$(C(R^9)_2)_nOR^4$, —$(C(R^9)_2)_nR^5$, —$(C(R^9)_2)_nC(O)OR^4$, —$C(O)OR^4$ and —$S(O)_2R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —$(C(R^9)_2)_nOR^4$, —$(C(R^9)_2)_nR^5$, —$(C(R^9)_2)_nC(O)OR^4$ and —$S(O)_2R^4$;

t is 1, 2 or 3, and each n is independently selected from 1, 2, 3 and 4.

In certain embodiments of compounds of Formula (I) or Formula (II), m is 1 and $R^{20}$ is selected from H, —F, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9{}_2)_nOR^4$, —$C(O)R^4$, —$(CR^9{}_2)_nC(=O)OR^4$, $R^{10}$, (—$CR^9{}_2)_nR^{10}$, —$((CR^9{}_2)_nO)_tR^4$, —$(CR^9{}_2)_nO)_tR^4$, —$(CR^9{}_2)_nO(CR^9{}_2)_nR^7$, —$(CR^9{}_2)_nC(=O)R^4$, —$C(=O)N(R^4)_2$, —$OR^4$, and —$(CR^9{}_2)_nCN$;

or m is 4 and $R^{20}$ is deuterium;

$R^1$ is selected from $C_1$-$C_6$alkyl and halo;

each $R^{11}$ is independently selected from H, halo and $C_1$-$C_6$alkyl;

$L_1$ is a bond, —NH— or —C(O)NH—;

$L_2$ is —$(CR^9{}_2)_n$—, —$CHR^6$—, —$(CR^9{}_2)_nO$—, —NH—, —$(CR^9{}_2)_nC(=O)$—, —$C(=O)O(CR^9{}_2)_n$—, —$(CR^9{}_2)_n$ $OC(=O)NR^4$—, —$(CR^9{}_2)_nNR^4C(=O)$ $(CR^9{}_2)_n$—, —$(CR^9{}_2)_nNR^4C(=O)$—, or —$(CR^9{}_2)_n$ $NR^4C(=O)O$—;

$R^2$ is $R^3$ or $L_2R^3$;

$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —$C(=O)OR^4$, —$C(=O)R^4$, —$C(=O)R^7$, —$C(=O)OR^5$, —$(CR^9{}_2)_nOR^4$, —$O(CR^9{}_2)_nOR^4$, —$C(=O)O(CR^9{}_2)_nOR^4$, —$N(R^4)_2$, —$C(=O)NR^4{}_2$, —$NR^4C(=O)OR^4$, —$NR^4C(=O)(CR^9{}_2)_nOR^4$, —$NR^4(CR^9{}_2)_nOR^4$, —$NR^4S(=O)_2R^4$, —$N(C(=O)OR^4)_2$, $R^8$, —$(CR^9{}_2)_nR^8$, deuterated $C_1$-$C_6$alkoxy, —$S(=O)_2R^4$, —$S(=O)_2R^7$, —$S(=O)_2R^8$, —$S(=O)_2N(R^4)_2$, —$S(=O)_2NHC(=O)OR^4$, —$S(=O)_2(CR^9{}_2)_nC(=O)OR^4$, $S(=O)_2(CR^9{}_2)_nOR^4$, a Spiro attached dioxolane, a spiro attached dioxolane which is substituted with $C_1$-$C_6$alkyl, a spiro attached dioxane, a spiro attached tetrahydrofuranyl, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, —$OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl;

each $R^6$ is independently selected from —$NR^4C(O)OR^4$, —$OR^4$ and —$(CR^9{}_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —(C($R^9$)$_2$)$_n$O$R^4$, —(C($R^9$)$_2$)$_n$$R^5$, —(C($R^9$)$_2$)$_n$C(O)O$R^4$, —C(O)O$R^4$ and —S(O)$_2$$R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —(C($R^9$)$_2$)$_n$O$R^4$, —(C($R^8$)$_2$)$_n$$R^5$, —(C($R^9$)$_2$)$_n$C(O)O$R^4$ and —S(O)$_2$$R^4$;

t is 1, 2 or 3, and each n is independently selected from 1, 2, 3 and 4.

In certain embodiments of compounds of Formula (I) or Formula (II), and the pharmaceutically acceptable salts, pharmaceutically acceptable solvates (e.g. hydrates), the N-oxide derivatives, protected derivatives, individual isomers and mixture of isomers thereof, the compound of Formula (I) or Formula (II) is a compound having a structure of Formula (Ia), Formula (IIa) Formula (Ib), Formula (IIb), Formula (Ic), Formula (IIc), Formula (Id), Formula (IId), Formula (Ie), Formula (IIe), Formula (If) or Formula (IIf):

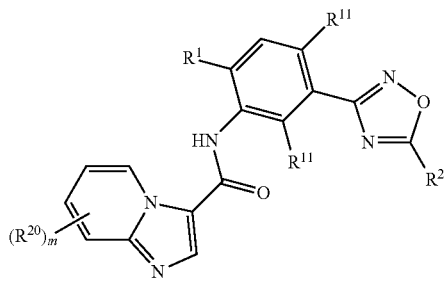

Formula (Ia)

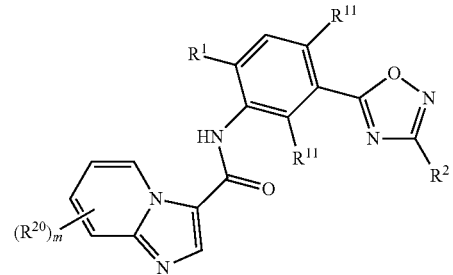

Formula (IIa)

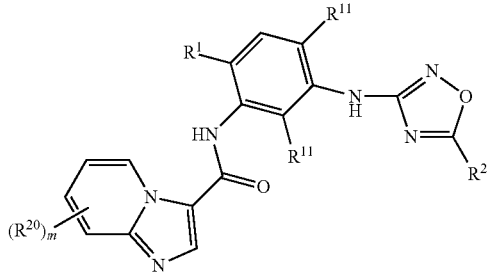

Formula (Ib)

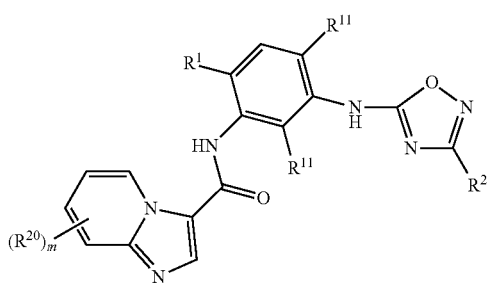

Formula (IIb)

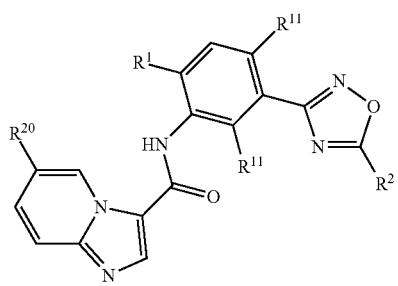

Formula (Ic)

Formula (IIc)
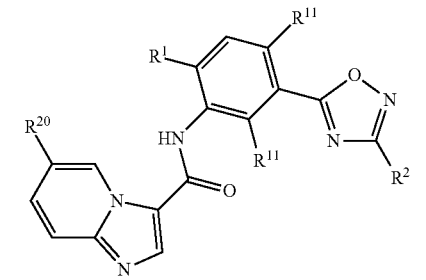

Formula (Id)
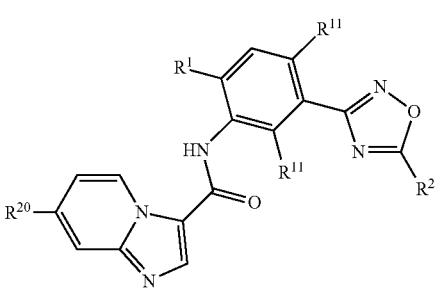

Formula (IId)
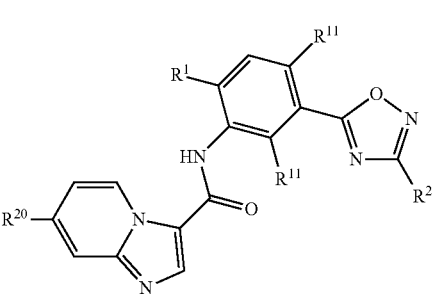

Formula (Ie)
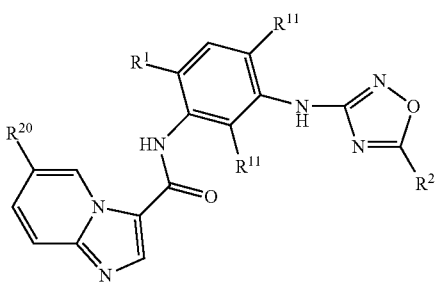

Formula (IIe)
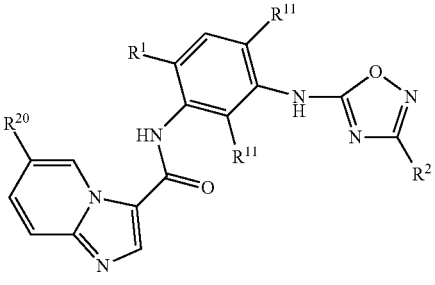

Formula (If)
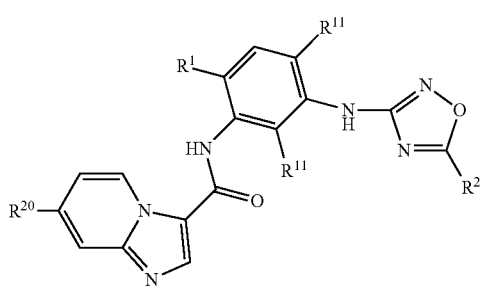

Formula (IIf)
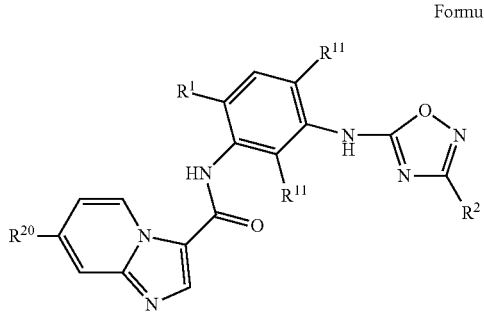

wherein:
m is 1 and $R^{20}$ is selected from H, halo, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9{}_2)_n$—, —$OR^4$, —C(O)$R^4$, —$(CR^9{}_2)_n$C(=O)$OR^4$, $R^{10}$, —$(CR^9{}_2)_n$O)$R^4$, —$(CR^9{}_2)_n$ O$(CR^9{}_2)_n R^7$, —$(CR^9{}_2)_n$C(=O)$R^4$, —C(=O)$_N(R^4)_2$, —$OR^4$, and —$(CR^9{}_2)_n$CN;
or m is 4 and $R^{20}$ is deuterium;
$R^1$ is selected from $C_1$-$C_6$alkyl and halo;
each $R^{11}$ is independently selected from H, halo and $C_1$-$C_6$alkyl;
$L_2$ is —$(CR^9{}_2)_n$—, —$CHR^6$—, —$(CR^9{}_2)_n$O—, —NH—, —$(CR^9{}_2)_n$C(=O)—, —C(=O)O$(CR^9{}_2)_n$—, —$(CR^9{}_2)_n$ OC(=O)$NR^4$—, —$(CR^9{}_2)_n NR^4$C(=O) $(CR^9{}_2)_n$—, —$(CR^9{}_2)_n NR^4$C(=O)—, or —$(CR^9{}_2)_n$ $NR^4$C(=O)O—;
$R^2$ is $R^3$ or $L_2R^3$;
$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —C(=O)$OR^4$, —C(=O)$R^4$, —C(=O)$R^7$, —C(=O) $OR^5$, —$(CR^9{}_2)_n OR^4$, —O$(CR^9{}_2)_n OR^4$, —C(=O)O $(CR^9{}_2)_n OR^4$, —N$(R^4)_2$, —C(=O)$NR^4{}_2$, —$NR^4$C (=O)$OR^4$, —$NR^4$C(=O)$(CR^9{}_2)_n OR^4$, —$NR^4(CR^9{}_2)_n$ $OR^4$, —$NR^4$S(=O)$_2 R^4$, —N(C(=O)$OR^4$)$_2$, $R^8$, —$(CR^9{}_2)_n R^8$, deuterated $C_1$-$C_6$alkoxy, —S(=O)$_2 R^4$, —S(=O)$_2 R^7$, —S(=O)$_2 R^8$, —S(=O)$_2 N(R^4)_2$, —S(=O)$_2$NHC(=O)$OR^4$, —S(=O)$_2(CR^9{}_2)_n$C(=O) $OR^4$, S(=O)$_2(CR^9{}_2)_n OR^4$, a spiro attached dioxolane, a spiro attached dioxolane which is substituted with $C_1$-$C_6$alkyl, a spiro attached dioxane, a spiro attached tetrahydrofuranly, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, —$OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl;

each $R^6$ is independently selected from —$NR^4C(O)OR^4$, —$OR^4$ and —$(CR^9{}_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —$(C(R^9)_2)_nOR^4$, —$(C(R^9)_2)_nR^5$, —$(C(R^9)_2)_nC(O)OR^4$, —$C(O)OR^4$ and —$S(O)_2R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —$(C(R^9)_2)_nOR^4$, —$(C(R^9)_2)_nR^5$, —$(C(R^9)_2)_nC(O)OR^4$ and —$S(O)_2R^4$;

t is 1, 2 or 3, and each n is independently selected from 1, 2, 3 and 4.

In certain embodiments of compounds of Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), m is 1 and $R^{20}$ is selected from H, —F, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9{}_2)_nOR^4$, —$C(O)R^4$, —$(CR^9{}_2)_nC(=O)OR^4$, $R^{10}$, —$(CR^9{}_2)_nR^{10}$, —$((CR^9{}_2)_nO)_tR^4$, —$(CR^9{}_2)_nO(CR^9{}_2)_nR^7$, —$(CR^9{}_2)_nC(=O)R^4$, —$C(=O)N(R^4)_2$, —$OR^4$, and —$(CR^9{}_2)_nCN$;

or m is 4 and $R^{20}$ is deuterium;

$R^1$ is selected from $C_1$-$C_6$alkyl and halo;

each $R^{11}$ is independently selected from H, halo and $C_1$-$C_6$alkyl;

$L_2$ is —$(CR^9{}_2)_n$—, —$CHR^6$—, —$(CR^9{}_2)_nO$—, —NH—, —$(CR^9{}_2)_nC(=O)$—, —$C(=O)O(CR^9{}_2)_n$—, —$(CR^9{}_2)_n$ $OC(=O)NR^4$—, —$(CR^9{}_2)_nNR^4C(=O)(CR^9{}_2)_n$—, —$(CR^9{}_2)_nNR^4C(=O)$—, or —$(CR^9{}_2)_nNR^4C(=O)O$—;

$R^2$ is $R^3$ or $L_2R^3$;

$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —$C(=O)OR^4$, —$C(=O)R^4$, —$C(=O)R^7$, —$C(=O)OR^5$, —$(CR^9{}_2)_nOR^4$, —$O(CR^9{}_2)_nOR^4$, —$C(=O)O(CR^9{}_2)_nOR^4$, —$N(R^4)_2$, —$C(=O)NR^4{}_2$, —$NR^4C(=O)OR^4$, —$NR^4C(=O)(CR^9{}_2)_nOR^4$, —$NR^4(CR^9{}_2)_nOR^4$, —$NR^4S(=O)_2R^4$, —$N(C(=O)OR^4)_2$, $R^8$, —$(CR^9{}_2)_nR^8$, deuterated $C_1$-$C_6$alkoxy, —$S(=O)_2R^4$, —$S(=O)_2R^7$, —$S(=O)_2R^8$, —$S(=O)_2N(R^4)_2$, —$S(=O)_2NHC(=O)OR^4$, —$S(=O)_2(CR^9{}_2)_nC(=O)OR^4$, $S(=O)_2(CR^9{}_2)_nOR^4$, a spiro attached dioxolane, a spiro attached dioxolane which is substituted with $C_1$-$C_6$alkyl, a spiro attached dioxane, a spiro attached tetrahydrofuranly, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, —$OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl, each $R^6$ is independently selected from —$NR^4C(O)OR^4$, —$OR^4$ and —$(CR^9{}_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —$(C(R^9)_2)_nOR^4$, —$(C(R^9)_2)_nR^5$, —$(C(R^9)_2)_nC(O)OR^4$, —$C(O)OR^4$ and —$S(O)_2R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —$(C(R^9)_2)_nOR^4$, —$(C(R^9)_2)_nR^5$, —$(C(R^9)_2)_nC(O)OR^4$ and —$S(O)_2R^4$;

t is 1, 2 or 3, and each n is independently selected from 1, 2, 3 and 4.

In certain embodiments of compounds of Formula (I) or Formula (II), and the pharmaceutically acceptable salts, pharmaceutically acceptable solvates (e.g. hydrates), the N-oxide derivatives, protected derivatives, individual isomers and mixture of isomers thereof, the compound of Formula (I) or Formula (II) is a compound having a structure of Formula (Ia), Formula (IIa) Formula (Ib) or Formula (IIb):

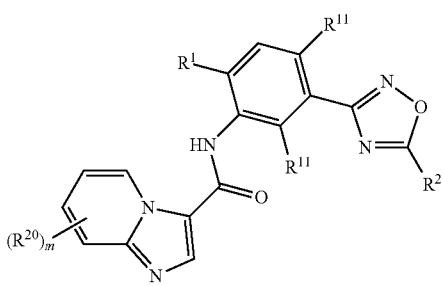

Formula (Ia)

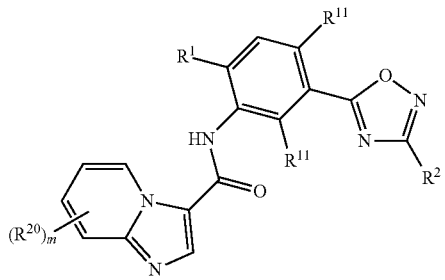

Formula (IIa)

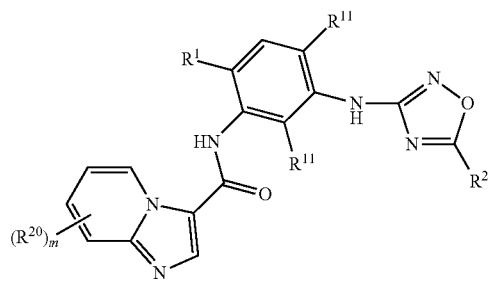

Formula (Ib)

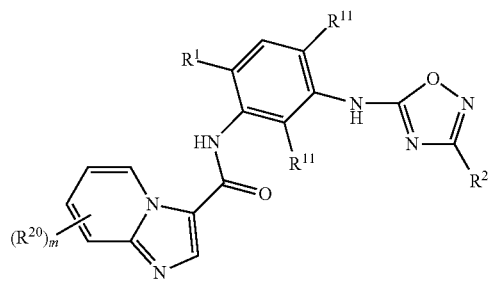

Formula (IIb)

wherein:

m is 1 and $R^{20}$ is selected from H, halo, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9_2)_nOR^4$, —$C(O)R^4$, —$(CR^9_2)_nC(=O)OR^4$, $R^{10}$, —$(CR^9_2)_nR_{10}$, —$((CR^9_2)_nO)_tR^4$, —$(CR^9_2)_nO(CR^9_2)_nR^7$, —$(CR^9_2)_nC(=O)R^4$, —$C(=O)N(R^4)_2$, —$OR^4$, and —$(CR^9_2)_nCN$;

or m is 4 and $R^{20}$ is deuterium;

$R^1$ is selected from $C_1$-$C_6$alkyl and halo;

each $R^{11}$ is independently selected from H, halo and $C_1$-$C_6$alkyl;

$L_2$ is —$(CR^9_2)_n$—, —$CHR^6$—, —$(CR^9_2)_nO$—, —NH—, —$(CR^9_2)_nC(=O)$—, —$C(=O)O(CR^9_2)_n$—, —$(CR^9_2)_n$ $OC(=O)NR^4$—, —$(CR^9_2)_nNR^4C(=O)$ $(CR^9_2)_n$—, —$(CR^9_2)_nNR^4C(=O)$—, or —$(CR^9_2)_n$ $NR^4C(=O)O$—;

$R^2$ is $R^3$ or $L_2R^3$;

$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —$C(=O)OR^4$, —$C(=O)R^4$, —$C(=O)R^7$, —$C(=O)OR^5$, —$(CR^9_2)_nOR^4$, —$O(CR^9_2)_nOR^4$, —$C(=O)O$ $(CR^9_2)_nOR^4$, $-N(R^4)_2$, $-C(=O)NR^4_2$, $-NR^4C(=O)OR^4$, $-NR^4C(=O)(CR^9_2)_nOR^4$, $-NR^4(CR^9_2)_nOR^4$, $-NR^4S(=O)_2R^4$, $-N(C(=O)OR^4)_2$, $R^8$, $-(CR^9_2)_nR^8$, deuterated $C_1$-$C_6$alkoxy, $-S(=O)_2R^4$, $-S(=O)_2R^7$, $-S(=O)_2R^8$, $-S(=O)_2N(R^4)_2$, $-S(=O)_2NHC(=O)OR^4$, $-S(=O)_2(CR^9_2)_nC(=O)OR^4$, $S(=O)_2(CR^9_2)_nOR^4$, a spiro attached dioxolane, a spiro attached dioxolane which is substituted with $C_1$-$C_6$alkyl, a spiro attached dioxane, a spiro attached tetrahydrofuranyl, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, $-OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl, each $R^6$ is independently selected from $-NR^4C(O)OR^4$, $-OR^4$ and $-(CR^9_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, $-(C(R^9)_2)_nOR^4$, $-(C(R^9)_2)_nR^5$, $-(C(R^9)_2)_nC(O)OR^4$, $-C(O)OR^4$ and $-S(O)_2R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], $-(C(R^9)_2)_nOR^4$, $-(C(R^9)_2)_nR^5$, $-(C(R^9)_2)_nC(O)OR^4$ and $-S(O)_2R^4$;

t is 1, 2 or 3, and each n is independently selected from 1, 2, 3 and 4.

In certain embodiments of compounds of Formula (Ia), Formula (IIa), Formula (Ib), or Formula (IIb), m is 1 and $R^{20}$ is selected from H, $-F$, $C_1$-$C_6$alkyl, $C_1$-$C_6$haloalkyl, $C_1$-$C_6$haloalkoxy, deuterium, deuterated $C_1$-$C_6$alkyl, $-CN$, $-(CR^9_2)_nOR^4$, $-C(O)R^4$, $-(CR^9_2)_nC(=O)OR^4$, $R^{10}$, $-(CR^9_2)_nR^{10}$, $-((CR^9_2)_nO)_tR^4$, $-(CR^9_2)_nO(CR^9_2)_nR^7$, $-(CR^9_2)_nC(=O)R^4$, $-C(=O)N(R^4)_2$, $-OR^4$, and $-(CR^9_2)_nCN$;

or m is 4 and $R^{20}$ is deuterium;

$R^1$ is selected from $C_1$-$C_6$alkyl and halo;

each $R^{11}$ is independently selected from H, halo and $C_1$-$C_6$alkyl;

$L_2$ is $-(CR^9_2)_n-$, $-CHR^6-$, $-(CR^9_2)_nO-$, $-NH-$, $-(CR^9_2)_nC(=O)-$, $-C(=O)O(CR^9_2)_n-$, $-(CR^9_2)_n$ $OC(=O)NR^4-$, $-(CR^9_2)_nNR^4C(=O)(CR^9_2)_n-(CR^9_2)_nNR^4C(=O)-$, or $-(CR^9_2)_nNR^4C(=O)O-$;

$R^2$ is $R^3$ or $L_2R^3$;

$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, $-CN$, $C_1$-$C_6$haloalkyl, $-OR^4$, $-C(=O)OR^4$, $-C(=O)R^4$, $-C(=O)R^7$, $-C(=O)OR^5$, $-(CR^9_2)_nOR^4$, $-O(CR^9_2)_nOR^4$, $-C(=O)O(CR^9_2)_nOR^4$, $-N(R^4)_2$, $-C(=O)NR^4_2$, $-NR^4C(=O)OR^4$, $-NR^4C(=O)(CR^9_2)_nOR^4$, $-NR^4(CR^9_2)_nOR^4$, $-NR^4S(=O)_2R^4$, $-N(C(=O)OR^4)_2$, $R^8$, $-(CR^9_2)_nR^8$, deuterated $C_1$-$C_6$alkoxy, $-S(=O)_2R^4$, $-S(=O)_2R^7$, $-S(=O)_2R^8$, $-S(=O)_2N(R^4)_2$, $-S(=O)_2NHC(=O)OR^4$, $-S(=O)_2(CR^9_2)_nC(=O)OR^4$, $S(=O)_2(CR^9_2)_nOR^4$, a spiro attached dioxolane, a spiro attached dioxolane which is substituted with $C_1$-$C_6$alkyl, a spiro attached dioxane, a spiro attached tetrahydrofuranyl, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, $-OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl;

each $R^6$ is independently selected from —$NR^4C(O)OR^4$, —$OR^4$ and —$(CR^9{}_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one,
wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —$(C(R^9)_2)_nOR^4$, —$(C(R^9)_2)_nR^5$, —$(C(R^9)_2)_nC(O)OR^4$, —$C(O)OR^4$ and —$S(O)_2R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one,
wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —$(C(R^9)_2)_nOR^4$, —$(C(R^9)_2)_nR^5$, —$(C(R^9)_2)_nC(O)OR^4$ and —$S(O)_2R^4$;

t is 1, 2 or 3, and each n is independently selected from 1, 2, 3 and 4.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^1$ is selected from —$CH_3$ and F.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^{11}$ is —$CH_3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^{11}$ is independently selected from H, F and —$CH_3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^{11}$ is H.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^3$ is selected from an unsubstituted 4-6 membered heterocycloalkyl with 1-2 heteroatoms independently selected from N and O, a piperidinone, a oxazolidin-2-one, pyrrolidinone, a pyrrolidin-2-one and a substituted 4-6 membered heterocycloalkyl with 1-2 heteroatoms independently selected from N and O, wherein the substituted 4-6 membered heterocycloalkyl of $R^3$ is substituted with 1-4 substituents independently selected from $C_1$-$C_6$alkyl, halo, —CN, $C_1$-$C_6$haloalkyl, —$OR^4$, —$C(=O)OR^4$, —$C(=O)R^4$, —$C(=O)R^7$, —$C(=O)OR^5$, —$(CR^9{}_2)_nOR^4$, —$C(=O)O(CR^9{}_2)_nOR^4$, —$C(=O)NR^4{}_2$, —$NR^4C(=O)OR^4$, —$NR^4C(=O)(CR^9{}_2)_nOR^4$, —$R^8$, —$(CR^9{}_2)_nR^8$, —$S(=O)_2R^4$, —$S(=O)_2R^7$, —$S(=O)_2R^8$, —$S(=O)_2N(R^4)_2$, —$S(=O)_2NHC(=O)OR^4$, —$S(=O)_2(CR^9{}_2)_nOR^4$, —$S(=O)_2(CR^9{}_2)_nC(=O)OR^4$ and a $C_1$ alkyl bridge.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^6$ is independently selected from —$NHC(O)OR^4$ and —$(CR^9{}_2)_nOR^4$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^6$ is independently selected from H, methyl, ethyl, propyl, butyl, i-propyl and t-butyl.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^4$ is independently selected from cyclopropyl, cyclopropyl substituted with a methyl or morpholinyl.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^5$ is —$CH_2OCH_3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^7$ is independently selected from $CH_2F$, —$CHF_2$, —$CH_2CHF_2$, —$CH_2CF_3$ and —$CF_3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), each $R^9$ is independently selected from H, methyl and ethyl.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^8$ is selected from an unsubstituted phenyl, unsubstituted 5-6 membered heteroaryl with 1-3 heteroatoms independently selected from N and O, an unsubstituted 5 membered heteroaryl with 1-4 heteroatoms selected from N, an unsubstituted 4-6 membered heterocycloalkyl with 1-2 heteroatoms independently selected from N and O, a substituted 5-6 membered heteroaryl with 1-3 heteroatoms independently selected from N and O, a substituted 5 membered heteroaryl with 1-4 heteroatoms selected from N, a substituted 4-6 membered heterocycloalkyl with 1-2 heteroatoms independently selected from N and O, and a tetrahydro-1H-oxazolo[3,4-a]pyrazin-3(5H)-one, wherein the substituted 5-6 membered heteroaryl with 1-3 heteroatoms independently selected from N and O, the substituted 5 membered heteroaryl with 1-4 heteroatoms selected from N and substituted 4-6 membered heterocycloalkyl of $R^8$ are substituted with 1-3 substituents independently selected from $C_1$-$C_6$alkyl and —C(=O)OR$^4$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^8$ is selected from pyridinyl, pyrazolyl tetrahydrofuranyl, tetrahydropyranyl, pyrrolidinyl, piperidinyl, pyrimidinyl and oxadiazolyl, each of which is unsubstituted or substituted with 1-2 substituents independently selected from —CH$_3$ and —C(=O)OC(CH$_3$)$_3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^2$ is $R^3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^3$ is selected from azetidinyl, azetidin-1-yl, azetidin-2-yl, azetidin-3-yl, pyrrolidinyl, pyrrolidin-1-yl, pyrrolidin-2-yl, pyrrolidin-3-yl, piperidinyl, piperidin-1-yl, piperidin-2-yl, piperidin-3-yl, piperidin-4-yl, tetrahydropyranyl, tetrahydropyran-2-yl, tetrahydropyran-3-yl, tetrahydropyran-4-yl, tetrahydrofuranyl, tetrahydrofuran-2-yl, tetrahydrofuran-3-yl, oxetanyl, oxetan-2-yl, oxetan-3-yl, morpholinyl, morpholin-2-yl, morpholin-3-yl and morpholin-4-yl, each of which is unsubstituted or each of which is substituted with 1-4 substituents independently selected from —CH$_3$, —CH$_2$CH$_3$, F, —CF$_3$, —CN, —OH, —C(=O)CF$_3$, —OCH$_3$, —C(=O)OCH$_3$, —C(=O)CH$_3$, —C(=O)OCH$_2$CH$_2$OCH$_3$, —C=(O)OCH$_2$CH$_3$, —C(=O)OC(CH$_3$)$_3$, —CH$_2$OH, —CH$_2$OCH$_3$, —CH$_2$CH$_2$CH$_2$OCH$_3$, —NHC(=O)OC(CH$_3$)$_3$, —NHC(=O)OCH$_3$, —C(=O)N(CH$_3$)$_2$, —S(=O)$_2$CH$_3$, —S(=O)$_2$ CH$_2$CH$_3$, —S(=O)$_2$CH$_2$CH$_2$CH$_3$, —S(=O)$_2$CH$_2$CH$_2$CH$_2$CH$_3$, —S(=O)$_2$CH(CH$_3$)$_2$, —S(=O)$_2$CH$_2$CH$_2$C(=O)OCH$_3$, —S(=O)$_2$CH$_2$CH$_2$OCH$_3$, —S(=O)$_2$CHF$_2$, —S(=O)$_2$NH$_2$, —S(=O)$_2$NHC(=O)OC(CH$_3$)$_3$, a C$_1$alkyl bridge, —C(=O)OR$^5$, —S(=O)$_2$R$^8$, —(CR$^9_2$)$_n$R$^8$ and R$^8$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^3$ is azetidinyl substituted with —C(=O)OCH$_3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), m is 1 and $R^{20}$ is selected from H, halo, $C_1$-$C_6$alkyl, $C_1$-$C_6$haloalkyl, deuterium, deuterated $C_1$-$C_6$alkyl, —CN, —(CR$^9_2$)$_n$OR$^4$, —C(O)R$^4$, —(CR$^9_2$)$_n$C(=O)OR$^4$, R$^{10}$, —(CR$^9_2$)$_n$R$^{10}$, —(CR$^9_2$)$_n$O(CR$^9_2$)$_n$R$^7$, —(CR$^9_2$)$_n$C(=O)R$^4$, —OR$^4$, and —(CR$^9_2$)$_n$CN.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), m is 1 $R^{20}$ is selected from H, -D, —F, —CH$_3$, —CF$_3$, —CN, —CH$_2$CH$_2$CH$_2$CN, —CH$_2$CH$_2$CN, —OCH3, —CH$_2$CH$_2$C(=O)OC(CH$_3$)$_3$, —C(=O)CH$_3$, —CH$_2$CH$_2$C(=O)CH$_3$, —CD$_3$, —CH$_2$OH, —CH$_2$CH$_2$C(CH$_3$)$_2$OH, —CH$_2$C(CH$_3$)$_2$OH, —C(CH$_3$)$_2$OH, —CH$_2$OCH$_3$, —CH$_2$OCH$_2$CF$_3$, —CH$_2$OCH$_2$CHF$_2$, and —CH$_2$OCH$_2$CH$_2$F.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), m is 1 and $R^{20}$ is —CH$_3$.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), m is 1 and $R^{20}$ is H.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^{10}$ is selected from morpholinyl, piperidinyl, piperidin-1-yl, piperidin-2-yl, piperidin-3-yl, piperidin-4-yl, piperazinyl, piperazin-1-yl, pyrazolyl, pyrazol-1-yl, pyrazol-3-yl, pyrazol-4-yl, triazolyl, 1H-1,2,3-triazol-4-yl, 4H-1,2,4-triazol-3-yl, 1H-1,2,4-triazol-5-yl, thiazolyl, thiazol-4-yl, thiazol-5-yl, imidazolyl, imidazol-1-yl, imidazol-2-yl, each of which is unsubstituted or each of which is substituted with 1-3 substituents independently selected from $C_1$-$C_6$alkyl, —(CR$^9_2$)$_n$OR$^4$, —(C(R$^9$)$_2$)$_n$ C(O)OR$^4$, —(C(R$^9$)$_2$)$_n$R$^5$ and —S(=O)$_2$R$^4$, or $R^{10}$ is selected from a oxazolidin-2-one and a pyrrolidin-2-one.

In certain embodiments of any of the aforementioned compounds of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), $R^{10}$ is selected from morpholinyl, piperidinyl, piperidin-1-yl, piperidin-2-yl, piperidin-3-yl, piperidin-4-yl, piperazinyl, piperazin-1-yl, pyrazolyl, pyrazol-1-yl, pyrazol-3-yl, pyrazol-4-yl, triazolyl, 1H-1,2,3-triazol-4-yl, 4H-1,2,4-triazol-3-yl, 1H-1,2,4-triazol-5-yl, thiazolyl, thiazol-4-yl, thiazol-5-yl, imidazolyl, imidazol-1-yl, imidazol-2-yl, each of which is unsubstituted or each of which is substituted with 1-3 substituents independently selected from —CH$_3$, —CH$_2$CH$_2$OH, —CH$_2$C(O)OH, —CH$_2$CH$_2$OH, —CH$_2$C(CH$_3$)$_2$OH, —S(O)$_2$CH$_3$ and —CH$_2$CH$_2$—R$_5$.

In certain embodiments of any of the aforementioned compounds of Formula (I), Formula (II), Formula (Ia), Formula (IIa), Formula (Ib) or Formula (IIb), m is 4 and $R^{20}$ is deuterium.

Certain embodiments of the compounds of Formula (I) or Formula (II) are selected from: N-{5-[3-(azetidin-1-yl)-1,2,4-oxadiazol-5-yl]-2-methylphenyl}imidazo[1,2-a]pyridine-3-carboxamide; N-{5-[3-(3,3-difluoroazetidin-1-yl)-1,2,4-oxadiazol-5-yl]-2-methylphenyl}imidazo[1,2-a]pyridine-3-carboxamide; N-(2-methyl-5-{3-[(1S,4S)-2-oxa-5-azabicyclo[2.2.1]heptan-5-yl]-1,2,4-oxadiazol-5-yl}phenyl)imidazo[1,2-a]pyridine-3-carboxamide; N-{5-[3-(4,4-difluoropiperidin-1-yl)-1,2,4-oxadiazol-5-yl]-2-methylphenyl}imidazo[1,2-a]pyridine-3-carboxamide; N-{5-[3-(4-fluoropiperidin-1-yl)-1,2,4-oxadiazol-5-yl]-2-methylphenyl}imidazo[1,2-a]pyridine-3-carboxamide; N-(5-{5-[3-hydroxy-3-(trifluoromethyl)azetidin-1-yl]-1,2,4-oxadiazol-3-yl}-2-methylphenyl)-6-methylimidazo[1,2-a]pyridine-3-carboxamide; N-{2-methyl-5-[5-(oxolan-3-yl)-1,2,4-oxadiazol-3-yl]phenyl}imidazo[1,2-a]pyridine-3-carboxamide; N-{2-methyl-5-[5-(oxan-2-yl)-1,2,4-oxadiazol-3-yl]phenyl}imidazo[1,2-a]pyridine-3-carboxamide; methyl 2-[3-(3-{imidazo[1,2-a]pyridine-3-amido}-4-methylphenyl)-1,2,4-oxadiazol-5-yl]piperidine-1-carboxylate; N-{5-[5-(5,5-difluorooxan-2-yl)-1,2,4-oxadiazol-3-yl]-2-methylphenyl}imidazo[1,2-a]pyridine-3-carboxamide; N-(5-{5-[(2S)-5,5-difluorooxan-2-yl]-1,2,4-oxadiazol-3-yl}-2-methylphenyl)imidazo[1,2-a]pyridine-3-carboxamide; N-(5-{5-[(2R)-5,5-difluorooxan-2-yl]-1,2,4-oxadiazol-3-yl}-2-methylphenyl)imidazo[1,2-a]pyridine-3-carboxamide; tert-butyl 3-[3-(3-{imidazo[1,2-a]pyridine-3-amido}-4-methylphenyl)-1,2,4-oxadiazol-5-yl]azetidine-1-carboxylate; N-{5-[5-(1-methanesulfonylazetidin-3-yl)-1,2,4-oxadiazol-3-yl]-2-methylphenyl}imidazo[1,2-a]pyridine-3-carboxamide; methyl 3-[3-(3-{imidazo[1,2-a]pyridine-3-amido}-4-methylphenyl)-1,2,4-oxadiazol-5-yl]azetidine-1-carboxylate; N-(2-methyl-5-{5-[1-(propane-1-sulfonyl)azetidin-3-yl]-1,2,4-oxadiazol-3-yl}phenyl)imidazo[1,2-a]pyridine-3-carboxamide; N-{2-methyl-5-[5-(oxan-4-ylmethyl)-1,2,4-oxadiazol-3-yl]phenyl}imidazo[1,2-a]pyridine-3-carboxamide; N-{2-methyl-5-[5-(oxolan-2-ylmethyl)-1,2,4-oxadiazol-3-yl]phenyl}imidazo[1,2-a]pyridine-3-carboxamide; N-(5-{5-[1-(ethanesulfonyl)azetidin-3-yl]-1,2,4-oxadiazol-3-yl}-2-methylphenyl)imidazo[1,2-a]pyridine-3-carboxamide; N-(2-methyl-5-{5-[3-(morpholin-4-yl)propyl]-1,2,4-oxadiazol-3-yl}phenyl)imidazo[1,2-a]pyridine-3-carboxamide; N-(5-{5-[(3,3-difluoroazetidin-1-yl)methyl]-1,2,4-oxadiazol-3-yl}-2-methylphenyl)imidazo[1,2-a]pyridine-3-carboxamide; N-{2-methyl-5-[5-(morpholin-4-ylmethyl)-1,2,4-oxadiazol-3-yl]phenyl}imidazo[1,2-a]pyridine-3-carboxamide; N-{2-methyl-5-[5-(1-sulfamoylazetidin-3-yl)-1,2,4-oxadiazol-3-yl]phenyl}imidazo[1,2-a]pyridine-3-carboxamide; tert-butyl (2S)-2-[3-(3-{imidazo[1,2-a]pyridine-3-amido}-4-methylphenyl)-1,2,4-oxadiazol-5-yl]azetidine-1-carboxylate; N-(5-{5-[(2S)-1-methanesulfonylazetidin-2-yl]-1,2,4-oxadiazol-3-yl}-2-methylphenyl)imidazo[1,2-a]pyridine-3-carboxamide; methyl N-{3-[3-(3-{imidazo[1,2-a]pyridine-3-amido}-4-methylphenyl)-1,2,4-oxadiazol-5-yl]oxetan-3-yl}carbamate; tert-butyl 3-[3-(4-fluoro-3-{imidazo[1,2-a]pyridine-3-amido}phenyl)-1,2,4-oxadiazol-5-yl]azetidine-1-carboxylate; N-(5-{5-[1-(ethanesulfonyl)azetidin-3-yl]-1,2,4-oxadiazol-3-yl}-2-fluorophenyl)imidazo[1,2-a]pyridine-3-carboxamide; N-(5-{5-[(3,3-difluoropyrrolidin-1-yl)methyl]-1,2,4-oxadiazol-3-yl}-2-methylphenyl)imidazo[1,2-a]pyridine-3-carboxamide; N-(5-{5-[(4,4-difluoropiperidin-1-yl)methyl]-1,2,4-oxadiazol-3-yl}-2-methylphenyl)imidazo[1,2-a]pyridine-3-carboxamide; N-(5-{5-[1-(butane-1-sulfonyl)azetidin-3-yl]-1,2,4-oxadiazol-3-yl}-2-methylphenyl)imidazo[1,2-a]pyridine-3-carboxamide; N-(5-{5-[(2S)-4,4-difluoro-1-methanesulfonylpyrrolidin-2-yl]-1,2,4-oxadiazol-3-yl}-2-methylphenyl)imidazo[1,2-a]pyridine-3-carboxamide; methyl 4-[3-(3-{imidazo[1,2-a]pyridine-3-amido}-4-methylphenyl)-1,2,4-oxadiazol-5-yl]piperidine-1-carboxylate; N-{5-[5-(1-methanesulfonylpiperidin-4-yl)-1,2,4-oxadiazol-3-yl]-2-methylphenyl}imidazo[1,2-a]pyridine-3-carboxamide; N-{5-[5-(4-methanesulfonylmorpholin-2-yl)-1,2,4-oxadiazol-3-yl]-2-methylphenyl}imidazo[1,2-a]pyridine-3-carboxamide; N-(5-{5-[(2S)-1-methanesulfonylpyrrolidin-2-yl]-1,2,4-oxadiazol-3-yl}-2-methylphenyl)imidazo[1,2-a]pyridine-3-carboxamide; N-(5-{5-[(2R)-4-methanesulfonylmorpholin-2-yl]-1,2,4-oxadiazol-3-yl}-2-methylphenyl)imidazo[1,2-a]pyridine-3-carboxamide; N-[5-(5-{[(3S)-1-methanesulfonylpyrrolidin-3-yl]methyl}-1,2,4-oxadiazol-3-yl)-2-methylphenyl]imidazo[1,2-a]pyridine-3-carboxamide; N-(5-{5-[(3R)-1-methanesulfonylpiperidin-3-yl]-1,2,4-oxadiazol-3-yl}-2-methylphenyl)imidazo[1,2-a]pyridine-3-carboxamide; methyl (2S)-2-{[3-(3-{imidazo[1,2-a]pyridine-3-amido}-4-methylphenyl)-1,2,4-oxadiazol-5-yl]methyl}pyrrolidine-1-carboxylate; N-[5-(5-{[(2S)-1-methanesulfonylpyrrolidin-2-yl]methyl}-1,2,4-oxadiazol-3-yl)-2-methylphenyl]imidazo[1,2-a]pyridine-3-carboxamide; N-(2-methyl-5-{5-[(3,3,4,4-tetrafluoropyrrolidin-1-yl)methyl]-1,2,4-oxadiazol-3-yl}phenyl)imidazo[1,2-a]pyridine-3-carboxamide; N-(5-{5-[1-(difluoromethane)sulfonylazetidin-3-yl]-1,2,4-oxadiazol-3-yl}-2-methylphenyl)imidazo[1,2-a]pyridine-3-carboxamide; N-{2-methyl-5-[5-(oxan-2-ylmethyl)-1,2,4-oxadiazol-3-yl]phenyl}imidazo[1,2-a]pyridine-3-carboxamide; N-(5-{5-[(3,3-difluoropyrrolidin-1-yl)methyl]-1,2,4-oxadiazol-3-yl}-2-fluorophenyl)imidazo[1,2-a]pyridine-3-carboxamide; N-(5-{5-[(4,4-difluoropiperidin-1-yl)methyl]-1,2,4-oxadiazol-3-yl}-2-fluorophenyl)imidazo[1,2-a]pyridine-3-carboxamide; N-(2-methyl-5-{5-[(2S)-1-(propane-2-sulfonyl)azetidin-2-yl]-1,2,4-oxadiazol-3-yl}phenyl)imidazo[1,2-a]pyridine-3-carboxamide; methyl 3-[3-(4-methyl-3-{pyrazolo[1,5-a]pyridine-3-amido}phenyl)-1,2,4-oxadiazol-5-yl]azetidine-1-carboxylate; N-{2-methyl-5-[5-(oxan-3-ylmethyl)-1,2,4-oxadiazol-3-yl]phenyl}imidazo[1,2-a]pyridine-3-carboxamide; N-(5-{5-[(1S)-1-(3,3-difluoroazetidin-1-yl)ethyl]-1,2,4-oxadiazol-3-yl}-2-methylphenyl)imidazo[1,2-a]pyridine-3-carboxamide; N-(5-{5-[(1S)-1-(3,3-difluoropyrrolidin-1-yl)ethyl]-1,2,4-oxadiazol-3-yl}-2-methylphenyl)imidazo[1,2-a]pyridine-3-carboxamide; methyl 3-(3-{4-methyl-3-[6-(trifluoromethyl)imidazo[1,2-a]pyridine-3-amido]phenyl}-1,2,4-oxadiazol-5-yl) azetidine-1-carboxylate; ethyl 3-[3-(3-{imidazo[1,2-a]pyridine-3-amido}-4-methylphenyl)-1,2,4-oxadiazol-5-yl]azetidine-1-carboxylate; methyl 3-[3-(3-{7-fluoroimidazo[1,2-a]pyridine-3-amido}-4-methylphenyl)-1,2,4-oxadiazol-5-yl]azetidine-1-carboxylate; methyl 3-[3-(3-{6-fluoroimidazo[1,2-a]pyridine-3-amido}-4-methylphenyl)-1,2,4-oxadiazol-5-yl]azetidine-1-carboxylate; methyl 3-(3-{4-methyl-3-[7-(1-methyl-1H-pyrazol-3-yl)imidazo[1,2-a]pyridine-3-amido]phenyl}-1,2,4-oxadiazol-5-yl)azetidine-1-carboxylate; methyl 3-(3-{4-methyl-3-[7-(trifluoromethyl)imidazo[1,2-a]pyridine-3-amido]phenyl}-1,2,4-oxadiazol-5-yl)azetidine-1-carboxylate; N-{5-[5-(1-methanesulfonyl-3-methylazetidin-3-yl)-1,2,4-oxadiazol-3-yl]-2-methylphenyl}imidazo[1,2-a]pyridine-3-carboxamide; methyl 3-(3-{3-[6-(3-cyanopropyl)imidazo[1,2-a]pyridine-3-amido]-4-methylphenyl}-1,2,4-oxadiazol-5-yl)azetidine-1-carboxylate; methyl 3-[3-(3-{6- methoxyimidazo[1,2-a]pyridine-3-amido}-4-methylphenyl)-1,2,4-oxadiazol-5-yl]azetidine-1-carboxylate; methyl 3-[3-(4-methyl-3-{7-methylimidazo[1,2-a]pyridine-3-amido}phenyl)-1,2,4-oxadiazol-5-yl]azetidine-1-carboxylate; methyl 3-[3-(4-methyl-3-{6-methylimidazo[1,2-a]pyridine-3-amido}phenyl)-1,2,4-oxadiazol-5-yl]azetidine-1-carboxylate; methyl 3-{3-[4-methyl-3-(7-{1-[2-(morpholin-4-yl)ethyl]-1H-pyrazol-4-yl}imidazo[1,2-a]pyridine-3-amido)phenyl]-1,2,4-oxadiazol-5-yl}azetidine-1-carboxylate; methyl 3-(3-{3-[6-(2-cyanoethyl)imidazo[1,2-a]pyridine-3-amido]-4-methylphenyl}-1,2,4-oxadiazol-5-yl)azetidine-1-carboxylate; methyl 3-(3-{4-methyl-3-[6-(3-oxobutyl)imidazo[1,2-a]pyridine-3-amido]phenyl}-1,2,4-oxadiazol-5-yl)azetidine-1-carboxylate; methyl 3-[3-(4-methyl-3-{6-[2-(morpholin-4-yl)ethyl]imidazo[1,2-a]pyridine-3-amido}phenyl)-1,2,4-oxadiazol-5-yl]azetidine-1-carboxylate; methyl 3-(3-{3-[6-(3-hydroxy-3-methylbutyl)imidazo[1,2-a]pyridine-3-amido]4-methylphenyl}-1,2,4-oxadiazol-5-yl)azetidine-1-carboxylate; methyl 3-(3-{4-methyl-3-[7-(1H-pyrazol-3-yl)imidazo[1,2-a]pyridine-3-amido]phenyl}-1,2,4-oxadiazol-5-yl)azetidine-1-carboxylate; N-(2-methyl-5-{[5-(oxan-4-yl)-1,2,4-oxadiazol-3-yl]amino}phenyl)imidazo[1,2-a]pyridine-3-carboxamide; N-(2-methyl-5-{[5-(oxan-2-yl)-1,2,4-oxadiazol-3-yl]amino}phenyl)imidazo[1,2-a]pyridine-3-carboxamide; N-[2-methyl-5-({5-[(2R)-oxolan-2-yl]-1,2,4-oxadiazol-3-yl}amino)phenyl]imidazo[1,2-a]pyridine-3-carboxamide; N-[2-methyl-5-({5-[(2S)-oxolan-2-yl]-1,2,4-oxadiazol-3-yl}amino)phenyl]imidazo[1,2-a]pyridine-3-carboxamide; methyl 3-(3-{4-methyl-3-[7-(3-oxobutyl)imidazo[1,2-a]pyridine-3-amido]phenyl}-1,2,4-oxadiazol-5-yl)azetidine-1-carboxylate; methyl 3-(3-{3-[7-(3-hydroxy-3-methylbutyl)imidazo[1,2-a]pyridine-3-amido]4-methylphenyl}-1,2,4-oxadiazol-5-yl)azetidine-1-carboxylate; N-{2-methyl-5-[3-(morpholin-4-yl)-1,2,4-oxadiazol-5-yl]phenyl}imidazo[1,2-a]pyridine-3-carboxamide; methyl 3-[3-(4-methyl-3-{5,6,7,8-tetradeuteroimidazo[1,2-a]pyridine-3-amido}phenyl)-1,2,4-oxadiazol-5-yl]azetidine-1-carboxylate; N-{5-[5-(azetidin-1-yl)-1,2,4-oxadiazol-3-yl]-2-methylphenyl}imidazo[1,2-a]pyridine-3-carboxamide; N-{5-[5-(3,3-difluoroazetidin-1-yl)-1,2,4-oxadiazol-3-yl]-2-methylphenyl}imidazo[1,2-a]pyridine-3-carboxamide; methyl 3-[3-(5-{imidazo[1,2-a]pyridine-3-amido}-2,4-dimethylphenyl)-1,2,4-oxadiazol-5-yl]azetidine-1-carboxylate; methyl 3-[3-(4-methyl-3-{7-methylimidazo[1,2-a]pyridine-3-amido}phenyl)-1,2,4-oxadiazol-5-yl]azetidine-1-carboxylate; 7-fluoro-N-{2-methyl-5-[5-(oxan-4-ylamino)-1,2,4-oxadiazol-3-yl]phenyl}imidazo[1,2-a]pyridine-3-carboxamide; 6-methyl-N-{2-methyl-5-[5-(oxan-4-ylamino)-1,2,4-oxadiazol-3-yl]phenyl}imidazo[1,2-a]pyridine-3-carboxamide; methyl 3-(3-{4-methyl-3-[6-(morpholin-4-yl)imidazo[1,2-a]pyridine-3-amido]phenyl}-1,2,4-oxadiazol-5-yl)azetidine-1-carboxylate; methyl 3-[3-(4-methyl-3-{6-[(2,2,2-trifluoroethoxy)methyl]imidazo[1,2-a]pyridine-3-amido}phenyl)-1,2,4-oxadiazol-5-yl]azetidine-1-carboxylate; N-(5-{5-[3-hydroxy-3-(trifluoromethyl)azetidin-1-yl]-1,2,4-oxadiazol-3-yl}-2-methylphenyl)-6-methylimidazo[1,2-a]pyridine-3-carboxamide; N-{5-[5-(3,3-difluoroazetidin-1-yl)-1,2,4-oxadiazol-3-yl]-2-methylphenyl}-7-methylimidazo[1,2-a]pyridine-3-carboxamide; N-{5-[5-(3,3-difluoroazetidin-1-yl)-1,2,4-oxadiazol-3-yl]-2-methylphenyl}-7-fluoroimidazo[1,2-a]pyridine-3-carboxamide; N-{5-[5-(3-hydroxy-3-methylazetidin-1-yl)-1,2,4-oxadiazol-3-yl]-2-methylphenyl}-7-methylimidazo[1,2-a]pyridine-3-carboxamide; N-{5-[5-(4,4-difluoropiperidin-1-yl)-1,2,4-oxadiazol-3-yl]-2-methylphenyl}-7-methylimidazo[1,2-a]pyridine-3-carboxamide; N-{5-[5-(4-fluoropiperidin-1-yl)-1,2,4-oxadiazol-3-yl]-2-methylphenyl}-7-methylimidazo[1,2-a]pyridine-3-carboxamide; 7-methyl-N-{2-methyl-5-[5-(morpholin-4-yl)-1,2,4-oxadiazol-3-yl]phenyl}imidazo[1,2-a]pyridine-3-carboxamide; N-{5-[5-(3,3-difluoropyrrolidin-1-yl)-1,2,4-oxadiazol-3-yl]-2-methylphenyl}-7-methylimidazo[1,2-a]pyridine-3-carboxamide; 7-methyl-N-(2-methyl-5-{5-[3-(trifluoromethyl)piperidin-1-yl]-1,2,4-oxadiazol-3-yl}phenyl)imidazo[1,2-a]pyridine-3-carboxamide; N-(2-methyl-5-{3-[(1S,4S)-2-oxa-5-azabicyclo[2.2.1]heptan-5-yl]-1,2,4-oxadiazol-5-yl}phenyl)imidazo[1,2-a]pyridine-3-carboxamide; methyl 3-[3-(3-{6-[(2,2-difluoroethoxy)methyl]imidazo[1,2-a]pyridine-3-amido}-4-methylphenyl)-1,2,4-oxadiazol-5-yl]azetidine-1-carboxylate; methyl 3-[3-(3-{6-[(2-fluoroethoxy)methyl]imidazo[1,2-a]pyridine-3-amido}-4-methylphenyl)-1,2,4-oxadiazol-5-yl]azetidine-1-carboxylate; methyl 3-[3-(3-{7-hydrogenioimidazo[1,2-a]pyridine-3-amido}-4-methylphenyl)-1,2,4-oxadiazol-5-yl]azetidine-1-carboxylate; methyl 3-[3-(3-{6-hydrogenioimidazo[1,2-a]pyridine-3-amido}-4-methylphenyl)-1,2,4-oxadiazol-5-yl]azetidine-1-carboxylate, and N-(5-{5-[(3-cyanoazetidin-1-yl)methyl]-1,2,4-oxadiazol-3-yl}-2-methylphenyl)-6-(2,4-dimethyl-1,3-thiazol-5-yl)imidazo[1,2-a]pyridine-3-carboxamide.

A preferred embodiment of the compounds of Formula (I) is methyl 3-[3-(4-methyl-3-{5,6,7,8-tetradeuteroimidazo[1,2-a]pyridine-3-amido}phenyl)-1,2,4-oxadiazol-5-yl]azetidine-1-carboxylate.

Certain other embodiments of the compounds of Formula (I) or Formula (II) are selected from: N-[5-(3-{2-[(1-benzylpiperidin-4-yl)oxy]ethyl}-1,2,4-oxadiazol-5-yl)-2-methylphenyl]imidazo[1,2-a]pyridine-3-carboxamide; methyl 3-[5-(3-{imidazo[1,2-a]pyridine-3-amido}-4-methylphenyl)-1,2,4-oxadiazol-3-yl]azetidine-1-carboxylate; N-{2-methyl-5-[5-(oxan-4-yl)-1,2,4-oxadiazol-3-yl]phenyl}imidazo[1,2-a]pyridine-3-carboxamide; N-(2-methyl-5-{5-[(2R)-oxolan-2-yl]-1,2,4-oxadiazol-3-yl}phenyl)imidazo[1,2-a]pyridine-3-carboxamide; N-(2-methyl-5-{5-[(2S)-oxolan-2-yl]-1,2,4-oxadiazol-3-yl}phenyl)imidazo[1,2-a]pyridine-3-carboxamide; tert-butyl 4-[3-(3-{imidazo[1,2-a]pyridine-3-amido}-4-methylphenyl)-1,2,4-oxadiazol-5-yl]piperidine-1-carboxylate; tert-butyl 2-[3-(3-{imidazo[1,2-a]pyridine-3-amido}-4-methylphenyl)-1,2,4-oxadiazol-5-yl]pyrrolidine-1-carboxylate; tert-butyl 3-[3-(3-{imidazo[1,2-a]pyridine-3-amido}-4-methylphenyl)-1,2,4-oxadiazol-5-yl]pyrrolidine-1-carboxylate; N-{2-methyl-5-[5-(pyrrolidin-2-yl)-1,2,4-oxadiazol-3-yl]phenyl}imidazo[1,2-a]pyridine-3-carboxamide; N-{2-methyl-5-[5-(piperidin-2-yl)-1,2,4-oxadiazol-3-yl]phenyl}imidazo[1,2-a]pyridine-3-carboxamide; N-{5-[5-(1-methanesulfonylpiperidin-2-yl)-1,2,4-oxadiazol-3-yl]-2-methylphenyl}imidazo[1,2-a]pyridine-3-carboxamide; N-{2-methyl-5-[5-(1-methylpiperidin-2-yl)-1,2,4-oxadiazol-3-yl]phenyl}imidazo[1,2-a]pyridine-3-carboxamide; N-{5-[5-(5-hydroxyoxan-2-yl)-1,2,4-oxadiazol-3-yl]-2-methylphenyl}imidazo[1,2-a]pyridine-3-carboxamide; tert-butyl 3-[3-(3-{imidazo[1,2-a]pyridine-3-amido}-4-methylphenyl)-1,2,4-oxadiazol-5-yl]azetidine-1-carboxylate; N-(5-{5-[(5S)-5-hydroxyoxan-2-yl]-1,2,4-oxadiazol-3-yl}-2-methylphenyl)imidazo[1,2-a]pyridine-3-carboxamide; N-{5-[5-(1-acetylazetidin-3-yl)-1,2,4-oxadiazol-3-yl]-2-methylphenyl}imidazo[1,2-a]pyridine-3-carboxamide; tert-butyl (3S)-3-[3-(3-{imidazo[1,2-a]pyridine-3-amido}-4-methylphenyl)-1,2,4-oxadiazol-5-yl]morpholine-4-carboxylate; tert-butyl (3R)-3-[3-(3-{imidazo[1,2-a]pyridine-3-amido}-4-methylphenyl)-1,2,4- oxadiazol-5-yl]morpholine-4-carboxylate; N-(2-methyl-5-{5-[(3R)-morpholin-3-yl]-1,2,4-oxadiazol-3-yl}phenyl)imidazo[1,2-a]pyridine-3-carboxamide; N-(2-methyl-5-{5-[(2S)-6-oxopiperidin-2-yl]-1,2,4-oxadiazol-3-yl}phenyl)imidazo[1,2-a]pyridine-3-carboxamide; tert-butyl (2S)-4,4-difluoro-2-[3-(3-{imidazo[1,2-a]pyridine-3-amido}-4-methylphenyl)-1,2,4-oxadiazol-5-yl]pyrrolidine-1-carboxylate; N-(5-{5-[(2S)-4,4-difluoropyrrolidin-2-yl]-1,2,4-oxadiazol-3-yl}-2-methylphenyl)imidazo[1,2-a]pyridine-3-carboxamide; tert-butyl (2S)-2-[3-(3-{imidazo[1,2-a]pyridine-3-amido}-4-methylphenyl)-1,2,4-oxadiazol-5-yl]morpholine-4-carboxylate; N-(2-methyl-5-{5-[(2S)-morpholin-2-yl]-1,2,4-oxadiazol-3-yl}phenyl)imidazo[1,2-a]pyridine-3-carboxamide; N-(2-methyl-5-{5-[3-(morpholin-4-yl)-3-oxopropyl]-1,2,4-oxadiazol-3-yl}phenyl)imidazo[1,2-a]pyridine-3-carboxamide; N-(5-{5-[3-(3,3-difluoropyrrolidin-1-yl)-3-oxopropyl]-1,2,4-oxadiazol-3-yl}-2-methylphenyl)imidazo[1,2-a]pyridine-3-carboxamide; 1-methylcyclopropyl 3-[3-(3-{imidazo[1,2-a]pyridine-3-amido}-4-methylphenyl)-1,2,4-oxadiazol-5-yl]azetidine-1-carboxylate; 2-methoxyethyl 3-[3-(3-{imidazo[1,2-a]pyridine-3-amido}-4-methylphenyl)-1,2,4-oxadiazol-5-yl]azetidine-1-carboxylate; N-{2-methyl-5-[5-(3-methyloxetan-3-yl)-1,2,4-oxadiazol-3-yl]phenyl}imidazo[1,2-a]pyridine-3-carboxamide; N-(5-{5-[(3-cyanoazetidin-1-yl)methyl]-1,2,4-oxadiazol-3-yl}-2-methylphenyl)imidazo[1,2-a]pyridine-3-carboxamide; N-(5-{5-[(3-fluoroazetidin-1-yl)methyl]-1,2,4-oxadiazol-3-yl}-2-methylphenyl)imidazo[1,2-a]pyridine-3-carboxamide; N-(5-{5-[(3-hydroxyazetidin-1-yl)methyl]-1,2,4-oxadiazol-3-yl}-2-methylphenyl)imidazo[1,2-a]pyridine-3-carboxamide; N-(5-{5-[(3-methoxyazetidin-1-yl)methyl]-1,2,4-oxadiazol-3-yl}-2-methylphenyl)imidazo[1,2-a]pyridine-3-carboxamide; tert-butyl N-{3-[3-(3-{imidazo[1,2-a]pyridine-3-amido}-4-methylphenyl)-1,2,4-oxadiazol-5-yl]azetidine-1-sulfonyl}carbamate; 2-(morpholin-4-yl)ethyl 3-[3-(3-{imidazo[1,2-a]pyridine-3-amido}-4-methylphenyl)-1,2,4-oxadiazol-5-yl]azetidine-1-carboxylate; 3-(morpholin-4-yl)propyl 3-[3-(3-{imidazo[1,2-a]pyridine-3-amido}-4-methylphenyl)-1,2,4-oxadiazol-5-yl]azetidine-1-carboxylate; N-(5-{5-[(2S)-azetidin-2-yl]-1,2,4-oxadiazol-3-yl}-2-methylphenyl)imidazo[1,2-a]pyridine-3-carboxamide; [3-(3-{imidazo[1,2-a]pyridine-3-amido}-4-methylphenyl)-1,2,4-oxadiazol-5-yl]methyl N-(1-methylazetidin-3-yl)carbamate; [3-(3-{imidazo[1,2-a]pyridine-3-amido}-4-methylphenyl)-1,2,4-oxadiazol-5-yl]methyl 3-methoxyazetidine-1-carboxylate; tert-butyl N-{3-[3-(3-{imidazo[1,2-a]pyridine-3-amido}-4-methylphenyl)-1,2,4-oxadiazol-5-yl]oxetan-3-yl}carbamate; methyl N-{3-[3-(3-{imidazo[1,2-a]pyridine-3-amido}-4-methylphenyl)-1,2,4-oxadiazol-5-yl]oxetan-3-yl}carbamate; N-(5-{5-[3-(2-methoxyacetamido)oxetan-3-yl]-1,2,4-oxadiazol-3-yl}-2-methylphenyl) imidazo[1,2-a]pyridine-3-carboxamide; N-(2-methyl-5-{5-[(2-oxo-1,3-oxazolidin-3-yl)methyl]-1,2,4-oxadiazol-3-yl}phenyl)imidazo[1,2-a]pyridine-3-carboxamide; N-(2-methyl-5-{5-[(2-oxopyrrolidin-1-yl)methyl]-1,2,4-oxadiazol-3-yl}phenyl)imidazo[1,2-a]pyridine-3-carboxamide; N-[2-methyl-5-(5-{[2-(morpholin-4-yl)acetamido]methyl}-1,2,4-oxadiazol-3-yl)phenyl]imidazo[1,2-a]pyridine-3-carboxamide; N-[2-methyl-5-(5-{[2-(oxolan-2-yl)acetamido]methyl}-1,2,4-oxadiazol-3-yl)phenyl]imidazo[1,2-a]pyridine-3-carboxamide; N-[2-methyl-5-(5-{[(2R)-oxolan-2-ylformamido]methyl}-1,2,4-oxadiazol-3-yl)phenyl]imidazo[1,2-a]pyridine-3-carboxamide; N-[2-methyl-5-(5-{[(2S)-oxolan-2-ylformamido]methyl}-1,2,4-oxadiazol-3-yl)phenyl]imidazo[1,2-a]pyridine-3-carboxamide; N-[2-methyl-5-(5-{[(3-methyloxetan-3-yl)formamido]methyl}-1,2,4-oxadiazol-3-yl)phenyl]imidazo[1,2-a]pyridine-3-carboxamide; N-(2-methyl-5-{5-[(oxan-4-ylformamido)methyl]-1,2,4-oxadiazol-3-yl}phenyl)imidazo[1,2-a]pyridine-3-carboxamide; 2-hydroxyethyl 3-[3-(3-{imidazo[1,2-a]pyridine-3-amido}-4-methylphenyl)-1,2,4-oxadiazol-5-yl]azetidine-1-carboxylate; methyl (2S)-2-[3-(3-{imidazo[1,2-a]pyridine-3-amido}-4-methylphenyl)-1,2,4-oxadiazol-5-yl]azetidine-1-carboxylate; N-(5-{5-[(2S)-1-acetylazetidin-2-yl]-1,2,4-oxadiazol-3-yl}-2-methylphenyl)imidazo[1,2-a]pyridine-3-carboxamide; tert-butyl 3-[3-(4-fluoro-3-{imidazo[1,2-a]pyridine-3-amido}phenyl)-1,2,4-oxadiazol-5-yl]azetidine-1-carboxylate; N-{2-fluoro-5-[5-(1-methanesulfonylazetidin-3-yl)-1,2,4-oxadiazol-3-yl]phenyl}imidazo[1,2-a]pyridine-3-carboxamide; N-(5-{5-[1-(ethanesulfonyl)azetidin-3-yl]-1,2,4-oxadiazol-3-yl}-2-fluorophenyl)imidazo[1,2-a]pyridine-3-carboxamide; N-(2-fluoro-5-{5-[1-(propane-1-sulfonyl)azetidin-3-yl]-1,2,4-oxadiazol-3-yl}phenyl)imidazo[1,2-a]pyridine-3-carboxamide; N-(2-methyl-5-{5-[1-(pyridine-3-sulfonyl)azetidin-3-yl]-1,2,4-oxadiazol-3-yl}phenyl)imidazo[1,2-a]pyridine-3-carboxamide; N-(2-methyl-5-{5-[1-(1-methyl-1H-pyrazole-3-sulfonyl)azetidin-3-yl]-1,2,4-oxadiazol-3-yl}phenyl)imidazo[1,2-a]pyridine-3-carboxamide; N-(2-methyl-5-{5-[1-(oxolane-3-sulfonyl)azetidin-3-yl]-1,2,4-oxadiazol-3-yl}phenyl)imidazo[1,2-a]pyridine-3-carboxamide; N-(2-methyl-5-{5-[1-(oxane-4-sulfonyl)azetidin-3-yl]-1,2,4-oxadiazol-3-yl}phenyl)imidazo[1,2-a]pyridine-3-carboxamide; methyl 3-{3-[3-(3-{imidazo[1,2-a]pyridine-3-amido}-4-methylphenyl)-1,2,4-oxadiazol-5-yl]azetidine-1-sulfonyl}propanoate; tert-butyl 3-{3-[3-(3-{imidazo[1,2-a]pyridine-3-amido}-4-methylphenyl)-1,2,4-oxadiazol-5-yl]azetidine-1-sulfonyl}pyrrolidine-1-carboxylate; tert-butyl 4-{3-[3-(3-{imidazo[1,2-a]pyridine-3-amido}-4-methylphenyl)-1,2,4-oxadiazol-5-yl]azetidine-1-sulfonyl}piperidine-1-carboxylate; methyl (3S)-3-[3-(3-{imidazo[1,2-a]pyridine-3-amido}-4-methylphenyl)-1,2,4-oxadiazol-5-yl]morpholine-4-carboxylate; N-(5-{5-[(3S)-4-methanesulfonylmorpholin-3-yl]-1,2,4-oxadiazol-3-yl}-2-methylphenyl)imidazo[1,2-a]pyridine-3-carboxamide; methyl (3R)-3-[3-(3-{imidazo[1,2-a]pyridine-3-amido}-4-methylphenyl)-1,2,4-oxadiazol-5-yl]morpholine-4-carboxylate; N-(5-{5-[(3R)-4-methanesulfonylmorpholin-3-yl]-1,2,4-oxadiazol-3-yl}-2-methylphenyl)imidazo[1,2-a]pyridine-3-carboxamide; N-(5-{5-[(3R)-4-acetylmorpholin-3-yl]-1,2,4-oxadiazol-3-yl}-2-methylphenyl)imidazo[1,2-a]pyridine-3-carboxamide; methyl 3-[3-(3-{imidazo[1,2-a]pyridine-3-amido}-4-methylphenyl)-1,2,4-oxadiazol-5-yl]pyrrolidine-1-carboxylate; N-{5-[5-(1-methanesulfonylpyrrolidin-3-yl)-1,2,4-oxadiazol-3-yl]-2-methylphenyl}imidazo[1,2-a]pyridine-3-carboxamide; N-{5-[5-(1-acetylpyrrolidin-3-yl)-1,2,4-oxadiazol-3-yl]-2-methylphenyl}imidazo[1,2-a]pyridine-3-carboxamide; methyl (2S)-4,4-difluoro-2-[3-(3-{imidazo[1,2-a]pyridine-3-amido}-4-methylphenyl)-1,2,4-oxadiazol-5-yl]pyrrolidine-1-carboxylate; N-(5-{5-[(2S)-1-acetyl-4,4-difluoropyrrolidin-2-yl]-1,2,4-oxadiazol-3-yl}-2-methylphenyl)imidazo[1,2-a]pyridine-3-carboxamide; 3-[3-(3-{imidazo[1,2-a]pyridine-3-amido}-4-methylphenyl)-1,2,4-oxadiazol-5-yl]-N,N-dimethylazetidine-1-carboxamide; tert-butyl 2-[3-(3-{imidazo[1,2-a]pyridine-3-amido}-4-methylphenyl)-1,2,4-oxadiazol-5-yl]morpholine-4-carboxylate; tert-butyl (2S)-2-[3-(3-{imidazo[1,2-a]pyridine-3-amido}-4-methylphenyl)-1,2,4-oxadiazol-5-yl]pyrrolidine-1-carboxylate; methyl 3-{[3-(3-{imidazo[1,2-a]pyridine-3-amido}-4-methylphenyl)-1,2,4-oxadiazol-5-yl]methyl}azetidine-1-carboxylate; N-(5-{5-[(1-methanesulfonylazetidin-3-yl)methyl]-1,2,4-oxadiazol-3- yl}-2-methylphenyl)imidazo[1,2-a]pyridine-3-carboxamide; N-(5-{5-[2-(3,3-difluoroazetidin-1-yl)ethyl]-1,2,4-oxadiazol-3-yl}-2-methylphenyl)imidazo[1,2-a]pyridine-3-carboxamide; N-(2-methyl-5-{5-[2-(morpholin-4-yl)ethyl]-1,2,4-oxadiazol-3-yl}phenyl)imidazo[1,2-a]pyridine-3-carboxamide; N-[5-(5-{[3-(hydroxymethyl)azetidin-1-yl]methyl}-1,2,4-oxadiazol-3-yl)-2-methylphenyl]imidazo[1,2-a]pyridine-3-carboxamide; N-[5-(5-{[3-(methoxymethyl)azetidin-1-yl]methyl}-1,2,4-oxadiazol-3-yl)-2-methylphenyl]imidazo[1,2-a]pyridine-3-carboxamide; tert-butyl N-{[3-(3-{imidazo[1,2-a]pyridine-3-amido}-4-methylphenyl)-1,2,4-oxadiazol-5-yl](oxetan-3-yl)methyl}carbamate; tert-butyl (3S)-3-{[3-(3-{imidazo[1,2-a]pyridine-3-amido}-4-methylphenyl)-1,2,4-oxadiazol-5-yl]methyl}pyrrolidine-1-carboxylate; tert-butyl (3R)-3-{[3-(3-{imidazo[1,2-a]pyridine-3-amido}-4-methylphenyl)-1,2,4-oxadiazol-5-yl]methyl}pyrrolidine-1-carboxylate; tert-butyl (3R)-3-[3-(3-{imidazo[1,2-a]pyridine-3-amido}-4-methylphenyl)-1,2,4-oxadiazol-5-yl]piperidine-1-carboxylate; tert-butyl (3S)-3-[3-(3-{imidazo[1,2-a]pyridine-3-amido}-4-methylphenyl)-1,2,4-oxadiazol-5-yl]piperidine-1-carboxylate; N-{2-methyl-5-[5-(morpholin-2-yl)-1,2,4-oxadiazol-3-yl]phenyl}imidazo[1,2-a]pyridine-3-carboxamide; N-(2-methyl-5-{5-[(2R)-morpholin-2-yl]-1,2,4-oxadiazol-3-yl}phenyl)imidazo[1,2-a]pyridine-3-carboxamide; N-(2-methyl-5-{5-[(2S)-pyrrolidin-2-yl]-1,2,4-oxadiazol-3-yl}phenyl)imidazo[1,2-a]pyridine-3-carboxamide; N-(2-methyl-5-{5-[(2S)-5-oxopyrrolidin-2-yl]-1,2,4-oxadiazol-3-yl}phenyl)imidazo[1,2-a]pyridine-3-carboxamide; N-{2-methyl-5-[5-(5-oxopyrrolidin-2-yl)-1,2,4-oxadiazol-3-yl]phenyl}imidazo[1,2-a]pyridine-3-carboxamide; N-{5-[5-(1-acetylpiperidin-4-yl)-1,2,4-oxadiazol-3-yl]-2-methylphenyl}imidazo[1,2-a]pyridine-3-carboxamide; methyl 2-[3-(3-{imidazo[1,2-a]pyridine-3-amido}-4-methylphenyl)-1,2,4-oxadiazol-5-yl]morpholine-4-carboxylate; N-{5-[5-(4-acetylmorpholin-2-yl)-1,2,4-oxadiazol-3-yl]-2-methylphenyl}imidazo[1,2-a]pyridine-3-carboxamide; methyl (2S)-2-[3-(3-{imidazo[1,2-a]pyridine-3-amido}-4-methylphenyl)-1,2,4-oxadiazol-5-yl]pyrrolidine-1-carboxylate; N-(5-{5-[(2S)-1-acetylpyrrolidin-2-yl]-1,2,4-oxadiazol-3-yl}-2-methylphenyl)imidazo[1,2-a]pyridine-3-carboxamide; methyl (2R)-2-[3-(3-{imidazo[1,2-a]pyridine-3-amido}-4-methylphenyl)-1,2,4-oxadiazol-5-yl]morpholine-4-carboxylate; N-(5-{5-[(2R)-4-acetylmorpholin-2-yl]-1,2,4-oxadiazol-3-yl}-2-methylphenyl)imidazo[1,2-a]pyridine-3-carboxamide; N-(2-methyl-5-{5-[(2R)-pyrrolidin-2-yl]-1,2,4-oxadiazol-3-yl}phenyl)imidazo[1,2-a]pyridine-3-carboxamide; methyl 3-[3-(4-fluoro-3-{imidazo[1,2-a]pyridine-3-amido}phenyl)-1,2,4-oxadiazol-5-yl]azetidine-1-carboxylate; 1-methylcyclopropyl (2S)-2-[3-(3-{imidazo[1,2-a]pyridine-3-amido}-4-methylphenyl)-1,2,4-oxadiazol-5-yl]azetidine-1-carboxylate; N-(2-methyl-5-{5-[(3R)-piperidin-3-yl]-1,2,4-oxadiazol-3-yl}phenyl)imidazo[1,2-a]pyridine-3-carboxamide; methyl (3S)-3-{[3-(3-{imidazo[1,2-a]pyridine-3-amido}-4-methylphenyl)-1,2,4-oxadiazol-5-yl]methyl}pyrrolidine-1-carboxylate; methyl (3R)-3-{[3-(3-{imidazo[1,2-a]pyridine-3-amido}-4-methylphenyl)-1,2,4-oxadiazol-5-yl]methyl}pyrrolidine-1-carboxylate; N-[5-(5-{[(3R)-1-methanesulfonylpyrrolidin-3-yl]methyl}-1,2,4-oxadiazol-3-yl)-2-methylphenyl]imidazo[1,2-a]pyridine-3-carboxamide; methyl (3R)-3-[3-(3-{imidazo[1,2-a]pyridine-3-amido}-4-methylphenyl)-1,2,4-oxadiazol-5-yl]piperidine-1-carboxylate; methyl (3S)-3-[3-(3-{imidazo[1,2-a]pyridine-3-amido}-4-methylphenyl)-1,2,4-oxadiazol-5-yl]piperidine-1-carboxylate; N-(5-{5-[(3S)-1-methanesulfonylpiperidin-3-yl]-1,2,4-oxadiazol-3-yl}-2-methylphenyl)imidazo[1,2-a]pyridine-3-carboxamide; tert-butyl 4-{[3-(3-{imidazo[1,2-a]pyridine-3-amido}-4-methylphenyl)-1,2,4-oxadiazol-5-yl]methyl}piperidine-1-carboxylate; tert-butyl (2S)-2-{[3-(3-{imidazo[1,2-a]pyridine-3-amido}-4-methylphenyl)-1,2,4-oxadiazol-5-yl]methyl}pyrrolidine-1-carboxylate; methyl (2R)-2-[3-(3-{imidazo[1,2-a]pyridine-3-amido}-4-methylphenyl)-1,2,4-oxadiazol-5-yl]pyrrolidine-1-carboxylate; N-(5-{5-[(2R)-1-methanesulfonylpyrrolidin-2-yl]-1,2,4-oxadiazol-3-yl}-2-methylphenyl)imidazo[1,2-a]pyridine-3-carboxamide; methyl 4-{[3-(3-{imidazo[1,2-a]pyridine-3-amido}-4-methylphenyl)-1,2,4-oxadiazol-5-yl]methyl}piperidine-1-carboxylate; N-(5-{5-[(1-methanesulfonylpiperidin-4-yl)methyl]-1,2,4-oxadiazol-3-yl}-2-methylphenyl)imidazo[1,2-a]pyridine-3-carboxamide; N-(2-methyl-5-{5-[(2S)-pyrrolidin-2-ylmethyl]-1,2,4-oxadiazol-3-yl}phenyl)imidazo[1,2-a]pyridine-3-carboxamide; N-(2-methyl-5-{5-[1-(1-methyl-1H-pyrazole-4-sulfonyl)azetidin-3-yl]-1,2,4-oxadiazol-3-yl}phenyl)imidazo[1,2-a]pyridine-3-carboxamide; N-(2-methyl-5-{5-[1-(1H-pyrazole-4-sulfonyl)azetidin-3-yl]-1,2,4-oxadiazol-3-yl}phenyl)imidazo[1,2-a]pyridine-3-carboxamide; N-(5-{5-[1-(butane-1-sulfonyl)azetidin-3-yl]-1,2,4-oxadiazol-3-yl}-2-fluorophenyl)imidazo[1,2-a]pyridine-3-carboxamide; N-(2-fluoro-5-{5-[1-(pyridine-3-sulfonyl)azetidin-3-yl]-1,2,4-oxadiazol-3-yl}phenyl)imidazo[1,2-a]pyridine-3-carboxamide; N-(2-fluoro-5-{5-[1-(1-methyl-1H-pyrazole-3-sulfonyl)azetidin-3-yl]-1,2,4-oxadiazol-3-yl}phenyl)imidazo[1,2-a]pyridine-3-carboxamide; N-[2-fluoro-5-(5-{1-[(2-methoxyethane)sulfonyl]azetidin-3-yl}-1,2,4-oxadiazol-3-yl)phenyl]imidazo[1,2-a]pyridine-3-carboxamide; N-(5-{5-[1-(difluoromethane)sulfonylazetidin-3-yl]-1,2,4-oxadiazol-3-yl}-2-fluorophenyl)imidazo[1,2-a]pyridine-3-carboxamide; N-(2-fluoro-5-{5-[1-(1-methyl-1H-pyrazole-4-sulfonyl)azetidin-3-yl]-1,2,4-oxadiazol-3-yl}phenyl)imidazo[1,2-a]pyridine-3-carboxamide; N-(5-{5-[1-(3-methoxypropyl)azetidin-3-yl]-1,2,4-oxadiazol-3-yl}-2-methylphenyl)imidazo[1,2-a]pyridine-3-carboxamide; N-(5-{5-[(1R)-1-(3,3-difluoroazetidin-1-yl)ethyl]-1,2,4-oxadiazol-3-yl}-2-methylphenyl)imidazo[1,2-a]pyridine-3-carboxamide; N-(5-{5-[(1R)-1-(3,3-difluoropyrrolidin-1-yl)ethyl]-1,2,4-oxadiazol-3-yl}-2-methylphenyl)imidazo[1,2-a]pyridine-3-carboxamide; N-(5-{5-[(3,3-difluoroazetidin-1-yl)methyl]-1,2,4-oxadiazol-3-yl}-2-fluorophenyl)imidazo[1,2-a]pyridine-3-carboxamide; N-{2-fluoro-5-[5-(morpholin-4-ylmethyl)-1,2,4-oxadiazol-3-yl]phenyl}imidazo[1,2-a]pyridine-3-carboxamide; N-(2-methyl-5-{5-[1-(2,2,2-trifluoroacetyl)azetidin-3-yl]-1,2,4-oxadiazol-3-yl}phenyl)imidazo[1,2-a]pyridine-3-carboxamide; methyl 3-[3-(2-fluoro-5-{imidazo[1,2-a]pyridine-3-amido}-4-methylphenyl)-1,2,4-oxadiazol-5-yl]azetidine-1-carboxylate; N-{4-fluoro-5-[5-(1-methanesulfonylazetidin-3-yl)-1,2,4-oxadiazol-3-yl]-2-methylphenyl}imidazo[1,2-a]pyridine-3-carboxamide; methyl 3-(3-{4-methyl-3-[6-(trifluoromethyl)imidazo[1,2-a]pyridine-3-amido]phenyl}-1,2,4-oxadiazol-5-yl)azetidine-1-carboxylate; propan-2-yl 3-[3-(3-{imidazo[1,2-a]pyridine-3-amido}-4-methylphenyl)-1,2,4-oxadiazol-5-yl]azetidine-1-carboxylate; methyl 3-[3-(3-{7-cyanoimidazo[1,2-a]pyridine-3-amido}-4-methylphenyl)-1,2,4-oxadiazol-5-yl]azetidine-1-carboxylate; methyl 3-[3-(3-{6-cyanoimidazo[1,2-a]pyridine-3-amido}-4-methylphenyl)-1,2,4-oxadiazol-5-yl]azetidine-1-carboxylate; N-(5-{5-[1-(3,3-difluoropyrrolidin-1-yl)-2-methoxyethyl]-1,2,4-oxadiazol-3-yl}-2-methylphenyl)imidazo[1,2-a]pyridine-3-carboxamide; methyl 3-(3-{4-methyl-3-[7-(trifluoromethyl)imidazo[1,2-a]pyridine-3-amido]phenyl}-

1,2,4-oxadiazol-5-yl)azetidine-1-carboxylate; tert-butyl 3-[3-(3-{imidazo[1,2-a]pyridine-3-amido}-4-methylphenyl)-1,2,4-oxadiazol-5-yl]-3-methylazetidine-1-carboxylate; methyl 3-[3-(3-{imidazo[1,2-a]pyridine-3-amido}-4-methylphenyl)-1,2,4-oxadiazol-5-yl]-3-methylazetidine-1-carboxylate; methyl 3-[3-(3-{6-[3-(tert-butoxy)-3-oxopropyl]imidazo[1,2-a]pyridine-3-amido}-4-methylphenyl)-1,2,4-oxadiazol-5-yl]azetidine-1-carboxylate; methyl 3-[3-(3-{8-fluoroimidazo[1,2-a]pyridine-3-amido}-4-methylphenyl)-1,2,4-oxadiazol-5-yl]azetidine-1-carboxylate; N-(2-methyl-5-{5-[1-(pyrazin-2-yl)azetidin-3-yl]-1,2,4-oxadiazol-3-yl}phenyl)imidazo[1,2-a]pyridine-3-carboxamide; N-(2-methyl-5-{5-[1-(5-methyl-1,2,4-oxadiazol-3-yl)azetidin-3-yl]-1,2,4-oxadiazol-3-yl}phenyl)imidazo[1,2-a]pyridine-3-carboxamide; methyl 3-[3-(3-{6-acetylimidazo[1,2-a]pyridine-3-amido}-4-methylphenyl)-1,2,4-oxadiazol-5-yl]azetidine-1-carboxylate; methyl 3-(3-{3-[6-(2-hydroxypropan-2-yl)imidazo[1,2-a]pyridine-3-amido]-4-methylphenyl}-1,2,4-oxadiazol-5-yl)azetidine-1-carboxylate; methyl 3-(3-{3-[6-(2-hydroxy-2-methylpropyl)imidazo[1,2-a]pyridine-3-amido]-4-methylphenyl}-1,2,4-oxadiazol-5-yl)azetidine-1-carboxylate; N-{5-[5-(azetidin-1-yl)-1,2,4-oxadiazol-3-yl]-2-methylphenyl}imidazo[1,2-a]pyridine-3-carboxamide; methyl 3-[3-(3-{imidazo[1,2-a]pyridine-3-amido}-2,4-dimethylphenyl)-1,2,4-oxadiazol-5-yl]azetidine-1-carboxylate; methyl 3-(3-{4-methyl-3-[7-(2-oxo-1,3-oxazolidin-3-yl)imidazo[1,2-a]pyridine-3-amido]phenyl}-1,2,4-oxadiazol-5-yl)azetidine-1-carboxylate; N-{5-[3-(3-hydroxy-3-methylazetidin-1-yl)-1,2,4-oxadiazol-5-yl]-2-methylphenyl}imidazo[1,2-a]pyridine-3-carboxamide; methyl 3-(3-{3-[6-(1H-imidazol-1-yl)imidazo[1,2-a]pyridine-3-amido]-4-methylphenyl}-1,2,4-oxadiazol-5-yl)azetidine-1-carboxylate; methyl 3-[3-(3-{6-[3-(methoxymethyl)-1H-1,2,4-triazol-5-yl]imidazo[1,2-a]pyridine-3-amido}-4-methylphenyl)-1,2,4-oxadiazol-5-yl]azetidine-1-carboxylate; N-{5-[5-(3-methoxyazetidin-1-yl)-1,2,4-oxadiazol-3-yl]-2-methylphenyl}-7-methylimidazo[1,2-a]pyridine-3-carboxamide; N-(5-{5-[(3aS)-1-oxo-hexahydro-1H-[1,3]oxazolo[3,4-a]piperazin-5-yl]-1,2,4-oxadiazol-3-yl}-2-methylphenyl)-7-methylimidazo[1,2-a]pyridine-3-carboxamide; N-(5-{5-[(3-cyanoazetidin-1-yl)methyl]-1,2,4-oxadiazol-3-yl}-2-methylphenyl)-6-(1-methyl-1H-pyrazol-4-yl)imidazo[1,2-a]pyridine-3-carboxamide; methyl 3-(3-{4-methyl-3-[7-(trifluoromethyl)imidazo[1,2-a]pyridine-3-amido]phenyl}-1,2,4-oxadiazol-5-yl)azetidine-1-carboxylate; N-(5-{5-[(3-cyanoazetidin-1-yl)methyl]-1,2,4-oxadiazol-3-yl}-2-methylphenyl)-6-[1-(2-hydroxy-2-methylpropyl)-1H-pyrazol-4-yl]imidazo[1,2-a]pyridine-3-carboxamide; 2,2-difluoroethyl 3-[3-(3-{imidazo[1,2-a]pyridine-3-amido}-4-methylphenyl)-1,2,4-oxadiazol-5-yl]azetidine-1-carboxylate; 6-methyl-N-(2-methyl-5-{5-[(oxetan-3-yloxy)methyl]-1,2,4-oxadiazol-3-yl}phenyl)imidazo[1,2-a]pyridine-3-carboxamide; tert-butyl (2S)-2-[3-(4-methyl-3-{6-methylimidazo[1,2-a]pyridine-3-amido}phenyl)-1,2,4-oxadiazol-5-yl]azetidine-1-carboxylate; methyl (2S)-2-[3-(4-methyl-3-{6-methylimidazo[1,2-a]pyridine-3-amido}phenyl)-1,2,4-oxadiazol-5-yl]azetidine-1-carboxylate; N-{2-methyl-5-[5-(oxetan-2-yl)-1,2,4-oxadiazol-3-yl]phenyl}imidazo[1,2-a]pyridine-3-carboxamide; 2,2,2-trifluoroethyl 3-[3-(3-{imidazo[1,2-a]pyridine-3-amido}-4-methylphenyl)-1,2,4-oxadiazol-5-yl]azetidine-1-carboxylate; tert-butyl 4-[3-(3-{imidazo[1,2-a]pyridine-3-amido}-4-methylphenyl)-1,2,4-oxadiazol-5-yl]piperidine-1-carboxylate; methyl 3-(3-{3-[6-(hydroxymethyl)imidazo[1,2-a]pyridine-3-amido]-4-methylphenyl}-1,2,4-oxadiazol-5-yl)azetidine-1-carboxylate; tert-butyl 3-{[3-(4-methyl-3-{6-methylimidazo[1,2-a]pyridine-3-amido}phenyl)-1,2,4-oxadiazol-5-yl]methoxy}azetidine-1-carboxylate; tert-butyl 3-[3-(3-{imidazo[1,2-a]pyridine-3-amido}-4-methylphenyl)-1,2,4-oxadiazol-5-yl]pyrrolidine-1-carboxylate; N-(5-{5-[(2R)-1-acetylpyrrolidin-2-yl]-1,2,4-oxadiazol-3-yl}-2-methylphenyl)imidazo[1,2-a]pyridine-3-carboxamide, and N-[2-methyl-5-(5-{[2-(oxan-4-ypacetamido]methyl}-1,2,4-oxadiazol-3-yl)phenyl]imidazo[1,2-a]pyridine-3-carboxamide.

Another aspect provided herein are pharmaceutical compositions that include a therapeutically effective amount of a compound of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), and a pharmaceutically acceptable carrier. In certain embodiments of such pharmaceutical compositions, the pharmaceutical composition is formulated for intravenous administration, intravitrial administration, intramuscular administration, oral administration, rectal administration, transdermal administration, pulmonary administration, inhalation administration, nasal administration, topical administration, ophthalmic administration or otic administration. In other embodiments, such pharmaceutical compositions are in the form of a tablet, a pill, a capsule, a liquid, an inhalant, a nasal spray solution, a suppository, a solution, an emulsion, an ointment, eye drop or ear drop. In other embodiments, such pharmaceutical compositions are formulated for oral administration and are in the form of a tablet, a pill, a capsule, a liquid, a solution, or an emulsion. In other embodiments, such pharmaceutical compositions are formulated for oral administration and are in the form of a tablet, a pill, or a capsule. In other embodiments, such pharmaceutical compositions further include one or more additional therapeutic agents. In other embodiments, such aforementioned pharmaceutical compositions further include one or more additional therapeutic agents.

Another aspect provided herein are medicaments for treating a patient with a disease or disorder associated with c-kit or PDGFR kinase activity, or c-kit and PDGFR kinase activity, and such medicaments include a therapeutically effective amount of a compound of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf). In certain embodiments of this aspect the disease is a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, pulmonary arterial hypertension (PAH) or primary pulmonary hypertension (PPH). In other embodiments of this aspect, the disease is asthma, allergic rhinitis, pulmonary arterial hypertension (PAH), pulmonary fibrosis, hepatic fibrosis, cardiac fibrosis, scleroderma, irritable bowel syndrome (IBS), inflammatory bowel disease (IBD), uticaria, dermatosis, type I diabetes or type II diabetes.

Another aspect provided herein are medicaments for treating a disease mediated by c-kit or PDGFR kinase activity, or c-kit and PDGFR kinase activity, in a patient in need thereof, and such medicaments include a therapeutically effective amount of a compound of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), and the disease is a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, pulmonary arterial hypertension (PAH) or primary pulmonary hypertension (PPH).

In certain embodiments of this aspect, the disease is asthma, allergic rhinitis, pulmonary arterial hypertension (PAH), pulmonary fibrosis, hepatic fibrosis, cardiac fibrosis, scleroderma, irritable bowel syndrome (IBS), inflammatory bowel disease (IBD), uticaria, dermatosis, type I diabetes or type II diabetes.

Another aspect provided herein is the use of a compound of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf) in the manufacture of a medicament for treating a disease or disorder in a patient where c-kit or PDGFR kinase activity, or c-kit and PDGFR kinase activity is implicated.

Another aspect provided herein includes methods for treating a disease or disorder where c-kit or PDGFR kinase activity, or c-kit and PDGFR kinase activity is implicated, wherein the method includes administering to a system or subject in need of such treatment an effective amount of a compound of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf), or pharmaceutically acceptable salts or pharmaceutical compositions thereof, thereby treating the disease or disorder. In certain embodiments of such methods, the methods include administering the compound to a cell or tissue system or to a human or animal subject. In certain embodiments of such methods, the disease or condition is a metabolic disease, a fibrotic disease, a respiratory disease, an inflammatory disease or disorder, a dermatological disease or an autoimmune disease. In certain embodiments of such methods, the disease or condition is asthma, allergic rhinitis, irritable bowel syndrome (IBS), inflammatory bowel disease (IBD), pulmonary arterial hypertension (PAH), pulmonary fibrosis, liver fibrosis, cardiac fibrosis, scleroderma, urticaria, dermatoses, atopic dermatitis, type I diabetes or type II diabetes.

Another aspect provided herein is a compound of Formula (I), Formula (II), Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf) for use in treating a disease mediated by c-kit, PDGFRα, PDGFRβ or combination thereof, wherein the disease is selected from a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, pulmonary arterial hypertension (PAH) and primary pulmonary hypertension (PPH). In certain embodiments of this aspect, the disease is selected from a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, pulmonary arterial hypertension (PAH) and primary pulmonary hypertension (PPH). In other embodiments the disease is asthma, allergic rhinitis, pulmonary arterial hypertension (PAH), pulmonary fibrosis, hepatic fibrosis, cardiac fibrosis, scleroderma, irritable bowel syndrome (IBS), inflammatory bowel disease (IBD), uticaria, dermatosis, type I diabetes or type II diabetes.

DETAILED DESCRIPTION OF THE INVENTION

Definitions

The term "alkyl," as used herein, refers to a saturated branched or straight chain hydrocarbon. In certain embodiments such alkyl groups are optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. If not otherwise specified, an alkyl group generally is a $C_1$-$C_6$ alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkoxy," as used herein, refers to the group —$OR_a$, where $R_a$ is an alkyl group as defined herein. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "cycloalkyl," as used herein, refers to a saturated, monocyclic, fused bicyclic, fused tricyclic, spirocyclic or bridged polycyclic ring assembly. As used herein, the terms "$C_3$-$C_5$cycloalkyl", "$C_3$-$C_6$cycloalkyl", "$C_3$-$C_7$cycloalkyl", "$C_3$-$C_8$cycloalkyl, "$C_3$-$C_9$cycloalkyl and "$C_3$-$C_{10}$cycloalkyl refer to a cycloalkyl group wherein the saturated monocyclic, fused bicyclic or bridged polycyclic ring assembly contain at least 3, and at most 5, 6, 7, 8, 9 or 10, carbon atoms. Non-limiting examples of cycloalkyl groups, as used herein, include cyclopropyl, cyclobutyl, cyclopentyl, cyclohexyl, cycloheptyl, cyclooctyl, cyclononyl, cyclodecyl, and the like.

The term "halo," as used herein, refers to fluorine (F), chlorine (Cl), bromine (Br), or iodine (I) substituents.

The terms "haloalkyl" or "halo-substituted alkyl," as used herein, refers to an alkyl group as defined herein, substituted with one or more halo groups as defined herein. The halo groups are the same or different. The haloalkyl can be monohaloalkyl, dihaloalkyl or polyhaloalkyl, including perhaloalkyl. A perhalo-alkyl refers to an alkyl having all hydrogen atoms replaced with halo atoms. A monohaloalkyl can have one iodo, bromo, chloro or fluoro within the alkyl group. Dihaloalky and polyhaloalkyl groups can have two or more of the same halo atoms or a combination of different halo groups within the alkyl. Such haloalkyl groups are also referred to herein as "$C_1$-$C_3$haloalkyl", "$C_1$-$C_4$haloalkyl", "$C_1$-$C_5$haloalkyl", "$C_1$-$C_6$haloalkyl", "$C_1$-$C_7$haloalkyl" and "$C_1$-$C_6$haloalkyl" wherein the alkyl group contains at least 1, and at most 3, 4, 5, 6, 7 or 8 carbon atoms, respectively. Non-limiting examples of such branched or straight chained haloalkyl groups, as used herein, include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. In certain embodiments, a haloalkyl group is trifluoromethyl.

The term "heteroaryl," as used herein, refers to a 5-6 membered heteroaromatic monocyclic ring having 1 to 4 heteroatoms independently selected from nitrogen, oxygen and sulfur, an 8-10 membered fused bicyclic ring having 1 to 4 heteroatoms independently selected from nitrogen, oxygen and sulfur and where at least one of the rings is aromatic, or a 12-14 membered fused tricyclic ring having 1 to 4 heteroatoms independently selected from nitrogen, oxygen and sulfur and where at least one of the rings is aromatic. Such fused bicyclic and tricyclic ring systems may be fused to one or more aryl, cycloalkyl, or heterocycloalkyl rings. Non-limiting examples of heteroaryl groups, as used herein, include 2- or 3-furyl; 1-, 2-, 4-, or 5-imidazolyl; 3-, 4-, or 5-isothiazolyl; 3-, 4-, or 5-isoxazolyl; 2-, 4-, or 5-oxazolyl; 4- or 5-1,2,3-oxadiazolyl; 2- or 3-pyrazinyl; 1-, 3-, 4-, or 5-pyrazolyl; 3-, 4-, 5- or 6-pyridazinyl; 2-, 3-, or 4-pyridyl; 2-, 4-, 5- or 6-pyrimidinyl; 1-, 2- or 3-pyrrolyl; 1- or 5-tetrazolyl; 2- or 5-1,3,4-thiadiazolyl; 2-, 4-, or 5-thiazolyl; 2- or 3-thienyl; 2-, 4- or 6-1,3,5-triazinyl; 1-, 3- or 5-1,2,4-triazolyl; 1-, 4- or 5-1,2,3-triazolyl; 1-, 2-, 3-, 4-, 5-, 6-, 7-, 8-, or 9-acridinyl; 1-, 3-, 4-, 5-, 6-, 7-, 8-, 9-, or 10-benzo[g]isoquinoline; 2-, 4-, 5-, 6-, or 7-benzoxazolyl; 1-, 2-, 4-, 5-, 6-, or 7-benzimidazolyl; 2-, 4-, 5-, 6-, or 7-benzothiazolyl; 2-, 3-, 4-, 5-, 6-, 7-benzo[b]thienyl; 2-, 3-, 4-, 5-, 6-, 7-, 8-, 9-benzo[b]oxepine; 2-, 4-, 5-, 6-, 7-, or 8-benzoxazinyl; 1-, 2-, 3-, 4-, 5-, 6-, 7-, 8, or 9-carbazolyl; 3-, 4-, 5-, 6-, 7-, or 8-cinnolinyl; 2-, 4-, or 5-4H-imidazo[4,5-d]thiazolyl; 2-, 3-, 5-, or 6-imidazo[2,1-b]thiazolyl; 2-, 3-, 6-, or 7-imidazo[1,2-b][1,2,4]triazinyl; 1-, 3-, 4-, 5-, 6-, or 7-indazolyl; 1-, 2-, 3-, 5-, 6-, 7-, or 8-indolizinyl; 1-, 2-, 3-, 4-, 5-, 6-, or 7-indolyl; 1-, 2-, 3-, 4-, 5-, 6-, or 7-isoindolyl; 1-, 3-, 4-, 5-, 6-, 7-, or 8-isoquinoliylo; 2-, 3-, 4-, 5-, 6-, or 7-naphthyridinyl; 1-, 2-, 4-, 5-, 6-, 7-, 8-, or 9-perimidinyl; 1-, 2-, 3-, 4-, 6-, 7-, 8-, 9-, or 10-phenanthridinyl; 1-, 2-, 3-, 4-, 5-, 6-, 7-, 8-, 9-, or 10-phenanthrolinyl; 1-, 2-, 3-, 4-, 6-, 7-, 8-, or 9-phenazinyl; 1-, 2-, 3-, 4-, 6-, 7-, 8-, 9-, or 10-phenothiazinyl; 1-, 2-, 3-, 4-, 6-, 7-, 8-, 9-, or 10-phenoxazinyl; 1-, 4-, 5-, 6-, 7-, or 8-phthalazinyl; 2-, 4-, 6-, or 7-pteridinyl; 2-, 6-, 7-, or 8-purinyl; 2-, 3-, 5-, 6-, 7-, 8-, 9-, 10-, or 11-7H-pyrazino[2,3-c]carbazolyl; 2-, 3-, 5-, 6-, or 7-furo[3,2-b]-pyranyl; 1-, 3-, or 5-1H-pyrazolo[4,3-d]-oxazolyl; 2-, 3-, 5-, or 8-pyrazino[2,3-d]pyridazinyl; 1-, 2-, 3-, 4-, 5-, or 8-5H-pyrido[2,3-d]-o-oxazinyl; 1-, 2-, 3-, 4-, 6-, 7-, 8-, or 9-quinolizinyl; 2-, 3-, 4-, 5-, 6-, 7-, or 8-quinolinyl; 2-, 3-, 4-, 5-, 6-, 7-, or 8-quinazolinyl; 2-, 3-, 4-, or 5-thieno[2,3-b]furanyl, and 1-, 3-, 6-, 7-, 8-, or 9-furo[3,4-c]cinnolinyl.

The term "hetero atoms," as used herein, refers to nitrogen (N), oxygen (O) or sulfur (S) atoms.

The term "heterocycloalkyl," as used herein refers to a to saturated 3-6 membered monocyclic hydrocarbon ring structure, a saturated 6-9 membered fused bicyclic hydrocarbon ring structure, or a saturated 10-14 membered fused tricyclic hydrocarbon ring structure, wherein one to four of the ring carbons of the hydrocarbon ring structure are replaced by one to four groups independently selected from —O—, —NR—, or —S—, wherein R is hydrogen, $C_1$-$C_4$alkyl or an amino protecting group.

Non-limiting examples of heterocycloalkyl groups, as used herein, include aziridinyl, aziridin-1-yl, aziridin-2-yl, aziridin-3-yl, oxiranyl, oxiran-2-yl, oxiran-3-yl, thiiranyl, thiiran-2-yl, thiiran-3-yl, azetadinyl, azetadin-1-yl, azetadin-2-yl, azetadin-3-yl, oxetanyl, oxetan-2-yl, oxetan-3-yl, oxetan-4-yl, thietanyl, thietan-2-yl, thietan-3-yl, thietan-4-yl, pyrrolidinyl, pyrrolidin-1-yl, pyrrolidin-2-yl, pyrrolidin-3-yl, pyrrolidin-4-yl, pyrrolidin-5-yl, tetrahydrofuranyl, tetrahydrofuran-2-yl, tetrahydrofuran-3-yl, tetrahydrofuran-4-yl, tetrahydrofuran-5-yl, tetrahydrothienyl, tetrahydrothien-2-yl, tetrahydrothien-3-yl, tetrahydrothien-4-yl, tetrahydrothien-5-yl, piperidinyl, piperidin-1-yl, piperidin-2-yl, piperidin-3-yl, piperidin-4-yl, piperidin-5-yl, piperidin-6-yl, tetrahydropyranyl, tetrahydropyran-2-yl, tetrahydropyran-3-yl, tetrahydropyran-4-yl, tetrahydropyran-5-yl, tetrahydropyran-6-yl, tetrahydrothiopyranyl, tetrahydrothiopyran-2-yl, tetrahydrothiopyran-3-yl, tetrahydrothiopyran-4-yl, tetrahydrothiopyran-5-yl, tetrahydrothiopyran-6-yl, piperazinyl, piperazin-1-yl, piperazin-2-yl, piperazin-3-yl, piperazin-4-yl, piperazin-5-yl, piperazin-6-yl, morpholinyl, morpholin-2-yl, morpholin-3-yl, morpholin-4-yl, morpholin-5-yl, morpholin-6-yl, thiomorpholinyl, thiomorpholin-2-yl, thiomorpholin-3-yl, thiomorpholin-4-yl, thiomorpholin-5-yl, thiomorpholin-6-yl, oxathianyl, oxathian-2-yl, oxathian-3-yl, oxathian-5-yl, oxathian-6-yl, dithianyl, dithian-2-yl, dithian-3-yl, dithian-5-yl, dithian-6-yl, azepanyl, azepan-1-yl, azepan-2-yl, azepan-3-yl, azepan-4-yl, azepan-5-yl, azepan-6-yl, azepan-7-yl, oxepanyl, oxepan-2-yl, oxepan-3-yl, oxepan-4-yl, oxepan-5-yl, oxepan-6-yl, oxepan-7-yl, thiepanyl, thiepan-2-yl, thiepan-3-yl, thiepan-4-yl, thiepan-5-yl, thiepan-6-yl, thiepan-7-yl, dioxolanyl, dioxolan-2-yl, dioxolan-4-yl, dioxolan-5-yl, thioxanyl, thioxan-2-yl, thioxan-3-yl, thioxan-4-yl, thioxan-5-yl, dithiolanyl, dithiolan-2-yl, dithiolan-4-yl, dithiolan-5-yl, pyrrolinyl, pyrrolin-1-yl, pyrrolin-2-yl, pyrrolin-3-yl, pyrrolin-4-yl, pyrrolin-5-yl, imidazolinyl, imidazolin-1-yl, imidazolin-3-yl, imidazolin-4-yl, imidazolin-5-yl, imidazolidinyl, imidazolidin-1-yl, imidazolidin-2-yl, imidazolidin-3-yl, imidazolidin-4-yl, imidazolidin-4-yl, pyrazolinyl, pyrazolin-1-yl, pyrazolin-3-yl, pyrazolin-4-yl, pyrazolin-5-yl, pyrazolidinyl, pyrazolidin-1-yl, pyrazolidin-2-yl, pyrazolidin-3-yl, pyrazolidin-4-yl, pyrazolidin-5-yl, hexahydro-1,4-diazepinyl, dihydrofuranyldihydropyranyl, 1,2,3,6-tetrahydropyridinyl, 2H-pyranyl, 4H-pyranyl, dihydropyranyl, dihydrothienyl, dihydrofuranyl, 3-azabicyclo[3.1.0]hexanyl, 3-azabicyclo[4.1.0]heptanyl, pyrrolidinyl-2-one, piperidinyl-3-one piperidinyl-2-one, piperidinyl-4-one, and 2H-pyrrolyl.

The term "acceptable" with respect to a compound, formulation, composition or ingredient, as used herein, means having no persistent detrimental effect on the general health of the subject being treated.

The term "administration" or "administering" of the subject compound means providing a compound of Formula (I) or Formula (II), a pharmaceutically acceptable salt, a pharmaceutically acceptable solvate, or solvate thereof to a subject in need of treatment.

The term "autoimmune disease," or "autoimmune disorder," as used herein, refers diseases wherein cells uncontrollably attack the body's own tissues and organs (autoimmunity), producing inflammatory reactions and other serious symptoms and diseases. Non-limiting examples of autoimmune diseases include idiopathic thrombocytopenic purpura, hemolytic anemia, systemic lupus erythematosus, rheumatoid arthritis (RA), multiple sclerosis (MS), immune-mediated or type 1 diabetes mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, and Hashimoto's disease, Hashimoto's thyroiditis, dermatomyositis, goodpasture syndrome, myasthenia gravis pseudoparalytica, ophtalmia sympatica, phakogene uveitis, chronical aggressive hepatitis, primary billiary cirrhosis, autoimmune hemolytic anemy, Werlof disease, vitiligo vulgaris, Behcet's disease, collagen disease, uveitis, Sjogren's syndrome, autoimmune myocarditis, autoimmune hepatic diseases, autoimmune gastritis, pemphigus, Guillain-Barre syndrome, and HTLV-1-associated myelopathy.

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disease" or "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, actinic keratosis, basal cell carcinoma and urticaria.

The term "diluent," as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosis disease," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "inflammatory disease or disorders," as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arthritis); joints (arthritis: crystalline, osteo-, psoriatic, reactive, rheumatoid, Reiter's); gastrointestinal tract (Disease); skin (dermatitis); or multiple organs and tissues (systemic lupus erythematosus).

As used herein, the term "inhibit", "inhibition" or "inhibiting" refers to the reduction or suppression of a given condition, symptom, or disorder, or disease, or a significant decrease in the baseline activity of a biological activity or process.

The term "pharmaceutically acceptable," as used herein, refers to a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable" carrier, as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "pharmaceutically acceptable salt," as used herein, refers to a formulation of a compound that does not cause significant irritation to an organism to which it is administered and does not abrogate the biological activity and properties of the compounds described herein.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of Formula (I) or Formula (II) and an additional therapeutic agent, are both administered to a patient simultaneously in the form of a single entity or dosage. The term "non-fixed combination" means that the active ingredients, by way of example, a compound of Formula (I) or Formula (II) and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "composition" or "pharmaceutical composition," as used herein, refers to a mixture of at least one compound, such as the compounds of Formula (I) or Formula (II) provided herein, with at least one and optionally more than one other pharmaceutically acceptable chemical components, such as carriers, stabilizers, diluents, dispersing agents, suspending agents, thickening agents, and/or excipients.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient," as used herein, encompasses mammals and non-mammals. Examples of mammals include, but are not limited to, humans, chimpanzees, apes, monkeys, cattle, horses, sheep, goats, swine; rabbits, dogs, cats, rats, mice, guinea pigs, and the like. Examples of non-mammals include, but are not limited to, birds, fish and the like. Frequently the subject is a human, and may be a human who has been diagnosed as in need of treatment for a disease or disorder disclosed herein.

As used herein, a subject is "in need of" a treatment if such subject would benefit biologically, medically or in quality of life from such treatment.

The term "c-kit inhibitor," as used herein, refers to a compound which inhibits c-kit kinase.

The term "disease or disorder associated with c-kit activity," as used herein, refers to any disease state associated with a c-kit kinase. Such diseases or disorders include, but are not limited to, a mast-cell associated disease, inflammatory diseases, respiratory diseases, fibrosis diseases, a dermatological disease, metabolic diseases and autoimmune diseases, such as, by way of example only, asthma, dermatitis, allergic rhinitis, pulmonary fibrosis, hepatic fibrosis, cardiac fibrosis, scleroderma, irritable bowel syndrome (IBS), inflammatory bowel disease (IBD), urticaria, rheumatoid arthritis, multiple sclerosis, uticaria, pulmonary arterial hypertension (PAH), primary pulmonary hypertension (PPH), dermatosis, diabetes, type I diabetes and type II diabetes.

The term "PDGFR inhibitor," as used herein, refers to a compound which inhibits PDGFR kinase.

The term "disease or disorder associated with PDGFR activity," as used herein, refers to any disease state associated with a PDGFR kinase. Such diseases or disorders include, but are not limited to, inflammatory diseases, respiratory diseases, fibrosis diseases, metabolic diseases and autoimmune diseases, such as, by way of example only, asthma, dermatitis, allergic rhinitis, scleroderma, irritable bowel syndrome (IBS), inflammatory bowel disease (IBD), urticaria, rheumatoid arthritis, multiple sclerosis, pulmonary arterial hypertension and diabetes.

The term "an optical isomer" or "a stereoisomer", as used herein, refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)—.

The term "a therapeutically effective amount" of a compound of the present invention, as used herein, refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by c-kit kinase or c-kit and PDGFR kinases, or (ii) associated with c-kit kinase or c-kit and PDGFR kinase activity, or (iii) characterized by activity (normal or abnormal) of c-kit kinase or c-kit and PDGFR kinases; or (2) reducing or inhibiting the activity of c-kit kinase or c-kit and PDGFR kinases; or (3) reducing or inhibiting the expression of c-kit kinase or c-kit and PDGFR kinases. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of c-kit kinase or c-kit and PDGFR kinases; or at least partially reducing or inhibiting the expression of c-kit kinase or c-kit and PDGFR kinases.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

In addition, as used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The compound names provided herein were obtained using ChemDraw Ultra 10.0 (CambridgeSoft®) or JChem version 5.3.1 (ChemAxon).

Unless specified otherwise, the term "compounds of the present invention" or "compounds provided herein" refers to compounds of Formula (I) and Formula (II), and subformulae thereof (such as Formula (Ia), Formula (IIa), Formula (Ib), Formula (IIb), Formula (Ic), Formula (IIc), Formula (Id), Formula (IId), Formula (Ie), Formula (IIe), Formula (If) and Formula (IIf)), and pharmaceutically acceptable salts, hydrates or solvates, stereoisomers (including diastereoisomers and enantiomers), tautomers and isotopically labeled compounds (including deuterium substitutions) thereof. Compounds of the present invention further comprise polymorphs of compounds of Formula (I) and Formula (II) (or subformulae thereof) and salts thereof.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Various enumerated embodiments of the invention are described herein. It will be recognized that features specified in each embodiment may be combined with other specified features to provide further embodiments of the present invention.

DESCRIPTION OF THE PREFERRED EMBODIMENTS

Provided herein are compounds, pharmaceutically acceptable salts, solvates, N-oxides and isomers thereof, that are inhibitors of c-kit kinase or c-kit and PDGFR kinases. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 750 to 1000. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 500 to 750. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 250 to 500. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 100 to 250. Certain embodiments of compounds provided herein have an $IC_{50}$ for PDGFR inhibition to $IC_{50}$ for c-kit inhibition ratio ($IC_{50}$ PDGFR/$IC_{50\ c\text{-}kit}$) in the range of 75 to 100. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 50 to 75. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 25 to 50. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 10 to 25. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 7.5 to 10. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 5 to 7.5. Certain embodiments of compounds provided herein have an $IC_{50}$ for PDGFR inhibition to $IC_{50}$ for c-kit inhibition ratio ($IC_{50\ PDGFR}/IC_{50\ c\text{-}kit}$) in the range of 2.5 to 5. Certain embodiments of compounds provided herein have an $IC_{50}$ for PDGFR inhibition to $IC_{50}$ for c-kit inhibition ratio ($IC_{50}$ PDGFR/$IC_{50\ c\text{-}kit}$) in the range of 1 to 2.5. Certain embodiments of compounds provided herein have an $IC_{50}$ for $IC_{50}$ for PDGFR inhibition to c-kit inhibition ratio ($IC_{50\ PDGFR}/IC_{50\ c\text{-}kit}$) in the range of 0.95 to 2.5.

Also provided herein are pharmaceutical compositions that include such compounds. Further provided herein are methods for the treatment of diseases and/or disorders associated with c-kit kinase or c-kit and PDGFR kinases using such compounds and pharmaceutical compositions.

The c-kit kinase, or c-kit and PDGFR kinase, inhibitors of the present invention are compounds having the structure of Formula (I) or Formula (II), and pharmaceutically acceptable salts, pharmaceutically acceptable solvates (e.g. hydrates), the N-oxide derivatives, protected derivatives, individual isomers and mixture of isomers thereof:

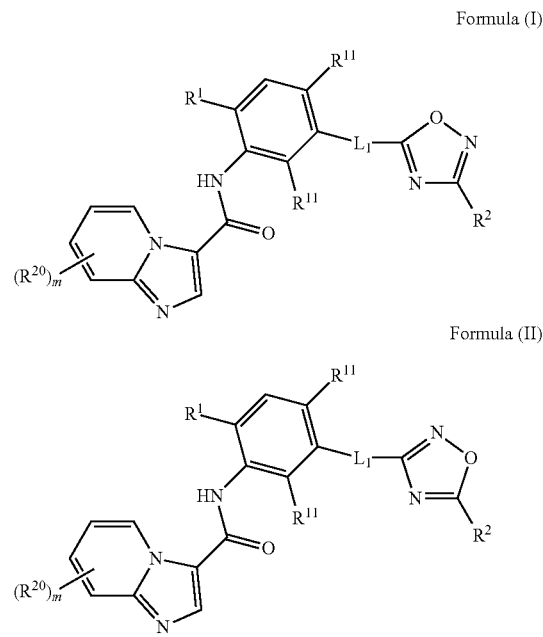

Formula (I)

Formula (II)

wherein:
m is 1 and $R^{20}$ is selected from H, halo, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9_2)_nOR^4$, —C(O)$R^4$, —$(CR^9_2)_nC(=O)OR^4$, $R^{10}$, —$(CR^9_2)_nR^{10}$, —$((CR^9_2)_nO)_nR^4$, —$(CR^9_2)_nO(CR^9_2)_nR^7$, —$(CR^9_2)_nC(=O)R^4$, —C(=O)N$(R^4)_2$, —$OR^4$, and —$(CR^9_2)_nCN$;
or m is 4 and $R^{20}$ is deuterium;
$R^1$ is selected from $C_1$-$C_6$alkyl and halo;
each $R^{11}$ is independently selected from H, halo and $C_1$-$C_6$alkyl;
$L_1$ is a bond, —NH— or —C(O)NH—;
$L_2$ is —$(CR^9_2)_n$—, —CHR$^6$—, —$(CR^9_2)_nO$—, —NH—, —$(CR^9_2)_nC(=O)$—, —C(=O)O$(CR^9_2)_n$—, —$(CR^9_2)_n$ OC(=O)N$R^4$—, —$(CR^9_2)_nNR^4C(=O)$ $(CR^9_2)_n$—$(CR^9_2)_nNR^4C(=O)$—, or —$(CR^9_2)_nNR^4C(=O)O$—;
$R^2$ is $R^3$ or $L_2R^3$;
$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —C(=O)O$R^4$, —C(=O)$R^4$, —C(=O)$R^7$, —C(=O) $OR^5$, —$(CR^9_2)_nOR^4$, —O$(CR^9_2)_nOR^4$, —C(=O)O $(CR^9_2)_nOR^4$, —N$(R^4)_2$, —C(=O)N$R^4_2$, —NR$^4$C (=O)OR⁴, —NR⁴C(=O)(CR⁹₂)ₙOR⁴, —NR⁴(CR⁹₂)ₙOR⁴, —NR⁴S(=O)₂R⁴, —N(C(=O)OR⁴)₂, R⁸, —(CR⁹₂)ₙR⁸, deuterated C₁-C₆alkoxy, —S(=O)₂R⁴, —S(=O)₂R⁷, —S(=O)₂R⁸, —S(=O)₂N(R⁴)₂, —S(=O)₂NHC(=O)OR⁴, —S(=O)₂(CR⁹₂)ₙC(=O)OR⁴, S(=O)₂(CR⁹₂)ₙOR⁴, a spiro attached dioxolane, a spiro attached dioxolane which is substituted with C₁-C₆alkyl, a spiro attached dioxane, a spiro attached tetrahydrofuranly, a spiro attached oxetane, a spiro attached cyclobutanone, a spiro attached cyclobutanol, a C₁ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from C₁-C₆alkyl, halo, C₁-C₆haloalkyl, C₁-C₆haloalkoxy, —OR⁴ and R⁸;

each R⁴ is independently selected from H and C₁-C₆alkyl;
R⁵ is an unsubstituted C₃-C₈cycloalkyl, an unsubstituted 5-6 membered heterocycloalkyl with 1-2 heteroatoms independently selected from N or O or a C₃-C₈cycloalkyl substituted with 1-3 substituents independently selected from C₁-C₆alkyl;
each R⁶ is independently selected from —NR⁴C(O)OR⁴, —OR⁴ and —(CR⁹₂)ₙOR⁴;
each R⁷ is independently selected from C₁-C₆haloalkyl;
R⁸ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted C₃-C₈cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted C₃-C₈cycloalkyl, a tetrahydro-1H-oxazolo[3,4-a]pyrazin-3(5H)-one, a oxazolidin-2-one, pyrrolidinone and a pyrrolidin-2-one,
  wherein the substituted phenyl, the substituted 5-6 membered heteroaryl with 1-2 heteroatoms independently selected from N, O and S, the substituted 5 membered heteroaryl with 1-4 heteroatoms selected from N, substituted C₃-C₈cycloalkyl and substituted 4-6 membered heterocycloalkyl of R⁸ are substituted with 1-3 substituents independently selected from C₁-C₆alkyl, —(C(R⁹)₂)ₙOR⁴, —(C(R⁹)₂)ₙR⁵, —(C(R⁹)₂)ₙC(O)OR⁴, —C(O)OR⁴ and —S(O)₂R⁴;

each R⁹ is independently selected from H and C₁-C₆alkyl;
R¹⁰ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted C₃-C₈cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted C₃-C₈cycloalkyl, a oxazolidin-2-one, pyrrolidinone and a pyrrolidin-2-one,
  wherein the substituted phenyl, the substituted 5-6 membered heteroaryl with 1-2 heteroatoms independently selected from N, O and S, the substituted 5 membered heteroaryl with 1-4 heteroatoms selected from N, substituted C₃-C₈cycloalkyl and substituted 4-6 membered heterocycloalkyl of R⁸ are substituted with 1-3 substituents independently selected from C₁-C₆alkyl [Me], —(C(R⁹)₂)ₙOR⁴, —(C(R⁹)₂)ₙR⁵, —(C(R⁹)₂)ₙC(O)OR⁴ and —S(O)₂R⁴;

t is 1, 2 or 3, and
each n is independently selected from 1, 2, 3 and 4.

In certain embodiments of compounds of Formula (I) or Formula (II), and the pharmaceutically acceptable salts, pharmaceutically acceptable solvates (e.g. hydrates), the N-oxide derivatives, protected derivatives, individual isomers and mixture of isomers thereof, the compound of Formula (I) or Formula (II) is a compound having a structure of Formula (Ia), Formula (IIa), Formula (Ib) or Formula (IIb):

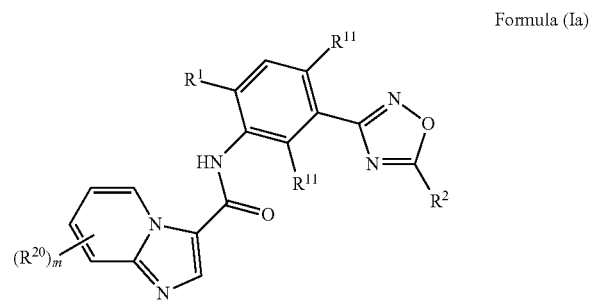

Formula (Ia)

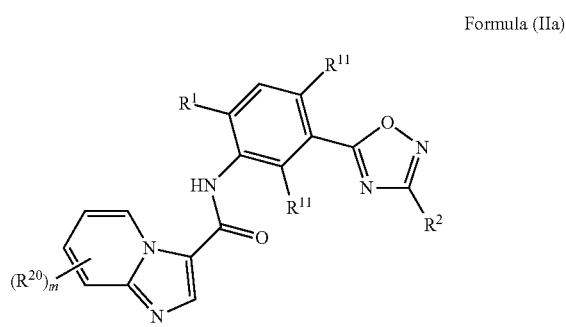

Formula (IIa)

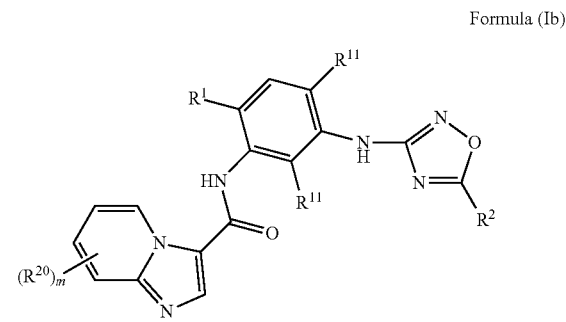

Formula (Ib)

-continued

Formula (IIb)

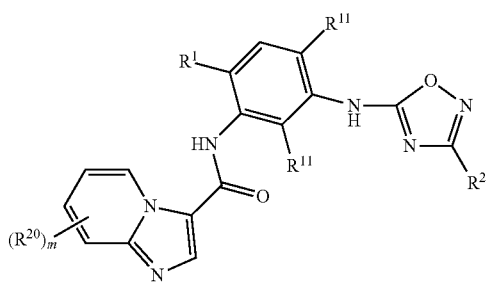

wherein:
m is 1 and R$^{20}$ is selected from H, halo, C$_1$-C$_6$alkyl, C$_1$-C$_6$haloalkyl, C$_1$-C$_6$haloalkoxy, deuterium, deuterated C$_1$-C$_6$alkyl, —CN, —(CR$^9_2$)$_n$OR$^4$, —C(O)R$^4$, —(CR$^9_2$)$_n$C(=O)OR$^4$, R$^{10}$, —((CR$^9_2$)$_n$O)$_t$R$^4$, —(CR$^9_2$)$_n$O(CR$^9_2$)$_n$R$^7$, —(CR$^9_2$)$_n$C(=O)R$^4$, —C(=O)$_N$(R$^4$)$_2$, —OR$^4$, and —(CR$^9_2$)$_n$CN;
or m is 4 and R$^{20}$ is deuterium;
R$^1$ is selected from C$_1$-C$_6$alkyl and halo;
each R$^{11}$ is independently selected from H, halo and C$_1$-C$_6$alkyl;
L$_2$ is —(CR$^9_2$)$_n$—, —CHR$^6$—, —(CR$^9_2$)$_n$O—, —NH—, —(CR$^9_2$)$_n$C(=O)—, —C(=O)O(CR$^9_2$)$_n$—, —(CR$^9_2$)$_n$OC(=O)NR$^4$—, —(CR$^9_2$)$_n$NR$^4$C(=O)(CR$^9_2$)$_n$—, —(CR$^9_2$)$_n$NR$^4$C(=O)—, or —(CR$^9_2$)$_n$NR$^4$C(=O)O—;
R$^2$ is R$^3$ or L$_2$R$^3$;
R$^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of R$^3$ is substituted with 1-4 substituents independently selected from C$_1$-C$_6$alkyl halo, —CN, C$_1$-C$_6$haloalkyl, —OR$^4$, —C(=O)OR$^4$, —C(=O)R$^4$, —C(=O)R$^7$, —C(=O)OR$^5$, —(CR$^9_2$)$_n$OR$^4$, —O(CR$^9_2$)$_n$OR$^4$, —C(=O)O(CR$^9_2$)$_n$OR$^4$, —N(R$^4$)$_2$, —C(=O)NR$^4_2$, —NR$^4$C(=O)OR$^4$, —NR$^4$C(=O)(CR$^9_2$)$_n$OR$^4$, —NR$^4$(CR$^9_2$)$_n$OR$^4$, —NR$^4$S(=O)$_2$R$^4$, —N(C(=O)OR$^4$)$_2$, R$^8$, —(CR$^9_2$)$_n$R$^8$, deuterated C$_1$-C$_6$alkoxy, —S(=O)$_2$R$^4$, —S(=O)$_2$R$^7$, —S(=O)$_2$R$^8$, —S(=O)$_2$N(R$^4$)$_2$, —S(=O)$_2$NHC(=O)OR$^4$, —S(=O)$_2$(CR$^9_2$)$_n$C(=O)OR$^4$, S(=O)$_2$(CR$^9_2$)$_n$OR$^4$, a spiro attached dioxolane, a spiro attached dioxolane which is substituted with C$_1$-C$_6$alkyl, a spiro attached dioxane, a spiro attached tetrahydrofuranly, a spiro attached oxetane, a spiro attached cyclobutanone, a spiro attached cyclobutanol, a C$_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from C$_1$-C$_6$alkyl, halo, C$_1$-C$_6$haloalkyl, C$_1$-C$_6$haloalkoxy, —OR$^4$ and R$^8$;
each R$^4$ is independently selected from H and C$_1$-C$_6$alkyl;
R$^5$ is an unsubstituted C$_3$-C$_8$cycloalkyl, an unsubstituted 5-6 membered heterocycloalkyl with 1-2 heteroatoms independently selected from N or O or a C$_3$-C$_8$cycloalkyl substituted with 1-3 substituents independently selected from C$_1$-C$_6$alkyl;
each R$^6$ is independently selected from —NR$^4$C(O)OR$^4$, —OR$^4$ and —(CR$^9_2$)$_n$OR$^4$;
each R$^7$ is independently selected from C$_1$-C$_6$haloalkyl;
R$^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted C$_3$-C$_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted C$_3$-C$_8$cycloalkyl, a tetrahydro-1H-oxazolo[3,4-a]pyrazin-3(5H)-one, a oxazolidin-2-one, pyrrolidinone and a pyrrolidin-2-one,
wherein the substituted phenyl, the substituted 5-6 membered heteroaryl with 1-2 heteroatoms independently selected from N, O and S, the substituted 5 membered heteroaryl with 1-4 heteroatoms selected from N, substituted C$_3$-C$_8$cycloalkyl and substituted 4-6 membered heterocycloalkyl of R$^8$ are substituted with 1-3 substituents independently selected from C$_1$-C$_6$alkyl, —(C(R$^9$)$_2$)$_n$OR$^4$, —(C(R$^9$)$_2$)$_n$R$^5$, —(C(R$^9$)$_2$)$_n$C(O)OR$^4$, —C(O)OR$^4$ and —S(O)$_2$R$^4$;
each R$^9$ is independently selected from H and C$_1$-C$_6$alkyl;
R$^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted C$_3$-C$_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted C$_3$-C$_8$cycloalkyl, a oxazolidin-2-one, pyrrolidinone and a pyrrolidin-2-one,
wherein the substituted phenyl, the substituted 5-6 membered heteroaryl with 1-2 heteroatoms independently selected from N, O and S, the substituted 5 membered heteroaryl with 1-4 heteroatoms selected from N, substituted C$_3$-C$_8$cycloalkyl and substituted 4-6 membered heterocycloalkyl of R$^8$ are substituted with 1-3 substituents independently selected from C$_1$-C$_6$alkyl [Me], —(C(R$^9$)$_2$)$_n$OR$^4$, —(C(R$^8$)$_2$)$_n$R$^5$, —(C(R$^9$)$_2$)$_n$C(O)OR$^4$ and —S(O)$_2$R$^4$;
t is 1, 2 or 3, and
each n is independently selected from 1, 2, 3 and 4.

In certain embodiments of compounds of Formula (I) or Formula (II), and the pharmaceutically acceptable salts, pharmaceutically acceptable solvates (e.g. hydrates), the N-oxide derivatives, protected derivatives, individual isomers and mixture of isomers thereof, the compound of Formula (I) or Formula (II), is a compound having a structure of Formula (Ia), Formula (IIa), Formula (Ib), Formula (IIb), Formula (Ic), Formula (IIc), Formula (Id), Formula (IId), Formula (Ie), Formula (IIe), Formula (If) or Formula (IIf):

Formula (Ia)
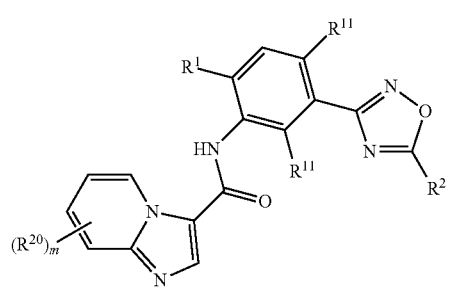
Formula (IIc)
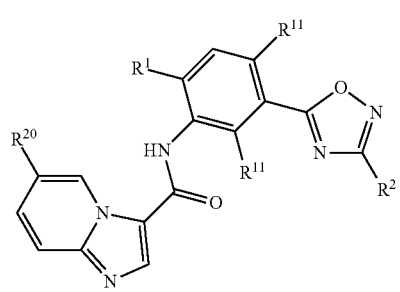
Formula (IIa)
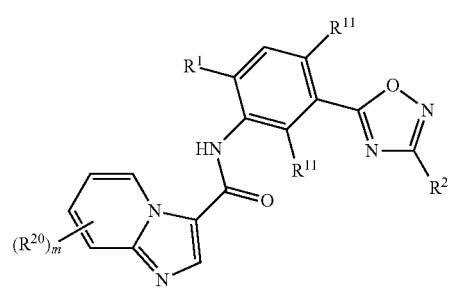
Formula (Id)
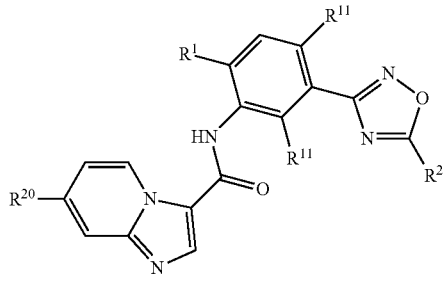
Formula (Ib)
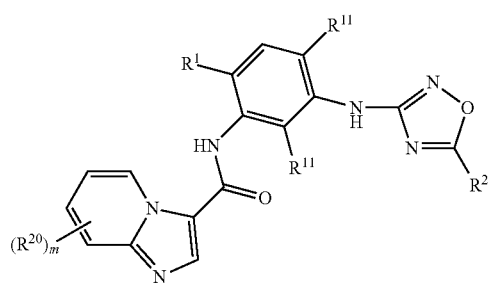
Formula (IId)
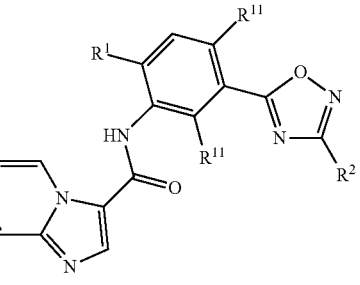
Formula (IIb)
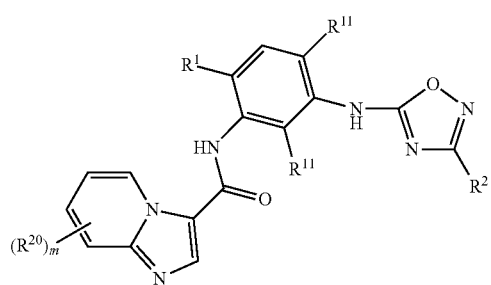
Formula (Ie)
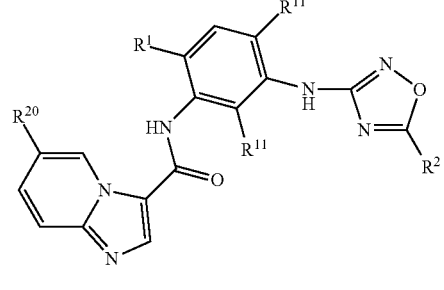
Formula (Ic)
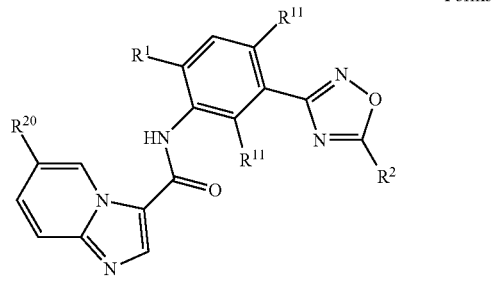
Formula (IIe)
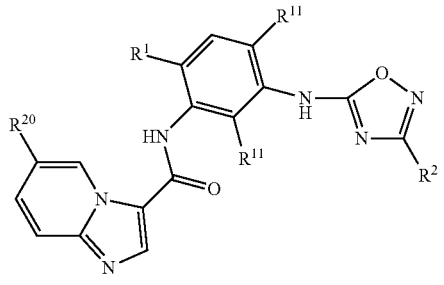

-continued

Formula (If)

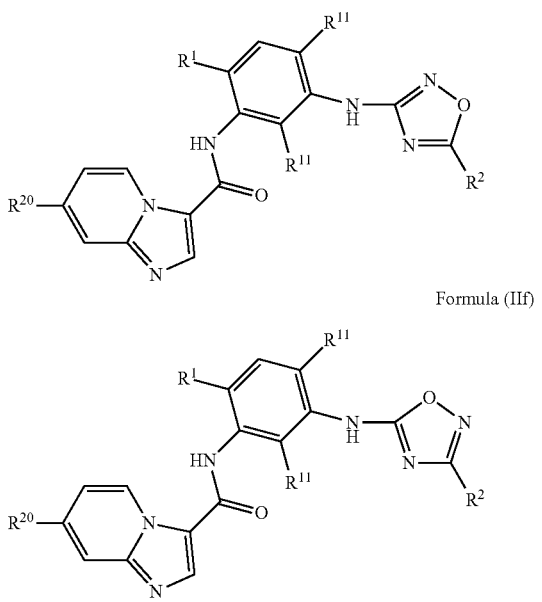

Formula (IIf)

wherein:
m is 1 and $R^{20}$ is selected from H, halo, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9_2)_nOR^4$, —$C(O)R^4$, —$(CR^9_2)_nC(=O)OR^4$, $R^{10}$, —$(CR^9_2)_nO)_tR^4$, —$(CR^9_2)_n$ $O(CR^9_2)_nR^7$, —$(CR^9_2)_nC(=O)R^4$, —$C(=O)_N(R^4)_2$, —$OR^4$, and —$(CR^9_2)_nCN$;
or m is 4 and $R^{20}$ is deuterium;
$R^1$ is selected from $C_1$-$C_6$alkyl and halo;
each $R^{11}$ is independently selected from H, halo and $C_1$-$C_6$alkyl;
$L_2$ is —$(CR^9_2)_n$—, —$CHR^6$—, —$(CR^9_2)_nO$—, —NH—, —$(CR^9_2)_nC(=O)$—, —$C(=O)O(CR^9_2)_n$—, —$(CR^9_2)_n$ $OC(=O)NR^4$—, —$(CR^9_2)_nNR^4C(=O)$ $(CR^9_2)_n$—, —$(CR^9_2)_nNR^4C(=O)$—, or —$(CR^9_2)_nNR^4C(=O)O$—;
$R^2$ is $R^3$ or $L_2R^3$;
$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —$C(=O)OR^4$, —$C(=O)R^4$, —$C(=O)R^7$, —$C(=O)$ $OR^5$, —$(CR^9_2)_nOR^4$, —$O(CR^9_2)_nOR^4$, —$C(=O)O(CR^9_2)_nOR^4$, —$N(R^4)_2$, —$C(=O)NR^4_2$, —$NR^4C(=O)OR^4$, —$NR^4C(=O)(CR^9_2)_nOR^4$, —$NR^4(CR^9_2)_n$ $OR^4$, —$NR^4S(=O)_2R^4$, —$N(C(=O)OR^4)_2$, $R^8$, —$(CR^9_2)_nR^8$, deuterated $C_1$-$C_6$alkoxy, —$S(=O)_2R^4$, —$S(=O)_2R^7$, —$S(=O)_2R^8$, —$S(=O)_2N(R^4)_2$, —$S(=O)_2NHC(=O)OR^4$, —$S(=O)_2(CR^9_2)_nC(=O)$ $OR^4$, $S(=O)_2(CR^9_2)_nOR^4$, a spiro attached dioxolane, a spiro attached dioxolane which is substituted with $C_1$-$C_6$alkyl, a spiro attached dioxane, a spiro attached tetrahydrofuranyl, a spiro attached oxetane, a spiro attached cyclobutanone, a spiro attached cyclobutanol, a $C_1$ alkyl bridge, an unsubstituted 5-6 membered hetero-cycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, —$OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl;

each $R^6$ is independently selected from —$NR^4C(O)OR^4$, —$OR^4$ and —$(CR^9_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one,
wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —$(C(R^9)_2)_nOR^4$, —$(C(R^9)_2)_nR^5$, —$(C(R^9)_2)_nC(O)OR^4$, —$C(O)OR^4$ and —$S(O)_2R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one,
wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —$(C(R^9)_2)_n OR^4$, —$(C(R^9)_2)_n R^5$, —$(C(R^9)_2)_n C(O)OR^4$ and —$S(O)_2R^4$;

t is 1, 2 or 3, and each n is independently selected from 1, 2, 3 and 4.

The compounds of Formula (I) or Formula (II), pharmaceutically acceptable salts, solvates, N-oxides and isomers thereof, and pharmaceutical compositions provided herein also includes all suitable isotopic variations of such compounds, and pharmaceutically acceptable salts, solvates, N-oxides and isomers thereof, and pharmaceutical compositions. Therefore, any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of Formula (I) and Formula (II) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of Formula (I) and Formula (II).

Processes for Making Compounds of Formula (I) or Formula (II)

General procedures for preparing compounds of Formula (I) or Formula (II) are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) or Formula (II) provided herein are prepared as a pharmaceutically acceptable acid addition salt by reacting the free base form of the compound of Formula (I) or Formula (II) with a stoichiometric amount of an appropriate pharmaceutically acceptable organic acid or inorganic acid or a suitable anion exchange reagent. In other embodiments, a pharmaceutically acceptable base addition salt of compounds of Formula (I) or Formula (II) is prepared by reacting the free acid form of the compound of Formula (I) or Formula (II) with a stoichiometric amount of an appropriate pharmaceutically acceptable organic base or inorganic base or a suitable ion exchange reagent. Such reactions are typically carried out in water or in an organic solvent, or in a mixture of the two. Generally, use of non-aqueous media like ether, ethyl acetate, ethanol, isopropanol, or acetonitrile is desirable, where practicable.

Alternatively, the salt forms of the compounds of Formula (I) or Formula (II) are prepared using salts of the starting materials or intermediates. In certain embodiments, the compounds of Formula (I) or Formula (II) are in the form of other salts including, but not limited to, oxalates and trifluoroacetates. In certain embodiments, hemisalts of acids and bases are formed, for example, hemisulphate and hemicalcium salts.

Such pharmaceutically acceptable acid addition salts of compounds of Formula (I) or Formula (II) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, ethanedisulfonate, camphorsulfonate, chlortheophyllonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hippurate, hydrochloride/chloride, hydrobromide/bromide, hydroiodide/iodide, isethionate, lactobionate, laurylsulphate, malate, malonate, mandelate, mesylate, methylsulphate, naphthoate, napsylate, naphthylate, 2-napsylate, nicotinate, octadecanoate, oleate, orotate, oxalate, palmitate, pamoate, phosphate/hydrogen phosphate/dihydrogen phosphate, polygalacturonate, pyroglutamate, saccharate, stearate, sulfosalicylate, tannate, tosylate, trifluoroacetate and xinofoate salts.

The organic acid or inorganic acids used to form certain pharmaceutically acceptable acid addition salts of compounds of Formula (I) or Formula (II) include, but are not limited to, hydrobromic acid, hydrochloric acid, sulfuric acid, nitric acid, phosphoric acid, succinic acid, maleic acid, malonic acid, mandelic acid, formic acid, acetic acid, propionic acid, glycolic acid, oxalic acid, fumaric acid, citric acid, tartaric acid, lactic acid, benzoic acid, salicylic acid, glutamic acid, aspartic acid, toluenesulfonic acid, sulfosalicylic acid, benzenesulfonic acid, methanesulfonic acid, ethanesulfonic acid, naphthalenesulfonic acid, such as 2-naphthalenesulfonic acid, or hexanoic acid.

Such pharmaceutically acceptable base addition salt of compounds of Formula (I) or Formula (II) include, but are not limited to, ammonium, aluminium, arginine, benzathine, calcium, choline, copper, diethylamine, diolamine, glycine, isopropylamine, cholinate, diethanolamine, piperazine, iron, lysine, magnesium, meglumine, olamine, potassium, silver, sodium, tromethamine and zinc salts.

The organic or inorganic bases used to form certain pharmaceutically acceptable base addition salt of compounds of Formula (I) or Formula (II) include, but are not limited to, salts derived from ammonium salts and metals from columns I to XII of the periodic table, or salts derived from primary, secondary, and tertiary amines, substituted amines including naturally occurring substituted amines, cyclic amines, basic ion exchange resins, and the like.

In certain embodiments, the free acid or free base forms of the compounds of Formula (I) or Formula (II) provided herein are prepared from the corresponding base addition salt or acid addition salt from, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002.

In certain embodiments, compounds of Formula (I) or Formula (II) in unoxidized form are prepared from N-oxides of compounds Formula (I) or Formula (II) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, compounds of Formula (I) or Formula (II) are prepared as protected derivatives using methods known to those of ordinary skill in the art. A detailed description of the techniques applicable to the creation of protecting groups and their removal can be found in T. W. Greene, "Protecting Groups in Organic Chemistry," $3^{rd}$ edition, John Wiley and Sons, Inc., 1999.

In certain embodiments, compounds of Formula (I) or Formula (II) are prepared or formed, as solvates (e.g., hydrates). In certain embodiments, hydrates of compounds of Formula (I) or Formula (II) are prepared by recrystallization from an aqueous/organic solvent mixture, using organic solvents such as dioxin, tetrahydrofuran or methanol.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70 enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

In certain embodiments, compounds of Formula (I) or Formula (II) are prepared as their individual stereoisomers. In other embodiments, the compounds of Formula (I) or Formula (II) provided herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I) or Formula (II), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Depending on the choice of the starting materials and procedures, certain embodiments of the compounds of the present invention are present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of Formula (I) or Formula (II) are made by processes described herein and as illustrated in the Examples. Intermediates and final products can be worked up and/or purified according to standard methods, e.g. using chromatographic methods, distribution methods, (re-) crystallization, and the like. The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ. All starting materials, building blocks, reagents, acids, bases, dehydrating agents, solvents and catalysts utilized to synthesize the compounds of the present invention are either commercially available or can be produced by organic synthesis methods known to one of ordinary skill in the art.

Non-limiting examples of synthetic schemes used to make compounds of the invention are illustrated in reaction schemes (I)-(IV). The $R_1$, $R_{20}$, $R_{11}$ and $R_2$ groups as defined herein.

Scheme (I) illustrates the synthesis of compounds of Formula (I) by coupling the amine with the carboxylic acid in the presence of a base and a coupling reagent. By way of example only, the coupling reagent is HATU and the base is diisopropylethylamine.

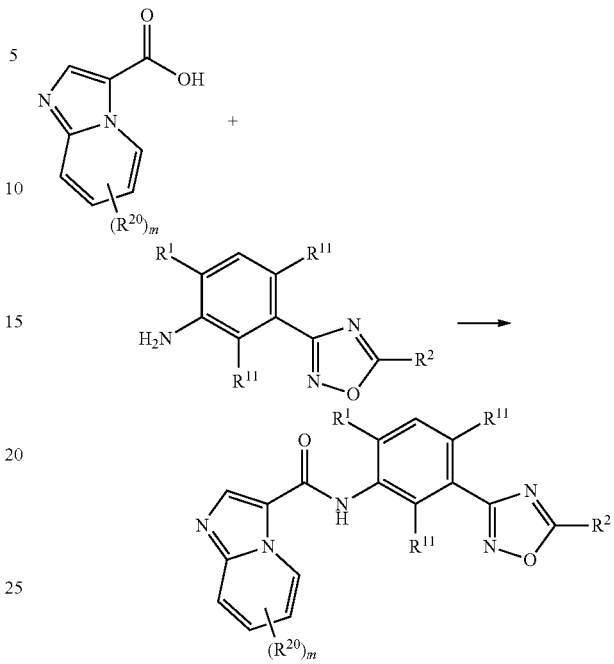

Scheme (I)

Scheme (II) illustrates the synthesis of compounds of Formula (II) by coupling the amine with the carboxylic acid in the presence of a base and a coupling reagent. By way of example only, the coupling reagent is HATU and the base is diisopropylethylamine.

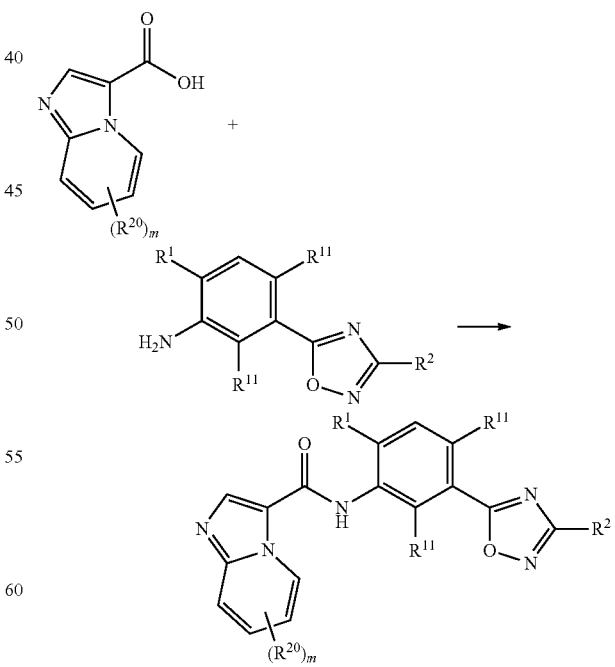

Scheme (II)

Scheme (III) illustrates the synthesis of compounds of Formula (I) by formation of the oxadiazole from the corresponding N'-hydroxyformimidamide and carboxylic acid.

Scheme (III)

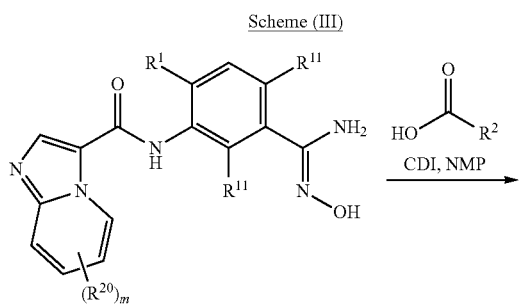

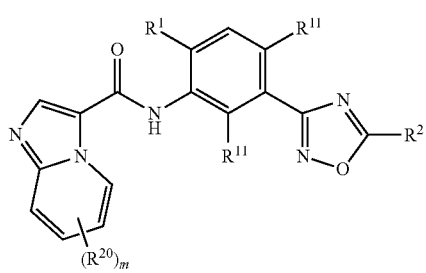

Scheme (IV) illustrates the synthesis of compounds of Formula (II) by formation of the oxadiazole from the corresponding N'-hydroxyformimidamide and carboxylic acid.

Scheme (IV)

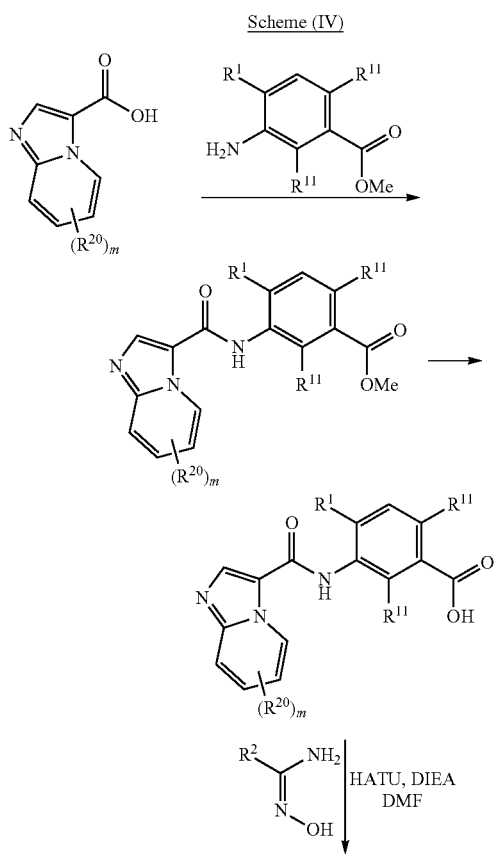

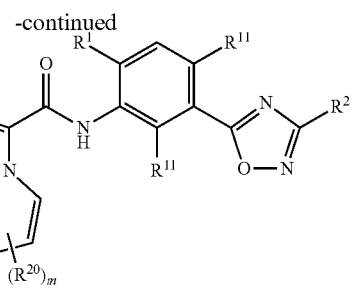

The examples provided herein are offered to illustrate, but not to limit, the compounds of Formula (I) or Formula (II) provided herein, and the preparation of such compounds.

Pharmacology and Utility

Protein tyrosine kinases (PTK) play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone-related diseases.

Examples of protein-tyrosine kinases include, but are not limited to, (a) tyrosine kinases such as Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (α and β), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1), and (b) and serine/threonine kinases such as Aurora, c-RAF, SGK, MAP kinases (e.g., MKK4, MKK6, etc.), SAPK2α, SAPK2β, Ark, ATM (1-3), CamK (1-IV), CamKK, Chk1 and 2 (Checkpoint kinases), CK1, CK2, Erk, IKK-I (also IKK-α or CHUK), IKK-2 (also IKK-β), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAKI, FRK, SGK, TAK1 and Tp1-2 (also COT).

Phosphorylation modulates or regulates a variety of cellular processes such as proliferation, growth, differentiation, metabolism, apoptosis, motility, transcription, translation and other signaling processes. Aberrant or excessive PTK activity has been observed in many disease states including, but not limited to, benign and malignant proliferative disorders, diseases resulting from inappropriate activation of the immune system and diseases resulting from inappropriate activation of the nervous systems. Specific diseases and disease conditions include, but are not limited to, autoimmune disorders, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, rheumatoid arthritis, atherosclerosis, restenosis, auto-immune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

Tyrosine kinases can be broadly classified as receptor-type (having extracellular, transmembrane and intracellular domains) or the non-receptor type (being wholly intracellular) protein tyrosine kinases. Tyrosine kinases transfer the terminal phosphate of ATP to tyrosine residues of proteins thereby activating or inactivating signal transduction pathways. Inappropriate or uncontrolled activation of many of these kinase (aberrant protein tyrosine kinase activity), for example by over-expression or mutation, results in uncontrolled cell growth. Many of the protein tyrosine kinases, whether a receptor or non-receptor tyrosine kinase have been found to be involved in cellular signaling pathways involved in numerous pathogenic conditions, including, but not limited to, immunomodulation, inflammation, or proliferative disorders such as cancer.

cKit

Mast cells are tissue elements derived from a particular subset of hematopoietic stem cells that express CD34, c-kit and CD13 antigens. Mast cells are characterized by their heterogeneity, not only regarding tissue location and structure but also at the functional and histochemical levels. Immature mast cell progenitors circulate in the bloodstream and differentiate into various tissues. These differentiation and proliferation processes are under the influence of cytokines, one of importance being Stem Cell Factor (SCF), also termed c-Kit ligand, Steel factor or Mast Cell Growth Factor. The Stem Cell Factor receptor is encoded by the protooncogene, c-kit, which is expressed in hematopoietic progenitor cells, mast cells, germ cells, interstitial cells of Cajal (ICC), and some human tumors, and is also expressed by non hematopoietic cells.

Stem cell factor (SCF), also known as c-kit ligand, is the primary regulating factor for human mast cell growth and function. The SCF receptor, c-kit receptor, is a Type III transmembrane receptor protein tyrosine kinase which initiates cell growth and proliferation signal transduction cascades in response to SCF binding. Ligation of c-kit receptor by SCF induces its dimerization followed by its transphorylation, leading to the recruitment and activation of various intracytoplasmic substrates. These activated substrates induce multiple intracellular signaling pathways responsible for cell proliferation and activation. These proteins are known to be involved in many cellular mechanisms, which in case of disruption, lead to disorders such as abnormal cell proliferation and migration, as well as inflammation.

The relationship between mast cells, SCF and c-kit receptor is discussed in the following references: Huang, E. et al., The hematopoietic growth factor KL is encoded by the SI locus and is the ligand of the c-kit receptor, the gene product of the W locus", *Cell*, 63, 225-233, 1990; Zsebo, K. M. et al., "Stem cell factor is encoded at the SI locus of the mouse and is the ligand for the c-kit tyrosine kinase receptor", *Cell*, 63, 213-224, 1990; Zhang, S. et al., "Cytokine production by cell cultures from bronchial subepithelial myofibroblasts", *J. Pathol.*, 180, 95-10, 1996; Zhang, S. et al., "Human mast cells express stem cell factor", *J. Pathol.*, 186, 59-66, 1998; Kassel, O. et al., "Up and down-regulation by glucocorticoids of the constitutive expression of the mast cell growth factor stem cell factor by human lung fibroblasts in culture", *Mol. Pharmacol.*, 54, 1073-1079, 1998; Kassel, O. et al., "Human bronchial smooth muscle cells in culture produce Stem Cell Factor", *Eur. Respir J.*, 13, 951-954, 1999; Kassel, O. et al., "The Stem Cell Factor, Stem cell factor, its Properties and Potential Role in the Airways", *Pulmonary Pharmacology & Therapeutics*, 14, 227-288, 2001; de Paulis, A. et al, "Stem cell factor is localized in, released from, and cleaved by human mast cells", *J. Immunol.*, 163, 2799-2808, 1999; Mol, C. D. et al., "Structure of a c-kit product complex reveals the basis for kinase transactivation", *J. Biol. Chem.*, 278, 31461-31464, 2003; lemura, A. et al., "The c-kit ligand, stem cell factor, promotes mast cell survival by suppressing apoptosis", *Am, J. Pathol.*, 144, 321-328, 1994; Nilsson, G. et al., "Stem cell factor is a chemotactic factor for human mast cells", *J. Immunol*, 153, 3717-3723, 1994; Meininger, C. J. et al., "The c-kit receptor ligand functions as a mast cell chemoattractant", *Blood*, 79, 958-963, 1992, and Kinashi, T. et al., "Steel factor and c-kit regulate cell-matrix adhesion", *Blood*, 83, 1033-1038, 1994.

The following references discuss the c-kit signaling pathway and its relationship with various downstream pathways and the relationship with diseases associated with mast cells: Thommes, K. et al., "Identification of Tyr-703 and Tyr-936 as the primary association sites for Grb2 and Grb7 in the c-Kit/stem cell factor receptor", *Biochem, J.* 341, 211-216, 1999; Ishizuka, T. et al., "Stem cell factor augments Fc epsilon RI-mediated TNF-alpha production and stimulates MAP kinases via a different pathway in MC/9 mast cells", *J. Immunol.*, 161, 3624-3630, 1998; Timokhina, I. et al., "Kit signaling through PI 3-kinase and Src kinase pathways: an essential role for Rac1 and JNK activation in mast cell proliferation", *EMBO J.*, 17, 6250-6262, 1998; Tang, B. et al., "Tec kinase associates with c-kit and is tyrosine phosphorylated and activated following stem cell factor binding", *Mol. Cell. Biol.*, 14, 8432-8437, 1994, and Ueda. S. et al., "Critical roles of c-Kit tyrosine residues 567 and 719 in stem cell factor-induced chemotaxis: contribution of src family kinase and PI3-kinase on calcium mobilization and cell migration", *Blood*, 99, 3342-3349, 2002.

Mast cells are the primary effector cells in allergic inflammation. Mast cells are also involved in other pathogenic processes such as acute inflammation and fibrosis. Mast cells present in tissues of patients are implicated in or contribute to the genesis of diseases such as autoimmune diseases (multiple sclerosis, rheumatoid arthritis, inflammatory bowel diseases (IBD)), allergic diseases (allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and bronchial asthma), tumor angiogenesis, germ cell tumors, mast cell tumors, gastrointestinal stromal tumors, small-cell lung cancer, melanoma, breast cancer, acute myelogenous leukemia, glioblastoma, neuroblastoma and mastocytosis, inflammatory diseases, diabetes, type I diabetes, type II diabetes, irritable bowel syndrome (IBS), CNS disorders and interstitial cystitis. In these diseases, mast cells participate in the destruction of tissues by releasing a cocktail of different proteases and mediators categorized into three groups: preformed granule-associated mediators (histamine, proteoglycans, and neutral proteases), lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-Lα, MIP-Iβ, MIP-2 and IFN-γ). The liberation by activated mast cells of mediators (TNF-α, histamine, leukotrienes, prostaglandins etc.) as well as proteases may i) induce inflammation and vasodilatation and ii) participate in the tissue destruction process.

In addition, mast cell activation induces diverse effector responses, such as secretion of allergic mediators, proteases, chemokines such as MCP-1 and RANTES, leukotrienes, prostaglandins and neurotrophins; and induction of cytokine gene transcription (IL-4, IL-5, IL-6, IL-13, TNFα and GM-CSF). These mediators contribute to creating the asthmatic phenotype by their effects on endothelial cells, smooth muscle cells and fibroblasts and on extracellular matrix, and by recruiting other inflammatory cells.

Asthma is characterized by airflow obstruction, bronchial hyper responsiveness and airway inflammation. Airway inflammation is the major factor in the development and perpetuation of asthma. In allergic asthma, allergens are thought to initiate the inflammatory process by inducing a T-lymphocyte mediated response (TH2) that results in the production of allergen-specific IgE. IgE binds to its high-affinity receptor FcεRI on pulmonary mast cells, triggering a type I (IgE-mediated) immediate allergic response. Thus, mast cells play a role in asthma.

The activation of mast cells by different stimuli such as stress, trauma, infection and neurotransmitters, also participate in the exacerbation of the chemical imbalance causing CNS disorders. More specifically, mast cell degranulation is stimulated by common neurotransmitters such as neurotensin, somatostatin, substance P and acetylcholine, by growth or survival factors, notably such as NGF. Mast cells involved in the response to such stimulus can be brain mast cells but also other mast cells releasing the content of their granules in the blood stream that ultimately reach sensory, motor or brain neurons. Following mast cells activation, released granules liberate various factors capable of modulating and altering neurotransmission and neurons survival. Among such factors, serotonin is important since an increase of the level of free serotonin has been observed in depressed patients. Alternatively, the sudden burst of serotonin may be followed by a period of serotonin shortage, leading to pain and migraine. As a consequence, it is believed that mast cells exacerbate in autocrine or paracrine manner the deregulation of neurotransmission. For example, anxiety or stress-induced release of neurotransmitters such as serotonin activates mast cells, which in turn release the content of their granules, further contributing to the chemical imbalance in the brain leading to CNS disorders.

Other mediators released by mast cells can be categorized into vasoactive, nociceptive, proinflammatory and other neurotransmitters. Taken together, these factors are able to induce disturbance in the activity of neurons, whether they are sensory, motor, or CNS neurons. In addition, patients afflicted with mastocytosis are more inclined to develop CNS disorders than the normal population. This can be explained by the presence of activating mutations in the c-kit receptor, which induce degranulation of mast cells and a burst of factors contributing to chemical imbalance and neurotransmission alteration.

The activation of mast cells by different drugs, including, but not limited to, salicylic derivatives, morphine derivatives, opioids, heroin, amphetamines, alcohol, nicotine, analgesics, anesthetics, and anxyolitics results in the degranulation of mast cells, which participate in the exacerbation of the chemical imbalance responsible for drug habituation and withdrawal syndrome. Following mast cells activation, released granules liberate various factors capable of modulating and altering neurotransmission. Among such factors is morphine which is bound or stored in mast cells granules. Tobacco smoke also induces the release of mediators from canine mast cells and modulates prostaglandin production leading to asthma. In addition, patients afflicted with mastocytosis are more incline to develop substance use disorders than the normal population. This can be explained by the presence of activating mutations in the c-kit receptor, which induce degranulation of mast cells and a burst of factors contributing to chemical imbalance and neurotransmission alteration.

Mast cells have also been identified to be involved in or to contribute to drug dependence and withdrawal symptoms.

The relationship between mast cells, SOF and c-kit kinase in various diseases is discussed in the following ferefernces: Oliveira et al., "Stem Cell Factor: A Hemopoietic Cytokine with Important Targets in Asthma", *Current Drug Targets*, 2: 313-318, 2003; Puxeddu et al., "Mast cells in allergy and beyond", *The International Journal of Biochemistry & Cell Biology*, 35: 1601-1607, 2003; Rottem et al., "Mast cells and autoimmunity", *Autoimmunity Reviews*, 4: 21-27, 2005; Woolley, D. E. et al., "The mast cell in inflammatory arthritis", *N. Engl. J. Med.*, 348:1709-1711, 2003; Benoist, C. et al., "Mast cells in autoimmune disease", *Nature*, 420:875-878, 2002; Nigrovic, P. A. et al., "Mast cells in inflammatory arthritis", *Arthritis Res. Ther.*, 7:1-11, 2005; Wang, H. W. et al., "Mast cell accumulation and cytokine expression in the tight skin mouse model of scleroderrna", *Exp. Dermatol.*, 14, 295-302, 2005; Olsson, N. et al., "Demonstration of mast cell chemotactic activity in bronchoalveolar lavage, fluid collected from asthmatic patients before and during pollen season", *J. Allergy Clin. Immunol*, 105, 455-461, 2000; Ma, Y. et al., "Indolinone derivatives inhibit constitutively activated KIT mutants and kill neoplastic mast cells", *J. Invest. Dermatol.*, 114, 392-394, 2000; Kobayashi, Y. et al., "Mst Cells as a Target of Rheumatoid Arthritis Treatment", *Jpn. J. Pharmacol.*, 7-11, 2002, and Al-Muhsen, S. Z. et al., "The expression of stem cell factor and c-kit receptor in human asthrnatic airways", *Ciin. Exp. Allergy*, 34, 911-916, 2004.

In addition, the treatment of asthma and arthritis with administration of a c-kit inhibitor is presented in the following references: Takeuchi et al., "STI571 inhibits growth and adhesion of human mast cells in culture", Journal of Leukocyte Biology, 74: 1026-1034, 2003; Berlin et al., "Treatment of Cockroach Allergen Asthma Model with imatinib Attenuates Airway Responses", American Journal of Respiratory and Critical care Medicine, 171: 35-39, 2005; Ekland et al., "Treatment of rheumatoid arthritis with imatinib mesylate: clinical improvement in three refractory cases", *Annals of*

*Medicine,* 35: 362-367, 2003; Miyachi et al., "Efficacy of imatinib mesylate (STI571) treatment for a patient with rheumatoid arthritis developing chronic myelogenous leukemia", *Clinical Rheumatology,* 22: 329-332, 2003; Juurikivi et al., "Inhibition of c-kit tyrosine kinase by imatinib mesylate induces apoptosis in mast cells in rheumatoid synovial: a potential approach to the treatment of arthritis", *Ann. Rheum. Dis.,* 64: 1126-1131, 2005; Wolf, A. M., et al, "The kinase inhibitor imatinib mesylate inhibits TNF-alpha production in vitro and prevents TNF-dependent acute hepatic inflammation", *Proc. Natl. Acad. Sci.* U.S.A. 102:13622-13627, 2005; Leath et al., "Novel and emerging therapies for asthma", *Drug Discovery Today,* 10(23/24): 1647-1655, 2005; Berlin et al., "Inhibition of SCF attenuates peribronchial remodeling in chronic cockroach allergen-induced asthma", *Laboratory Investigations,* 86: 557-565, 2006; Paniagua et al., "Selective tyrosine kinase inhibition by imatinib mesylate for the treatment of autoimmune arthritis", *The Journal of Clinical Investigation,* 116(10): 2633-2642, 2006; Wenzel et al., "Update in Asthma", *American Journal of Respiratory and Critical care Medicine,* 173: 698-706, 2006; Chaudhary et al., "Pharmacological Differentiation of Inflammation and Fibrosis in the Bleomycin Model", *American Journal of Respiratory and Critical care Medicine,* 173: 769-776, 2006, and Reber et al., "Review: Stem cell factor and its receptor c-Kit as targets for inflammatory diseases", *European Journal of Pharmacology,* 533: 327-340, 2006.

The activity of the c-kit receptor is regulated in normal cells, and the normal functional activity of this c-kit gene product is important for the maintenance of normal hematopoeisis, melanogenesis, genetogensis, and growth and differentiation of mast cells. Inhibition of c-kit kinase activity reduces the growth and differentiation of mast cells and thereby mediates the diseases and/or conditions associated with mast cells, such as autoimmune diseases, multiple sclerosis, rheumatoid arthritis, inflammatory bowel diseases (IBD), respiratory diseases, allergic diseases, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation, bronchial asthma, tumor angiogenesis, germ cell tumors, mast cell tumors, gastrointestinal stromal tumors, small-cell lung cancer, melanoma, breast cancer, acute myelogenous leukemia, glioblastoma, neuroblastoma and mastocytosis, inflammatory diseases, diabetes, type I diabetes, type II diabetes, irritable bowel syndrome (IBS), CNS disorders and interstitial cystitis In addition to its importance in normal cellular physiologic activities, c-kit kinase plays a role in the biological aspects of certain human cancers, and unregulated c-kit kinase activity is implicated in the pathogenesis of human cancers, and in certain tumors types. Proliferation of tumor cell growth mediated by c-kit can occur by a specific mutation of the c-kit polypeptide that results in ligand independent activation or by autocrine stimulation of the receptor. In the former case, mutations that cause constitutive activation of c-kit kinase activity in the absence of SCF binding are implicated in malignant human cancers, including germ cell tumors, mast cell tumors, gastrointestinal stromal tumors, small-cell lung cancer, melanoma, breast cancer, acute myelogenous leukemia, glioblastoma, neuroblastoma and mastocytosis.

A proliferation assay for the evaluation of the efficacy of c-kit inhibitors and PDGFR inhibitors is given in Kuriu et al., "Proliferation of human myeloid leukemia cell line associated with the tyrosine-phosphorylation and activation of the proto-oncogene c-kit product", Blood, 78(11): 2834-2840, 1991; Heinrich et al., "Inhibition of c-kit receptor tyrosine kinase activity by STI571, a selective tyrosine kinase inhibitor", Blood, 96(3): 925-932, 2000; Buchdunger et al., "Abl Protein-Tyrosine Kinase Inhibitor STI571 Inhibits In Vitro Signal Transduction Mediated by c-Kit and Platelet-Derived Growth Factor Receptors", The Journal of Pharmacology and Experimental Therapeutics, 295(1): 139-145, 2000; and Simlich et al., "The antiangiogenic protein kinase inhibitors SU5416 and SU6668 inhibit the SCE receptor (c-kit) in a human myeloid leukemia cell line and in acute myeloid leukemia blasts", Blood, 97(5): 1413-1421, 2001. This assay use MO7e cells, which are a human promegakaryocytic leukemia cell line that depend on SCF for proliferation. These references in combination with Berlin et al., Ekland et al., and Miyachi et al., (cited above) show that that a c-kit kinase inhibitor screened via this proliferation assay was later found to treat rheumatoid arthritis and asthma.

In addition, a compound that was initially evaluated for its efficacy as a c-kit inhibit)i using a proliferation assay based on Ba/F3 cells and Ba/F3-derived cells (see WO 2004/01903) was later found to be effective in the treatment of mast cell tumours and asthma (see Bellamy F, et al., "Pharmacokinetics of masitinib in cats", Vet. Res, Commun., June 16 (epub) 2009; Hahn K. A. et al., "Mastinib is safe and effective for treatment of canine mact cell tumours', J. Vet. Intern. Med., 22, 1301-1309, 2008 and Humbert M. et al., "Mastinib, a c-kit/PDGF receptor tyrosine kinase inhibitor, improves disease control in severe corticosteroid-dependent asthmatics", 64, 1194-1201, 2009.

c-kit receptor has a substantial homology to the PDGF receptor and to the CSF-1 receptor (c-Fms).

Platelet-Derived Growth Factor (PDGF) Receptor Family

PDGF (Platelet-derived Growth Factor) is commonly occurring growth factor which plays an important role both in normal growth and in pathological cell proliferation. By way of example, such as that observed in carcinogenesis and in diseases of the smooth-muscle cells of blood vessels, for example in atherosclerosis and thrombosis. The PDGF growth factor family consists of PDGF-A, PDGF-B, PDGF-C and PDGF-D, which form either homo- or heterodimers (AA, AB, BB, CC, DD) that bind to the protein tyrosine kinase receptors PDGFR-α and PDGFR-β. Dimerization of the growth factors is a prerequisite for activation of the kinase, as the monomeric forms are inactive. The two receptor isoforms dimerize upon binding resulting in three possible receptor combinations, PDGFR-αα, PDGFR-ββ and PDGFRαβ. Growth factor AA binds only to −αα, growth factor BB can bind with −αα, −ββ and −αβ, growth factors CC and AB specifically interact with −αα and −αβ, and growth factor DD binds to −ββpp. The PDGF-receptor plays an important role in the maintenance, growth and development of hematopoietic and non-hematopoietic cells.

Key downstream mediators of PDGFR signaling are Ras/ mitogen-activated protein kinase (MAPK), PI-3 kinase and phospholipase-γ (PLCγ) pathways. MAPK family members regulate various biological functions by phosphorylation of target molecules (transcription factors and other kinases) and thus contribute to regulation of cellular processes such as proliferation, differentiation, apoptosis and immunoresponses. PI-3 kinase activation generated PIP3 which functions as a second messenger to activate downstream tyrosine kinases Btk and Itk, the Ser/Thr kinases PDK1 and Akt (PKB). Akt activation is involved in survival, proliferation and cell growth. After activation PLC hydrolyses its substrate, Ptdlns(4,5)P2, and forms two secondary messengers, diacylglycerol and Ins(1,4,5)P3 which stimulates intracellular processes such as proliferation, angiogenesis and cell motility.

PDGFR is expressed on early stem cells, mast cells, myeloid cells, mesenchymal cells and smooth muscle cells. Only PDGFR-β is implicated in myeloid leukemias-usually as a translocation partner with Tel, Huntingtin interacting protein (HIP1) or Rabaptin5. Activation mutations in PDGFR-α kinase domain are associated with gastrointestinal stromal tumors (GIST).

Certain embodiments of compounds of Formula (I) and Formula (II) provided herein inhibit PDGF receptor (PDGFRα and PDGFRp) activity and c-kit kinase activity, and are useful for the treatment of diseases, which respond to an inhibition of the PDGF receptor kinase. Therefore, certain compounds of Formula (I) and Formula (II) provided herein are useful for the treatment of tumor diseases, such as gliomas, sarcomas, prostate tumors, small cell lung cancer and tumors of the colon, breast, and ovary. In addition certain embodiments of compounds of Formula (I) and Formula (II) provided herein are useful to treat disorders, such as thrombosis, psoriasis, scleroderma, fibrosis, asthma, metabolic diseases and hypereosinophilia. Compounds of Formula (I) and Formula (II) provided herein are also effective against diseases associated with vascular smooth-muscle cell migration and proliferation, such as restenosis and atherosclerosis.

Patients with obliterative bronchiolitis (OB), a chronic rejection of allogenic lung transplants, often show an elevated PDGF concentration in bronchoalveolar lavage fluids. In certain embodiments, compounds of Formula (I) and Formula (II) provided herein exhibit useful effects in the treatment of disorders arising as a result of transplantation, for example, allogenic transplantation, especially tissue rejection, such as obliterative bronchiolitis (OB).

In certain embodiments, compounds of Formula (I) and Formula (II) provided herein are useful for the protection of stem cells, for example to combat the hemotoxic effect of chemotherapeutic agents, such as 5-fluorouracil.

The compounds of Formula (I) and Formula (II) provided herein, and the pharmaceutically acceptable salts, pharmaceutically acceptable solvates (e.g. hydrates), the N-oxide derivatives, protected derivatives, individual isomers and mixture of isomers thereof, are inhibitors of c-kit kinase activity or are inhibitors of c-kit kinase activity and PDGFR (α and β) kinase activity. In certain embodiments, the compounds of Formula (I) and Formula (II) provided herein, and the pharmaceutically acceptable salts, pharmaceutically acceptable solvates (e.g. hydrates), the N-oxide derivatives, protected derivatives, individual isomers and mixture of isomers thereof, are inhibitors of c-kit kinase activity and PDGFR (α and β) kinase activity. In other embodiments, the compounds of Formula (I) and Formula (II) provided herein, and the pharmaceutically acceptable salts, pharmaceutically acceptable solvates (e.g. hydrates), the N-oxide derivatives, protected derivatives, individual isomers and mixture of isomers thereof, are inhibitors of either c-kit kinase activity. Such compounds of Formula (I) and Formula (II) provided herein, and the pharmaceutically acceptable salts, pharmaceutically acceptable solvates (e.g. hydrates), the N-oxide derivatives, protected derivatives, individual isomers and mixture of isomers thereof, are useful for treating diseases or disorders in which c-kit kinase, or c-kit and PDGFR (α and/or β) kinase, contributes to the pathology and/or symptomology of a disease or disorder. Such diseases or disorders include, but are not limited to, a mast cell associated disease, inflammatory diseases, respiratory diseases, an allergy disorder, fibrosis diseases, metabolic diseases, autoimmune diseases, a CNS related disorder, a neurodegenerative disorder, neurological diseases, dermatoligical diseases, a graft-versus-host disease, a pain condition, a neoplastic disorder, a cardiovascular disease and cancer.

Non-limiting examples of such diseases include asthma, allergic rhinitis, allergic sinusitis, bronchial asthma, irritable bowel syndrome (IBS), inflammatory bowel disease (IBD), pulmonary arterial hypertension (PAH), idiopathic arterial hypertension (IPAH), primary pulmonary hypertension (PPH), pulmonary fibrosis, liver fibrosis, cardiac fibrosis, scleroderma, urticaria, dermatoses, atopic dermatitis, allergic contact dermatitis, diabetes, type I diabetes, type II diabetes, rheumatoid arthritis, multiple scherosis, cytopenias (by way of example only, anemia, leucopenia, neutropenia, thrombocytopenia, granuloctopenia, pancytoia and idiopathic thrombocytopenic purpura), systemic lupus erythematosus, chronic obstructive pulmonary disease (COPD), adult respiratory distress syndrome (ARDS), ulcerative colitis, Crohns disease, psoriasis, lymphomas (by way of example only, B and T cell lymphomas), myelodysplasic syndrome, breast cancer, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, chronic myeloid leukemia metastasis, cancer-related pain, neuroblastoma, osteosarcoma, melanoma, bone metastases, a tumor of breast, renal, lung, prostate, pancreas, colon, ovary, thyroid, colorectal tumors, neuronal tumors, uterine tumors, gastrointestinal stromal tumors (GIST), gliomas, sarcomas, tumor angiogenesis, germ cell tumors, mast cell tumors, glioblastoma, neuroblastoma, mastocytosis, osteoporosis, hypereosinophilia, restenosis, atherosclerosis, anaphylactic syndrome, angioedema, erythema nodosum, erythema multiforme, cutaneous necrotizing venulitis, insect bite skin inflammation, CNS disorders and interstitial cystitis.

In certain embodiments, the compounds of Formula (I) and Formula (II) provided herein, and the pharmaceutically acceptable salts, pharmaceutically acceptable solvates (e.g. hydrates), the N-oxide derivatives, protected derivatives, individual isomers and mixture of isomers thereof, are useful for treating diseases or disorders in which c-kit kinase contributes to the pathology and/or symptomology of a disease or disorder. Non-limiting examples of such diseases include asthma, allergic rhinitis, allergic sinusitis, bronchial asthma, irritable bowel syndrome (IBS), inflammatory bowel disease (IBD), pulmonary arterial hypertension (PAH), pulmonary fibrosis, liver fibrosis, cardiac fibrosis, scleroderma, urticaria, dermatoses, atopic dermatitis, allergic contact dermatitis, diabetes, type I diabetes, type II diabetes, rheumatoid arthritis, multiple scherosis, cytopenias (by way of example only, anemia, leucopenia, neutropenia, thrombocytopenia, granuloctopenia, pancytoia and idiopathic thrombocytopenic purpura), systemic lupus erythematosus, chronic obstructive pulmonary disease (COPD), adult respiratory distress syndrome (ARDS), ulcerative colitis, Crohns disease, psoriasis, lymphomas (by way of example only, B and T cell lymphomas), myelodysplasic syndrome, breast cancer, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, chronic myeloid leukemia metastasis, cancer-related pain, neuroblastoma, osteosarcoma, melanoma, bone metastases, a tumor of breast, renal, lung, prostate, pancreas, colon, ovary, thyroid, colorectal tumors, neuronal tumors, uterine tumors, gastrointestinal stromal tumors (GIST), gliomas, sarcomas, tumor angiogenesis, germ cell tumors, mast cell tumors, glioblastoma, neuroblastoma, mastocytosis, osteoporosis, hypereosinophilia, restenosis, atherosclerosis, anaphylactic syndrome, angioedema, erythema nodosum, erythema multiforme, cutaneous necrotizing venulitis, insect bite skin inflammation, CNS disorders and interstitial cystitis.

In certain embodiments, the compounds of Formula (I) and Formula (II) provided herein, and the pharmaceutically acceptable salts, pharmaceutically acceptable solvates (e.g. hydrates), the N-oxide derivatives, protected derivatives, individual isomers and mixture of isomers thereof, are useful for treating diseases or disorders in which c-kit kinase and PDGFR (a and/or p) kinase contribute to the pathology and/or symptomology of a disease or disorder. Non-limiting examples of such diseases include asthma, allergic rhinitis, allergic sinusitis, bronchial asthma, irritable bowel syndrome (IBS), inflammatory bowel disease (IBD), pulmonary arterial hypertension (PAH), pulmonary fibrosis, liver fibrosis, cardiac fibrosis, scleroderma, urticaria, dermatoses, atopic dermatitis, allergic contact dermatitis, diabetes, type I diabetes, type II diabetes, rheumatoid arthritis, multiple scherosis, cytopenias (by way of example only, anemia, leucopenia, neutropenia, thrombocytopenia, granuloctopenia, pancytoia and idiopathic thrombocytopenic purpura), systemic lupus erythematosus, chronic obstructive pulmonary disease (COPD), adult respiratory distress syndrome (ARDS), ulcerative colitis, Crohns disease, psoriasis, lymphomas (by way of example only, B and T cell lymphomas), myelodysplasic syndrome, breast cancer, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, chronic myeloid leukemia metastasis, cancer-related pain, neuroblastoma, osteosarcoma, melanoma, bone metastases, a tumor of breast, renal, lung, prostate, pancreas, colon, ovary, thyroid, colorectal tumors, neuronal tumors, uterine tumors, gastrointestinal stromal tumors (GIST), gliomas, sarcomas, tumor angiogenesis, germ cell tumors, mast cell tumors, glioblastoma, neuroblastoma, mastocytosis, osteoporosis, hypereosinophilia, restenosis, atherosclerosis, anaphylactic syndrome, angioedema, erythema nodosum, erythema multiforme, cutaneous necrotizing venulitis, insect bite skin inflammation, CNS disorders and interstitial cystitis.

Another aspect provided herein includes methods for treating a cell-proliferative disease, comprising administering to a system or subject in need of such treatment an effective amount of a compound of Formula (I) and Formula (II), or pharmaceutically acceptable salts or pharmaceutical compositions thereof; wherein the cell-proliferative disease is lymphoma, osteosarcoma, melanoma, or a tumor of breast, renal, prostate, colorectal, thyroid, ovarian, pancreatic, neuronal, lung, uterine or gastrointestinal tumor.

In certain embodiments, the compounds of Formula (I) and Formula (II), pharmaceutically acceptable salts, solvates, N-oxides and isomers thereof, pharmaceutical compositions, and/or combinations provided herein are used in the treatment diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, including infectious and eosinophilic bronchitis; emphysema; bronchiectasis; cystic fibrosis; sarcoidosis; farmers lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

In certain embodiments, the compounds of Formula (I) and Formula (II), pharmaceutically acceptable salts, solvates, N-oxides and isomers thereof, pharmaceutical compositions, and/or combinations provided herein are used in the treatment of dermatological disorders including, but not limited to, psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, basal cell carcinoma, actinic keratosis, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

In certain embodiments, the compounds of Formula (I) and Formula (II), pharmaceutically acceptable salts, solvates, N-oxides and isomers thereof, pharmaceutical compositions, and/or combinations provided herein are used in the treatment of rheumatoid arthritis, irritable bowel syndrome, systemic lupus erythematosus, multiple sclerosis, Hashimoto's thyroiditis, Crohns disease, inflammatory bowel disease (IBD), Graves' disease, Addison's disease, diabetes mellitus, idiopathic thrombocytopaenic purpura, eosinophilic fasciitis, hyper-IgE syndrome, antiphospholipid syndrome and Sazary syndrome.

In certain embodiments, the compounds of Formula (I) and Formula (II), pharmaceutically acceptable salts, solvates, N-oxides and isomers thereof, and pharmaceutical compositions provided herein are used in the treatment of cancer including, but not limited to, prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes.

Provided herein are compounds of Formula (I) and Formula (II), pharmaceutically acceptable salts, pharmaceutically acceptable solvates (e.g. hydrates), the N-oxide derivatives, protected derivatives, individual isomers and mixture of isomers thereof, and pharmaceutical compositions containing at least one compound of Formula (I) or Formula (II), or pharmaceutically acceptable salts, pharmaceutically acceptable solvates (e.g. hydrates), the N-oxide derivatives, protected derivatives, individual isomers or mixture of isomers thereof, for use in activating c-kit kinase activity, or c-kit kinase and PDGFR (a and/or p) kinase activity, and thereby are used to in the prevention or treatment of diseases and/or disorders associated with c-kit kinase activity, or c-kit kinase and PDGFR (α and/or β) kinase activity.

Also provided herein are methods for the treatment of a subject suffering from a disease and/or disorder associated with c-kit kinase activity, wherein the method includes administering to the subject in need thereof, an effective amount of a compound of Formula (I) or Formula (II), or pharmaceutically acceptable salts, pharmaceutically acceptable solvates (e.g. hydrates), the N-oxide derivatives, protected derivatives, individual isomers or mixture of isomers thereof, either alone or as part of a pharmaceutical composition as described herein.

Also provided herein are methods for the treatment of a subject suffering from a disease and/or disorder associated with c-kit kinase activity and PDGFR (α and/or β) kinase activity, wherein the method includes administering to the subject in need thereof, an effective amount of a compound of Formula (I) or Formula (II), or pharmaceutically acceptable salts, pharmaceutically acceptable solvates (e.g. hydrates), the N-oxide derivatives, protected derivatives, individual isomers or mixture of isomers thereof, either alone or as part of a pharmaceutical composition as described herein.

Provided herein is the use of a compound of Formula (I) or Formula (II), or pharmaceutically acceptable salts, pharmaceutically acceptable solvates (e.g. hydrates), the N-oxide derivatives, protected derivatives, individual isomers or mixture of isomers thereof, in the manufacture of a medicament for the treatment of a disease or disorder associated with c-kit kinase activity. Also provided herein is the use of a compound of Formula (I) or Formula (II), or pharmaceutically acceptable salts, pharmaceutically acceptable solvates (e.g. hydrates), the N-oxide derivatives, protected derivatives, individual isomers or mixture of isomers thereof, in the manufacture of a medicament for the treatment of a disease or disorder associated with c-kit kinase activity and PDGFR (α and/or β) kinase activity.

Furthermore, provided herein is the use of a compound having Formula (I) or Formula (II), or pharmaceutically acceptable salts or pharmaceutical compositions thereof, and optionally in combination with a therapeutically effective amount of a second agent, in the manufacture of a medicament for treating a disease or condition modulated by kinase activity, particularly c-kit, or c-kit and PDGFR (α and β).

In accordance with the foregoing, the present invention further provides a method for preventing or treating any of the diseases or disorders described above in a subject in need of such treatment, which method comprises administering to said subject a therapeutically effective amount of a compound of Formula (I) or Formula (II), or a pharmaceutically acceptable salt thereof. For any of the above uses, the required dosage will vary depending on the mode of administration, the particular condition to be treated and the effect desired. (See, "Administration and Pharmaceutical Compositions," infra).

Administration and Pharmaceutical Compositions

For the therapeutic uses of compounds of Formula (I) and Formula (II), or pharmaceutically acceptable salts, solvates, N-oxides or isomers thereof, described herein, such compounds are administered in therapeutically effective amounts either alone or as part of a pharmaceutical composition. Accordingly, provided herein are pharmaceutical compositions, which comprise at least one compound of Formula (I) or Formula (II), or pharmaceutically acceptable salts solvates, N-oxides or isomers thereof, and one or more pharmaceutically acceptable carriers, diluents, or excipients. In addition, such compounds and compositions are administered singly or in combination with one or more additional therapeutic agents. The method of administration of such compounds and compositions include, but are not limited to, oral administration, rectal administration, transdermal administration, parenteral, intravenous administration, intravitreal administration, intramuscular administration, pulmonary administration, inhalation administration, intranasal administration, topical administration, ophthalmic administration or otic administration. In certain embodiments the method of administration of such compounds and compositions is oral administration. In other embodiments the method of administration of such compounds and compositions is pulmonary administration, inhalation administration or intranasal administration.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I) and Formula (II), satisfactory results are indicated to be obtained systemically at daily dosages of from about 0.03 to 2.5 mg/kg per body weight. In certain embodiments, the daily dosage of a compound of Formula (I) and Formula (II), administered by inhalation, is in the range from 0.05 micrograms per kilogram body weight (μg/kg) to 100 micrograms per kilogram body weight (μg/kg). In other embodiments, the daily dosage of a compound of Formula (I) and Formula (II), administered orally, is in the range from 0.01 micrograms per kilogram body weight (μg/kg) to 100 milligrams per kilogram body weight (mg/kg). An indicated daily dosage in the larger mammal, e.g. humans, is in the range from about 0.5 mg to about 100 mg of a compound of Formula (I) and Formula (II), conveniently administered, e.g. in divided doses up to four times a day or in controlled release form. In certain embodiment, unit dosage forms for oral administration comprise from about 1 to 50 mg of a compound of Formula (I) and Formula (II).

Other aspects provided herein are processes for the preparation of pharmaceutical composition which comprise at least one compound of Formula (I) or Formula (II), or pharmaceutically acceptable salts, solvates, N-oxides or isomers thereof. In certain embodiments, such processes include admixing a compound of the Formula (I) or Formula (II), or pharmaceutically acceptable salts, solvates, N-oxides or isomers thereof, with one or more pharmaceutically acceptable carriers, diluents or excipients. In certain embodiments, the pharmaceutical compositions comprising a compound of Formula (I) or Formula (II) in free form, or in a pharmaceutically acceptable salt, solvate, N-oxide or isomeric form, in association with at least one pharmaceutically acceptable carrier, diluent or excipient are manufactured by mixing, granulating and/or coating methods. In other embodiments, such compositionsoptionally contain excipients, such as preserving, stabilizing, wetting or emulsifying agents, solution promoters, salts for regulating the osmotic pressure and/or buffers. In other embodiments, such compositions are sterilized.

In certain embodiments, the pharmaceutical compositions comprising at least one compound of Formula (I) or Formula (II) are adapted for oral administration for the treatment of diseases and/or disorders associated with c-kit kinase activity. In other embodiments, the pharmaceutical compositions comprising at least one compound of Formula (I) or Formula (II) are adapted for oral administration for the treatment of diseases and/or disorders associated with c-kit kinase and PDGFR (a and/or p) kinase activity.

In certain embodiments, the pharmaceutical compositions comprising at least one compound of Formula (I) or Formula (II) are adapted for inhalation adminitsation, including pulmonary administration, inhalation administration or intranasal administration, for the treatment of diseases and/or disorders associated with c-kit kinase activity. In other embodiments, the pharmaceutical compositions comprising at least one compound of Formula (I) or Formula (II) are adapted for inhalation adminitsation, including pulmonary administration, inhalation administration or intranasal administration, for the treatment of diseases and/or disorders associated with c-kit kinase and PDGFR (α and/or β) kinase activity.

In certain embodiments, the pharmaceutical compositions comprising at least one compound of Formula (I) or Formula (II) are adapted for inhalation adminitsation, including pulmonary administration, inhalation administration or intranasal administration, for the treatment of respiratory diseases with c-kit kinase activity. In certain embodiments, the respiratory disease is allergic rhinitis or asthma. In other embodiments, the pharmaceutical compositions comprising at least one compound of Formula (I) or Formula (II) are adapted for inhalation adminitsation, including pulmonary administration, inhalation administration or intranasal administration, for the treatment of respiratory diseases associated with c-kit kinase and PDGFR (α and/or β) kinase activity. In certain embodiments, the respiratory disease is allergic rhinitis or asthma.

In certain embodiments, the pharmaceutical compositions comprising at least one compound of Formula (I) or Formula (II) are adapted for parenteral or intravenous administration, for the treatment of diseases and/or disorders associated with c-kit kinase activity. In other embodiments, the pharmaceutical compositions comprising at least one compound of Formula (I) or Formula (II) are adapted for parenteral or intravenous administration, for the treatment of diseases and/or disorders associated with c-kit kinase and PDGFR (a and/or p) kinase activity.

Oral Dosage Forms

In certain embodiments, the pharmaceutical compositions containing at least one compound of Formula (I) or Formula (II) are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I) and Formula (II) are prepared by admixing at least one compound of Formula (I) and Formula (II) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) or Formula (II) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) or Formula (II) is orally administered as a controlled release dosage form. Such dosage forms are used to provide slow or controlled-release of one or more compounds of Formula (I) or Formula (II). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I) or Formula (II), reduce dosage frequency, and increase patient compliance.

Administration of compounds of Formula (I) or Formula (II) as oral fluids such as solution, syrups and elixirs are prepared in unit dosage forms such that a given quantity of solution, syrups or elixirs contains a predetermined amount of a compound of Formula (I) or Formula (II). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) or Formula (II) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing at least one compound of Formula (I) or Formula (II) are administered transdemally. Such transdermal dosage forms include "reservoir type" or "matrix type" patches, which are applied to the skin and worn for a specific period of time to permit the penetration of a desired amount of a compound of Formula (I) or Formula (II). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I) or Formula (II) include an effective amount of a compound of Formula (I) or Formula (II), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I) or Formula (II) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I) or Formula (II). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I) or Formula (II) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compounds of Formula (I) or Formula (II) are used to further adjust the properties of the resulting composition.

In certain embodiments compounds of Formula (I) or Formula (II) are transderrmally delivered from a patch by iontophoresis.

Topical Dosage Forms

In certain embodiments at least one compound of Formula (I) or Formula (II) is administered by topical application of pharmaceutical composition containing at least one compound of Formula (I) or Formula (II) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I) or Formula (II) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Inhalation Administration

In certain embodiments pharmaceutical compositions containing at least one compound of Formula (I) or Formula (II) are administered by inhalation. Inhalation refers to administration into the patient's lungs whether inhaled through the mouth or through the nasal passages. Dosage forms for inhaled administration are formulated as aerosols, dry powders, suspensions, or solution compositions. Dry powder compositions contain at least one compound of Formula (I) or Formula (II) or a pharmaceutically acceptable salt thereof as a finely divided powder together with one or more pharmaceutically-acceptable excipients as finely divided powders. Such pharmaceutically-acceptable excipients used in dry powders include, but are not limited to, lactose, starch, mannitol, and mono-, di-, and polysaccharides. In certain embodiments, the finely divided powder is prepared by micronisation and milling, wherein the size-reduced (micronised) compound is defined by a $D_{50}$ value of about 1 to about 10 microns.

Aerosol formulations for inhalation administration comprise a solution or fine suspension of at least one compound of Formula (I) or Formula (II) in a pharmaceutically acceptable aqueous or non-aqueous solvent/propellant. Suitable propellants include halocarbons, hydrocarbons, and other liquified gases. Representative propellants include: trichlorofluoromethane (propellant 1 1), dichlorofluoromethane (propellant 12), dichlorotetrafluoroethane (propellant 1 14), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate. Aerosol also optionally contain additional pharmaceutically-acceptable excipients such as surfactants, lubricants, cosolvents and other excipients to improve the physical stability of the formulation, to improve solubility, or to improve taste.

The particle size of a micronized compound of Formula (I) or Formula (II) contained in an aerosol formulation is less than 100 microns, while in other embodiments less than 20 microns. In certain embodiments the particle size is in the range of from 1 to 10 microns, in other embodiments from 1 to 5 microns, while in still other embodiments from 2 to 3 microns.

Thus provided herein is a pharmaceutical aerosol formulation comprising at least one compound of Formula (I) or Formula (II) or a pharmaceutically acceptable salt thereof and a fluorocarbon or hydrogen-containing chlorofluorocarbon as propellant, optionally in combination with a surfactant and/or a cosolvent. In certain embodiments, in such pharmaceutical aerosol formulation the propellant is selected from 1,1,1,2-tetrafluoroethane, 1,1,1,2,3,3,3-heptafluoro-n-propane and mixtures thereof.

In certain embodiments, suspensions and solutions comprising at least one compound of Formula (I) or Formula (II), or a pharmaceutically acceptable salt thereof, formulated for inhalation administration are administered via a nebulizer. The solvent or suspension agent utilized for nebulization is any pharmaceutically-acceptable liquid such as water, aqueous saline, alcohols or glycols, (by way of example only, ethanol, isopropylalcohol, glycerol, propylene glycol, polyethylene glycol or mixtures thereof). Saline solutions utilize salts which display little or no pharmacological activity after administration. Such salt include, but are not limited to, alkali metal or ammonium halogen salts or organic acids (by way of example only, ascorbic acid, citric acid, acetic acid and tartaric acid). Such suspensions optionally contain other pharmaceutically-acceptable excipients provided herein.

In certain embodiments, compounds of Formula (I) or Formula (II) are administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) or Formula (II) and a powder base such as lactose or starch. In certain embodiments, compounds of Formula (I) or Formula (II) are delivered to the lung using a liquid spray device, wherein such devices use extremely small nozzle holes to aerosolize liquid drug formulations that can then be directly inhaled into the lung. In other embodiments, compounds of Formula (I) or Formula (II) are delivered to the lung using a nebulizer device, wherein a nebulizers creates an aerosols of liquid drug formulations by using ultrasonic energy to form fine particles that can be readily inhaled. In other embodiments, compounds of Formula (I) or Formula (II) are delivered to the lung using an electrohydrodynamic ("EHD") aerosol device wherein such EHD aerosol devices use electrical energy to aerosolize liquid drug solutions or suspensions.

In certain embodiments, the proportion of Formula (I) or Formula (II) or pharmaceutically acceptable salt thereof used in powders for inhalation or insufflation is within the range of from 0.1 to 10%. In other embodiments, the proportion of Formula (I) or Formula (II) or pharmaceutically acceptable salt thereof used in powders for inhalation or insufflation is within the range of from 0.1 to 5%. In certain embodiments, aerosol formulations contain from 20 μg to 10 mg of a compound of Formula (I) or Formula (II), while in other embodiments, aerosol formulations contain from 20 μg to 2000 μg of a compound of Formula (I) or Formula (II). In certain embodiments, aerosol formulations contain from 20 μg to 500 μg of a compound of Formula (I) or Formula (II). In certain embodiments, a compound of Formula (I) or Formula (II) is administered once daily by inhalation administration, while in other embodiments a compound of Formula (I) or Formula (II) is administered several times daily by inhalation administration, By way of example only, such multiple daily dosages occur 2, 3, 4 or 8 times daily, giving for example 1, 2 or 3 doses each time.

In certain embodiments, the pharmaceutical composition containing at least one compound of Formula (I) or Formula (II), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) or Formula (II) are administered intranasally. The dosage forms for nasal administration are formulated as aerosols, solutions, drops, gels or dry powders. Aqueous formulations for administration to the lung or nose optionally include conventional excipients as provided herein, such as buffering agents, tonicity modifying agents and the like.

Rectal Administration

In certain embodiments pharmaceutical compositions containing at least one compound of Formula (I) or Formula (II) are administered rectally in the form of suppositories, enemas, ointment, creams rectal foams or rectal gels. In certain embodiments such suppositories are prepared from fatty emulsions or suspensions, cocoa butter or other glycerides.

In certain embodiments pharmaceutical compositions containing at least one compound of Formula (I) or Formula (II) are administered opthamically as eye drops. Such formulations are aqueous solutions that optionally contain solubilizers, stabilizers, tonicity enhancing agents, buffers and preservatives.

Otic Administration

In certain embodiments pharmaceutical compositions containing at least one compound of Formula (I) or Formula (II)

are administered optically as ear drops. Such formulations are aqueous solutions that optionally contain solubilizers, stabilizers, tonicity enhancing agents, buffers and preservatives.

Depot Administration

In certain embodiments pharmaceutical compositions containing at least one compound of Formula (I) or Formula (II) are formulated as a depot preparation. Such formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

Combination Treatment

In certain embodiments, a compound of Formula (I) or Formula (II) of the present invention, or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II) provided herein, is administered alone (without an additional therapeutic agent) for the treatment of a disease or disorder associated with c-kit kinase activity.

In certain embodiments, a compound of Formula (I) or Formula (II) of the present invention, or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II) provided herein, is administered alone (without an additional therapeutic agent) for the treatment of a disease or disorder associated with c-kit kinase activity and PDGFR ($\alpha$ and/or $\beta$) kinase activity.

In other embodiments, a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), is administered in combination with one or more additional therapeutic agents, for the treatment of a disease or disorder associated with c-kit kinase activity.

In other embodiments, a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), is administered in combination with one or more additional therapeutic agents, for the treatment of a disease or disorder associated with c-kit kinase activity and PDGFR ($\alpha$ and/or $\beta$) kinase activity.

In other embodiments, a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), is formulated in combination with one or more additional therapeutic agents and administered for the treatment of a disease or disorder associated with c-kit kinase activity.

In other embodiments, a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), is formulated in combination with one or more additional therapeutic agents and administered for the treatment of a disease or disorder associated with c-kit kinase activity and PDGFR ($\alpha$ and/or $\beta$) kinase activity.

In other embodiments, a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), is administered sequentially with one or more additional therapeutic agents, for the treatment of a disease or disorder associated with c-kit kinase activity.

In other embodiments, a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), is administered sequentially with one or more additional therapeutic agents, for the treatment of a disease or disorder associated with c-kit kinase activity and PDGFR ($\alpha$ and/or $\beta$) kinase activity.

In other embodiments, the combination treatments provided herein include administration of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), prior to administration of one or more additional therapeutic agents, for the treatment of a disease or disorder associated with c-kit kinase activity.

In other embodiments, the combination treatments provided herein include administration of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), prior to administration of one or more additional therapeutic agents, for the treatment of a disease or disorder associated with c-kit kinase activity and PDGFR ($\alpha$ and/or $\beta$) kinase activity.

In other embodiments, the combination treatments provided herein include administration of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), subsequent to administration of one or more additional therapeutic agents, for the treatment of a disease or disorder associated with c-kit kinase activity.

In other embodiments, the combination treatments provided herein include administration of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), subsequent to administration of one or more additional therapeutic agents, for the treatment of a disease or disorder associated with c-kit kinase activity and PDGFR ($\alpha$ and/or $\beta$) kinase activity.

In certain embodiments, the combination treatments provided herein include administration of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), concurrently with one or more additional therapeutic agents, for the treatment of a disease or disorder associated with c-kit kinase activity.

In certain embodiments, the combination treatments provided herein include administration of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing at least one compound of Formula (I) or Formula (II), concurrently with one or more additional therapeutic agents, for the treatment of a disease or disorder associated with c-kit kinase activity and PDGFR (α and/or β) kinase activity.

In certain embodiments of the combination therapies described herein, the compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, and the additional therapeutics agent(s) act additively. In certain embodiments of the combination therapies described herein, the compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, and the additional therapeutics agent(s) act synergistically.

The additional therapeutic agents used in combination with at least one compound of Formula (I) or Formula (II) of the present invention, or a pharmaceutically acceptable salts, pharmaceutically acceptable solvates (e.g. hydrates), the N-oxide derivatives, protected derivatives, individual isomers and mixture of isomers thereof, include, but are not limited to antiemetic agents, anti-inflammatory agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function, anticancer agents and toll-like receptor modulators.

In some embodiments, the compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, are used in combination with a second therapeutic agent for treating asthma. In certain combinations, the second therapeutic agent is a bronchodilator, an anti-inflammatory agent, a leukotriene antagonist, or an IgE blocker.

The antiemetic agents used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and combinations thereof.

The anti-inflammatory agents used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide, leukotriene antagonists including, but not limited to, zileuton, aurothioglucose, gold sodium thiomalate and auranofin, steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

The immunomodulatory agents used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, azathioprine, tacrolimus, cyclosporin methothrexate, leflunomide, corticosteroids, cyclophosphamide, cyclosporine A, cyclosporin G, mycophenolate mofetil, ascomycin, rapamycin (sirolimus), FK-506, mizoribine, deoxyspergualin, brequinar, mycophenolic acid, malononitriloamindes (such as, by way of example only, leflunamide), T cell receptor modulators, and cytokine receptor modulators, peptide mimetics, and antibodies (such as, by way of example only, human, humanized, chimeric, monoclonal, polyclonal, Fvs, ScFvs, Fab or F(ab)$_2$ fragments or epitope binding fragments), nucleic acid molecules (such as, by way of example only, antisense nucleic acid molecules and triple helices), small molecules, organic compounds, and inorganic compounds. Examples of T cell receptor modulators include, but are not limited to, anti-T cell receptor antibodies (such as, by way of example only, anti-CD4 antibodies (such as, by way of example only, cM-T412 (Boehringer), IDEC-CE9.1™ (IDEC and SKB), mAB 4162W94, Orthoclone and OKTcdr4a (Janssen-Cilag)), anti-CD3 antibodies (such as, by way of example only, Nuvion (Product Design Labs), OKT3 (Johnson & Johnson), or Rituxan (IDEC)), anti-CD5 antibodies (such as, by way of example only, an anti-CD5 ricin-linked immunoconjugate), anti-CD7 antibodies (such as, by way of example only, CHH-380 (Novartis)), anti-CD8 antibodies, anti-CD40 ligand monoclonal antibodies (such as, by way of example only, IDEC-131 (IDEC)), anti-CD52 antibodies (such as, by way of example only, CAMPATH 1H (Ilex)), anti-CD2 antibodies, anti-CD11a antibodies (such as, by way of example only, Xanelim (Genentech)), anti-B7 antibodies (such as, by way of example only, IDEC-114 (IDEC)), CTLA4-immunoglobulin, and toll receptor-like (TLR) modulators. Examples of cytokine receptor modulators include, but are not limited to, soluble cytokine receptors (such as, by way of example only, the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (such as, by way of example only, interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (such as, by way of example only, anti-IFN receptor antibodies, anti-IL-2 receptor antibodies (such as, by way of example only, Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (such as, by way of example only, anti-IFN antibodies, anti-TNF-α antibodies, anti-IL-1β antibodies, anti-IL-6 antibodies, anti-IL-8 antibodies (such as, by way of example only, ABX-IL-8 (Abgenix)), and anti-IL-12 antibodies).

The alkylating agents used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, nitrogen mustards, ethylenimines, methylmelamines, alkyl sulfonates, nitrosoureas, carmustine, lomustine, triazenes, melphalan, mechlorethamine, cisplatin, oxaliplatin, carboplatin, cyclophosphamide, ifosfamide, melphalan, chlorambucil, hexamethylmelaine, thiotepa, busulfan, carmustine, streptozocin, dacarbazine and temozolomide.

The antimetabolites used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, cytarabile, gemcitabine and antifolates such as, by way of example only, fluoropyrimidines (by way of example only, 5-fluorouracil and tegafur), raltitrexed, methotrexate, cytosine arabinoside, and hydroxyurea.

The antitumour antibiotics used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, anthracyclines, bleomycin, doxorubicin, daunomycin, epirubicin, idarubicin, mitomycin-C, dactinomycin and mithramycin.

The antimitotic agents used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, vinca alkaloids (by way of example only, vincristine, vinblastine, vindesine and vinorelbine), taxoids (by way of example only, taxol, paclitaxel and taxotere) and polokinase inhibitors.

The topoisomerase inhibitors used in combination with compounds of Formula (I) or Formula (II), or a pharmaceutically acceptable salts, pharmaceutically acceptable solvates (e.g. hydrates), the N-oxide derivatives, protected derivatives, individual isomers and mixture of isomers thereof, include, but are not limited to, epipodophyllotoxins by way of example only, etoposide and teniposide, amsacrine, topotecan, irinotecan and camptothecin.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with a receptor antagonist for leukotrienes (LTB4, LTC4, LTD4, and LTE4) selected from the group consisting of the phenothiazin-3-Is such as L-651,392; amidino compounds such as CGS-25019c; benzoxalamines such as ontazolast; benzenecarboximidamides such as BIIL 284/260; and compounds such as zafirlukast, ablukast, montelukast, SINGULAIR™, pranlukast, verlukast (MK-679), RG-12525, Ro-245913, iralukast (CGP 45715A), and BAYx7195.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with a phosphodiesterase (PDE) inhibitor such as a methylxanthanine including theophylline and aminophylline; a selective PDE isoenzyme inhibitor including a PDE4 inhibitor, including, but not limited to, cilomilast or roflumilast, an inhibitor of the isoform PDE4D, or an inhibitor of PDE5.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with a gastroprotective histamine type 2 receptor antagonist. In other embodiments, the combinations described herein include combination of a compound of Formula (I) and Formula (II), or a pharmaceutically acceptable salt or solvate thereof, described herein, with an antagonist of the histamine type 4 receptor.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with an alpha-l/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with a glucocorticoid, such as flunisolide, triamcinolone acetonide, beclomethasone dipropionate, budesonide, fluticasone propionate, ciclesonide or mometasone furoate.

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with an immunoglobulin (Ig), gamma globulin, Ig preparation or an antagonist or antibody modulating Ig function such as anti-IgE (omalizumab).

In other embodiments, the combinations described herein include combination of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor. Non-limiting examples of chemotherapeutic agents used in such combinations are anthracyclines, alkylating agents (e.g., mitomycin C), alkyl sulfonates, aziridines, ethylenimines, methylmelamines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins. Other non-limiting examples of chemotherapeutic agents used in such combinations are busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycins, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, teniposide, tenuazonic acid, triaziquone, 2,2',2"-trichlorotriethylamine, urethane, vinblastine, vincristine, and vindesine.

In certain embodiments, the combination treatments provided herein include administration of a compound of Formula (I) or Formula (II), or a pharmaceutically acceptable salts, pharmaceutically acceptable solvates (e.g. hydrates), the N-oxide derivatives, protected derivatives, individual isomers and mixture of isomers thereof, or a pharmaceutical composition containing a compound of Formula (I) and Formula (II) in combination with one or more additional therapeutic agents, for the treatment of Pulmonary Arterial Hypertension (PAH). Such additional therapeutic agents include phosphodiesterase-5 inhibitors, prostanoids, endothelin receptor antagonists, calcium channel blockers, oxygen therapy, iloprost, sildenafil, tadalifil, digoxin, furosemide, spironolactone, warfarin, epoprostenol, treprostinil, bosentan and ambrisentan.

EXAMPLES

The following examples were offered to illustrate, but not to limit, the compounds of Formula (I) or Formula (II) of the present invention, and the preparation of such compounds.

Synthesis of intermediates

Synthesis of 3-(imidazo[1,2-a]pyridine-3-carboxamido)-4-methylbenzoic acid (4)

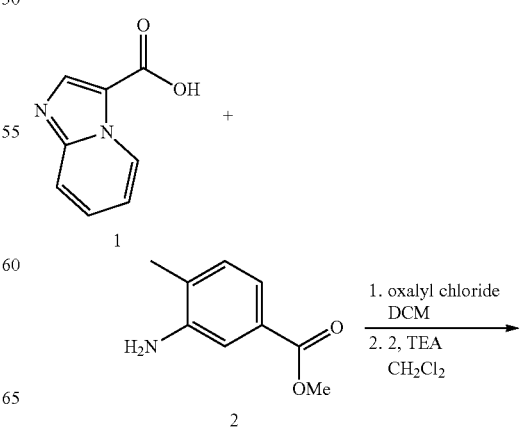

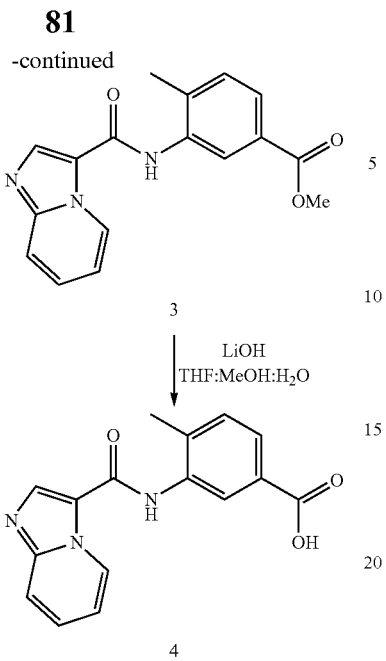

To a suspension of imidazo[1,2-a]pyridine-3-carboxylic acid (1) (4.09 g, 25.3 mmol) in dichloromethane (100 mL) and DMF (0.25 mL) at 0° C. was added oxalyl chloride (4.15 mL, 48.0 mmol) dropwise over 10 minutes. The reaction was slowly warmed to room temperature and stirred until complete conversion was detected by LCMS. The reaction was subsequently reduced to dryness and suspended in dichloromethane (100 mL) and was added a solution of methyl 3-amino-4-methylbenzoate (2) (4.6 g, 27.9 mmol) in dichloromethane (100 mL) and triethylamine (7.1 mL). Contents were stirred at room temperature for 4 hours and diluted with dichloromethane (100 mL). The reaction was washed with water, saturated NaHCO₃, brine, dried over magnesium sulfate, filtered and reduced to dryness. The crude solid was triturated with diethyl ether to remove excess aniline and dried to afford methyl 3-(imidazo[1,2-a]pyridine-3-carboxamido)-4-methylbenzoate (3) as a white solid. MS m/z 310.1 (M+1)⁺.

To a suspension of 3-(imidazo[1,2-a]pyridine-3-carboxamido)-4-methylbenzoate (3) (5.43 g, 17.6 mmol) in THF (225 ml) and MeOH (150 mL) was added LiOH 3 M (17.5 mL) and water (50 mL). The reaction was stirred at room temperature for 12 hours then reduced in volume on roto-vap to remove THF and MeOH. The mixture was diluted with water (75 mL) and neutralized with HCl (17.5 mL of a 3M solution). The resulting precipitate was filtered, washed with water and dried under vacuum to afford 3-(imidazo[1,2-a]pyridine-3-carboxamido)-4-methylbenzoic acid (4) as a white solid. ¹H NMR (400 MHz, d₆-DMSO) δ 10.0 (s, 1H), 9.45 (dt, J=6.8, 1.2 Hz, 1H), 8.58 (s, 1H), 7.98 (d, J=2.0 Hz, 1H), 7.79 (dt, J=9.2, 1.2 Hz, 1H), 7.76 (dd, J=8.0, 1.6 Hz, 1H), 7.52 (ddd, J=9.2, 9.2, 1.2 Hz, 1H), 7.43 (d, J=8.0 Hz, 1H), 7.17 (td, J=6.8, 1.2 Hz, 1H), 2.35 (s, 3H). MS m/z 296.1 (M+1)⁺.

Synthesis of 2-hydroxy-1-bhenylquanidine (5)

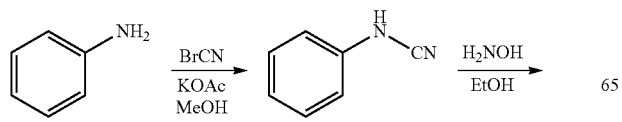

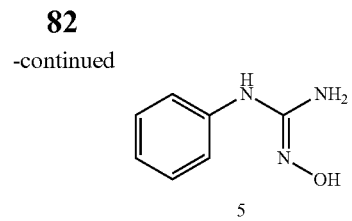

To a solution of BrCN (0.11 g, 1.1 mmo) in MeOH (10 mL) at 0° C. was added solid KOAc (0.32 g, 3.3 mmol) and a solution of aniline (0.1 mL, 1.1 mmol) in MeOH (1 mL). The reaction was stirred for 3 hours then partitioned with water (15 mL) and dichloromethane (25 mL). The organic layer was separated, washed with brine, dried over magnesium sulfate, filtered and reduced to dryness to afford N-phenylcyanamide, which was immediately used without purification.

N-phenylcyanamide was dissolved in EtOH (7 mL) and treated with H₂NOH (1.5 eq of a 50% aq solution). The mixture was stirred at room temperature for 12 hours then reduced to dryness to afford 2-hydroxy-1-phenylguanidine (5) as a clear yellow oil, which was used without purification.

Synthesis of N'-hydroxy-6-methylpicolinimidamide (6)

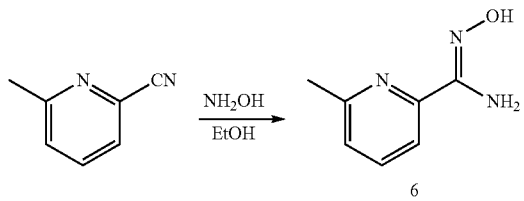

6-Methylpicolinonitrile (12 mg, 0.1 mmol) was dissolved in EtOH (0.5 mL) and treated with NH₂OH (1.5 eq of a 50% aq solution). The mixture was stirred at room temperature for 12 hours then reduced to dryness to afford N'-hydroxy-6-methylpicolinimidamide (6) as a clear yellow oil, which was used without purification.

Synthesis of N-(5-(N'-hydroxycarbamimidoyl)-2-methylphenyl)imidazo[1,2-a]pyridine-3-carboxamide (9)

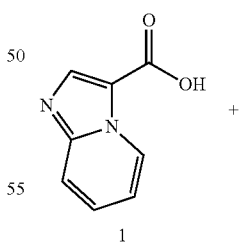
+
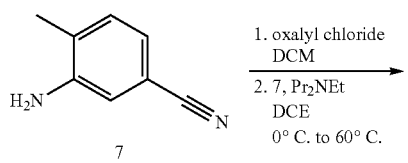

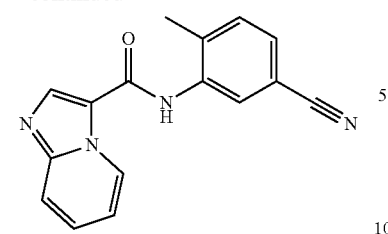

8

| NH₂OH,
| EtOH,
| 0° C. to 50° C.

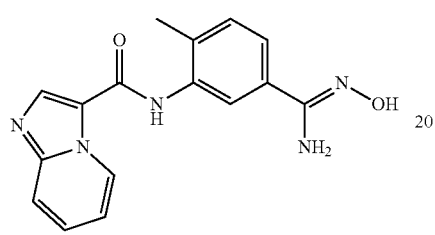

9

To a suspension of imidazo[1,2-a]pyridine-3-carboxylic acid (1) (16.6 g, 102 mmol) in dichloromethane (300 mL) and DMF (0.5 mL) at 0° C. was added oxalyl chloride (45 mL, 510 mmol) dropwise over 10 minutes. The reaction was slowly warmed to room temperature and stirred until complete conversion was detected by LCMS in MeOH. The reaction was subsequently reduced to dryness and suspended in dichloroethane (100 mL) and was added to a solution of 3-amino-4-methylbenzonitrile (7) (15 g, 113 mmol) in dichloroethane (200 mL) and Pr₂NEt (55 mL) at 0° C. After the addition, the cold bath was removed and contents were stirred at room temperature for 1 hour and then heated to 50° C. for another 2 hours. After the completion of the reaction, the mixture was cooled and a white precipitate formed. The mixture was filtered and the solid was washed with cold dichloromethane. About 10 g of the desired N-(5-cyano-2-methylphenyl)imidazo[1,2-a]pyridine-3-carboxamide (8) was obtained. The filtrate was washed with saturated NH₄Cl, saturated NaHCO₃, brine, dried over magnesium sulfate, filtered and reduced to dryness. The crude solid was triturated with diethyl ether to remove excess aniline and filtered to afford another crop of N-(5-cyano-2-methylphenyl)imidazo[1,2-a]pyridine-3-carboxamide (8) as a white solid. MS m/z 277.1 (M+1).

To a stirred and cooled (0° C.) suspension of N-(5-cyano-2-methylphenyl)imidazo[1,2-a]pyridine-3-carboxamide (8) (10 g, 36.2 mmol) in EtOH (225 ml) was added NH₂OH (6 mL, 50% in water solution). After the addition, the reaction was stirred at room temperature for 2 hours then heated at 50° C. for another 2 hours. After cooling to room temperature, the mixture was stored in the fridge overnight. The resulting precipitate was filtered, washed with cold EtOH and dried under vacuum to afford N-(5-(N'-hydroxycarbamimidoyl)-2-methylphenyl)imidazo[1,2-a]pyridine-3-carboxamide (9) as a white solid. ¹H NMR (400 MHz, d₆-DMSO) δ 9.40 (dt, J=6.8, 1.2 Hz, 1H), 8.15 (s, 1H), 7.88 (d, J=2.0 Hz, 1H), 7.79 (dt, J=9.2, 1.2 Hz, 1H), 7.76 (dd, J=8.0, 1.6 Hz, 1H), 7.52 (ddd, J=9.2, 9.2, 1.2 Hz, 1H), 7.43 (d, J=8.0 Hz, 1H), 7.17 (td, J=6.8, 1.2 Hz, 1H), 2.49 (s, 3H). MS m/z 310.1 (M+1)⁺.

Synthesis of
5,5-difluorotetrahydro-2H-pyran-2-carboxylic acid
(17)

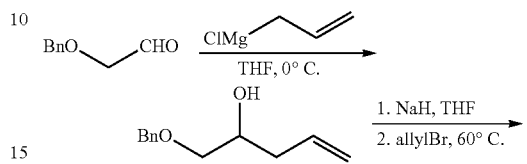

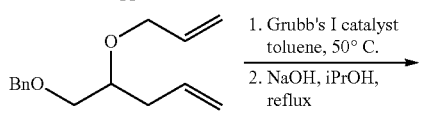

12

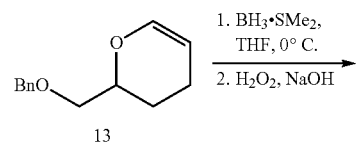

13

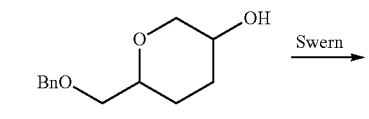

14

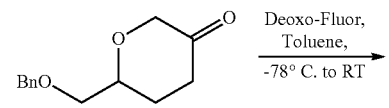

15

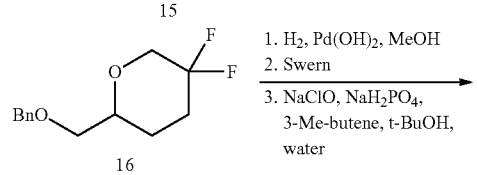

16

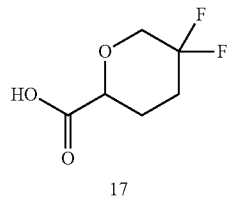

17

2-(Benzyloxy)acetaldehyde (5 g, 33.3 mmol) in dry THF (10 mL) was added dropwise to a stirred and cooled solution of allylmagnesium chloride (25 mL, 2 M in THF, 50 mmol) in THF (100 mL) at −78° C. After the addition, the solution was allowed to warm to 0° C. and quenched with saturated NH₄Cl solution. After standard aqueous work up, the residue was purified over silica using EtOAc and hexane to give 1-(benzyloxy)pent-4-en-2-ol (11).

NaH (4.8 g, 120 mmol) was added portion wise to a stirred solution of 1-(benzyloxy)pent-4-en-2-ol (11) (15.3 g, 79.6 mmol) in THF (100 mL) at 0° C. After addition, the mixture was warmed to room temperature and stirred for another hour before it was cooled to 0° C. Allyl bromide (9 mL, 103.5 mmol) was added to the reaction and the resulting mixture was warmed to room temperature and then heated to 50° C. overnight. After cooling to room temperature, the mixture was quenched with saturated NH$_4$Cl and worked up under standard conditions. The residue was purified over silica using Et$_2$O and hexane to give ((2-(allyloxy)pent-4-enyloxy)methyl)benzene (12).

Benzylidene-bis(tricyclohexylphosphine)dichlororuthenium, bis(tricyclohexylphosphine)benzylidine ruthenium (IV) chloride-Grubbs 1 generation catalyst (0.5 g, 0.54 mmol) was added in one portion to a stirred solution of ((2-(allyloxy)pent-4-enyloxy)methyl)benzene (12) (4 g, 17.2 mmol) in toluene (200 mL). The resulting mixture was heated at 50° C. under N$_2$ for 2 hours before isopropanol (18 mL) and NaOH (0.17 g) were added. The mixture was then heated at 120° C. overnight. The solvent was evaporated and the residue was purified over silica gel using Et$_2$O and hexane to give 2-(benzyloxymethyl)-3,4-dihydro-2H-pyran (13).

BH$_3$.SMe$_2$ (17 mL, 1 M in THF) was added slowly to a stirred solution of 2-(benzyloxymethyl)-3,4-dihydro-2H-pyran (2.87 g, 14.06 mmol) (13) in THF (100 mL) at −78° C. The resulting mixture was allowed to warm to room temperature overnight. The mixture was quenched by the slow addition of 1M NaOH (50 mL) at 0° C. followed by H$_2$O$_2$ (13 mL, 30% in water). The resulting mixture was stirred for 2 hours at room temperature. After aqueous work up the residue was purified on silica gel using EtOAc and hexane to give 6-(benzyloxymethyl)tetrahydro-2H-pyran-3-ol (14).

DMSO (1.15 mL, 16.2 mmol) was added to a stirred solution of oxalyl chloride (1 mL, 10.8 mmol) in dichloromethane (60 mL) at −78° C. After 10 minutes, a dichlotomethane solution of 6-(benzyloxymethyl)tetrahydro-2H-pyran-3-ol (14) (1.20 g, 5.40 mmol) was added. Stirring was continued for one hour then triethylamine (3.8 mL, 27 mmol) was added and slowly warmed to 0° C. The reaction was poured into saturated NH$_4$Cl solution and the organic phase was washed with brine and dried (NaSO$_4$). The residue was purified over silica gel using EtOAc and hexanes to give 6-(benzyloxymethyl)dihydro-2H-pyran-3(4H)-one (15).

Deoxo-Fluor (4.6 mL, 25 mmol) was added dropwise to a −78° C. solution of 6-(benzyloxymethyl)dihydro-2H-pyran-3(4H)-one (15) (1.1 g, 5.06 mmol) in toluene (20 mL) in a plastic container. The mixture was warmed to room temperature overnight and poured into saturated NaHCO$_3$ solution and extracted with Et$_2$O. After washing with brine and drying over MgSO$_4$, the residue was purified over silica gel using EtOAc and hexane to give 2-(benzyloxymethyl)-5,5-difluorotetrahydro-2H-pyran (16).

H$_2$ (balloon) was introduced to a stirred mixture of Pd(OH)$_2$/C (0.2 g) and 2-(benzyloxymethyl)-5,5-difluorotetrahydro-2H-pyran (16) (1.05 g, 4.3 mmol) in MeOH (20 mL). After 2 hours, the mixture was filtered through a pad of Celite and the solvent was evaporated to give the crude alcohol product. The oil was azeotroped with toluene to remove residual water and the product was used directly in the following step.

DMSO (0.3 mL, 4.11 mmol) was added to a stirred solution of oxalyl chloride (0.28 mL, 3.15 mmol) in dichlorometane (20 mL) at −78° C. After 10 minutes, a dichlorometane solution of the alcohol from previous step (0.33 g, 1.37 mmol) was added. The stirring continued for one hour before triethylamine (1.0 mL, 6.85 mmol) was added and after 10 minutes the reaction was warmed to 0° C. The reaction was poured into saturated NH$_4$Cl solution and the organic phase was washed with brine and dried (NaSO$_4$). The crude aldehyde was filtration through a pad of silica gel and used directly in the following step.

NaClO$_2$ (0.74 g, 8.22 mmol) was added in one portion to a stirred mixture of the aldehyde from previous step (1.37 mmol), 3-methyl-2-butene (2 mL) and NaH$_2$PO$_4$ (2.81 g, 20.5 mmol) in water (10 mL) and t-BuOH (10 mL) at 0° C. After stirring at room temperature for 2 hours, the mixture was partitioned with EtOAc and brine. The organic phase was dried (MgSO$_4$) and filtered. The residue was purified over silica gel using EtOAc and hexane to give 5,5-difluorotetrahydro-2H-pyran-2-carboxylic acid (17) as a clear oil. MS m/z 167.1 (M+1)$^+$.

Synthesis of N-(5-(5-(azetidin-3-yl)-1,2,4-oxadiazol-3-yl)-2-methylphenyl)imidazo[1,2-a]pyridine-3-carboxamide (21)

F39

4N HCl
Dioxane
CH$_3$CN

21

To a vial was added tert-butyl 3-(3-(3-(imidazo[1,2-a]pyridine-3-carboxamido)-4-methylphenyl)-1,2,4-oxadiazol-5-yl)azetidine-1-carboxylate (F39) (145 mg, 0.3 mmol) and 4N HCl in 1,4-dioxane (2 mL) and CH$_3$CN (1 mL). The reaction was stirred for 45 minutes. The solvent was concentrated and placed under high vacuum. The solid was taken in water/acetonitrile and the pH was adjusted to neutral with an aqueous solution of ammonium carbonate and lyophilized to afford N-(5-(5-(azetidin-3-yl)-1,2,4-oxadiazol-3-yl)-2-methylphenyl)imidazo[1,2-a]pyridine-3-carboxamide (21) which was used directly in the next step. $^1$H NMR (400 MHz, d$_6$-DMSO) δ 10.85 (s, 1 H), 9.66-9.64 (m, 1 H), 9.42 (bs, 1 H), 9.28 (s, 1 H), 8.10-8.08 (m, 2 H), 8.02-7.98 (m, 1 H), 7.89-

7.87 (m, 1H), 7.59-7.53 (m, 2 H), 4.53-4.47 (m, 1 H), 4.36-4.29 (m, 4 H), 2.40 (s, 3 H). MS m/z 375.1 (M+1)+.

Synthesis of 7-(trifluoromethyl)imidazo[1,2-a]pyridine-3-carboxylic acid (24)

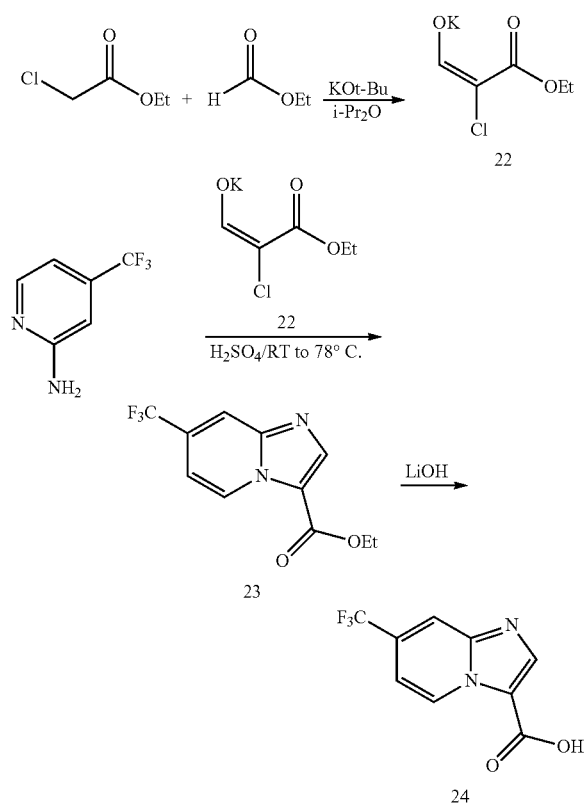

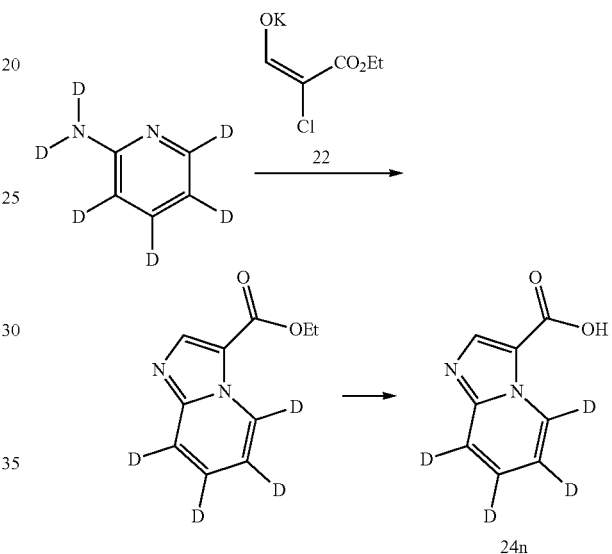

Ethyl 2-chloroacetate (20 mL, 187 mmol) and ethyl formate (15.1 mL, 187 mmol) were added simultaneously to a stirred and cooled suspension of potassium tert-butoxide (21.4 g, 188 mmol) in dry diisopropylether (300 mL). After the addition, the reaction was warmed to room temperature and stirred overnight. The yellow suspension was filtered and the solid potassium 2-chloro-3-ethoxy-3-oxoprop-1-en-1-olate (22) was vacuum dried and used directly in the following step.

To a stirring suspension of 4-(trifluoromethyl)pyridin-2-amine (128 mg, 0.791 mmol) and potassium 2-chloro-3-ethoxy-3-oxoprop-1-en-1-olate (22) (500 mg, 2.64 mmol) in EtOH (5 mL) at room temperature was added sulfuric acid (70 µL, 1.32 mmol) dropwise. The reaction mixture was stirred at room temperature overnight then heated at 78° C. for 3 hours. The reaction was cooled to room temperature and the solvent was concentrated. The residue was taken in water and the pH was adjusted between 6-8 with saturated sodium bicarbonate. The crude product was extracted with ethyl acetate. The organic was washed with brine and dried over anhydrous sodium sulfate. The crude product 7-(trifluoromethyl)imidazo[1,2-a]pyridine-3-carboxylate (23) was purified by silica chromatography. MS m/z 259.3 (M+1)+.

To a stirring solution of ethyl 7-(trifluoromethyl)imidazo[1,2-a]pyridine-3-carboxylate (23) (100 mg, 0.387 mmol) in THF:MeOH (4:1, 1.5 mL) was added 2N LiOH (0.25 mL). The reaction was heated at 60° C. for 1 hour. Then, cooled to room temperature and the pH was adjusted between 4-5 with 1N HCl. The solvent was partially concentrated and the resulting aqueous layer was lyophilized to give 7-(trifluoromethyl)imidazo[1,2-a]pyridine-3-carboxylic acid (24). $^1$H NMR (400 MHz, d$_6$-DMSO) δ 9.44 (d, J=7.2 Hz, 1 H), 8.40 (s, 1 H), 8.31-8.30 (m, 1 H), 7.48 (dd, J=2.0, 7.6 Hz, 1 H). MS m/z 231.2 (M+1)+.

The following compounds were prepared according to the protocol described for 7-(trifluoromethyl)imidazo[1,2-a]pyridine-3-carboxylic acid (24).

Synthesis of 5,6,7,8-deutero-imidazo[1,2-a]pyridine-3-carboxylic acid (24n)

2-aminopyridine (D6) (10 g, 99.91 mmol) and potassium 2-chloro-3-ethoxy-3-oxoprop-1-en-1-olate (22) (46.93 g, 250 mmol) were suspended in dry EtOH (300 mL) and H$_2$SO$_4$ (6.65 mL, 128.8 mmol) was added dropwise at ambient temperature. After the addition, the resulting mixture was heated at reflux for 3 hours before pyridine (20 mL) was added and reflux continued overnight. The reaction was then cooled and solvent evaporated. The residue was partitioned between saturated NaHCO$_3$ solution and EtOAc. The aqueous phase was further extracted with EtOAc and the combined organic phase was washed with brine and dried (MgSO$_4$). After filtration and concentration, the residue was purified over silica using EtOAc/hexane to give ethyl 5,6,7,8-deutero-imidazo[1,2-a]pyridine-3-carboxylate. $^1$H NMR (400 MHz, CDCl$_3$) δ 8.30 (s, 1 H), 4.42 (q, J=8.4 Hz, 2 H), 1.34 (t, J=8.4 Hz, 3 H). MS m/z 195.1 (M+1)+.

LiOH (15.8 g, 377.1 mmol) was added to a stirred solution of ethyl 5,6,7,8-deutero-imidazo[1,2-a]pyridine-3-carboxylate (18.7 g, 95.3 mmol) in THF (100 mL), MeOH (100 mL) and H$_2$O (100 mL). After 3 hours, the solvent was evaporated and the solid was resuspended in water. NaHSO$_4$ (50 g) was added to neutralize the solution and the precipitate was filtered. The solid 5,6,7,8-deutero-imidazo[1,2-a]pyridine-3-carboxylic acid (24 n) was dried in vacuum oven and used without further purification. $^1$H NMR (400 MHz, d$_6$-DMSO) δ 8.22 (s, 1 H). MS m/z 167.0 (M+1)+.

| Intermediate number | Structure | Physical Data |
|---|---|---|
| 24a | 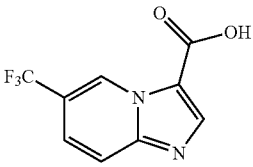 [SMILES: O=C(O)c1cnc2ccc(C(F)(F)F)cn12] | $^1$H NMR (400 MHz, d$_6$-DMSO) δ 9.64-9.62 (m, 1 H), 8.39 (s, 1 H), 8.01 (d, J = 9.2 Hz, 1 H), 7.81 (dd, J = 2.0, 9.2 Hz, 1 H). MS m/z 231.2 (M + 1)$^+$. |
| 24b | 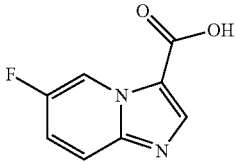 [SMILES: O=C(O)c1cnc2ccc(F)cn12] | MS m/z 181.2 (M + 1)$^+$. |
| 24c | 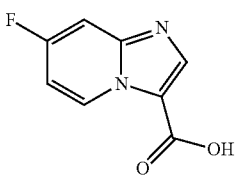 [SMILES: O=C(O)c1cnc2cc(F)ccn12] | MS m/z 181.2 (M + 1)$^+$. |
| 24d | 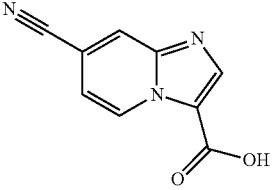 [SMILES: N#Cc1ccn2c(C(=O)O)cnc2c1] | MS m/z 188.1 (M + 1)$^+$. |
| 24e | 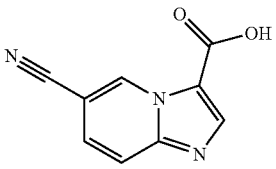 [SMILES: N#Cc1ccc2ncc(C(=O)O)n2c1] | MS m/z 188.1 (M + 1)$^+$. |
| 24f | 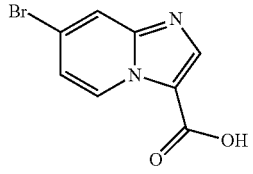 | MS m/z 241.0 (M + 1)$^+$. |
| 24g | 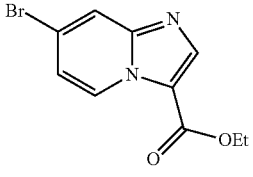 [SMILES: CCOC(=O)c1cnc2cc(Br)ccn12] | MS m/z 270.0 (M + 1)$^+$. |
| 24h | 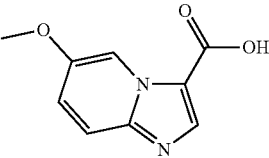 | $^1$H NMR (400 MHz, d$_6$-DMSO) δ 8.94 (d, J = 2.0 Hz, 1H), 8.13 (s, 1 H), 7.70 (d, J = 9.6 Hz, 1 H), 7.31 (dd, J = 2.8, 9.8 Hz, 1 H), 3.85 (s, 3H). MS m/z 193.1 (M + 1)$^+$. |

| Intermediate number | Structure | Physical Data |
|---|---|---|
| 24i | 7-methyl-imidazo[1,2-a]pyridine-3-carboxylic acid | MS m/z 177.6 (M + 1)+. |
| 24j | 6-methyl-imidazo[1,2-a]pyridine-3-carboxylic acid | MS m/z 177.6 (M + 1)+. |
| 24k | 8-fluoro-imidazo[1,2-a]pyridine-3-carboxylic acid | MS m/z 209.06 (M + 1)+. |
| 24l | 6-(2-morpholinoethyl)-imidazo[1,2-a]pyridine-3-carboxylic acid | 1H NMR (400 MHz, d6-DMSO) δ 9.21 (s, 1 H), 8.22 (s, 1 H), 7.76 (d, J = 9.2 Hz, 1 H), 7.50 (dd, J = 1.6, 9.2 Hz, 1 H), 3.72-3.69 (m, 4 H), 3.40-3.28 (m, 2 H), 2.99-2.92 (m, 4 H), 2.88-2.82 (m, 2 H). MS m/z 276.13 (M + 1)+. |
| 24m | imidazo[1,2-a]pyrazine-3-carboxylic acid | 1H NMR (400 MHz, d6-DMSO) δ 9.29 (d, J = 1.6 Hz, 1 H), 9.15 (dd, J = 1.6, 4.4 Hz, 1 H), 8.4 (s, 1 H), 8.20 (d, J = 4.4 Hz, 1 H). MS m/z 164.1 (M + 1)+. |
| 24n | deuterated imidazo[1,2-a]pyridine-3-carboxylic acid | MS m/z 167.0 (M + 1)+. |
| 24o | 6-morpholino-imidazo[1,2-a]pyridine-3-carboxylic acid | 1H NMR (400 MHz, d6-DMSO) δ 8.79 (s, 1 H), 8.49 (s, 1 H), 7.84 (m, 2 H), 3.80 (m, 4 H), 3.16 (m, 4 H). MS m/z 248.1 (M + 1)+. |
| 24p | 6-(1H-imidazol-1-yl)-imidazo[1,2-a]pyridine-3-carboxylic acid | 1H NMR (400 MHz, d6-DMSO) δ 9.69 (dd, J = 0.8, 2.0 Hz, 1 H), 9.54 (s, 1 H), 8.42 (s, 1 H), 8.23 (s, 1 H), 8.09 (dd, J = 0.8, 9.6 Hz, 1 H), 7.95 (dd, J = 2.0, 9.6 Hz, 1 H), 7.87 (s, 1 H). MS m/z 248.1 (M + 1)+. |

-continued
| Intermediate number | Structure | Physical Data |
|---|---|---|
| 24q | 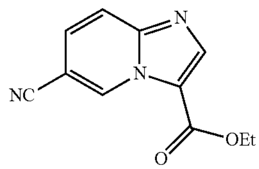 [SMILES: CCOC(=O)c1cnc2ccc(C#N)cn12] | MS m/z 216.0 (M + 1)+. |
| 24r | 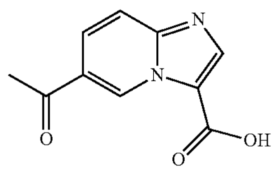 | MS m/z 205.0 (M + 1)+. |
| 24s | 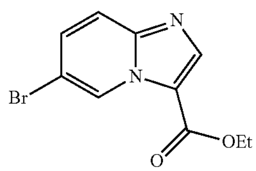 [SMILES: CCOC(=O)c1cnc2ccc(Br)cn12] | MS m/z 270.0 (M + 1)+. |
| 24t | 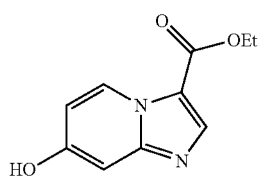 [SMILES: CCOC(=O)c1cnc2cc(O)ccn12] | MS m/z 207.1 (M + 1)+. |
| 24u | 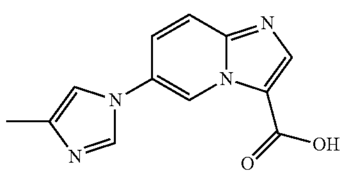 [SMILES: Cc1cn(-c2ccc3ncc(C(=O)O)n3c2)cn1] | MS m/z 243.1 (M + 1)+. |
Synthesis of 6-(3-cyanopropyl)imidazo[1,2-a]pyridine-3-carboxylic acid (25)
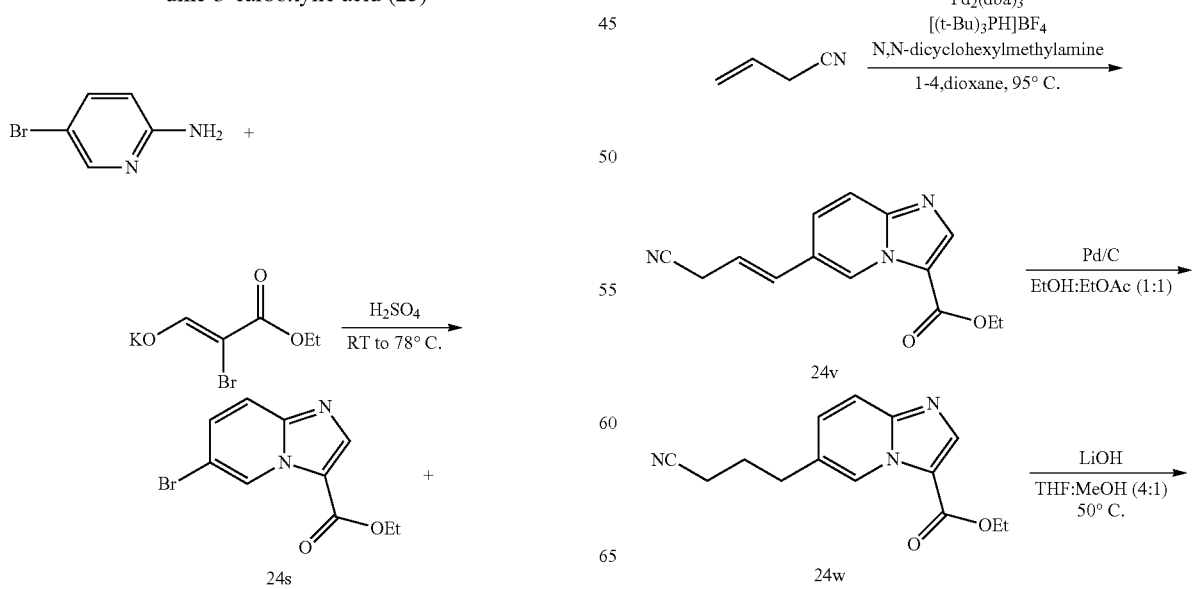

-continued

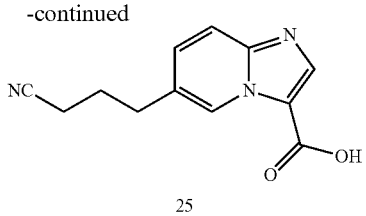

25

To a stirring suspension of 5-bromopyridin-2-amine (1.2 g, 7.05 mmol) and ethyl 2-chloro-3-hydroxyacrylate potassium salt (6.6 g, 28.19 mmol) (prepared in a similar manner as 22) in EtOH (100 mL) at room temperature was added sulfuric acid (751 µL, 14.10 mmol) dropwise. The reaction mixture was heated at 78° C. overnight. The reaction was cooled to room temperature and the solvent was concentrated. The residue was taken in water and the pH was adjusted between 6-8 with saturated sodium bicarbonate. The crude product was extracted with ethyl acetate. The organic was washed with brine and dried over anhydrous sodium sulfate. The crude product was purified by silica chromatography to yield ethyl 6-bromoimidazo[1,2-a]pyridine-3-carboxylate (24s). MS m/z 270.2 (M+1)+.

A stirring mixture of ethyl 6-bromoimidazo[1,2-a]pyridine-3-carboxylate (24s) (500 mg, 1.86 mmol), allyl cyanide (224 uL, 2.79 mmol), tris(dibenzylideneacetone)dipalladium (0) (26 mg, 0.028 mmol), [(t-Bu)$_3$PH]BF$_4$ (16 mg, 0.056 mmol), and N,N-dicyclohexylmethylamine (433 µL, 2.04 mmol) in anhydrous 1,4-dioxane (6 mL) was heated at 95° C. overnight. The reaction was cooled to room temperature and filtered. The solvent was concentrated. The crude product was purified by silica chromatography to give ethyl 6-(3-cyanoprop-1-enyl)imidazo[1,2-a]pyridine-3-carboxylate (24v). MS m/z 256.4 (M+1)+.

To a stirring solution of ethyl 6-(3-cyanoprop-1-enyl)imidazo[1,2-a]pyridine-3-carboxylate (24v) (400 mg, 1.57 mmol) in EtOH:EtOAc (1:1, 10 mL) was added catalytic Pd/C (10 wt %, wet basis). The reaction was hydrogenated by balloon overnight then filtered through celite. The crude product ethyl 6-(3-cyanopropyl)imidazo[1,2-a]pyridine-3-carboxylate (24w) was used in the next step without further purification. MS m/z 258.4 (M+1)+.

To a stirring solution of ethyl 6-(3-cyanopropyl)imidazo[1,2-a]pyridine-3-carboxylate (24w) (375 mg, 1.46 mmol) in THF:MeOH (4:1, 5 mL) was added 2N LiOH (500 µL). The reaction was heated at 50° C. for 45 minutes then cooled to room temperature and the pH was adjusted between 3-4 with 1N HCl. The solvent was partially concentrated and the remaining aqueous was lyophilized to yield 6-(3-cyanopropyl)imidazo[1,2-a]pyridine-3-carboxylic acid (25). $^1$H NMR (400 MHz, d$_6$-DMSO) δ 9.21-9.19 (m, 1 H), 8.45 (s, 1 H), 7.85 (dd, J=0.8, 9.2 Hz, 1 H), 7.70 (dd, J=1.6, 9.2 Hz, 1 H), 2.82 (t, J=7.2 Hz, 2 H), 2.55 (t, J=7.2 Hz, 2 H), 1.97-1.90 (m, 2 H). MS m/z 230.3 (M+1)+.

Synthesis of N-(5-(5-(aminomethyl)-1,2,4-oxadiazol-3-yl)-2-methylphenyl)imidazo[1,2-a]pyridine-3-carboxamide (26)

F54

26

To a stirring suspension of tert-butyl (3-(3-(imidazo[1,2-a]pyridine-3-carboxamido)-4-methylphenyl)-1,2,4-oxadiazol-5-yl)methyl(methyl)carbamate (F54) (90 mg, 0.195 mmol) in acetonitrile (1 mL) was added 4N HCl in dioxane (1 mL) and water (0.5 mL). The reaction mixture was stirred at room temperature for 45 minutes. Then, the solvent was concentrated and the crude product was dried under high vacuum. The crude product N-(5-(5-(aminomethyl)-1,2,4-oxadiazol-3-yl)-2-methylphenyl)imidazo[1,2-a]pyridine-3-carboxamide (26) was used in the next step without further purification. $^1$H NMR (400 MHz, d$_6$-DMSO) δ 10.04 (s, 1 H), 9.46-9.44 (m, 1 H), 8.74 (s, 2 H), 8.63 (s, 1 H), 8.15 (d, J=2.0 Hz, 1 H), 7.86-7.80 (m, 2 H), 7.59-7.54 (m, 1 H), 7.55 (d, J=8.4 Hz, 1 H), 7.23-7.20 (m, 1 H), 4.62 (s, 2 H), 2.39 (s, 3 H). MS m/z 349.4 (M+1)+.

Synthesis of methyl 3-(3-(3-amino-4-methylphenyl)-1,2,4-oxadiazol-5-yl)azetidine-1-carboxylate (31)

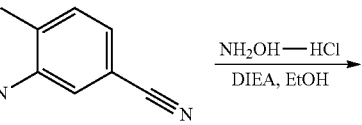

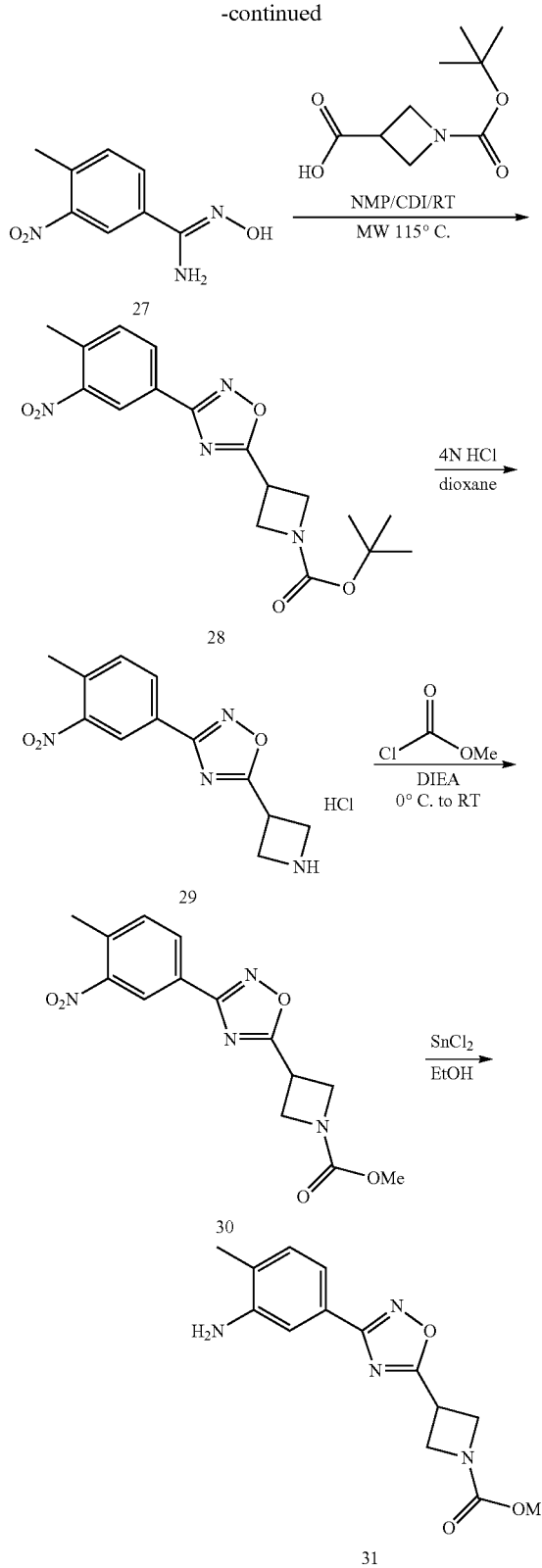

water and the solid was collected by vacuum filtration. The crude product (27) was used in the next step without further purification. MS m/z 196.3 (M+1)⁺.

To a stirring solution of boc-azetidine-3-carboxylic acid (1.9 g, 9.22 mmol) in anhydrous NMP (12 mL) was added 1,1'-carbonyldiimidazole (CDI) (1.5 g, 9.22 mmol). The reaction was stirred for 5 minutes. Then, N'-hydroxy-4-methyl-3-nitrobenzimidamide (27) (1.2 g, 6.1 mmol) was added and the reaction was stirred for 25 minutes. Next, the reaction was heated in the microwave at 115° C. for 12 minutes. The crude product was extracted with ethyl acetate. The organic was washed with water/brine mixture followed by brine and dried over anhydrous sodium sulfate. The solvent was concentrated and the crude product tert-butyl 3-(3-(4-methyl-3-nitrophenyl)-1,2,4-oxadiazol-5-yl)azetidine-1-carboxylate (28) was taken in dichloromethane and minimal tetrahydrofuran and purified by silica chromatography. MS m/z 361.4 (M+1)⁺.

To stirring suspension of tert-butyl 3-(3-(4-methyl-3-nitrophenyl)-1,2,4-oxadiazol-5-yl)azetidine-1-carboxylate (28) (1 g, 2.78 mmol) in acetonitrile (2 mL) was added 4 N HCl in dioxane (5 mL). The reaction was stirred at room temperature for 1 hour. The solvent was concentrated and the crude product was dried under high vacuum to yield 5-(azetidin-3-yl)-3-(4-methyl-3-nitrophenyl)-1,2,4-oxadiazole hydrochloride (29). MS m/z 261.4 (M+1)⁺.

To a stirring suspension of 5-(azetidin-3-yl)-3-(4-methyl-3-nitrophenyl)-1,2,4-oxadiazole hydrochloride (29) (825 mg, 2.78 mmol) in anhydrous dichloromethane (20 mL) at 0° C. was added N,N-diisopropylethylamine (1.2 mL, 6.95 mmol) and methyl chloroformate (215 μL, 2.78 mmol) dropwise. The reaction was stirred to room temperature for 25 minutes. The crude product was purified by silica chromatography to yield 3-(3-(4-methyl-3-nitrophenyl)-1,2,4-oxadiazol-5-yl) azetidine-1-carboxylate (30). MS m/z 425.39 (M+1)⁺.

To a stirring suspension of methyl 3-(3-(4-methyl-3-nitrophenyl)-1,2,4-oxadiazol-5-yl)azetidine-1-carboxylate (30) (795 mg, 2.50 mmol) in EtOH (20 mL) was added stannous chloride dihydrate (2.3 g, 9.99 mmol). The reaction mixture was heated at 78° C. for 3 hours. Then, the reaction was cooled to room temperature and the solvent was partially concentrated. The pH was adjusted to slightly basic pH with a saturated solution of sodium bicarbonate. The resulting white suspension was filtered and washed with water and ethyl acetate. The aqueous was extracted with ethyl acetate and washed with water, brine and dried over anhydrous sodium sulfate. The solvent was concentrated to give methyl 3-(3-(3-amino-4-methylphenyl)-1,2,4-oxadiazol-5-yl)azetidine-1-carboxylate (31). ¹H NMR (400 MHz, d₆-DMSO) δ 7.32 (d, J=1.6 Hz, 1 H), 7.12 (dd, J=1.6, 7.6 Hz, 1 H), 7.30 (d, J=7.6 Hz, 1 H), 5.19 (s, 2 H), 4.38-4.31 (m, 2 H), 4.27-4.20 (m, 1 H), 4.19-4.16 (m, 2 H), 3.60 (s, 3 H), 2.10 (s, 3 H). MS m/z 289.12 (M+1)⁺.

Synthesis of N-(5-(5-(chloromethyl)-1,2,4-oxadiazol-3-yl)-2-methylphenyl)imidazo[1,2-a]pyridine-3-carboxamide (38)

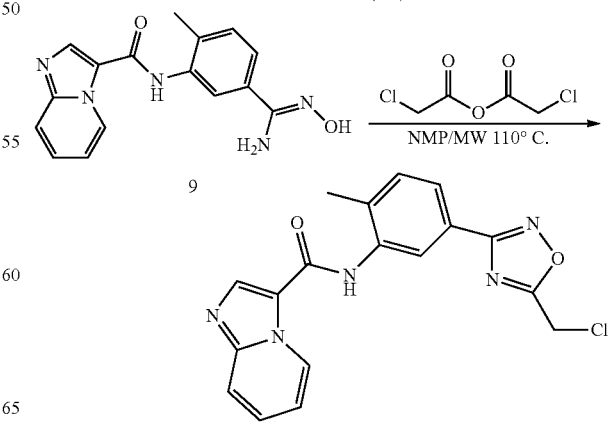

A stirring mixture of 4-methyl-3-nitrobenzonitrile (2 g, 12.33 mmol), hydroxylamine hydrogen chloride (1 g, 14.80 mmol) and N,N-diisopropylethylamine (3.2 mL, 18.50 mmol) in EtOH (20 mL) was heated at 78° C. for 3 hours. Then, the solvent was concentrated and the crude product was dried under high vacuum. The crude product was taken in A mixture of N-(5-(N'-hydroxycarbamimidoyl)-2-methylphenyl)imidazo[1,2-a]pyridine-3-carboxamide (9) (500 mg, 1.62 mmol) and 2-chloroacetic anhydride (553 mg, 3.23 mmol) in anhydrous NMP (10 mL) was heated in the microwave at 110° C. for 12 minutes. The crude was diluted with water and extracted with ethyl acetate. The organic was washed with a water/brine mixture and dried over anhydrous sodium sulfate. The solvent was concentrated and the crude product was purified by silica chromatography to yield N-(5-(5-(chloromethyl)-1,2,4-oxadiazol-3-yl)-2-methylphenyl)imidazo[1,2-a]pyridine-3-carboxamide (38). MS m/z 378.9 (M+1)$^+$.

Synthesis of (Z)-6-fluoro-N-(5-(N'-hydroxycarbamimidoyl)-2-methylphenyl)imidazo[1,2-a]pyridine-3-carboxamide (40)

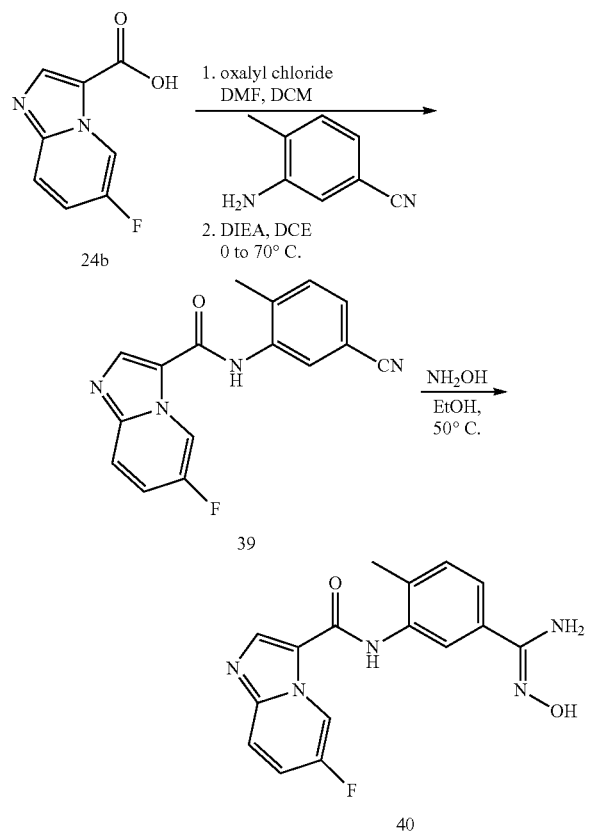

Oxalyl chloride (10 mL, 110 mmol) was added dropwise to a stirred suspension of 6-fluoroimidazo[1,2-a]pyridine-3-carboxylic acid (24b) (2 g, 11 mmol) and catalytic amounts of DMF in dichloromethane (20 mL). After 5 hours, the solvent was evaporated and the solid was suspended in dry DCE (20 mL) and added to a stirred solution of 3-amino-4-methylbenzonitrile (1.45 g, 11 mmol) and DIEA (6 mmol) in DCE (10 mL) at 0° C. After the addition, the reaction was heated at 60° C. for 5 hours. The mixture was subjected to standard aqueous work and silica purification to give N-(5-cyano-2-methylphenyl)-6-fluoroimidazo[1,2-a]pyridine-3-carboxamide (39) as a solid. $^1$H NMR (400 MHz, d$_6$-DMSO) δ 10.14 (s, 1 H), 9.45 (dd, J=5.2, 2.0 Hz, 1 H), 8.62 (s, 1 H), 7.90-7.87 (m, 2 H), 7.68-7.63 (m, 1 H), 7.53 (d, J=8.0 Hz, 1 H), 2.37 (s, 3 H). MS m/z 295.1 (M+1)$^+$.

NH$_2$OH (5 mL, 16.1 mmol) was added in one portion to a stirred suspension of N-(5-cyano-2-methylphenyl)-6-fluoroimidazo[1,2-a]pyridine-3-carboxamide (39) (0.95 g, 3.23 mmol). The resulting suspension was heated at 60° C. overnight and then cooled to 0° C. The product, (Z)-6-fluoro-N-(5-(N'-hydroxycarbamimidoyl)-2-methylphenyl)imidazo[1,2-a]pyridine-3-carboxamide (40) was collected by filtration. MS m/z 328.1 (M+1)$^+$.

Synthesis of methyl 3-(3-(3-(7-bromoimidazo[1,2-a]pyridine-3-carboxamido)-4-methylphenyl)-1,2,4-oxadiazol-5-yl)azetidine-1-carboxylate (42)

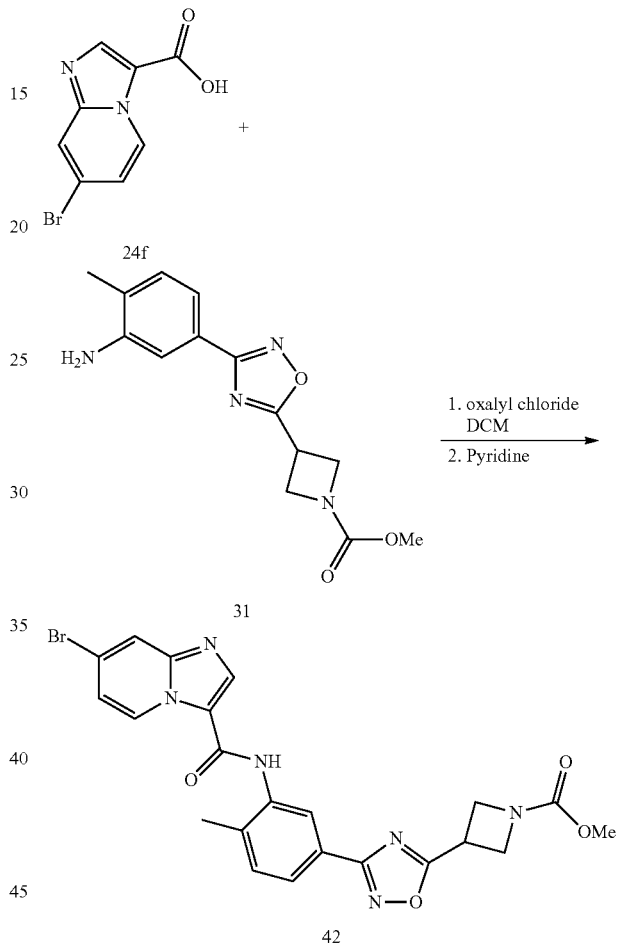

To a stirring suspension of 7-bromoimidazo[1,2-a]pyridine-3-carboxylic acid (24f) (400 mg, 1.67 mmol), in anhydrous dichloromethane (2 mL) at 0° C. under Argon was added dropwise oxalyl chloride (325 μL, 3.72 mmol). Then, a drop of anhydrous DMF was added and the reaction mixture was stirred at room temperature for 1.5 hour. The solvent was concentrated and the crude solid was added portion-wise to a stirring solution of methyl 3-(3-(3-amino-4-methylphenyl)-1,2,4-oxadiazol-5-yl)azetidine-1-carboxylate (31) (429 mg, 1.49 mmol) in anhydrous pyridine (1 mL) at 0° C. The reaction was stirred to room temperature under Argon for 30 minutes. Then, the reaction was quenched with water. The solvent was concentrated and the crude product was purified by silica chromatography to yield methyl 3-(3-(3-(7-bromoimidazo[1,2-a]pyridine-3-carboxamido)-4-methylphenyl)-1,2,4-oxadiazol-5-yl)azetidine-1-carboxylate (42). MS m/z 511.1 (M+1)$^+$.

The following compounds were prepared according to the protocol described for methyl 3-(3-(3-(7-bromoimidazo[1,2-a]pyridine-3-carboxamido)-4-methylphenyl)-1,2,4-oxadiazol-5-yl)azetidine-1-carboxylate (42).

| Intermediate number | Structure | Physical Data |
|---|---|---|
| 42g | 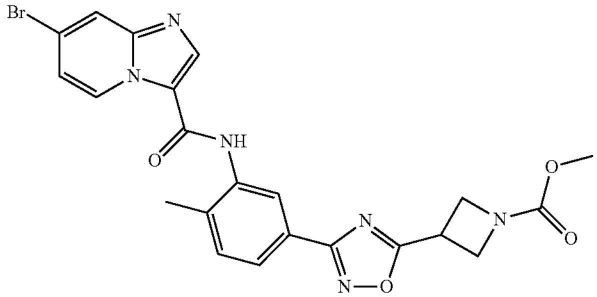 [SMILES: COC(=O)N1CC(c2nc(-c3ccc(C)c(NC(=O)c4cnc5cc(Br)ccn45)c3)no2)C1] | $^1$H NMR (400 MHz, d$_6$-DMSO) δ 10.12 (s, 1H), 9.38 (dd, J = 0.8, 7.2 Hz, 1H), 8.59 (s, 1H), 8.14 (dd, J = 0.8, 2.4 Hz, 1H), 8.09 (d, J = 1.6 Hz, 1H), 7.85 (dd, J = 2.0, 8.0 Hz, 1H), 7.51 (d, J = 8.0 Hz, 1H), 7.35 (dd, J = 2.0, 7.6 Hz, 1H), 4.16-4.42 (m, 5H), 3.60 (s, 3H), 2.37 (s, 3H). MS m/z 511.0, 513.0 (M + 1)$^+$. |
| 42j | 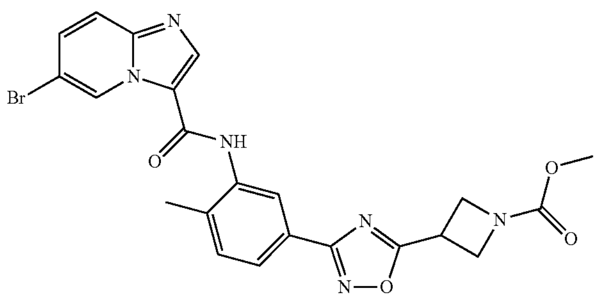 [SMILES: COC(=O)N1CC(c2nc(-c3ccc(C)c(NC(=O)c4cnc5ccc(Br)cn45)c3)no2)C1] | MS m/z 511.0, 513.0 (M + 1)$^+$. |

Synthesis of (3-(3-(imidazo[1,2-a]pyridine-3-carboxamido)-4-methylphenyl)-1,2,4-oxadiazol-5-yl)methyl methanesulfonate (44)

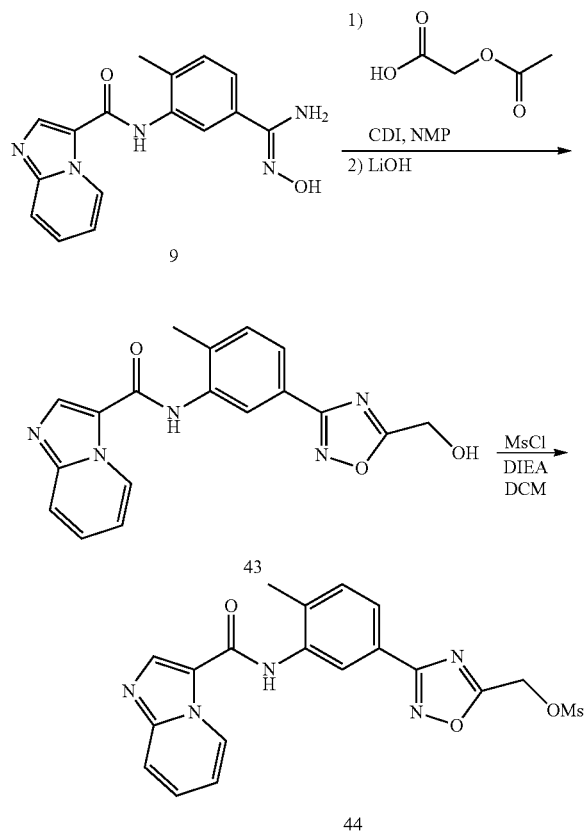

Carbonyl diimidazole (CDI) (324 mg, 2.0 mmol) was added to a stirred solution of 2-acetoxyacetic acid (236 mg, 2.0 mmol) in NMP. After 20 minutes, N-(5-(N'-hydroxycarbamimidoyl)-2-methylphenyl)imidazo[1,2-a]pyridine-3-carboxamide (9) (310 mg, 1.0 mmol) was added in one portion and the resulting solution was stirred for 1 hour before it was heated at 125° C. for 15 minutes in a microwave reactor. The reaction solution was subjected to standard aqueous work up to afford a residue which was hydrolyzed by lithium hydroxide monohydrate (252 mg, 6.0 mmol) in THF/MeOH/H$_2$O (3:2:1). After removal of all solvents 2M NaHCO$_3$ (10 mL) was added. The precipitate was filtered and dried in air to afford N-(5-(5-(hydroxymethyl)-1,2,4-oxadiazol-3-yl)-2-methylphenyl)imidazo[1,2-a]pyridine-3-carboxamide (43). $^1$H NMR (400 MHz, d$_6$-DMSO) δ 10.02 (s, 1 H), 9.46 (d, J=6.8 Hz, 1 H), 8.59 (s, 1 H), 8.11 (s, 1 H), 7.82 (m, 2 H), 7.53 (m, 2 H), 7.18 (m, 1 H), 6.08 (m, 1 H), 4.80 (d, J=6.0 Hz, 2 H), 2.37 (s, 3 H). MS m/z 350.1 (M+1)$^+$.

To a solution of N-(5-(5-(hydroxymethyl)-1,2,4-oxadiazol-3-yl)-2-methylphenyl)imidazo[1,2-a]pyridine-3-carboxamide (43) (210 mg, 0.6 mmol) and DIEA (0.32 mL, 1.8 mmol) in DCM (5 mL) was added MsCl (138 mg, 1.2 mmol). The mixture was stirred at room temperature for 10 minutes then subjected to standard aqueous work up. The crude product was purified by silica chromatography to yield (3-(3-(imidazo[1,2-a]pyridine-3-carboxamido)-4-methylphenyl)-1,2,4-oxadiazol-5-ylmethyl methanesulfonate (44) (180 mg, 70% yield). MS m/z 428.1 (M+1)$^+$.

The following compounds were prepared according to the protocol described for (3-(3-(imidazo[1,2-a]pyridine-3-carboxamido)-4-methylphenyl)-1,2,4-oxadiazol-5-ylmethyl methanesulfonate (44).

| Intermediate number | Structure | Physical Data |
|---|---|---|
| 44a | 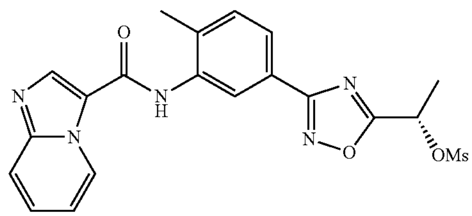 [SMILES: Cc1ccc(-c2noc([C@H](C)OS(C)(=O)=O)n2)cc1NC(=O)c1cnc2ccccn12] | MS m/z 442.1 (M + 1)⁺. |
| 44b | (crude used without isolation) | MS m/z 442.1 (M + 1)⁺. |
| 44c | (crude used without isolation) | MS m/z 432.1 (M + 1)⁺. |
| 44d | 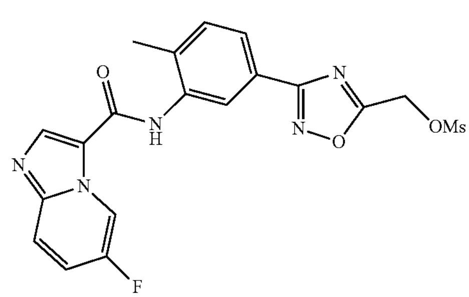 [SMILES: Cc1ccc(-c2noc(COS(C)(=O)=O)n2)cc1NC(=O)c1cnc2ccc(F)cn12] | MS m/z 446.1 (M + 1)⁺. |

Synthesis of N-(5-(5-(3-aminooxetan-3-yl)-1,2,4-oxadiazol-3-yl)-2-methylphenyl)imidazo[1,2-a]pyridine-3-carboxamide (47)

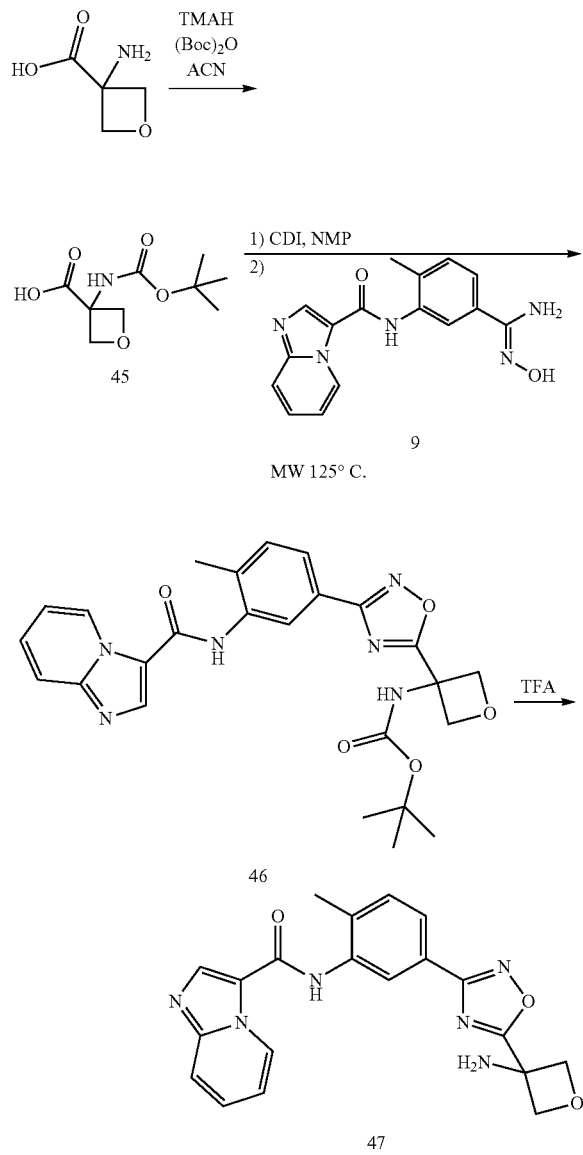

A mixture of 3-aminooxetane-3-carboxylic acid (117.0 mg, 1.0 mmol) and $NMe_4OH \cdot 5H_2O$ (TMAH) (181.0 mg, 1.0 mmol) in $CH_3CN$ (10 mL) was stirred at room temperature for 30 minutes. Then $(Boc)_2O$ (327.3 mg, 1.5 mmol) was added and the resulting mixture was stirred overnight. Water (10 mL) was added and the mixture was extracted with ether (20 mL). The aqueous layer was acidified to pH=2 by addition of citric acid (solid) and extracted with EtOAc (2×20 mL). The organic layers were combined, dried over $Na_2SO_4$, filtered and concentrated to yield crude 3-((tert-butoxycarbonyl)amino)oxetane-3-carboxylic acid (45) which was used without further purification. MS m/z 218.1 $(M+1)^+$.

Carbonyl diimidazole (CDI) (162.2 mg, 1.0 mmol) was added to a stirred solution of 3-((tert-butoxycarbonyl)amino)oxetane-3-carboxylic acid (45) (217.1 mg, 1.0 mmol)) in NMP (1.0 mL). After 20 minutes, N-(5-(N'-hydroxycarbamimidoyl)-2-methylphenyl)imidazo[1,2-a]pyridine-3-carboxamide (9) (150.0 mg, 0.5 mmol) was added in one portion and the resulting solution was stirred for 1 hour before it was heated at 125° C. for 15 minutes in a microwave reactor. The reaction solution was subjected to standard aqueous work up to afford a residue which was purified by silica chromatography to yield tert-butyl (3-(3-(3-(imidazo[1,2-a]pyridine-3-carboxamido)-4-methylphenyl)-1,2,4-oxadiazol-5-yl)oxetan-3-yl)carbamate (46) (159 mg, 65% yield). MS m/z 491.2 $(M+1)^+$.

(3-(3-(3-(Imidazo[1,2-a]pyridine-3-carboxamido)-4-methylphenyl)-1,2,4-oxadiazol-5-yl)oxetan-3-yl)carbamate (46) (29.5 mg, 0.06 mmol) was dissolved in TFA (0.5 mL) and stirred at room temperature for 10 minutes. Then TFA was removed under vacuum to yield crude N-(5-(5-(3-aminooxetan-3-yl)-1,2,4-oxadiazol-3-yl)-2-methylphenyl)imidazo[1,2-a]pyridine-3-carboxamide (47) as a TFA salt which was used without further purification. MS m/z 391.1 $(M+1)^+$.

Synthesis of N-(2-fluoro-5-(N'-hydroxycarbamimidoyl)phenyl)imidazo[1,2-a]pyridine-3-carboxamide (50)

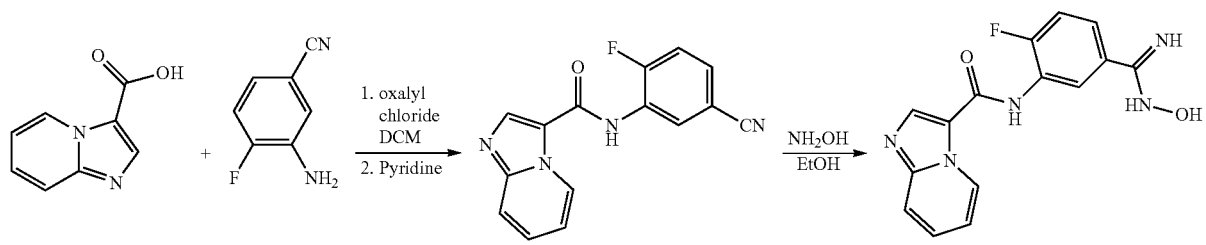

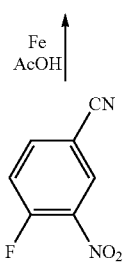

A mixture of 4-fluoro-3-nitrobenzonitrile (5.0 g, 30.1 mmol) and Fe powder (5.05 g, 90.3 mmol) in AcOH (100 mL) was heated at 80° C. for 1 hour under $N_2$. Then the solvent was removed under vacuum and water (200 mL) was added to the residue. The solution was adjusted to pH 6 by addition of $Na_2CO_3$ and extracted with DCM (2×200 mL). The organic layers were combined, dried over $Na_2SO_4$, filtered and concentrated to yield 3-amino-4-fluorobenzonitrile (48), which was used without further purification. MS m/z 137.0 $(M+1)^+$.

To a stirring suspension of imidazo[1,2-a]pyridine-3-carboxylic acid (1) (3.0 g, 18.5 mmol) in anhydrous dichloromethane (50 mL) at 0° C. was added dropwise oxalyl chloride (4.84 mL, 55.5 mmol). Then, three drops of anhydrous DMF was added and the reaction mixture was stirred at room temperature for 15 minutes. The solvent was concentrated and the crude solid was added to a stirring solution of 3-amino-4-fluorobenzonitrile (48) (2.5 g, 18.5 mmol) in anhydrous pyridine (50 mL) at room temperature. The reaction was stirred for 20 minutes and quenched with water (200 mL) with stirring for another 10 minutes. Then the precipitate was filtered and dried in air to yield N-(5-cyano-2-fluorophenyl)imidazo[1,2-a]pyridine-3-carboxamide (49). $^1$H NMR (400 MHz, $d_6$-DMSO) δ 10.40 (s, 1H), 9.43 (td, J=1.2, 6.8 Hz, 1H), 8.63 (s, 1H), 8.21 (dd, J=2.0, 7.2 Hz, 1H), 7.78-7.84 (m, 2H), 7.54-7.63 (m, 2H), 7.22 (dt, J=1.2, 6.8, 1H). MS m/z 281.1 $(M+1)^+$.

$NH_2OH$ (10 mL, 32.1 mmol) was added in one portion to a stirred suspension of N-(5-cyano-2-fluorophenyl)imidazo[1,2-a]pyridine-3-carboxamide (49) (3.6 g, 12.85 mmol) in EtOH (100 mL). The resulting suspension was heated at 70° C. for 3 hours and then the solvent was removed to yield N-(2-fluoro-5-(N'-hydroxycarbamimidoyl)phenyl)imidazo[1,2-a]pyridine-3-carboxamide (50). $^1$H NMR (400 MHz, $d_6$-DMSO) δ 10.21 (s, 1H), 9.70 (s, 1H), 9.45 (td, J=1.2, 7.2 Hz, 1H), 8.61 (s, 1H), 7.95 (dd, J=2.4, 7.6 Hz, 1H), 7.79 (td, J=1.2, 8.8 Hz, 1H), 7.51-7.60 (m, 2H), 7.31-7.37 (m, 1H), 7.19 (dt, J=1.2, 6.8, 1H), 5.88 (s, 2H). MS m/z 314.1 $(M+1)^+$.

The following compounds were prepared according to the protocol described for N-(2-fluoro-5-(N'-hydroxycarbamimidoyl)phenyl)imidazo[1,2-a]pyridine-3-carboxamide (50).

| Intermediate number | Structure | Physical Data |
|---|---|---|
| 50a | 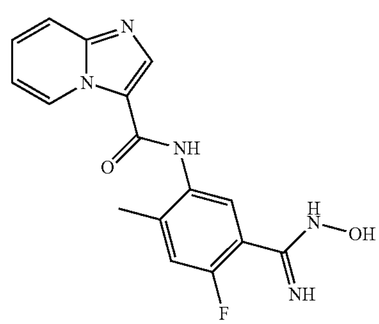 [SMILES: Cc1cc(F)c(C(=N)NO)cc1NC(=O)c1cnc2ccccn12] | $^1$H NMR (400 MHz, $d_6$-DMSO) δ 9.96 (s, 1H), 9.65 (s, 1H), 9.44 (td, J = 0.8, 6.8 Hz, 1H), 8.55 (s, 1H), 7.78 (td, J = 1.2, 9.2 Hz, 1H), 7.52 (m, 2H), 7.21 (d, J = 11.6 Hz, 1H), 7.17 (dt, J = 1.2, 6.8, 1H), 5.81 (s, 2H), 2.28 (s, 3H). MS m/z 328.1 $(M + 1)^+$. |
| 50b | 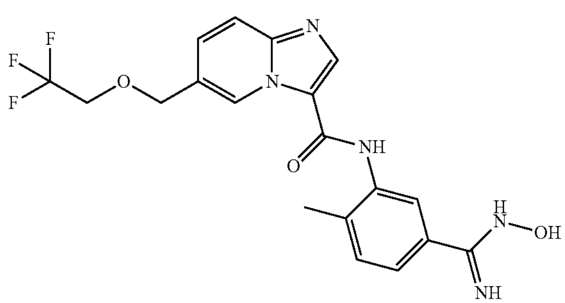 [SMILES: Cc1ccc(C(=N)NO)cc1NC(=O)c1cnc2ccc(COCC(F)(F)F)cn12] | MS m/z 422.1 $(M + 1)^+$. |

| Intermediate number | Structure | Physical Data |
|---|---|---|
| 50c | 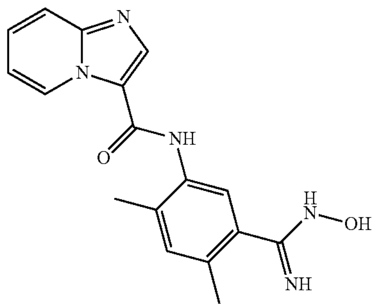 [SMILES: Cc1cc(C)c(C(=N)NO)cc1NC(=O)c1cnc2ccccn12] | ¹H NMR (400 MHz, d₆-DMSO) δ 9.89 (s, 1H), 9.44 (dt, J = 6.8, 1.2 Hz, 1H), 9.33 (s, 1H), 8.55 (s, 1H), 7.76 (dt, J = 9.2, 1.2 Hz, 1H), 7.49-7.52 (m, 1H), 7.28 (s, 1H), 7.14-7.18 (m, 2H), 5.72 (s, 2H), 2.34 (s, 3H), 2.24 (s, 3H). MS m/z 324.1 (M + 1)⁺. |
| 50d | 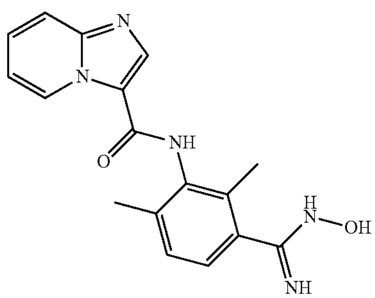 [SMILES: Cc1ccc(C(=N)NO)c(C)c1NC(=O)c1cnc2ccccn12] | ¹H NMR (400 MHz, d₆-DMSO) δ 9.84 (s, 1H), 9.43 (d, J = 6.8 Hz, 1H), 8.59 (s, 1H), 7.78 (d, J = 8.8 Hz, 1H), 7.50 (d, J = 8.0 Hz, 1H), 7.17 (m, 3H), 5.76 (s, 2H), 2.25 (s, 3H), 2.24 (s, 3H). MS m/z 324.1 (M + 1)⁺. |
| 50e | 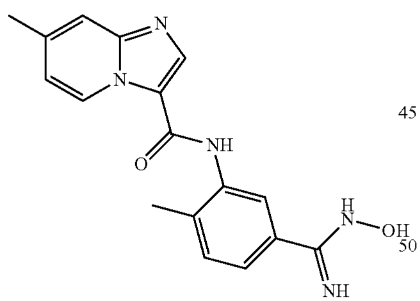 | ¹H NMR (400 MHz, d₆-DMSO) δ 9.90 (s, 1H), 9.60 (s, 1H), 9.32 (d, J = 7.2 Hz, 1H), 8.50 (s, 1H), 7.69 (d, J = 2.20 Hz, 1H), 7.56 (m, 1H), 7.50 (dd, J = 1.6, 8.0 Hz, 1H), 7.29 (d, J = 8.0 Hz, 1H), 7.02 (dd, J = 1.6, 7.2 Hz, 1H), 5.80 (s, 2H), 2.42 (s, 3H), 2.27 (s, 3H). MS m/z 324.1 (M + 1)⁺. |
| 50f | 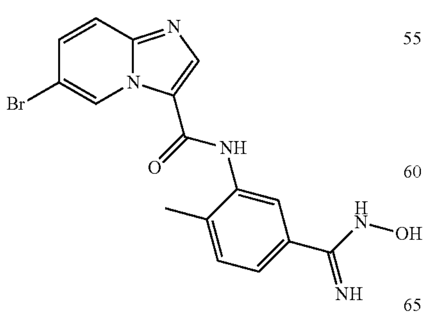 | ¹H NMR (400 MHz, d₆-DMSO) δ 10.09 (s, 1H), 9.63 (m, 1H), 9.60 (s, 1H), 8.58 (s, 1H), 7.78 (dd, J = 0.8, 9.6 Hz, 1H), 7.69 (d, J = 1.6 Hz, 1H), 7.66 (dd, J = 2.0, 9.2 Hz, 1H), 7.52 (dd, J = 1.6, 8.0 Hz, 1H), 7.31 (d, J = 8.0 Hz, 1H), 5.81 (s, 2H), 2.27 (s, 3H). MS m/z 388.0, 390.0 (M + 1)⁺. |

Synthesis of 5-amino-2-fluoro-4-methylbenzonitrile (51)

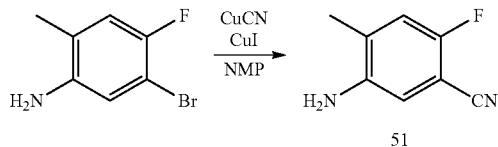

A mixture of 5-bromo-4-fluoro-2-methylaniline (2.04 g, 10.0 mmol), CuCN (889 mg, 10.0 mmol) and CuI (1.9 g, 10.0 mmol) in NMP was purged with $N_2$ for 5 minutes and then sealed and heated at 195° C. for 30 minutes under microwave condition. The mixture was subjected to standard aqueous workup to give a residue which was purified by silica chromatography to yield 5-amino-2-fluoro-4-methylbenzonitrile (51) (540 mg, 36% yield). MS m/z 151.0 (M+1)$^+$.

Synthesis of N-(5-(5-(azetidin-3-ylmethyl)-1,2,4-oxadiazol-3-yl)-2-methylphenyl)imidazo[1,2-a]pyridine-3-carboxamide (55)

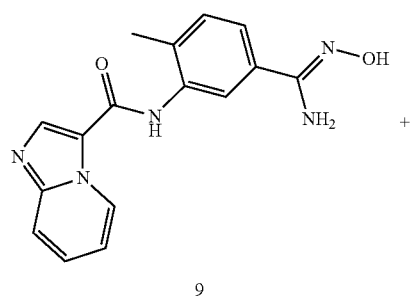

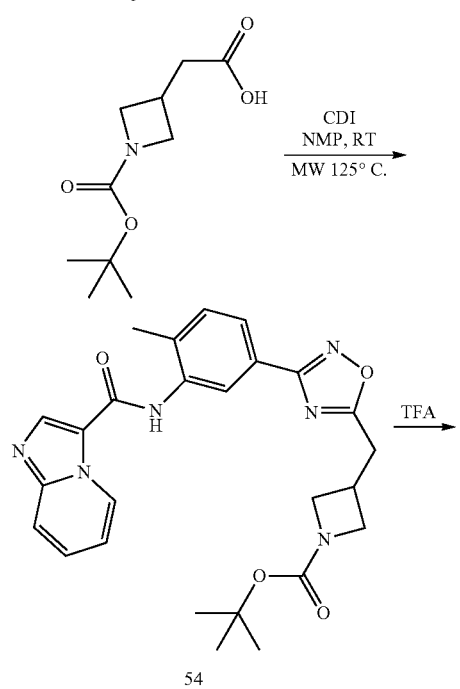

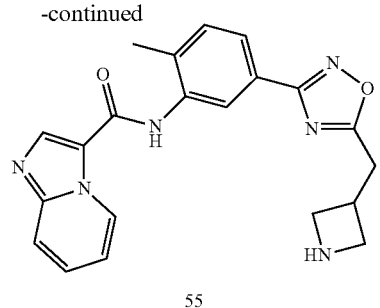

Carbonyl diimidazole (CDI) (52.0 mg, 0.32 mmol) was added to a stirred solution of 2-(1-(tert-butoxycarbonyl)azetidin-3-yl)acetic acid (69.0 mg, 0.32 mmol) in NMP (1.0 mL). After 20 minutes, N-(5-(N'-hydroxycarbamimidoyl)-2-methylphenyl)imidazo[1,2-a]pyridine-3-carboxamide (9) (49.5 mg, 0.16 mmol) was added in one portion and the resulting solution was stirred for 30 minutes before it was heated at 125° C. for 15 minutes in a microwave reactor. The reaction mixture was added dropwise to water (20 mL) with stirring. The precipitate was filtered and dried to give tert-butyl 3-((3-(3-(imidazo[1,2-a]pyridine-3-carboxamido)-4-methylphenyl)-1,2,4-oxadiazol-5-yl)methyl)azetidine-1-carboxylate (54). MS m/z 489.2 (M+1)$^+$.

3-((3-(3-(Imidazo[1,2-a]pyridine-3-carboxamido)-4-methylphenyl)-1,2,4-oxadiazol-5-yl)methyl)azetidine-1-carboxylate (54) (29.3 mg, 0.06 mmol) was dissolved in TFA (0.5 mL) and stirred at room temperature for 10 minutes. Then TFA was removed under vacuum to yield crude N-(5-(5-(azetidin-3-ylmethyl)-1,2,4-oxadiazol-3-yl)-2-methylphenyl)imidazo[1,2-a]pyridine-3-carboxamide (55) which was used without further purification. MS m/z 389.2 (M+1)$^+$.

Synthesis of 2-(3,3-difluoropyrrolidin-1-yl)-3-methoxypropanoic acid (58)

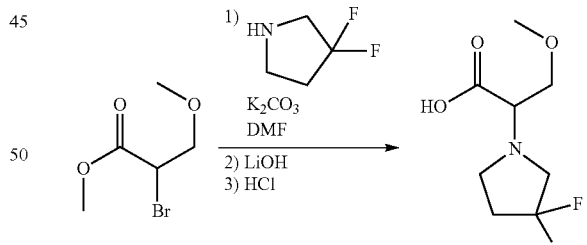

A mixture of methyl 2-bromo-3-methoxypropanoate (132.0 mg, 0.66 mmol), 3,3-difluoropyrrolidine (70.6 mg, 0.66 mmol) and $K_2CO_3$ (91.2 mg, 0.66 mmol) in DMF (2 mL) was heated at 90° C. for 3 hours. The mixture was subjected to standard aqueous workup to afford a residue which was dissolved in THF/MeOH/$H_2O$ (3:2:1, 5 mL). LiOH (6N, 3.3 mmol) was added and the resulting mixture was stirred at room temperature for 30 minutes. The solution was acidified to pH5 by addition of 6N HCl. All solvents were removed under vacuum to give a crude 2-(3,3-difluoropyrrolidin-1- yl)-3-methoxypropanoic acid (58) which was used without purification. MS m/z 210.1 (M+1)+.

Synthesis of 6-(((triisopropylsilyl)oxy)methyl)imidazo[1,2-a]pyridine-3-carboxylic acid (61)

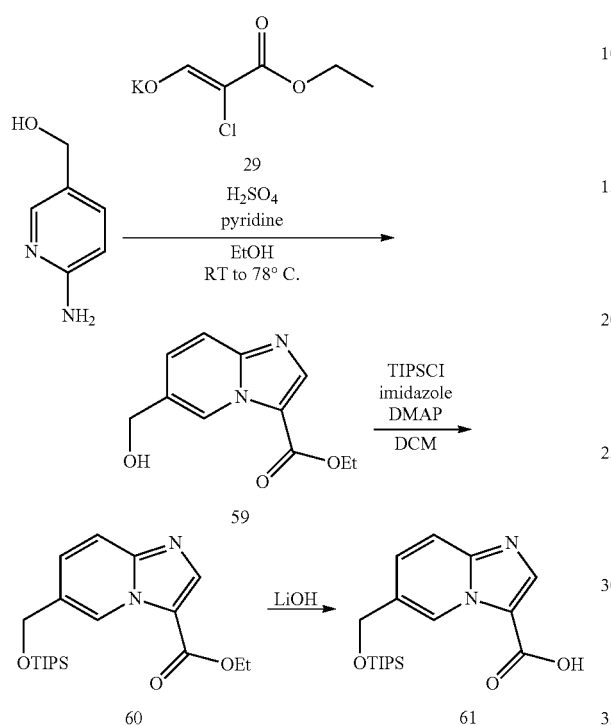

To a stirring suspension of (6-aminopyridin-3-yl)methanol (1.24 mg, 10.0 mmol) and ethyl 2-chloro-3-hydroxyacrylate, potassium salt (29) (3.76 g, 20.0 mmol) in EtOH (10 mL) at room temperature was added conc sulfuric acid (10.0 mmol) dropwise. The reaction mixture was stirred at room temperature for 15 minutes and pyridine (0.92 g, 12.0 mmol) was added. The resulting mixture was heated at 85° C. overnight. The reaction was cooled to room temperature and the solvent was concentrated. The residue was taken in water and the solution was adjusted to pH 8 with saturated sodium bicarbonate. The crude product was extracted with ethyl acetate. The organic layer was washed with brine and dried over anhydrous sodium sulfate. The crude product ethyl 6-(hydroxymethyl)imidazo[1,2-a]pyridine-3-carboxylate (59) was purified by silica chromatography. $^1$H NMR (400 MHz, $d_6$-DMSO) δ 9.16 (d, J=6.8 Hz, 1H), 8.26 (s, 1H), 7.67 (s, 1H), 7.19 (dd, J=1.6, 6.8 Hz, 1H), 5.57 (t, J=6.4 Hz, 1H), 4.63 (d, J=6.0, 2H), 4.36 (q, J=7.2 Hz, 2H), 1.35 (t, J=6.8 Hz, 3H). MS m/z 221.1 (M+1)+.

To a suspension of ethyl 6-(hydroxymethyl)imidazo[1,2-a]pyridine-3-carboxylate (59) (497.0 mg, 2.26 mmol), DMAP (12.2 mg, 0.1 mmol) and 1H-imidazole (154.0 mg, 2.26 mmol) in dichloromethane (10 mL), was added TIPSCI (523.0 mg, 2.71 mmol). The resulting mixture was stirred overnight at room temperature. The solvent was removed under vacuum to yield crude ethyl 6-(((triisopropylsilyl)oxy)methyl)imidazo[1,2-a]pyridine-3-carboxylate (60). MS m/z 377.2 (M+1)+.

The crude ethyl 6-(((triisopropylsilyl)oxy)methyl)imidazo[1,2-a]pyridine-3-carboxylate (60) obtained above was dissolved in THF/MeOH/H$_2$O (3:2:1, 5 mL). 6N LiOH (2.27 mL, 13.6 mmol) was added and the reaction mixture was stirred at room temperature for 2 hours. All solvents were removed and 6N HCl was added until pH 5-6. EtOAc (5 mL) was added and the mixture was stirred for 1 hour. The precipitate was filtered and dried to give 6-(((triisopropylsilyl)oxy)methyl)imidazo[1,2-a]pyridine-3-carboxylic acid (61). $^1$H NMR (400 MHz, $d_6$-DMSO) δ 9.37 (s, 1H), 8.21 (s, 1H), 7.76 (dd, J=1.2, 9.2 Hz, 1H), 7.46 (dd, J=2.0, 9.2 Hz, 1H), 4.94 (s, 2H), 1.20 (m, 3H), 1.08 (d, J=6.8 Hz, 18H). MS m/z 349.2 (M+1)+.

Synthesis of 7-(1H-pyrazol-3-yl)imidazo[1,2-a]pyridine-3-carboxylic acid (63)

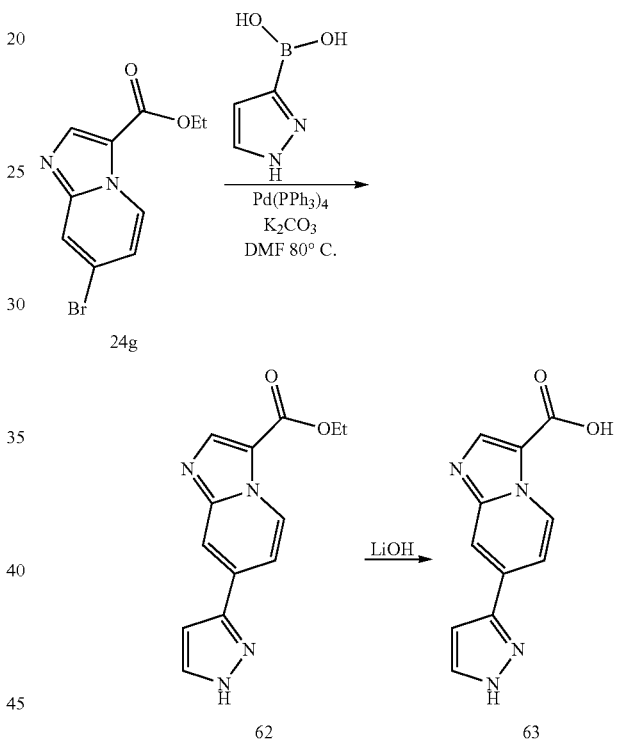

To a solution of 5-ethyl 7-bromoimidazo[1,2-a]pyridine-3-carboxylate 24 g (202 mg, 0.75 mmol) in DMF (2 mL) was added (1H-pyrazol-3-yl)boronic acid (101 mg, 0.903 mmol), 1.8 M K$_2$CO$_3$ (1.3 mL, 2.26 mmol) and Pd(PPh$_3$)$_4$ (87 mg, 0.075 mmol). The reaction was evacuated and backfilled with nitrogen twice then heated at 160° C. for 10 minutes in a microwave oven. After the reaction mixture was filtered through a pad of Celite, the mixture was diluted with a saturated solution of NH$_4$Cl and extracted with ethyl acetate. The organic layer was washed with brine, dried over Na$_2$SO$_4$ and concentrated to give ethyl 7-(1H-pyrazol-3-yl)imidazo[1,2-a]pyridine-3-carboxylate (62). MS (m/z) 257.1 (M+1)+.

To a stirring solution of ethyl 7-(1H-pyrazol-3-yl)imidazo[1,2-a]pyridine-3-carboxylate (62) (103 mg, 0.4 mmol) in THF:MeOH:H$_2$O (3:2:1, 1.6 mL) was added 6N LiOH (0.035 mL). The reaction was stirred at room temperature for 20 minutes. The pH was adjusted between 4-5 with 3N HCl. The resulting mixture was concentrated to yield 7-(1H-pyrazol-3-yl)imidazo[1,2-a]pyridine-3-carboxylic acid (63). MS (m/z) 229.2 (M+1)⁺.

Synthesis of N-(5-amino-2-methylphenyl)imidazo[1,2-a]pyridine-3-carboxamide (67)

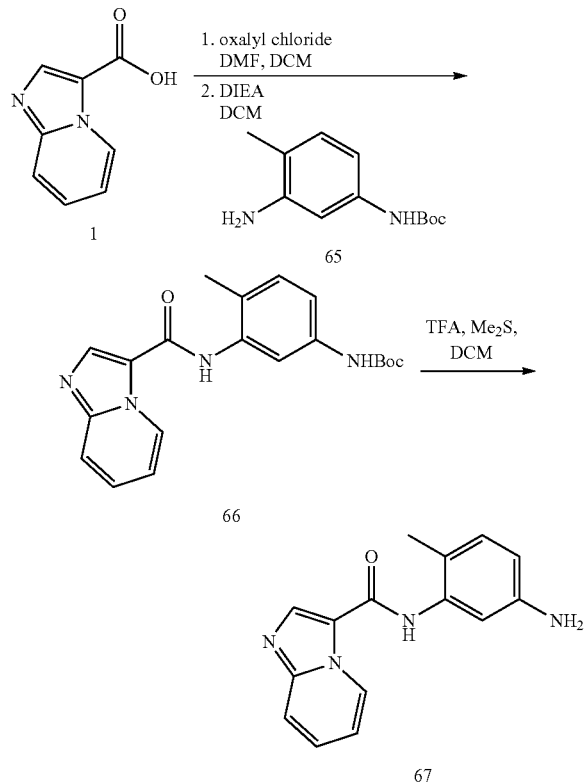

Oxalyl chloride (10 mL) was added dropwise to a stirred solution of imidazo[1,2-a]pyridine-3-carboxylic acid (1) (3 g, 18.5 mmol) in dry dichloromethane (100 mL) and a few drops of DMF. The resulting solution was stirred at room temperature for 5 hours before it was evaporated to dryness and fresh dichloromethane was added to the resulting acid chloride to make a suspension. In a separate flask, tert-butyl 3-amino-4-methylphenylcarbamate (65) (4.5 g, 20.3 mmol) and DIEA (10 mL) was dissolved in dichloromethane (100 mL) and the above acid chloride solution was added slowly. The resulting solution was stirred overnight at room temperature. Saturated NH₄Cl was added to the reaction solution and the phases were separated. The organic layer was dried over Na₂SO₄ and filtered. After evaporation, the residue was purified over silica gel column using hexane and EtOAc to give tert-butyl 3-(imidazo[1,2-a]pyridine-3-carboxamido)-4-methylphenylcarbamate (66) as a slightly yellow solid.

TFA (50 mL) was added to a stirred suspension of tert-butyl 3-(imidazo[1,2-a]pyridine-3-carboxamido)-4-methylphenylcarbamate (66) in Me₂S (5 mL) and dichloromethane (10 mL). After 2 hours the solution was evaporated and partitioned with dichloromethane and saturated NaHCO₃. The aqueous layer was extracted several times with dichloromethane and the combined organic layers were dried over Na₂SO₄. N-(5-amino-2-methylphenyl)imidazo[1,2-a]pyridine-3-carboxamide (67) was isolated and used without further purification. ¹H NMR (400 MHz, CDCl₃) δ 9.44 (d, J=6.8 Hz, 1 H), 8.05 (s, 1 H), 7.67 (d, J=8.8 Hz, 1 H), 7.38-7.33 (m, 2 H), 6.98-6.94 (m, 2 H), 2.19 (s, 3 H). MS m/z 267.1 (M+1)⁺.

Synthesis of (E)-N-(5-(2-hydroxyguanidino)-2-methylphenyl)imidazo[1,2-a]pyridine-3-carboxamide (69)

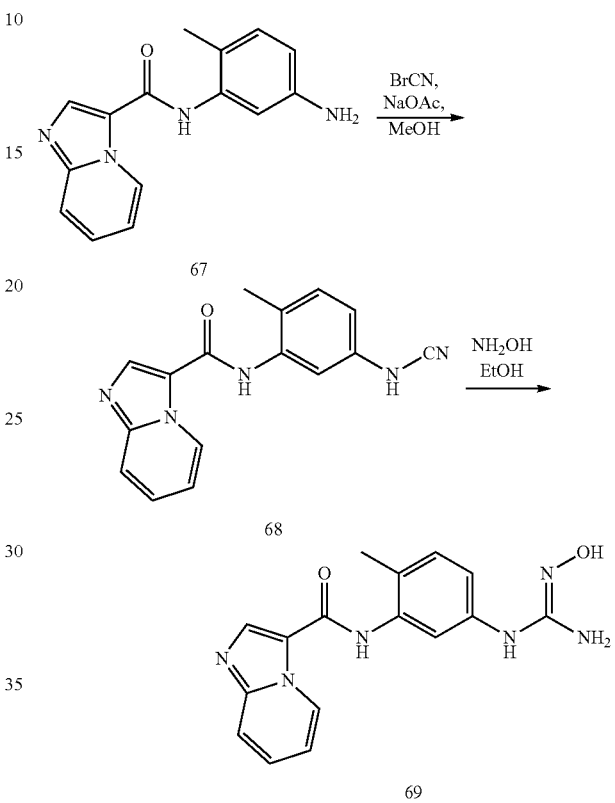

To N-(5-amino-2-methylphenyl)imidazo[1,2-a]pyridine-3-carboxamide (67) (4.53 g, 15 mmol) in MeOH (100 mL) was added KOAc (4.41 g, 45 mmol) and the mixture was stirred at room temperature for 5 minutes then cooled to 0° C. before a solution of BrCN (1.62 g, 15 mmol) in MeOH (30 mL) was added dropwise. The resulting mixture was slowly warmed to room temperature and stirred overnight. The solvent was evaporated and to the residue was added water (150 mL). The mixture was stirred at room temperature for 1 hour, filtered and washed with water (2×20 mL), then air dried to give N-(5-cyanamido-2-methylphenyl)imidazo[1,2-a]pyridine-3-carboxamide (68) as a white solid.

To a suspension of N-(5-cyanamido-2-methylphenyl)imidazo[1,2-a]pyridine-3-carboxamide (68) 3.52 g (12.1 mmol) in 200 mL of EtOH was added 0.75 mL NH₂OH (50 wt % in water, 12.1 mmol). The resulting mixture was stirred at room temperature overnight. The precipitate was filtered, washed with EtOH (10 mL) and air dried to give N-(5-(2-hydroxyguanidino)-2-methylphenyl)imidazo[1,2-a]pyridine-3-carboxamide (69) as a white solid, which was used directly in the next step without further purification. ¹H NMR (400 MHz, d6-DMSO) δ 9.44 (s, 1 H), 9.46 (dd, J=6.8, 0.8 Hz, 1 H), 8.54

(s, 1 H), 8.34 (s, 1 H), 7.76 (dd, J=7.2, 2.2 Hz, 1 H), 7.59 (s, 1 H), 7.52-7.43 (m, 2 H), 7.18-7.06 (m, 2 H), 2.13 (s, 3 H). MS m/z 325.1 (M+1)+.

Synthesis of 6-(3-(tert-butoxy)-3-oxopropyl)imidazo [1,2-a]pyridine-3-carboxylic acid (72)

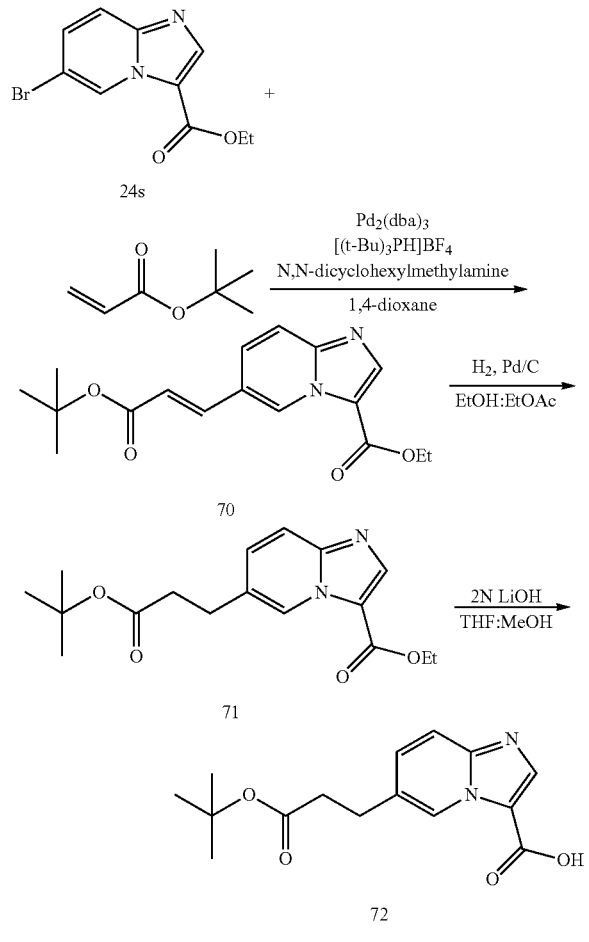

A stirring mixture of ethyl 6-bromoimidazo[1,2-a]pyridine-3-carboxylate (24s) (500 mg, 1.86 mmol), tert-butyl acrylate (408 uL, 2.79 mmol), tris(dibenzylideneacetone)diplalladium(0) (51 mg, 0.056 mmol), [(t-Bu)$_3$PH]BF$_4$ (27 mg, 0.093 mmol) and N,N-dicyclohexylmethylamine (738 uL, 3.48 mmol) in anhydrous 1,4-dioxane (5 mL) was heated at 95° C. overnight. The reaction was cooled to room temperature and filtered. The solvent was concentrated and the crude product was purified by silica chromatography to yield ethyl 6-(3-(tert-butoxy)-3-oxoprop-1-en-1-yl)imidazo[1,2-a]pyridine-3-carboxylate (70). MS m/z 317.14 (M+1)+.

A stirring mixture of ethyl 6-(3-(tert-butoxy)-3-oxoprop-1-en-1-yl)imidazo[1,2-a]pyridine-3-carboxylate (70) (460 mg, 1.80 mmol) and 10 wt % Pd/C (wet) in ethanol:ethylacetate (1:1, 10 mL) was hydrogenated overnight. The reaction was filtered over celite and the solvent was concentrated. Crude ethyl 6-(3-tert-butoxy-3-oxopropyl)imidazo[1,2-a]pyridine-3-carboxylate (71) was used in the next step without further purification. MS m/z 319.16 (M+1)+.

A stirring mixture of ethyl 6-(3-tert-butoxy-3-oxopropyl)imidazo[1,2-a]pyridine-3-carboxylate (71) (400 mg, 1.26 mmol) and 2N LiOH (1 mL) in THF:MeOH (4:1, 4 mL) was heated at 60° C. for 30 minutes. The reaction was cooled to room temperature and the pH was adjusted between 3-5 with 10% citric acid. The solvent was partially reduced. The resulting solid was collected by vacuum filtration and washed with excess water. Crude 6-(3-(tert-butoxy)-3-oxopropyl)imidazo [1,2-a]pyridine-3-carboxylic acid (72) was dried and used in the next step without further purification. $^1$H NMR (400 MHz, d$_6$-DMSO) δ 9.11 (s, 1 H), 8.20 (s, 1 H), 7.72 (dd, J=0.8, 9.2 Hz, 1 H), 7.50 (dd, J=1.6, 9.2 Hz, 1H), 2.91 (t, J=6.8 Hz, 2 H), 2.60 (t, J=7.2, 2 H), 1.33 (s, 9 H). MS m/z 291.13 (M+1)+.

Synthesis of 6(2-cyanoethyl)imidazo[1,2-a]pyridine-3-carboxylic acid (75)

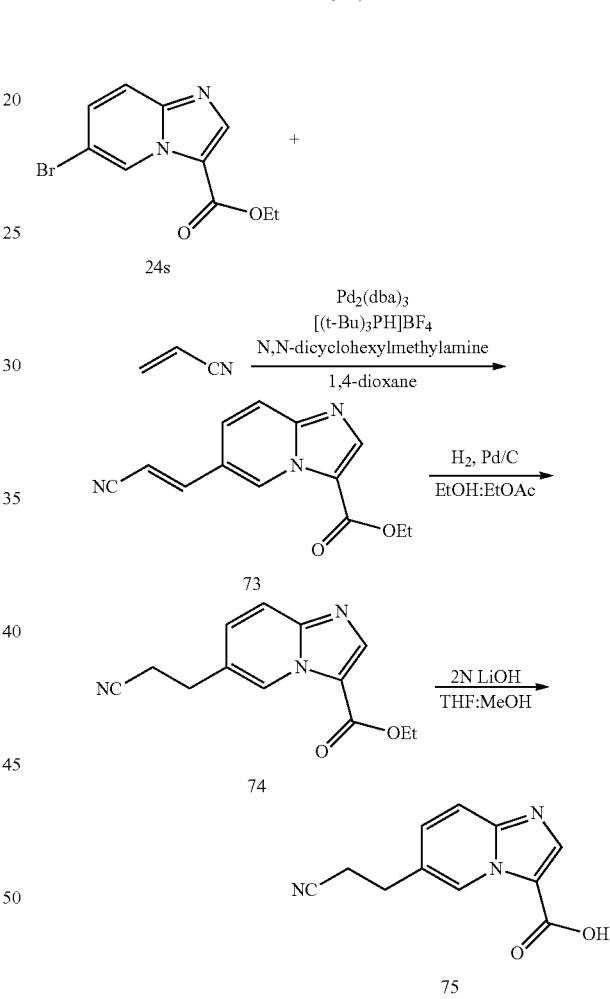

A stirring mixture of ethyl 6-bromoimidazo[1,2-a]pyridine-3-carboxylate (24s) (250 mg, 0.929 mmol), acrylonitrile (92 uL, 1.39 mmol), tris(dibenzylideneacetone)diplalladium (0) (26 mg, 0.0279 mmol), [(t-Bu)$_3$PH]BF$_4$ (13 mg, 0.0465 mmol) and N,N-dicyclohexylmethylamine (217 uL, 1.02 mmol) in anhydrous 1,4-dioxane (4 mL) was heated at 95° C. overnight. The reaction was cooled to room temperature and filtered. The solvent was concentrated and crude 6-(2-cyanovinyl)imidazo[1,2-a]pyridine-3-carboxylate (73) was purified by silica chromatography. MS m/z 242.09 (M+1)+.

A stirring mixture of ethyl 6-(2-cyanovinyl)imidazo[1,2-a]pyridine-3-carboxylate (73) (115 mg, 0.451 mmol) and 10 wt % Pd/C (wet) in ethanol:ethylacetate (1:1, 5 mL) was hydrogenated overnight. The reaction was filtered over celite and the solvent was removed. Crude ethyl 6-(2-cyanoethyl)imidazo[1,2-a]pyridine-3-carboxylate (74) was used in the next step without further purification. MS m/z 244.10 (M+1)+.

A stirring mixture of ethyl 6-(2-cyanoethyl)imidazo[1,2-a]pyridine-3-carboxylate (74) (100 mg, 0.411 mmol) and 2N LiOH (0.2 mL) in THF:MeOH (4:1, 3 mL) was heated at 50° C. for 45 minutes. The reaction was cooled to room temperature and the pH was adjusted between 3-5 with 10% citric acid. The solvent was partially reduced. The resulting solid was collected by vacuum filtration and washed with excess water. Crude 6-(2-cyanoethyl)imidazo[1,2-a]pyridine-3-carboxylic acid (75) was dried and used in the next step without further purification. MS m/z 416.07 (M+1)+.

Synthesis of 6-(3-oxobutyl)imidazo[1,2-a]pyridine-3-carboxylic acid (78)

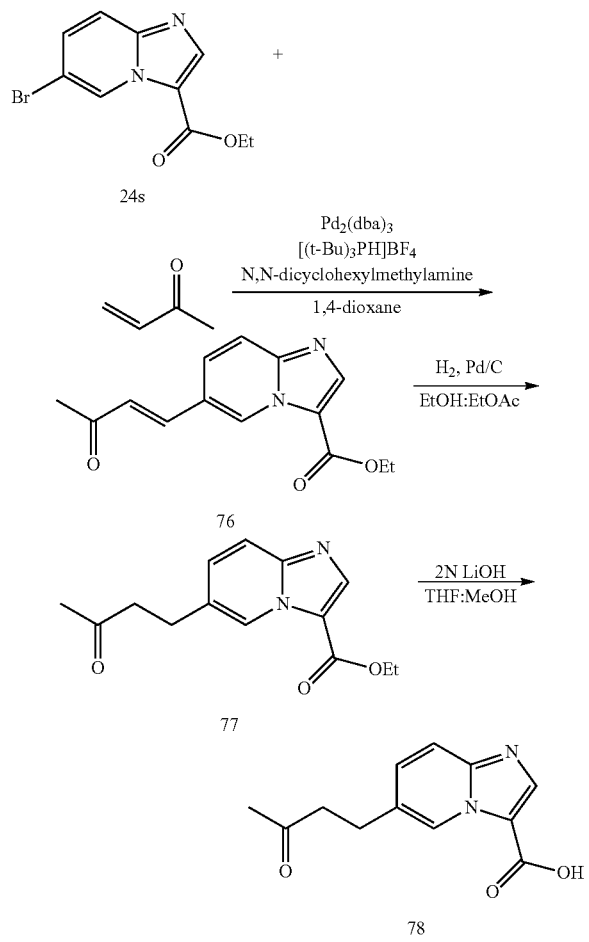

A stirring mixture of ethyl 6-bromoimidazo[1,2-a]pyridine-3-carboxylate (24s) (250 mg, 0.929 mmol), methyl vinyl ketone (151 uL, 1.86 mmol), tris(dibenzylideneacetone)diplalladium(0) (26 mg, 0.0279 mmol), [(t-Bu)3PH]BF4 (13 mg, 0.0465 mmol) and N,N-dicyclohexylmethylamine (217 uL, 1.02 mmol) in anhydrous 1,4-dioxane (4 mL) was heated at 95° C. overnight. The reaction was cooled to room temperature and filtered. The solvent was concentrated and crude 6-(3-oxobut-1-enyl)imidazo[1,2-a]pyridine-3-carboxylate (76) was purified by silica chromatography. MS m/z 259.10 (M+1)+.

A stirring mixture of ethyl 6-(3-oxobut-1-enyl)imidazo[1,2-a]pyridine-3-carboxylate (76) (200 mg, 0.774 mmol) and 10 wt % Pd/C (wet) in ethanol:ethylacetate (1:1, 8 mL) was hydrogenated overnight. The reaction was filtered over celite and the solvent was concentrated. Crude 6-(3-oxobutyl)imidazo[1,2-a]pyridine-3-carboxylate (77) was used in the next step without further purification. MS m/z 261.12 (M+1)+.

A stirring mixture of ethyl 6-(3-oxobutyl)imidazo[1,2-a]pyridine-3-carboxylate (77) (190 mg, 0.730 mmol) and 2N LiOH (0.2 mL) in THF:MeOH (4:1, 3 mL) was heated at 50° C. for 45 minutes. The reaction was cooled to room temperature and the pH was adjusted between 3-5 with 10% citric acid. The solvent was partially reduced. The resulting solid was collected by vacuum filtration and washed with excess water. Crude 6-(3-oxobutyl)imidazo[1,2-a]pyridine-3-carboxylic acid (78) was dried and used in the next step without further purification. MS m/z 233.08 (M+1)+.

Synthesis of 6-(3-oxobutyl)imidazo[1,2-a]pyridine-3-carboxylic acid (80)

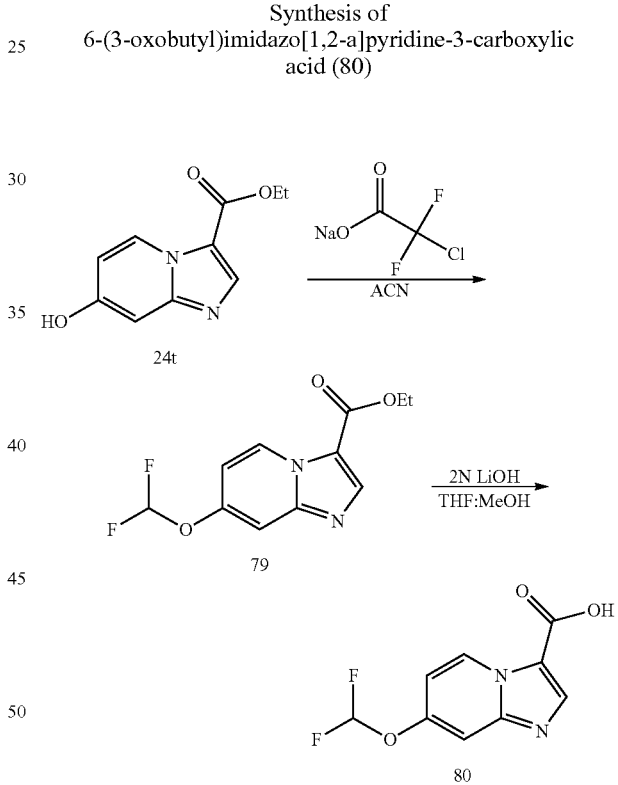

A mixture of ethyl 7-hydroxyimidazo[1,2-a]pyridine-3-carboxylate (24t) (500 mg, 2.43 mmol) and sodium chlorodifluoroacetate (444 mg, 2.91 mmol) in anhydrous acetonitrile (8 mL) was heated in the microwave at 125° C. for 12 minutes. The solvent was concentrated and the crude product ethyl 7-(difluoromethoxy)imidazo[1,2-a]pyridine-3-carboxylate (79) was purified by silica chromatography. MS m/z 257.07 (M+1)+.

A stirring mixture of ethyl 7-(difluoromethoxy)imidazo[1,2-a]pyridine-3-carboxylate (79) (150 mg, 0.585 mmol) and 2N LiOH (1 mL) in THF:MeOH (4:1, 5 mL) was heated at 60° C. for 45 minutes. The reaction was cooled to room temperature and the pH was adjusted between 4-5 with 1N HCl. The solvent was partially reduced and the crude product was purified by reverse phase preparative HPLC to yield 6-(3-oxobutyl)imidazo[1,2-a]pyridine-3-carboxylic acid (80). MS m/z 229.03 (M+1)⁺.

Synthesis of N-(5-(5-(1-(N'-hydroxycarbamimidoyl)azetidin-3-yl)-1,2,4-oxadiazol-3-yl)-2-methylphenyl)imidazo[1,2-a]pyridine-3-carboxamide (83)

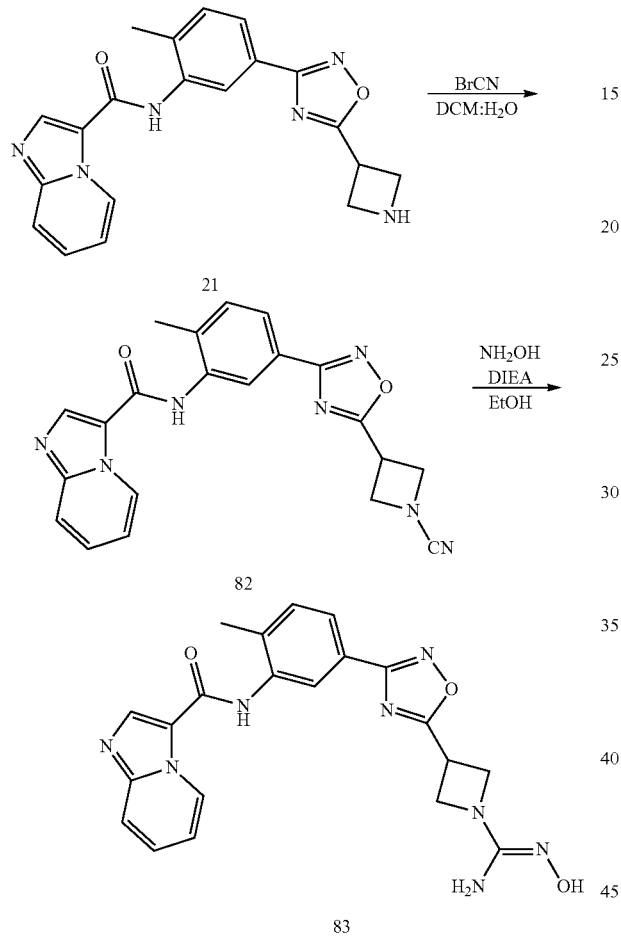

To a stirring mixture of N-(5-(5-(azetidin-3-yl)-1,2,4-oxadiazol-3-yl)-2-methylphenyl)imidazo[1,2-a]pyridine-3-carboxamide hydrochloride (21) (200 mg, 0.487 mmol), potassium carbonate (202 mg, 1.46 mmol) and cyanogen bromide (103 mg, 0.974 mmol) in dichloromethane:water (1:1, 15 mL) were heated at 45° C. for 1.5 hours. The reaction was cooled to room temperature and the layers were separated. The aqueous layer was washed with 3 times with DCM and dried over anhydrous sodium sulfate. The combined organics were concentrated. The resulting solid was washed with hexanes to give N-(5-(5-(1-cyanoazetidin-3-yl)-1,2,4-oxadiazol-3-yl)-2-methylphenyl)imidazo[1,2-a]pyridine-3-carboxamide (82). MS m/z 400.14 (M+1)⁺.

A stirring mixture of N-(5-(5-(1-cyanoazetidin-3-yl)-1,2,4-oxadiazol-3-yl)-2-methylphenyl)imidazo[1,2-a]pyridine-3-carboxamide (82) (50 mg, 0.125 mmol), hydroxylamine HCl (13 mg, 0.188 mmol) and DIEA (44 uL, 0.250 mmol) in ethanol was heated at 78° C. for 2 hours. The solvent was concentrated and dried under high vacuum. Crude N-(5-(5-(1-(N'-hydroxycarbamimidoyl)azetidin-3-yl)-1,2,4-oxadiazol-3-yl)-2-methylphenyl)imidazo[1,2-a]pyridine-3-carboxamide (83) was used in the next step without further purification. MS m/z 433.17 (M+1)⁺.

Synthesis of 7-(3-oxobutyl)imidazo[1,2-a]pyridine-3-carboxylic acid (86)

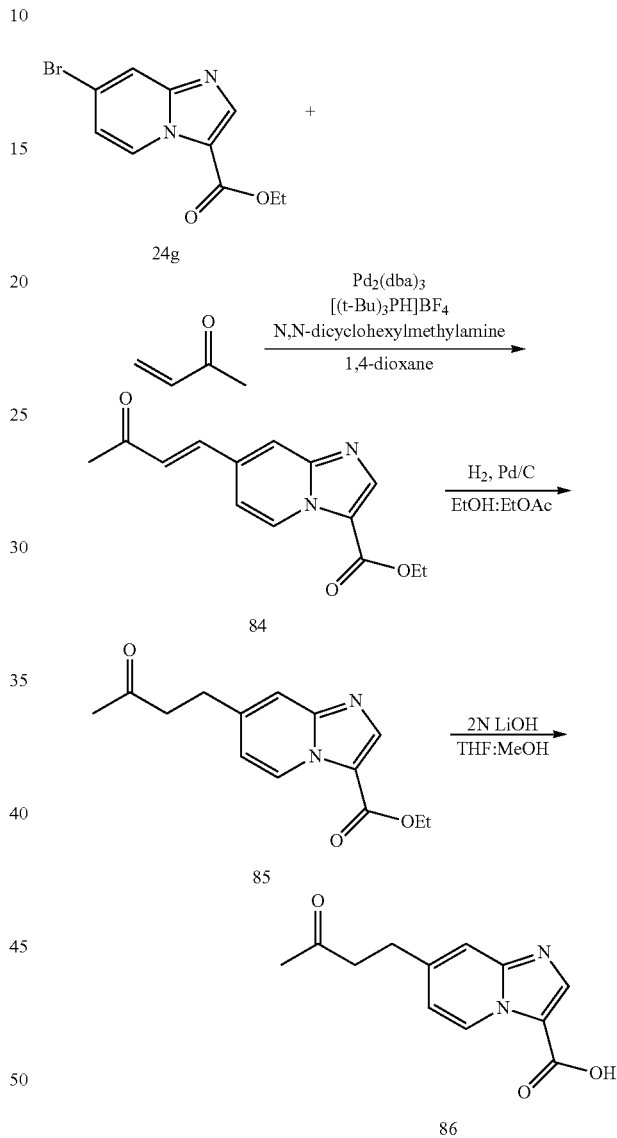

A stirring mixture of ethyl 7-bromoimidazo[1,2-a]pyridine-3-carboxylate (24g) (500 mg, 1.86 mmol), methyl vinyl ketone (301 uL, 3.72 mmol), tris(dibenzylideneacetone)diplalladium(0) (51 mg, 0.056 mmol), [(t-Bu)₃PH]BF₄ (27 mg, 0.093 mmol) and N,N-dicyclohexylmethylamine (433 uL, 2.04 mmol) in anhydrous 1,4-dioxane (10 mL) was heated at 95° C. overnight. The reaction was cooled to room temperature and filtered. The solvent was concentrated and crude ethyl 7-(3-oxobut-1-enyl)imidazo[1,2-a]pyridine-3-carboxylate (84) was purified by silica chromatography. MS m/z 259.10 (M+1)⁺.

A stirring mixture of ethyl 7-(3-oxobut-1-enyl)imidazo[1,2-a]pyridine-3-carboxylate (84) (92 mg, 0.356 mmol) and 10 wt % Pd/C (wet) in ethanol:ethylacetate (1:1, 8 mL) was hydrogenated overnight. The reaction was filtered over celite and the solvent was concentrated. Crude ethyl 7-(3-oxobutyl)imidazo[1,2-a]pyridine-3-carboxylate (85) was used in the next step without further purification. MS m/z 261.12 (M+1)$^+$.

A stirring mixture of ethyl 7-(3-oxobutyl)imidazo[1,2-a]pyridine-3-carboxylate (85) (90 mg, 0.346 mmol) and 2N LiOH (0.5 mL) in THF:MeOH (4:1, 3 mL) was heated at 60° C. for 45 minutes. The reaction was cooled to room temperature and the pH was adjusted between 3-5 with 10% citric acid. The solvent was partially concentrated and the crude product was purified by reverse phase preparative HPLC to yield 7-(3-oxobutyl)imidazo[1,2-a]pyridine-3-carboxylic acid (86). MS m/z 233.08 (M+1)$^+$.

Synthesis of 7-meth 1-d$_3$-imidazo[1,2-a]pyridine-3-carboxylic acid (95)

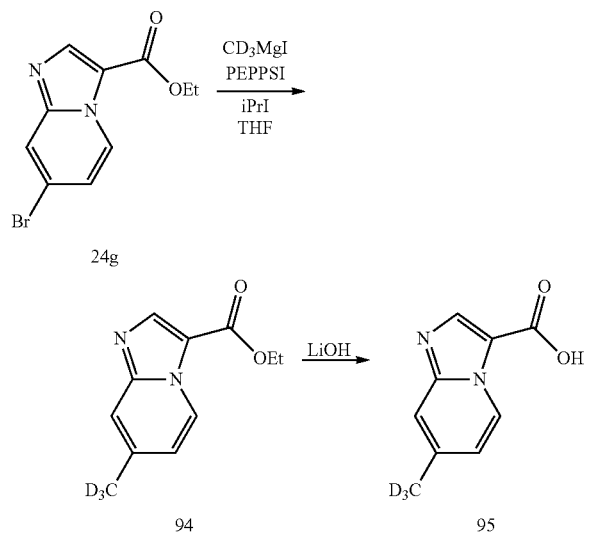

To a stirring solution of ethyl 7-bromoimidazo[1,2-a]pyridine-3-carboxylate (24g) (500 mg, 1.86 mmol), PEPPSI (63.2 mg, 0.093 mmol) and 2-iodopropane (928 uL, 9.3 mmol) in anhydrous THF (3 mL) at 0° C. under a stream of nitrogen was added methyl-d$_3$-magnesium iodide (5.6 mL, 5.57 mmol). The reaction was stirred to room temperature for 5 hours. Then, the reaction was quenched with NH$_4$Cl. The crude product was extracted with ether, washed with water and brine and dried over sodium sulfate. The product was purified on silica gel using 10% MeOH in dichloromethane to yield ethyl 7-methyl-d$_3$-imidazo[1,2-a]pyridine-3-carboxylate (94). $^1$H NMR (400 MHz, d$_6$-DMSO) δ 8.85 (dd, J=0.4, 7.0 Hz, 1H), 7.98 (s, 1H), 7.36 (s, 1H), 6.86 (dd, J=1.6, 7.2 Hz, 1H), 4.10 (q, J=7.2 Hz, 2H), 1.09 (t, J=7.2 Hz, 3H). MS m/z 208.1 (M+1)$^+$.

To a stirring suspension of ethyl 7-methyl-d$_3$-imidazo[1,2-a]pyridine-3-carboxylate (94) (142 mg, 0.69 mmol) in THF:MeOH: H$_2$O (3:2:1, 3 mL) was added 6N LiOH (0.34 mL). The reaction was stirred at room temperature for 2 hours then neutralized with sodium bisulfate monohydrate and concentrated to afford 7-methyl-d$_3$-imidazo[1,2-a]pyridine-3-carboxylic acid (95), which was immediately used without purification. MS (m/z) 180.1 (M+1)$^+$.

Synthesis of 6((2,2,2-trifluoroethoxy)methyl)imidazo[1,2-a]pyridine-3-carboxylic acid (98)

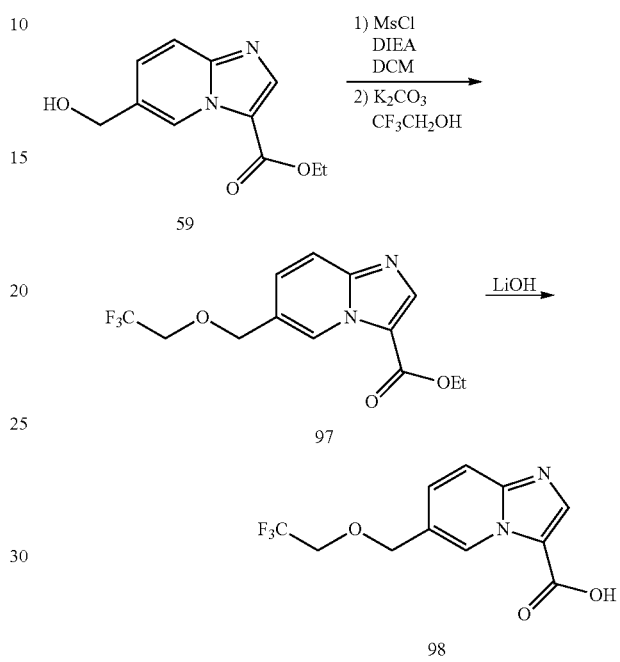

To a solution of ethyl 6-(hydroxymethyl)imidazo[1,2-a]pyridine-3-carboxylate (59) (460 mg, 2.2 mmol) and DIEA (0.78 mL, 4.4 mmol) in DCM (5 mL) was added MsCl (303 mg, 2.64 mmol). The mixture was stirred at room temperature for 10 minutes then subjected to standard aqueous work up to give a residue. The crude product was dissolved in 2,2,2-trifluoroethanol (2 mL) and was added K$_2$CO$_3$ (608 mg, 4.4 mmol). The reaction mixture was heated at 80° C. for 2 hours. Once complete, the reaction mixture was diluted and extracted with EtOAc. The organic layers were combined, dried over Na$_2$SO$_4$, filtered and concentrated to afford a residue which was purified by silica chromatography to yield ethyl 6-((2,2,2-trifluoroethoxy)methyl)imidazo[1,2-a]pyridine-3-carboxylate (97). $^1$H NMR (400 MHz, CDCl$_3$) δ 9.33 (m, 1H), 8.32 (s, 1H), 7.76 (dd, J=0.8, 9.2 Hz, 1H), 7.47 (dd, J=2.0, 9.2 Hz, 1H), 4.76 (s, 2H), 4.44 (q, J=7.2 Hz, 2H), 3.92 (q, J=8.4 Hz, 2H), 1.45 (t, J=7.2 Hz, 3H). MS m/z 303.1 (M+1)$^+$.

A solution of ethyl 6-((2,2,2-trifluoroethoxy)methyl)imidazo[1,2-a]pyridine-3-carboxylate (97) (280 mg, 0.92 mmol) in THF/MeOH/H$_2$O (3:2:1, 5 mL) was treated with 6N LiOH (0.92 mL, 5.52 mmol) and stirred at room temperature for 1 hour. All solvents were removed and 6N HCl was added to adjust pH 5-6. Then the mixture was purified by HPLC to give 6-((2,2,2-trifluoroethoxy)methyl)imidazo[1,2-a]pyridine-3-carboxylic acid (98). $^1$H NMR (400 MHz, d$_6$-DMSO) δ 9.34 (m, 1H), 8.40 (s, 1H), 7.88 (dd, J=0.8, 9.2 Hz, 1H), 7.65 (dd, J=1.6, 9.2 Hz, 1H), 4.83 (s, 2H), 4.18 (q, J=9.6 Hz, 2H). MS m/z 275.1 (M+1)$^+$.

Synthesis of 6-(3-(methoxymethyl)-1H-1,2,4-triazol-5-yl)imidazo[1,2-a]pyridine-3-carboxylic acid (99)

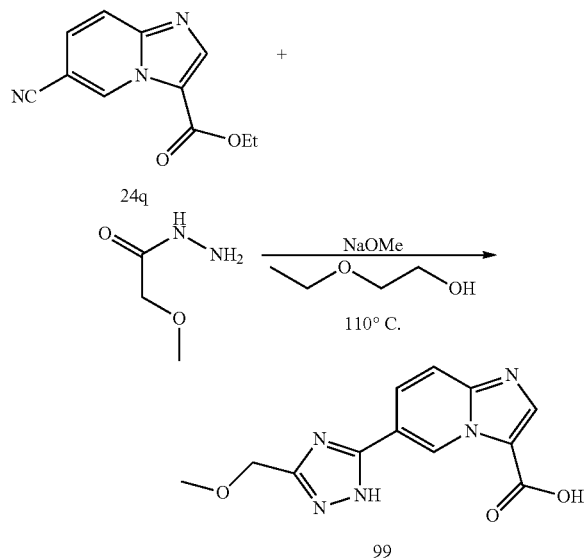

To a solution of ethyl 6-cyanoimidazo[1,2-a]pyridine-3-carboxylate (24q) (265 mg, 1.23 mmol) and 2-methoxyacetohydrazide (193 mg, 1.85 mmol) in 2-ethoxyethanol (5 mL) was added NaOMe (0.5 M in MeOH, 3.7 mL). The mixture was heated at 110° C. in a sealed vial overnight. The reaction mixture was purified by HPLC to give 6-(3-(methoxymethyl)-1H-1,2,4-triazol-5-yl)imidazo[1,2-a]pyridine-3-carboxylic acid (99). MS m/z 274.1 (M+1)$^+$.

Synthesis of 5-(5-(azetidin-1-yl)-1,2,4-oxadiazol-3-yl)-2-methylaniline (109)

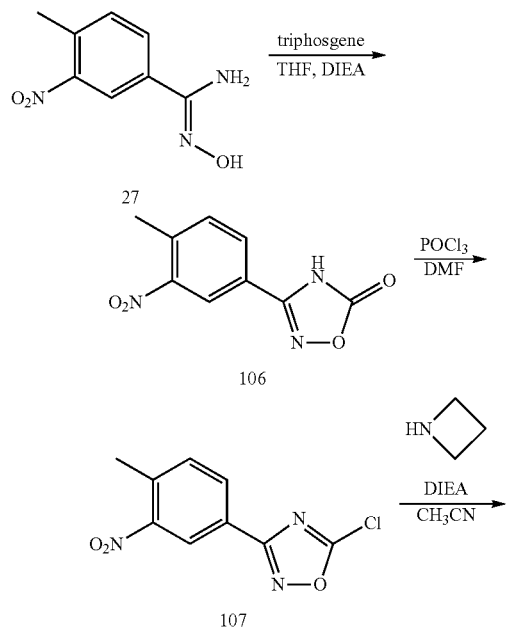

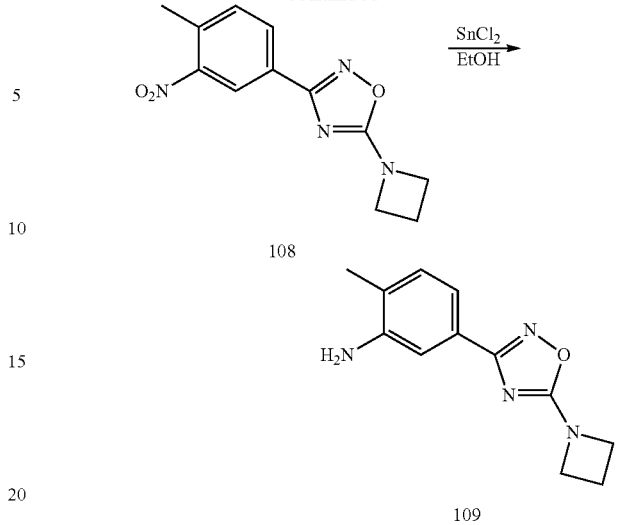

To a solution of (Z)—N'-hydroxy-4-methyl-3-nitrobenzimidamide (27) (30 g, 153.71 mmol, 1.00 equiv) and DIEA (39.7 g, 307.18 mmol, 2.00 equiv) in tetrahydrofuran (300 mL) was added dropwise to a solution of triphosgene (18.2 g) in tetrahydrofuran (50 mL). The reaction was stirred for 1 hour at room temperature then heated to reflux for an additional hour. The resulting solution was poured into 500 mL of water and extracted with 3×300 mL of ethyl acetate. The combined organic layers were washed with brine (3×200 mL), dried over anhydrous sodium sulfate, concentrated under vacuum, and purified by flash chromatography (DCM/MeOH=20:1) to afford of 3-(4-methyl-3-nitrophenyl)-1,2,4-oxadiazol-5(4H)-one as a pale yellow solid (106). MS m/z 222.1 (M+1)$^+$.

To a solution of 3-(4-methyl-3-nitrophenyl)-1,2,4-oxadiazol-5(4H)-one (106) (12 g, 54.26 mmol) in POCl$_3$ (120 mL) was added N,N-dimethylformamide (12 mL). The resulted solution was heated to reflux for 72 hours then concentrated under vacuum. The residue was dissolved in water (250 mL) and extracted with ethyl acetate (3×250 mL). The combined organic layers were washed with brine (3×250 mL), dried over anhydrous sodium sulfate and concentrated under vacuum. The residue was purified by flash chromatography (PE/EA=10:1) to afford 5-chloro-3-(4-methyl-3-nitrophenyl)-1,2,4-oxadiazole (107) as a white solid. $^1$H NMR (300 MHz, CDCl$_3$) δ 8.64 (dd, J=1.5, 8.4 Hz, 1H), 8.18 (dd, J=1.5, 7.8 Hz, 1H), 7.56 (d, J=8.1 Hz, 1H), 2.70 (s, 3H). MS m/z 240.7 (M+1)$^+$.

To a solution of 5-chloro-3-(4-methyl-3-nitrophenyl)-1,2,4-oxadiazole (107) (3.6 g, 15.02 mmol, 1.00 equiv) in CH$_3$CN (40 mL) was added triethylamine (3.03 g, 29.94 mmol) and azetidine hydrochloride (1.68 g, 17.96 mmol). The resulting solution was stirred for 1 hour at room temperature, concentrated under vacuum and purified by prep-HPLC to afford 5-(azetidin-1-yl)-3-(4-methyl-3-nitrophenyl)-1,2,4-oxadiazole (108) as a white solid. MS m/z 261.1 (M+1)$^+$.

To a stirred solution of 5-(azetidin-1-yl)-3-(4-methyl-3-nitrophenyl)-1,2,4-oxadiazole (108) (1.4 g, 5.38 mmol) in ethanol (25 mL) was added SnCl$_2$.2H$_2$O (6.07 g, 26.90 mmol). The resulting solution was stirred for 20 min at reflux then cooled to room temperature and concentrated under vacuum. The residue was poured into saturated sodium hydroxide (50 mL) and extracted with ethyl acetate (3×50 mL). The combined organic layers were washed with brine (3×250 mL), dried over anhydrous sodium sulfate, concentrated under vacuum and purified by flash chromatography (PE/EA=10:1) to afford 5-(5-(azetidin-1-yl)-1,2,4-oxadiazol-3-yl)-2-methylaniline (109) (0.8 g, 65% yield) as a white solid. $^1$H NMR (300 MHz, CDCl$_3$) δ 7.28-7.36 (m, 2H), 7.12 (d, J=7.8 Hz, 1H), 4.32 (t, J=7.5 Hz, 4H), 3.69 (brs, 2H), 2.47-2.57 (m, 2H), 2.21 (s, 3H). MS m/z 231.1 (M+1)$^+$.

Synthesis of 6-carbamoylimidazo[1,2-a]pyridine-3-carboxylic acid (110)

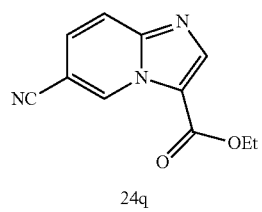

24q

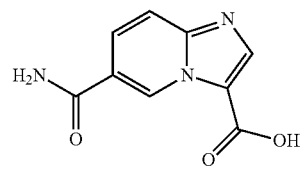

110

To a stirring solution of ethyl 6-cyanoimidazo[1,2-a]pyridine-3-carboxylate (24q) (500 mg, 2.32 mmol) in THF:MeOH (4:1, 5 mL) was added 2N LiOH (4 mL). The reaction was heated at 60° C. for 2 h then acidified with 10% citric acid. The solvent was partially concentrated and the resulting solid was collected by vacuum filtration and was washed with excess water. The product was purified from the crude solid to afford 6-carbamoylimidazo[1,2-a]pyridine-3-carboxylic acid (110). $^1$H NMR (400 MHz, d$_6$-DMSO) δ 9.80 (s, 1H), 8.33-8.31 (m, 1H), 8.29 (s, 1H), 7.95 (dd, J=2.0, 9.6 Hz, 1H), 7.83 (dd, J=0.8, 9.2 Hz, 1H), 7.69 (s, 1H). MS m/z 205.05 (M+1)$^+$.

Synthesis of 6-(2-(4-methylpiperazin-1-yl)ethyl) imidazo[1,2-a]pyridine-3-carboxylic acid (114)

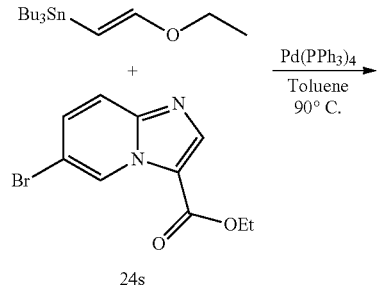

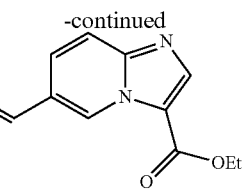

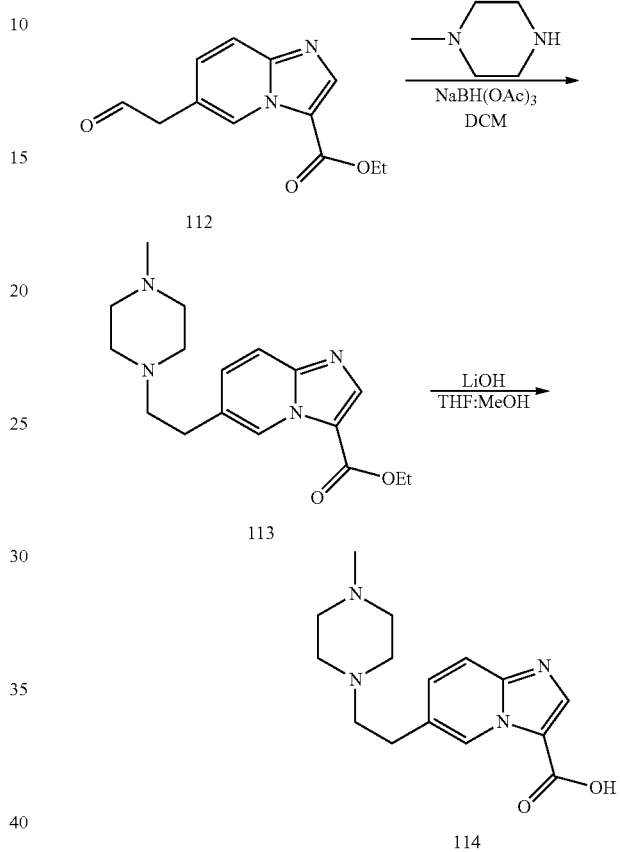

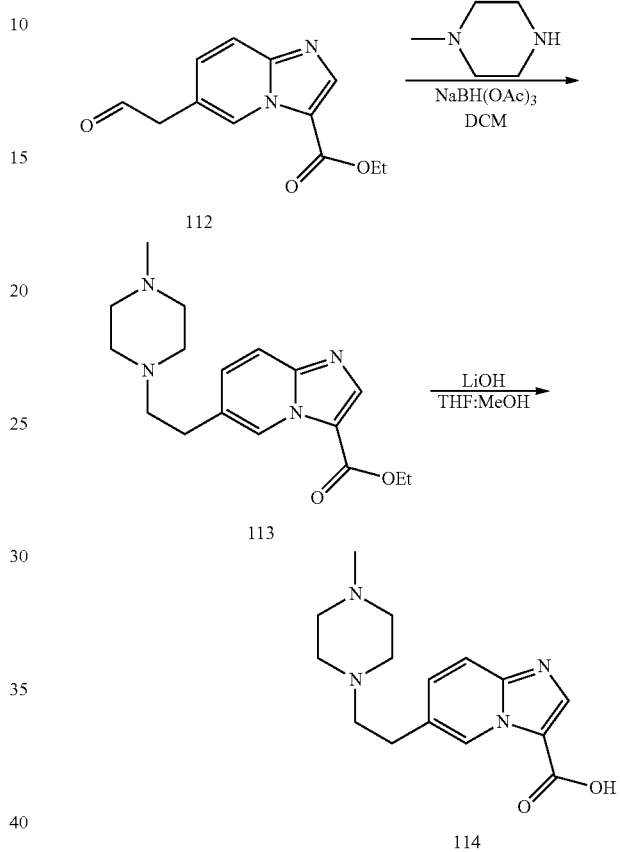

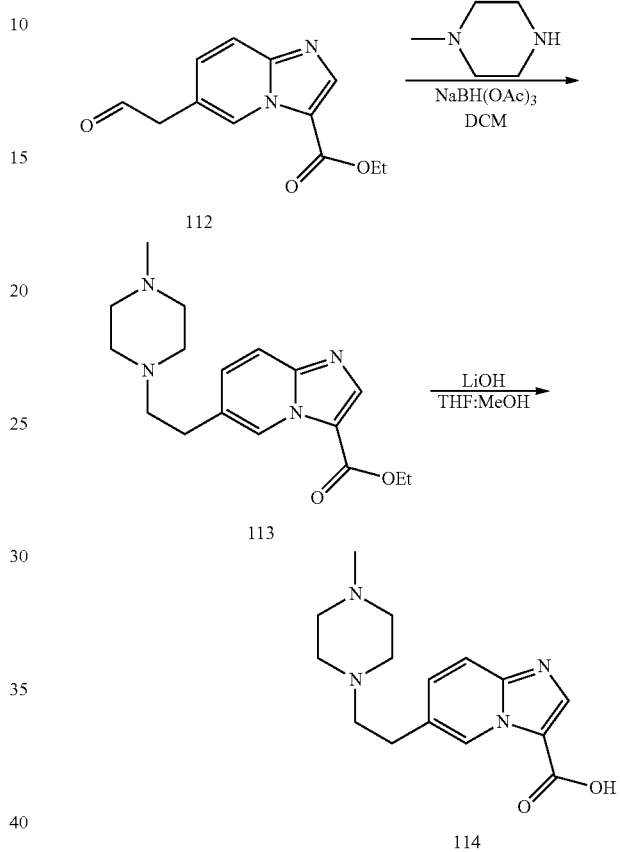

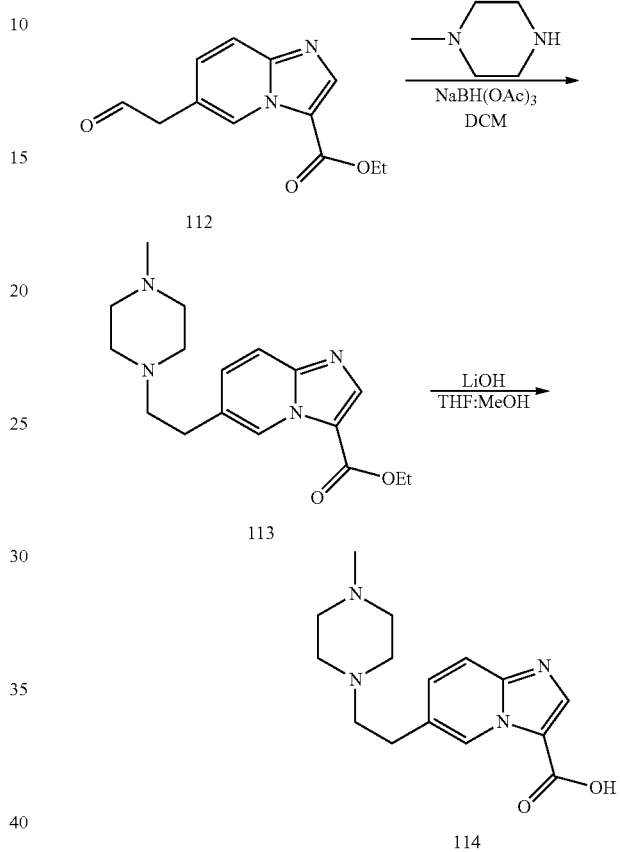

To a stirring mixture of ethyl 6-bromoimidazo[1,2-a]pyridine-3-carboxylate (24s) (1 g, 3.72 mmol) and tetrakis(triphenylphosphine)palladium(0) (215 mg, 0.19 mmol) in anhydrous toluene (10 mL) under argon was added tributyl[2-ethoxyethenyl]stannane (1.7 g, 4.65 mmol). The reaction mixture was heated in a microwave sealed tube overnight at 90° C. The reaction was cooled to room temperature and was filtered through celite. The solvent was concentrated and the crude product was purified by silica chromatography to afford (E)-ethyl 6-(2-ethoxyvinyl)imidazo[1,2-a]pyridine-3-carboxylate (111). MS m/z 261.3 (M+1)$^+$.

A stirring solution of ethyl 6-(2-ethoxyvinyl)imidazo[1,2-a]pyridine-3-carboxylate (111) (240 mg, 1.15 mmol) in THF:H$_2$O (1:1, 4 mL) was heated at 50° C. overnight. The reaction was cooled to room temperature and neutralized with saturated solution of sodium bicarbonate. The crude product was extracted with ethyl acetate. The organic layer was washed with water, brine and dried over anhydrous sodium sulfate. The solvent was concentrated and crude ethyl 6-(2-oxoethyl)imidazo[1,2-a]pyridine-3-carboxylate (112) was used in the next step without further purification. MS m/z 233.3 (M+1)$^+$.

To a stirring solution of crude ethyl 6-(2-oxoethyl)imidazo[1,2-a]pyridine-3-carboxylate (112) (214 mg, 0.92 mmol) in DCM (5 mL) and 1-methylpiperazine (231 μL, 2.30 mmol) at room temperature was added portion-wise sodium triacetoxyborohydride (586 mg, 2.77 mmol). The reaction was stirred at room temperature overnight. The solvent was concentrated. The crude was taken in 10% sodium bicarbonate and ethyl acetate. The organic was washed with water, brine and dried over anhydrous sodium sulfate. The solvent was concentrated and the crude product was purified by silica chromatography to afford methyl 6-(2-(4-methylpiperazin-1-yl)ethyl)imidazo[1,2-a]pyridine-3-carboxylate (113). MS m/z 304.4 (M+1)$^+$.

To a stirring solution of methyl 6-(2-(4-methylpiperazin-1-yl)ethyl)imidazo[1,2-a]pyridine-3-carboxylate (113) (215 mg, 0.68 mmol) in THF:MeOH (4:1, 4 mL) was added 2N LiOH (3 mL). The reaction was heated at 60° C. for 45 minutes. The pH was adjusted between 4-5 with 1N HCl and concentrated. The crude product was purified by preparative HPLC to afford 6-(2-(4-methylpiperazin-1-yl)ethyl)imidazo[1,2-a]pyridine-3-carboxylic acid (114). $^1$H NMR (400 MHz, d$_6$-DMSO) δ 9.25 (s, 1H), 8.35 (s, 1H), 7.83 (d, J=9.2 Hz, 1H), 7.61 (dd, J=1.6, 9.2 Hz, 1H), 4.65-4.19 (m, 8H), 3.49-3.30 (m, 2H), 3.04-2.99 (m, 2H), 2.81 (s, 3H). MS m/z 316.1 (M+1)$^+$.

Synthesis of tert-butyl 3-(3-(3-(imidazo[1,2-a]pyridine-3-carboxamido)-4-methylphenyl)-1,2,4-oxadiazol-5-yl)azetidin-1-ylsulfonylcarbamate (128)

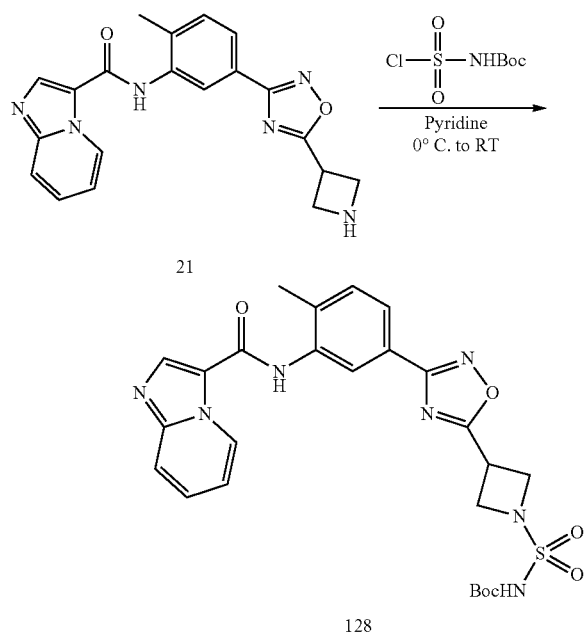

To a stirring solution of N-(5-(5-(azetidin-3-yl)-1,2,4-oxadiazol-3-yl)-2-methylphenyl)imidazo[1,2-a]pyridine-3-carboxamide (21) (50 mg, 0.133 mmol) in anhydrous pyridine (1.5 mL) at 0° C. was added tert-butyl chlorosulfonylcarbamate (35 mg, 0.160 mmol). The reaction was stirred to room temperature for 1 hour. The reaction was quenched with water and the solvent was concentrated. The crude product tert-butyl 3-(3-(3-(imidazo[1,2-a]pyridine-3-carboxamido)-4-methylphenyl)-1,2,4-oxadiazol-5-yl)azetidin-1-ylsulfonylcarbamate (128) was purified by preparative HPLC. $^1$H NMR (400 MHz, d$_6$-DMSO) δ 11.27 (s, 1H), 10.25 (s, 1H), 9.55-9.53 (m, 1H), 8.76 (s, 1H), 8.07 (d, J=1.6 Hz, 1H), 7.93-7.90 (m, 1H), 7.84 (dd, J=1.6, 8.0 Hz, 1H), 7.75-7.71 (m, 1H), 7.52 (d, J=8.4 Hz, 1H), 7.37-7.34 (m, 1H), 4.37-4.33 (m, 5H), 2.38 (s, 3H), 1.38 (s, 9H). MS m/z 554.17 (M+1)$^+$.

Synthesis of methyl 3-(3-(4-methyl-3-(6-(((methylsulfonyl)oxy)methyl)imidazo[1,2-a]pyridine-3-carboxamido)phenyl)-1,2,4-oxadiazol-5-yl)azetidine-1-carboxylate (133)

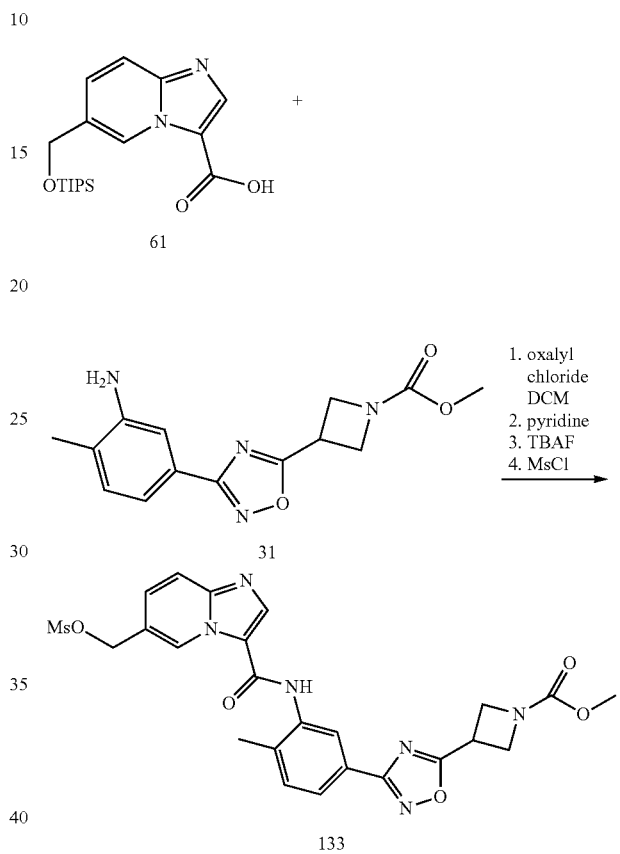

To a stirring suspension of 6-(((triisopropylsilyl)oxy)methyl)imidazo[1,2-a]pyridine-3-carboxylic acid (61) (70 mg, 0.20 mmol) in anhydrous dichloromethane (5 mL) at room temperature oxalyl chloride was added dropwise (0.05 mL, 2.22 mmol). Then, one drop of anhydrous DMF was added and the reaction mixture was stirred at room temperature for 15 minutes. The solvent was concentrated and the crude solid was added to a stirring solution of methyl 3-(3-(3-amino-4-methylphenyl)-1,2,4-oxadiazol-5-yl)azetidine-1-carboxylate (31) (51.1 mg, 0.18 mmol) in anhydrous pyridine (5 mL) at room temperature. The reaction was stirred for 20 minutes. Water (20 mL) was added to the reaction mixture and extraction with EtOAc afforded a residue after removing organic solvents. To the above residue, was added THF (0.5 mL) and TBAF (1M in THF, 0.30 mL) and the resulting mixture was stirred for 30 minutes. THF was removed and the residue was dissolved in EtOAc (20 mL) and washed with water twice. The organic layers were combined, dried over Na$_2$SO$_4$, filtered and concentrated to give a crude residue which was dissovled in DCM (1 mL) and followed by addition of DIEA (52 mg, 0.40 mmol) and MsCl (46 mg, 0.4 mmol). The reaction was stirred for 10 minutes. The mixture was diluted with DCM (10 mL) and washed with water. The organic layers were combined, dried over Na₂SO₄, filtered and concentrated to give methyl 3-(3-(4-methyl-3-(6-(((methylsulfonyl)oxy)methyl)imidazo[1,2-a]pyridine-3-carboxamido)phenyl)-1,2,4-oxadiazol-5-yl)azetidine-1-carboxylate (133) which was used without further purification. MS m/z 541.1 (M+1)⁺.

Synthesis of 5-(4-methyl-1H-imidazol-1-yl)pyridin-2-amine (134)

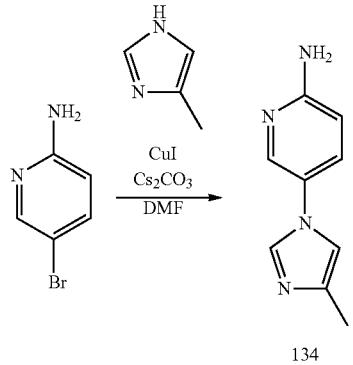

134

To a microwave tube with a magnetic stirring bar was charged CuI (382 mg, 2.0 mmol), Cs₂CO₃ (6.5 g, 20.0 mmol), 4-methyl-1H-imidazole (1.15 g, 14.0 mmol), 5-bromopyridin-2-amine (1.75 g, 10.0 mmol), and DMF (10 mL) under N₂. The system was sealed and then evacuated twice and back filled with N₂. The reaction mixture was stirred for 30 min at room temperature, and then heated at 120° C. for 48 h. The reaction mixture was then cooled to ambient temperature, diluted with 30 mL of ethyl acetate, washed with water. The combined organic layers were concentrated, and the resulting residue was purified by column chromatography on silica gel to provide 5-(4-methyl-1H-imidazol-1-yl)pyridin-2-amine (134). ¹H NMR (400 MHz, d₆-DMSO) δ 8.09 (m, 1H), 7.85 (d, J=1.6 Hz, 1H), 7.56 (dd, J=2.8, 8.8 Hz, 1H), 7.22 (t, J=1.2 Hz, 1H), 6.51 (dd, J=0.8, 8.8 Hz, 1H), 6.15 (s, 2H), 2.14 (d, J=1.2 Hz, 3H). MS m/z 175.1 (M+1)⁺.

Synthesis of 6-bromo-N-(5-(5-((3-cyanoazetidin-1-yl)methyl)-1,2,4-oxadiazol-3-yl)-2-methylphenyl)imidazo[1,2-a]pyridine-3-carboxamide (143)

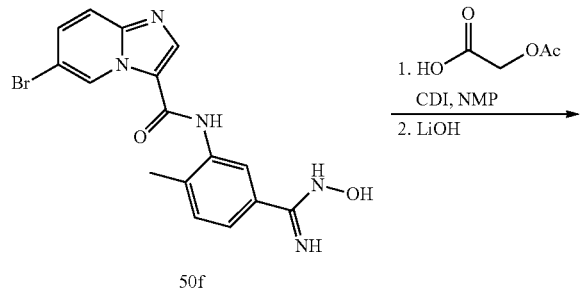

50f

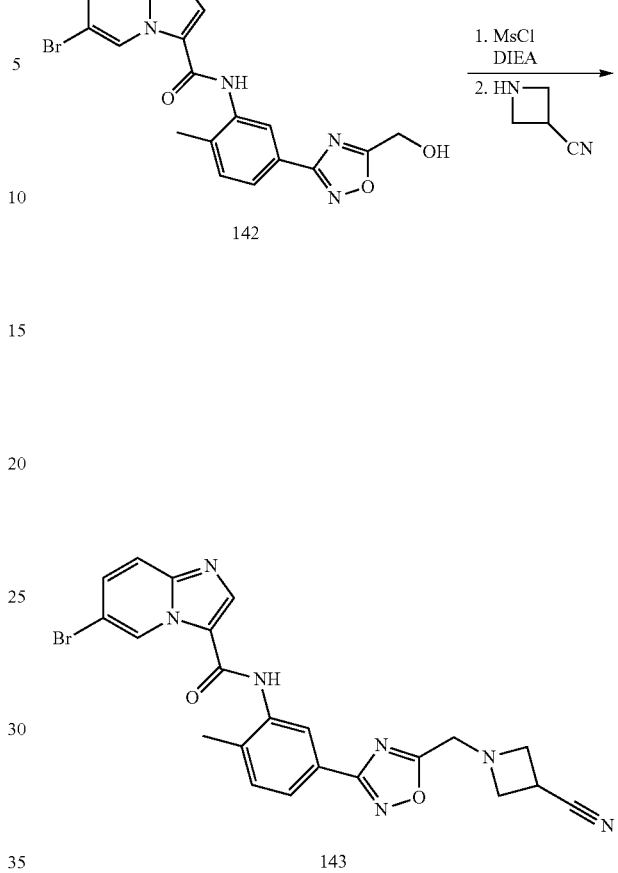

Carbonyl diimidazole (CDI) (2.3 g, 14.24 mmol) was added to a stirred solution of 2-acetoxyacetic acid (1.68 g, 14.24 mmol) in NMP (10 mL). After 30 minutes, 6-bromo-N-(5-(N-hydroxycarbamimidoyl)-2-methylphenyl)imidazo[1,2-a]pyridine-3-carboxamide (50f) (1.38 g, 3.56 mmol) was added in one portion and the resulting solution was stirred for 30 minutes before it was heated at 125° C. for 15 minutes in a microwave reactor. The reaction solution was subjected to standard aqueous work up to afford a residue which was hydrolyzed by lithium hydroxide monohydrate (897 mg, 21.36 mmol) in THF/MeOH/H₂O (3:2:1). After removal of all solvents 2M NaHCO₃ (10 mL) was added. The precipitate was filtered and dried in air to afford 6-bromo-N-(5-(5-(hydroxymethyl)-1,2,4-oxadiazol-3-yl)-2-methylphenyl)imidazo[1,2-a]pyridine-3-carboxamide (142). ¹H NMR (400 MHz, d₆-DMSO) δ 10.14 (s, 1H), 9.64 (d, J=1.2 Hz, 1H), 8.60 (s, 1H), 8.11 (d, J=1.6 Hz, 1H), 7.83 (dd, J=1.6, 8.0 Hz, 1H), 7.79 (dd, J=0.8, 9.6 Hz, 1H), 7.67 (dd, J=2.0, 9.6 Hz, 1H), 7.51 (d, J=8.0 Hz, 1H), 6.09 (s, 1H), 4.81 (s, 2H), 2.37 (s, 3H). MS m/z 427.9, 429.9 (M+1)⁺.

To a solution of 6-bromo-N-(5-(5-(hydroxymethyl)-1,2,4-oxadiazol-3-yl)-2-methylphenyl)imidazo[1,2-a]pyridine-3-carboxamide (142) (200 mg, 0.47 mmol) and DIEA (0.25 mL, 1.41 mmol) in dichloromethane (5 mL) was added MsCl (108.1 mg, 0.94 mmol). The mixture was stirred at room temperature for 10 minutes and then diluted with dichloromethane (10 mL) and washed with water. The organic layers were dried over Na₂SO₄, filtered and concentrated to give a residue which was dissolved in DMF (2 mL). Then azetidine-3-carbonitrile (116 mg, 1.41 mmol) was added and the reaction mixture was heated at 80° C. for 1 hour. The reaction mixture was diluted with water (50 mL) and extracted with EtOAc. The organic layers were dried over $Na_2SO_4$, filtered and concentrated to give the crude product which was purified by silica chromatography to yield 6-bromo-N-(5-(5-((3-cyanoazetidin-1-yl)methyl)-1,2,4-oxadiazol-3-yl)-2-methylphenyl)imidazo[1,2-a]pyridine-3-carboxamide (143). $^1$H NMR (400 MHz, $d_6$-DMSO) δ 10.15 (s, 1H), 9.62 (dd, J=0.8, 2.0 Hz, 1H), 8.60 (s, 1H), 8.07 (d, J=1.6 Hz, 1H), 7.83 (dd, J=1.6, 8.0 Hz, 1H), 7.79 (dd, J=0.8, 9.6 Hz, 1H), 7.68 (dd, J=2.0, 9.6 Hz, 1H), 7.51 (d, J=8.4 Hz, 1H), 4.06 (s, 2H), 3.67 (m, 2H), 3.51-3.60 (m, 3H), 2.37 (s, 3H). MS m/z 492.0, 494.0 (M+1)$^+$.

Synthesis of 6-(2,4-dimethylthiazol-5-yl)imidazo[1,2-a]pyridine-3-carboxylic acid (146) was collected by vacuum filtration to give 6-(2,4-dimethylthiazol-5-yl)imidazo[1,2-a]pyridine-3-carboxylic acid (146). $^1$H NMR (400 MHz, $d_6$-DMSO) δ 9.34 (s, 1H), 8.29 (s, 1H), A mixture of ethyl 6-(2,4-dimethylthiazol-5-yl)imidazo[1,2-a]pyridine-3-carboxylate (145) (190 mg, 0.630 mmol) and 2N LiOH (1 mL) in THF:MeOH (4:1, 4 mL) was heated at 60° C. for 30 minutes. The reaction was cooled to room temperature and the pH was adjusted between 4-5 with 10% citric acid. The solvent was partially reduced and the resulting solid 7.87 (dd, J=0.8, 9.2 Hz, 1H), 7.62 (dd, J=2.0, 9.2 Hz, 1H), 2.66 (s, 3H), 2.41 (s, 3H). MS m/z 274.06 (M+1)$^+$.

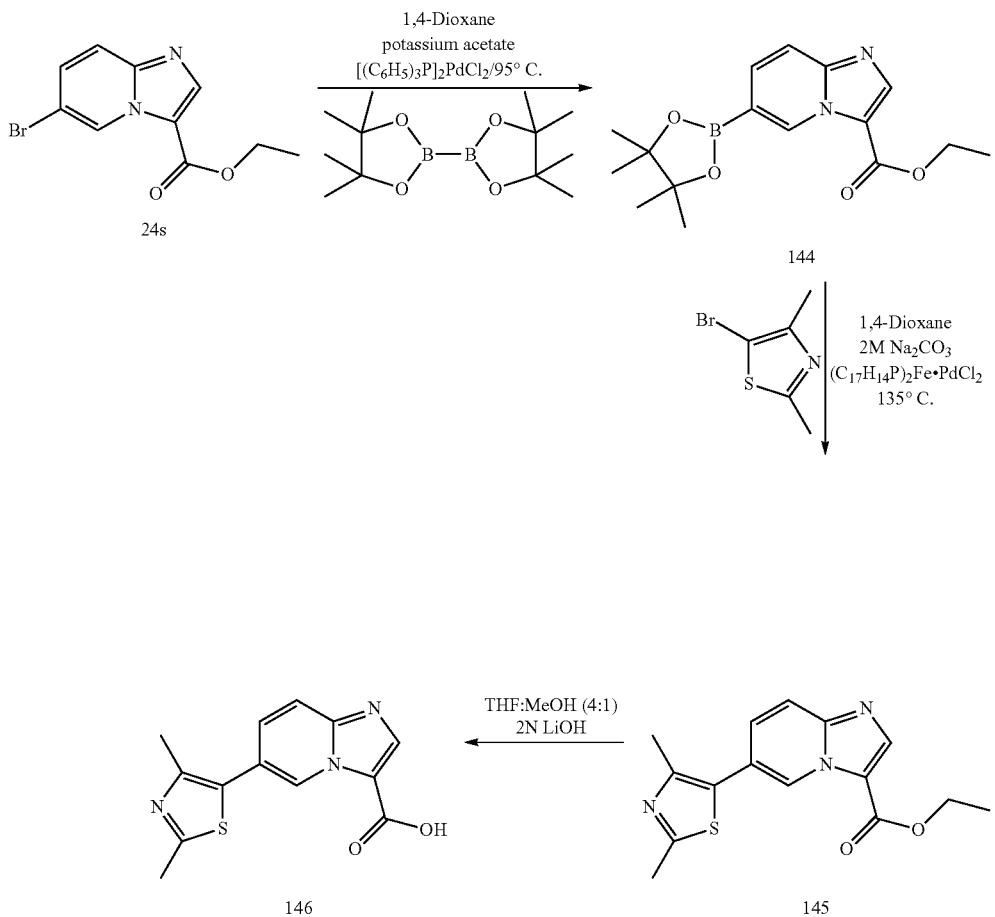

A mixture of ethyl 6-bromoimidazo[1,2-a]pyridine-3-carboxylate (24s) (500 mg, 1.86 mmol), bis(pinacolato)diboron (472 mg, 1.86 mmol), dichloro-bis(triphenylphosphine)palladium (65 mg, 0.093 mmol) and potassium acetate (456 mg, 4.65 mmol) in anhydrous dioxane (8 mL) was heated at 95° C. for 4 hours. The reaction turned black. The reaction was cooled and filtered through celite. The solvent was concentrated. The oil was taken in EtOAc. The organic was washed with water/brine mixture, brine and dried over anhydrous sodium sulfate. The crude product was purified by silica chromatography. MS m/z 317 (M+1)+.

A mixture of 5-bromo-2,4-dimethylthiazole (171 mg, 0.89 mmol), ethyl 6-(4,4,5,5-tetramethyl-1,3,2-dioxaborolan-2-yl)imidazo[1,2-a]pyridine-3-carboxylate (144) (250 mg, 1.07 mmol), [1,1'-Bis(diphenylphosphino)ferrocene]dichloropalladium(11) (39 mg, 0.05 mmol) and a solution of 2M sodium carbonate (300 uL) in anhydrous dioxane (4 mL) was heated in the microwave at 135° C. for 25 minutes. The reaction was filtered through celite. The crude product was taken in water and ethylacetate. The organic was washed with water/brine mixture and dried over anhydrous sodium sulfate. The crude product was purified by silica chromatography. MS m/z 302.09 (M+1)+.

Synthesis of N-(5-(5-(chloromethyl)-1,2,4-oxadiazol-3-O-2-methylphenyl)imidazo[1,2-a]pyridine-3-carboxamide (151)

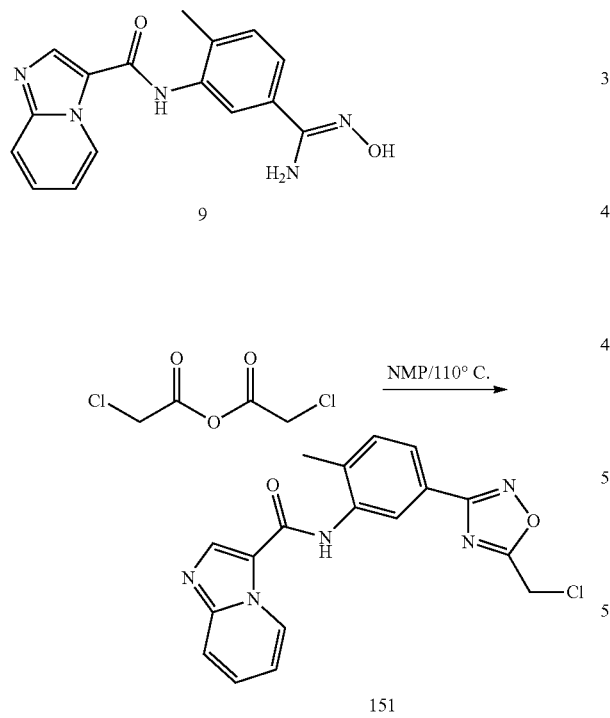

A mixture of N-(5-(N'-hydroxycarbamimidoyl)-2-methylphenyl)imidazo[1,2-a]pyridine-3-carboxamide 9 (500 mg, 1.62 mmol) and 2-chloroacetic anhydride (553 mg, 3.23 mmol) in anhydrous 1-methyl-2-pyrrolidinone (10 mL) was heated in the microwave at 110° C. for 12 minutes. The crude was diluted with water and extracted with ethyl acetate. The organic was washed with water/brine mixture and dried over anhydrous sodium sulfate. The crude product was purified by silica chromatography. MS m/z 368.08 (M+1)+.

Synthesis of Final Compounds

Synthesis of N-(5-(5-(5,5-difluorotetrahydro-2H-pyran-2-yl)-1,2,4-oxadiazol-3-yl)-2-methylphenyl)imidazo[1,2-a]pyridine-3-carboxamide (F10)

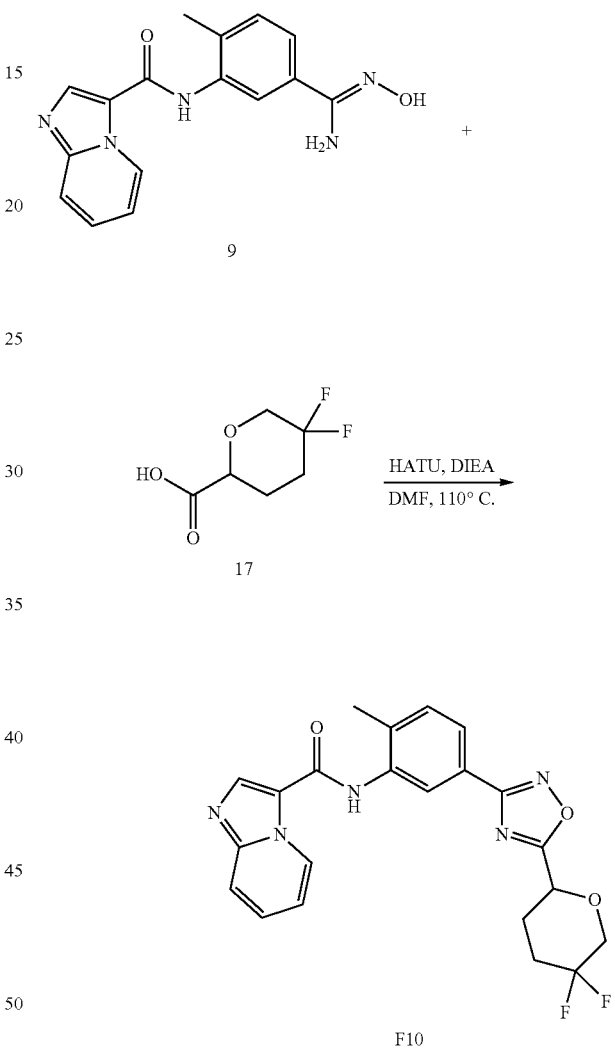

HATU (0.134 g, 0.355 mmol) was added in one portion to a stirred solution of 5,5-difluorotetrahydro-2H-pyran-2-carboxylic acid (17) (53 mg, 0.31 mmol) and DIEA (60 L, 0.355 mmol) in dry DMF (3 mL). After 10 minutes, N-(5-(N'-hydroxycarbamimidoyl)-2-methylphenyl)imidazo[1,2-a]pyridine-3-carboxamide (9) (0.1 g, 0.323 mmol) was added in one portion and continued to stir for another 30 minutes, then heated at 110° C. for 30 minutes. The reaction was filtered and purified by preparative reverse phase HPLC to afford N-(5-(5-(5,5-difluorotetrahydro-2H-pyran-2-yl)-1,2,4-oxadiazol-3-yl)-2-methylphenyl)imidazo[1,2-a]pyridine-3-carboxamide (F10) as a white solid. $^1$H NMR (400 MHz, d$_4$-MeOH) δ 9.73 (d, J=7.2 Hz, 1H), 8.74 (s, 1H), 8.17 (m, 1H), 7.98-7.95 (m, 3H), 7.52-7.50 (m, 2H), 5.06 (dd, J=8.4, 2.8 Hz, 1H), 4.07-4.00 (m, 1H), 3.91-3.81 (m, 1H), 2.44 (s, 3H), 2.40-2.21 (m, 4H). MS m/z 440.1 (M+1)⁺.

Synthesis of tert butyl 3-(3-(3-(imidazo[1,2-a]pyridine-3-carboxamido)-4-methylphenyl)-1,2,4-oxadiazol-5-yl)azetidine-1-carboxylate (F13)

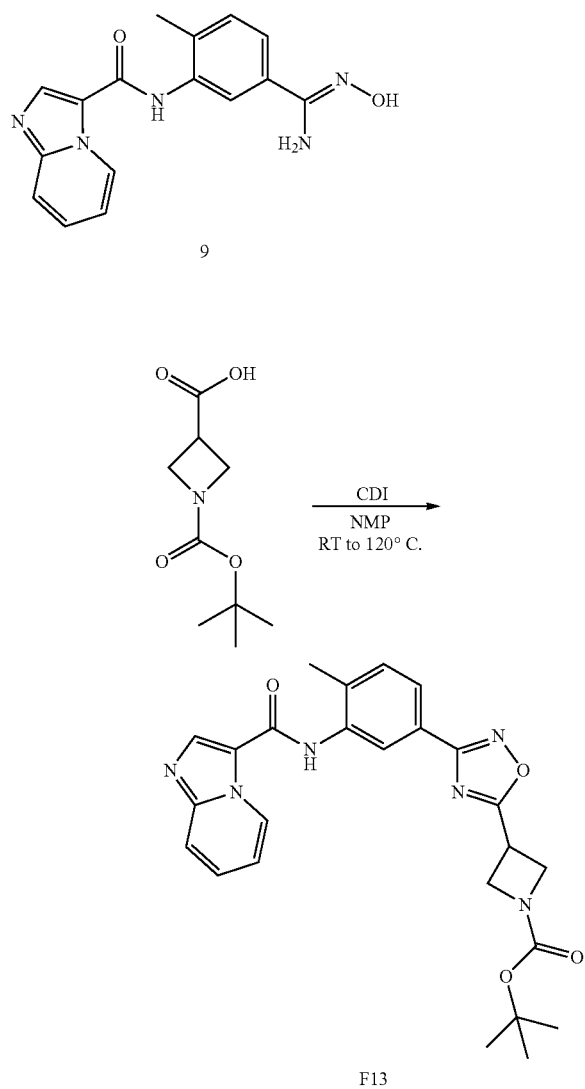

To a stirring solution of Boc-azetidine-3-carboxylic acid (162 mg, 0.8 mmol) in anhydrous NMP (4 mL) was added CDI (131 mg, 0.8 mmol). The reaction was stirred for 2 minutes. N-(5-(N'-hydroxycarbamimidoyl)-2-methylphenyl)imidazo[1,2-a]pyridine-3-carboxamide (9) (250 mg, 0.8 mmol) was added and the reaction was stirred for 15 minutes, then heated via microwave at 120° C. for 15 minutes. The crude was purified by reverse phase HPLC to afford tert-butyl 3-(3-(3-(imidazo[1,2-a]pyridine-3-carboxamido)-4-methylphenyl)-1,2,4-oxadiazol-5-yl)azetidine-1-carboxylate (F13) as a white solid. ¹H NMR (400 MHz, d₆-DMSO) δ 10.17 (s 1H), 9.51 (d, J=6.8 Hz, 1H), 8.70 (s, 1H), 8.10 (d, J=2.0 Hz, 1H), 7.86 (dt, J=12, 2.0 Hz, 2H), 7.68 (t, J=8.0 Hz, 1H), 7.51 (d, J=8 Hz, 1H), 7.31 (td, J=6.8, 0.8 Hz, 1H), 4.06-4.38 (m, 5H) 2.37 (s, 3H), 1.40 (s, 9H). MS m/z 476.2 (M+1)⁺.

Synthesis of methyl 3-(3-(3-(imidazo[1,2-a]pyridine-3-carboxamido)-4-methylphenyl)-1,2,4-oxadiazol-5-yl)azetidine-1-carboxylate (F15)

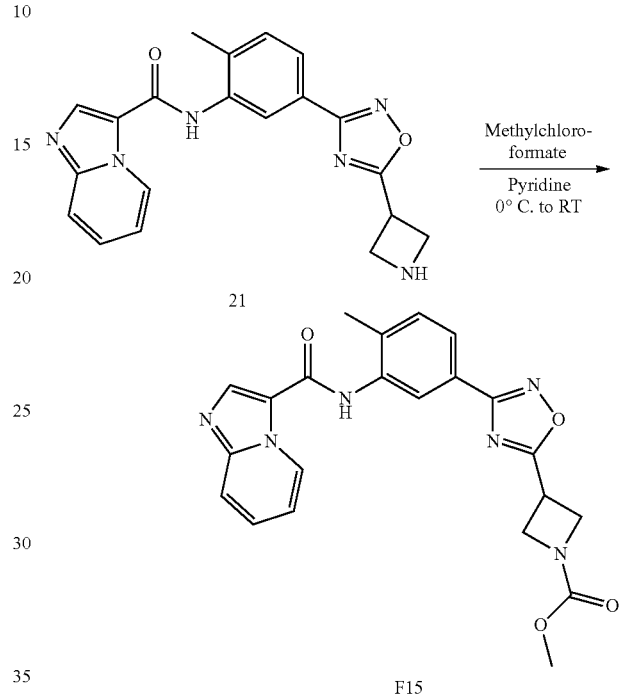

To a stirring solution of N-(5-(5-(azetidin-3-yl)-1,2,4-oxadiazol-3-yl)-2-methylphenyl)imidazo[1,2-a]pyridine-3-carboxamide (21) (25 mg, 0.0667 mmol) in anhydrous pyridine (1 mL) was added methylchloroformate (5 μL, 0.667 mmol). The reaction was stirred to room temperature for 10 minutes. The pH was adjusted to neutral with 10% citric acid. The crude was purified by reverse phase HPLC to afford methyl 3-(3-(3-(imidazo[1,2-a]pyridine-3-carboxamido)-4-methylphenyl)-1,2,4-oxadiazol-5-yl)azetidine-1-carboxylate (F15) as a white solid. ¹H NMR (400 MHz, d₆-DMSO) δ 10.18 (s 1H), 9.52 (d, J=7.2 Hz, 1H), 8.71 (s, 1H), 8.10 (s, 1H), 7.82-7.91 (m, 2H), 7.69 (t, J=8.0 Hz, 1H), 7.51 (d, J=8.4 Hz, 1H), 7.31 (td, J=7.2, 0.8 Hz, 1H), 4.15-4.44 (m, 5H) 3.59 (s, 3H), 2.37 (s, 3H). MS m/z 433.3 (M+1)⁺.

Synthesis of N-(2-methyl-5-(5-(morpholinomethyl)-1,2,4-oxadiazol-3-yl)phenyl)imidazo[1,2-a]pyridine-3-carboxamide (F22)

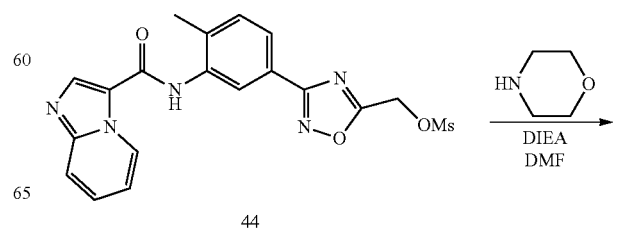

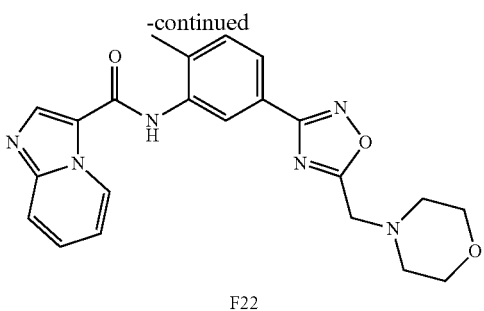

F22

A solution of (3-(3-(imidazo[1,2-a]pyridine-3-carboxamido)-4-methylphenyl)-1,2,4-oxadiazol-5-yl)methyl methanesulfonate (44) (21.4 mg, 0.05 mmol), DIEA (13.0 mg, 0.1 mmol) and morpholine (13.0 mg, 0.15 mmol) in DMF (1 mL) was heated at 80° C. for 4 hours. The crude product was purified by preparative HPLC to yield N-(2-methyl-5-(5-(morpholinomethyl)-1,2,4-oxadiazol-3-yl)phenyl)imidazo[1,2-a]pyridine-3-carboxamide (F22). $^1$H NMR (400 MHz, CD$_2$Cl$_2$) δ 9.60 (d, J=6.8 Hz, 1H), 8.60 (d, J=1.6 Hz, 1H), 8.45 (s, 1H), 8.06 (s, 1H), 7.89 (dd, J=2.0, 8.0 Hz, 1H), 7.80 (d, J=8.8 Hz, 1H), 7.54 (m, 1H), 7.43 (d, J=8.0 Hz, 1H), 7.15 (m, 1H), 3.93 (s, 2H), 3.75 (m, 4H), 2.67 (m, 4H), 2.48 (s, 3H). MS m/z 419.2 (M+1)$^+$. Note: if HCl salt of morpholine (0.15 mmol) was used, AgNO$_3$ (0.15 mmol) was needed to avoid replacement of OMs group by Cl.

Synthesis of N-(2-methyl-5-(5-(1-sulfamoylazetidin-3-yl)-1,2,4-oxadiazol-3-yl)phenyl)imidazo[1,2-a]pyridine-3-carboxamide (F23)

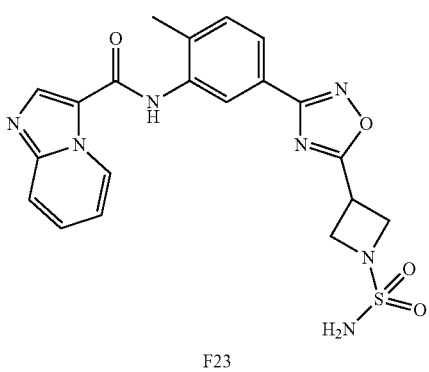

To a stirring solution of tert-butyl 3-(3-(3-(imidazo[1,2-a]pyridine-3-carboxamido)-4-methylphenyl)-1,2,4-oxadiazol-5-yl)azetidin-1-ylsulfonylcarbamate (128) (25 mg, 0.0452 mmol) in CH$_3$CN (0.5 mL) was added HCl (4N in dioxane, 1 mL). The reaction was stirred for 30 minutes. The solvent was concentrated and the crude was purified by preparative HPLC to give N-(2-methyl-5-(5-(1-sulfamoylazetidin-3-yl)-1,2,4-oxadiazol-3-yl)phenyl)imidazo[1,2-a]pyridine-3-carboxamide (F23). $^1$H NMR (400 MHz, d$_6$-DMSO) δ 10.14 (s, 1H), 9.51-9.48 (m, 1H), 8.67 (s, 1H), 8.11 (d, J=1.6 Hz, 1H), 7.87-7.84 (m, 2H), 7.66-7.61 (m, 1H), 7.52 (d, J=8.0 Hz, 1H), 7.29-7.25 (m, 1H), 7.13 (s, 2H), 4.24-4.18 (m, 1H), 4.16-4.12 (m, 2H), 4.05-4.01 (m, 2H), 2.37 (s, 3H). MS m/z 454.59 (M+1)$^+$.

Synthesis of (3-(3-(3-(imidazo[1,2-a]pyridine-3-carboxamido)-4-methylphenyl)-1,2,4-oxadiazol-5-yl)oxetan-3-yl)carbamate (F26)

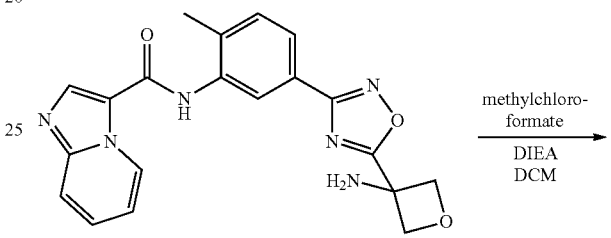

47

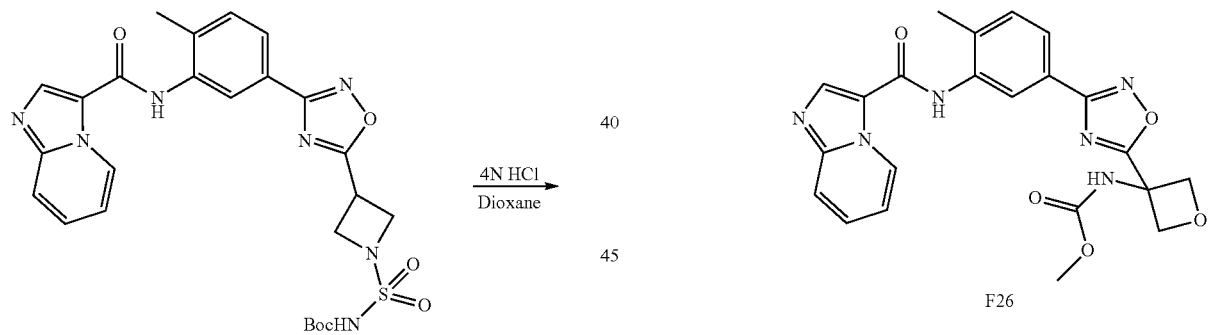

F26

To a stirring solution of N-(5-(5-(3-aminooxetan-3-yl)-1,2,4-oxadiazol-3-yl)-2-methylphenyl)imidazo[1,2-a]pyridine-3-carboxamide (47) (8.0 mg, 0.02 mmol) and DIEA (5.2 mg, 0.04 mmol) in anhydrous dichloromethane (1 mL) was added methylchloroformate (2.3 mg, 0.024 mmol). The reaction was stirred to room temperature for 10 minutes. The solvent was removed and the crude was purified by preparative HPLC to afford methyl methyl (3-(3-(3-(imidazo[1,2-a]pyridine-3-carboxamido)-4-methylphenyl)-1,2,4-oxadiazol-5-yl)oxetan-3-yl)carbamate (F26). $^1$H NMR (400 MHz, CDCl$_3$) δ 9.46 (m, 1H), 8.48 (s, 1H), 8.14 (s, 1H), 7.81 (dd, J=1.6, 8.0 Hz, 1H), 7.69 (d, J=7.2 Hz, 1H), 7.56 (s, 1H), 7.38 (m, 1H), 7.31 (d, J=8.0 Hz, 1H), 6.98 (dt, J=0.8, 6.8 Hz, 1H), 5.12 (m, 2H), 4.91 (m, 2H), 3.66 (s, 3H), 2.36 (s, 3H). MS m/z 449.1 (M+1)$^+$.

Synthesis of 3-(3-(4-fluoro-3-(imidazo[1,2-a]pyridine-3-carboxamido)phenyl)-1,2,4-oxadiazol-5-yl)azetidine-1-carboxylate (F27)

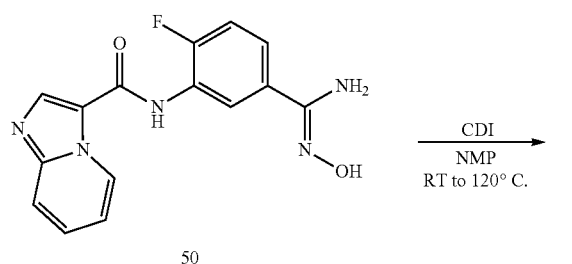

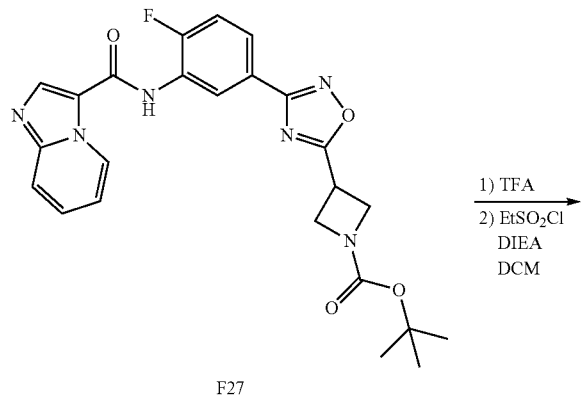

To a stirring solution of Boc-azetidine-3-carboxylic acid (162 mg, 0.8 mmol) in anhydrous NMP (4 mL) was added CDI (131 mg, 0.8 mmol). The reaction was stirred for 10 minutes. N-(2-fluoro-5-(N'-hydroxycarbamimidoyl)phenyl)imidazo[1,2-a]pyridine-3-carboxamide (50) (125 mg, 0.4 mmol) was added and the reaction was stirred for 15 minutes, then heated via microwave at 125° C. for 15 minutes. The crude was purified via reverse phase HPLC to afford tert-butyl 3-(3-(4-fluoro-3-(imidazo[1,2-a]pyridine-3-carboxamido)phenyl)-1,2,4-oxadiazol-5-yl)azetidine-1-carboxylate (F27) as a white solid. MS m/z 479.2 (M+1)$^+$.

Synthesis of N-(5-(5-(1-(ethylsulfonyl)azetidin-3-yl)-1,2,4-oxadiazol-3-yl)-2-fluorophenyl)imidazo[1,2-a]pyridine-3-carboxamide (F28)

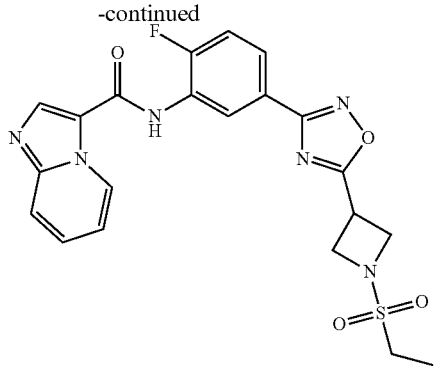

Tert-butyl 3-(3-(4-fluoro-3-(imidazo[1,2-a]pyridine-3-carboxamido)phenyl)-1,2,4-oxadiazol-5-yl)azetidine-1-carboxylate (F27) (14.4 mg, 0.03 mmol) was dissolved in TFA (0.5 mL) and stirred at room temperature for 10 minutes. Then TFA was removed under vacuum. The residue was dissolved in anhydrous dichloromethane (1 mL) and DIEA (13.0 mg, 0.10 mmol) and ethanesulfonyl chloride (5.8 mg, 0.045 mmol) were added. The reaction was stirred at room temperature for 10 minutes. The solvent was removed and the crude was purified by preparative HPLC to afford N-(5-(5-(1-(ethylsulfonyl)azetidin-3-yl)-1,2,4-oxadiazol-3-yl)-2-fluorophenyl)imidazo[1,2-a]pyridine-3-carboxamide (F28). $^1$H NMR (400 MHz, CDCl$_3$) δ 9.50 (d, J=2 Hz, 1H), 9.09 (dd, J=2, 7.2 Hz, 1H), 8.21 (s, 1H), 7.87 (m, 1H), 7.79 (m, 1H), 7.71 (d, J=9.2 Hz, 1H), 7.41 (m, 1H), 7.22 (dd, J=8.8, 10.4 Hz, 1H), 7.02 (dt, J=0.8, 6.8 Hz, 1H), 4.34 (m, 4H), 4.07 (m, 1H), 3.00 (q, J=7.6 Hz, 2H), 1.35 (t, J=7.6 Hz, 3H). MS m/z 471.1 (M+1)$^+$.

Synthesis of methyl 3-(3-(4-methyl-3-(6-(trifluoromethyl)imidazo[1,2-a]pyridine-3-carboxamido)phenyl)-1,2,4-oxadiazol-5-yl)azetidine-1-carboxylate (F52)

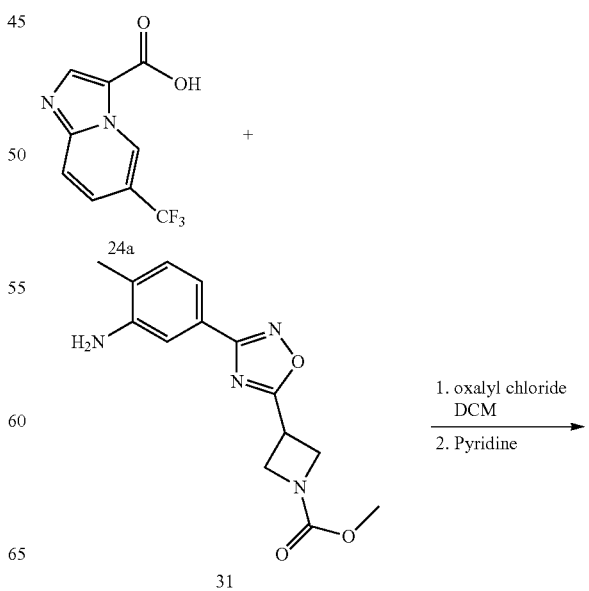

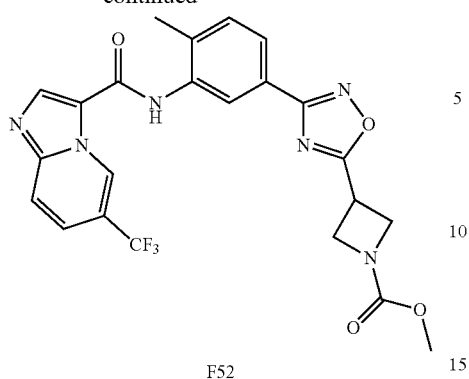

F52

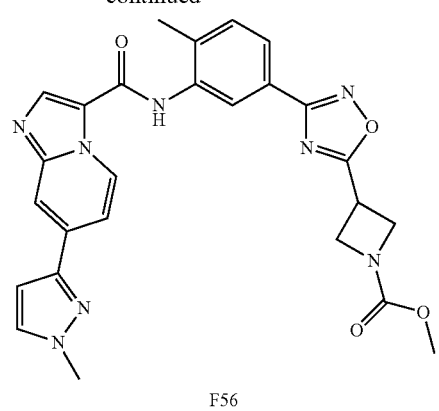

F56

To a stirring suspension of 6-(trifluoromethyl)imidazo[1,2-a]pyridine-3-carboxylic acid (24a) (50 mg, 0.217 mmol) in anhydrous dichloromethane (2 mL) at 0° C. under Argon was added dropwise oxalyl chloride (19 μL, 0.228 mmol). Then, a drop of anhydrous DMF was added and the reaction mixture was stirred at room temperature for 1.5 hours. The solvent was concentrated and the crude solid was added portion-wise to a stirring solution of methyl 3-(3-(3-amino-4-methylphenyl)-1,2,4-oxadiazol-5-yl)azetidine-1-carboxylate (31) (47 mg, 0.163 mmol) in anhydrous pyridine (1 mL) at 0° C. The reaction was stirred at room temperature under Argon for 10 minutes and quenched with water. The crude product was purified by preparative HPLC to yield methyl 3-(3-(4-methyl-3-(6-(trifluoromethyl)imidazo[1,2-a]pyridine-3-carboxamido)phenyl)-1,2,4-oxadiazol-5-yl)azetidine-1-carboxylate (F52). $^1$H NMR (400 MHz, $d_6$-DMSO) δ 10.27 (s, 1H), 9.90-9.85 (m, 1H), 8.72 (s, 1H), 8.08 (d, J=1.6 Hz, 1H), 8.02-7.99 (m, 1H), 7.86 (dd, J=2.0, 8.0 Hz, 1H), 7.79 (dd, J=2.0, 9.2 Hz, 1H), 7.52 (d, J=8.0 Hz, 1H), 4.37-4.19 (m, 5H), 3.59 (s, 3H), 2.37 (s, 3H). MS m/z 501.43 (M+1)$^+$.

Synthesis of methyl 3-(3-(4-methyl-3-(7-(1-methyl-1H-pyrazol-3-yl)imidazo[1,2-a]pyridine-3-carboxamido)phenyl)-1,2,4-oxadiazol-5-yl)azetidine-1-carboxylate (F56)

Methyl 3-(3-(3-(7-bromoimidazo[1,2-a]pyridine-3-carboxamido)-4-methylphenyl)-1,2,4-oxadiazol-5-yl)azetidine-1-carboxylate (42) (40 mg, 0.078 mmol), 1-methyl-3-(4,4,5,5-tetramethyl-1,3,2-dioxaborolan-2-yl)-1H-pyrazole (19.6 mg, 0.094 mmol) and Pd(PPh$_3$)$_4$ (9 mg, 0.0078 mmol) were added to a flask equipped with a stir bar. The flask was evacuated and backfilled with nitrogen several times. DMF (1 mL) and 1.8 M K$_2$CO$_3$ (0.094 mmol) were added by syringe. The flask was sealed and heated at 80° C. for 12 hours. The reaction was filtered and directly purified by preparative reverse phase HPLC to afford methyl 3-(3-(4-methyl-3-(7-(1-methyl-1H-pyrazol-3-yl)imidazo[1,2-a]pyridine-3-carboxamido)phenyl)-1,2,4-oxadiazol-5-yl)azetidine-1-carboxylate (F56). MS m/z 513.2 (M+1)$^+$.

Synthesis of methyl 3-(3-(4-methyl-3-(7-(trifluoromethyl)imidazo[1,2-a]pyridine-3-carboxamido)phenyl)-1,2,4-oxadiazol-5-yl)azetidine-1-carboxylate (F57)

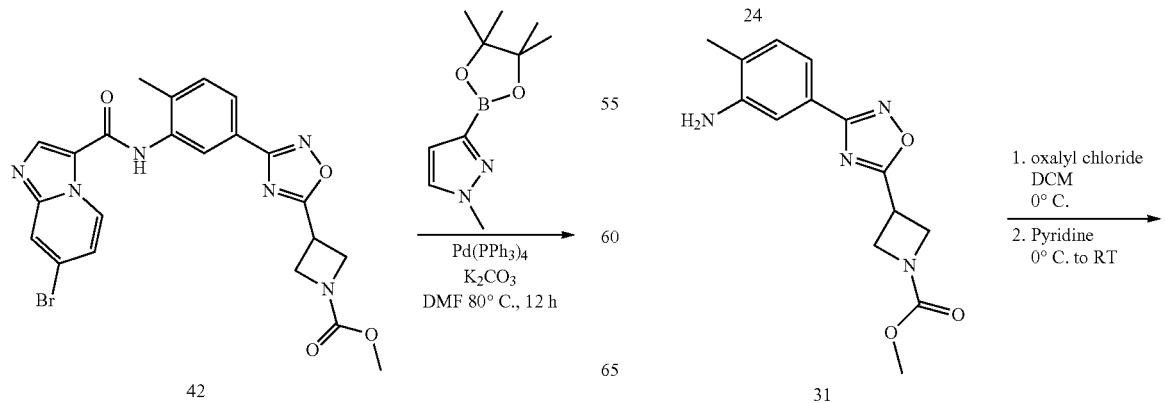

-continued

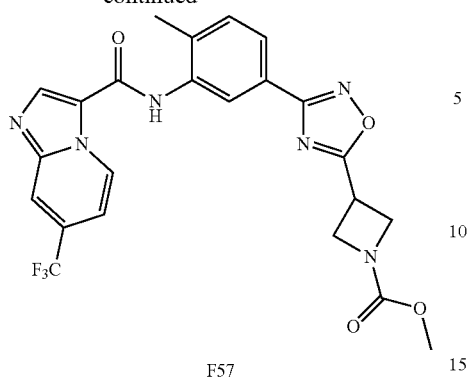

F57

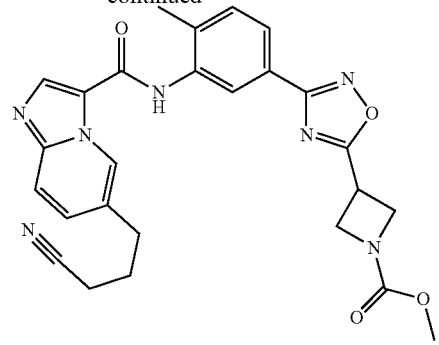

F59

To a stirring suspension of 7-(trifluoromethyl)imidazo[1,2-a]pyridine-3-carboxylic acid (24) (89 mg, 0.387 mmol) in anhydrous dichloromethane (3 mL) at 0° C. under Argon oxalyl chloride (34 uL, 0.407 mmol) was added dropwise. Then, a drop of anhydrous DMF was added and the reaction mixture was stirred at 0° C. for 1.5 hours. The solvent was concentrated and the crude solid was added to a stirring solution of methyl 3-(3-(3-amino-4-methylphenyl)-1,2,4-oxadiazol-5-yl)azetidine-1-carboxylate (31) (19 mg, 0.0645 mmol) in anhydrous pyridine (1.5 mL) at 0° C. The reaction was stirred at room temperature under Argon for 20 minutes. The crude product was filtered and purified by preparative HPLC to give methyl 3-(3-(4-methyl-3-(7-(trifluoromethyl)imidazo[1,2-a]pyridine-3-carboxamido)phenyl)-1,2,4-oxadiazol-5-yl)azetidine-1-carboxylate (F57). $^1$H NMR (400 MHz, d$_6$-DMSO) δ 10.25 (s, 1H), 9.64-9.61 (m, 1H), 9.75 (s, 1H), 8.33-8.30 (m, 1H), 8.10 (dd, J=1.6 Hz, 1H), 7.86 (dd, J=1.6, 8.0 Hz, 1H), 7.52 (d, J=8.4 Hz, 1H), 7.46 (dd, J=2.0, 7.6 Hz, 1H), 4.40-4.33 (m, 2H), 4.31-4.25 (m, 1H), 4.22-4.18 (m, 2H), 3.59 (s, 3H), 2.38 (s, 3H). MS m/z 501.43 (M+1)$^+$.

Synthesis of methyl 3-(3-(3-(6-(3-cyanopropyl)imidazo[1,2-a]pyridine-3-carboxamido)-4-methylphenyl)-1,2,4-oxadiazol-5-yl)azetidine-1-carboxylate (F59)

To a stirring suspension of 6-(3-cyanopropyl)imidazo[1,2-a]pyridine-3-carboxylic acid (25) (50 mg, 0.218 mmol) in anhydrous dichloromethane (2 mL) at 0° C. under Argon was added dropwise oxalyl chloride (20 μL, 0.240 mmol). Then, a drop of anhydrous DMF was added and the reaction mixture was stirred at 0° C. for 1 hour. The solvent was concentrated and the crude solid was dried under vacuum. To a mixture of the acid chloride and methyl 3-(3-(3-amino-4-methylphenyl)-1,2,4-oxadiazol-5-yl)azetidine-1-carboxylate (31) (31 mg, 0.109 mmol) cooled to ° C. under Argon was added anhydrous pyridine (2 mL). The reaction was stirred to room temperature under Argon for 20 minutes. The solvent was concentrated. The crude product methyl 3-(3-(3-(6-(3-cyanopropyl)imidazo[1,2-a]pyridine-3-carboxamido)-4-methylphenyl)-1,2,4-oxadiazol-5-yl)azetidine-1-carboxylate (F59) was purified by silica chromatography. $^1$H NMR (400 MHz, d$_6$-DMSO) δ 10.13 (s, 1H), 9.38-9.36 (m, 1H), 8.66 (s, 1H), 8.11 (d, J=1.6 Hz, 1H), 7.86-7.82 (m, 2H), 7.63-7.60 (m, 1H), 7.51 (d, J=8.0 Hz, 1H), 4.39-4.34 (m, 2H), 4.31-4.24 (m, 1H), 4.21-4.18 (m, 2H), 3.59 (s, 3H), 2.81-2.77 (m, 2H), 2.60-2.52 (m, 2H), 2.38 (s, 3H), 1.97-1.90 (m 2H). MS m/z 500.52 (M+1)$^+$.

Synthesis of methyl 3-(3-(4-methyl-3-(7-methylimidazo[1,2-a]pyridine-3-carboxamido)phenyl)-1,2,4-oxadiazol-5-yl)azetidine-1-carboxylate (F61)

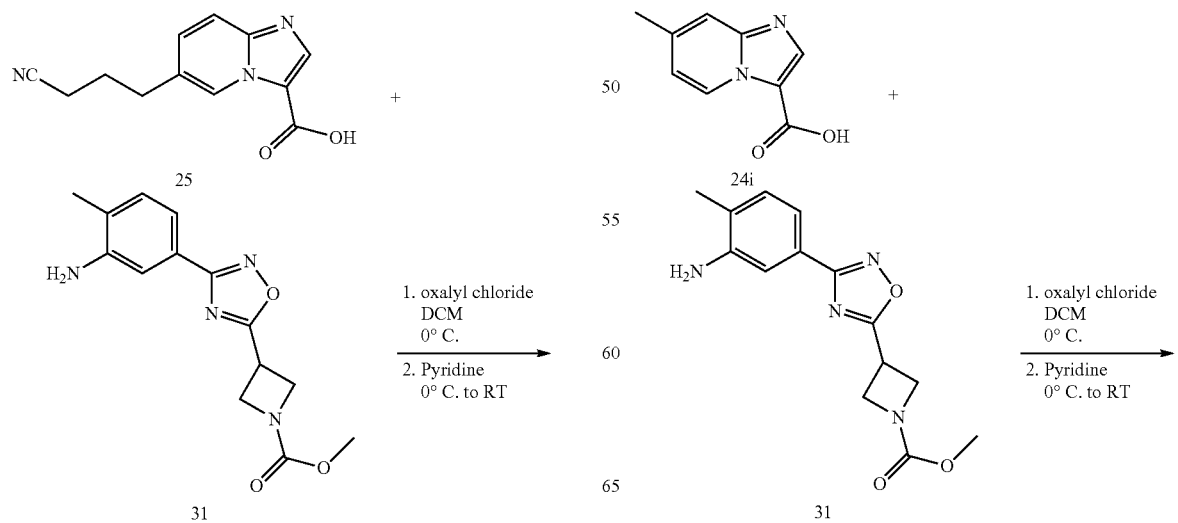

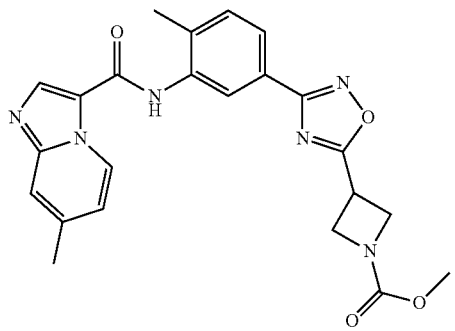

F61

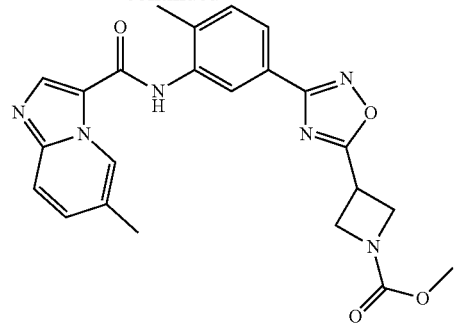

F62

To a stirring suspension of 7-methylimidazo[1,2-a]pyridine-3-carboxylic acid (24i) (100 mg, 0.568 mmol) in anhydrous dichloromethane (5 mL) at 0° C. under Argon was added dropwise oxalyl chloride (53 uL, 0.624 mmol). Then, a drop of anhydrous N,N-dimethylformamide was added and the reaction mixture was stirred at 0° C. for 1 hour. The solvent was concentrated. A stirring mixture of the acid chloride and methyl 3-(3-(3-amino-4-methylphenyl)-1,2,4-oxadiazol-5-yl)azetidine-1-carboxylate (31) (82 mg, 0.283 mmol) in anhydrous pyridine (2 mL) was stirred at room temperature for 2 hour. The solvent was concentrated and the crude product was purified by silica chromatography to give methyl 3-(3-(4-methyl-3-(7-methylimidazo[1,2-a]pyridine-3-carboxamido)phenyl)-1,2,4-oxadiazol-5-yl)azetidine-1-carboxylate (F61). $^1$H NMR (400 MHz, $d_6$-DMSO) δ 9.97 (s, 1H), 9.33 (d, J=7.2 Hz, 1H), 8.52 (s, 1H), 8.09 (d, J=1.6 Hz, 1H), 7.83 (dd, J=1.6, 7.6 Hz, 1H), 7.58 (s, 1H), 7.50 (d, J=8.0 Hz, 1H), 7.03 (dd, J=1.6, 7.2 Hz, 1H), 4.39-4.33 (m, 2H), 4.31-4.24 (m, 1H), 4.22-4.16 (m, 2H), 3.59 (s, 3H), 2.43 (s, 3H), 2.36 (s, 3H). MS m/z 447.17 (M+1)$^+$.

To a stirring suspension of 6-methylimidazo[1,2-a]pyridine-3-carboxylic acid (24j) (35 mg, 0.196 mmol) in anhydrous dichloromethane (2 mL) at 0° C. under Argon was added dropwise oxalyl chloride (17 uL, 0.206 mmol). Then, a drop of anhydrous N,N-dimethylformamide was added and the reaction mixture was stirred at 0° C. for 1 hour. The solvent was concentrated. A stirring mixture of the acid chloride and methyl 3-(3-(3-amino-4-methylphenyl)-1,2,4-oxadiazol-5-yl)azetidine-1-carboxylate (31) (28 mg, 0.098 mmol) in anhydrous pyridine (1.5 mL) was stirred at room temperature for 2 hours. The solvent was concentrated and the crude product was purified by silica chromatography to give methyl 3-(3-(4-methyl-3-(6-methylimidazo[1,2-a]pyridine-3-carboxamido)phenyl)-1,2,4-oxadiazol-5-yl)azetidine-1-carboxylate (F62). $^1$H NMR (400 MHz, $d_6$-DMSO) δ 10.15 (s, 1H), 9.36 (s, 1H), 8.67 (s, 1H), 8.11 (d, J=2.0 Hz, 1H), 7.85 (dd, J=2.0, 8.0 Hz, 1H), 7.81 (d, J=9.2 Hz, 1H), 7.57 (dd, J=1.2, 9.2 Hz, 1H), 7.51 (d, J=8.0 Hz, 1H), 4.39-4.34 (m, 2H), 4.31-4.24 (m, 1H), 4.22-4.17 (m, 2H), 3.59 (s, 3H), 2.41 (s, 3H), 2.37 (s, 3H). MS m/z 447.17 (M+1)$^+$.

Synthesis of methyl 3-(3-(4-methyl-3-(6-methylimidazo[1,2-a]pyridine-3-carboxamido)phenyl)-1,2,4-oxadiazol-5-yl)azetidine-1-carboxylate (F62)

Synthesis of methyl 3-(3-(3-(6-(2-cyanoethyl)imidazo[1,2-a]pyridine-3-carboxamido)-4-methylphenyl)-1,2,4-oxadiazol-5-yl)azetidine-1-carboxylate (F64)

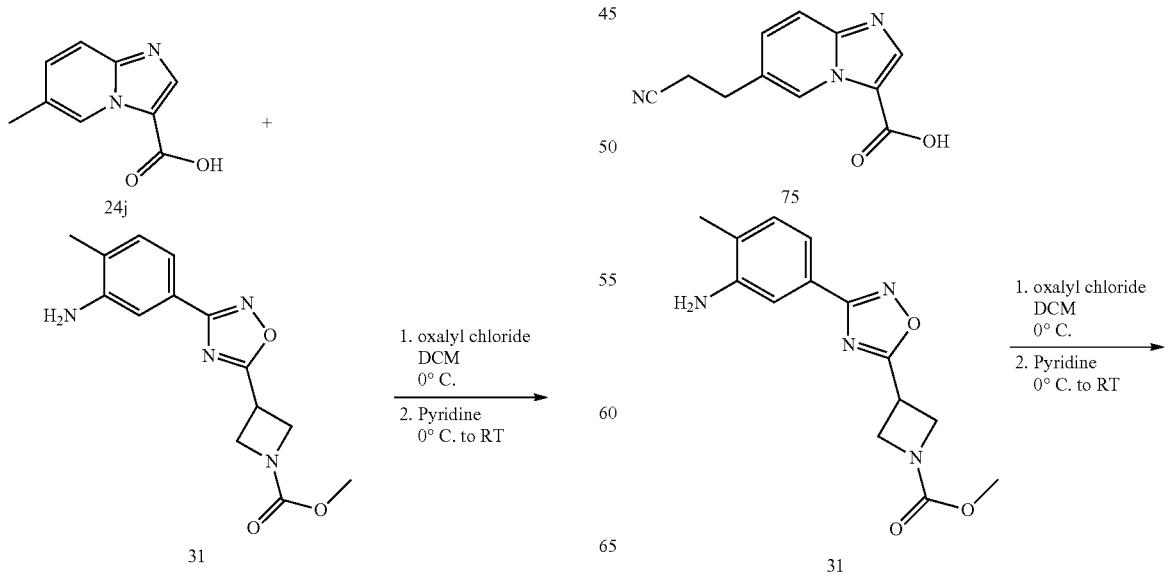

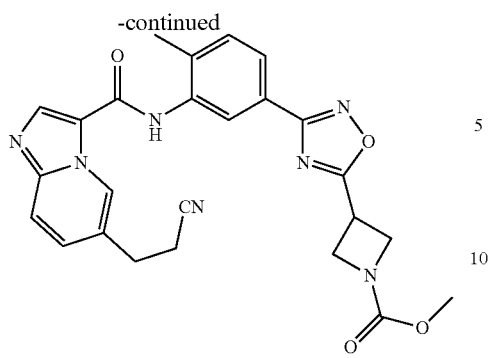

F64

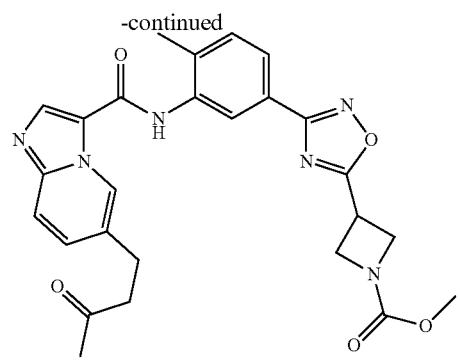

F65

To a stirring suspension of 6-(2-cyanoethyl)imidazo[1,2-a]pyridine-3-carboxylic acid (75) (50 mg, 0.232 mmol) in anhydrous dichloromethane (2 mL) at 0° C. under Argon was added dropwise oxalyl chloride (22 uL, 0.256 mmol). Then, a drop of anhydrous N,N-dimethylformamide was added and the reaction mixture was stirred at 0° C. for 1 hour. The solvent was concentrated and the crude solid was dried under vacuo. Methyl 3-(3-(3-amino-4-methylphenyl)-1,2,4-oxadiazol-5-yl)azetidine-1-carboxylate (31) (33 mg, 0.116 mmol) and anhydrous pyridine (2 mL) were added to the acid chloride. The reaction was stirred to room temperature under Argon for 20 minutes. The crude product was purified by reverse phase preparative HPLC to give methyl 3-(3-(3-(6-(2-cyanoethyl)imidazo[1,2-a]pyridine-3-carboxamido)-4-methylphenyl)-1,2,4-oxadiazol-5-yl)azetidine-1-carboxylate (F64). $^1$H NMR (400 MHz, d$_6$-DMSO) δ 10.08 (s, 1H), 9.45 (s, 1H), 8.63 (s, 1H), 8.12 (d, J=1.6 Hz, 1H), 7.85 (dd, J=2.0, 5.6 Hz, 1H), 7.82 (d, J=6.8 Hz, 1H), 7.60 (dd, J=1.6, 9.2 Hz, 1H), 7.51 (d, J=8.0 Hz, 1H), 4.38-4.33 (m, 2H), 4.31-4.24 (m, 1H), 4.21-4.18 (m, 2H), 3.59 (s, 3H), 3.01 (t, J=7.6 Hz, 2H), 2.91 (t, J=6.4 Hz, 2H), 2.38 (s, 3H). MS m/z 486.18 (M+1)$^+$.

Synthesis of methyl 3-(3-(4-methyl-3-(6-(3-oxobutyl)imidazo[1,2-a]pyridine-3-carboxamido)phenyl)-1,2,4-oxadiazol-5-yl)azetidine-1-carboxylate (F65)

To a stirring suspension of 6-(3-oxobutyl)imidazo[1,2-a]pyridine-3-carboxylic acid (78) (50 mg, 0.215 mmol) in anhydrous dichloromethane (2 mL) at 0° C. under Argon was added dropwise oxalyl chloride (20 uL, 0.237 mmol). Then, a drop of anhydrous N,N-dimethylformamide was added and the reaction mixture was stirred at 0° C. for 1 hour. The solvent was concentrated and the crude solid was dried under vacuo. Next, methyl 3-(3-(3-amino-4-methylphenyl)-1,2,4-oxadiazol-5-yl)azetidine-1-carboxylate (31) (27 mg, 0.0796 mmol) and anhydrous pyridine (1 mL) were added to the acid chloride. The reaction was stirred to room temperature under Argon for 20 minutes. The crude product was purified by reverse phase preparative HPLC to give methyl 3-(3-(4-methyl-3-(6-(3-oxobutyl)imidazo[1,2-a]pyridine-3-carboxamido)phenyl)-1,2,4-oxadiazol-5-yl)azetidine-1-carboxylate (F65). $^1$H NMR (400 MHz, d$_6$-DMSO) δ 10.02 (s, 1H), 9.31 (s, 1H), 8.55 (s, 1H), 8.10 (d, J=1.6 Hz, 1H), 7.83 (dd, J=2.0, 8.0 Hz, 1H), 7.73 (d, J=9.2 Hz, 1H), 7.50 (d, J=8.0 Hz, 1H), 7.46 (dd, J=1.6, 9.2 Hz, 1H), 4.39-4.34 (m, 2H), 4.31-4.25 (m, 1H), 4.22-4.18 (m, 2H), 3.59 (s, 3H), 2.85 (s, 4H), 2.37 (s, 3H), 2.10 (s, 3H). MS m/z 503.2 (M+1)$^+$.

Synthesis of methyl 3-(3-(4-methyl-3-(6-(2-morpholinoethyl)imidazo[1,2-a]pyridine-3-carboxamido)phenyl)-1,2,4-oxadiazol-5-yl)azetidine-1-carboxylate (F66)

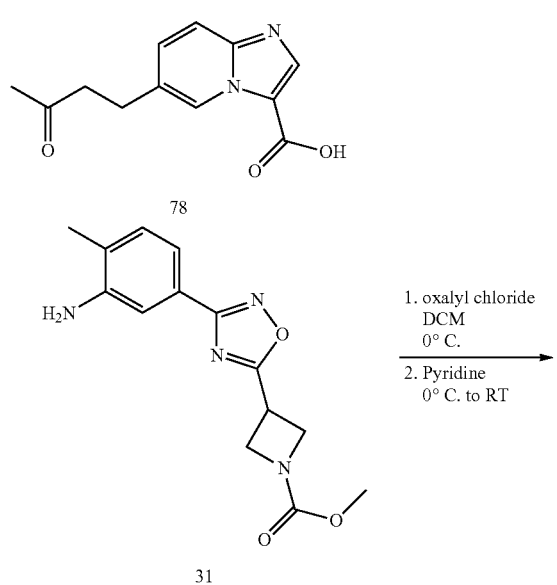

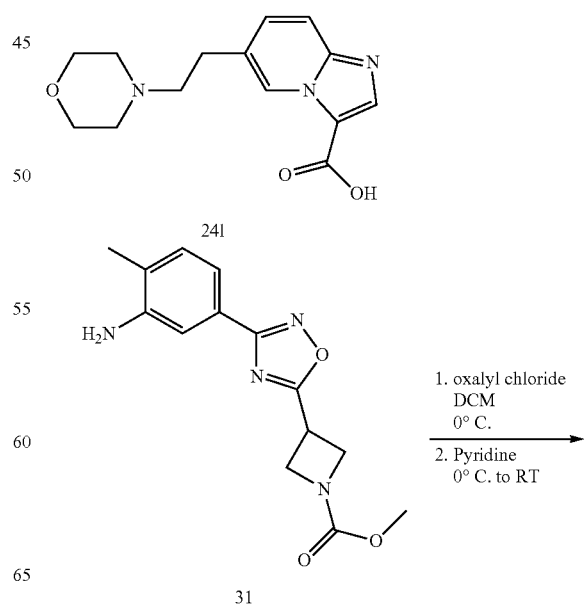

151

-continued

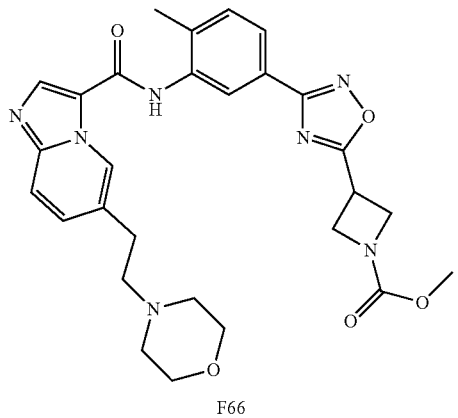

F66

To a stirring suspension of 6-(2-morpholinoethyl)imidazo[1,2-a]pyridine-3-carboxylic acid (24l) (50 mg, 0.182 mmol) in anhydrous dichloromethane (2 mL) at 0° C. under Argon was added dropwise oxalyl chloride (17 uL, 0.200 mmol). Then, a drop of anhydrous N,N-dimethylformamide was added and the reaction mixture was stirred at 0° C. for 1 hour. The solvent was concentrated. A stirring mixture of the acid chloride and methyl 3-(3-(3-amino-4-methylphenyl)-1,2,4-oxadiazol-5-yl)azetidine-1-carboxylate (31) (26 mg, 0.0908 mmol) in anhydrous pyridine (1.5 mL) was stirred at room temperature for 2 hours. The crude product was purified by reverse phase preparative HPLC to give methyl 3-(3-(4-methyl-3-(6-(2-morpholinoethyl)imidazo[1,2-a]pyridine-3-carboxamido)phenyl)-1,2,4-oxadiazol-5-yl)azetidine-1-carboxylate (F66). $^1$H NMR (400 MHz, $d_6$-DMSO) δ 10.07 (s, 1H), 9.46 (s, 1H), 8.61 (s, 1H), 8.12 (d, J=1.6 Hz, 1H), 7.86-7.83 (m, 2H), 7.52-7.49 (m, 2H), 4.39-4.36 (m, 2H), 4.31-4.26 (m, 1H), 4.21-4.17 (m, 2H), 4.03-4.00 (m, 2H), 3.69-3.63 (m, 2H), 3.59 (s, 3H), 3.54-3.44 (m, 4H), 3.14-3.10 (m, 4H), 2.38 (s, 3H). MS m/z 546.24 (M+1)$^+$.

Synthesis of methyl 3-(3-(3-(6-(3-hydroxy-3-methylbutyl)imidazo[1,2-a]pyridine-3-carboxamido)-4-methylphenyl)-1,2,4-oxadiazol-5-yl)azetidine-1-carboxylate (F67)

152

-continued

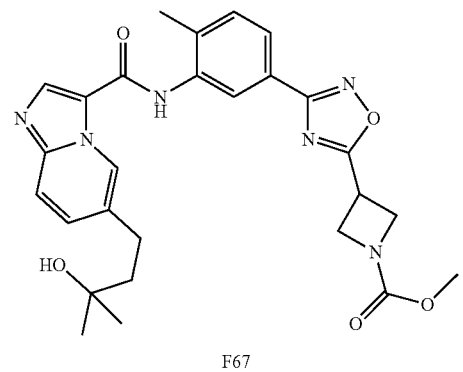

F67

To a stirring solution of methyl 3-(3-(4-methyl-3-(6-(3-oxobutyl)imidazo[1,2-a]pyridine-3-carboxamido)phenyl)-1,2,4-oxadiazol-5-yl)azetidine-1-carboxylate (F65) (10 mg, 0.0199 mmol) in anhydrous THF (1 mL) at −78° C. under a stream of Argon was added methylmagnesium bromide (27 uL, 0.080 mmol). The reaction was stirred to room temperature for 15 minutes then cooled to 0° C. and quenched with 1N HCl. The crude product was purified by reverse phase preparative HPLC to give methyl 3-(3-(3-(6-(3-hydroxy-3-methylbutyl)imidazo[1,2-a]pyridine-3-carboxamido)-4-methylphenyl)-1,2,4-oxadiazol-5-yl)azetidine-1-carboxylate (F67). $^1$H NMR (400 MHz, $d_6$-DMSO) δ 10.10 (s, 1H), 9.34 (s, 1H), 8.63 (s, 1H), 8.10 (d, J=1.6 Hz, 1H), 7.84 (dd, J=1.6, 8.0 Hz, 1H), 7.78 (d, J=9.2 Hz, 1H), 7.56-7.54 (m, 1H), 7.51 (d, J=8.4 Hz, 1H), 4.39-4.34 (m, 2H), 4.31-4.25 (m, 1H), 4.22-4.17 (m, 2H), 3.59 (s, 3H), 2.76-2.72 (m, 2H), 2.37 (s, 3H), 1.71-1.67 (m, 2H), 1.15 (s, 6H). MS m/z 519.23 (M+1)$^+$.

Synthesis of (methyl 3-(3-(3-(7-(1H-pyrazol-3-yl)imidazo[1,2-a]pyridine-3-carboxamido)-4-methylphenyl)-1,2,4-oxadiazol-5-yl)azetidine-1-carboxylate (F68)

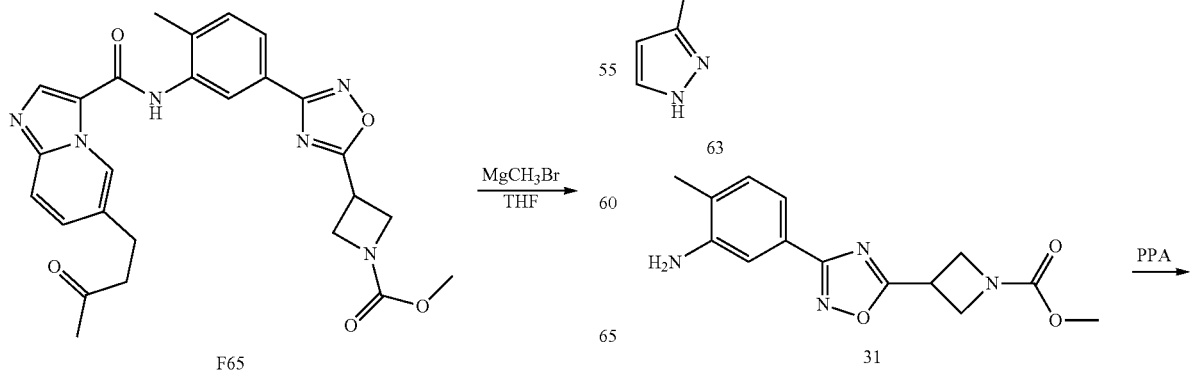

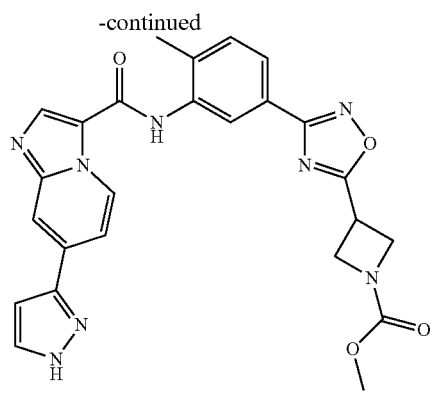

F68

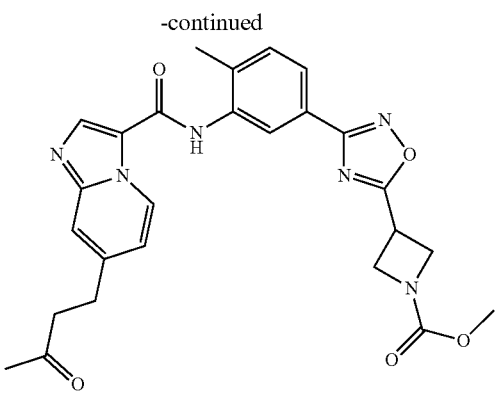

F73

To a stirring solution of 7-(1H-pyrazol-3-yl)imidazo[1,2-a]pyridine-3-carboxylic acid (63) (31.7 mg, 0.14 mmol), and methyl (3-(3-amino-4-methylphenyl)-1,2,4-oxadiazol-5-yl)methylcarbamate (31) (52 mg, 0.18 mmol) in ethyl acetate (0.1 mL) was added propylphosphonic anhydride (50 wt % in ethyl acetate 0.41 mL). The reaction was heated at 80° C. for 12 hours. The resulting mixture was diluted in ethyl acetate and washed with 1N $Na_2CO_3$. After aqueous workup, the residue was purified by reverse phase HPLC to afford methyl 3-(3-(3-(7-(1H-pyrazol-3-yl)imidazo[1,2-a]pyridine-3-carboxamido)-4-methylphenyl)-1,2,4-oxadiazol-5-yl)azetidine-1-carboxylate (F68). MS (m/z) 499.1 $(M+1)^+$.

Synthesis methyl 3-(3-(4-methyl-3-(7-(3-oxobutyl)imidazo[1,2-a]pyridine-3-carboxamido)phenyl)-1,2,4-oxadiazol-5-yl)azetidine-1-carboxylate (F73)

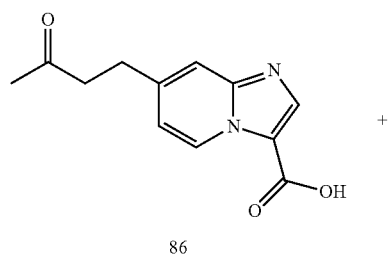

86

To a stirring suspension of 7-(3-oxobutyl)imidazo[1,2-a]pyridine-3-carboxylic acid (86) (40 mg, 0.172 mmol) in anhydrous dichloromethane (2 mL) at 0° C. under Argon was added dropwise oxalyl chloride (16 uL, 0.189 mmol). Then, a drop of anhydrous N,N-dimethylformamide was added and the reaction mixture was stirred at 0° C. for 1 hour. The solvent was concentrated and the crude solid was dried under vacuum. Methyl 3-(3-(3-amino-4-methylphenyl)-1,2,4-oxadiazol-5-yl)azetidine-1-carboxylate (31) (25 mg, 0.086 mmol) and anhydrous pyridine (1 mL) were added to the acid chloride. The reaction was stirred to room temperature under Argon for 20 minutes. The crude product was purified by reverse phase preparative HPLC to give methyl 3-(3-(4-methyl-3-(7-(3-oxobutyl)imidazo[1,2-a]pyridine-3-carboxamido)phenyl)-1,2,4-oxadiazol-5-yl)azetidine-1-carboxylate (F73). $^1$H NMR (400 MHz, $d_6$-DMSO) δ 10.24 (s, 1H), 9.44-9.41 (m, 1H), 8.73 (s, 1H), 8.09 (d, J=1.6 Hz, 1H), 7.85 (dd, J=1.6, 8.0 Hz, 1H), 7.73 (s, 1H), 7.51 (d, J=8.4 Hz, 1H), 7.32-7.29 (m, 1H), 4.39-4.35 (m, 2H), 4.31-4.24 (m, 1H), 4.21-4.17 (m, 2H), 3.59 (s, 3H), 2.98-2.91 (m, 4H), 2.37 (s, 3H), 2.13 (s, 3H). MS m/z 503.2 $(M+1)^+$.

Synthesis of methyl 3-(3-(3-(7-(3-hydroxy-3-methylbutyl)imidazo[1,2-a]pyridine-3-carboxamido)-4-methylphenyl)-1,2,4-oxadiazol-5-yl)azetidine-1-carboxylate (F74)

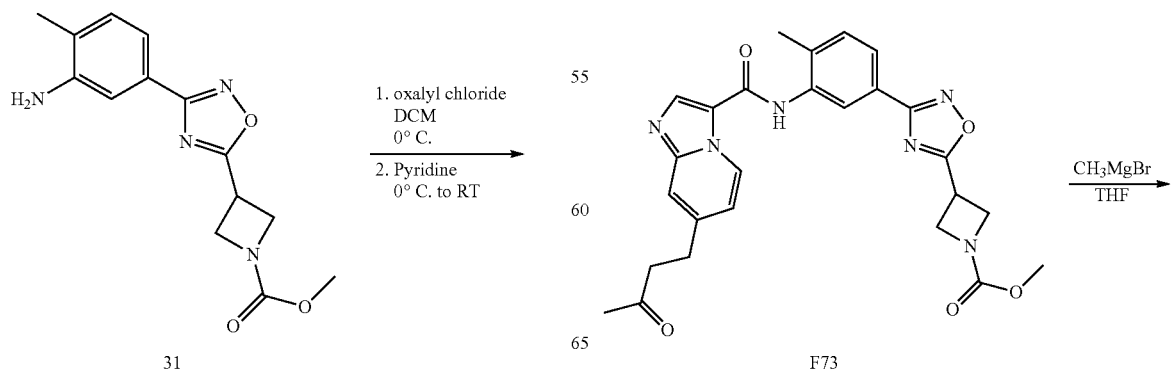

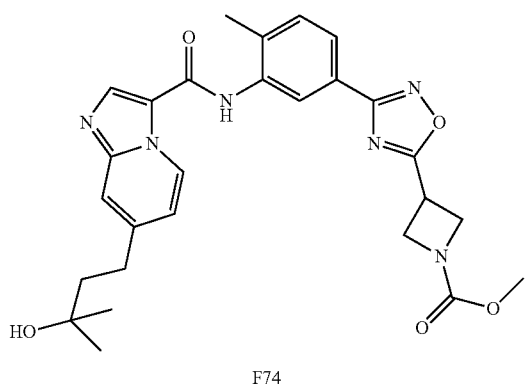

F74

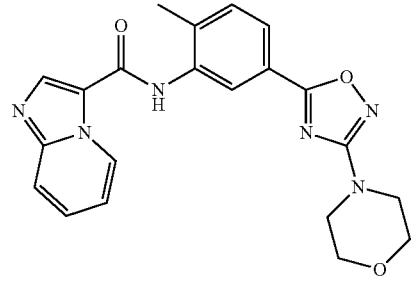

F75

To a stirring solution of methyl 3-(3-(4-methyl-3-(7-(3-oxobutyl)imidazo[1,2-a]pyridine-3-carboxamido)phenyl)-1,2,4-oxadiazol-5-yl)azetidine-1-carboxylate (F194) (10 mg, 0.0199 mmol) in anhydrous THF (1 mL) at −78° C. under a stream of Argon was added methylmagnesium bromide (27 uL, 0.080 mmol). The reaction was stirred to room temperature for 15 minutes and quenched at 0° C. with 1N HCl. The crude product was purified by reverse phase preparative HPLC to give methyl 3-(3-(3-(6-(3-hydroxy-3-methylbutyl)imidazo[1,2-a]pyridine-3-carboxamido)-4-methylphenyl)-1,2,4-oxadiazol-5-yl)azetidine-1-carboxylate (F74). $^1$H NMR (400 MHz, d$_6$-DMSO) δ 10.11 (s, 1H), 9.41-9.38 (m, 1H), 8.64 (s, 1H), 8.10 (s, 1H), 7.84 (dd, J=1.2, 7.6 Hz, 1H), 7.65 (s, 1H), 7.50 (d, J=8.0 Hz, 1H), 7.21-7.17 (m, 1H), 4.39-4.35 (m, 2H), 4.31-4.24 (m, 1H), 4.22-4.18 (m, 2H), 3.59 (s, 3H), 2.82-2.77 (m, 2H), 2.37 (s, 3H), 1.74-1.69 (m, 2H), 1.17 (s, 6H). MS m/z 519.23 (M+1)$^+$.

Synthesis of N-(2-methyl-5-(3-morpholino-1,2,4-oxadiazol-5-yl)phenyl)imidazo[2-a]pyridine-3-carboxamide (F75)

A stirring suspension of 3-(imidazo[1,2-a]pyridine-3-carboxamido)-4-methylbenzoic acid (4) (41 mg, 0.138 mmol) in anhydrous NMP (1 mL) was heated in the microwave at 105° C. for 2 minutes to dissolve all solid. Then, 1,1'-carbonyldiimidazole (22 mg, 0.138 mmol) was added and the reaction was stirred at room temperature for 15 minutes. N'-hydroxymorpholine-4-carboximidamide (20 mg, 0.138 mmol) was added and the reaction was stirred for 30 minutes. The reaction was heated in the microwave at 130° C. for 15 minutes. The crude product was purified by reverse phase preparative HPLC to give N-(2-methyl-5-(3-morpholino-1,2,4-oxadiazol-5-yl)phenyl)imidazo[1,2-a]pyridine-3-carboxamide (F75). $^1$H NMR (400 MHz, d$_6$-DMSO) δ 10.18 (s, 1H), 9.52-9.48 (m, 1H), 8.68 (s, 1H), 8.11 (d, J=2.0 Hz, 1H), 7.88-7.83 (m, 2H), 7.68-7.63 (m, 1H), 7.54 (d, J=8.0 Hz, 1H), 7.31-7.27 (m, 1H), 3.72-3.69 (m, 4H), 3.41-3.38 (m, 4H), 2.39 (s, 3H). MS m/z 405.16 (M+1)$^+$.

Synthesis of methyl 3-(3-(4-methyl-3-(5,6,7,8-(D$_4$)imidazo[1,2-a]pyridine-3-carboxamido)phenyl)-1,2,4-oxadiazol-5-yl)azetidine-1-carboxylate (F76)

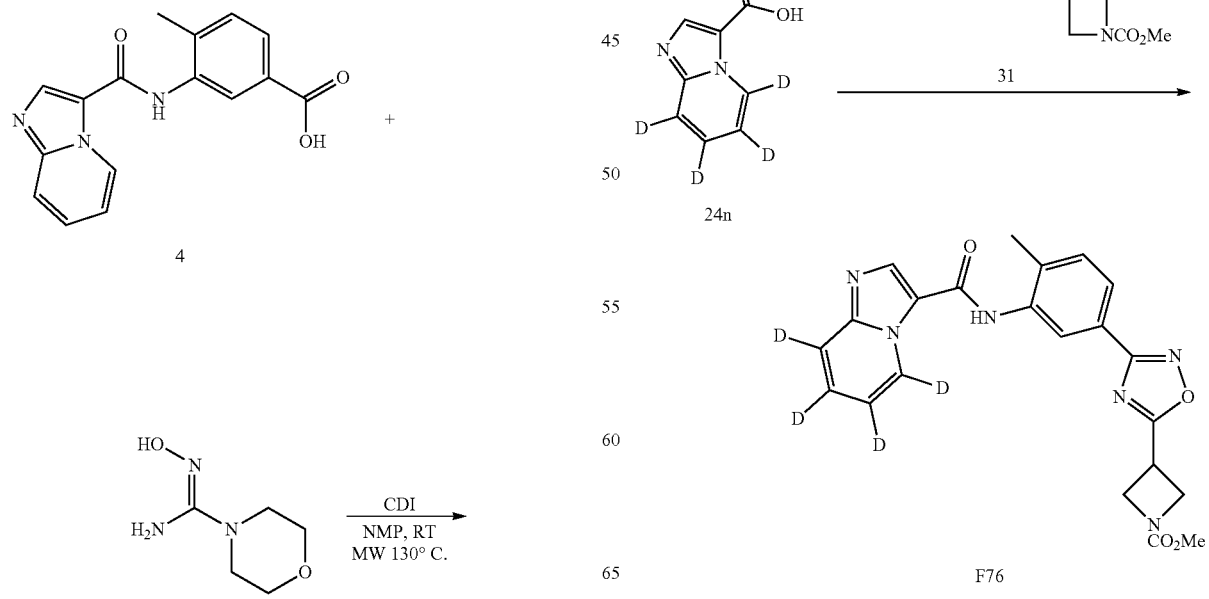

Oxalyl chloride (6 mL, 69 mmol) was added dropwise to a stirred suspension of 5,6,7,8-deutero-imidazo[1,2-a]pyridine-3-carboxylic acid (24n) (1.91 g, 11.5 mmol) and DMF (0.1 ml). The mixture was stirred overnight and the volatiles were evaporated. Methyl 3-(3-(3-amino-4-methylphenyl)-1,2,4-oxadiazol-5-yl)azetidine-1-carboxylate (31) (3.23 g, 11.2 mmol) in dry pyridine (50 mL) was added to the solid acid chloride at 0° C. After the addition, the mixture was warmed to room temperature and stirred for 3 hours before it was heated (50° C.) for 5 hours. The solvent was evaporated and the residue was stirred in saturated NH$_4$Cl and EtOAc. A precipitate formed and was filtered and washed with water, and EtOAc to give methyl 3-(3-(4-methyl-3-(5,6,7,8-(D$_4$)imidazo[1,2-a]pyridine-3-carboxamido)phenyl)-1,2,4-oxadiazol-5-yl)azetidine-1-carboxylate (F76) as a grey solid. $^1$H NMR (400 MHz, d$_4$-MeOH) 8.70 (s, 1H), 8.16 (s, 1H), 7.96 (dd, J=7.6, 1.6 Hz, 1H), 7.49 (d, J=7.6 Hz, 1H), 4.48-4.44 (m, 2H), 4.32-4.29 (m, 2H), 4.24-4.19 (m, 1H), 3.69 (s, 3H), 2.42 (s, 3H). MS m/z 438.1 (M+1)$^+$.

Synthesis of N-(5-(5-(azetidin-1-yl)-1,2,4-oxadiazol-3-yl)-2-methylphenyl)imidazo[1,2-a]pyridine-3-carboxamide (F77)

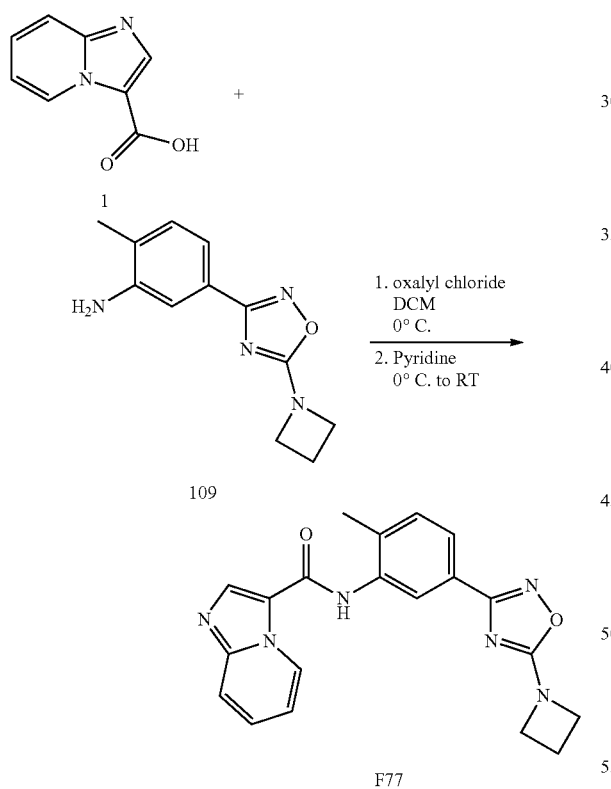

To a stirring suspension of imidazo[1,2-a]pyridine-3-carboxylic acid (1) (71 mg, 0.39 mmol) in anhydrous dichloromethane (2 mL) was added dropwise oxalyl chloride (173 uL, 1.98 mmol). Then, a drop of anhydrous N,N-dimethylformamide was added and the reaction mixture was stirred at room temperature for 30 minutes. The solvent was concentrated. A stirring mixture of the acid chloride and 5-(azetidin-1-yl)-3-(4-methyl-3-nitrophenyl)-1,2,4-oxadiazole (109) (85 mg, 0.29 mmol) in anhydrous pyridine (2 mL) was stirred at room temperature for 30 minutes. The crude product was purified on silica gel using 10% MeOH in dichloromethane to give N-(5-(5-(azetidin-1-yl)-1,2,4-oxadiazol-3-yl)-2-methylphenyl)imidazo[1,2-a]pyridine-3-carboxamide (F77). $^1$H NMR (400 MHz, CD$_2$Cl$_2$) δ 10.10 (s, 1H), 9.51-9.48 (m, 1H), 8.65 (s, 1H), 7.94 (d, J=1.6 Hz, 1H), 7.86-7.83 (m, 1H), 7.71 (dd, J=1.6, 7.6 Hz, 1H), 7.64-7.60 (m, 1H), 7.43 (d, J=8.0 Hz, 1H), 7.27-7.24 (m, 1H), 4.26-4.22 (m, 4H), 2.48-2.40 (m, 2H), 2.34 (s, 3H). MS m/z 374.15 (M+1)$^+$.

Synthesis of methyl 3-(3-(5-(imidazo[1,2-a]pyridine-3-carboxamido)-2,4-dimethylphenyl)-1,2,4-oxadiazol-5-yl)azetidine-1-carboxylate (F79)

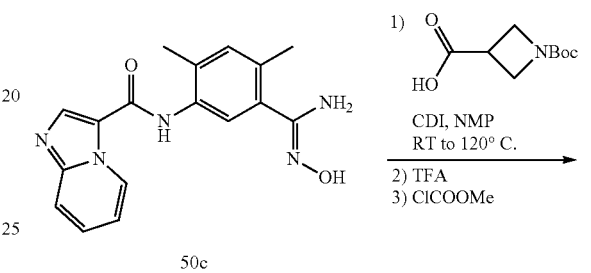

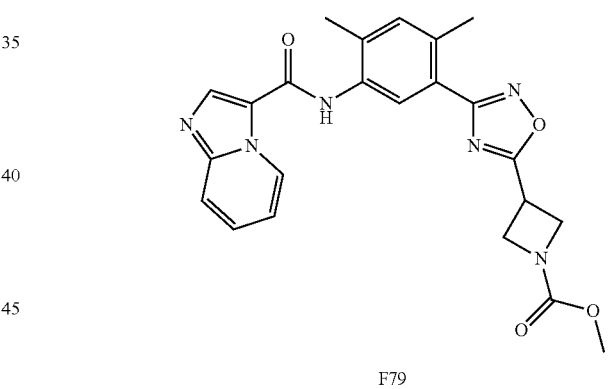

To a stirring solution of Boc-azetidine-3-carboxylic acid (20 mg, 0.1 mmol) in anhydrous NMP (1 mL) was added CDI (16.3 mg, 0.1 mmol). The reaction was stirred for 10 minutes. Then, N-(5-(N'-hydroxycarbamimidoyl)-2,4-dimethylphenyl)imidazo[1,2-a]pyridine-3-carboxamide (50c) (15 mg, 0.05 mmol) was added and the reaction was stirred for 15 minutes. The reaction was heated in the microwave at 125° C. for 15 minutes. The reaction mixture was added dropwise to water (20 mL) and extracted with EtOAc. The organic layers were combined, dried over Na$_2$SO$_4$, filtered and concentrated to afford a residue which was dissolved in 0.5 mL of TFA and stirred for 10 minutes. Then TFA was removed under vacuum and the residue was dissolved in DCM (1 mL) followed by addition of TEA (15 mg, 0.15 mmol) and methyl chloroformate (6 mg, 0.06 mmol). The solvent was removed and the residue was purified by HPLC to give methyl 3-(3-(5-(imidazo[1,2-a]pyridine-3-carboxamido)-2,4-dimethylphenyl)-1,2,4-oxadiazol-5-yl)azetidine-1-carboxylate (F79). MS m/z 447.1 (M+1)+.

Synthesis of methyl 3-(3-(4-methyl-3-(7-methyl-d3-imidazo[1,2-a]pyridine-3-carboxamido)phenyl)-1,2,4-oxadiazol-5-yl)azetidine-1-carboxylate (F80)

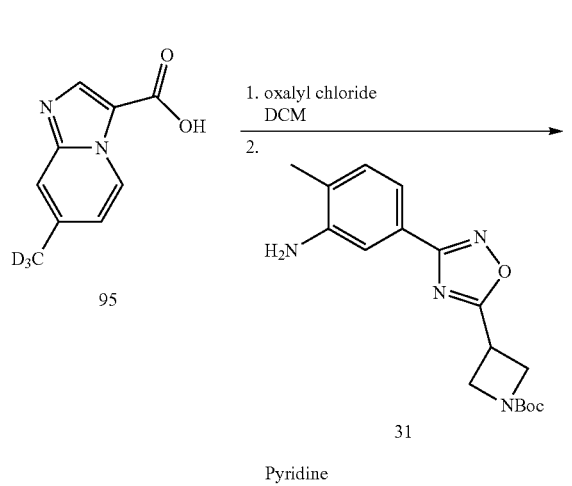

J=6.0 Hz, 1H), 4.37 (d, J=6.0 Hz, 1H), 4.16 (m, 1H), 3.72 (s, 3H), 2.77 (s, 3H). MS m/z 450.1 (M+1)+.

Synthesis of N-(5-(5-(azetidin-1-yl)-1,2,4-oxadiazol-3-yl)-2-methylphenyl)imidazo[1,2-a]pyridine-3-carboxamide (F77)

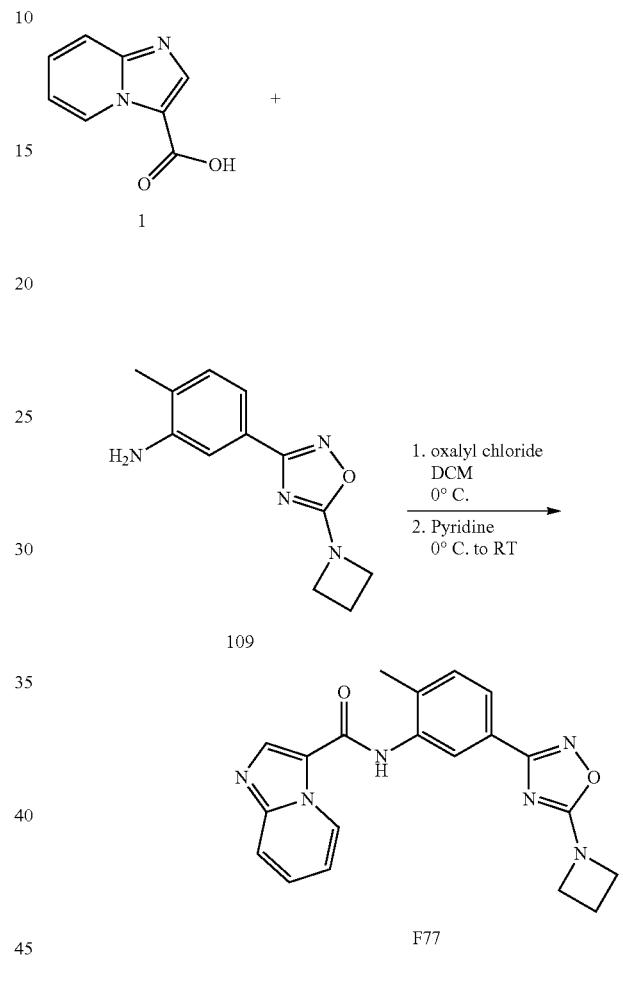

To a stirring suspension of 7-methyl-d$_3$-imidazo[1,2-a]pyridine-3-carboxylic acid (95) (71 mg, 0.39 mmol) in anhydrous dichloromethane (2 mL) was added dropwise oxalyl chloride (173 uL, 1.98 mmol). Then, a drop of anhydrous N,N-dimethylformamide was added and the reaction mixture was stirred at room temperature for 30 minutes. The solvent was concentrated. A stirring mixture of the acid chloride and methyl 3-(3-(3-amino-4-methylphenyl)-1,2,4-oxadiazol-5-yl)azetidine-1-carboxylate (31) (85 mg, 0.29 mmol) in anhydrous pyridine (2 mL) was stirred at room temperature for 30 minutes. The crude product was purified on silica gel using 10% MeOH in dichloromethane to give methyl 3-(3-(4-methyl-3-(7-methyl-d$_3$-imidazo[1,2-a]pyridine-3-carboxamido)phenyl)-1,2,4-oxadiazol-5-yl)azetidine-1-carboxylate (F80). $^1$H NMR (400 MHz, CD$_2$Cl$_2$) δ 9.71 (d, J=7.2 Hz, 1H), 9.15 (s, 1H), 9.04 (s, 1H), 8.33 (s, 1H), 7.95 (dd, J=1.2, 8.2 Hz, 1H), 7.93 (s, 1H), 7.46 (d, J=8.0 Hz, 1H), 7.37 (d, J=7.2 Hz, 1H), 4.48 (d, J=9.2 Hz, 1H), 4.46 (d, J=8.4 Hz, 1H), 4.39 (d, To a stirring suspension of imidazo[1,2-a]pyridine-3-carboxylic acid (1) (71 mg, 0.39 mmol) in anhydrous dichloromethane (2 mL) was added dropwise oxalyl chloride (173 uL, 1.98 mmol). Then, a drop of anhydrous N,N-dimethylformamide was added and the reaction mixture was stirred at room temperature for 30 minutes. The solvent was concentrated. A stirring mixture of the acid chloride and 5-(azetidin-1-yl)-3-(4-methyl-3-nitrophenyl)-1,2,4-oxadiazole (109) (85 mg, 0.29 mmol) in anhydrous pyridine (2 mL) was stirred at room temperature for 30 minutes. The crude product was purified on silica gel using 10% MeOH in dichloromethane to give N-(5-(5-(azetidin-1-yl)-1,2,4-oxadiazol-3-yl)-2-methylphenyl)imidazo[1,2-a]pyridine-3-carboxamide (F77). $^1$H NMR (400 MHz, CD$_2$Cl$_2$) δ 10.10 (s, 1H), 9.51-9.48 (m, 1H), 8.65 (s, 1H), 7.94 (d, J=1.6 Hz, 1H), 7.86-7.83 (m, 1H), 7.71 (dd, J=1.6, 7.6 Hz, 1H), 7.64-7.60 (m, 1H), 7.43 (d, J=8.0 Hz, 1H), 7.27-7.24 (m, 1H), 4.26-4.22 (m, 4H), 2.48-2.40 (m, 2H), 2.34 (s, 3H). MS m/z 374.15 (M+1)+.

Synthesis of methyl 3-(3-(3-(6-((2,2-difluoroethoxy)methyl)imidazo[1,2-a]pyridine-3-carboxamido)-4-methylphenyl)-1,2,4-oxadiazol-5-yl)azetidine-1-carboxylate (F95)

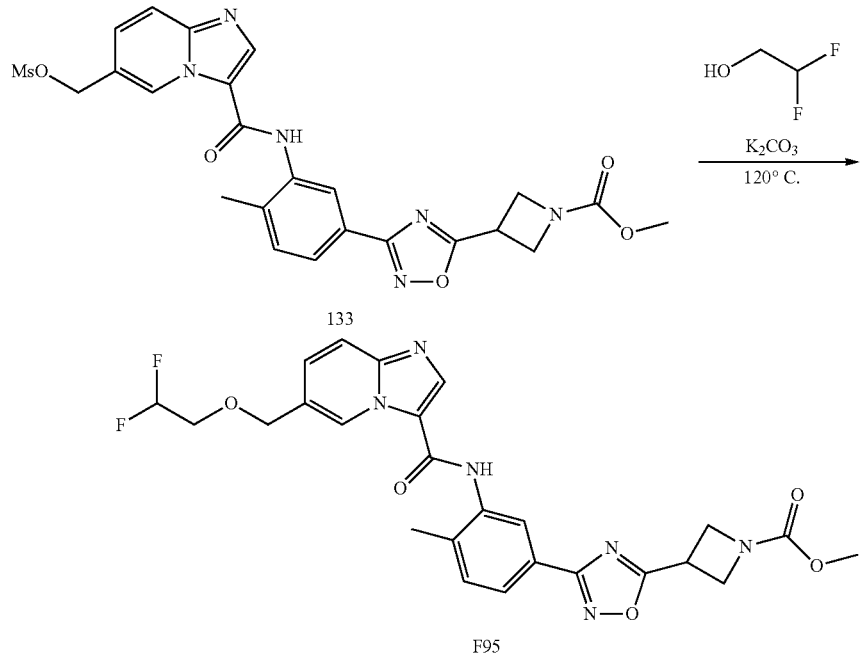

Methyl 3-(3-(4-methyl-3-(6-((((methylsulfonyl)oxy)methyl)imidazo[1,2-a]pyridine-3-carboxamido)phenyl)-1,2,4-oxadiazol-5-yl)azetidine-1-carboxylate (133) (15.0 mg, 0.028 mmol) and K$_2$CO$_3$ (8.3 mg, 0.06 mmol) in 2,2-difluoroethanol (0.5 mL) was heated at 120° C. for 5 minutes. The reaction mixture was purified by preparative HPLC to afford methyl 3-(3-(3-(6-((2,2-difluoroethoxy)methyl)imidazo[1,2-a]pyridine-3-carboxamido)-4-methylphenyl)-1,2,4-oxadiazol-5-yl)azetidine-1-carboxylate (F95). MS m/z 527.1 (M+1)$^+$.

Synthesis of methyl 3-(3-(3-(7-deuteroimidazo[1,2-a]pyridine-3-carboxamido)-4-methylphenyl)-1,2,4-oxadiazol-5-yl)azetidine-1-carboxylate (F97)

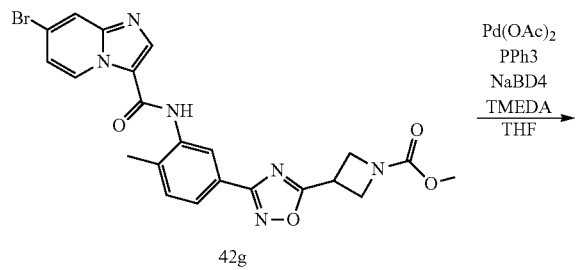

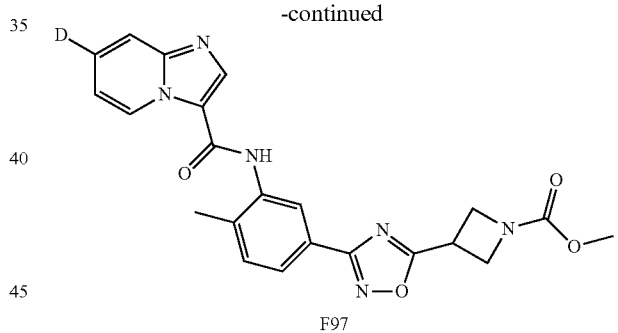

Method A:

A mixture of methyl 3-(3-(3-(7-bromoimidazo[1,2-a]pyridine-3-carboxamido)-4-methylphenyl)-1,2,4-oxadiazol-5-yl)azetidine-1-carboxylate (42g) (0.185 g, 0.36 mmol) in anhydrous THF (5 mL) was degassed by bubbling argon for few minutes. Then, Pd(OAc)$_2$ (7.9 mg, 0.036 mmol, PPh$_3$ (38.0 mg, 0.144 mmol), TMEDA (83.4 mg, 0.72 mmol) and finally NaBD$_4$ (60.6 mg, 1.44 mmol) were introduced in sequence. The mixture was heated at 65° C. under argon for 2 hours. The residue was taken up in brine and extracted with ethyl acetate. The organic phase was separated, dried over Na$_2$SO$_4$, the solvent was evaporated and the residue was purified by flash chromatography to give methyl 3-(3-(3-(7-deuteroimidazo[1,2-a]pyridine-3-carboxamido)-4-methylphenyl)-1,2,4-oxadiazol-5-yl)azetidine-1-carboxylate (F97). $^1$H NMR (400 MHz, CD$_4$OD) δ 9.53 (dd, J=0.8, 7.2 Hz, 1H), 8.49 (s, 1H), 8.16 (d, J=1.6 Hz, 1H), 7.94 (dd, J=1.6, 8.0 Hz, 1H), 7.75 (m, 1H), 7.49 (d, J=8.0 Hz, 1H), 7.18 (dd, J=0.8, 7.2 Hz, 1H), 4.47 (m, 2H), 4.33 (m, 2H), 4.24 (m, 1H), 3.70 (s, 3H), 2.43 (s, 3H). MS m/z 434.1 (M+1)$^+$.

Method B:

Methyl 3-(3-(3-(7-bromoimidazo[1,2-a]pyridine-3-carboxamido)-4-methylphenyl)-1,2,4-oxadiazol-5-yl)azetidine-1-carboxylate (42g) (0.20 g, 0.39 mmol) was treated with MeOD (1 mL), stirred for 10 minutes and concentrated. Then the residue was added to MeOD (5 mL) and followed by addition of 5% Pd on alumina (150 mg). The reaction mixture was charged with $D_2$ balloon and stirred at room temperature for 2 hours. After the reaction was completed, the mixture was filtered through a pad of celite and the filtrate was concentrated to give a crude which was purified by flash chromatography to give methyl 3-(3-(3-(7-deuteroimidazo[1,2-a]pyridine-3-carboxamido)-4-methylphenyl)-1,2,4-oxadiazol-5-yl)azetidine-1-carboxylate (F97). $^1$H NMR (400 MHz, CD40D) δ 9.53 (dd, J=0.8, 7.2 Hz, 1H), 8.49 (s, 1H), 8.16 (d, J=1.6 Hz, 1H), 7.94 (dd, J=1.6, 8.0 Hz, 1H), 7.75 (m, 1H), 7.49 (d, J=8.0 Hz, 1H), 7.18 (dd, J=0.8, 7.2 Hz, 1H), 4.47 (m, 2H), 4.33 (m, 2H), 4.24 (m, 1H), 3.70 (s, 3H), 2.43 (s, 3H). MS m/z 434.1 (M+1)+.

Representative compounds of Formula (I) and Formula (II) with $IC_{50}$ values in the range of 1 nM to 100 nM, and prepared following the procedures described above, are set forth in Table 1.

TABLE 1

| Cmpd No. | Structure | Physical Data | c-kit (Mo7e) μM |
|---|---|---|---|
| F1 | 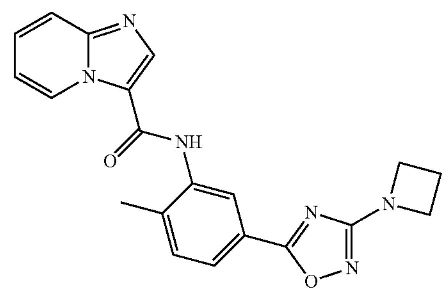 [SMILES: Cc1ccc(-c2nc(N3CCC3)no2)cc1NC(=O)c1cnc2ccccn12] | $^1$H NMR (400 MHz, $d_6$-DMSO) δ 10.13 (s, 1H), 9.50-9.48 (m, 1H), 8.66 (s, 1H), 8.10 (d, J = 1.6 Hz, 1H), 7.86-7.82 (m, 2H), 7.65-7.61 (m, 1H), 7.53 (d, J = 8.4 Hz, 1H), 7.28-7.25 (m, 1H), 4.06-4.02 (m, 4H), 2.44-2.36 (m, 2H), 2.39 (, 3H). MS m/z 374.1 (M + 1)+. | 0.049 |
| F2 | 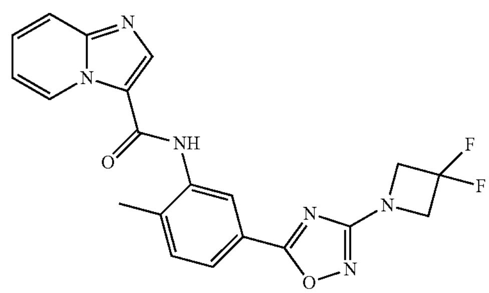 [SMILES: Cc1ccc(-c2nc(N3CC(F)(F)C3)no2)cc1NC(=O)c1cnc2ccccn12] | $^1$H NMR (400 MHz, $d_6$-DMSO) δ 10.15 (s, 1H), 9.51-9.48 (m, 1H), 8.68 (s, 1H), 8.13 (d, J = 1.6 Hz, 1H), 7.87-7.85 (m, 2H), 7.67-7.63 (m, 1H), 7.55 (d, J = 8.0 Hz, 1H), 7.30-7.27 (, m, 1H), 4.57-4.50 (m, 4H), 2.40 (s, 3H). MS m/z 410.1 (M + 1)+. | 0.013 |
| F3 | 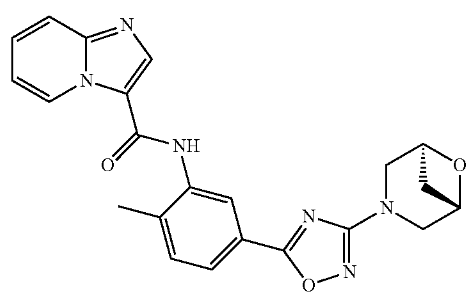 [SMILES: Cc1ccc(-c2nc(N3C[C@@H]4C[C@@H](C3)O4)no2)cc1NC(=O)c1cnc2ccccn12] | MS m/z 417.4 (M + 1)+. | 0.09 |
| F4 | 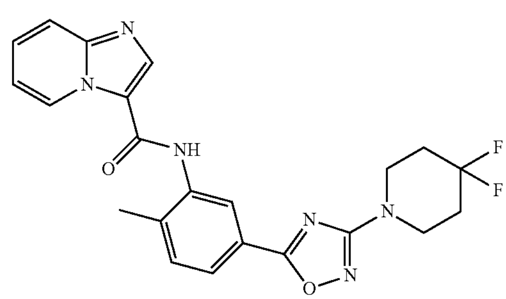 [SMILES: Cc1ccc(-c2nc(N3CCC(F)(F)CC3)no2)cc1NC(=O)c1cnc2ccccn12] | $^1$H NMR (400 MHz, $d_6$-DMSO) δ 10.16 (s, 1H), 9.51-9.49 (m, 1H), 8.68 (s, 1H), 8.12 (d, J = 1.2 Hz, 1H), 7.87-7.85 (m, 2H), 7.67-7.64 (m, 1H), 7.55 (d, J = 5.2 Hz, 1H), 7.30-7.28 (m, 1H), 3.60-3.58 (m, 4H), 2.39 (s, 3H), 2.12-2.06 (m, 4H). MS m/z 438.16 (M + 1)+. | 0.035 |

TABLE 1-continued

| Cmpd No. | Structure | Physical Data | c-kit (Mo7e) μM |
|---|---|---|---|
| F5 | 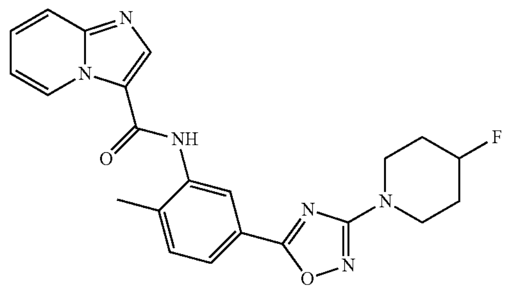 [SMILES: Cc1ccc(-c2nc(N3CCC(F)CC3)no2)cc1NC(=O)c1cnc2ccccn12] | $^1$H NMR (400 MHz, d$_6$-DMSO) δ 10.19 (s, 1H), 9.52-9.51 (m, 1H), 8.71 (s, 1H), 8.11 (d, J = 1.2 Hz, 1H), 7.90-7.88 (m, 1H), 7.85 (dd, J = 1.2, 5.2 Hz, 1H), 7.71-7.68 (m, 1H), 7.55 (d, J = 5.2 Hz, 1H), 7.33-7.31 (m, 1H), 4.96-4.85 (m, 1H), 3.61-3.57 (m, 2H), 3.45-3.41 (m, 2H), 2.39 (s, 3H), 2.02-1.93 (m, 2H), 1.81-1.74 (m, 2H). MS m/z 420.17 (M + 1)$^+$. | 0.034 |
| F6 | 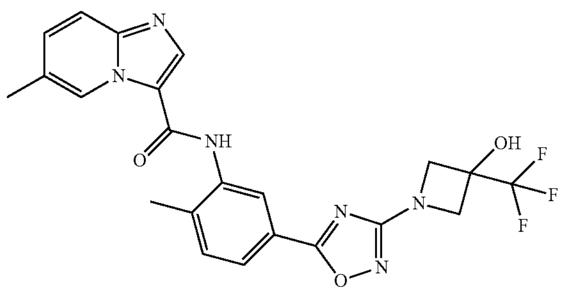 [SMILES: Cc1ccc2ncc(C(=O)Nc3cc(-c4nc(N5CC(O)(C(F)(F)F)C5)no4)ccc3C)n2c1] | $^1$H NMR (400 MHz, d$_6$-DMSO) δ 10.11 (s, 1H), 9.34 (s, 1H), 8.64 (s, 1H), 7.97 (d, J = 1.6 Hz, 1H), 7.80 (d, J = 9.2 Hz, 1H), 7.72 (dd, J = 1.6, 8.0 Hz, 1H), 7.57-7.54 (m, 1H), 7.45 (d, J = 8.0 Hz, 1H), 4.54-4.51 (m, 2H), 4.33-4.30 (m, 2H), 2.40 (s, 3H), 2.35 (s, 3H). MS m/z 472.15 (M + 1)$^+$. | 0.026 |
| F7 | 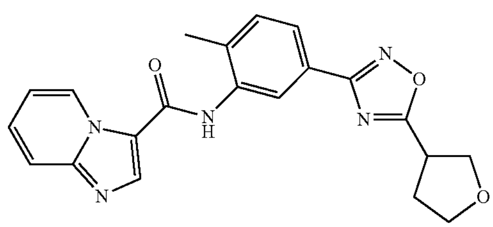 [SMILES: Cc1ccc(-c2noc(C3CCOC3)n2)cc1NC(=O)c1cnc2ccccn12] | MS m/z 390.1 (M + 1)$^+$. | 0.078 |
| F8 | 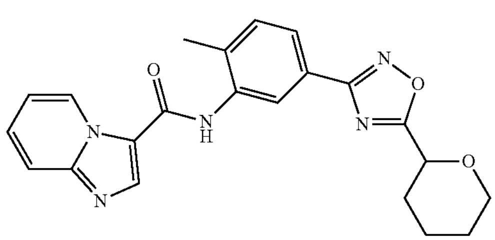 [SMILES: Cc1ccc(-c2noc(C3CCCCO3)n2)cc1NC(=O)c1cnc2ccccn12] | $^1$H NMR (400 MHz, d$_4$-MeOH) δ 9.73-9.76 (d, J = 7.2 Hz, 1H), 8.78 (s, 1H), 8.15-8.13 (m, 1H), 8.06-8.00 (m, 2H), 7.95-7.91 (m, 1H), 7.58-7.48 (m, 2H), 4.72 (dd, J = 12.4, 2.8, Hz, 1H), 4.14-4.09 (m, 1H), 3.63-3.57 (m, 1H), 2.35 (s, 3H), 2.06-1.86 (m, 4H), 1.72-1.55 (m, 2H). MS m/z 404.1 (M + 1)$^+$. | 0.042 |
| F9 | 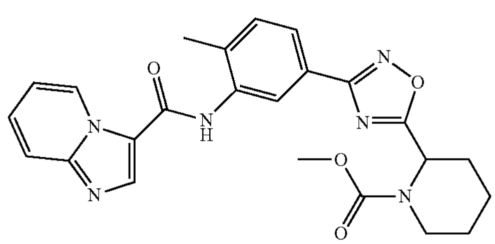 [SMILES: COC(=O)N1CCCCC1c1nc(-c2ccc(C)c(NC(=O)c3cnc4ccccn34)c2)no1] | $^1$H NMR (400 MHz, d$_4$-MeOH) δ 9.77 (d, J = 7.2 Hz, 1H), 8.78 (s, 1H), 8.14-8.13 (m, 1H), 8.04-8.03 (m, 2H), 7.95-7.93 (m, 1H), 7.57 (ddd, J = 6.8, 6.8, 1.2 Hz, 1H), 7.50 (d, J = 8.0, 1H), 5.71 (d, J = 4.4 Hz, 1H), 4.15-4.12 (m, 1H), 3.75 (s, 3H), 3.75-3.06 (m, 1H), 2.43 (s, 3H), 2.04-1.94 (m, 2H), 1.80-1.71 (m, 2H), 1.61-1.40 (m, 4H). MS m/z 461.1 (M + 1)$^+$. | 0.035 |

TABLE 1-continued

| Cmpd No. | Structure | Physical Data | c-kit (Mo7e) µM |
|---|---|---|---|
| F10 | 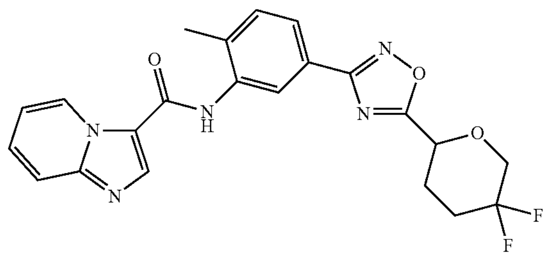 [SMILES: Cc1ccc(-c2noc(C3CCC(F)(F)CO3)n2)cc1NC(=O)c1cnc2ccccn12] | ¹H NMR (400 MHz, d₄-MeOH) δ 9.73 (d, J = 7.2 Hz, 1H), 8.74 (s, 1H), 8.17 (m, 1H), 7.98-7.95 (m, 3H), 7.52-7.50 (m, 2H), 5.06 (dd, J = 8.4, 2.8 Hz, 1H), 4.07-4.00 (m, 1H), 3.91-3.81 (m, 1H), 2.44 (s, 3H), 2.40-2.21 (m, 4H). MS m/z 440.1 (M + 1)⁺. | 0.023 |
| F11 | 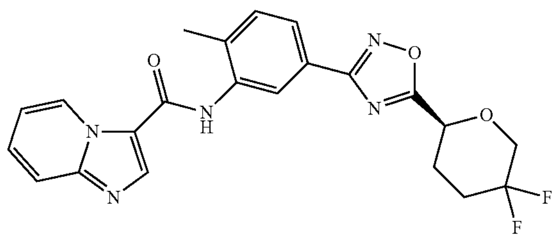 [SMILES: Cc1ccc(-c2noc([C@@H]3CCC(F)(F)CO3)n2)cc1NC(=O)c1cnc2ccccn12] | ¹H NMR (400 MHz, d₄-MeOH) δ 9.73 (d, J = 7.2 Hz, 1H), 8.74 (s, 1H), 8.17 (m, 1H), 7.98-7.95 (m, 3H), 7.52-7.50 (m, 2H), 5.06 (dd, J = 8.4, 2.8 Hz, 1H), 4.07-4.00 (m, 1H), 3.91-3.81 (m, 1H), 2.44 (s, 3H), 2.40-2.21 (m, 4H). MS m/z 440.1 (M + 1)⁺. | 0.023 |
| F12 | 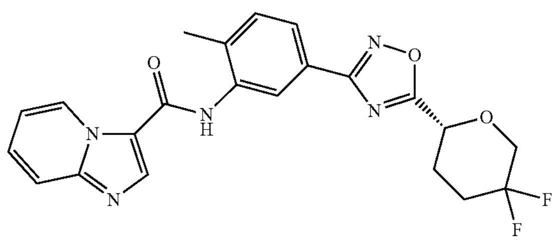 [SMILES: Cc1ccc(-c2noc([C@H]3CCC(F)(F)CO3)n2)cc1NC(=O)c1cnc2ccccn12] | ¹H NMR (400 MHz, d₄-MeOH) δ 9.73 (d, J = 7.2 Hz, 1H), 8.74 (s, 1H), 8.17 (m, 1H), 7.98-7.95 (m, 3H), 7.52-7.50 (m, 2H), 5.06 (dd, J = 8.4, 2.8 Hz, 1H), 4.07-4.00 (m, 1H), 3.91-3.81 (m, 1H), 2.44 (s, 3H), 2.40-2.21 (m, 4H). MS m/z 440.1 (M + 1)⁺. | 0.032 |
| F13 | 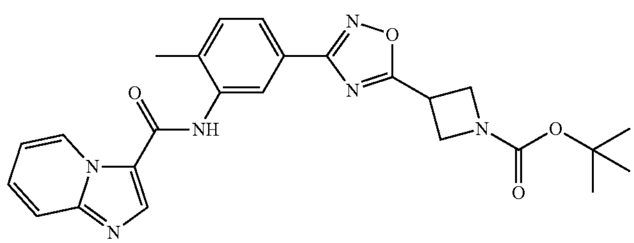 [SMILES: Cc1ccc(-c2noc(C3CN(C(=O)OC(C)(C)C)C3)n2)cc1NC(=O)c1cnc2ccccn12] | ¹H NMR (400 MHz, d₆-DMSO) δ 10.17 (s, 1H), 9.51 (d, J = 6.8 Hz, 1H), 8.70 (s, 1H), 8.10 (d, J = 2.0 Hz, 1H), 7.86 (dt, J = 12, 2.0 Hz, 2H), 7.68 (t, J = 8.0, 1H), 7.51 (d, J = 8 Hz, 1H), 7.31 (td, J = 6.8, 0.8 Hz, 1H), 4.06-4.38 (m, 5H) 2.37 (s, 3H), 1.04 (s, 9H). MS m/z 476.2 (M + 1). | 0.623 |
| F14 | 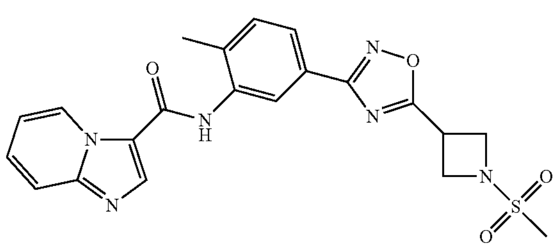 [SMILES: Cc1ccc(-c2noc(C3CN(S(C)(=O)=O)C3)n2)cc1NC(=O)c1cnc2ccccn12] | ¹H NMR (400 MHz, d₆-DMSO) δ 10.17 (s, 1H), 9.52-9.50 (m, 1H), 8.69 (s, 1H), 8.10 (d, J = 1.6 Hz, 1H), 7.88-7.85 (m, 2H), 7.68-7.64 (m, 1H), 7.52 (d, J = 8.0 Hz, 1H), 7.31-7.27 (m, 1H), 4.36-4.30 (m, 3H), 4.22-4.19 (m, 2H), 3.11 (s, 3H), 2.37 (s, 3H). MS m/z 453.4 (M + 1)⁺. | 0.042 |
| F15 | 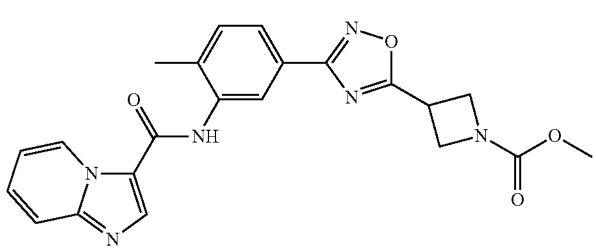 [SMILES: COC(=O)N1CC(c2nc(-c3ccc(C)c(NC(=O)c4cnc5ccccn45)c3)no2)C1] | ¹H NMR (400 MHz, d₆-DMSO) δ 10.18 (s, 1H), 9.52 (d, J = 7.2 Hz, 1H), 8.71 (s, 1H), 8.10 (s, 1H), 7.82-7.91 (m, 2H), 7.69 (t, J = 8.0 Hz, 1H), 7.51 (d, J = 8.4 Hz, 1H), 7.31 (td, J = 7.2, 0.8 Hz, 1H), 4.15-4.44 (m, 5H) 3.59 (s, 3H), 2.37 (s, 3H) MS m/z 433.3 (M + 1). | 0.02 |

TABLE 1-continued

| Cmpd No. | Structure | Physical Data | c-kit (Mo7e) μM |
|---|---|---|---|
| F16 | 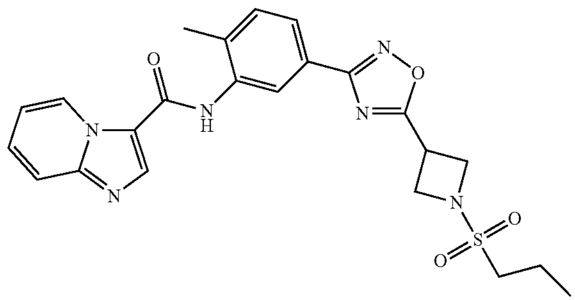 [SMILES: CCCS(=O)(=O)N1CC(c2nc(-c3ccc(C)c(NC(=O)c4cnc5ccccn45)c3)no2)C1] | $^1$H NMR (400 MHz, d$_6$-DMSO) δ $^1$H NMR (400 MHz, d$_6$-DMSO) δ 10.07 (s, 1H), 9.43 (d, J = 7.0, 1H), 8.59 (s, 1H), 8.03 (s, 1H), 7.81-7.71 (m, 2H), 7.56 (s, 1H), 7.45 (d, J = 8.1 Hz, 1H), 7.19 (s, 1H), 4.24 (d, J = 3.2 Hz, 3H), 4.14 (s, 2H), 3.20-3.07 (m ,3H), 2.31 (s, 3H), 1.66 (dd, J = 7.5 Hz, 15.2, 2H), 0.92 (d, J = 7.5 Hz, 2H). MS m/z 481.5 (M + 1)$^+$. | 0.035 |
| F17 | 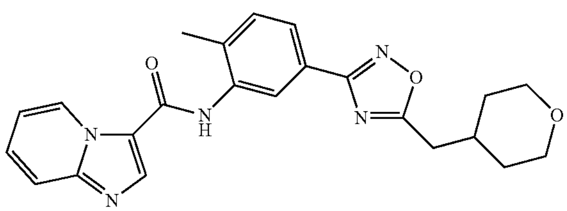 [SMILES: Cc1ccc(-c2noc(CC3CCOCC3)n2)cc1NC(=O)c1cnc2ccccn12] | $^1$H NMR (400 MHz, d$_6$-DMSO) δ 10.12 (s, 1H), 9.49 (d, J = 6.9 Hz, 1H), 8.06 (s, 1H), 7.82 (d, J = 7.8 Hz, 2H), 7.63-7.57 (m, 1H), 7.50 (d, J = 8.1 Hz, 1H), 7.25 (s, 1H), 3.82 (s, 2H), 3.31 (t, J = 7.1 Hz, 2H), 2.98 (d, J = 7.1 Hz, 2H), 2.37 (s, 3H), 2.01-2.11 (m, 1H), 1.62 (s, 2H), 1.41-1.25 (m, 2H). MS m/z 418.4 (M + 1)$^+$. | 0.027 |
| F18 | 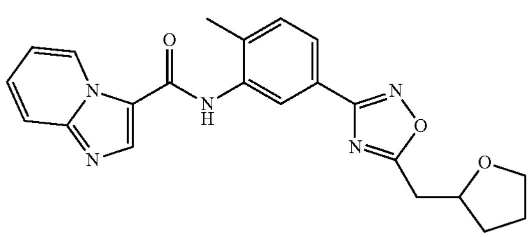 [SMILES: Cc1ccc(-c2noc(CC3CCCO3)n2)cc1NC(=O)c1cnc2ccccn12] | $^1$H NMR (400 MHz, d$_6$-DMSO) δ 10.15 (s, 1H), 9.51 (d, J = 6.9 Hz, 1H), 8.68 (s, 1H), 8.07 (s, 1H), 7.96-7.75 (m, 2H), 7.66 (s, 1H), 7.50 (d, J = 8.1 Hz, 1H), 7.29 (s, 1H), 4.30 (d, J = 5.1 Hz, 1H), 3.83-3.73 (m, 1H), 3.72-3.51 (m, 1H), 3.09-3.28 (m, 2H), 2.37 (s, 3H), 2.02-2.14 (m, 1H), 1.81-1.91 (m, 2H), 1.61-1.78 (m, 2H). MS m/z 404.4 (M + 1)$^+$. | 0.064 |
| F19 | 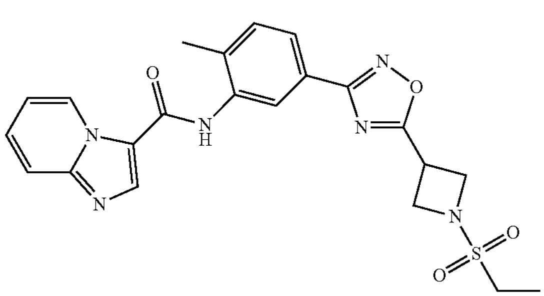 [SMILES: CCS(=O)(=O)N1CC(c2nc(-c3ccc(C)c(NC(=O)c4cnc5ccccn45)c3)no2)C1] | $^1$H NMR (400 MHz, d$_6$-DMSO) δ 10.05 (s, 1H), 9.47-9.45 (m, 1H), 8.59 (s, 1H), 8.10-8.09 (d, J = 1.6 Hz, 1H), 7.76-7.91 (m, 2H), 7.55-7.49 (m, 2H), 7.20-7.16 (m, 1H), 4.35-4.28 (m, 3H), 4.25-4.20 (m, 2H), 3.22 (q, J = 7.2 Hz, 2H), 2.37 (s, 3H), 1.25 (t, J = 7.2 Hz, 3H). MS m/z 467.5 (M + 1)$^+$. | 0.033 |

TABLE 1-continued

| Cmpd No. | Structure | Physical Data | c-kit (Mo7e) μM |
|---|---|---|---|
| F20 | 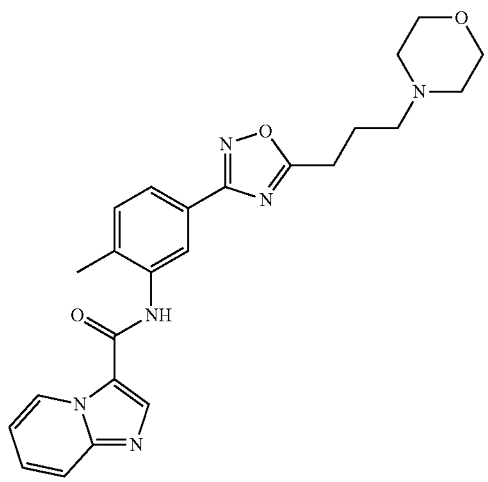 [SMILES: Cc1ccc(-c2noc(CCCN3CCOCC3)n2)cc1NC(=O)c1cnc2ccccn12] | $^1$H NMR (400 MHz, d$_6$-DMSO) δ 10.06 (s, 1H), 9.46 (d, J = 7.0 Hz, 1H), 8.63 (s, 1H), 8.09 (s, 1H), 7.82 (d, J = 8.7 Hz, 2H), 7.58 (s, 1H), 7.51 (d, J = 8.1 Hz, 1H), 7.22 (s, 1H), 3.91-4.01 (m, 2H), 3.53-3.65 (m, 5H), 3.47 (s, 3H), 3.32-3.20 (m, 2H), 3.12 (d, J = 7.4 Hz, 4H), 2.37 (s, 3H), 2.21 (s, 2H). MS m/z 446.5 (M + 1)$^+$. | 0.095 |
| F21 | 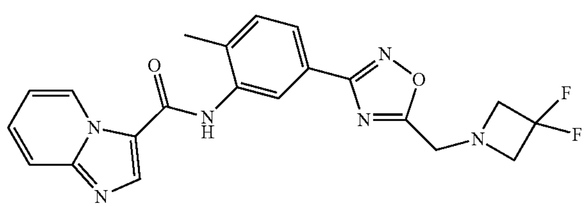 [SMILES: Cc1ccc(-c2noc(CN3CC(F)(F)C3)n2)cc1NC(=O)c1cnc2ccccn12] | $^1$H NMR (400 MHz, CDCl$_3$) δ 9.47 (d, J = 7.2 Hz, 1H), 8.51 (d, J = 1.2 Hz, 1H), 8.13 (s, 1H), 7.81 (dd, J = 1.2, 7.6 Hz, 1H), 7.68 (d, J = 9.2 Hz, 1H), 7.54 (s, 1H), 7.38 (m, 1H), 7.32 (d, J = 8.0 Hz, 1H), 6.99 (t, J = 7.2 Hz, 1H), 4.10 (s, 2H), 3.82 (t, J = 12.0 Hz, 4H). MS m/z 425.1 (M + 1)$^+$. | 0.044 |
| F22 | 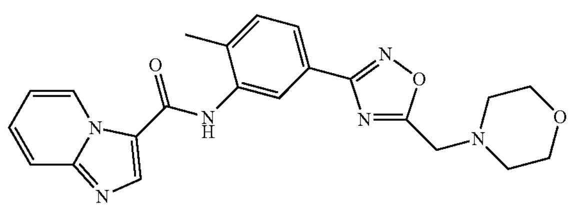 [SMILES: Cc1ccc(-c2noc(CN3CCOCC3)n2)cc1NC(=O)c1cnc2ccccn12] | MS m/z 419.2 (M + 1)$^+$. | 0.073 |
| F23 | 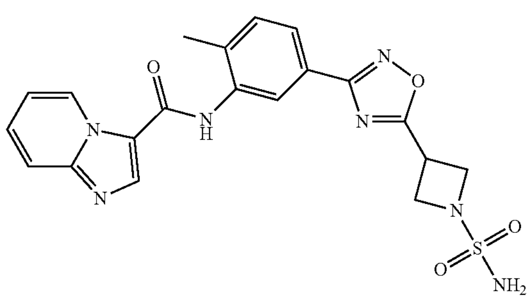 [SMILES: Cc1ccc(-c2noc(C3CN(S(N)(=O)=O)C3)n2)cc1NC(=O)c1cnc2ccccn12] | $^1$H NMR (400 MHz, d$_6$-DMSO) δ 10.14 (s, 1H), 9.51-9.48 (m, 1H), 8.67 (s, 1H), 8.11 (d, J = 1.6 Hz, 1H), 7.87-7.84 (m, 2H), 7.66-7.61 (m, 1H), 7.52 (d, J = 8.0 Hz, 1H), 7.29-7.25 (m, 1H), 7.13 (s, 2H), 4.24-4.18 (m, 1H), 4.16-4.12 (m, 2H), 4.05-4.01 (m, 2H), 2.37 (s, 3H). MS m/z 454.5 (M + 1)$^+$. | 0.088 |
| F24 | 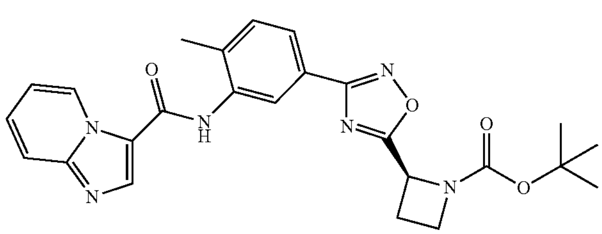 [SMILES: Cc1ccc(-c2noc([C@@H]3CCN3C(=O)OC(C)(C)C)n2)cc1NC(=O)c1cnc2ccccn12] | $^1$H NMR (400 MHz, d$_6$-DMSO) δ 10.15 (s, 1H), 9.51 (d, J = 6.9 Hz, 1H), 8.68 (s, 1H), 8.10 (s, 1H), 7.86 (d, J = 9.0 Hz, 2H), 7.65 (s, 1H), 7.52 (d, J = 8.1 Hz, 1H), 7.28 (s, 1H), 5.50 (s, 1H), 4.02 (s, 4H), 2.76-2.64 (m, 1H), 2.37 (s, 3H), 1.22 (s, 9H). MS m/z 475.5 (M + 1)$^+$. | 0.08 |

TABLE 1-continued

| Cmpd No. | Structure | Physical Data | c-kit (Mo7e) μM |
|---|---|---|---|
| F25 | 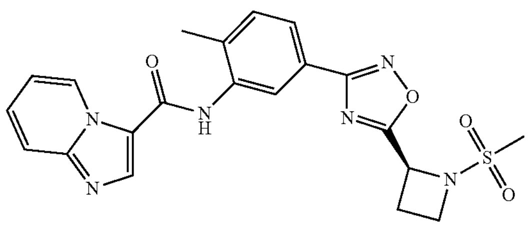 [SMILES: Cc1ccc(-c2noc([C@@H]3CCN3S(C)(=O)=O)n2)cc1NC(=O)c1cnc2ccccn12] | ¹H NMR (400 MHz, d₆-DMSO) δ 10.12 (s, 1H), 9.51-9.49 (m, 1H), 8.66 (s, 1H), 8.12 (d, J = 1.6 Hz, 1H), 7.86-7.83 (m, 2H), 7.64-7.60 (m, 1H), 7.52 (d, J = 8.4 Hz, 1H), 7.28-7.24 (m, 1H), 5.74 (t, J = 8.0 Hz, 1H), 4.13 (q, J = 8.8 Hz, 2H), 3.87 (q, J = 7.2 Hz, 2H), 3.17 (s, 3H), 2.38 (s, 3H). MS m/z 453.5 (M + 1)⁺. | 0.046 |
| F26 | 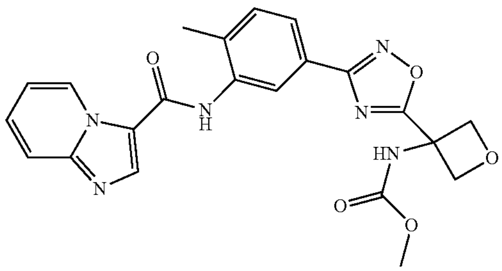 | ¹H NMR (400 MHz, CDCl₃) δ 9.46 (m, 1H), 8.48 (s, 1H), 8.14 (s, 1H), 7.81 (dd, J = 1.6, 8.0 Hz, 1H), 7.69 (d, J = 7.2 Hz, 1H), 7.56 (s, 1H), 7.38 (m, 1H), 7.31 (d, J = 8.0 Hz, 1H), 6.98 (dt, J = 0.8, 6.8 Hz, 1H), 5.12 (m, 2H), 4.91 (m, 2H), 3.66 (s, 3H), 2.36 (s, 3H). MS m/z 499.0 (M + 1)⁺. | 0.103 |
| F27 | 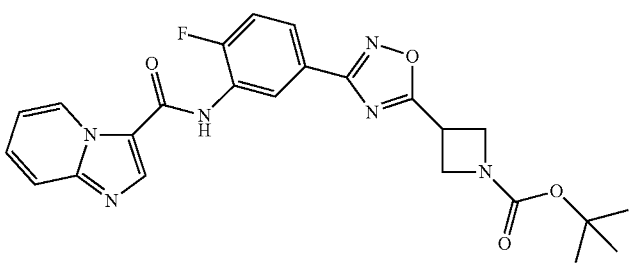 [SMILES: CC(C)(C)OC(=O)N1CC(c2nc(-c3ccc(F)c(NC(=O)c4cnc5ccccn45)c3)no2)C1] | MS m/z 479.2 (M + 1)⁺. | 0.997 |
| F28 | 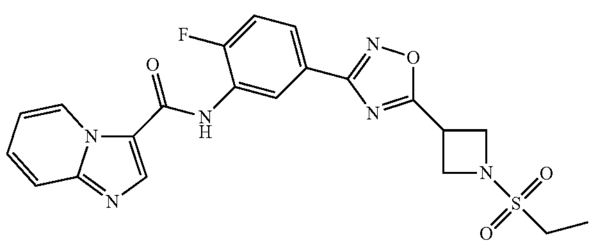 [SMILES: CCS(=O)(=O)N1CC(c2nc(-c3ccc(F)c(NC(=O)c4cnc5ccccn45)c3)no2)C1] | ¹H NMR (400 MHz, CDCl₃) δ 9.50 (d, J = 2 Hz, 1H), 9.09 (dd, J = 2, 7.2 Hz, 1H), 8.21 (s, 1H), 7.87 (m, 1H), 7.79 (m, 1H), 7.71 (d, J = 9.2 Hz, 1H), 7.41 (m, 1H), 7.22 (dd, J = 8.8, 10.4 Hz, 1H), 7.02 (dt, J = 0.8, 6.8 Hz, 1H), 4.34 (m, 4H), 4.07 (m, 1H), 3.00 (q, J = 7.6 Hz, 2H), 1.35 (t, J = 7.6 Hz, 3H). MS m/z 471.2 (M + 1)⁺. | 0.12 |
| F29 | 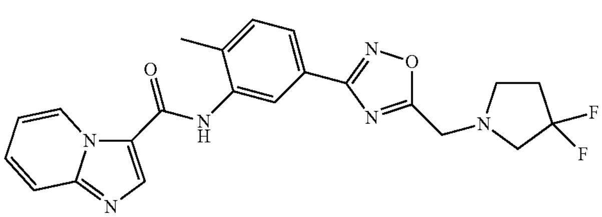 [SMILES: Cc1ccc(-c2noc(CN3CCC(F)(F)C3)n2)cc1NC(=O)c1cnc2ccccn12] | MS m/z 439.2 (M + 1)⁺. | 0.016 |
| F30 | 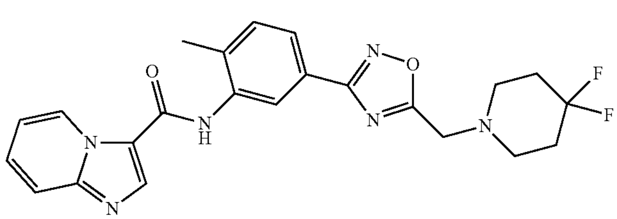 [SMILES: Cc1ccc(-c2noc(CN3CCC(F)(F)CC3)n2)cc1NC(=O)c1cnc2ccccn12] | ¹H NMR (400 MHz, CD₂Cl₂) δ = 9.71 (d, J = 6.9 Hz, 1H), 9.37 (s, 1H), 9.01 (s, 1H), 8.10 (s, 1H), 8.00 (d, J = 8.8 Hz, 1H), 7.89 (d, J = 7.3 Hz, 1H), 7.75 (d, J = 7.9 Hz, 1H), 7.41 (t, J = 6.9 Hz, 1H), 7.29 (d, J = 8.0 Hz, 1H), 4.42 (s, 2H), 3.36 (s, 3H), 2.31 (d, J = 9.8 Hz, 8H). MS m/z 453.2 (M + 1)⁺. | 0.02 |

TABLE 1-continued

| Cmpd No. | Structure | Physical Data | c-kit (Mo7e) μM |
|---|---|---|---|
| F31 | 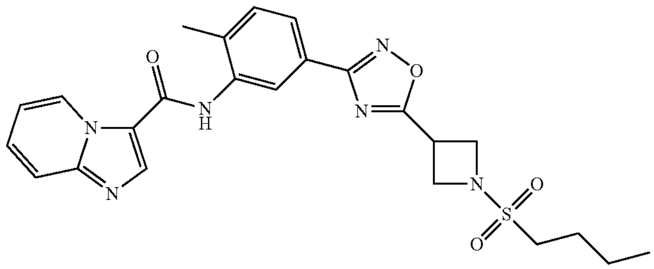 [SMILES: CCCCS(=O)(=O)N1CC(c2nc(-c3ccc(C)c(NC(=O)c4cnc5ccccn45)c3)no2)C1] | MS m/z 495.2 (M + 1)+. | 0.054 |
| F32 | 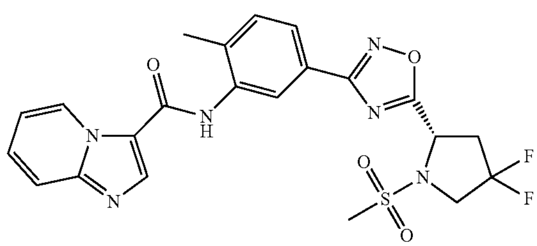 [SMILES: Cc1ccc(-c2noc([C@@H]3CC(F)(F)CN3S(C)(=O)=O)n2)cc1NC(=O)c1cnc2ccccn12] | ¹H NMR (400 MHz, d₆-DMSO) δ 10.16 (s, 1H), 9.50 (d, J = 6.9 Hz, 1H), 8.68 (s, 1H), 8.08 (d, J = 1.7 Hz, 1H), 7.84 (dd, J = 5.5, 13.5 Hz, 2H), 7.68-7.60 (m, 1H), 7.52 (d, J = 8.1 Hz, 1H), 7.28 (t, J = 6.9 Hz, 1H), 5.61-5.74 (m, 1H), 4.10 (dd, J = 11.7, 23.8 Hz, 1H), 3.95 (dd, J = 11.7, 23.8 Hz, 1H), 3.21 (s, 3H), 3.10-3.21 (m, 1H), 2.81-2.87 (m, 1H), 2.37 (s, 3H). MS m/z 503.4 (M + 1)+. | 0.055 |
| F33 | 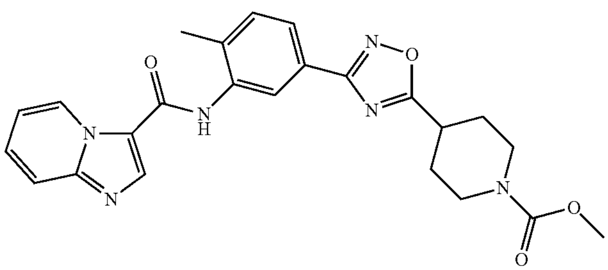 [SMILES: COC(=O)N1CCC(c2nc(-c3ccc(C)c(NC(=O)c4cnc5ccccn45)c3)no2)CC1] | ¹H NMR (400 MHz, d₆-DMSO) δ 10.17 (s, 1H), 8.69 (s, 1H), 8.06 (d, J = 1.6 Hz, 1H), 7.92-7.78 (m, 2H), 7.72-7.61 (m, 1H), 7.50 (d, J = 8.1 Hz, 1H), 7.30 (t, J = 6.9 Hz, 1H), 3.60 (s, 3H), 3.37 (t, J = 11.0 Hz, 1H), 3.05 (br s, 2H), 2.36 (s, 3H), 2.10 (d, J = 10.4 Hz, 2H), 1.70 (dd, J = 11.3, 20.4 Hz, 2H). MS m/z 461.5 (M + 1)+. | 0.084 |
| F34 | 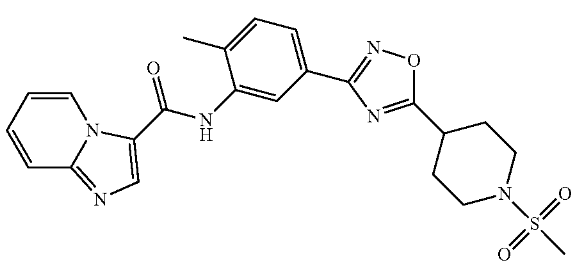 [SMILES: Cc1ccc(-c2noc(C3CCN(S(C)(=O)=O)CC3)n2)cc1NC(=O)c1cnc2ccccn12] | ¹H NMR (400 MHz, d₆-DMSO) δ 10.12 (s, 1H), 9.48 (d, J = 6.9 Hz, 1H), 8.64 (s, 1H), 8.06 (s, 1H), 7.83 (d, J = 8.0 Hz, 2H), 7.60 (s, 1H), 2.85-3.15 (m, 4H), 2.36 (s, 3H), 2.22 (d, J = 9.5 Hz, 2H), 1.87 (q, J = 9.5 Hz, 2H). MS m/z 481.5 (M + 1)+. | 0.095 |
| F35 | 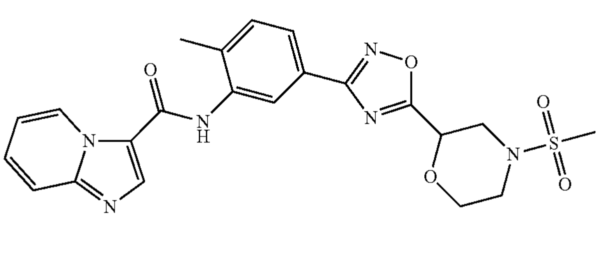 [SMILES: Cc1ccc(-c2noc(C3CN(S(C)(=O)=O)CCO3)n2)cc1NC(=O)c1cnc2ccccn12] | ¹H NMR (400 MHz, d₆-DMSO) δ 10.16 (s, 1H), 9.51 (d, J = 7.0 Hz, 1H), 8.68 (s, 1H), 8.11 (d, J = 1.7 Hz, 1H), 7.90-7.80 (m, 2H), 7.73-7.57 (m, 1H), 7.53 (d, J = 8.1 Hz, 1H), 7.29 (t, J = 6.9 Hz, 1H), 5.20 (dd, J = 3.1, 8.9 Hz, 1H), 4.06 (d, J = 11.8 Hz, 2H), 3.94-3.74 (m, 3H), 3.52-3.31 (m, 2H), 3.00 (s, 3H), 2.38 (s, 3H). MS m/z 483.5 (M + 1)+. | 0.066 |

TABLE 1-continued

| Cmpd No. | Structure | Physical Data | c-kit (Mo7e) μM |
|---|---|---|---|
| F36 | 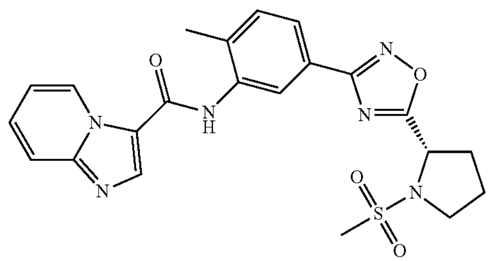 [SMILES: Cc1ccc(-c2noc([C@@H]3CCCN3S(C)(=O)=O)n2)cc1NC(=O)c1cnc2ccccn12] | ¹H NMR (400 MHz, d₆-DMSO) δ 10.16 (s, 1H), 9.51 (d, J = 6.9 Hz, 1H), 8.68 (s, 1H), 8.07 (s, 1H), 7.91-7.73 (m, 2H), 7.65 (s, 1H), 7.51 (d, J = 8.1 Hz, 1H), 7.28 (s, 1H), 5.32 (dd, J = 3.9, 8.5 Hz, 1H), 3.50 (s, 3H), 3.01-3.21 (m, 2H), 2.37 (s, 3H), 2.21-1.87 (m, 4H). MS m/z 467.51 (M + 1)⁺. | 0.093 |
| F37 | 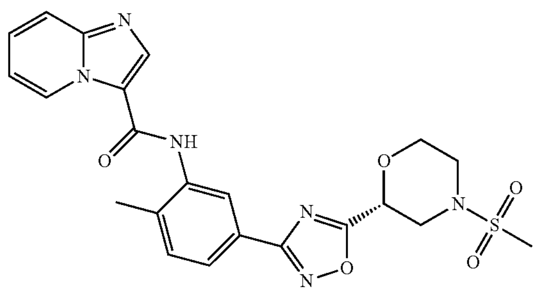 [SMILES: Cc1ccc(-c2noc([C@H]3CN(S(C)(=O)=O)CCO3)n2)cc1NC(=O)c1cnc2ccccn12] | ¹H NMR (400 MHz, d₆-DMSO) δ 10.15 (s, 1H), 9.50 (d, J = 6.9 Hz, 1H), 8.68 (s, 1H), 8.11 (d, J = 1.7 Hz, 1H), 7.88-7.83 (m, 2H), 7.68-7.62 (m, 1H), 7.53 (d, J = 8.1 Hz, 1H), 7.28 (t, J = 6.5 Hz, 1H), 5.15-5.21 (m, 1H), 4.06 (d, J = 11.8 Hz, 2H), 3.86-3.78 (m, 2H), 3.43-3.34 (m, 2H), 3.08 (d, J = 9.2 Hz, 1H), 3.00 (s, 3H), 2.38 (s, 3H). MS m/z 483.51 (M + 1)⁺. | 0.06 |
| F38 | 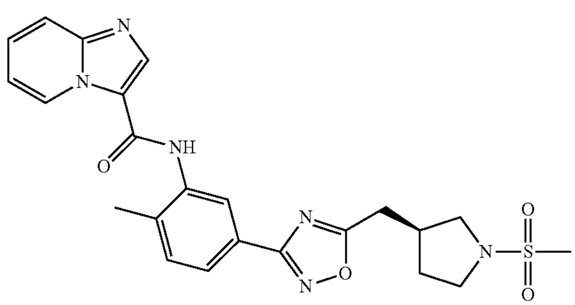 [SMILES: Cc1ccc(-c2noc(C[C@@H]3CCN(S(C)(=O)=O)C3)n2)cc1NC(=O)c1cnc2ccccn12] | ¹H NMR (400 MHz, d₆-DMSO) δ 10.21 (s, 1H), 9.52 (d, J = 7.0 Hz, 1H), 8.72 (s, 1H), 8.07 (d, J = 1.7 Hz, 1H), 7.90 (d, J = 9.0 Hz, 1H), 7.84 (dd, J = 1.7, 7.9 Hz, 1H), 7.74-7.66 (m, 1H), 7.51 (d, J = 8.1 Hz, 1H), 7.33 (t, J = 6.9 Hz, 1H), 3.51-3.54 (m, 1H), 3.41-3.33 (m, 1H), 3.30-3.21 (m, 1H), 3.11-3.19 (m, 2H), 3.00-3.08 (m, 1H), 2.91 (s, 3H), 2.70-2.81 (m, 1H), 2.37 (s, 3H), 2.11-2.21 (m, 1H), 1.62-1.74 (m, 1H). MS m/z 481.54 (M + 1)⁺. | 0.09 |
| F39 | 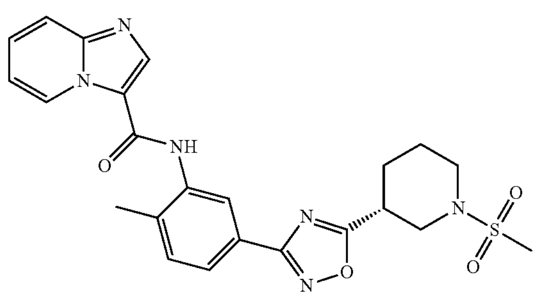 [SMILES: Cc1ccc(-c2noc([C@@H]3CCCN(S(C)(=O)=O)C3)n2)cc1NC(=O)c1cnc2ccccn12] | ¹H NMR (400 MHz, d₆-DMSO) δ 10.20 (s, 1H), 9.52 (dd, J = 3.5, 4.5 Hz, 1H), 8.71 (s, 1H), 8.07 (d, J = 1.7 Hz, 1H), 7.92-7.81 (m, 2H), 7.73-7.66 (m, 1H), 7.51 (d, J = 8.1 Hz, 1H), 7.32 (dd, J = 5.9, 6.9 Hz, 1H), 3.84 (d, J = 11.7 Hz, 1H), 3.49-3.41 (m, 2H), 3.18-3.29 (m, 1H), 2.96-2.86 (m, 3H), 2.37 (s, 3H), 2.23-2.13 (m, 1H), 1.70-1.94 (m, 3H). MS m/z 481.54 (M + 1)⁺. | 0.049 |
| F40 | 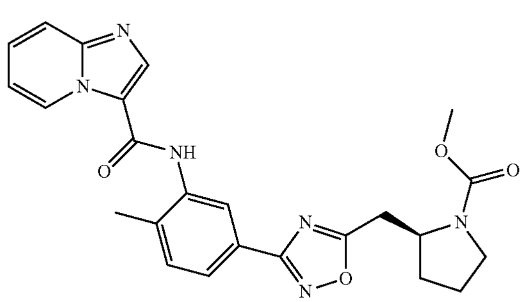 [SMILES: COC(=O)N1CCC[C@H]1Cc1nc(-c2ccc(C)c(NC(=O)c3cnc4ccccn34)c2)no1] | ¹H NMR (400 MHz, d₆-DMSO) δ 10.18 (s, 1H), 9.52 (d, J = 6.9 Hz, 1H), 8.70 (s, 1H), 8.06 (s, 1H), 7.92-7.76 (m, 2H), 7.72-7.64 (m, 1H), 7.51 (d, J = 8.1 Hz, 1H), 7.31 (t, J = 6.9 Hz, 1H), 4.27 (s, 2H), 3.34-3.21 (m, 4H), 2.37 (s, 3H), 1.94-2.04 (m, 1H), 1.72-1.88 (m, 3H). MS m/z 461.49 (M + 1)⁺. | 0.094 |

TABLE 1-continued

| Cmpd No. | Structure | Physical Data | c-kit (Mo7e) μM |
|---|---|---|---|
| F41 | 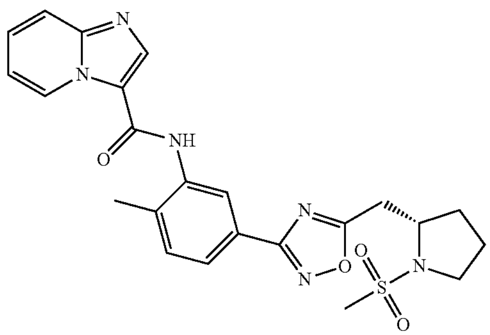 [SMILES: Cc1ccc(-c2noc(C[C@@H]3CCCN3S(C)(=O)=O)n2)cc1NC(=O)c1cnc2ccccn12] | $^1$H NMR (400 MHz, d$_6$-DMSO) δ 10.18 (s, 1H), 9.52 (d, J = 6.9 Hz, 1H), 8.70 (s, 1H), 8.06 (s, 1H), 7.92-7.76 (m, 2H), 7.72-7.64 (m, 1H), 7.51 (d, J = 8.1 Hz, 1H), 7.31 (t, J = 6.9 Hz, 1H), 4.17 (s, 2H), 3.34-3.21 (m, 4H), 2.37 (s, 3H), 1.94-2.04 (m, 1H), 1.72-1.88 (m, 3H). MS m/z 481.54 (M + 1)$^+$. | 0.092 |
| F42 | 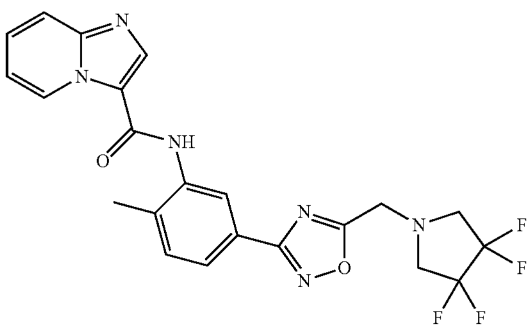 [SMILES: Cc1ccc(-c2noc(CN3CC(F)(F)C(F)(F)C3)n2)cc1NC(=O)c1cnc2ccccn12] | MS m/z 475.2 (M + 1)$^+$. | 0.013 |
| F43 | 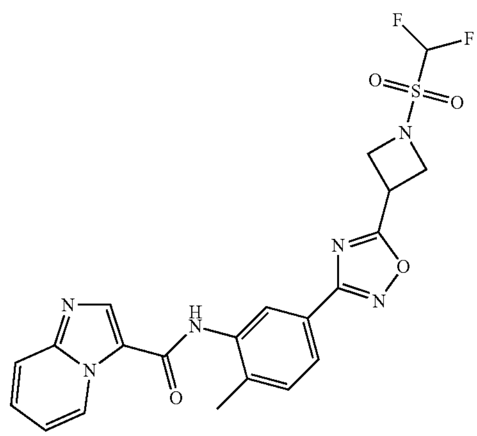 [SMILES: Cc1ccc(-c2noc(C3CN(S(=O)(=O)C(F)F)C3)n2)cc1NC(=O)c1cnc2ccccn12] | $^1$H NMR (400 MHz, d$_6$-DMSO) δ 10.18 (s, 1H), 9.52 (d, J = 6.8 Hz, 1H), 8.70 (s, 1H), 8.10 (d, J = 2.5 Hz, 1H), 7.88 (m, 2H), 7.67 (m ,1H), 7.53 (d, J = 8.4 Hz, 1H), 7.30 (t, J = 7.2 Hz, 1H), 7.26 (t, J = 52 Hz, 1H), 4.59 (m, 2H), 4.47 (m, 3H), 2.38 (s, 3H). MS m/z 489.2 (M + 1)$^+$. | 0.024 |
| F44 | 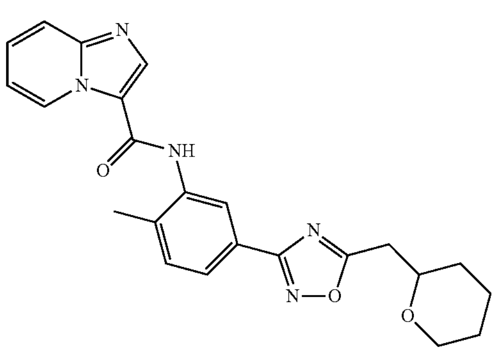 [SMILES: Cc1ccc(-c2noc(CC3CCCCO3)n2)cc1NC(=O)c1cnc2ccccn12] | $^1$H NMR (400 MHz, d$_6$-DMSO) δ 10.03 (s, 1H), 9.46 (d, J = 6.9 Hz, 1H), 8.59 (s, 1H), 8.07 (d, J = 1.6 Hz, 1H), 7.84-7.76 (m, 2H), 7.55-7.46 (m, 2H), 7.11-7.15 (m, 1H), 3.07-3.37 (m, 5H), 2.37 (s, 3H), 1.68-1.80 (m, 3H), 1.23-1.59 (m, 6H) MS m/z 418.46 (M + 1)$^+$. | 0.017 |

TABLE 1-continued

| Cmpd No. | Structure | Physical Data | c-kit (Mo7e) μM |
|---|---|---|---|
| F45 | 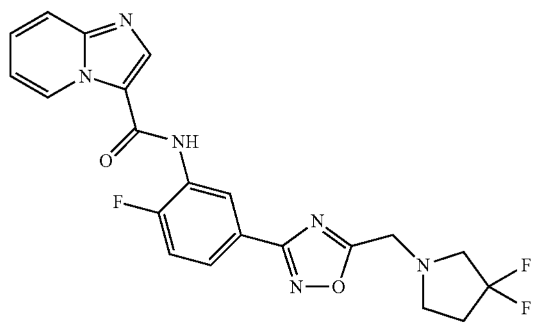 [SMILES: O=C(Nc1cc(-c2noc(CN3CCC(F)(F)C3)n2)ccc1F)c1cnc2ccccn12] | ¹H NMR (400 MHz, CDCl₃) δ 9.48 (d, J = 7.2 Hz, 1H), 9.08 (dd, J = 2.0, 7.6 Hz, 1H), 8.19 (s, 1H), 7.81 (m, 2H), 7.70 (d, J = 8.8 Hz, 1H), 7.40 (m, 1H), 7.22 (m, 1H), 7.01 (m, 1H), 4.00 (s, 2H), 3.11 (t, J = 13.2 Hz, 2H), 2.94 (t, J = 7.2 Hz, 2H), 2.29 (m, 2H). MS m/z 443.1 (M + 1)⁺. | 0.09 |
| F46 | 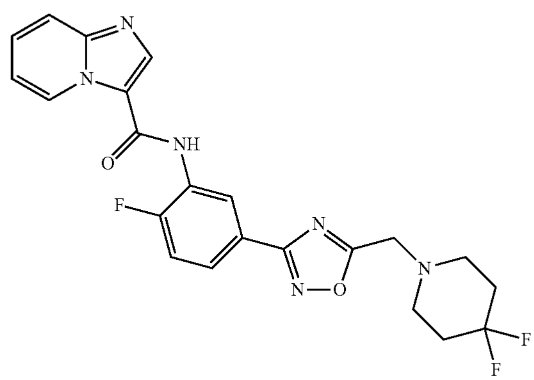 [SMILES: O=C(Nc1cc(-c2noc(CN3CCC(F)(F)CC3)n2)ccc1F)c1cnc2ccccn12] | ¹H NMR (400 MHz, CDCl₃) δ 9.49 (m, 1H), 9.07 (dd, J = 2.0, 7.6 Hz, 1H), 8.18 (s, 1H), 7.81 (m, 2H), 7.70 (m, 1H), 7.40 (m, 1H), 7.22 (m, 1H), 7.01 (m, 1H), 3.91 (s, 4H), 2.02 (m, 4H). MS m/z 457.1 (M + 1)⁺. | 0.073 |
| F47 | 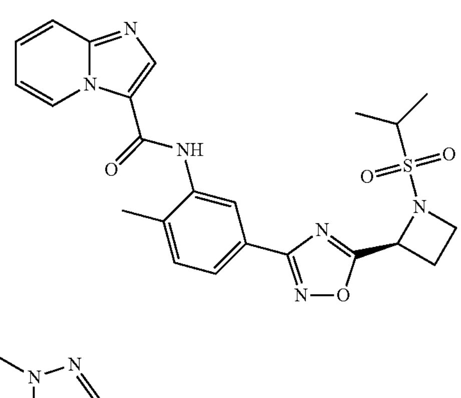 | MS m/z 481.54 (M + 1)⁺. | 0.047 |
| F48 | 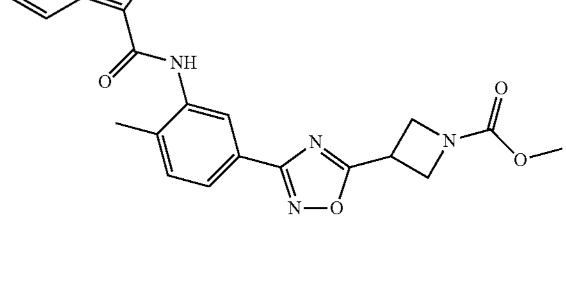 | ¹H NMR (400 MHz, CDCl₃) δ 8.54 (d, J = 6.5 Hz, 1H), 8.53 (s, 1H), 8.36 (m, 2H), 7.81 (d, J = 7.9 Hz, 1H), 7.76 (s, 1H), 7.41 (dd, J = 8.9, 6.9 Hz, 1H), 7.35 (d, J = 7.9 Hz, 1H), 6.99 (t, J = 6.1 Hz, 1H), 4.41 (m, 4H), 4.12 (m, 1H), 3.71 (s, 3H), 2.41 (s, 3H). MS m/z 433.2 (M + 1)⁺. | 0.08 |

TABLE 1-continued

| Cmpd No. | Structure | Physical Data | c-kit (Mo7e) µM |
|---|---|---|---|
| F49 | 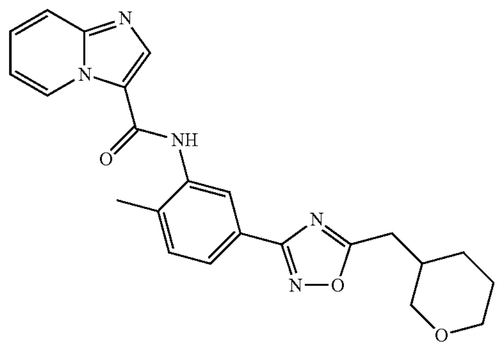 [SMILES: Cc1ccc(-c2noc(CC3CCCOC3)n2)cc1NC(=O)c1cnc2ccccn12] | ¹H NMR (400 MHz, d₆-DMSO) δ 10.19 (s, 1H), 9.54-9.50 (m, 1H), 8.71 (s, 1H), 8.06 (d, J = 1.7 Hz, 1H), 7.89 (d, J = 9.0 Hz, 1H), 7.83 (dd, J = 1.8, 7.9 Hz, 1H), 7.73-7.66 (m, 1H), 7.50 (d, J = 8.1 Hz, 1H), 7.32 (td, J = 1.1, 6.9 Hz, 1H), 3.83 (dd, J = 2.3, 11.1 Hz, 1H), 3.73 (dt, J = 3.6, 10.9 Hz, 1H), 3.34 (td, J = 3.0, 10.8 Hz, 1H), 3.18 (dd, J = 9.3, 11.1 Hz, 1H), 2.93 (qd, J = 7.2, 15.6 Hz, 2H), 2.36 (s, 3H), 2.15-2.05 (m, 1H), 1.88-1.78 (m, 1H), 1.64-1.44 (m, 2H), 1.30-1.41 (m, 1H). MS m/z 418.46 (M + 1)⁺. | 0.04 |
| F50 | 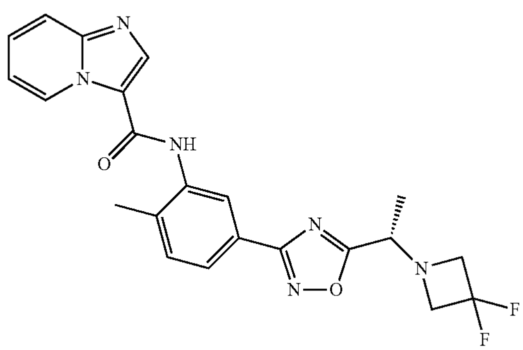 [SMILES: Cc1ccc(-c2noc([C@H](C)N3CC(F)(F)C3)n2)cc1NC(=O)c1cnc2ccccn12] | MS m/z 439.0 (M + 1)⁺. | 0.077 |
| F51 | 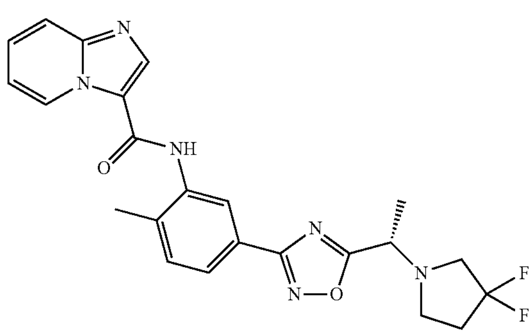 [SMILES: Cc1ccc(-c2noc([C@H](C)N3CCC(F)(F)C3)n2)cc1NC(=O)c1cnc2ccccn12] | MS m/z 453.2 (M + 1)⁺. | 0.043 |
| F52 | 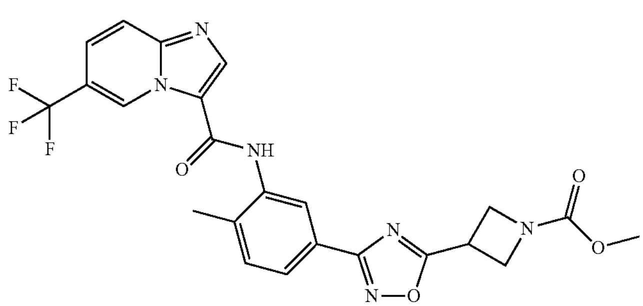 [SMILES: COC(=O)N1CC(c2nc(-c3ccc(C)c(NC(=O)c4cnc5ccc(C(F)(F)F)cn45)c3)no2)C1] | ¹H NMR (400 MHz, d₆-DMSO) δ 10.27 (s, 1H), 9.88 (s, 1H), 8.72 (s, 1H), 8.08 (d, J = 1.6 Hz, 1H), 8.01 (d, J = 9.5 Hz, 1H), 7.86 (dd, J = 1.7, 7.9 Hz, 1H), 7.79 (dd, J = 1.9, 9.5 Hz, 1H), 7.52 (d, J = 8.1 Hz, 1H), 4.39-4.10 (m, 6H), 3.59 (s, 3H), 2.37 (s, 3H). MS m/z 501.43 (M + 1)⁺. | 0.218 |

TABLE 1-continued

| Cmpd No. | Structure | Physical Data | c-kit (Mo7e) μM |
|---|---|---|---|
| F53 | 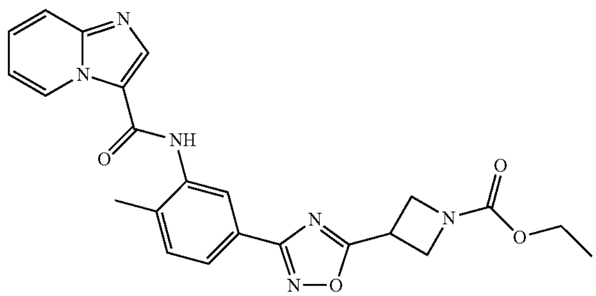 [SMILES: CCOC(=O)N1CC(c2nc(-c3ccc(C)c(NC(=O)c4cnc5ccccn45)c3)no2)C1] | ¹H NMR (400 MHz, d₆-DMSO) δ 10.16 (s, 1H), 9.51 (d, J = 6.9 Hz, 1H), 8.69 (s, 1H), 8.10 (d, J = 1.7 Hz, 1H), 7.86 (dd, J = 5.4, 11.7 Hz, 2H), 7.69-7.63 (m, 1H), 7.51 (d, J = 8.1 Hz, 1H), 7.29 (t, J = 6.9 1H), 4.37 (s, 3H), 4.27 (dd, J = 5.4, 8.6 Hz, 2H), 4.18 (s, 3H), 4.04 (q, J = 7.1 Hz, 3H), 2.37 (s, 3H), 1.17 (t, J = 7.1 Hz, 3H) MS m/z 447.46 (M + 1)⁺. | 0.093 |
| F54 | 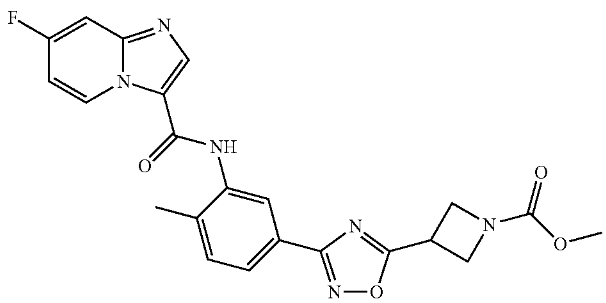 [SMILES: COC(=O)N1CC(c2nc(-c3ccc(C)c(NC(=O)c4cnc5cc(F)ccn45)c3)no2)C1] | ¹H NMR (400 MHz, d₆-DMSO) δ 10.15 (s, 1H), 9.49 (dd, J = 2.5, 5.0 Hz, 1H), 8.66 (s, 1H), 8.09 (d, J = 1.6 Hz, 1H), 7.88 (ddd, J = 3.4, 8.9, 9.6 Hz, 2H), 7.72-7.63 (m, 1H), 7.52 (d, J = 8.1 Hz, 1H), 4.38 (s, 2H), 4.34-4.24 (m, 1H), 4.23 (d, J = 19.4 Hz, 2H), 3.60 (s, 3H), 2.35 (d, J = 15.0 Hz, 3H) MS m/z 451.1 (M + 1)⁺. | 0.037 |
| F55 | 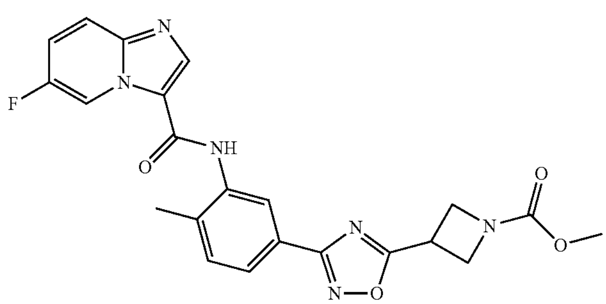 [SMILES: COC(=O)N1CC(c2nc(-c3ccc(C)c(NC(=O)c4cnc5ccc(F)cn45)c3)no2)C1] | ¹H NMR (400 MHz, d₆-DMSO) δ 10.13 (s, 1H), 9.48-9.46 (m, 1H), 8.64 (s, 1H), 8.08 (d, J = 1.6 Hz, 1H), 7.90-7.87 (m, 1H), 7.85 (dd, J = 2.0, 8.0 Hz, 1H), 7.67-7.62 (m, 1H), 7.51 (d, J = 8.4 Hz, 1H), 4.42-4.33 (m, 2H), 4.31-4.24 (m, 1H), 4.27-4.15 (m, 2H), 3.59 (s, 3H), 2.36 (s, 3H). MS m/z 451.42 (M + 1)⁺. | 0.054 |
| F56 | 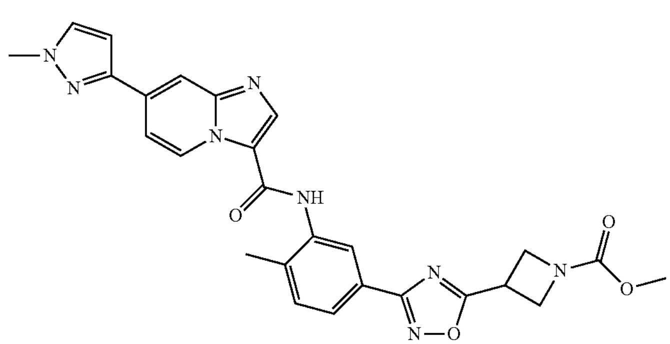 | MS m/z 513.2 (M + 1)⁺. | 0.006 |

TABLE 1-continued

| Cmpd No. | Structure | Physical Data | c-kit (Mo7e) μM |
|---|---|---|---|
| F57 | 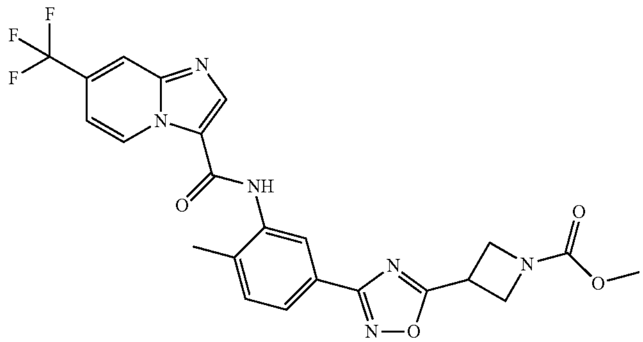 [SMILES: COC(=O)N1CC(c2nc(-c3ccc(C)c(NC(=O)c4cnc5cc(C(F)(F)F)ccn45)c3)no2)C1] | ¹H NMR (400 MHz, d₆-DMSO) δ 10.25 (s, 1H), 9.64-9.61 (m, 1H), 9.75 (s, 1H), 8.33-8.30 (m, 1H), 8.10 (dd, J = 1.6 Hz, 1H), 7.86 (dd, J = 1.6, 8.0 Hz, 1H), 7.52 (d, J = 8.4 Hz, 1H), 7.46 (dd, J = 2.0, 7.6 Hz, 1H), 4.40-4.33 (m, 2H), 4.31-4.25 (m, 1H), 4.22-4.18 (m, 2H), 3.59 (s, 3H), 2.38 (s, 3H).<br>MS m/z 501.43 (M + 1)⁺. | 0.13 |
| F58 | 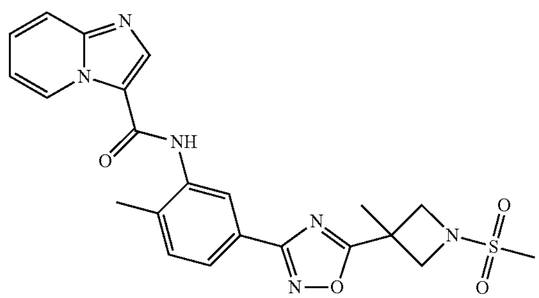 [SMILES: Cc1ccc(-c2noc(C3(C)CN(S(C)(=O)=O)C3)n2)cc1NC(=O)c1cnc2ccccn12] | MS m/z 467.1 (M + 1)⁺. | 0.089 |
| F59 | 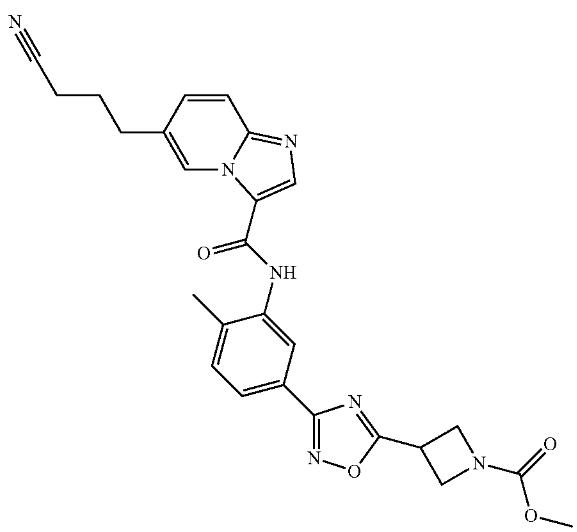 [SMILES: COC(=O)N1CC(c2nc(-c3ccc(C)c(NC(=O)c4cnc5ccc(CCCC#N)cn45)c3)no2)C1] | ¹H NMR (400 MHz, d₆-DMSO) δ 10.13 (s, 1H), 9.38-9.36 (m, 1H), 8.66 (s, 1H), 8.11 (d, J = 1.6 Hz, 1H), 7.86-7.82 (m, 2H), 7.63-7.60 (m, 1H), 7.51 (d, J = 8.0 Hz, 1H), 4.39-4.34 (m, 2H), 4.31-4.24 (m, 1H), 4.21-4.18 (m, 2H), 3.59 (s, 3H), 2.81-2.77 (m, 2H), 2.60-2.52 (m, 2H), 2.38 (s, 3H), 1.97-1.90 (m, 2H).<br>MS m/z 500.52 (M + 1)⁺. | 0.033 |
| F60 | 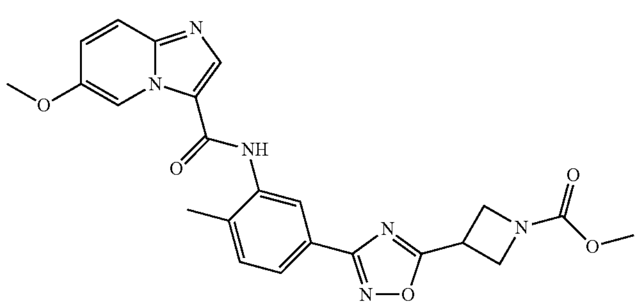 | ¹H NMR (400 MHz, d₆-DMSO) δ 10.01 (s, 1H), 9.12 (d, J = 2.4 Hz, 1H), 8.54 (s, 1H), 8.09 (d, J = 1.6 Hz, 1H), 7.85 (dd, J = 1.6, 7.8 Hz, 1H), 7.72 (d, J = 9.6 Hz, 1H), 7.51 (d, J = 8.0 Hz, 1H), 7.32 (dd, J = 2.4, 9.6 Hz, 1H), 4.38 (bs, 2H), 4.32-4.25 (m, 1H), 4.20 (bs, 2H), 3.83 (s, 3H), 3.59 (s, 3H), 2.37 (s, 3H).<br>MS m/z 463.1 (M + 1)⁺. | 0.028 |

TABLE 1-continued

| Cmpd No. | Structure | Physical Data | c-kit (Mo7e) μM |
|---|---|---|---|
| F61 | 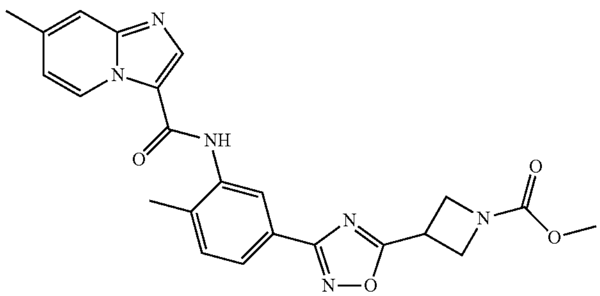 | $^1$H NMR (400 MHz, d$_6$-DMSO) δ 9.97 (s, 1H), 9.33 (d, J = 7.2 Hz, 1H), 8.52 (s, 1H), 8.09 (d, J = 1.6 Hz, 1H), 7.83 (dd, J = 1.6, 7.6 Hz, 1H), 7.58 (s, 1H), 7.50 (d, J = 8.0 Hz, 1H), 7.03 (dd, J = 1.6, 7.2 Hz, 1H), 4.39-4.33 (m, 2H), 4.31-4.24 (m, 1H), 4.22-4.16 (m, 2H), 3.59 (s, 3H), 2.43 (s, 3H), 2.36 (s, 3H).<br>MS m/z 447.17 (M + 1)$^+$. | 0.026 |
| F62 | 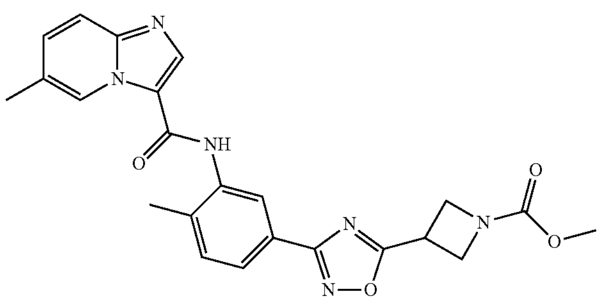 | $^1$H NMR (400 MHz, d$_6$-DMSO) δ 10.15 (s, 1H), 9.36 (s, 1H), 8.67 (s, 1H), 8.11 (d, J = 2.0 Hz, 1H), 7.85 (dd, J = 2.0, 8.0 Hz, 1H), 7.81 (d, J = 9.2 Hz, 1H), 7.57 (dd, J = 1.2, 9.2 Hz, 1H), 7.51 (d, J = 8.0 Hz, 1H), 4.39-4.34 (m, 2H), 4.31-4.24 (m, 1H), 4.22-4.17 (m, 2H), 3.59 (s, 3H), 2.41 (s, 3H), 2.37 (s, 3H).<br>MS m/z 447.17 (M + 1)$^+$. | 0.036 |
| F63 | 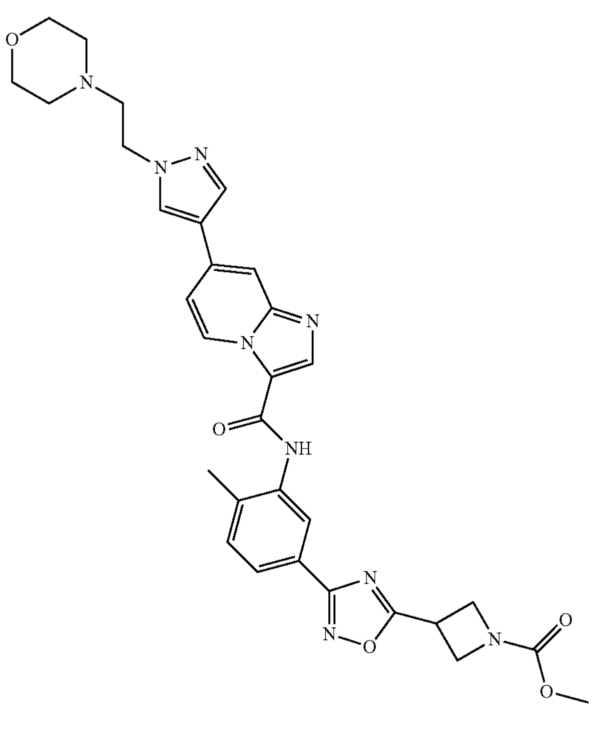 [SMILES: COC(=O)N1CC(c2nc(-c3ccc(C)c(NC(=O)c4cnc5cc(-c6cnn(CCN7CCOCC7)c6)ccn45)c3)no2)C1] | MS m/z 612.2 (M + 1)$^+$. | 0.013 |

TABLE 1-continued

| Cmpd No. | Structure | Physical Data | c-kit (Mo7e) μM |
|---|---|---|---|
| F64 | 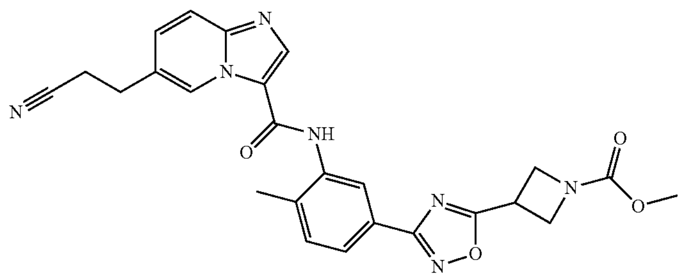 [SMILES: COC(=O)N1CC(c2nc(-c3ccc(C)c(NC(=O)c4cnc5ccc(CCC#N)cn45)c3)no2)C1] | $^1$H NMR (400 MHz, d$_6$-DMSO) δ 10.08 (s, 1H), 9.45 (s, 1H), 8.63 (s, 1H), 8.12 (d, J = 1.6 Hz, 1H), 7.85 (dd, J = 2.0, 5.6 Hz, 1H), 7.82 (d, J = 6.8 Hz, 1H), 7.60 (dd, J = 1.6, 9.2 Hz, 1H), 7.51 (d, J = 8.0 Hz, 1H), 4.38-4.33 (m, 2H), 4.31-4.24 (m, 1H), 4.21-4.18 (m, 2H), 3.59 (s, 3H), 3.01 (t, J = 7.6 Hz, 2H), 2.91 (t, J = 6.4 Hz, 2H), 2.38 (s, 3H). MS m/z 486.18 (M + 1)$^+$. | 0.064 |
| F65 | 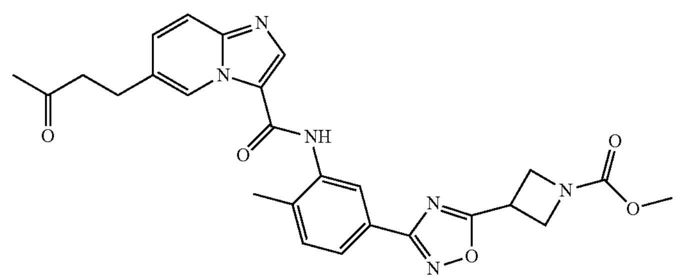 [SMILES: COC(=O)N1CC(c2nc(-c3ccc(C)c(NC(=O)c4cnc5ccc(CCC(C)=O)cn45)c3)no2)C1] | $^1$H NMR (400 MHz, d$_6$-DMSO) δ 10.02 (s, 1H), 9.31 (s, 1H), 8.55 (s, 1H), 8.10 (d, J = 1.6 Hz, 1H), 7.83 (dd, J = 2.0, 8.0 Hz, 1H), 7.73 (d, J = 9.2 Hz, 1H), 7.50 (d, J = 8.0 Hz, 1H), 7.46 (dd, J = 1.6, 9.2 Hz, 1H), 4.39-4.34 (m, 2H), 4.31-4.25 (m, 1H), 4.22-4.18 (m, 2H), 3.59 (s, 3H), 2.85 (s, 4H), 2.37 (s, 3H), 2.10 (s, 3H). MS m/z 503.2 (M + 1)$^+$. | 0.033 |
| F66 | 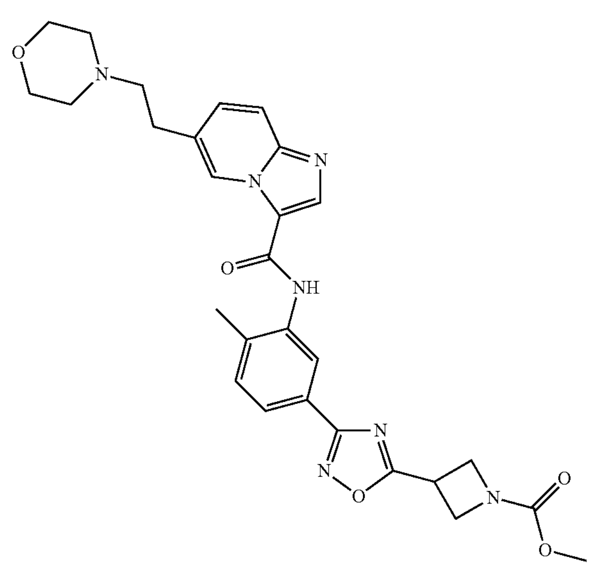 [SMILES: COC(=O)N1CC(c2nc(-c3ccc(C)c(NC(=O)c4cnc5ccc(CCN6CCOCC6)cn45)c3)no2)C1] | $^1$H NMR (400 MHz, d$_6$-DMSO) δ 10.07 (s, 1H), 9.46 (s, 1H), 8.61 (s, 1H), 8.12 (d, J = 1.6 Hz, 1H), 7.86-7.83 (m, 2H), 7.52-7.49 (m, 2H), 4.39-4.36 (m, 2H), 4.31-4.26 (m, 1H), 4.21-4.17 (m, 2H), 4.03-4.00 (m, 2H), 3.69-3.63 (m, 2H), 3.59 (s, 3H), 3.54-3.44 (m, 4H), 3.14-3.10 (m, 4H), 2.38 (s, 3H). MS m/z 546.24 (M + 1)$^+$. | 0.05 |

TABLE 1-continued

| Cmpd No. | Structure | Physical Data | c-kit (Mo7e) μM |
|---|---|---|---|
| F67 | 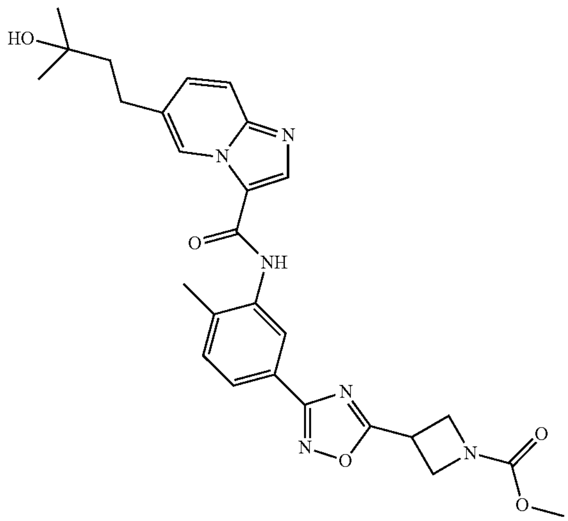 [SMILES: COC(=O)N1CC(c2nc(-c3ccc(C)c(NC(=O)c4cnc5ccc(CCC(C)(C)O)cn45)c3)no2)C1] | ¹H NMR (400 MHz, d₆-DMSO) δ 10.10 (s, 1H), 9.34 (s, 1H), 8.63 (s, 1H), 8.10 (d, J = 1.6 Hz, 1H), 7.84 (dd, J = 1.6, 8.0 Hz, 1H), 7.78 (d, J = 9.2 Hz, 1H), 7.56-7.54 (m, 1H), 7.51 (d, J = 8.4 Hz, 1H), 4.39-4.34 (m, 2H), 4.31-4.25 (m, 1H), 4.22-4.17 (m, 2H), 3.59 (s, 3H), 2.76-2.72 (m, 2H), 2.37 (s, 3H), 1.71-1.67 (m, 2H), 1.15 (s, 6H).<br>MS m/z 519.23 (M + 1)⁺. | 0.029 |
| F68 | 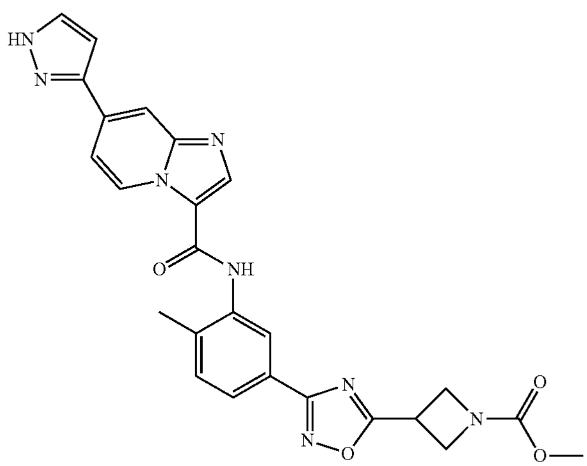 [SMILES: COC(=O)N1CC(c2nc(-c3ccc(C)c(NC(=O)c4cnc5cc(-c6cc[nH]n6)ccn45)c3)no2)C1] | MS m/z 499.1 (M + 1)⁺. | 0.013 |
| F69 | 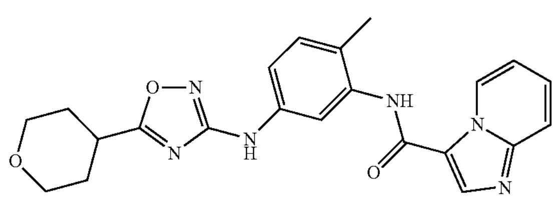 [SMILES: Cc1ccc(Nc2noc(C3CCOCC3)n2)cc1NC(=O)c1cnc2ccccn12] | MS m/z 419.1 (M + 1)⁺. | 0.039 |
| F70 | 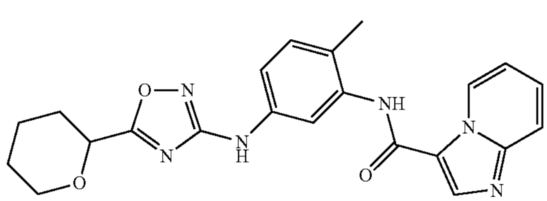 [SMILES: Cc1ccc(Nc2noc(C3CCCCO3)n2)cc1NC(=O)c1cnc2ccccn12] | MS m/z 419.1 (M + 1)⁺. | 0.006 |

TABLE 1-continued

| Cmpd No. | Structure | Physical Data | c-kit (Mo7e) μM |
|---|---|---|---|
| F71 | 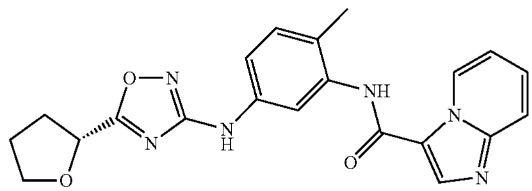 [SMILES: Cc1ccc(Nc2noc([C@H]3CCCO3)n2)cc1NC(=O)c1cnc2ccccn12] | MS m/z 405.2 (M + 1)+. | 0.011 |
| F72 | 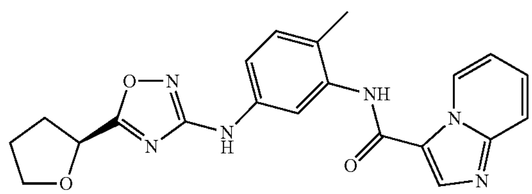 [SMILES: Cc1ccc(Nc2noc([C@@H]3CCCO3)n2)cc1NC(=O)c1cnc2ccccn12] | MS m/z 405.2 (M + 1)+. | 0.006 |
| F73 | 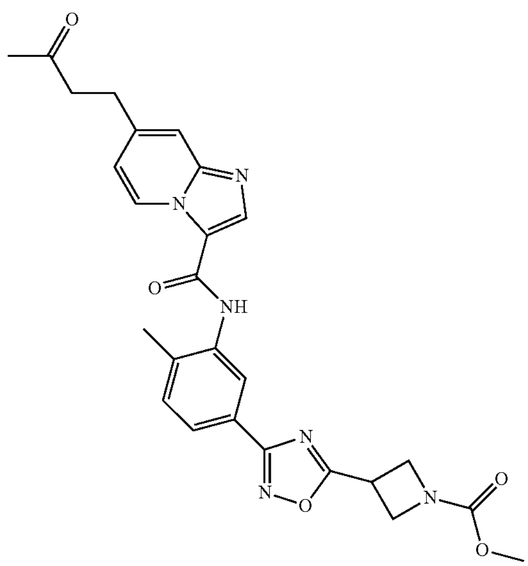 [SMILES: COC(=O)N1CC(c2nc(-c3ccc(C)c(NC(=O)c4cnc5cc(CCC(C)=O)ccn45)c3)no2)C1] | $^1$H NMR (400 MHz, d-DMSO) δ 10.24 (s, 1H), 9.44-9.41 (m, 1H), 8.73 (s, 1H), 8.09 (d, J = 1.6 Hz, 1H), 7.85 (dd, J = 1.6, 8.0 Hz, 1H), 7.73 (s, 1H), 7.51 (d, J = 8.4 Hz, 1H), 7.32-7.29 (m, 1H), 4.39-4.35 (m, 2H), 4.31-4.24 (m, 1H), 4.21-4.17 (m, 2H), 3.59 (s, 3H), 2.98-2.91 (m, 4H), 2.37 (s, 3H), 2.13 (s, 3H). MS m/z 503.2 (M + 1)+. | 0.03 |
| F74 | 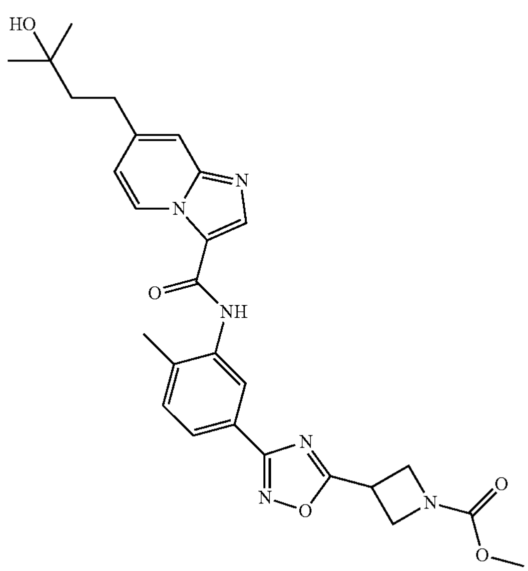 [SMILES: COC(=O)N1CC(c2nc(-c3ccc(C)c(NC(=O)c4cnc5cc(CCC(C)(C)O)ccn45)c3)no2)C1] | $^1$H NMR (400 MHz, d$_6$-DMSO) δ 10.11 (s, 1H), 9.41-9.38 (m, 1H), 8.64 (s, 1H), 8.10 (s, 1H), 7.84 (dd, J = 1.2, 7.6 Hz, 1H), 7.65 (s, 1H), 7.50 (d, J = 8.0 Hz, 1H), 7.21-7.17 (m, 1H), 4.39-4.35 (m, 2H), 4.31-4.24 (m, 1H), 4.22-4.18 (m, 2H), 3.59 (s, 3H), 2.82-2.77 (m, 2H), 2.37 (s, 3H), 1.74-1.69 (m, 2H), 1.17 (s, 6H). MS m/z 519.23 (M + 1)+. | 0.051 |

TABLE 1-continued

| Cmpd No. | Structure | Physical Data | c-kit (Mo7e) μM |
|---|---|---|---|
| F75 | 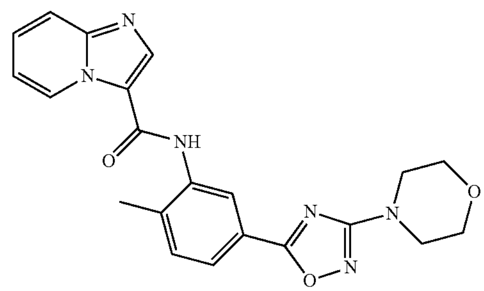 [SMILES: Cc1ccc(-c2nc(N3CCOCC3)no2)cc1NC(=O)c1cnc2ccccn12] | $^1$H NMR (400 MHz, d$_6$-DMSO) δ 10.18 (s, 1H), 9.52-9.48 (m, 1H), 8.68 (s, 1H), 8.11 (d, J = 2.0 Hz, 1H), 7.88-7.83 (m, 2H), 7.68-7.63 (m, 1H), 7.54 (d, J = 8.0 Hz, 1H), 7.31-7.27 (m, 1H), 3.72-3.69 (m, 4H), 3.41-3.38 (m, 4H), 2.39 (s, 3H). MS m/z 405.16 (M + 1)$^+$. | 0.061 |
| F76 | 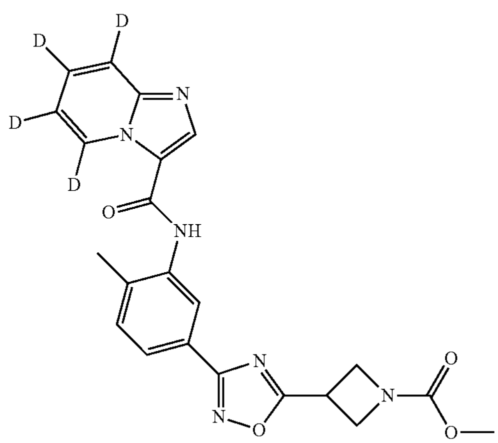 [SMILES: [2H]c1c([2H])c([2H])n2c(C(=O)Nc3cc(-c4noc(C5CN(C(=O)OC)C5)n4)ccc3C)cnc2c1[2H]] | $^1$H NMR (400 MHz, d$_4$-MeOH) δ 8.71 (s, 1H), 8.16 (s, 1H), 7.96 (dd, J = 7.6, 1.6 Hz, 1H), 7.49 (d, J = 7.6 Hz, 1H), 4.48-4.44 (m, 2H), 4.32-4.29 (m, 2H), 4.24-4.19 (m, 1H), 3.69 (s, 3H), 2.42 (s, 3H). MS m/z 438.1 (M + 1)$^+$. | 0.051 |
| F77 | 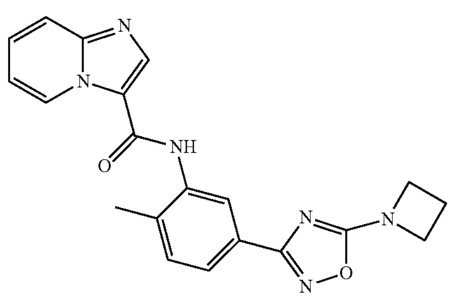 [SMILES: Cc1ccc(-c2noc(N3CCC3)n2)cc1NC(=O)c1cnc2ccccn12] | $^1$H NMR (400 MHz, d$_6$-DMSO) δ 10.10 (s, 1H), 9.51-9.48 (m, 1H), 8.65 (s, 1H), 7.94 (d, J = 1.6 Hz, 1H), 7.86-7.83 (m, 1H), 7.71 (dd, J = 1.6, 7.6 Hz, 1H), 7.64-7.60 (m, 1H), 7.43 (d, J = 8.0 Hz, 1H), 7.27-7.24 (m, 1H), 4.26-4.22 (m, 4H), 2.48-2.40 (m, 2H), 2.34 (s, 3H). MS m/z 374.15 (M + 1)$^+$. | 0.132 |
| F78 | 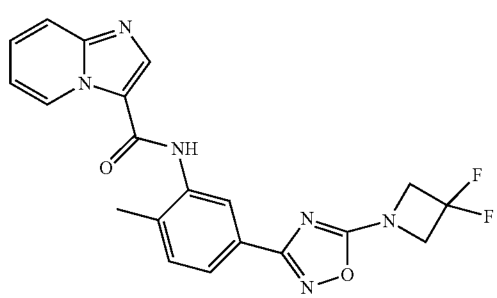 [SMILES: Cc1ccc(-c2noc(N3CC(F)(F)C3)n2)cc1NC(=O)c1cnc2ccccn12] | $^1$H NMR (400 MHz, d$_6$-DMSO) δ 10.16 (s, 1H), 9.52-9.50 (m, 1H), 8.69 (s, 1H), 7.97 (d, J = 1.6 Hz, 1H), 7.90-7.87 (m, 1H), 7.74 (dd, J = 1.6, 7.6 Hz, 1H), 7.71-7.67 (m, 1H), 7.46 (d, J = 8.4 Hz, 1H), 7.33-7.30 (m, 1H), 4.78-4.72 (m, 4H), 2.35 (s, 3H). MS m/z 410.13 (M + 1)$^+$. | 0.055 |

TABLE 1-continued

| Cmpd No. | Structure | Physical Data | c-kit (Mo7e) μM |
|---|---|---|---|
| F79 | 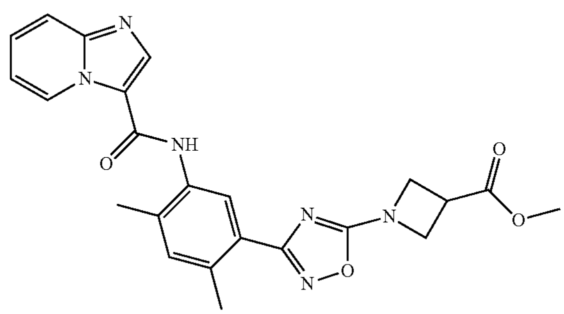 [SMILES: COC(=O)C1CN(c2nc(-c3cc(NC(=O)c4cnc5ccccn45)c(C)cc3C)no2)C1] | MS m/z 447.1 (M + 1)⁺. | 0.037 |
| F80 | 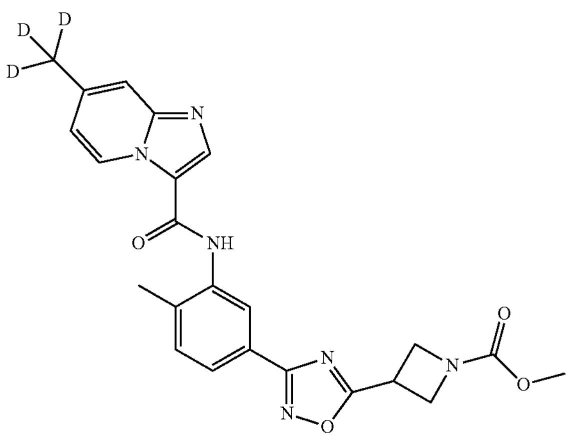 [SMILES: [2H]C([2H])([2H])c1ccn2c(C(=O)Nc3cc(-c4noc(C5CN(C(=O)OC)C5)n4)ccc3C)cnc2c1] | ¹H NMR (400 MHz, CD₂Cl₂) δ 9.71 (d, J = 7.2 Hz, 1H), 9.15 (s, 1H), 9.04 (s, 1H), 8.33 (s, 1H), 7.95 (dd, J = 1.2, 8.2 Hz, 1H), 7.93 (s, 1H), 7.46 (d, J = 8.0 Hz, 1H), 7.37 (d, J = 7.2 Hz, 1H), 4.48 (d, J = 9.2 Hz, 1H), 4.46 (d, J = 8.4 Hz, 1H), 4.39 (d, J = 6.0 Hz, 1H), 4.37 (d, J = 6.0 Hz, 1H), 4.16 (m, 1H), 3.72 (s, 3H), 2.77 (s, 3H). MS m/z 450.1 (M + 1)⁺. | 0.044 |
| F81 | 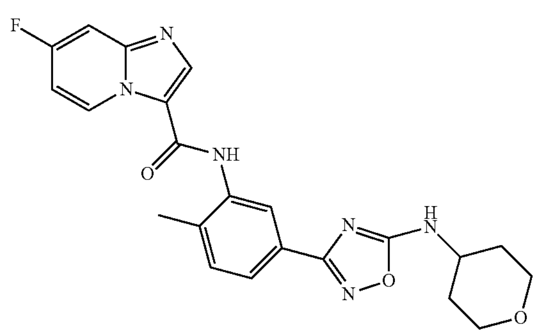 [SMILES: Cc1ccc(-c2noc(NC3CCOCC3)n2)cc1NC(=O)c1cnc2cc(F)ccn12] | ¹H NMR (400 MHz, d₆-DMSO) δ 10.11 (s, 1H), 9.51-9.47 (m, 1H), 8.60 (s, 1H), 8.55-8.53 (m, 1H), 7.90 (d, J = 1.6 Hz, 1H), 7.74-7.70 (m, 2H), 7.43 (d, J = 8.0 Hz, 1H), 7.30-7.26 (m, 1H), 3.89-3.84 (m, 2H), 3.79-3.71 (m, 1H), 3.43-3.37 (m, 2H), 2.32 (s, 3H), 1.93-1.89 (m, 2H), 1.58-1.48 (m, 2H). MS m/z 436.17 (M + 1)⁺. | 0.084 |
| F82 | 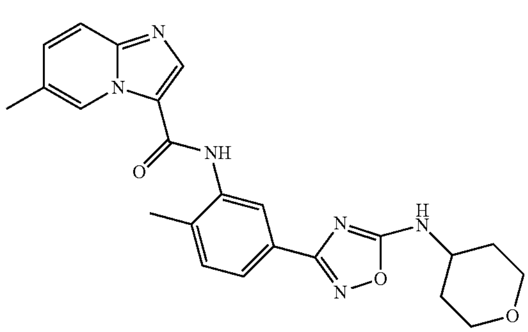 [SMILES: Cc1ccc2ncc(C(=O)Nc3cc(-c4noc(NC5CCOCC5)n4)ccc3C)n2c1] | ¹H NMR (400 MHz, d₆-DMSO) δ 10.15 (s, 1H), 9.35 (s, 1H), 8.65 (s, 1H), 8.54 (d, J = 7.6 Hz, 1H), 7.92 (d, J = 1.6 Hz, 1H), 7.81 (d, J = 9.2 Hz, 1H), 7.72 (dd, J = 1.6, 8.0 Hz, 1H), 7.60-7.57 (m, 1H), 7.43 (d, J = 8.4 Hz, 1H), 3.89-3.84 (m, 2H), 3.79-3.72 (m, 1H), 3.43-3.37 (m, 2H), 2.40 (s, 3H), 2.33 (s, 3H), 1.93-1.89 (m, 2H), 1.58-1.48 (m, 2H). MS m/z 432.19 (M + 1)⁺. | 0.055 |

TABLE 1-continued

| Cmpd No. | Structure | Physical Data | c-kit (Mo7e) μM |
|---|---|---|---|
| F83 | 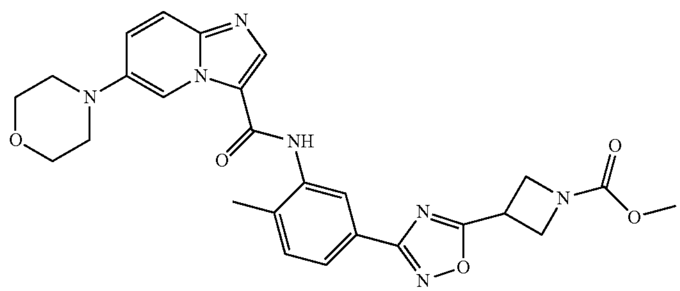 [SMILES: COC(=O)N1CC(c2nc(-c3ccc(C)c(NC(=O)c4cnc5ccc(N6CCOCC6)cn45)c3)no2)C1] | MS m/z 518.2 (M + 1)⁺. | 0.04 |
| F84 | 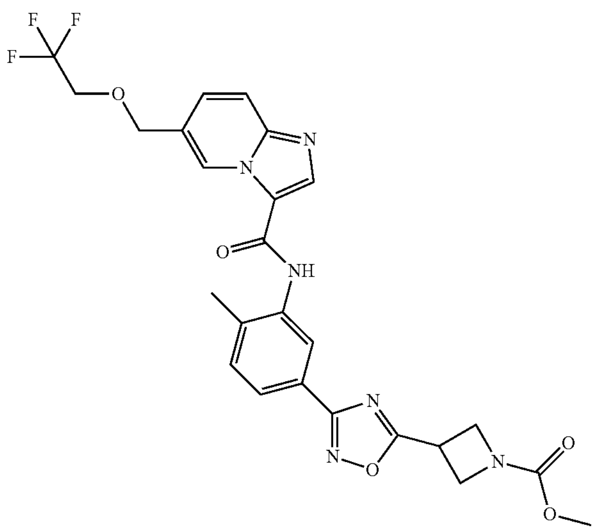 [SMILES: COC(=O)N1CC(c2nc(-c3ccc(C)c(NC(=O)c4cnc5ccc(COCC(F)(F)F)cn45)c3)no2)C1] | ¹H NMR (400 MHz, d6-DMSO) δ 10.13 (s, 1H), 9.52 (m, 1H), 8.65 (s, 1H), 8.12 (d, J = 1.6 Hz, 1H), 7.83-7.87 (m, 2H), 7.58 (dd, J = 1.6, 9.6 Hz, 1H), 7.51 (d, J = 8.0 Hz, 1H), 4.80 (s, 2H), 4.37 (m, 2H), 4.22-4.32 (m, 1H), 4.12-4.21 (m, 4H), 3.60 (s, 3H), 2.38 (s, 3H).<br>MS m/z 545.1 (M + 1)⁺. | 0.038 |
| F85 | 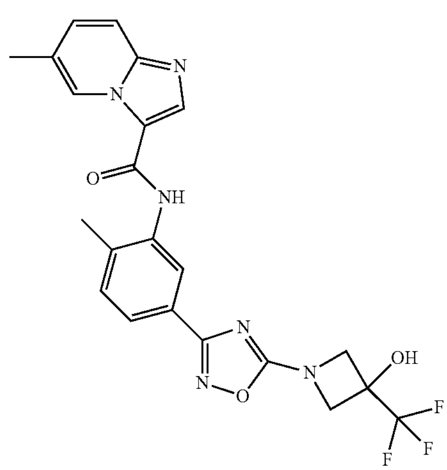 [SMILES: Cc1ccc2ncc(C(=O)Nc3cc(-c4noc(N5CC(O)(C(F)(F)F)C5)n4)ccc3C)n2c1] | ¹H NMR (400 MHz, d₆-DMSO) δ 10.11 (s, 1H), 9.34 (s, 1H), 8.64 (s, 1H), 7.97 (d, J = 1.6 Hz, 1H), 7.80 (d, J = 9.2 Hz, 1H), 7.72 (dd, J = 1.6, 8.0 Hz, 1H), 7.57-7.54 (m, 1H), 7.45 (d, J = 8.0 Hz, 1H), 4.54-4.51 (m, 2H), 4.33-4.30 (m, 2H), 2.40 (s, 3H), 2.35 (s, 3H).<br>MS m/z 472.15 (M + 1)⁺. | 0.026 |

TABLE 1-continued

| Cmpd No. | Structure | Physical Data | c-kit (Mo7e) μM |
|---|---|---|---|
| F86 | 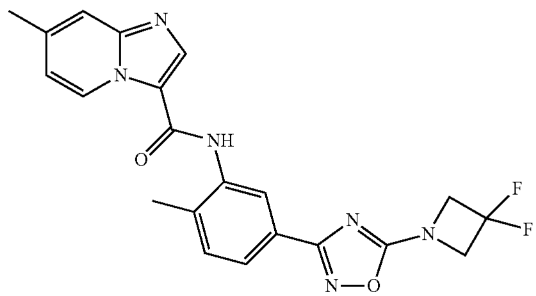 [SMILES: Cc1ccn2c(C(=O)Nc3cc(-c4noc(N5CC(F)(F)C5)n4)ccc3C)cnc2c1] | ¹H NMR (400 MHz, d₆-DMSO) δ 10.21 (s, 1H), 9.43-9.42 (m, 1H), 8.72 (s, 1H), 7.97 (d, J = 1.6 Hz, 1H), 7.75-7.73 (m, 2H), 7.46 (d, J = 8.0 Hz, 1H), 7.29-7.27 (m, 1H), 4.78-4.71 (m, 4H), 2.52 (s, 3H), 2.35 (s, 3H). MS m/z 424.15 (M + 1)⁺. | 0.093 |
| F87 | 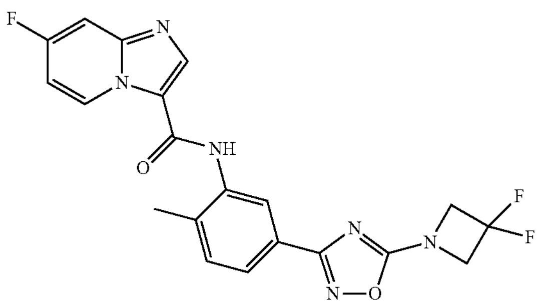 [SMILES: Cc1ccc(-c2noc(N3CC(F)(F)C3)n2)cc1NC(=O)c1cnc2cc(F)ccn12] | ¹H NMR (400 MHz, d₆-DMSO) δ 10.04 (s, 1H), 9.49-9.46 (m, 1H), 8.57 (s, 1H), 7.95 (d, J = 1.6 Hz, 1H), 7.72 (dd, J = 1.6, 8.0 Hz, 1H), 7.71-7.67 (m, 1H), 7.45 (d, J = 8.4 Hz, 1H), 7.26-7.22 (m, 1H), 4.78-4.71 (m, 4H), 2.34 (s, 3H). MS m/z 428.12 (M + 1)⁺. | 0.091 |
| F88 | 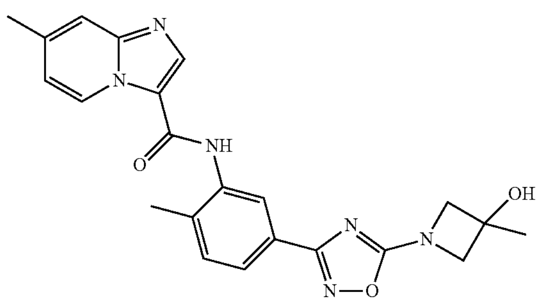 | ¹H NMR (400 MHz, d₆-DMSO) δ 9.94 (s, 1H), 9.33-9.31 (m, 1H), 8.50 (s, 1H), 7.93 (d, J = 1.6 Hz, 1H), 7.69 (dd, J = 2.0, 8.0 Hz, 1H), 7.57 (s, 1H), 7.42 (d, J = 8.0 Hz, 1H), 7.02 (dd, J = 1.6, 7.2 Hz, 1H), 5.89 (s, 1H), 4.12-4.07 (m, 4H), 2.42 (s, 3H), 2.33 (s, 3H), 1.45 (s, 3H). MS m/z 418.18 (M + 1)⁺. | 0.062 |
| F89 | 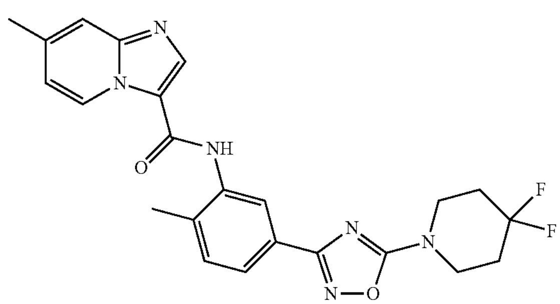 [SMILES: Cc1ccn2c(C(=O)Nc3cc(-c4noc(N5CCC(F)(F)CC5)n4)ccc3C)cnc2c1] | ¹H NMR (400 MHz, d₆-DMSO) δ 9.95 (s, 1H), 9.33-9.31 (m, 1H), 8.51 (s, 1H), 7.95 (d, J = 1.6 Hz, 1H), 7.71 (dd, J = 1.6, 7.6 Hz, 1H), 7.57 (s, 1H), 7.43 (d, J = 8.4 Hz, 1H), 7.03 (dd, J = 1.6, 7.2 Hz, 1H), 3.77-3.74 (m, 4H), 2.42 (s, 3H), 2.33 (s, 3H), 2.20-2.10 (m, 4H). MS m/z 452.18 (M + 1)⁺. | 0.031 |
| F90 | 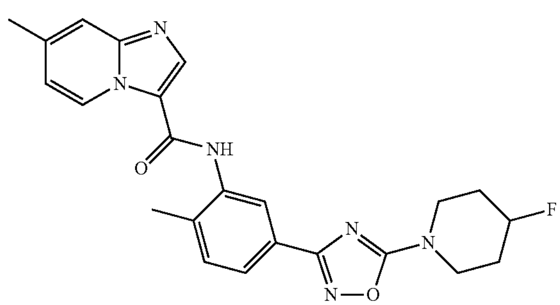 [SMILES: Cc1ccn2c(C(=O)Nc3cc(-c4noc(N5CCC(F)CC5)n4)ccc3C)cnc2c1] | ¹H NMR (400 MHz, d₆-DMSO) δ 9.95 (s, 1H), 9.33-9.31 (m, 1H), 8.51 (s, 1H), 7.93 (d, J = 2.0 Hz, 1H), 7.70 (dd, J = 1.6, 8.0 Hz, 1H), 7.57 (s, 1H), 7.42 (d, J = 8.0 Hz, 1H), 7.03 (dd, J = 2.0, 7.2 Hz, 1H), 5.02-4.86 (m, 1H), 3.72-3.62 (m, 4H), 2.42 (s, 3H), 2.33 (s, 3H), 2.06-1.94 (m, 2H), 1.87-1.81 (m, 2H). MS m/z 434.19 (M + 1)⁺. | 0.033 |

TABLE 1-continued

| Cmpd No. | Structure | Physical Data | c-kit (Mo7e) μM |
|---|---|---|---|
| F91 | 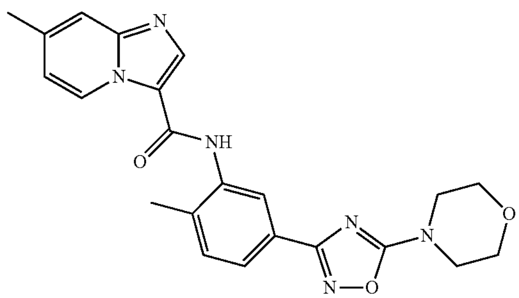 [SMILES: Cc1ccn2c(C(=O)Nc3cc(-c4noc(N5CCOCC5)n4)ccc3C)cnc2c1] | ¹H NMR (400 MHz, d₆-DMSO) δ 9.95 (s, 1H), 9.93-9.31 (m, 1H), 8.51 (s, 1H), 7.94 (d, J = 1.6 Hz, 1H), 7.71 (dd, J = 2.0, 8.0 Hz, 1H), 7.57 (s, 1H), 7.43 (d, J = 8.4 Hz, 1H), 7.02 (dd, J = 2.0, 7.2 Hz, 1H), 3.73-3.71 (m, 4H), 3.61-3.58 (m, 4H), 2.42 (s, 3H), 2.33 (s, 3H). MS m/z 418.18 (M + 1)⁺. | 0.064 |
| F92 | 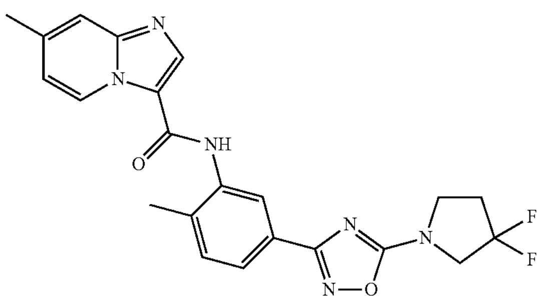 [SMILES: Cc1ccn2c(C(=O)Nc3cc(-c4noc(N5CCC(F)(F)C5)n4)ccc3C)cnc2c1] | ¹H NMR (400 MHz, d₆-DMSO) δ 9.96 (s, 1H), 9.93-9.31 (m, 1H), 8.51 (s, 1H), 7.94 (d, J = 2.0 Hz, 1H), 7.71 (dd, J = 1.6, 8.0 Hz, 1H), 7.57 (s, 1H), 7.43 (d, J = 8.0 Hz, 1H), 7.02 (dd, J = 1.6, 7.2 Hz, 1H), 4.05-3.99 (m, 2H), 3.85-3.81 (m, 2H), 2.64-2.54 (m, 2H), 2.42 (s, 3H), 2.33 (s, 3H). MS m/z 438.16 (M + 1)⁺. | 0.021 |
| F93 | 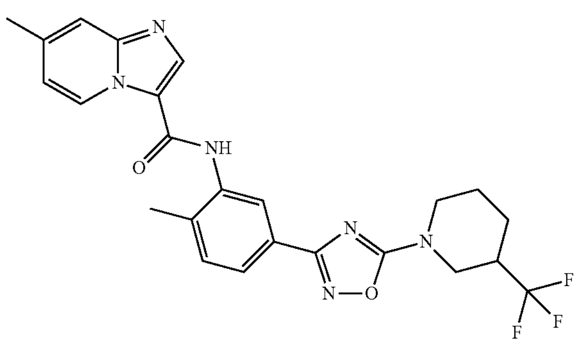 [SMILES: Cc1ccn2c(C(=O)Nc3cc(-c4noc(N5CCCC(C(F)(F)F)C5)n4)ccc3C)cnc2c1] | ¹H NMR (400 MHz, d₆-DMSO) δ 9.96 (s, 1H), 9.33-9.31 (m, 1H), 8.50 (s, 1H), 7.92 (d, J = 1.6 Hz, 1H), 7.71 (dd, J = 1.6, 7.6 Hz, 1H), 7.57 (s, 1H), 7.43 (d, J = 8.0 Hz, 1H), 7.02 (dd, J = 1.6, 7.2 Hz, 1H), 4.17-4.13 (m, 1H), 4.01-3.96 (m, 1H), 3.30-3.21 (m, 2H), 2.82-2.74 (m, 1H), 2.42 (s, 3H), 2.33 (s, 3H), 2.00-1.97 (m, 1H), 1.84-1.81 (m, 1H), 1.64-1.56 (m, 2H). MS m/z 484.18 (M + 1)⁺. | 0.048 |
| F94 | 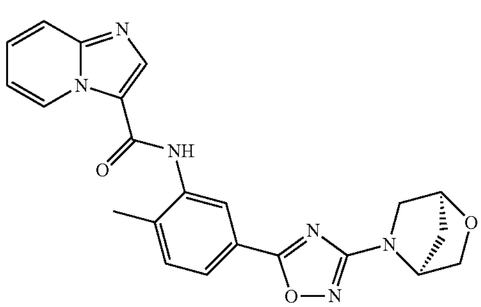 [SMILES: Cc1ccc(-c2nc(N3C[C@@H]4C[C@H]3CO4)no2)cc1NC(=O)c1cnc2ccccn12] | ¹H NMR (400 MHz, d₆-DMSO) δ 10.21 (s, 1H), 9.53-9.51 (m, 1H), 8.71 (s, 1H), 8.10 (d, J = 1.2 Hz, 1H), 7.91-7.88 (m, 1H), 7.85 (dd, J = 1.2, 5.6 Hz, 1H), 7.72-7.69 (m, 1H), 7.54 (d, J = 5.2 Hz, 1H), 7.34-7.32 (m, 1H), 4.66 (s, 1H), 4.54 (s, 1H), 3.77-3.74 (m, 2H), 3.48-3.46 (m, 1H), 3.29-3.27 (m, 1H), 2.39 (s, 3H), 1.96-1.94 (m, 1H), 1.88-1.86 (m, 1H). MS m/z 416.16 (M + 1)⁺. | 0.092 |

TABLE 1-continued
| Cmpd No. | Structure | Physical Data | c-kit (Mo7e) μM |
|---|---|---|---|
| F95 | 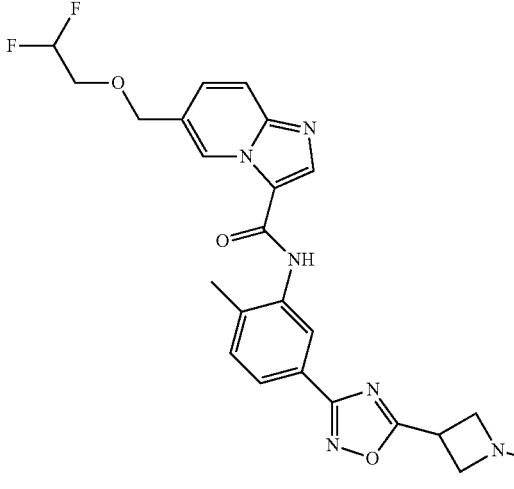 | MS m/z 527.1 (M + 1)+. | 0.019 |
| F96 | 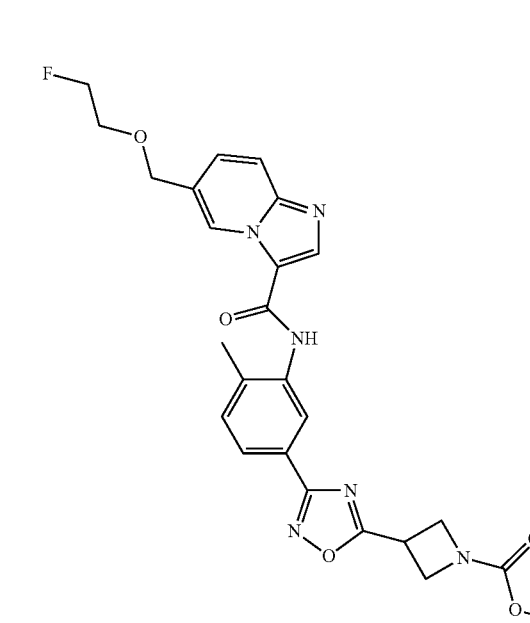 | MS m/z 509.1 (M + 1)+. | 0.026 |
| F97 | 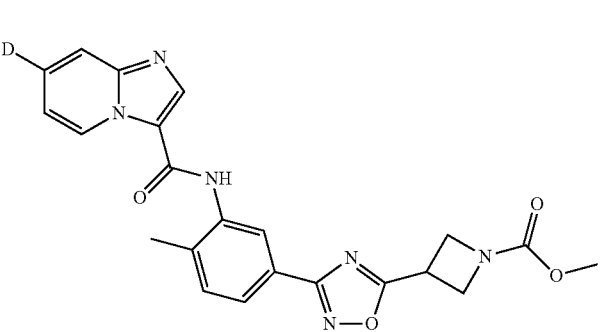 | 1H NMR (400 MHz, d4-MeOD) δ 9.53 (dd, J = 0.8, 7.2 Hz, 1H), 8.49 (s, 1H), 8.16 (d, J = 1.6 Hz, 1H), 7.94 (dd, J = 1.6, 8.0 Hz, 1H), 7.75 (m, 1H), 7.49 (d, J = 8.0 Hz, 1H), 7.18 (dd, J = 0.8, 7.2 Hz, 1H), 4.47 (m, 2H), 4.33 (m, 2H), 4.24 (m, 1H), 3.70 (s, 3H), 2.43 (s, 3H) MS m/z 434.1 (M + 1)+. | 0.044 |

TABLE 1-continued
| Cmpd No. | Structure | Physical Data | c-kit (Mo7e) μM |
|---|---|---|---|
| F98 | 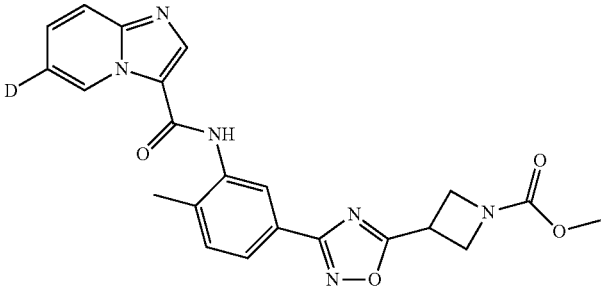 | ¹H NMR (400 MHz, d4-MeOD) δ 9.53 (s, 1H), 8.49 (s, 1H), 8.16 (d, J = 1.6 Hz, 1H), 7.94 (dd, J = 2.0, 8.0 Hz, 1H), 7.75 (dd, J = 0.8, 8.8 Hz, 1H), 7.58 (dd, J = 1.2, 8.8 Hz, 1H), 7.49 (d, J = 8.0 Hz, 1H), 4.47 (m, 2H), 4.33 (m, 2H), 4.24 (m, 1H), 3.70 (s, 3H), 2.43 (s, 3H) MS m/z 434.1 (M + 1)⁺. | 0.043 |
| F99 | 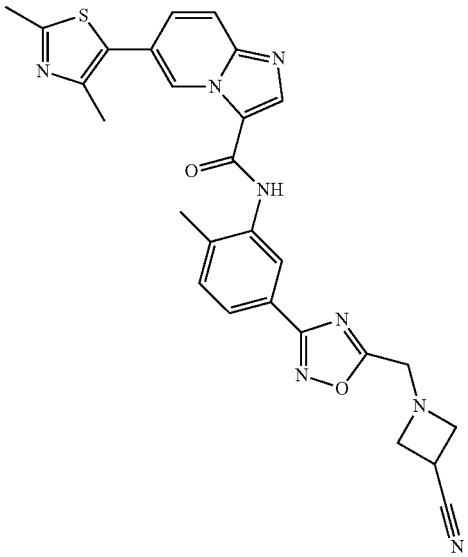 [SMILES: Cc1nc(C)c(-c2ccc3ncc(C(=O)Nc4cc(-c5noc(CN6CC(C#N)C6)n5)ccc4C)n3c2)s1] | MS m/z 525.1 (M + 1)⁺. | 0.049 |
*20% FBS, otherwise 1% FBS Representative compounds of Formula (I) and Formula (II) with C-kit inhibition IC$_{50}$ values greater than 100 nM and prepared following the procedures described above, are set forth in Table 2.

TABLE 2

| Cmpd No. | Structure | Physical Data | c-kit (Mo7e) μM |
|---|---|---|---|
| F100 | 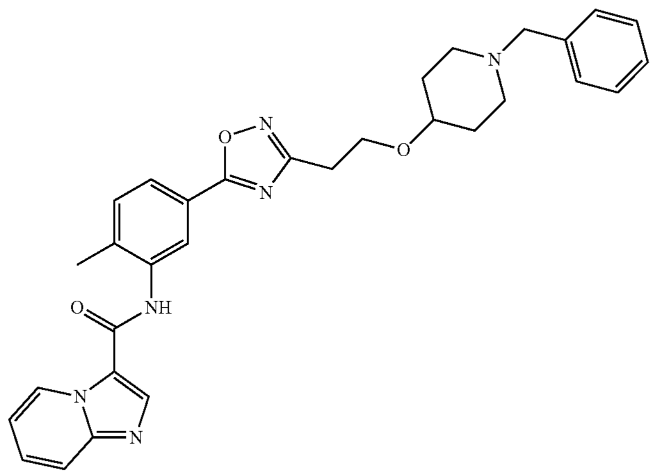 [SMILES: Cc1ccc(-c2nc(CCOC3CCN(Cc4ccccc4)CC3)no2)cc1NC(=O)c1cnc2ccccn12] | MS m/z 537.2 (M + 1)$^+$. | 0.198 |
| F101 | 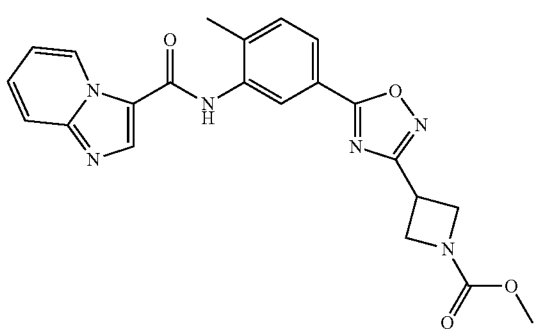 [SMILES: COC(=O)N1CC(c2noc(-c3ccc(C)c(NC(=O)c4cnc5ccccn45)c3)n2)C1] | MS m/z 433.2 (M + 1)$^+$. | 0.332 |
| F102 | 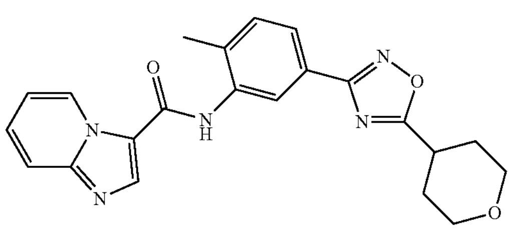 [SMILES: Cc1ccc(-c2noc(C3CCOCC3)n2)cc1NC(=O)c1cnc2ccccn12] | $^1$H NMR (400 MHz, d$_4$-MeOH) δ 9.73 (d, J = 7.2 Hz, 1H), 8.74 (s, 1H), 8.15-8.14 (m, 1H), 7.98-7.92 (m, 3H), 7.53-7.49 (m, 2H), 4.03 (ddd, J = 12, 4, 4, Hz, 2 H), 3.61 (ddd, J = 12, 12, 4 Hz, 2 H), 3.40-3.30 (m, 1H), 2.46 (s, 3H), 2.11-2.07 (m, 2H), 2.02-1.96 (m, 2H), MS m/z 404.1 (M + 1)$^+$. | 0.286 |
| F103 | 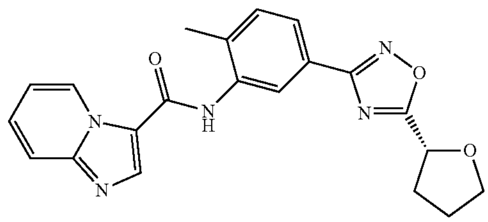 [SMILES: Cc1ccc(-c2noc([C@H]3CCCO3)n2)cc1NC(=O)c1cnc2ccccn12] | $^1$H NMR (400 MHz, d$_4$-MeOH) δ 9.77 (d, J = 7.1 Hz, 1H), 8.79 (d, J = 2.4 Hz, 1H), 8.16-8.15 (m, 1 H), 8.07-8.03 (m, 2H), 7.95-7.93 (m, 1H), 7.59-7.55 (m, 1H), 7.50 (d, J = 8 Hz, 1H), 4.85 (dd, J = 10.4, 2.8 Hz, 1H), 4.08 (d, J = 11.6, 1H), 3.70 (ddd, J = 11.6, 3.2, 3.2 Hz, 1H), 2.43 (s, 3 H), 2.11-2.07 (m, 1H), 2.01-1.87 (m, 1H), 1.82-1.63 (m, 2H), MS m/z 390.1 (M + 1)$^+$. | 0.229* |

TABLE 2-continued

| Cmpd No. | Structure | Physical Data | c-kit (Mo7e) μM |
|---|---|---|---|
| F104 | 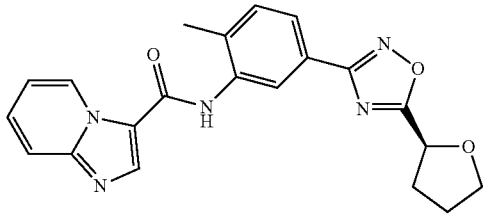 [SMILES: Cc1ccc(-c2noc([C@@H]3CCCO3)n2)cc1NC(=O)c1cnc2ccccn12] | ¹H NMR (400 MHz, d₄-MeOH) δ 9.77 (d, J = 7.1 Hz, 1H), 8.79 (d, J = 2.4 Hz, 1H), 8.16-8.15 (m, 1 H), 8.07-8.03 (m, 2H), 7.95-7.93 (m, 1H), 7.59-7.55 (m, 1H), 7.50 (d, J = 8 Hz, 1H), 4.85 (dd, J = 10.4, 2.8 Hz, 1H), 4.08 (d, J = 11.6, 1H), 3.70 (ddd, J = 11.6, 3.2, 3.2 Hz, 1H), 2.43 (s, 3 H), 2.11-2.07 (m, 1H), 2.01-1.87 (m, 1H), 1.82-1.63 (m, 2H), MS m/z 390.1 (M + 1)⁺. | 0.224* |
| F105 | 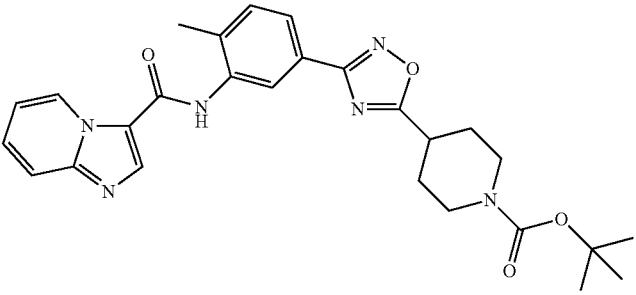 [SMILES: Cc1ccc(-c2noc(C3CCN(C(=O)OC(C)(C)C)CC3)n2)cc1NC(=O)c1cnc2ccccn12] | ¹H NMR (400 MHz, d₄-MeOH) δ 9.73-9.68 (m, 1H), 8.73-8.70 (m, 1H), 8.16-8.14 (m, 1H), 7.97-7.87 (m, 3H), 7.51-7.39 (m, 2H), 4.12-4.07 (m, 1H), 3.54-3.50 (m, 2H), 3.23-3.20 (m, 2H), 2.57 (s, 3H), 2.20-2.04 (m, 2H), 1.86-1.79 (m, 2H), 1.48 (s, 9H). MS m/z 503.1 (M + 1)⁺. | 0.505 |
| F106 | 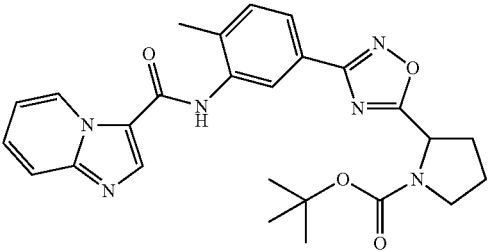 [SMILES: Cc1ccc(-c2noc(C3CCCN3C(=O)OC(C)(C)C)n2)cc1NC(=O)c1cnc2ccccn12] | ¹H NMR (400 MHz, d₄-MeOH) δ 9.73-9.76 (d, J = 7.2 Hz, 1H), 8.78 (s, 1H), 8.15-8.13 (m, 1 H), 8.06-8.00 (m, 2H), 7.95-7.91 (m, 1H), 7.58-7.48 (m, 2 H), 5.12 (dd, J = 8.0, 4.0, Hz, 1 H), 3.69-3.63 (m, 1H), 3.56-3.50 (m, 1H), 2.51-2.39 (m, 1 H), 2.43 (s, 3H), 2.18-2.03 (m, 3H), 1.28 (s, 9H). MS m/z 489.2 (M + 1)⁺. | 0.935 |
| F107 | 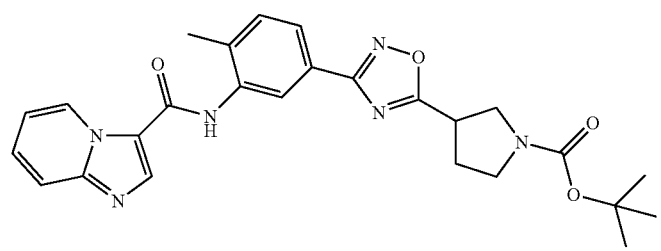 [SMILES: Cc1ccc(-c2noc(C3CCN(C(=O)OC(C)(C)C)C3)n2)cc1NC(=O)c1cnc2ccccn12] | MS m/z 489.2 (M + 1)⁺. | 0.912 |
| F108 | 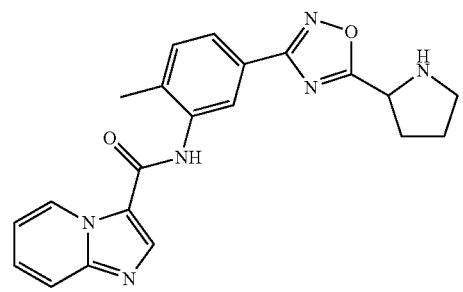 | ¹H NMR (400 MHz, d₄-MeOH) δ 9.73-9.76 (d, J = 7.2 Hz, 1H), 8.78 (s, 1H), 8.15-8.13 (m, 1 H), 8.06-8.00 (m, 2H), 7.95-7.91 (m, 1H), 7.58-7.48 (m, 2 H), 5.12 (dd, J = 8.0, 4.0, Hz, 1 H), 3.63-3.60 (m, 1H), 3.48-3.45 (m, 1H), 2.49-2.35 (m, 1 H), 2.41 (s, 3H), 2.10-2.05 (m, 3H). MS m/z 489.2 (M + 1)⁺. | 0.648* |

TABLE 2-continued

| Cmpd No. | Structure | Physical Data | c-kit (Mo7e) μM |
|---|---|---|---|
| F109 | 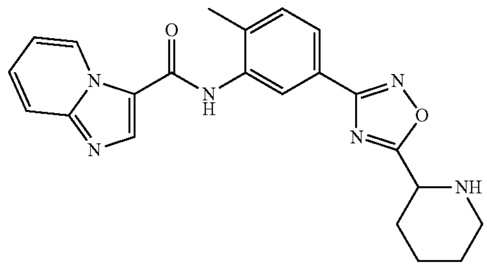 [SMILES: Cc1ccc(-c2noc(C3CCCCN3)n2)cc1NC(=O)c1cnc2ccccn12] | ¹H NMR (400 MHz, d₄-MeOH) δ 9.78 (d, J = 7.2 Hz, 1H), 8.79-8.70 (m, 1H), 8.15 (d, J = 2.0 Hz, 1H), 8.03-7.94 (m, 3H), 7.60-7.50 (m, 2H), 5.58 (m, 1H), 3.98-3.90 (m, 2H), 2.43 (s, 3H), 2.01-1.95 (m, 2H), 1.75-1.68 (m, 2H), 1.50-1.30 (m, 2H). MS m/z 403.2 (M + 1)⁺. | 0.215 |
| F110 | 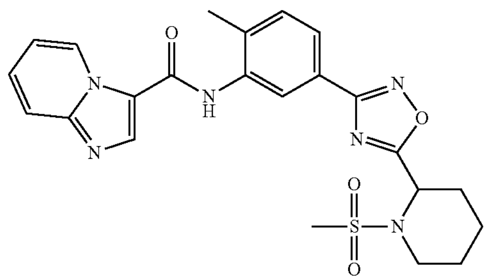 [SMILES: Cc1ccc(-c2noc(C3CCCCN3S(C)(=O)=O)n2)cc1NC(=O)c1cnc2ccccn12] | ¹H NMR (400 MHz, d₄-MeOH) δ 9.77 (d, J = 7.2 Hz, 1H), 8.78 (s, 1H), 8.14-8.13 (m, 1H), 8.04-8.03 (m, 2H), 7.95-7.93 (m, 1H), 7.57 (ddd, J = 6.8, 6.8, 1.2 Hz, 1H), 7.50 (d, J = 8.0, 1H), 5.54 (d, J = 4.4 Hz, 1H), 3.83-3.80 (m, 1H), 3.65-3.55 (m, 1H), 3.07 (s, 3H), 2.43 (s, 3H), 2.04-1.94 (m, 2H), 1.80-1.71 (m, 2H), 1.61-1.40 (m, 4H). MS m/z 481.2 (M + 1)⁺. | 0.227* |
| F111 | 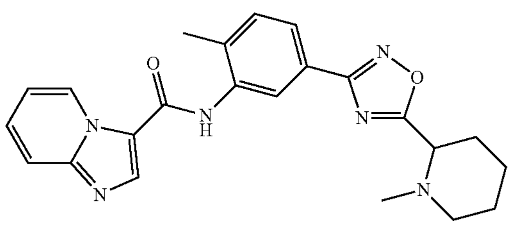 [SMILES: Cc1ccc(-c2noc(C3CCCCN3C)n2)cc1NC(=O)c1cnc2ccccn12] | ¹H NMR (400 MHz, d₄-MeOH) δ 9.76 (d, J = 7.2 Hz, 1H), 8.77 (s, 1H), 8.14-8.13 (m, 1H), 8.04-8.03 (m, 2H), 7.95-7.93 (m, 1H), 7.57 (ddd, J = 6.8, 6.8, 1.2 Hz, 1H), 7.52 (d, J = 8.0, 1H), 5.01-4.98 (m, 1H), 3.75-3.72 (m, 1H), 3.37-3.30 (m, 1H), 2.96 (s, 3H), 2.46 (s, 3H), 2.46-2.38 (m, 2H), 2.21-216 (m, 1H), 2.07-1.90 (m, 2H), 1.82-1.74 (m, 1H). MS m/z 417.2 (M + 1)⁺. | 0.243 |
| F112 | 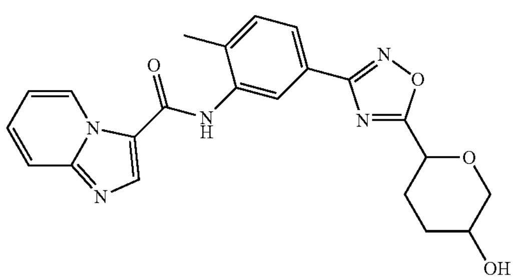 [SMILES: Cc1ccc(-c2noc(C3CCC(O)CO3)n2)cc1NC(=O)c1cnc2ccccn12] | ¹H NMR (400 MHz, d₄-MeOH) δ 9.76 (d, J = 7.2 Hz, 1H), 8.78 (s, 1H), 8.14-8.13 (m, 1H), 8.04-8.03 (m, 2H), 7.95-7.93 (m, 1H), 7.57 (ddd, J = 6.8, 6.8, 1.2 Hz, 1H), 7.52 (d, J = 8.0 1H), 4.79 (dd, J = 10.4, 2.4 Hz, 1H), 4.10-4.05 (m, 1H), 3.75-3.70 (m, 1H), 3.38-3.31 (m, 1H), 2.43 (s, 3H), 2.28-2.19 (m, 2H), 2.04-1.95 (m, 1H), 1.70-1.60 (m, 1H). MS m/z 420.1 (M + 1)⁺. | 0.227 |
| F113 | 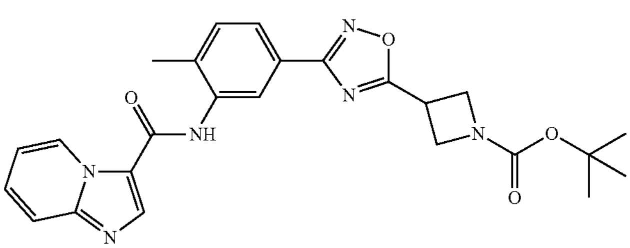 [SMILES: Cc1ccc(-c2noc(C3CN(C(=O)OC(C)(C)C)C3)n2)cc1NC(=O)c1cnc2ccccn12] | ¹H NMR (400 MHz, d₆-DMSO) δ 10.17 (s, 1H), 9.51 (d, J = 6.8 Hz, 1H), 8.70 (s, 1H), 8.10 (d, J = 2.0 Hz, 1H), 7.86 (dt, J = 12, 2.0 Hz, 2H), 7.68 (t, J = 8.0, 1H), 7.51 (d, J = 8 Hz, 1H), 7.31 (t, d, J = 6.8, 0.8 Hz, 1H), 4.06-4.38 (m, 5H) 2.37 (s, 3H), 1.40 (s, 9H) MS m/z 476.2 (M + 1). | 0.623 |

TABLE 2-continued

| Cmpd No. | Structure | Physical Data | c-kit (Mo7e) μM |
|---|---|---|---|
| F114 | 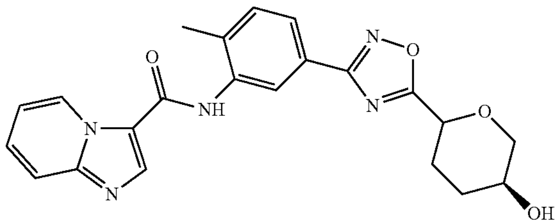 [SMILES: Cc1ccc(-c2noc(C3CC[C@H](O)CO3)n2)cc1NC(=O)c1cnc2ccccn12] | | 0.183 |
| F115 | 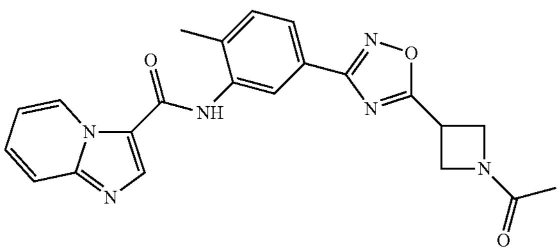 [SMILES: CC(=O)N1CC(c2nc(-c3ccc(C)c(NC(=O)c4cnc5ccccn45)c3)no2)C1] | ¹H NMR (400 MHz, d₆-DMSO) δ 10.14 (s, 1H), 9.51-9.49 (m, 1 H), 8.67 (s, 1H), 8.10 (d, J = 1.6, Hz, 1H), 7.86-7.84 (m, 2H), 7.66-7.61 (m, 1H), 7.51 (d, J = 8.0 Hz, 1H), 7.29-7.25 (m, 1 H), 4.60-4.56 (m, 1H), 4.43-4.40 (m, 1H), 4.31-4.25 (m, 2 H), 4.12-4.10 (m, 1H), 2.37 (s, 3H), 1.80 (s, 3H). MS m/z 417.43 (M + 1)⁺. | 0.464 |
| F116 | 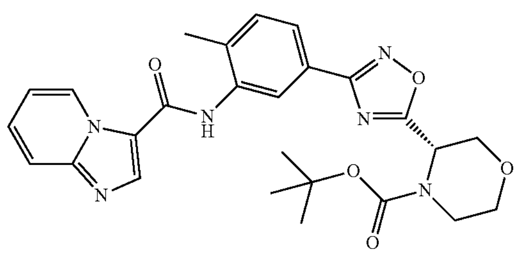 [SMILES: Cc1ccc(-c2noc([C@@H]3COCCN3C(=O)OC(C)(C)C)n2)cc1NC(=O)c1cnc2ccccn12] | ¹H NMR (400 MHz, d₆-DMSO) δ 10.19 (s, 1H), 9.52-9.49 (m, 1 H), 8.69 (s, 1H), 8.06 (s, 1H), 7.89-7.85 (m, 1H), 7.82 (dd, J = 1.2, 7.6 Hz, 1H), 7.69-7.64 (m, 1H), 7.52 (d, J = 8.0 Hz, 1H), 7.32-7.27 (m, 1H), 5.44-5.41 (m, 1H), 4.35-4.32 (m, 2H), 3.87-3.82 (m, 2H), 3.74-3.70 (m, 1H), 3.53-3.48 (m, 1H), 2.37 (s, 3H), 1.45 (s, 9H). MS m/z 505.54 (M + 1)⁺. | 0.792 |
| F117 | 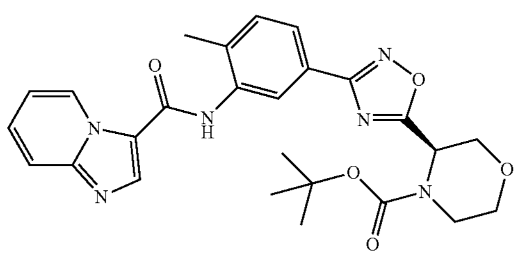 [SMILES: Cc1ccc(-c2noc([C@H]3COCCN3C(=O)OC(C)(C)C)n2)cc1NC(=O)c1cnc2ccccn12] | ¹H NMR (400 MHz, d₆-DMSO) δ 10.19 (s, 1H), 9.52-9.48 (m, 1 H), 8.69 (s, 1H), 8.06 (s, 1H), 7.89-7.85 (m, 1H), 7.82 (dd, J = 1.2, 7.6 Hz, 1H), 7.68-7.64 (m, 1H), 7.52 (d, J = 8.4 Hz, 1H), 7.32-7.28 (m, 1H), 5.44-5.41 (m, 1H), 4.35-4.31 (m, 2H), 3.87-3.83 (m, 2H), 3.74-3.70 (m, 1H), 3.53-3.47 (m, 1), 2.37 (s, 3H), 1.44 (s, 9H). MS m/z 505.54 (M + 1)⁺. | 0.629 |
| F118 | 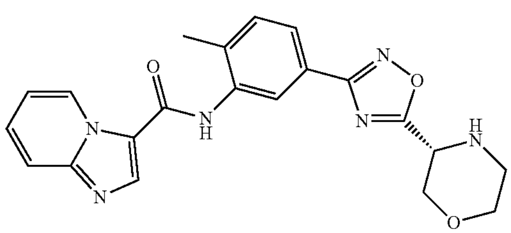 [SMILES: Cc1ccc(-c2noc([C@H]3COCCN3)n2)cc1NC(=O)c1cnc2ccccn12] | MS m/z 405.42 (M + 1)⁺. | 0.936 |
| F119 | 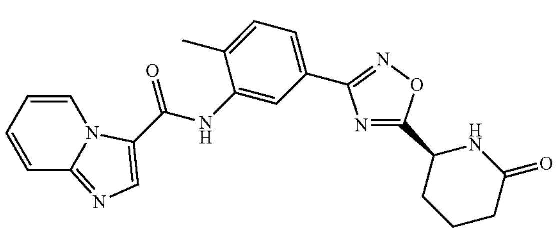 [SMILES: Cc1ccc(-c2noc([C@@H]3CCCC(=O)N3)n2)cc1NC(=O)c1cnc2ccccn12] | MS m/z 417.43 (M + 1)⁺. | 0.434 |

TABLE 2-continued

| Cmpd No. | Structure | Physical Data | c-kit (Mo7e) μM |
|---|---|---|---|
| F120 | 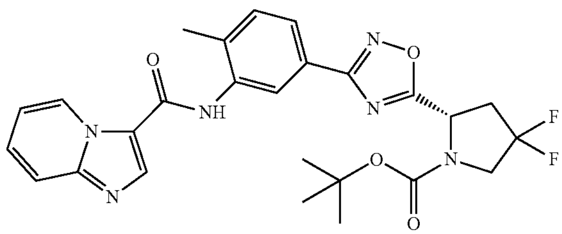 [SMILES: Cc1ccc(-c2noc([C@@H]3CC(F)(F)CN3C(=O)OC(C)(C)C)n2)cc1NC(=O)c1cnc2ccccn12] | ¹H NMR (400 MHz, d₆-DMSO) δ 10.16 (s, 1H), 9.51-9.48 (m, 1 H), 8.67 (s, 1H), 8.06 (s, 1H), 7.87-7.82 (m, 2H), 7.67-7.63 (m, 1H), 7.51 (d, J = 8.0 Hz, 1 H), 7.30-7.27 (m, 1H), 5.48-5.43 (m, 1H), 3.96-3.90 (m, 3 H), 3.18-3.06 (m, 1H), 2.37 (s, 3H), 1.30 (s, 9H). MS m/z 525.40 (M + 1)⁺. | 0.311 |
| F121 | 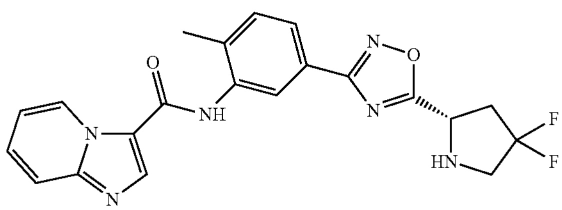 [SMILES: Cc1ccc(-c2noc([C@@H]3CC(F)(F)CN3)n2)cc1NC(=O)c1cnc2ccccn12] | ¹H NMR (400 MHz, d₆-DMSO) δ 10.11 (s, 1H), 9.49-9.47 (m, 1 H), 8.65 (s, 1H), 8.09 (d, J = 4.0 Hz, 1H), 7.85-7.82 (m, 2H), 7.61-7.57 (m, 1H), 7.51 (d, J = 8.0 Hz, 1H), 7.25-7.22 (m, 1 H), 4.97-4.93 (m, 1H), 3.40-3.34 (m, 2H), 2.94-2.68 (m, 2H), 2.37 (s, 3H). MS m/z 425.40 (M + 1)⁺. | 0.205 |
| F122 | 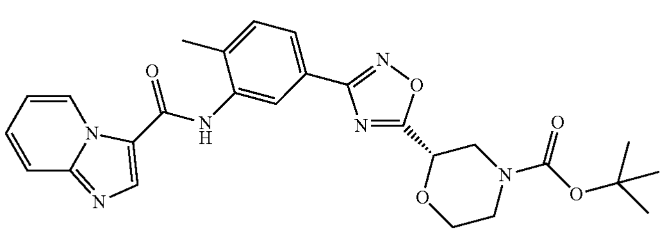 | ¹H NMR (400 MHz, d₆-DMSO) δ 10.16 (s, 1H), 9.52- (m, 1H), 8.69 (s, 1H), 8.10 (d, J = 2.0 Hz, 1H), 7.88-7.83 (m, 2H), 7.68-7.63 (m, 1H), 752 (d, J = 8.4 Hz, 1H), 7.31-7.27 (m, 1H), 5.08-5.05 (m, 1H), 3.94-3.89 (m, 2H), 3.71-3.60 (m ,3H), 3.26-3.19 (m, 1H), 2.38 (s, 3H), 1.40 (s, 9H). MS m/z 505.54 (M + 1)⁺. | 0.296 |
| F123 | 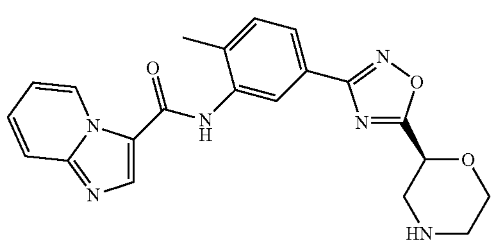 [SMILES: Cc1ccc(-c2noc([C@@H]3CNCCO3)n2)cc1NC(=O)c1cnc2ccccn12] | MS m/z 405.42 (M + 1)⁺. | 0.527 |
| F124 | 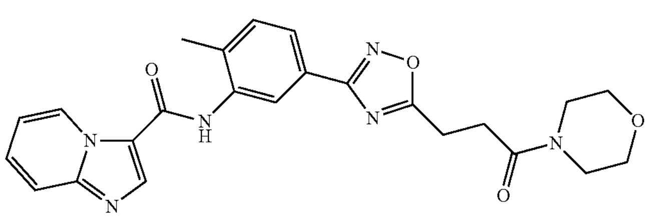 [SMILES: Cc1ccc(-c2noc(CCC(=O)N3CCOCC3)n2)cc1NC(=O)c1cnc2ccccn12] | ¹H NMR (400 MHz, d₆-DMSO) δ 10.14 (s, 1H), 9.46 (d, J = 7.2 Hz, 1H), 8.66 (s, 1H), 7.99 (s, 1H), 7.83 (d, J = 9.2 Hz, 1H), 7.75 (dd, J = 7.6, 1.6 Hz, 1H), 7.75 (dt, J = 7.6, 1.6 Hz, 1H), 7.43 (d, J = 8 Hz, 1H), 7.28 (t, J = 7.2 Hz, 1H), 3.53 (t, J = 4.4, Hz, 1H), 3.46 (t, J = 4.4, Hz, 2H), 3.43 (t, J = 4.4, Hz, 2H), 3.35 (t, J = 4.4, Hz, 2H), 2.30 (s, 3H). MS m/z 461.49 (M + 1)⁺. | 0.426 |

TABLE 2-continued

| Cmpd No. | Structure | Physical Data | c-kit (Mo7e) μM |
|---|---|---|---|
| F125 | 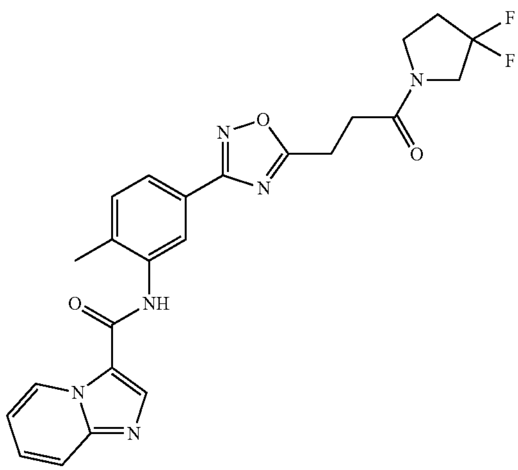 [SMILES: Cc1ccc(-c2noc(CCC(=O)N3CCC(F)(F)C3)n2)cc1NC(=O)c1cnc2ccccn12] | ¹H NMR (400 MHz, d₆-DMSO) δ 10.15 (s, 1H), 9.50 (d, J = 7.2 Hz, 1H), 8.68 (s, 1H), 8.05 (s, 1H), 7.68 (d, J = 8.8 Hz, 1H), 7.80 (dd, J = 8.0, 1.6 Hz, 1H), 7.65 (t, J = 8.8 Hz, 1H), 7.50 (d, J = 8 Hz, 1H), 7.29 (t, J = 6.8 Hz, 1H), 3.95-4.05 (m, 2H), 3.25-3.63 (m, 4H), 3.50 (t, J = 7.6 Hz, 2H), 3.15 (t, J = 7.2 Hz, 2H), 2.68 (t, J = 7.2 Hz, 2H), 2.36 (s, 3H). MS m/z 481.47 (M + 1)⁺. | 0.426 |
| F126 | 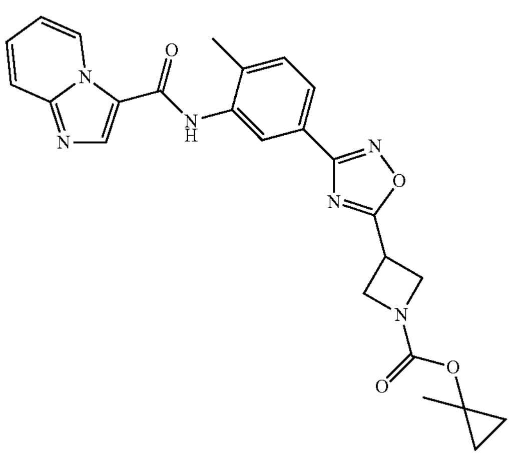 [SMILES: Cc1ccc(-c2noc(C3CN(C(=O)OC4(C)CC4)C3)n2)cc1NC(=O)c1cnc2ccccn12] | ¹H NMR (400 MHz, d₆-DMSO) δ ¹H NMR (400 MHz, d₆-DMSO) δ 10.16 (s, 1H), 9.52 (dt, J = 7.2, 1.2 Hz, 1H), 8.69 (s, 1H), 8.09 (d, J = 1.2 Hz, 1H), 7.84-7.89 (m, 2H), 7.67 (t, J = 8.0, 1H), 7.51 (d, J = 8.0 Hz, 1H), 7.30 (t, d, J = 7.2, 0.8 Hz, 1H), 4.11-4.34 (m, 5H), 2.37 (s, 3H), 1.46 (s, 3H), 0.76-0.81 (m, 2H), 0.57-0.62 (m, 2H). MS m/z 473.50 (M + 1). | 0.891 |
| F127 | 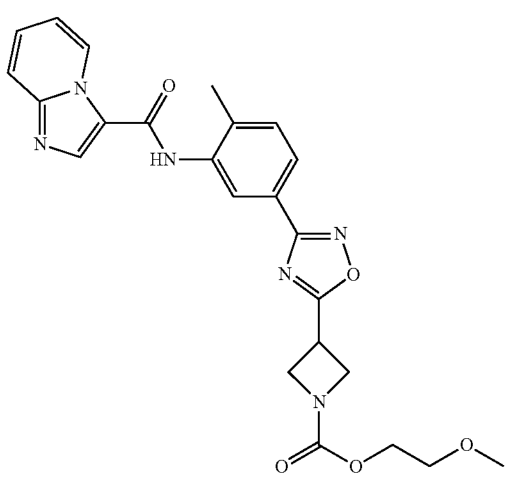 [SMILES: COCCOC(=O)N1CC(c2nc(-c3ccc(C)c(NC(=O)c4cnc5ccccn45)c3)no2)C1] | ¹H NMR (400 MHz, d₆-DMSO) δ 10.19 (s, 1H), 9.52 (d, J = 6.9, 1H), 8.71 (s, 1H), 8.09 (s, 1H), 7.76-7.91 (m, 2H), 7.72-7.62 (m, 1H), 7.51 (d, J = 8.1, 1H), 7.30 (d, J = 6.9, 1H), 4.32-4.23 (m, 2H), 4.14-4.08 (m, 3H), 3.53-3.46 (m, 2H), 3.24 (s, 3H), 2.37 (s, 4H). MS m/z 477.48 (M + 1)⁺. | 0.517 |

TABLE 2-continued

| Cmpd No. | Structure | Physical Data | c-kit (Mo7e) μM |
|---|---|---|---|
| F128 | 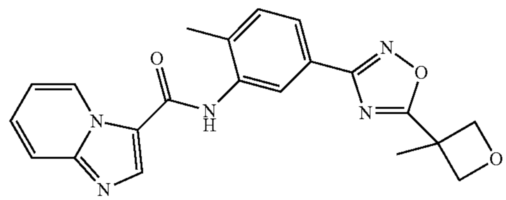 [SMILES: Cc1ccc(-c2noc(C3(C)COC3)n2)cc1NC(=O)c1cnc2ccccn12] | ¹H NMR (400 MHz, DMSO) δ 10.24 (s, 1H), 9.52 (dd, J = 7.5, 1.1 Hz, 1H), 8.73 (s, 1H), 8.05 (s, 1H), 7.86 (m, 2H), 7.69 (m, 1H), 7.51 (dd, J = 6.3, 1.6 Hz, 1H), 7.31 (m, 1H), 4.12 (d, J = 10.8 Hz, 1H), 3.98 (d, J = 10.7 Hz, 1H), 3.76 (m, 2H), 2.37 (s, 3H), 1.5 (s, 3H). MS m/z 390.2 (M + 1)⁺. | 0.14 |
| F129 | 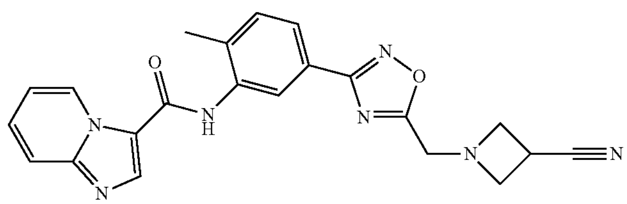 [SMILES: Cc1ccc(-c2noc(CN3CC(C#N)C3)n2)cc1NC(=O)c1cnc2ccccn12] | MS m/z 414.1 (M + 1)⁺. | 0.31 |
| F130 | 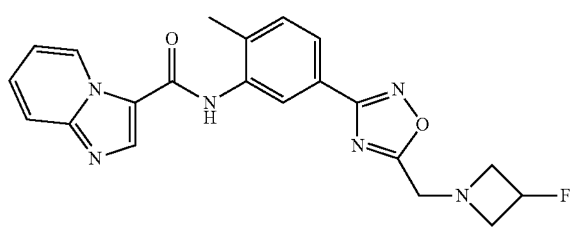 [SMILES: Cc1ccc(-c2noc(CN3CC(F)C3)n2)cc1NC(=O)c1cnc2ccccn12] | MS m/z 407.1 (M + 1)⁺. | 0.127 |
| F131 | 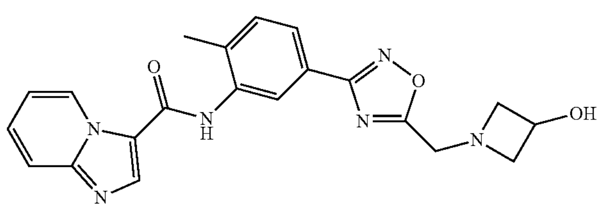 [SMILES: Cc1ccc(-c2noc(CN3CC(O)C3)n2)cc1NC(=O)c1cnc2ccccn12] | MS m/z 405.2 (M + 1)⁺. | 0.738 |
| F132 | 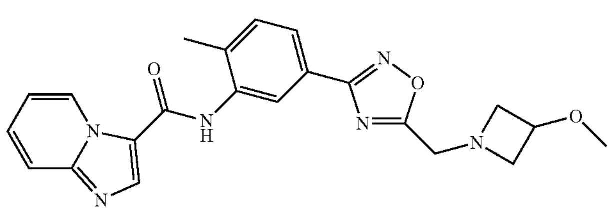 [SMILES: COC1CN(Cc2nc(-c3ccc(C)c(NC(=O)c4cnc5ccccn45)c3)no2)C1] | MS m/z 419.1 (M + 1)⁺. | 0.283 |

TABLE 2-continued

| Cmpd No. | Structure | Physical Data | c-kit (Mo7e) μM |
|---|---|---|---|
| F133 | 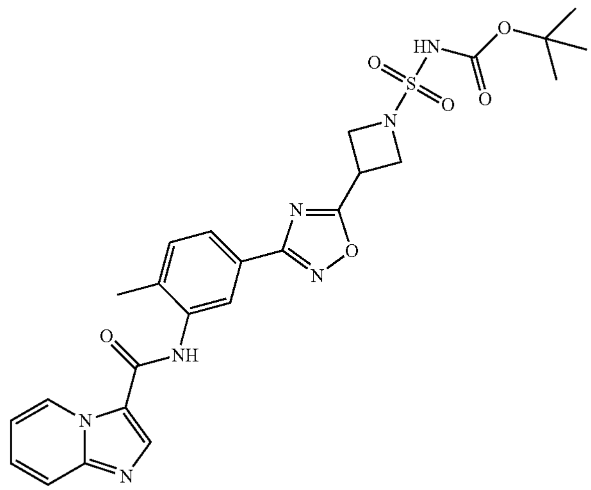 [SMILES: Cc1ccc(-c2noc(C3CN(S(=O)(=O)NC(=O)OC(C)(C)C)C3)n2)cc1NC(=O)c1cnc2ccccn12] | $^1$H NMR (400 MHz, d$_6$-DMSO) δ 11.27 (s, 1H), 10.25 (s, 1H), 9.55-9.51 (m, 1H), 8.76 (s, 1H), 8.07 (d, J = 1.6 Hz, 1H), 7.93-7.89 (m, 1H), 7.85 (dd, J = 1.6, 8.0 Hz, 1H), 7.75-7.71 (m, 1H), 7.52 (d, J = 8.4 Hz, 1H), 7.37-7.34 (m, 1H), 4.37-4.32 (m, 5H), 2.38 (s, 3H), 1.38 (s, 9H). MS m/z 554.59 (M + 1)$^+$. | 0.138 |
| F134 | 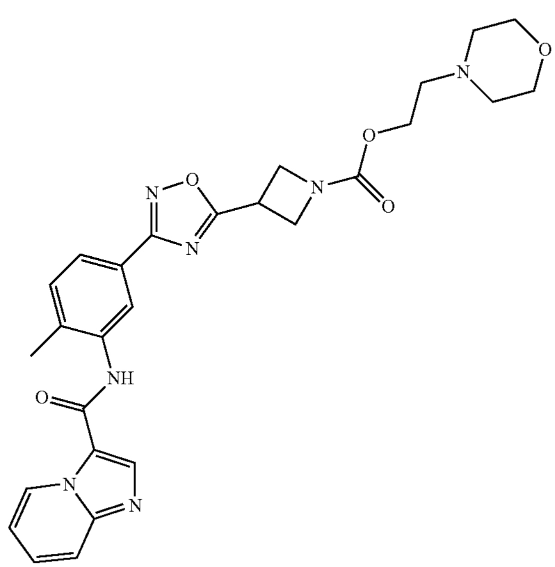 [SMILES: Cc1ccc(-c2noc(C3CN(C(=O)OCCN4CCOCC4)C3)n2)cc1NC(=O)c1cnc2ccccn12] | $^1$H NMR (400 MHz, d$_6$-DMSO) δ 10.08 (s, 1H), 9.48 (d, J = 6.9, 1H), 8.64 (s, 1H), 8.11 (s, 1H), 7.87-7.79 (m, 2H), 7.59 (s, 1H), 7.52 (d, J = 8.2, 1H), 7.23 (s, 1H), ), 4.24-4.18 (m, 1H), 4.16-4.12 (m, 2H), 4.05-4.01 (m, 2H), 3.31-3.38 (m, 12H), 2.37 (s, 3H). MS m/z 532.56 (M + 1)$^+$. | 0.892 |

TABLE 2-continued

| Cmpd No. | Structure | Physical Data | c-kit (Mo7e) μM |
|---|---|---|---|
| F135 | 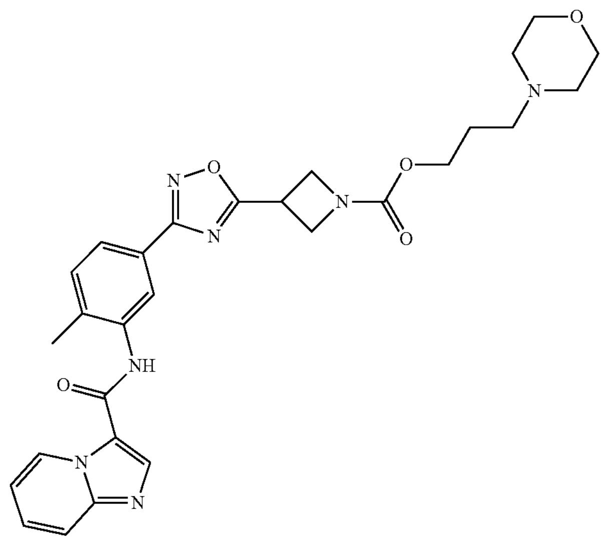 [SMILES: Cc1ccc(-c2noc(C3CN(C(=O)OCCCN4CCOCC4)C3)n2)cc1NC(=O)c1cnc2ccccn12] | ¹H NMR (400 MHz, d₆-DMSO) δ 10.12 (s, 1H), 9.46 (d, J = 7.0, 1H), 8.66 (s, 1H), 8.07 (d, J = 1.6, 1H), ), 7.93-7.83 (m, 2H), 7.67-7.57 (m, 1H), 7.48 (d, J = 8.1, 1H), 7.24 (t, J = 6.9, 1H),, 4.24-4.18 (m, 1H), 4.16-4.12 (m, 2H), 4.05-4.01 (m, 2H), 3.31-3.38 (m, 14H), 2.37 (s, 3H) 1.98-1.88 (m, 2H). MS m/z 546.59 (M + 1)⁺. | 0.75 |
| F136 | 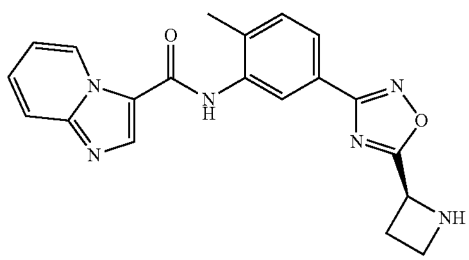 [SMILES: Cc1ccc(-c2noc([C@@H]3CCN3)n2)cc1NC(=O)c1cnc2ccccn12] | ¹H NMR (400 MHz, d₆-DMSO) δ 10.48 (s, 1H), 9.57 (d, J = 7.0, 1H), 8.96 (s, 1H), 8.13 (s, 1H), 7.97 (d, J = 9.0, 1H), 7.94-7.87 (m, 1H), 7.81 (s, 1H), 7.56 (d, J = 8.1, 1H), 7.42 (s, 1H), 5.96-5.80 (m, 1H), 4.19-4.02 (m, 3H), 3.00 (s, 1H), 2.88 (s, 1H), 2.40 (s, 3H). MS m/z 375.40 (M + 1)⁺. | 0.543 |
| F137 | 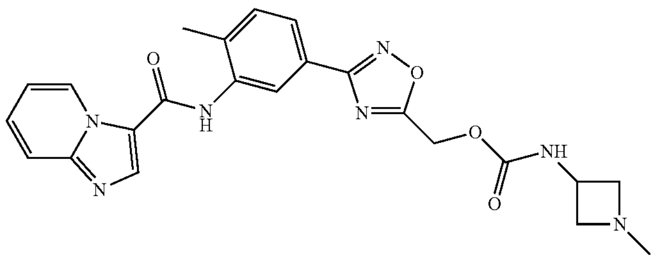 [SMILES: Cc1ccc(-c2noc(COC(=O)NC3CN(C)C3)n2)cc1NC(=O)c1cnc2ccccn12] | MS m/z 462.2 (M + 1)⁺. | 0.792 |
| F138 | 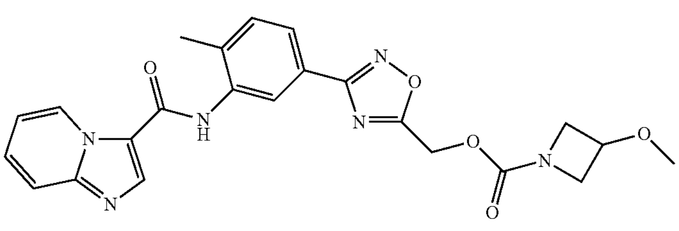 [SMILES: COC1CN(C(=O)OCc2nc(-c3ccc(C)c(NC(=O)c4cnc5ccccn45)c3)no2)C1] | MS m/z 463.1 (M + 1)⁺. | 0.27 |

TABLE 2-continued
| Cmpd No. | Structure | Physical Data | c-kit (Mo7e) μM |
|---|---|---|---|
| F139 | 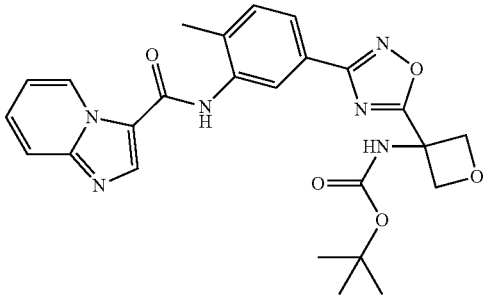 [SMILES: Cc1ccc(-c2noc(C3(NC(=O)OC(C)(C)C)COC3)n2)cc1NC(=O)c1cnc2ccccn12] | MS m/z 491.2 (M + 1)+. | 0.139 |
| F140 | 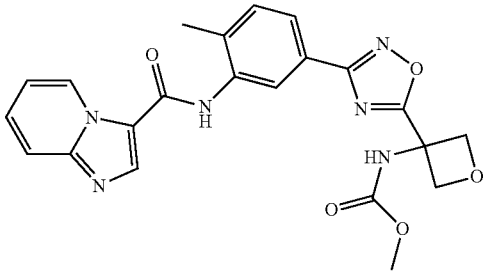 [SMILES: COC(=O)NC1(c2nc(-c3ccc(C)c(NC(=O)c4cnc5ccccn45)c3)no2)COC1] | 1H NMR (400 MHz, CDCl3) δ 9.46 (m, 1H), 8.48 (s, 1H), 8.14 (s, 1H), 7.81 (dd, J = 1.6, 8.0 Hz 1H), 7.69 (d, J = 7.2 Hz, 1H), 7.56 (s, 1H), 7.38 (m, 1H), 7.31 (d, J = 8.0 Hz, 1H), 6.98 (dt, J = 0.8, 6.8 Hz, 1H), 5.12 (m, 2H), 4.91 (m, 2H), 3.66 (s, 3H), 2.36 (s, 3H). MS m/z 449.0 (M + 1)+. | 0.103 |
| F141 | 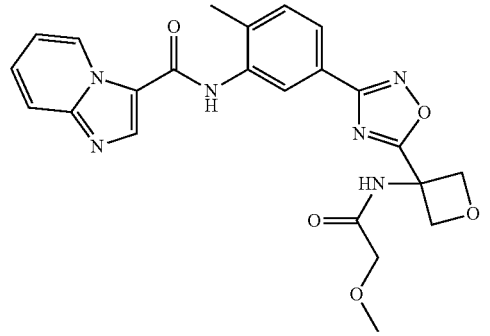 [SMILES: COCC(=O)NC1(c2nc(-c3ccc(C)c(NC(=O)c4cnc5ccccn45)c3)no2)COC1] | MS m/z 463.1 (M + 1)+. | 0.7 |
| F142 | 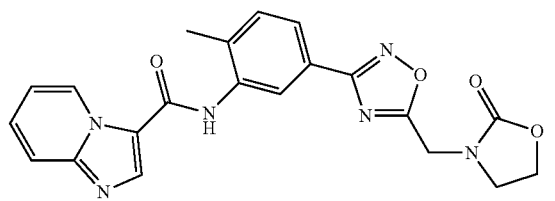 [SMILES: Cc1ccc(-c2noc(CN3CCOC3=O)n2)cc1NC(=O)c1cnc2ccccn12] | MS m/z 419.41 (M + 1)+. | 0.578 |
| F143 | 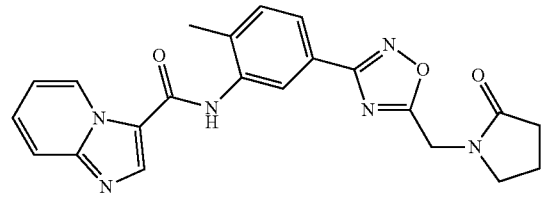 [SMILES: Cc1ccc(-c2noc(CN3CCCC3=O)n2)cc1NC(=O)c1cnc2ccccn12] | MS m/z 417.43 (M + 1)+. | 0.314 |

| Cmpd No. | Structure | Physical Data | c-kit (Mo7e) μM |
|---|---|---|---|
| F144 | 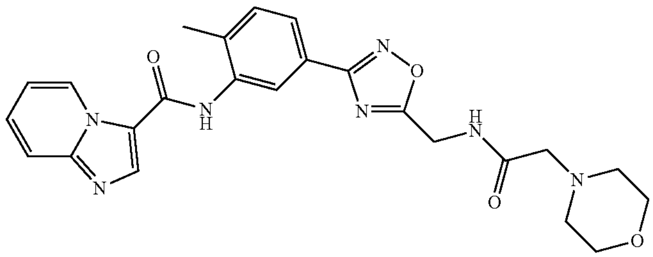 [SMILES: Cc1ccc(-c2noc(CNC(=O)CN3CCOCC3)n2)cc1NC(=O)c1cnc2ccccn12] | ¹H NMR (400 MHz, d₆-DMSO) δ 10.05 (s, 1H), 9.46 (d, J = 6.9, 2H), 8.63 (s, 1H), 8.07 (s, 1H), 7.88-7.73 (m, 2H), 7.51 (d, J = 8.2, 2H), 7.22 (s, 1H), 4.77 (d, J = 5.7, 2H), 4.17-4.08 (m, 2H), 3.4-3.98 (m, 10H), 2.37 (s, 3H) MS m/z 476.50 (M + 1)⁺. | 0.963 |
| F145 | 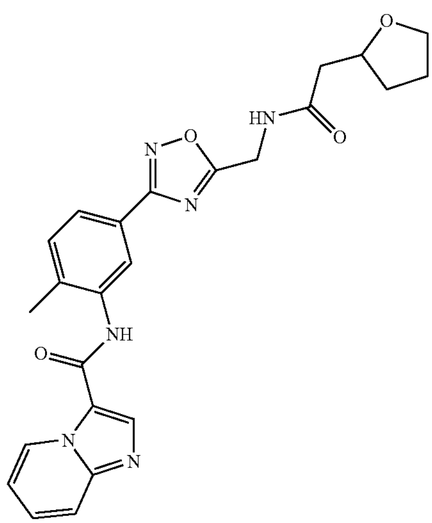 [SMILES: Cc1ccc(-c2noc(CNC(=O)CC3CCCO3)n2)cc1NC(=O)c1cnc2ccccn12] | MS m/z 461.49 (M + 1)⁺. | 0.447 |
| F146 | 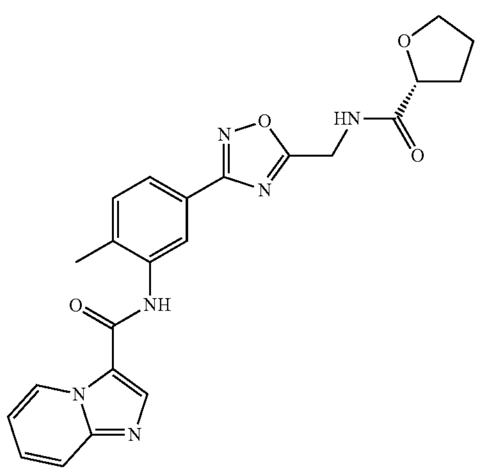 [SMILES: Cc1ccc(-c2noc(CNC(=O)[C@H]3CCCO3)n2)cc1NC(=O)c1cnc2ccccn12] | ¹H NMR (400 MHz, d₆-DMSO) δ 10.15 (s, 1H), 9.51 (d, J = 6.9 1H), 8.68 (s, 2H), 8.07 (s, 1H), 7.88-7.73 (m, 2H), 7.69-7.60 (m, 1H), 7.51 (d, J = 8.1, 1H), 7.29 (t, J = 6.9, 1H), 4.62 (d, J = 5.9, 2H), 4.32 (m, 2H), 3.94 (m, 2H), 3.80 (m, 2H), 2.37 (s, 3H), 2.10-2.15 (m, 1H), 1.96-1.76 (m, 3H). MS m/z 447.46 (M + 1)⁺. | 0.187 |

TABLE 2-continued

| Cmpd No. | Structure | Physical Data | c-kit (Mo7e) μM |
|---|---|---|---|
| F147 | 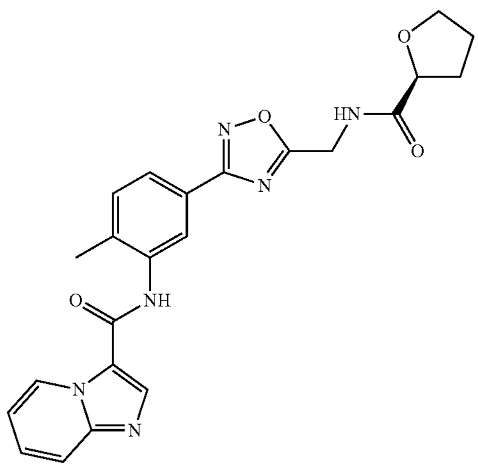 [SMILES: Cc1ccc(-c2noc(CNC(=O)[C@@H]3CCCO3)n2)cc1NC(=O)c1cnc2ccccn12] | $^1$H NMR (400 MHz, d$_6$-DMSO) δ 10.15 (s, 1H), 9.51 (d, J = 6.9, 1H), 8.68 (s, 2H), 8.07 (s, 1H), 7.88-7.73 (m, 2H), 7.69-7.60 (m, 1H), 7.51 (d, J = 8.1, 1H), 7.29 (t, J = 6.9, 1H), 4.62 (d, J = 5.9, 2H), 4.32 (m, 2H), 3.94 (m, 2H), 3.80 (m, 2H), 2.37 (s, 3H), 2.10-2.15 (m, 1H), 1.96-1.76 (m, 3H). MS m/z 447.46 (M + 1)$^+$. | 0.232 |
| F148 | 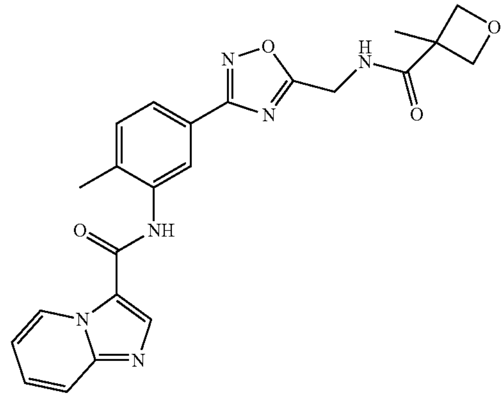 [SMILES: Cc1ccc(-c2noc(CNC(=O)C3(C)COC3)n2)cc1NC(=O)c1cnc2ccccn12] | $^1$H NMR (400 MHz, d$_6$-DMSO) δ 10.14 (s, 1H), 9.50 (d, J = 7.0, 1H), 8.81 (t, J = 5.7, 1H), 8.67 (s, 1H), 8.08 (d, J = 1.7, 1H), 7.87-7.77 (m, 2H), 7.68-7.60 (m, 1H), 7.51 (d, J = 8.1, 1H), 7.28 (t, J = 6.9, 1H), 4.75 (d, J = 5.9, 2H), 4.66 (d, J = 5.9, 2H), 4.27-4.34 (m, 3H), 2.37 (s, 3H), 1.54 (s, 3H). MS m/z 447.46 (M + 1)$^+$. | 0.15 |
| F149 | 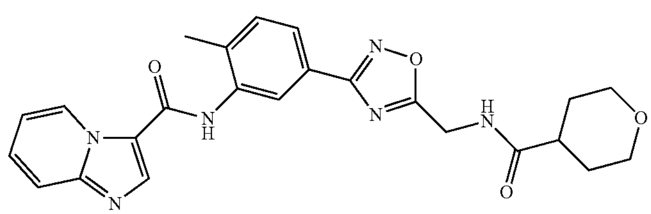 [SMILES: Cc1ccc(-c2noc(CNC(=O)C3CCOCC3)n2)cc1NC(=O)c1cnc2ccccn12] | $^1$H NMR (400 MHz, d$_6$-DMSO) δ 10.13 (s, 1H), 8.73 (s, 1H), 8.67 (s, 1H), 8.07 (s, 1H), 7.87-7.77 (m, 2H), 7.65 (s, 1H), 7.51 (d, J = 8.1, 1H), 7.28 (s, 1H), 4.61 (d, J = 5.7, 2H), 3.85 (t, J = 5.7, 2H), 3.32 (t, J = 5.7, 2H), 2.37 (s, 3H), 2.07 (s, 1H), 1.60-1.71 (m, 4H). MS m/z 461.49 (M + 1)$^+$. | 0.684 |
| F150 | 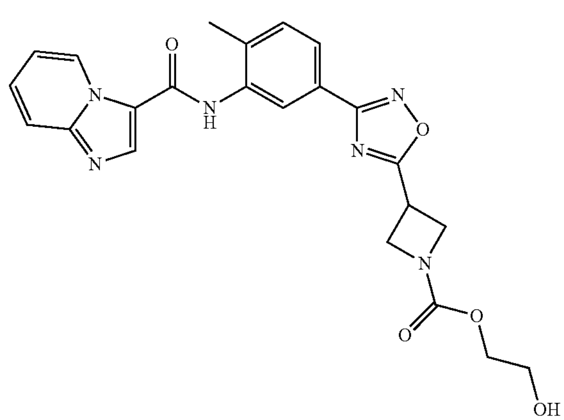 [SMILES: Cc1ccc(-c2noc(C3CN(C(=O)OCCO)C3)n2)cc1NC(=O)c1cnc2ccccn12] | $^1$H NMR (400 MHz, d$_6$-DMSO) δ 10.10 (s, 1H), 9.49 (d, J = 6.9, 1H), 8.71 (s, 1H), 8.65 (s, 1H), 8.07 (s, 1H), 7.87-7.77 (m, 2H), 7.68-7.58 (m, 1H), 7.51 (d, J = 8.1, 1H), 7.25 (s, 1H), 4.63 (d, J = 5.7, 2H), 2.37 (s, 3H), 2.31 (s, 2H), 1.19 (s, 6H). MS m/z 463.46 (M + 1)$^+$. | 0.718 |

TABLE 2-continued

| Cmpd No. | Structure | Physical Data | c-kit (Mo7e) μM |
|---|---|---|---|
| F151 | 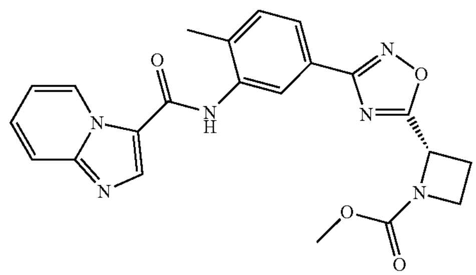 [SMILES: COC(=O)N1CC[C@H]1c1nc(-c2ccc(C)c(NC(=O)c3cnc4ccccn34)c2)no1] | ¹H NMR (400 MHz, d₆-DMSO) δ 10.18 (s, 1H), 9.53-9.50 (m, 1 H), 8.70 (s, 1H), 8.09 (d, J = 1.6 Hz, 1H), 7.89-7.84 (m, 2H), 7.69-7.65 (m, 1H), 7.52 (d, J = 8.0 Hz, 1H), 7.32-7.28 (m, 1 H), 5.60 (s, 1H), 4.05 (s, 2H), 3.56 (s, 3H), 2.79-2.68 (m, 1 H), 2.56-2.53 (m, 1H), 2.38 (s, 3H). MS m/z 433.43 (M + 1)⁺. | 0.357 |
| F152 | 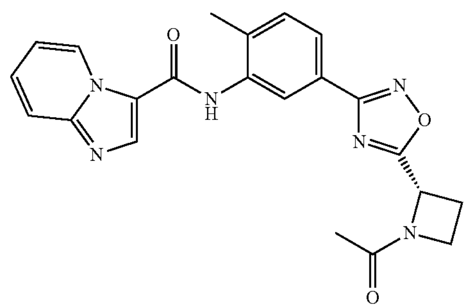 [SMILES: CC(=O)N1CC[C@H]1c1nc(-c2ccc(C)c(NC(=O)c3cnc4ccccn34)c2)no1] | ¹H NMR (400 MHz, d₆-DMSO) δ 10.17 (s, 1H), 9.52-9.50 (m, 1 H), 8.68 (s, 1H), 8.10-8.08 (m, 1H), 7.88-7.83 (m, 2H), 7.68-7.64 (m, 1H), 7.51 (d, J = 8.0 Hz, 1H), 7.31-7.27 (m, 1H), 5.52-5.48 (m, 1H), 4.31-4.20 (m, 2H), 3.97-3.93 (m, 1H), 2.77-2.67 (m, 1H), 2.37 (s, 3 H), 1.84 (s, 3H). MS m/z 417.43 (M + 1)⁺. | 0.738 |
| F153 | 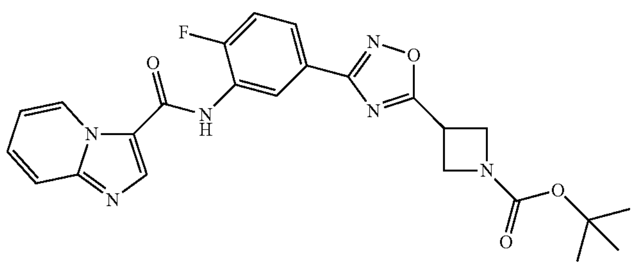 [SMILES: CC(C)(C)OC(=O)N1CC(c2nc(-c3ccc(F)c(NC(=O)c4cnc5ccccn45)c3)no2)C1] | MS m/z 479.2 (M + 1)⁺. | 0.997 |
| F154 | 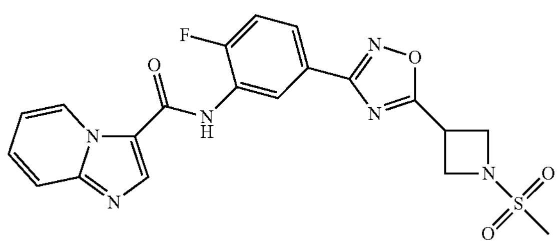 [SMILES: CS(=O)(=O)N1CC(c2nc(-c3ccc(F)c(NC(=O)c4cnc5ccccn45)c3)no2)C1] | MS m/z 457.1 (M + 1)⁺. | 0.472 |
| F155 | 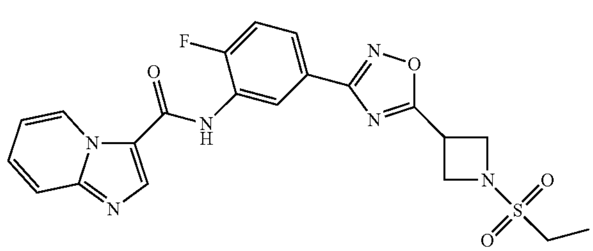 [SMILES: CCS(=O)(=O)N1CC(c2nc(-c3ccc(F)c(NC(=O)c4cnc5ccccn45)c3)no2)C1] | ¹H NMR (400 MHz, CDCl₃) δ 9.50 (d, J = 2 Hz, 1H), 9.09 (dd, J = 2, 7.2 Hz, 1H), 8.21 (s, 1H), 7.87 (m, 1H), 7.79 (m, 1H), 7.71 (d, J = 9.2 Hz, 1H), 7.41 (m, 1H), 7.22 (dd, J = 8.8, 10.4 Hz, 1H), 7.02 (dt, J = 0.8, 6.8 Hz, 1H), 4.34 (m, 4H), 4.07 (m, 1H), 3.00 (q, J = 7.6 Hz, 2H), 1.35 (t, J = 7.6 Hz, 3H). MS m/z 471.2 (M + 1)⁺. | 0.12 |

TABLE 2-continued

| Cmpd No. | Structure | Physical Data | c-kit (Mo7e) μM |
|---|---|---|---|
| F156 | 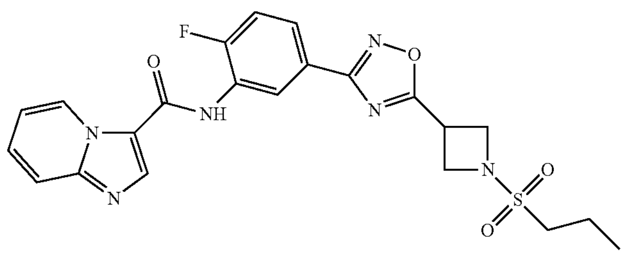 [SMILES: CCCS(=O)(=O)N1CC(c2nc(-c3ccc(F)c(NC(=O)c4cnc5ccccn45)c3)no2)C1] | ¹H NMR (400 MHz, CDCl₃) δ 9.50 (m, 1H), 9.10 (dd, J = 2, 7.2 Hz, 1H), 8.19 (s, 1H), 7.84 (m, 1H), 7.79 (m, 1H), 7.70 (m, 1H), 7.40 (m, 1H), 7.22 (dd, J = 8.8, 10.4 Hz, 1H), 7.09 (dt, J = 1.2, 6.8 Hz, 1H), 4.33 (m, 4H), 4.05 (m, 1H), 2.95 (m, 2H), 1.81 (m, 2H), 1.22 (t, J = 7.2 Hz, 3H). MS m/z 485.2 (M + 1)⁺. | 0.124 |
| F157 | 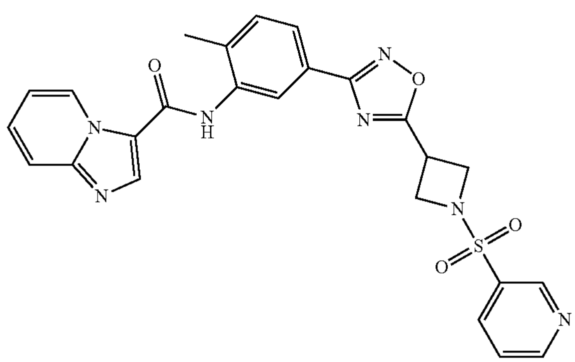 [SMILES: Cc1ccc(-c2noc(C3CN(S(=O)(=O)c4cccnc4)C3)n2)cc1NC(=O)c1cnc2ccccn12] | MS m/z 516.2 (M + 1)⁺. | 0.153 |
| F158 | 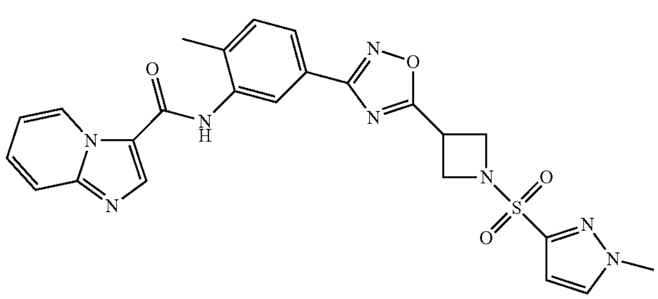 [SMILES: Cc1ccc(-c2noc(C3CN(S(=O)(=O)c4ccn(C)n4)C3)n2)cc1NC(=O)c1cnc2ccccn12] | MS m/z 519.2 (M + 1)⁺. | 0.527 |
| F159 | 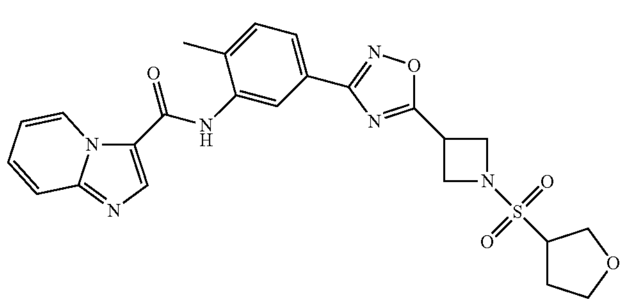 [SMILES: Cc1ccc(-c2noc(C3CN(S(=O)(=O)C4CCOC4)C3)n2)cc1NC(=O)c1cnc2ccccn12] | MS m/z 509.2 (M + 1)⁺. | 0.157 |

TABLE 2-continued

| Cmpd No. | Structure | Physical Data | c-kit (Mo7e) μM |
|---|---|---|---|
| F160 | 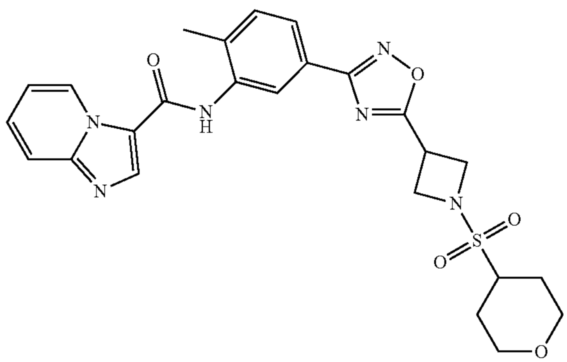 [SMILES: Cc1ccc(-c2noc(C3CN(S(=O)(=O)C4CCOCC4)C3)n2)cc1NC(=O)c1cnc2ccccn12] | MS m/z 523.2 (M + 1)+. | 0.38 |
| F161 | 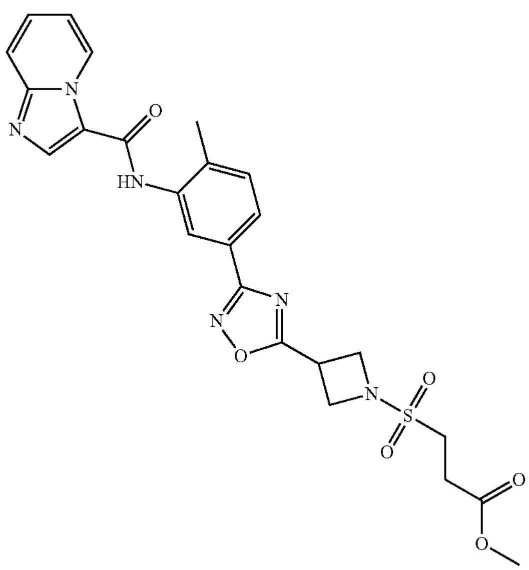 [SMILES: COC(=O)CCS(=O)(=O)N1CC(c2nc(-c3ccc(C)c(NC(=O)c4cnc5ccccn45)c3)no2)C1] | MS m/z 525.2 (M + 1)+. | 0.145 |
| F162 | 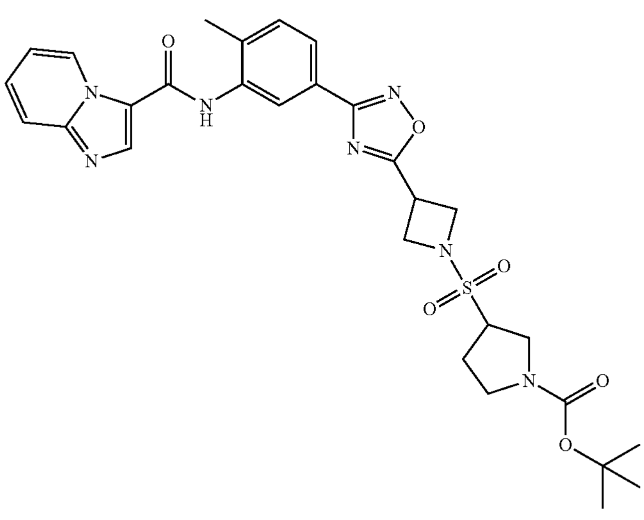 [SMILES: Cc1ccc(-c2noc(C3CN(S(=O)(=O)C4CCN(C(=O)OC(C)(C)C)C4)C3)n2)cc1NC(=O)c1cnc2ccccn12] | MS m/z 608.3 (M + 1)+. | 0.249 |

TABLE 2-continued

| Cmpd No. | Structure | Physical Data | c-kit (Mo7e) μM |
|---|---|---|---|
| F163 | 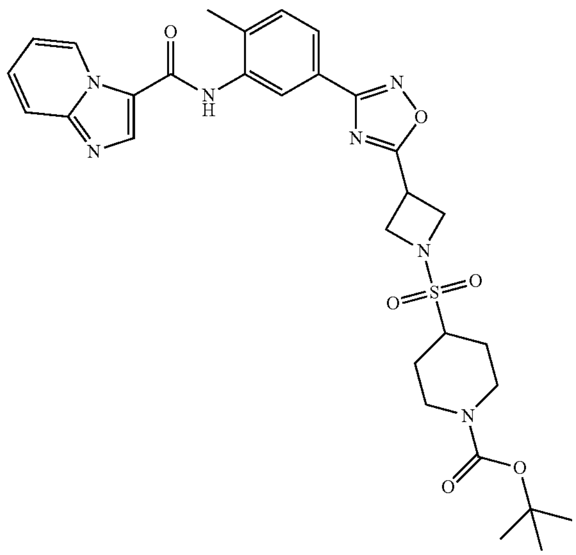 [SMILES: Cc1ccc(-c2noc(C3CN(S(=O)(=O)C4CCN(C(=O)OC(C)(C)C)CC4)C3)n2)cc1NC(=O)c1cnc2ccccn12] | MS m/z 622.4 (M + 1)+. | 0.185 |
| F164 | 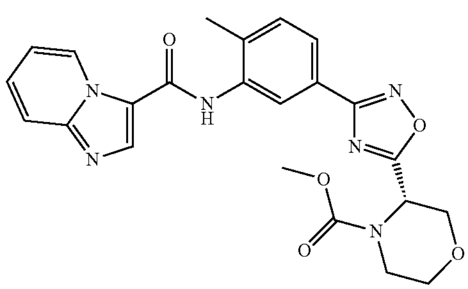 [SMILES: COC(=O)N1CCOC[C@H]1c1nc(-c2ccc(C)c(NC(=O)c3cnc4ccccn34)c2)no1] | ¹H NMR (400 MHz, d₆-DMSO) δ 10.21 (s, 1H), 9.51 (d, J = 7.0, 1H), 8.68 (s, 1H), 8.04 (d, J = 1.7, 1H), 7.89-7.81 (m, 2H), 7.70-7.62 (m, 1H), 7.52 (d, J = 8.1, 1H), 7.29 (t, J = 6.9, 1H), 5.53 (s, 1H), 4.34 (d, J = 12.0, 1H), 3.86 (m, 3H), 3.69 (m, 3H), 3.52 (m, 1H), 3.39-3.11 (m, 2H), 2.37 (s, 3H). MS m/z 464.46 (M + 1)+. | 0.269 |
| F165 | 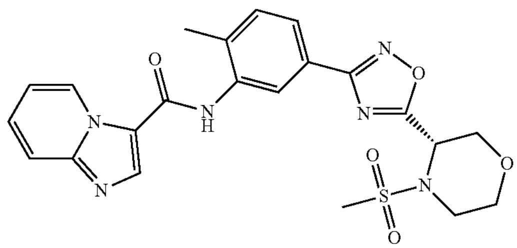 [SMILES: Cc1ccc(-c2noc([C@@H]3COCCN3S(C)(=O)=O)n2)cc1NC(=O)c1cnc2ccccn12] | ¹H NMR (400 MHz, d₆-DMSO) δ 10.17 (s, 1H), 9.49 (d, J = 6.9, 1H), 8.67 (s, 1H), 8.07 (s, 1H), 7.85 (d, J = 9.3, 2H), 7.66-7.59 (m, 1H), 7.53 (d, J = 8.1, 1H), 7.27 (t, J = 6.9, 1H), 5.40 (s, 1H), 4.31 (d, J = 11.7, 1H), 3.89 (d, J = 11.9, 3H), 3.57 (s, 3H), 3.51-3.44 (m, 1H), 3.16 (s, 3H), 2.37 (s, 3H). MS m/z 483.51 (M + 1)+. | 0.362 |
| F166 | 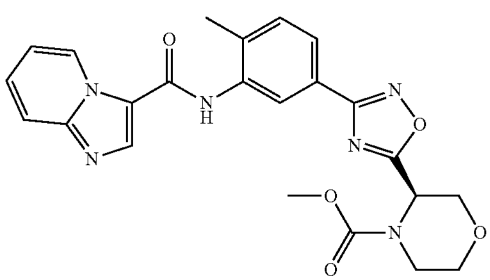 [SMILES: COC(=O)N1CCOC[C@@H]1c1nc(-c2ccc(C)c(NC(=O)c3cnc4ccccn34)c2)no1] | ¹H NMR (400 MHz, d₆-DMSO) δ 10.19 (s, 1H), 9.50 (d, J = 6.9, 1H), 8.67 (s, 1H), 8.03 (s, 1H), 7.89-7.84 (m, 2H), 7.68-7.61 (m, 1H), 7.52 (d, J = 8.1, 1H), 7.28 (t, J = 6.9, 1H), 5.53 (s, 1H), 4.34 (d, J = 12.0, 1H), 3.86 (m, 3H), 3.69 (m, 3H), 3.52 (m, 1H), 3.39-3.11 (m, 2H), 2.37 (s, 3H). MS m/z 463.46 (M + 1)+. | 0.163 |

TABLE 2-continued

| Cmpd No. | Structure | Physical Data | c-kit (Mo7e) μM |
|---|---|---|---|
| F167 | 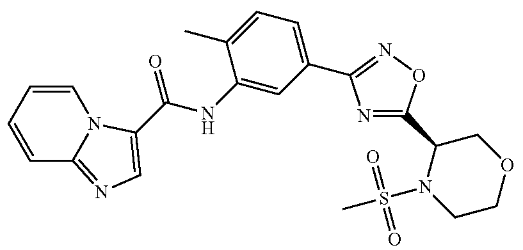 [SMILES: Cc1ccc(-c2noc([C@H]3COCCN3S(C)(=O)=O)n2)cc1NC(=O)c1cnc2ccccn12] | ¹H NMR (400 MHz, d₆-DMSO) δ 10.16 (s, 1H), 9.49 (d, J = 7.0, 1H), 8.67 (s, 1H), 8.07 (s, 1H), 7.84 (d, J = 9.3, 2H), 7.66-7.59 (m, 1H), 7.53 (d, J = 8.1, 1H), 7.27 (t, J = 6.9, 1H), 5.40 (s, 1H), 4.31 (d, J = 11.7, 1H), 3.89 (d, J = 11.9, 3H), 3.57 (s, 3H), 3.50-3.43 (m, 1H), 3.16 (s, 3H), 2.36 (s, 3H). MS m/z 483.51 (M + 1)⁺. | 0.102 |
| F168 | 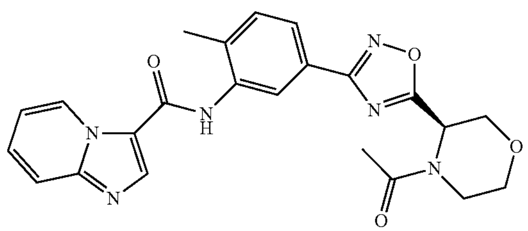 [SMILES: CC(=O)N1CCOC[C@@H]1c1nc(-c2ccc(C)c(NC(=O)c3cnc4ccccn34)c2)no1] | ¹H NMR (400 MHz, d₆-DMSO) δ 10.23 (d, J = 5.8, 1H), 9.51 (d, J = 6.9, 1H), 8.70 (s, 1H), 8.03 (s, 1H), 7.91-7.81 (m, 2H), 7.72-7.64 (m, 1H), 7.52 (d, J = 8.0, 1H), 7.31 (t, J = 6.9, 1H), 5.61 (s, 1H), 4.31-4.45 (m, 1H), 3.93-3.76 (m, 3H), 3.60-3.39 (m, 2H), 2.36 (s, 3H), 2.14 (s, 3H). MS m/z 447.46 (M + 1)⁺. | 0.358 |
| F169 | 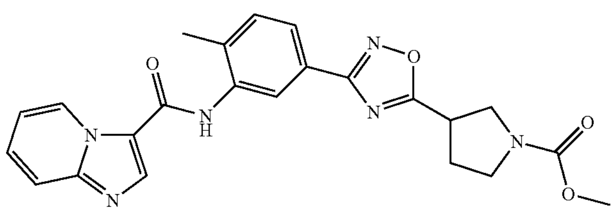 [SMILES: COC(=O)N1CCC(c2nc(-c3ccc(C)c(NC(=O)c4cnc5ccccn45)c3)no2)C1] | ¹H NMR (400 MHz, d₆-DMSO) δ 10.18 (s, 1H), 9.51 (d, J = 6.9, 1H), 8.69 (s, 1H), 8.06 (d, J = 1.7, 1H), 7.90-7.79 (m, 2H), 7.70-7.64 (m, 1H), 7.51 (d, J = 8.1, 1H), 7.30 (t, J = 6.5, 1H), 3.88-3.94 (m, 1H), 3.74-3.85 (m, 1H), 3.64-3.71 (m, 1H), 3.54-3.63 (m, 3H), 3.52-3.42 (m, 2H), 2.36 (s, 3H). MS m/z 447.46 (M + 1)⁺. | 0.132 |
| F170 | 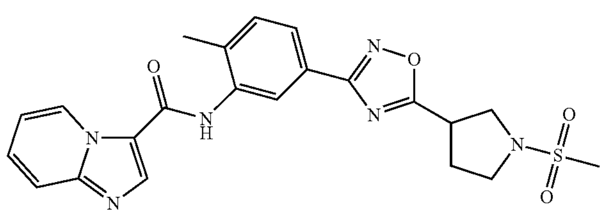 [SMILES: Cc1ccc(-c2noc(C3CCN(S(C)(=O)=O)C3)n2)cc1NC(=O)c1cnc2ccccn12] | ¹H NMR (400 MHz, d₆-DMSO) δ 10.14 (s, 1H), 9.50 (d, J = 6.9, 1H), 8.67 (s, 1H), 8.08 (d, J = 1.7, 1H), 7.89-7.84 (m, 2H), 7.67-7.61 (m, 1H), 7.51 (d, J = 8.1, 1H), 7.28 (t, J = 6.9, 1H), 4.02-3.93 (m, 2H), 3.74-3.85 (m, 1H), 3.51-3.55 (m, 1H), 3.41-3.45 (m, 2H), 2.98 (s, 3H), 2.37 (s, 3H), 2.33-2.22 (m, 1H). MS m/z 467.51 (M + 1)⁺. | 0.137 |
| F171 | 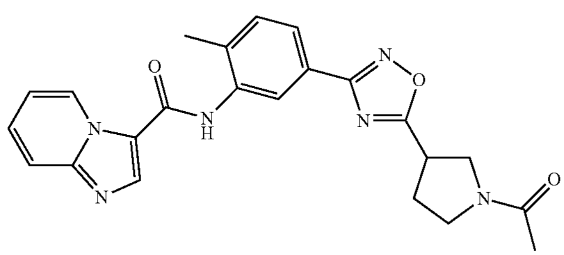 [SMILES: CC(=O)N1CCC(c2nc(-c3ccc(C)c(NC(=O)c4cnc5ccccn45)c3)no2)C1] | ¹H NMR (400 MHz, d₆-DMSO) δ 10.21 (s, 1H), 9.52 (d, J = 6.9, 1H), 8.71 (s, 1H), 8.06 (d, J = 1.6, 1H), 7.87 (dd, J = 8.4, 24.5, 2H), 7.71 (t, J = 8.0, 1H), 7.51 (d, J = 7.9, 1H), 7.33 (t, J = 6.9, 1H), 3.34-4.02 (m, 6H), 2.37 (s, 4H), 1.97 (s, 3H). MS m/z 431.46 (M + 1)⁺. | 0.24 |
| F172 | 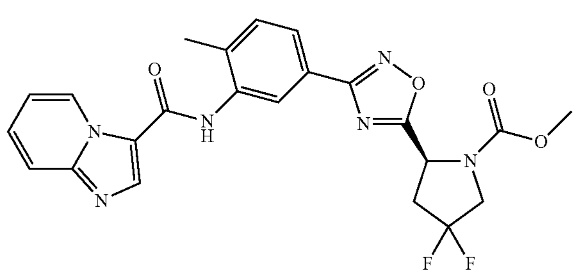 [SMILES: COC(=O)N1CC(F)(F)C[C@H]1c1nc(-c2ccc(C)c(NC(=O)c3cnc4ccccn34)c2)no1] | ¹H NMR (400 MHz, d₆-DMSO) δ 10.18 (s, 1H), 9.51 (d, J = 6.9, 1H), 8.68 (s, 1H), 8.05 (d, J = 1.6, 1H), 7.89-7.84 (m, 2H), 7.70-7.63 (m, 1H), 7.52 (d, J = 8.1, 1H), 7.29 (t, J = 6.9, 1H), 5.54 (s, 1H), 3.90-4.10 (m, 2H), 3.61-3.71 (m, 2H), 3.22-3.01 (m, 1H), 2.88-2.76 (m, 1H), 2.37 (s, 3H). MS m/z 483.44 (M + 1)⁺. | 0.122 |

TABLE 2-continued

| Cmpd No. | Structure | Physical Data | c-kit (Mo7e) μM |
|---|---|---|---|
| F173 | 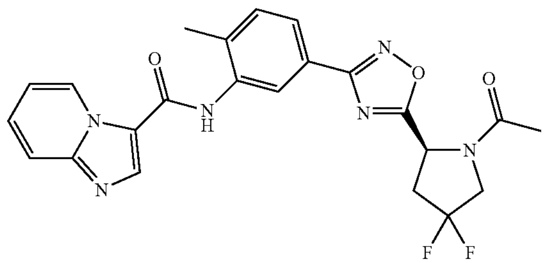 [SMILES: CC(=O)N1CC(F)(F)C[C@H]1c1nc(-c2ccc(C)c(NC(=O)c3cnc4ccccn34)c2)no1] | ¹H NMR (400 MHz, d₆-DMSO) δ 10.19 (d, J = 11.4, 1H), 9.50 (d, J = 6.9, 1H), 8.68 (s, 1H), 8.04 (s, 1H), 7.91-7.77 (m, 2H), 7.71-7.61 (m, 1H), 7.51 (d, J = 8.1, 1H), 7.29 (t, J = 6.6, 1H), 5.51-5.60 (m 1H), 4.20-4.29 (m ,2H), 3.01-3.08 (m, 1H), 2.71-2.91 (m, 1H), 2.37 (s, 3H), 2.01-2.09 (m, 3H). MS m/z 467.44 (M + 1)⁺. | 0.212 |
| F174 | 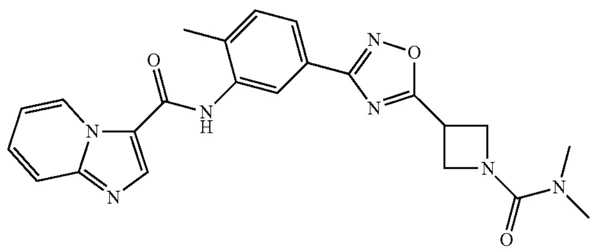 [SMILES: Cc1ccc(-c2noc(C3CN(C(=O)N(C)C)C3)n2)cc1NC(=O)c1cnc2ccccn12] | ¹H NMR (400 MHz, d₆-DMSO) δ 10.13 (s, 1H), 9.50 (d, J = 6.9, 1H), 8.66 (s, 1H), 8.09 (s, 1H), 7.85 (d, J = 9.3, 2H), 7.62 (s, 1H), 7.51 (d, J = 8.1, 1H), 7.26 (s, 1H), 4.32 (t, J = 7.9, 2H), 4.16 (d, J = 5.6, 2H), 2.78 (s, 6H), 2.38 (s, 3H). MS m/z 446.47 (M + 1)⁺. | 0.831 |
| F175 | 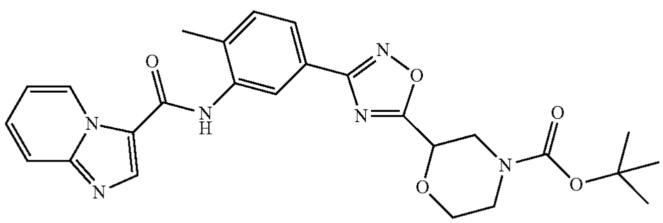 | ¹H NMR (400 MHz, d₆-DMSO) δ 10.15 (s, 1H), 9.51 (d, J = 6.9, 1H), 8.68 (s, 1H), 8.10 (s, 1H), 7.85 (t, J = 8.1, 2H), 7.65 (s, 1H), 7.52 (d, J = 8.1, 1H), 7.28 (s, 1H), 5.03-5.10 (m, 1H), 3.28-3.84 (m, 6H), 2.37 (s, 3H), 1.40 (s, 9H). MS m/z 505.54 (M + 1)⁺. | 0.728 |
| F176 | 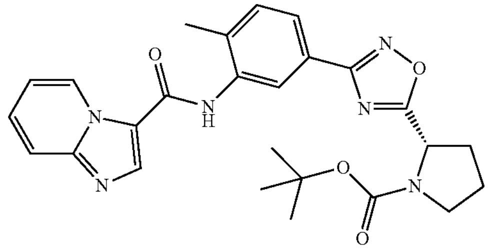 [SMILES: Cc1ccc(-c2noc([C@@H]3CCCN3C(=O)OC(C)(C)C)n2)cc1NC(=O)c1cnc2ccccn12] | MS m/z 489.54 (M + 1)⁺. | 0.452 |
| F177 | 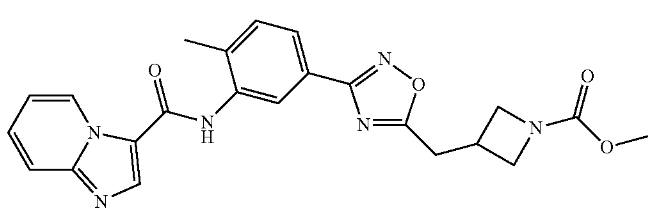 [SMILES: COC(=O)N1CC(Cc2nc(-c3ccc(C)c(NC(=O)c4cnc5ccccn45)c3)no2)C1] | MS m/z 447.1 (M + 1)⁺. | 0.398 |
| F178 | 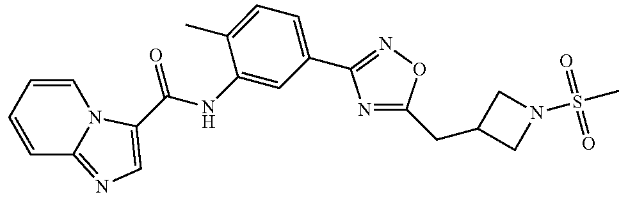 [SMILES: Cc1ccc(-c2noc(CC3CN(S(C)(=O)=O)C3)n2)cc1NC(=O)c1cnc2ccccn12] | MS m/z 467.1 (M + 1)⁺. | 0.476 |

TABLE 2-continued

| Cmpd No. | Structure | Physical Data | c-kit (Mo7e) μM |
|---|---|---|---|
| F179 | 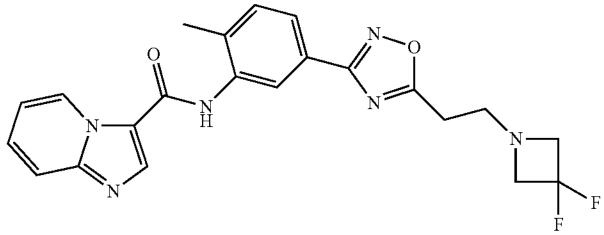 [SMILES: Cc1ccc(-c2noc(CCN3CC(F)(F)C3)n2)cc1NC(=O)c1cnc2ccccn12] | MS m/z 439.2 (M + 1)+. | 0.119 |
| F180 | 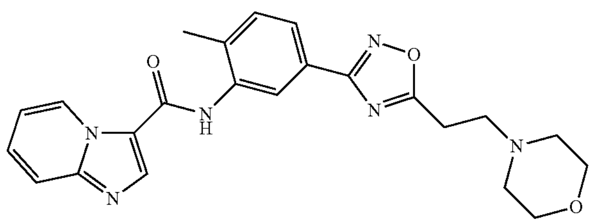 [SMILES: Cc1ccc(-c2noc(CCN3CCOCC3)n2)cc1NC(=O)c1cnc2ccccn12] | MS m/z 433.1 (M + 1)+. | 0.169 |
| F181 | 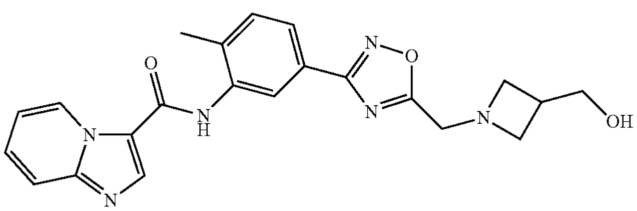 [SMILES: Cc1ccc(-c2noc(CN3CC(CO)C3)n2)cc1NC(=O)c1cnc2ccccn12] | MS m/z 419.1 (M + 1)+. | 0.337 |
| F182 | 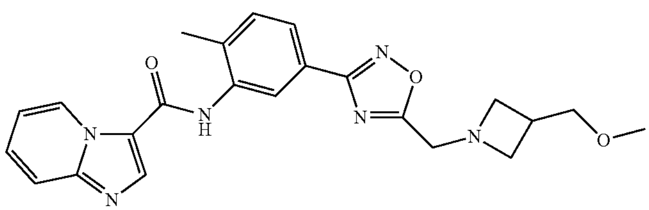 [SMILES: COCC1CN(Cc2nc(-c3ccc(C)c(NC(=O)c4cnc5ccccn45)c3)no2)C1] | MS m/z 433.1 (M + 1)+. | 0.259 |
| F183 | 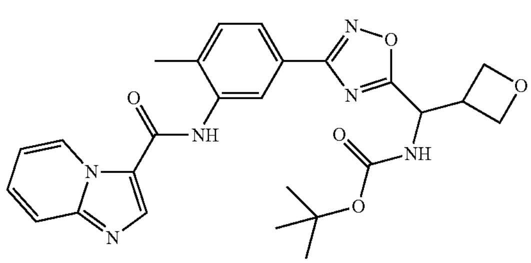 [SMILES: Cc1ccc(-c2noc(C(NC(=O)OC(C)(C)C)C3COC3)n2)cc1NC(=O)c1cnc2ccccn12] | 1H NMR (400 MHz, d6-DMSO) δ 10.15 (s, 1H), 9.51-9348 (m, 1 H), 8.66 (s, 1H), 8.03 (d, J = 1.6 Hz, 1H), 7.91-7.88 (m, 1H), 7.87-7.84 (m, 1H), 7.81-7.79 (m, 1H), 7.66-7.62 (m, 1H), 7.50 (d, J = 8.4 Hz, 1H), 5.32-5.27 (m, 1H), 4.71-4.65 (m, 2 H), 4.51-4.44 (m, 2H), 3.58-3.52 (m, 1H), 2.36 (s, 3H), 1.41 (s, 9H).<br>MS m/z 505.54 (M + 1)+. | 0.454 |
| F184 | 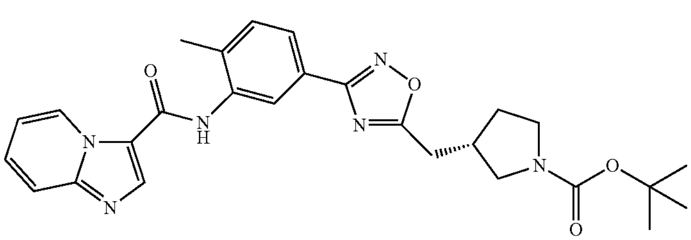 [SMILES: Cc1ccc(-c2noc(C[C@@H]3CCN(C(=O)OC(C)(C)C)C3)n2)cc1NC(=O)c1cnc2ccccn12] | 1H NMR (400 MHz, d6-DMSO) δ 10.19 (s, 1H), 9.53-9.51 (m, 1 H), 8.72 (s, 1H), 8.07-8.06 (m, 1H), 7.89 (d, J = 8.8 Hz, 1H), 7.84-7.82 (m, 1H), 7.73-7.68 (m, 1H), 7.51 (d, J = 8.0 Hz, 1 H), 7.35-7.31 (m, 1H), 3.56-3.52 (m, 1H), 3.40-3.34 (m, 1 H), 3.26-3.17 (m, 1H), 3.14-3.12 (m, 2H), 3.04-2.98 (m, 2 H), 2.37 (s, 3H), 2.09-2.01 (m, 1H), 1.70-1.61 (m, 1H), 1.38 (s, 9H).<br>MS m/z 503.56 (M + 1)+. | 0.496 |

TABLE 2-continued

| Cmpd No. | Structure | Physical Data | c-kit (Mo7e) μM |
|---|---|---|---|
| F185 | 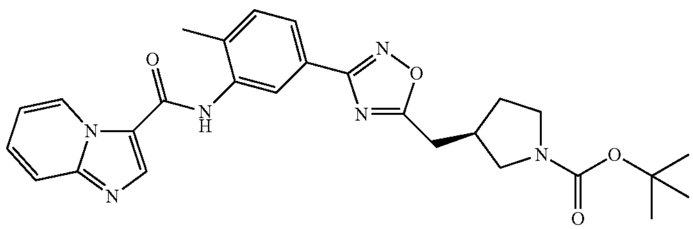 [SMILES: Cc1ccc(-c2noc(C[C@H]3CCN(C(=O)OC(C)(C)C)C3)n2)cc1NC(=O)c1cnc2ccccn12] | ¹H NMR (400 MHz, d₆-DMSO) δ 10.19 (s, 1H), 9.53-9.51 (m, 1 H), 8.71 (s, 1H), 8.07-8.06 (m, 1H), 7.89 (d, J = 8.8 Hz, 1H), 7.84-7.82 (m, 1H), 7.72-7.67 (m, 1H), 7.51 (d, J = 8.0 Hz, 1 H), 7.34-7.30 (m, 1H), 3.56-3.52 (m, 1H), 3.40-3.34 (m, 1 H), 3.26-3.17 (m, 1H), 3.14-3.12 (m, 2H), 3.04-2.98 (m, 1 H), 2.71-2.62 (m, 1H), 2.37 (s, 3H), 2.08-2.02 (m, 1H), 1.70-1.61 (m, 1H), 1.38 (s, 9H). MS m/z 503.56 (M + 1)⁺. | 0.452 |
| F186 | 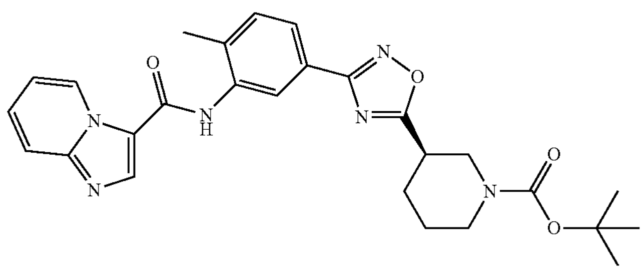 [SMILES: Cc1ccc(-c2noc([C@@H]3CCCN(C(=O)OC(C)(C)C)C3)n2)cc1NC(=O)c1cnc2ccccn12] | ¹H NMR (400 MHz, d₆-DMSO) δ 10.19 (s, 1H), 9.53-9.51 (m, 1 H), 8.70 (s, 1H), 8.06 (d, J = 1.2 Hz, 1H), 7.90-7.87 (m, 1H), 7.83 (dd, J = 1.6, 8.0 Hz, 1H), 7.71-7.67 (m, 1H), 7.50 (d, J = 8.0 Hz, 1H), 7.33-7.30 (m, 1 H), 3.72-3.62 (m, 1H), 3.29-3.21 (m, 2H), 2.36 (s, 3H), 2.15-2.07 (m, 1H), 1.98-1.87 (m, 1 H), 1.79-1.75 (m, 1H), 1.55-1.48 (m, 1H), 1.35 (s, 9H). MS m/z 503.56 (M + 1)⁺. | 0.291 |
| F187 | 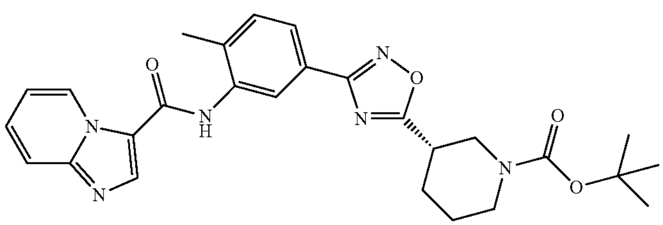 [SMILES: Cc1ccc(-c2noc([C@H]3CCCN(C(=O)OC(C)(C)C)C3)n2)cc1NC(=O)c1cnc2ccccn12] | ¹H NMR (400 MHz, d₆-DMSO) δ 10.20 (s, 1H), 9.53-9.50 (m, 1 H), 8.70 (s, 1H), 8.06 (d, J = 1.6 Hz, 1H), 7.90-7.87 (m, 1H), 7.83 (dd, J = 2.0, 8.0 Hz, 1H), 7.71-7.67 (m, 1H), 7.50 (d, J = 8.0 Hz, 1H), 7.34-7.30 (m, 1 H), 3.67-3.46 (m, 1H), 3.30-3.27 (m, 2H), 2.36 (s, 3H), 2.18-2.09 (m, 1H), 1.98-1.87 (m, 1 H), 1.79-1.75 (m, 1H), 1.55-1.49 (m, 1H), 1.35 (s, 9H). MS m/z 503.56 (M + 1)⁺. | 0.32 |
| F188 | 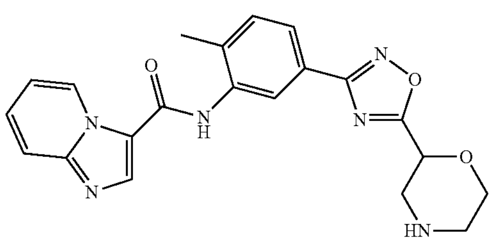 [SMILES: Cc1ccc(-c2noc(C3CNCCO3)n2)cc1NC(=O)c1cnc2ccccn12] | ¹H NMR (400 MHz, d₆-DMSO) δ 10.10 (s, 1H), 9.48 (d, J = 7.0, 1H), 9.25 (s, 2H), 8.65 (s, 1H), 8.11 (s, 1H), 7.84 (d, J = 7.9, 2H), 7.73-7.56 (m, 1H), 7.53 (d, J = 8.1, 1H), 7.25 (d, J = 6.9, 1H), 5.33 (t, J = 7.0, 1H), 4.10-4.15 (m, 2H), 3.91-4.01 (m, 2H), 3.79-3.69 (m, 2H), 3.30 (br s, 2H), 2.38 (s, 3H). MS m/z 405.42 (M + 1)⁺. | 0.399 |
| F189 | 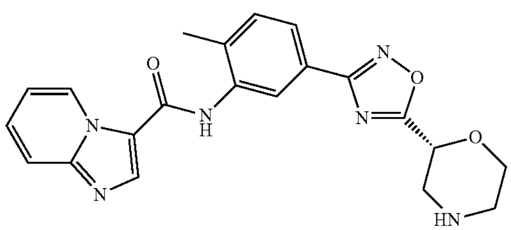 [SMILES: Cc1ccc(-c2noc([C@H]3CNCCO3)n2)cc1NC(=O)c1cnc2ccccn12] | ¹H NMR (400 MHz, d₆-DMSO) δ 10.13 (s, 1H), 9.49 (d, J = 6.9, 1H), 9.29 (s, 1H), 8.68 (s, 1H), 8.11 (d, J = 1.7, 1H), 7.93-7.81 (m, 2H), 7.69-7.57 (m, 1H), 7.53 (d, J = 8.2, 1H), 7.27 (t, J = 6.9, 1H), 5.37-5.26 (m, 1H), 4.15 (d, J = 12.9, 1H), 3.96 (s, 1H), 3.73 (s, 1H), 3.60-3.38 (m, 1H), 3.30 (br s, 2H), 2.38 (s, 3H). MS m/z 405.42 (M + 1)⁺. | 0.824 |

TABLE 2-continued

| Cmpd No. | Structure | Physical Data | c-kit (Mo7e) μM |
|---|---|---|---|
| F190 | 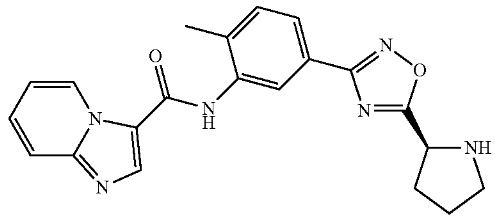 [SMILES: Cc1ccc(-c2noc([C@@H]3CCCN3)n2)cc1NC(=O)c1cnc2ccccn12] | ¹H NMR (400 MHz, d₆-DMSO) δ 10.10 (s, 1H), 9.46 (d, J = 6.9, 1H), 8.65 (s, 1H), 8.12 (s, 1H), 7.85 (t, J = 9.1, 2H), 7.65-7.49 (m, 2H), 7.25 (d, J = 7.0, 1H), 5.17 (s, 1H), 3.41 (m, 2H), 2.39 (s, 3H), 2.35-2.26 (m, 2H), 2.01-2.15 (m, 2H). MS m/z 389.42 (M + 1)⁺. | 0.476 |
| F191 | 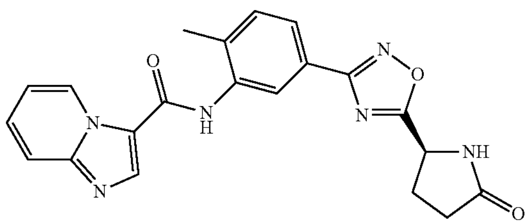 [SMILES: Cc1ccc(-c2noc([C@@H]3CCC(=O)N3)n2)cc1NC(=O)c1cnc2ccccn12] | ¹H NMR (400 MHz, d₆-DMSO) δ 10.15 (s, 1H), 9.50 (d, J = 7.0, 1H), 8.40 (s, 1H), 8.09 (s, 1H), 7.85 (t, J = 9.1, 2H), 7.65 (s, 1H), 7.51 (d, J = 8.1, 1H), 7.28 (s, 1H), 5.23-5.03 (m, 1H), 2.64-2.52 (m, 1H), 2.37 (s, 3H), 2.21-2.38 (m, 3H). MS m/z 403.41 (M + 1)⁺. | 0.465 |
| F192 | 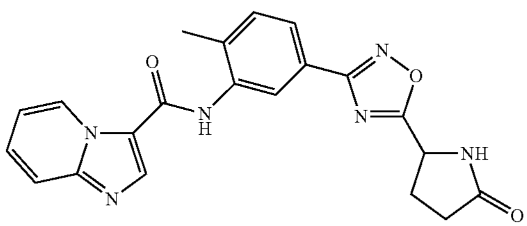 [SMILES: Cc1ccc(-c2noc(C3CCC(=O)N3)n2)cc1NC(=O)c1cnc2ccccn12] | ¹H NMR (400 MHz, d₆-DMSO) δ 10.17 (s, 1H), 9.51 (d, J = 7.0, 1H), 8.69 (s, 1H), 8.40 (s, 1H), 8.09 (s, 1H), 7.89-7.84 (m, 2H), 7.67 (s, 1H), 7.52 (d, J = 8.1, 1H), 7.30 (s, 1H), 5.12 (s, 1H), 2.72-2.52 (m, 1H), 2.37 (s, 3H), 2.33-2.20 (m, 2H). MS m/z 403.41 (M + 1)⁺. | 0.672 |
| F193 | 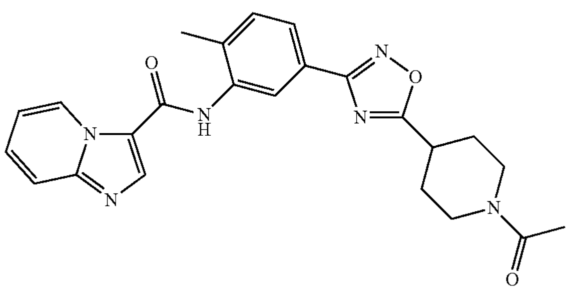 [SMILES: CC(=O)N1CCC(c2nc(-c3ccc(C)c(NC(=O)c4cnc5ccccn45)c3)no2)CC1] | ¹H NMR (400 MHz, d₆-DMSO) δ 10.18 (s, 1H), 9.51 (d, J = 7.0, 1H), 8.69 (s, 1H), 8.06 (s, 1H), 7.89-7.84 (m, 2H), 7.68 (s, 1H), 7.50 (d, J = 8.1, 1H), 7.30 (s, 1H), 4.35-4.25 (m, 1H), 3.36-3.41 (m, 1H), 3.24 (s, 1H), 2.96-2.78 (m, 1H), 2.36 (s, 3H), 2.01-2.15 (m, 2H), 2.02 (s, 3H), 1.86-1.71 (m, 1H), 1.68-1.55 (m, 1H). MS m/z 445.49 (M + 1)⁺. | 0.354 |
| F194 | 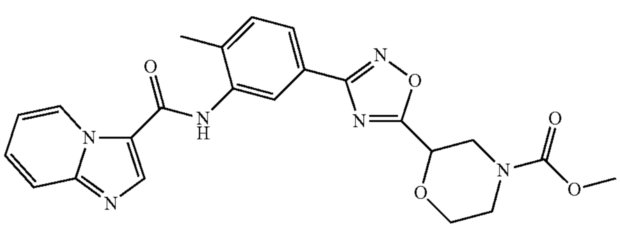 [SMILES: COC(=O)N1CCOC(c2nc(-c3ccc(C)c(NC(=O)c4cnc5ccccn45)c3)no2)C1] | ¹H NMR (400 MHz, d₆-DMSO) δ 10.13 (s, 1H), 9.50 (d, J = 6.9, 1H), 8.66 (s, 1H), 8.10 (s, 1H), 7.89-7.84 (m, 2H), 7.64 (d, J = 7.2, 1H), 7.52 (d, J = 8.1, 1H), 7.26 (t, J = 7.2, 1H), 5.01-5.11 (m, 1H), 3.94-4.19 (m, 6H), 3.65 (s, 3H), 2.37 (s, 3H). MS m/z 463.46 (M + 1)⁺. | 0.105 |
| F195 | 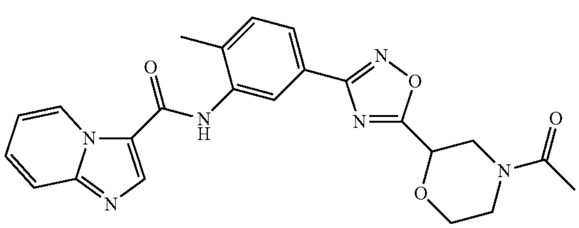 [SMILES: CC(=O)N1CCOC(c2nc(-c3ccc(C)c(NC(=O)c4cnc5ccccn45)c3)no2)C1] | ¹H NMR (400 MHz, d₆-DMSO) δ 10.12 (s, 1H), 9.57-9.44 (m, 1H), 8.66 (s, 1H), 8.11 (s, 1H), 7.85 (d, J = 9.0, 2H), 7.69-7.56 (m, 1H), 7.54-7.46 (m, 1H), 7.26 (s, 1H), 5.19-4.96 (m, 1H), 3.94-4.19 (m, 6H), 3.34-3.10 (m, 3H), 2.38 (s, 3H). MS m/z 447.46 (M + 1)⁺. | 0.566 |

TABLE 2-continued

| Cmpd No. | Structure | Physical Data | c-kit (Mo7e) μM |
|---|---|---|---|
| F196 | 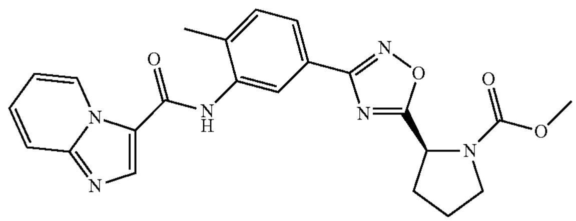 [SMILES: COC(=O)N1CCC[C@H]1c1nc(-c2ccc(C)c(NC(=O)c3cnc4ccccn34)c2)no1] | ¹H NMR (400 MHz, d₆-DMSO) δ 10.13 (s, 1H), 9.49 (d, J = 6.9, 1H), 8.64 (s, 1H), 8.04 (s, 1H), 7.83 (t, J = 7.6, 2H), 5.31-5.15 (m, 1H), 3.61 (s, 3H), 2.67 (s, 1H), 2.36 (s, 3H), 2.33 (s, 1H), 1.99 (br s, 3H). MS m/z 447.46 (M + 1)⁺. | 0.475 |
| F197 | 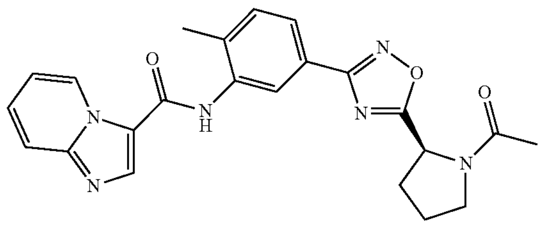 [SMILES: CC(=O)N1CCC[C@H]1c1nc(-c2ccc(C)c(NC(=O)c3cnc4ccccn34)c2)no1] | ¹H NMR (400 MHz, d₆-DMSO) δ 10.14 (s, 1H), 9.49 (d, J = 6.9, 1H), 8.65 (s, 1H), 8.03 (s, 1H), 7.89-7.84 (m, 2H), 7.69-7.57 (m, 1H), 7.50 (d, J = 8.1, 1H), 7.26 (s, 1H), 5.24-5.16 (m, 1H), 2.36 (s, 3H), 2.21-1.87 (m, 6H). MS m/z 431.46 (M + 1)⁺. | 0.46 |
| F198 | 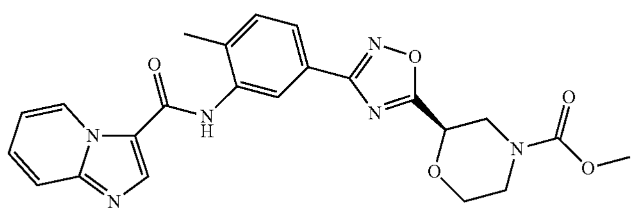 [SMILES: COC(=O)N1CCO[C@@H](c2nc(-c3ccc(C)c(NC(=O)c4cnc5ccccn45)c3)no2)C1] | ¹H NMR (400 MHz, d₆-DMSO) δ 10.13 (s, 1H), 9.50 (d, J = 6.9, 1H), 8.66 (s, 1H), 8.10 (s, 1H), 7.89-7.84 (m, 2H), 7.64 (d, J = 7.2, 1H), 7.52 (d, J = 8.1, 1H), 7.26 (t, J = 7.2, 1H), 5.01-5.11 (m,1H), 3.94-4.19 (m, 6H), 3.65 (s, 3H), 2.37 (s, 3H). MS m/z 463.46 (M + 1)⁺. | 0.142 |
| F199 | 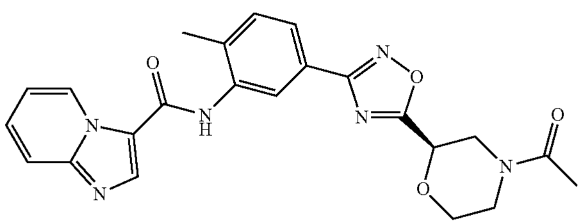 [SMILES: CC(=O)N1CCO[C@@H](c2nc(-c3ccc(C)c(NC(=O)c4cnc5ccccn45)c3)no2)C1] | ¹H NMR (400 MHz, d₆-DMSO) δ 10.12 (s, 1H), 9.57-9.44 (m, 1H), 8.66 (s, 1H), 8.11 (s, 1H), 7.85 (d, J = 9.0, 2H), 7.69-7.56 (m, 1H), 7.54-7.46 (m, 1H), 7.26 (s, 1H), 5.19-4.96 (m ,1H), 3.94-4.19 (m, 6H), 3.34-3.10 (m, 3H), 2.38 (s, 3H). MS m/z 447.46 (M + 1)⁺. | 0.509 |
| F200 | 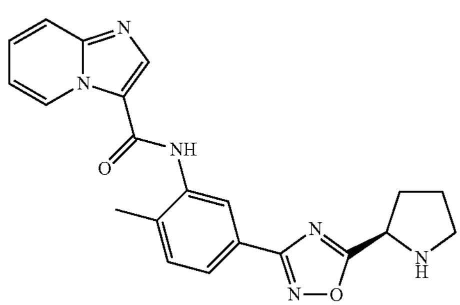 [SMILES: Cc1ccc(-c2noc([C@H]3CCCN3)n2)cc1NC(=O)c1cnc2ccccn12] | ¹H NMR (400 MHz, d₆-DMSO) δ 10.09 (s, 1H), 9.46 (d, J = 6.9, 2H), 8.65 (s, 1H), 8.13 (s, 1H), 7.85 (t, J = 9.1, 2H), 7.63-7.53 (m, 2H), 7.53 (s, 1H), 7.24 (s, 1H), 5.25-5.10 (m, 1H), 3.49-3.30 (m, 3H), 2.39 (s, 3H), 2.35-2.28 (m, 2H), 2.01-2.14 (m, 2H). MS m/z 389.42 (M + 1)⁺. | 0.395 |
| F201 | 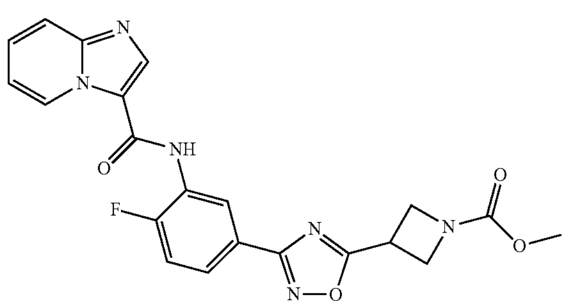 [SMILES: COC(=O)N1CC(c2nc(-c3ccc(F)c(NC(=O)c4cnc5ccccn45)c3)no2)C1] | MS m/z 437.2 (M + 1)⁺. | 0.443 |

TABLE 2-continued

| Cmpd No. | Structure | Physical Data | c-kit (Mo7e) μM |
|---|---|---|---|
| F202 | 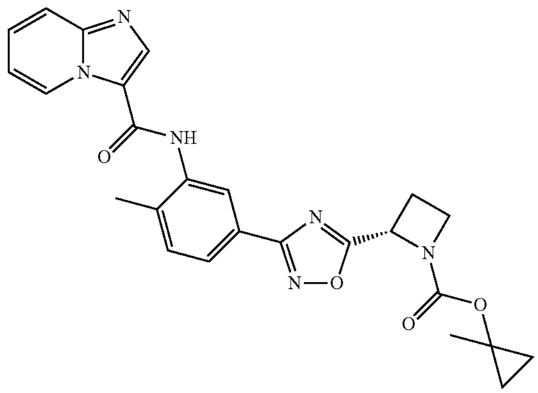 [SMILES: Cc1ccc(-c2noc([C@@H]3CCN3C(=O)OC3(C)CC3)n2)cc1NC(=O)c1cnc2ccccn12] | $^1$H NMR (400 MHz, d$_6$-DMSO) δ 10.17 (s, 1H), 9.51 (d, J = 6.9, 1H), 8.69 (s, 1H), 8.10 (s, 1H), 7.64-7.77 (m, 2H), 7.20-7.61 (m, 1H), 7.53 (d, J = 8.1, 1H), 7.29 (t, J = 6.9, 1H), 5.51-5.63 (m, 1H), 4.03 (s, 3H), 2.80-2.67 (m, 1H), 2.38 (s, 3H), 1.38 (s, 3H), 0.91-0.70 (m, 1H), 0.56 (s, 3H). MS m/z 473.50 (M + 1)$^+$. | 0.208 |
| F203 | 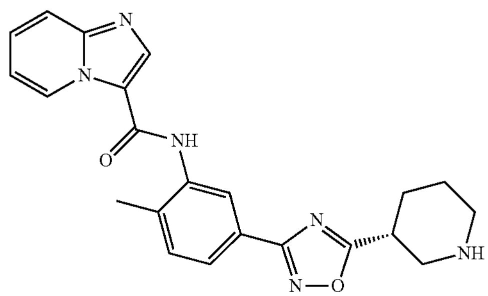 [SMILES: Cc1ccc(-c2noc([C@@H]3CCCNC3)n2)cc1NC(=O)c1cnc2ccccn12] | $^1$H NMR (400 MHz, d$_6$-DMSO) δ 10.11 (s, 1H), 9.48 (d, J = 7.0, 1H), 8.66 (s, 1H), 8.09 (d, J = 1.6, 1H), 7.86-7.80 (m, 2H), 7.64-7.58 (m, 1H), 7.52 (d, J = 8.1, 1H), 7.25 (t, J = 6.4, 1H), 3.61-3.74 (m, 1H), 3.51-3.58 (m, 1H), 3.29-3.38 (m, 2H), 2.37 (s, 3H), 1.81-1.92 (m, 4H). MS m/z 403.45 (M + 1)$^+$. | 0.826 |
| F204 | 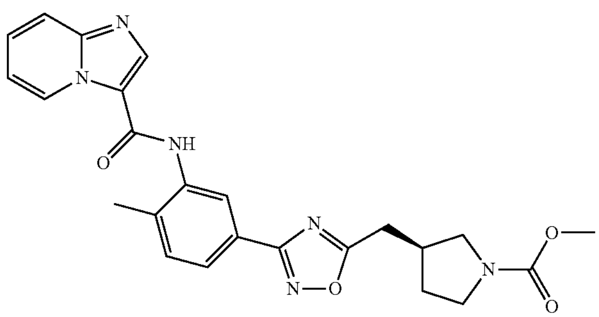 [SMILES: COC(=O)N1CC[C@@H](Cc2nc(-c3ccc(C)c(NC(=O)c4cnc5ccccn45)c3)no2)C1] | $^1$H NMR (400 MHz, d$_6$-DMSO) δ 10.22 (s, 1H), 9.53 (d, J = 6.9, 1H), 8.72 (s, 1H), 8.06 (s, 1H), 7.90 (d, J = 9.0, 1H), 7.83 (d, J = 7.9, 1H), 7.75-7.67 (m, 1H), 7.51 (d, J = 8.1, 1H), 7.34 (t, J = 6.9, 1H), 3.61-3.53 (m, 4H), 3.40-3.45 (m, 1H), 3.33-3.21 (m, 1H), 3.10-3.21 (m, 2H), 3.08 (t, J = 7.2, 1H), 2.76-2.59 (m, 1H), 2.37 (s, 3H), 2.07 (s, 1H), 1.69 (s, 1H). MS m/z 461.49 (M + 1)$^+$. | 0.2 |
| F205 | 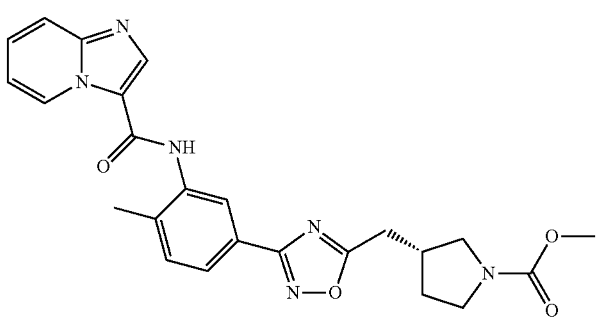 [SMILES: COC(=O)N1CC[C@H](Cc2nc(-c3ccc(C)c(NC(=O)c4cnc5ccccn45)c3)no2)C1] | $^1$H NMR (400 MHz, d$_6$-DMSO) δ 10.22 (s, 1H), 9.53 (d, J = 6.9, 1H), 8.72 (s, 1H), 8.06 (s, 1H), 7.90 (d, J = 9.0, 1H), 7.83 (d, J = 7.9, 1H), 7.75-7.67 (m, 1H), 7.51 (d, J = 8.1, 1H), 7.34 (t, J = 6.9, 1H), 3.61-3.53 (m, 4H), 3.40-3.45 (m, 1H), 3.33-3.21 (m, 1H), 3.10-3.21 (m, 2H), 3.08 (t, J = 7.2, 1H), 2.76-2.59 (m, 1H), 2.37 (s, 3H), 2.07 (s, 1H), 1.69 (s, 1H). MS m/z 461.49 (M + 1)$^+$. | 0.284 |

TABLE 2-continued

| Cmpd No. | Structure | Physical Data | c-kit (Mo7e) μM |
|---|---|---|---|
| F206 | 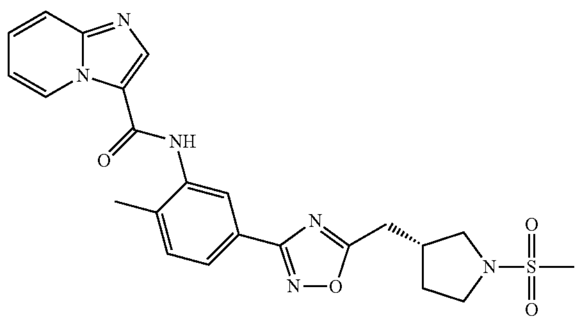 [SMILES: Cc1ccc(-c2noc(C[C@H]3CCN(S(C)(=O)=O)C3)n2)cc1NC(=O)c1cnc2ccccn12] | ¹H NMR (400 MHz, d₆-DMSO) δ 10.21 (s, 1H), 9.52 (d, J = 7.0, 1H), 8.72 (s, 1H), 8.07 (d, J = 1.7, 1H), 7.90 (d, J = 9.0, 1H), 7.84 (dd, J = 1.7, 7.9, 1H), 7.74-7.66 (m, 1H), 7.51 (d, J = 8.1, 1H), 7.33 (t, J = 6.9, 1H), 3.51-3.54 (m, 1H), 3.41-3.33 (m, 1H), 3.30-3.21 (m, 1H), 3.11-3.19 (m, 2H), 3.00-3.08 (m, J = 8.0, 10.0, 1H), 2.91 (s, 3H), 2.70-2.81 (m, 1H), 2.37 (s, 3H), 2.11-2.21 (m, 1H), 1.62-1.74 (m, 1H). MS m/z 481.54 (M + 1)⁺. | 0.169 |
| F207 | 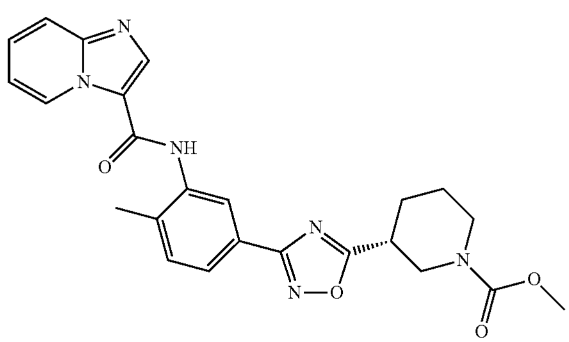 [SMILES: COC(=O)N1CCC[C@@H](c2nc(-c3ccc(C)c(NC(=O)c4cnc5ccccn45)c3)no2)C1] | ¹H NMR (400 MHz, d₆-DMSO) δ 10.17 (s, 1H), 9.51 (d, J = 6.9, 1H), 8.69 (s, 1H), 8.06 (s, 1H), 7.86-7.80 (m, 2H), 7.66 (s, 1H), 7.51 (d, J = 8.1, 1H), 7.29 (s, 1H), 3.81-3.71 (m, 2H), 3.59 (s, 3H), 3.36-3.23 (m, 2H), 3.12-3.03 (m, 1H), 2.36 (s, 3H), 2.25-2.15 (m, 1H), 1.94-1.80 (m, 1H), 1.79-1.69 (m, 1H), 1.59-1.43 (m, 1H). MS m/z 461.49 (M + 1)⁺. | 0.141 |
| F208 | 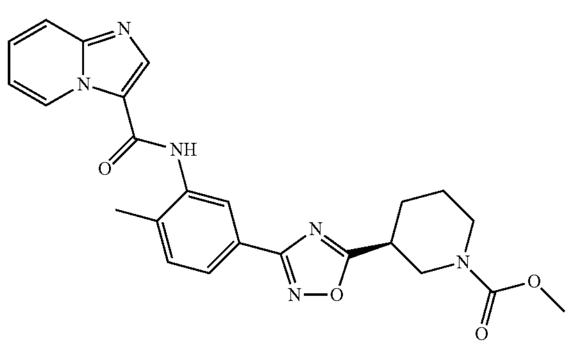 [SMILES: COC(=O)N1CCC[C@H](c2nc(-c3ccc(C)c(NC(=O)c4cnc5ccccn45)c3)no2)C1] | ¹H NMR (400 MHz, d₆-DMSO) δ 10.17 (s, 1H), 9.51 (d, J = 6.9, 1H), 8.69 (s, 1H), 8.06 (s, 1H), 7.86-7.80 (m, 2H), 7.66 (s, 1H), 7.51 (d, J = 8.1, 1H), 7.29 (s, 1H), 3.81-3.71 (m, 2H), 3.59 (s, 3H), 3.36-3.23 (m, 2H), 3.12-3.03 (m, 1H), 2.36 (s, 3H), 2.25-2.15 (m, 1H), 1.94-1.80 (m, 1H), 1.79-1.69 (m, 1H), 1.59-1.43 (m, 1H). MS m/z 461.49 (M + 1)⁺. | 0.134 |
| F209 | 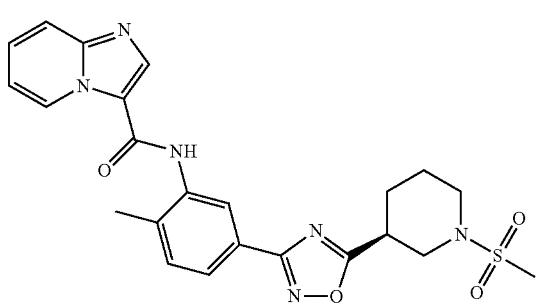 [SMILES: Cc1ccc(-c2noc([C@H]3CCCN(S(C)(=O)=O)C3)n2)cc1NC(=O)c1cnc2ccccn12] | ¹H NMR (400 MHz, d₆-DMSO) δ 10.20 (s, 1H), 9.52 (dd, J = 3.5, 4.5, 1H), 8.71 (s, 1H), 8.07 (d, J = 1.7, 1H), 7.92-7.81 (m, 2H), 7.73-7.66 (m, 1H), 7.51 (d, J = 8.1, 1H), 7.32 (dd, J = 5.9, 6.9, 1H), 3.84 (d, J = 11.7, 1H), 3.49-3.41 (m, 2H), 3.18-3.29 (m, 1H), 2.96-2.86 (m, 3H), 2.37 (s, 3H), 2.23-2.13 (m, 1H), 1.70-1.94 (m, 3H). MS m/z 481.54 (M + 1)⁺. | 0.148 |

TABLE 2-continued

| Cmpd No. | Structure | Physical Data | c-kit (Mo7e) μM |
|---|---|---|---|
| F210 | 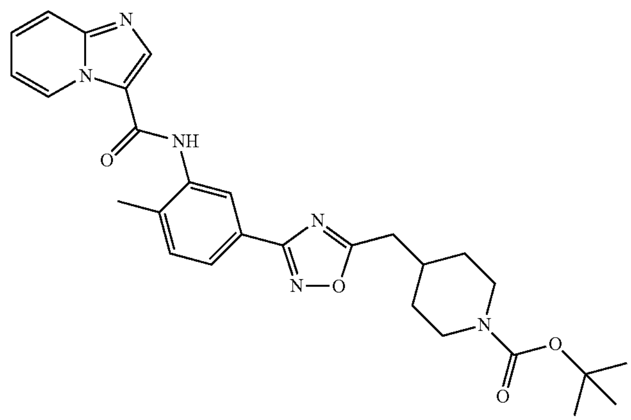 [SMILES: Cc1ccc(-c2noc(CC3CCN(C(=O)OC(C)(C)C)CC3)n2)cc1NC(=O)c1cnc2ccccn12] | $^1$H NMR (400 MHz, d$_6$-DMSO) δ 10.13 (s, 1H), 9.46 (d, J = 7.0, 1H), 8.65 (s, 1H), 7.99 (d, J = 1.7, 1H), 7.83 (d, J = 9.0, 1H), 7.76 (dd, J = 1.7, 7.9, 1H), 7.66-7.60 (m, 1H), 7.44 (d, J = 8.1, 1H), 7.26 (t, J = 6.9, 1H), 3.84 (s, 2H), 2.91 (d, J = 7.0, 2H), 2.63 (s, 2H), 2.30 (s, 3H), 1.88-2.01 (m, 1H), 1.61 (d, J = 11.1, 2H), 1.31 (s, 9H), 1.02-1.15 (m, 2H). MS m/z 517.59 (M + 1)$^+$. | 0.71 |
| F211 | 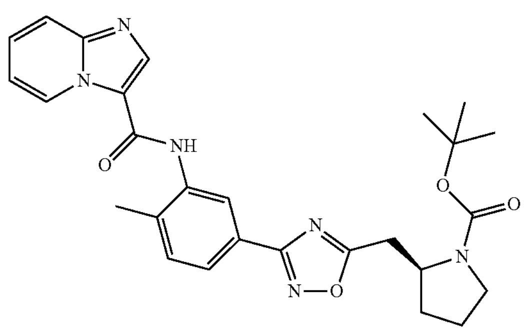 [SMILES: Cc1ccc(-c2noc(C[C@@H]3CCCN3C(=O)OC(C)(C)C)n2)cc1NC(=O)c1cnc2ccccn12] | $^1$H NMR (400 MHz, d$_6$-DMSO) δ 10.21 (s, 1H), 9.53 (d, J = 6.9, 1H), 8.73 (s, 1H), 8.07 (s, 1H), 7.90 (d, J = 9.1, 1H), 7.83 (d, J = 7.8, 1H), 7.75-7.68 (m, 1H), 7.50 (d, J = 8.0, 1H), 7.33 (t, J = 6.6, 1H), 4.16 (br s, 1H), 3.33-3.11 (m, 4H), 2.37 (s, 3H), 2.01 br (s, 1H), 1.81 (br s, 3H), 1.33 (s, 9H). MS m/z 503.56 (M + 1)$^+$. | 0.106 |
| F212 | 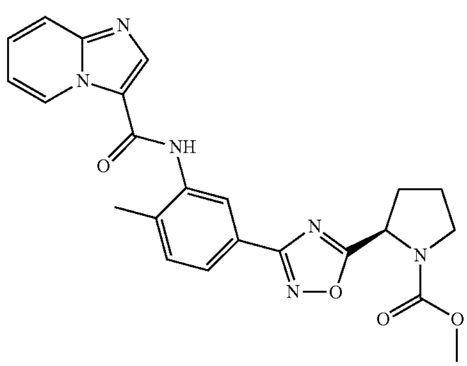 [SMILES: COC(=O)N1CCC[C@@H]1c1nc(-c2ccc(C)c(NC(=O)c3cnc4ccccn34)c2)no1] | $^1$H NMR (400 MHz, d$_6$-DMSO) δ 10.16 (s, 1H), 9.50 (d, J = 6.9, 1H), 8.67 (s, 1H), 8.03 (s, 1H), 7.91-7.83 (m, 2H), 7.66-7.56 (m, 1H), 7.50 (d, J = 8.1, 1H), 7.28 (s, 1H), 5.26-5.19 (m, 1H), 3.65-3.89 (m, 5H), 2.36 (s, 4H), 2.03 (s, 3H), 1.81-1.85 (m, 1H). MS m/z 447.46 (M + 1)$^+$. | 0.17 |
| F213 | 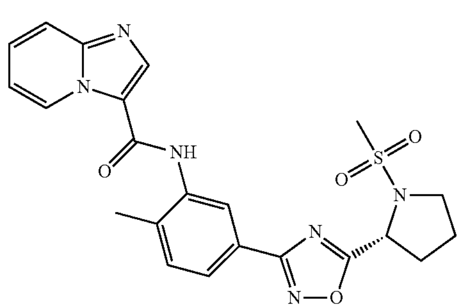 [SMILES: Cc1ccc(-c2noc([C@H]3CCCN3S(C)(=O)=O)n2)cc1NC(=O)c1cnc2ccccn12] | $^1$H NMR (400 MHz, d$_6$-DMSO) δ 10.10 (s, 1H), 9.48 (d, J = 6.9, 1H), 8.63 (s, 1H), 8.07 (d, J = 1.7, 1H), 7.93-7.79 (m, 2H), 7.64-7.46 (m, 2H), 7.22 (t, J = 6.9, 1H), 5.21-5.42 (m, 1H), 3.08 (s, 3H), 2.38 (s, 3H), 2.21-1.96 (m, 3H), 1.25 (q, J = 6.7, 4H). MS m/z 467.51 (M + 1)$^+$. | 0.137 |

TABLE 2-continued
| Cmpd No. | Structure | Physical Data | c-kit (Mo7e) μM |
|---|---|---|---|
| F214 | 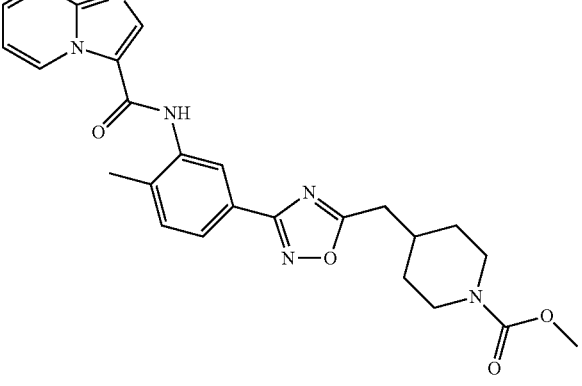 | ¹H NMR (400 MHz, d₆-DMSO) δ 10.19 (s, 1H), 9.52 (d, J = 7.0, 1H), 8.70 (s, 1H), 8.06 (d, J = 1.7, 1H), 7.94-7.77 (m, 2H), 7.72-7.66 (m, 1H), 7.50 (d, J = 8.1, 1H), 7.32 (t, J = 6.4, 1H), 3.95 (br s, 2H), 3.57 (s, 3H), 2.98 (d, J = 7.1, 2H), 2.81 (s, 2H), 2.36 (s, 3H), 2.06 (br s, 1H), 1.70 (d, J = 12.1, 2H), 1.19 (q, J = 12.1, 2H). MS m/z 475.51 (M + 1)⁺. | 0.142 |
| F215 | 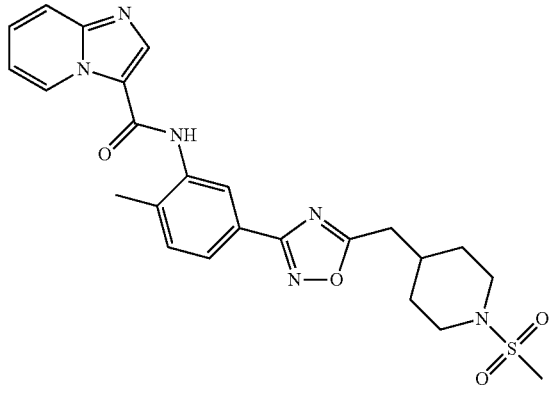 [SMILES: Cc1ccc(-c2noc(CC3CCN(S(C)(=O)=O)CC3)n2)cc1NC(=O)c1cnc2ccccn12] | ¹H NMR (400 MHz, d₆-DMSO) δ 10.17 (s, 1H), 9.51 (d, J = 6.9, 1H), 8.69 (s, 1H), 8.06 (d, J = 1.7, 1H), 7.88 (d, J = 9.0, 1H), 7.83 (dd, J = 1.7, 7.9, 1H), 7.70-7.64 (m, 1H), 7.51 (d, J = 8.1, 1H), 7.31 (t, J = 6.5, 1H), 3.55 (d, J = 11.9, 2H), 3.03 (d, J = 7.1, 2H), 2.84 (s, 3H), 2.45-2.59 (m, 2H), 2.37 (s, 3H), 2.00 (br s, 1H), 1.81 (d, J = 10.9, 2H), 1.29 (q, J = 10.9, 2H). MS m/z 495.57 (M + 1)⁺. | 0.175 |
| F216 | 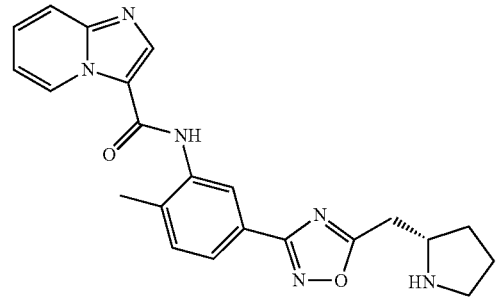 [SMILES: Cc1ccc(-c2noc(C[C@@H]3CCCN3)n2)cc1NC(=O)c1cnc2ccccn12] | MS m/z 403.45 (M + 1)⁺. | 0.519 |
| F217 | 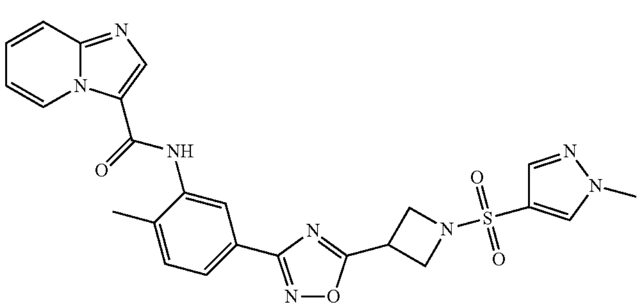 [SMILES: Cc1ccc(-c2noc(C3CN(S(=O)(=O)c4cnn(C)c4)C3)n2)cc1NC(=O)c1cnc2ccccn12] | MS m/z 519.2 (M + 1)⁺. | 0.173 |

TABLE 2-continued

| Cmpd No. | Structure | Physical Data | c-kit (Mo7e) μM |
|---|---|---|---|
| F218 | 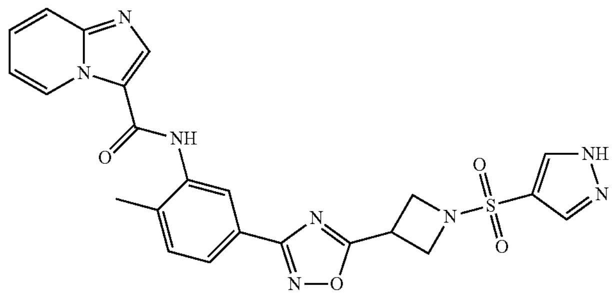 [SMILES: Cc1ccc(-c2noc(C3CN(S(=O)(=O)c4cn[nH]c4)C3)n2)cc1NC(=O)c1cnc2ccccn12] | MS m/z 505.1 (M + 1)+. | 0.155 |
| F219 | 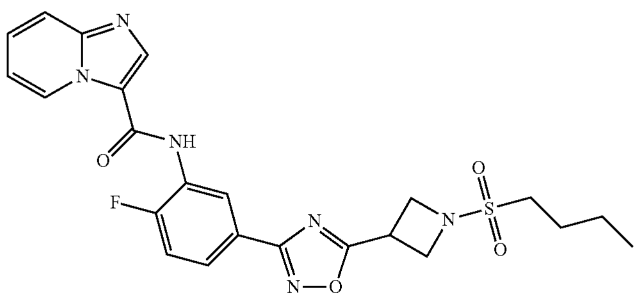 [SMILES: CCCCS(=O)(=O)N1CC(c2nc(-c3ccc(F)c(NC(=O)c4cnc5ccccn45)c3)no2)C1] | MS m/z 499.2 (M + 1)+. | 0.158 |
| F220 | 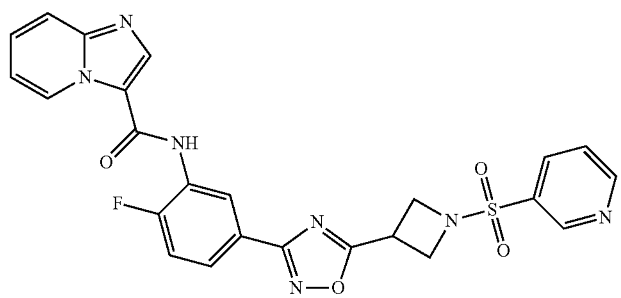 [SMILES: O=C(Nc1cc(-c2noc(C3CN(S(=O)(=O)c4cccnc4)C3)n2)ccc1F)c1cnc2ccccn12] | MS m/z 520.2 (M + 1)+. | 0.69 |
| F221 | 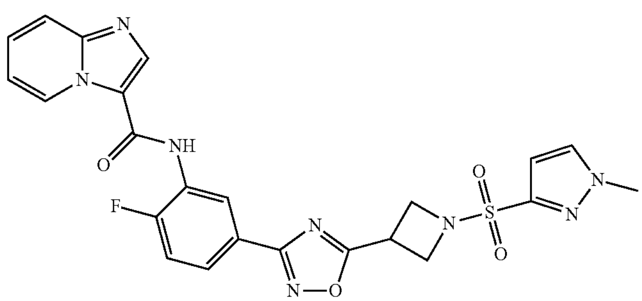 [SMILES: Cn1ccc(S(=O)(=O)N2CC(c3nc(-c4ccc(F)c(NC(=O)c5cnc6ccccn56)c4)no3)C2)n1] | MS m/z 523.0 (M + 1)+. | 0.851 |
| F222 | 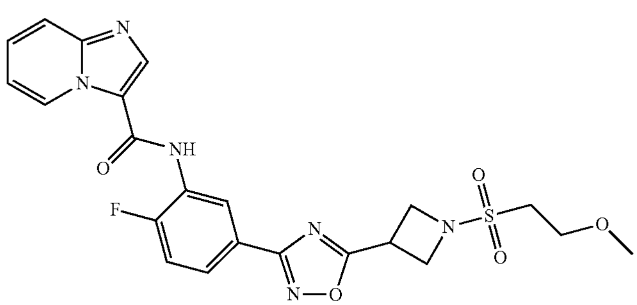 [SMILES: COCCS(=O)(=O)N1CC(c2nc(-c3ccc(F)c(NC(=O)c4cnc5ccccn45)c3)no2)C1] | MS m/z 501.0 (M + 1)+. | 0.376 |

TABLE 2-continued

| Cmpd No. | Structure | Physical Data | c-kit (Mo7e) μM |
|---|---|---|---|
| F223 | 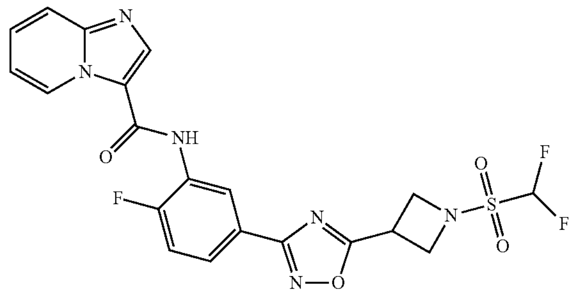 [SMILES: O=C(Nc1cc(-c2noc(C3CN(S(=O)(=O)C(F)F)C3)n2)ccc1F)c1cnc2ccccn12] | MS m/z 493.1 (M + 1)+. | 0.151 |
| F224 | 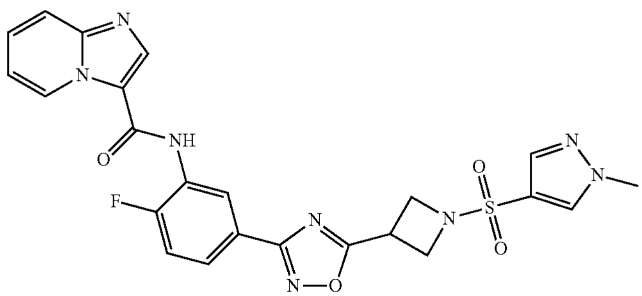 [SMILES: Cn1cc(S(=O)(=O)N2CC(c3nc(-c4ccc(F)c(NC(=O)c5cnc6ccccn56)c4)no3)C2)cn1] | MS m/z 523.2 (M + 1)+. | 0.854 |
| F225 | 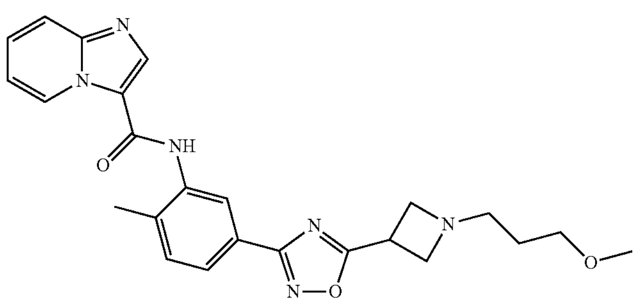 [SMILES: COCCCN1CC(c2nc(-c3ccc(C)c(NC(=O)c4cnc5ccccn45)c3)no2)C1] | 1H NMR (400 MHz, d6-DMSO) δ 10.18 (s, 1H), 9.52 (d, J = 6.9, 1H), 8.70 (s, 1H), 8.06 (s, 1H), 7.92-7.76 (m, 2H), 7.72-7.64 (m, 1H), 7.51 (d, J = 8.1, 1H), 7.31 (t, J = 6.9, 1H), 4.44-4.69 (m, 7H), 3.27-3.38 (m, 4H), 3.23 (s, 3H), 2.38 (s, 3H), 1.70-1.80 (m, 2H). MS m/z 447.50 (M + 1)+. | 0.239 |
| F226 | 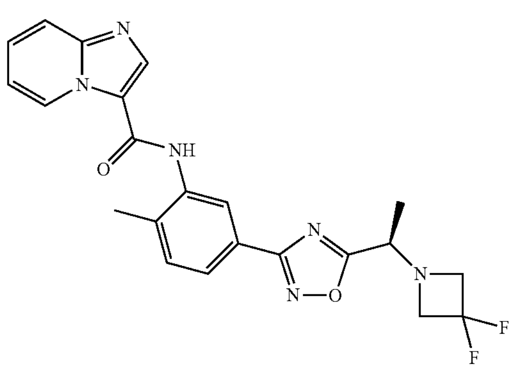 [SMILES: Cc1ccc(-c2noc([C@@H](C)N3CC(F)(F)C3)n2)cc1NC(=O)c1cnc2ccccn12] | MS m/z 439.2 (M + 1)+. | 0.112 |

| Cmpd No. | Structure | Physical Data | c-kit (Mo7e) μM |
|---|---|---|---|
| F227 | 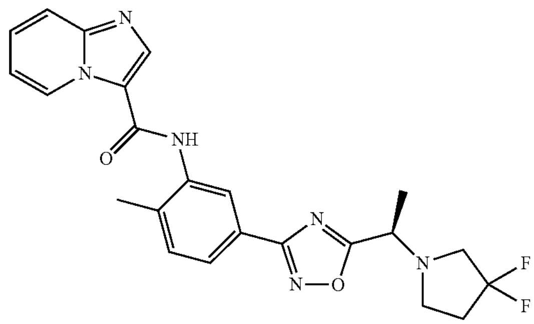 [SMILES: Cc1ccc(-c2noc([C@@H](C)N3CCC(F)(F)C3)n2)cc1NC(=O)c1cnc2ccccn12] | ¹H NMR (400 MHz, CDCl₃) δ 9.47 (d, J = 7.2 Hz, 1H), 8.49 (s, 1H), 8.13 (s, 1H), 7.81 (dd, J = 2.0, 8.0 Hz, 1H), 7.69 (m, 1H), 7.49 (s, 1H), 7.38 (m, 1H), 7.32 (d, J = 8.0 Hz, 1H), 6.99 (m, 1H), 4.14 (q, J = 6.8 Hz, 1H), 3.06 (t, J = 13.2 Hz, 2H), 2.85 (m, 2H), 2.37 (s, 3H), 2.22 (m, 2H), 1.54 (d, J = 6.8 Hz, 3H).<br>MS m/z 453.0 (M + 1)⁺. | 0.119 |
| F228 | 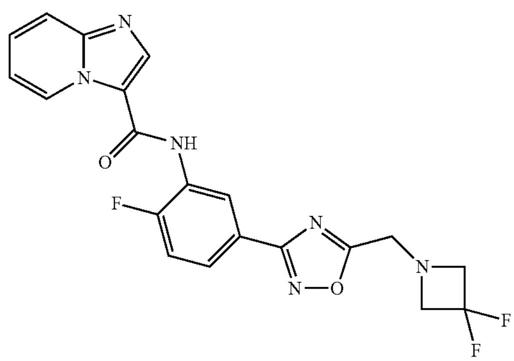 [SMILES: O=C(Nc1cc(-c2noc(CN3CC(F)(F)C3)n2)ccc1F)c1cnc2ccccn12] | MS m/z 429.1 (M + 1)⁺. | 0.341 |
| F229 | 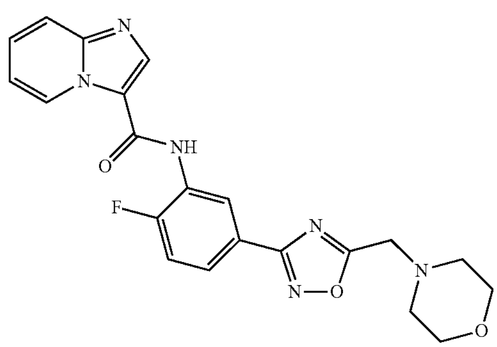 [SMILES: O=C(Nc1cc(-c2noc(CN3CCOCC3)n2)ccc1F)c1cnc2ccccn12] | MS m/z 423.1 (M + 1)⁺. | 0.245 |
| F230 | 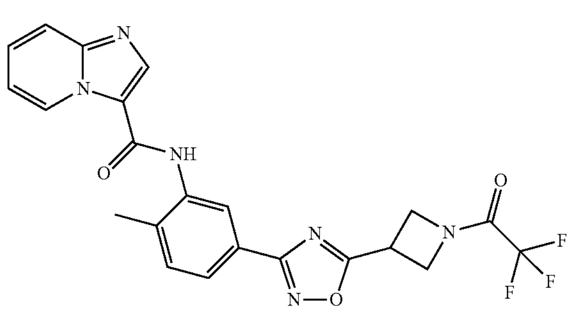 [SMILES: Cc1ccc(-c2noc(C3CN(C(=O)C(F)(F)F)C3)n2)cc1NC(=O)c1cnc2ccccn12] | MS m/z 471.2 (M + 1)⁺. | 0.217 |

TABLE 2-continued

| Cmpd No. | Structure | Physical Data | c-kit (Mo7e) μM |
|---|---|---|---|
| F231 | 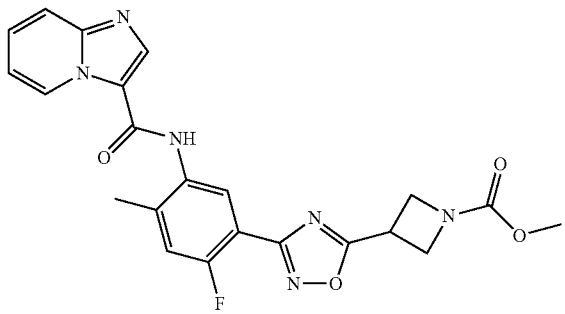 [SMILES: COC(=O)N1CC(c2nc(-c3cc(NC(=O)c4cnc5ccccn45)c(C)cc3F)no2)C1] | MS m/z 451.1 (M + 1)+. | 0.439 |
| F232 | 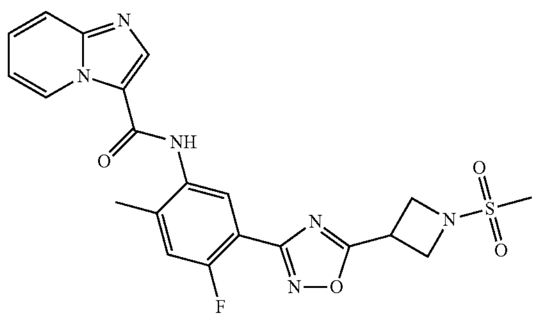 [SMILES: Cc1cc(F)c(-c2noc(C3CN(S(C)(=O)=O)C3)n2)cc1NC(=O)c1cnc2ccccn12] | MS m/z 471.1 (M + 1)+. | 0.489 |
| F233 | 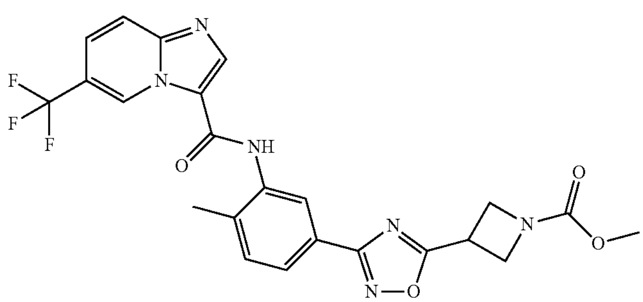 [SMILES: COC(=O)N1CC(c2nc(-c3ccc(C)c(NC(=O)c4cnc5ccc(C(F)(F)F)cn45)c3)no2)C1] | 1H NMR (400 MHz, d6-DMSO) δ 10.27 (s, 1H), 9.88 (s, 1H), 8.72 (s, 1H), 8.08 (d, J = 1.6, 1H), 8.01 (d, J = 9.5, 1H), 7.86 (dd, J = 1.7, 7.9, 1H), 7.79 (dd, J = 1.9, 9.5, 1H), 7.52 (d, J = 8.1, 1H), 4.39-4.10 (m, 6H), 3.59 (s, 3H), 2.37 (s, 3H). MS m/z 501.43 (M + 1)+. | 0.218 |
| F234 | 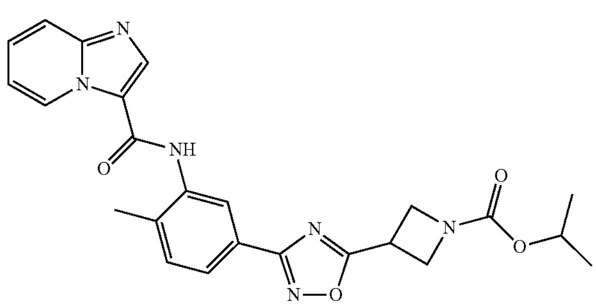 [SMILES: Cc1ccc(-c2noc(C3CN(C(=O)OC(C)C)C3)n2)cc1NC(=O)c1cnc2ccccn12] | 1H NMR (400 MHz, d6-DMSO) δ 10.17 (s, 1H), 9.52 (d, J = 7.0, 1H), 8.69 (s, 1H), 8.10 (d, J = 1.6, 1H), 7.86 (dd, J = 5.8, 13.8, 2H), 7.71-7.64 (m, 1H), 7.52 (d, J = 8.1, 1H), 7.30 (t, J = 6.9, 1H), 4.77 (dt, J = 6.3, 12.5, 1H), 4.35 (s, 2H), 4.26 (dd, J = 5.3, 8.6, 2H), 4.16 (s, 2H), 2.37 (s, 3H), 1.18 (d, J = 6.3, 6H). MS m/z 461.49 (M + 1)+. | 0.245 |

TABLE 2-continued

| Cmpd No. | Structure | Physical Data | c-kit (Mo7e) μM |
|---|---|---|---|
| F235 | 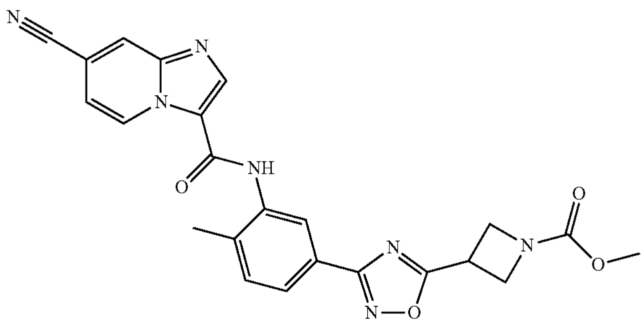 [SMILES: COC(=O)N1CC(c2nc(-c3ccc(C)c(NC(=O)c4cnc5cc(C#N)ccn45)c3)no2)C1] | MS m/z 458.1 (M + 1)+. | 0.181 |
| F236 | 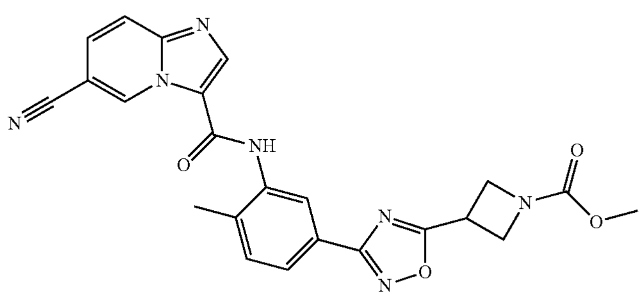 [SMILES: COC(=O)N1CC(c2nc(-c3ccc(C)c(NC(=O)c4cnc5ccc(C#N)cn45)c3)no2)C1] | MS m/z 457.9 (M + 1)+. | 0.103 |
| F237 | 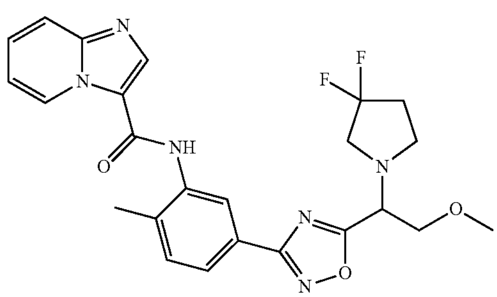 [SMILES: COCC(c1nc(-c2ccc(C)c(NC(=O)c3cnc4ccccn34)c2)no1)N1CCC(F)(F)C1] | MS m/z 483.2 (M + 1)+. | 0.109 |
| F238 | 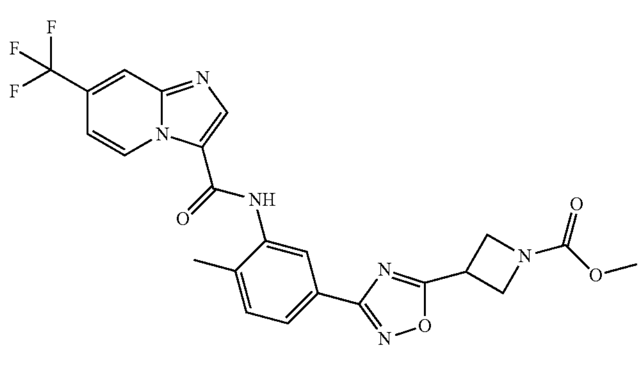 [SMILES: COC(=O)N1CC(c2nc(-c3ccc(C)c(NC(=O)c4cnc5cc(C(F)(F)F)ccn45)c3)no2)C1] | $^1$H NMR (400 MHz, d$_6$-DMSO) δ 10.25 (s, 1H), 9.64-9.61 (m, 1H), 9.75 (s, 1H), 8.33-8.30 (m, 1H), 8.10 (dd, J = 1.6 Hz, 1H), 7.86 (dd, J = 1.6, 8.0 Hz, 1H), 7.52 (d, J = 8.4 Hz, 1H), 7.46 (dd, J = 2.0, 7.6 Hz, 1H), 4.40-4.33 (m, 2H), 4.31-4.25 (m, 1H), 4.22-4.18 (m, 2H), 3.59 (s, 3H), 2.38 (s, 3H). MS m/z 501.43 (M + 1)+. | 0.13 |

TABLE 2-continued

| Cmpd No. | Structure | Physical Data | c-kit (Mo7e) μM |
|---|---|---|---|
| F239 | 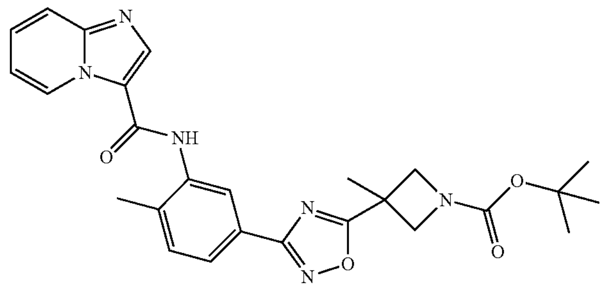 [SMILES: Cc1ccc(-c2noc(C3(C)CN(C(=O)OC(C)(C)C)C3)n2)cc1NC(=O)c1cnc2ccccn12] | $^1$H NMR (400 MHz, d$_6$-DMSO) δ 10.06 (s, 1H), 9.45 (td, J = 1.2, 6.0 Hz, 1H), 8.60 (s, 1H), 8.08 (d, J = 1.6 Hz, 1H), 7.85 (dd, J = 1.6, 8.0 Hz, 1H), 7.80 (dt, J = 8.8, 1.2, 1H), 7.53 (m, 2H), 7.18 (dt, J = 1.2, 8.0 Hz, 1H), 4.28 (d, J = 6.4 Hz, 2H), 3.93 (d, J = 8.0 Hz, 2H), 2.37 (s, 3H), 1.76 (s, 3H), 1.41 (s, 9H).<br>MS m/z 489.2 (M + 1)$^+$. | 0.831 |
| F240 | 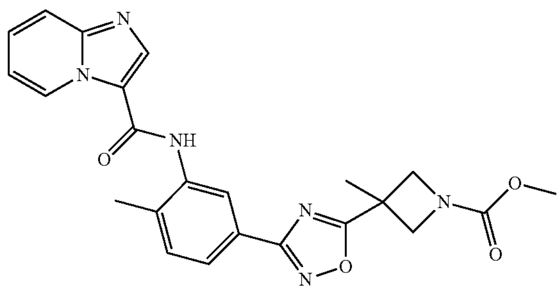 [SMILES: COC(=O)N1CC(C)(c2nc(-c3ccc(C)c(NC(=O)c4cnc5ccccn45)c3)no2)C1] | MS m/z 447.1 (M + 1)$^+$. | 0.249 |
| F241 | 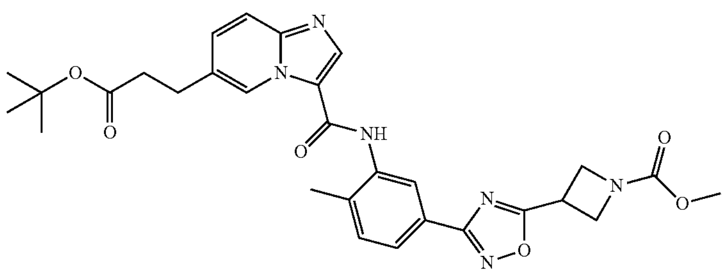 [SMILES: COC(=O)N1CC(c2nc(-c3ccc(C)c(NC(=O)c4cnc5ccc(CCC(=O)OC(C)(C)C)cn45)c3)no2)C1] | $^1$H NMR (400 MHz, d$_6$-DMSO) δ 10.10 (s, 1H), 9.36 (s, 1H), 8.63 (s, 1H), 8.10 (d, J = 1.6 Hz, 1H), 7.85 (dd, J = 1.6, 8.0 Hz, 1H), 7.79 (d, J = 9.6 Hz, 1H), 7.58 (dd, J = 0.8, 9.2 Hz, 1H), 7.51 (d, J = 8.0 Hz, 1H), 4.38-4.33 (m, 2H), 4.31-4.25 (m, 1H), 4.21-4.18 (m, 2H), 3.59 (s, 3H), 2.92 (t, J = 7.2 Hz, 2H), 2.61 (t, J = 7.2 Hz, 2H), 2.37 (s, 3H), 1.34 (s, 9H).<br>MS m/z 561.24 (M + 1)$^+$. | 0.115 |
| F242 | 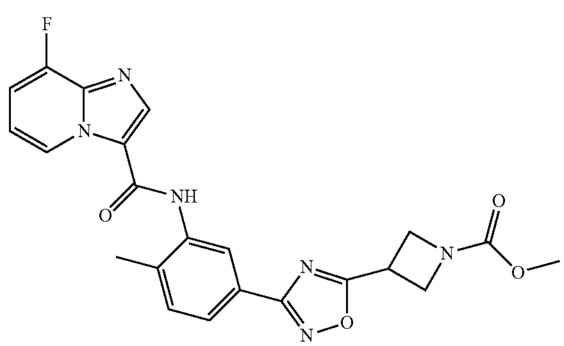 [SMILES: COC(=O)N1CC(c2nc(-c3ccc(C)c(NC(=O)c4cnc5c(F)cccn45)c3)no2)C1] | $^1$H NMR (400 MHz, d$_6$-DMSO) δ 10.18 (s, 1H), 9.29 (dd, J = 0.8, 7.2 Hz, 1H), 8.61 (s, 1H), 8.09 (d, J = 1.6 Hz, 1H), 7.85 (dd, J = 2.0, 8.0 Hz, 1H), 7.51 (d, J = 8.0 Hz, 1H), 7.48-7.43 (m, 1H), 4.38-4.36 (m, 2H), 4.31-4.24 (m, 1H), 4.22-4.18 (m, 2H), 3.59 (s, 3H), 2.37 (s, 3H).<br>MS m/z 451.15 (M + 1)$^+$. | 0.812 |
| F243 | 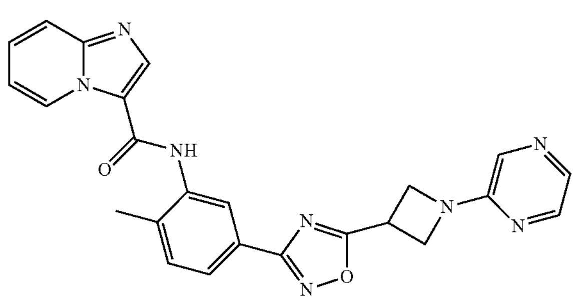 [SMILES: Cc1ccc(-c2noc(C3CN(c4cnccn4)C3)n2)cc1NC(=O)c1cnc2ccccn12] | $^1$H NMR (400 MHz, d$_6$-DMSO) δ 10.11 (s, 1H), 9.50-9.47 (m, 1H), 8.65 (s, 1H), 8.10-8.09 (m, 2H), 8.00 (d, J = 1.2 Hz, 1H), 7.92 (d, J = 2.8 Hz, 1H), 7.86-7.82 (m, 2H), 7.63-7.59 (m, 1H), 7.51 (d, J = 8.4 Hz, 1H), 7.27-7.23 (m, 1H), 4.54-4.44 (m, 3H), 4.36-4.33 (m, 2H), 2.37 (s, 3H).<br>MS m/z 453.17 (M + 1)$^+$. | 0.31 |

TABLE 2-continued

| Cmpd No. | Structure | Physical Data | c-kit (Mo7e) μM |
|---|---|---|---|
| F244 | 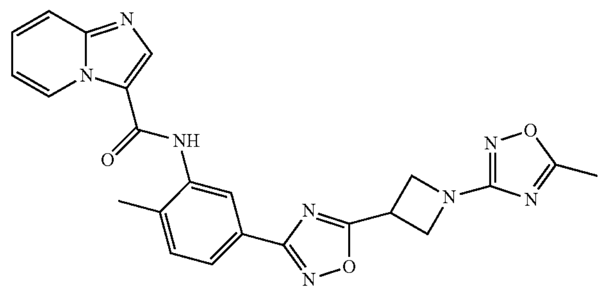 [SMILES: Cc1nc(N2CC(c3nc(-c4ccc(C)c(NC(=O)c5cnc6ccccn56)c4)no3)C2)no1] | ¹H NMR (400 MHz, d₆-DMSO) δ 10.16 (s, 1H), 9.52-9.49 (m, 1H), 8.68 (s, 1H), 8.10 (d, J = 1.6 Hz, 1H), 7.88-7.84 (m, 2H), 7.68-7.63 (m, 1H), 7.51 (d, J = 8.0 Hz, 1H), 7.30-7.27 (m, 1H), 4.48-4.41 (m, 3H), 4.27-4.24 (m, 2H), 2.46 (s, 3H), 2.37 (s, 3H). MS m/z 457.17 (M + 1)⁺. | 0.176 |
| F245 | 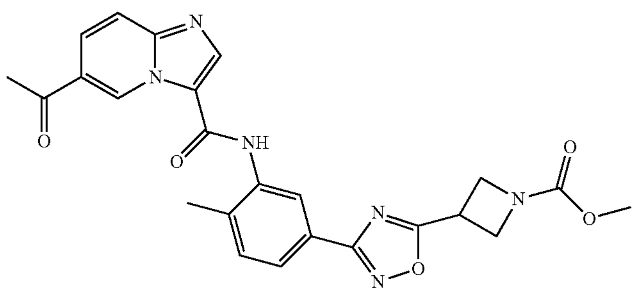 [SMILES: COC(=O)N1CC(c2nc(-c3ccc(C)c(NC(=O)c4cnc5ccc(C(C)=O)cn45)c3)no2)C1] | ¹H NMR (400 MHz, d₆-DMSO) δ 10.23 (s, 1H), 10.13-10.12 (m, 1H), 8.70 (s, 1H), 8.10 (d, J = 2.0 Hz, 1H), 7.95 (dd, J = 1.6, 9.2 Hz, 1H), 7.87-7.85 (m, 2H), 7.52 (d, J = 8.0 Hz, 1H), 4.39-4.33 (m, 2H), 4.31-4.25 (m, 1H), 4.22-4.18 (m, 2H), 3.59 (s, 3H), 2.64 (s, 3H), 2.38 (s, 3H). MS m/z 474.17 (M + 1)⁺. | 0.178 |
| F246 | 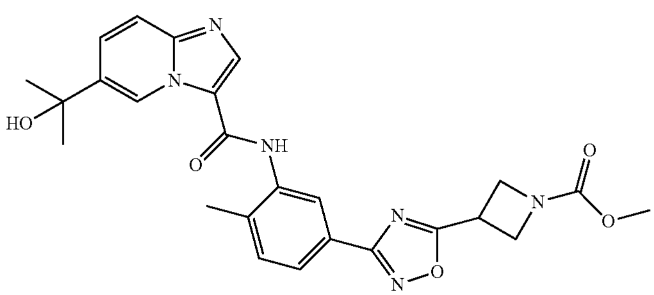 [SMILES: COC(=O)N1CC(c2nc(-c3ccc(C)c(NC(=O)c4cnc5ccc(C(C)(C)O)cn45)c3)no2)C1] | ¹H NMR (400 MHz, d₆-DMSO) δ 10.14 (s, 1H), 9.61 (s, 1H), 8.67 (s, 1H), 8.09 (d, J = 1.6 Hz, 1H), 7.85 (dd, J = 1.6, 7.6 Hz, 1H), 7.82-7.75 (m, 2H), 7.51 (d, J = 8.0 Hz, 1H), 4.39-4.33 (m, 2H), 4.31-4.25 (m, 1H), 4.22-4.18 (m, 2H), 3.59 (s, 3H), 2.37 (s, 3H), 1.50 (s, 6H). MS m/z 490.20 (M + 1)⁺. | 0.317 |
| F247 | 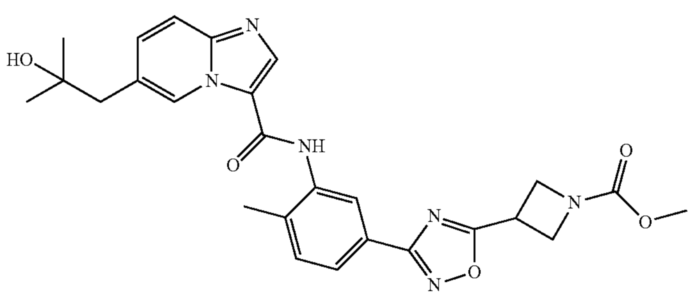 [SMILES: COC(=O)N1CC(c2nc(-c3ccc(C)c(NC(=O)c4cnc5ccc(CC(C)(C)O)cn45)c3)no2)C1] | MS m/z 505.1 (M + 1)⁺. | 0.328 |
| F248 | 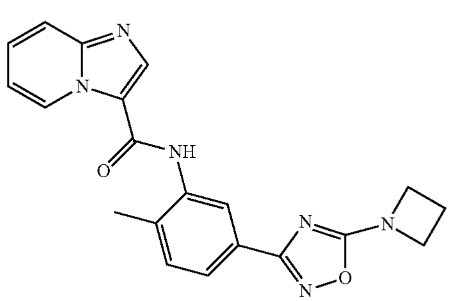 [SMILES: Cc1ccc(-c2noc(N3CCC3)n2)cc1NC(=O)c1cnc2ccccn12] | ¹H NMR (400 MHz, d₆-DMSO) δ 10.10 (s, 1H), 9.51-9.48 (m, 1H), 8.65 (s, 1H), 7.94 (d, J = 1.6 Hz, 1H), 7.86-7.83 (m, 1H), 7.71 (dd, J = 1.6, 7.6 Hz, 1H), 7.64-7.60 (m, 1H), 7.43 (d, J = 8.0 Hz, 1H), 7.27-7.24 (m, 1H), 4.26-4.22 (m, 4H), 2.48-2.40 (m, 2H), 2.34 (s, 3H). MS m/z 374.15 (M + 1)⁺. | 0.132 |

TABLE 2-continued

| Cmpd No. | Structure | Physical Data | c-kit (Mo7e) μM |
|---|---|---|---|
| F249 | 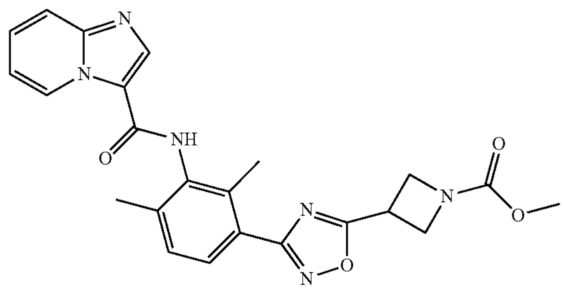 [SMILES: COC(=O)N1CC(c2nc(-c3ccc(C)c(NC(=O)c4cnc5ccccn45)c3C)no2)C1] | MS m/z 447.1 (M + 1)+. | 0.426 |
| F250 | 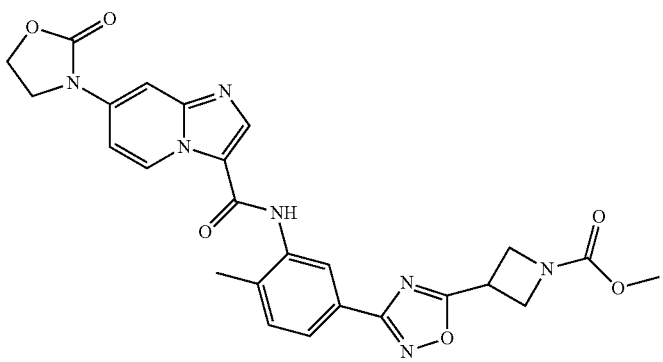 [SMILES: COC(=O)N1CC(c2nc(-c3ccc(C)c(NC(=O)c4cnc5cc(N6CCOC6=O)ccn45)c3)no2)C1] | MS m/z 518.1 (M + 1)+. | 0.114 |
| F251 | 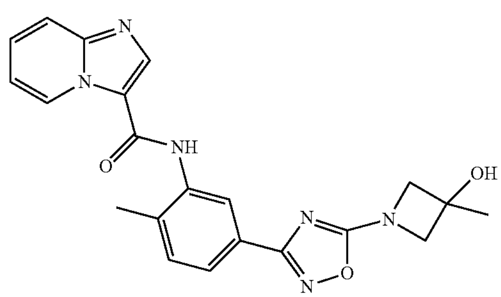 [SMILES: Cc1ccc(-c2noc(N3CC(C)(O)C3)n2)cc1NC(=O)c1cnc2ccccn12] | ¹H NMR (400 MHz, d₆-DMSO) δ 10.15 (s, 1H), 9.51-9.48 (m, 1H), 8.67 (s, 1H), 8.09 (d, J = 1.6 Hz, 1H), 7.87-7.82 (m, 2H), 7.66-7.62 (m, 1H), 7.53 (d, J = 8.4 Hz, 1H), 7.30-7.26 (m, 1H), 3.90 (s, 4H), 2.39 (s, 3H), 1.44 (s, 3H). MS m/z 404.16 (M + 1)+. | 0.157 |
| F252 | 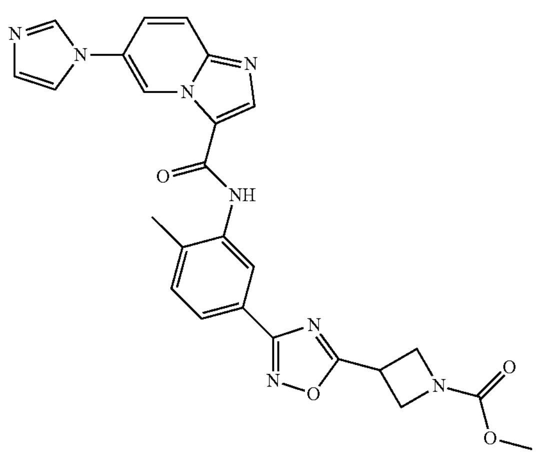 [SMILES: COC(=O)N1CC(c2nc(-c3ccc(C)c(NC(=O)c4cnc5ccc(-n6ccnc6)cn45)c3)no2)C1] | MS m/z 498.7 (M + 1)+. | 0.421 |

TABLE 2-continued

| Cmpd No. | Structure | Physical Data | c-kit (Mo7e) μM |
|---|---|---|---|
| F253 | 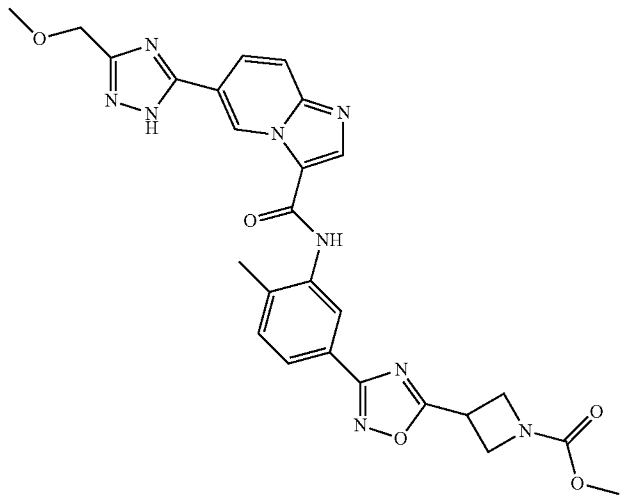 | MS m/z 543.7 (M + 1)+. | 0.215 |
| F254 | 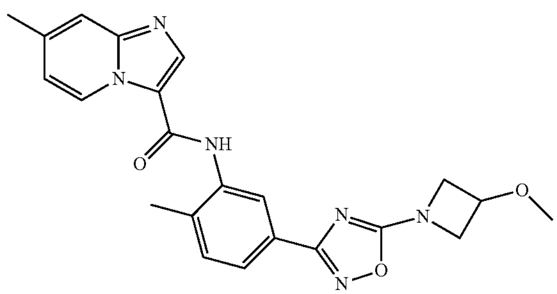 | 1H NMR (400 MHz, d6-DMSO) δ 9.93 (s, 1H), 9.33-9.31 (m, 1H), 8.50 (s, 1H), 7.93 (d, J = 1.6 Hz, 1H), 7.69 (dd, J = 1.6, 7.6 Hz, 1H), 7.57 (s, 1H), 7.42 (d, J = 8.0 Hz, 1H), 7.02 (dd, J = 1.6, 7.2 Hz, 1H), 4.45-4.38 (m, 3H), 4.10-4.06 (m, 2H), 3.25 (s, 3H), 2.42 (s, 3H), 2.33 (s, 3H). MS m/z 418.18 (M + 1)+. | 0.111 |
| F255 | 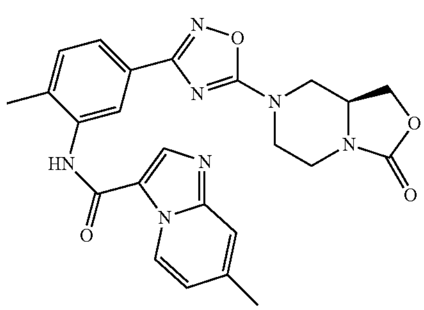 [SMILES: Cc1ccn2c(C(=O)Nc3cc(-c4noc(N5CCN6C(=O)OC[C@@H]6C5)n4)ccc3C)cnc2c1] | 1H NMR (400 MHz, d6-DMSO) δ 9.94 (s, 1H), 9.32-9.31 (m, 1H), 8.51 (s, 1H), 7.95 (d, J = 1.6 Hz, 1H), 7.71 (dd, J = 1.6, 8.0 Hz, 1H), 7.57 (s, 1H), 7.43 (d, J = 8.0 Hz, 1H), 7.03 (dd, J = 1.6, 7.2 Hz, 1H), 4.43-4.38 (m, 1H), 4.25-4.21 (m, 1H), 4.06-4.00 (m, 3H), 3.70-3.67 (m, 1H), 3.23-3.16 (m, 3H), 2.42 (s, 3H), 2.34 (s, 3H). MS m/z 473.18 (M + 1)+. | 0.129 |

TABLE 2-continued

| Cmpd No. | Structure | Physical Data | c-kit (Mo7e) μM |
|---|---|---|---|
| F256 | 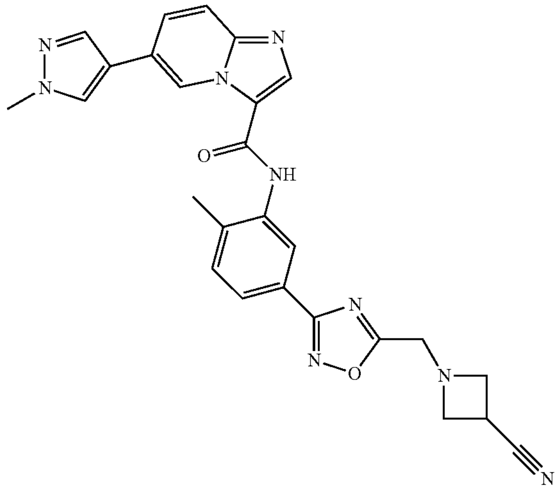 [SMILES: Cc1ccc(-c2noc(CN3CC(C#N)C3)n2)cc1NC(=O)c1cnc2ccc(-c3cnn(C)c3)cn12] | MS m/z 494.2 (M + 1)+. | 0.106 |
| F257 | 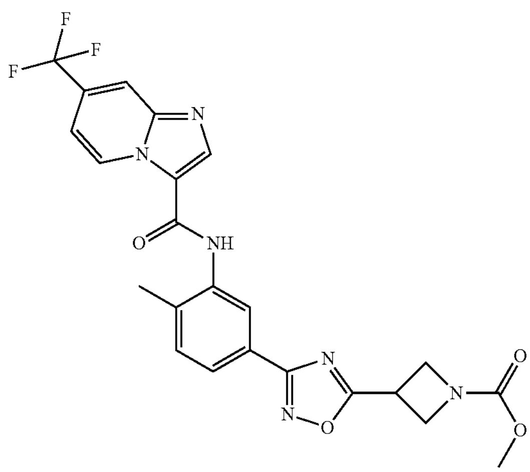 [SMILES: COC(=O)N1CC(c2nc(-c3ccc(C)c(NC(=O)c4cnc5cc(C(F)(F)F)ccn45)c3)no2)C1] | MS m/z 501.14 (M + 1)+. | 0.13 |
| F258 | 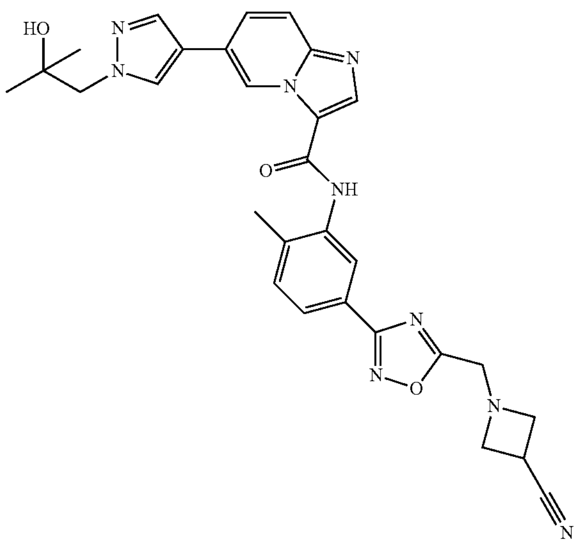 [SMILES: Cc1ccc(-c2noc(CN3CC(C#N)C3)n2)cc1NC(=O)c1cnc2ccc(-c3cnn(CC(C)(C)O)c3)cn12] | MS m/z 552.24 (M + 1)+. | 0.146 |

US 9,023,839 B2
TABLE 2-continued
| Cmpd No. | Structure | Physical Data | c-kit (Mo7e) μM |
|---|---|---|---|
| F259 | 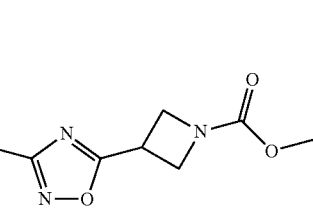 | MS m/z 483.15 (M + 1)+. | 0.177 |
| F260 | 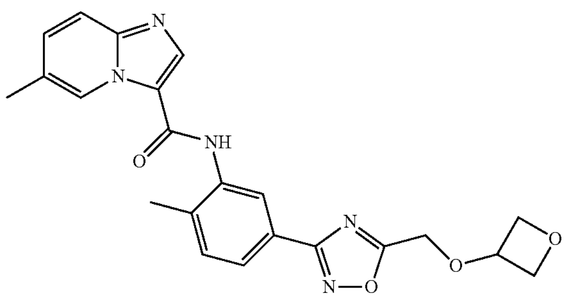 [SMILES: Cc1ccc2ncc(C(=O)Nc3cc(-c4noc(COC5COC5)n4)ccc3C)n2c1] | MS m/z 420.17 (M + 1)+. | 0.205 |
| F261 | 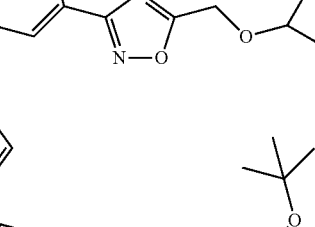 | MS m/z 489.22 (M + 1)+. | 0.291 |
| F262 | 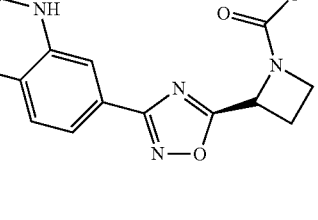 | MS m/z 447.17 (M + 1)+. | 0.309 |
| F263 | 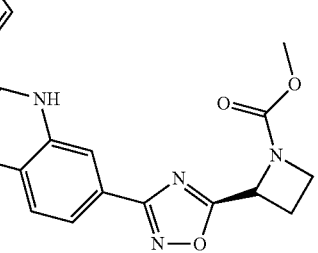 | MS m/z 376.13 (M + 1)+. | 0.35 |

TABLE 2-continued

| Cmpd No. | Structure | Physical Data | c-kit (Mo7e) μM |
|---|---|---|---|
| F264 | 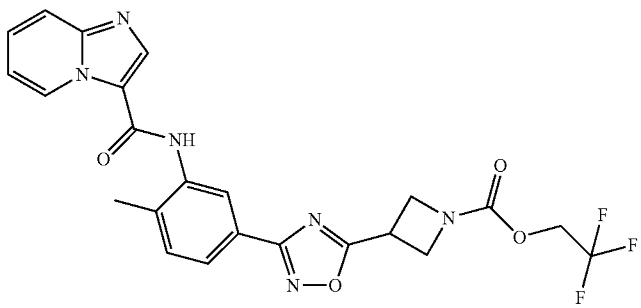 [SMILES: Cc1ccc(-c2noc(C3CN(C(=O)OCC(F)(F)F)C3)n2)cc1NC(=O)c1cnc2ccccn12] | MS m/z 501.14 (M + 1)+. | 0.438 |
| F265 | 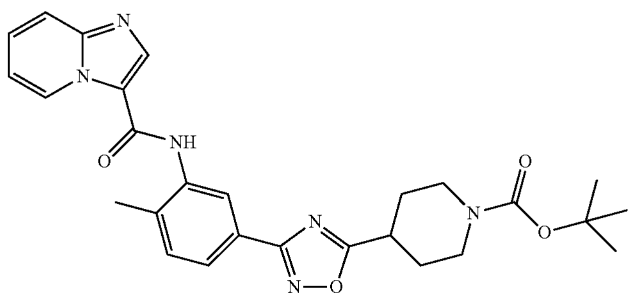 [SMILES: Cc1ccc(-c2noc(C3CCN(C(=O)OC(C)(C)C)CC3)n2)cc1NC(=O)c1cnc2ccccn12] | MS m/z 503.24 (M + 1)+. | 0.505 |
| F266 | 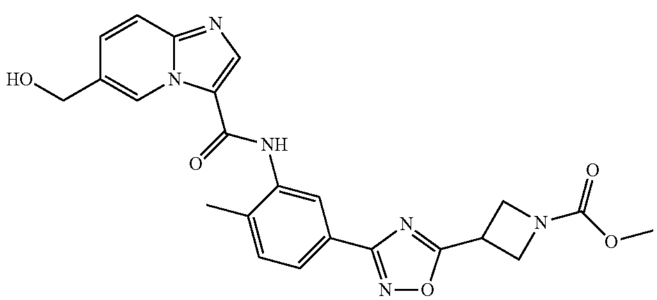 [SMILES: COC(=O)N1CC(c2nc(-c3ccc(C)c(NC(=O)c4cnc5ccc(CO)cn45)c3)no2)C1] | MS m/z 463.16 (M + 1)+. | 0.523 |
| F267 | 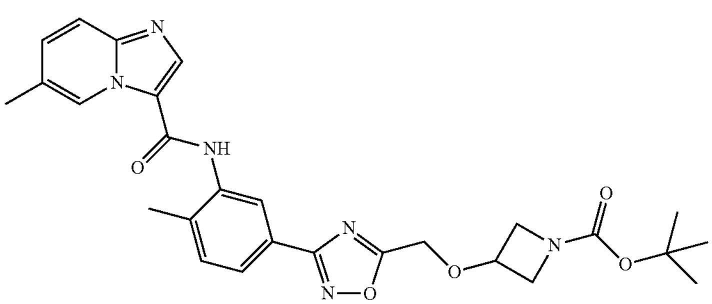 [SMILES: Cc1ccc2ncc(C(=O)Nc3cc(-c4noc(COC5CN(C(=O)OC(C)(C)C)C5)n4)ccc3C)n2c1] | MS m/z 519.23 (M + 1)+. | 0.65 |
| F268 | 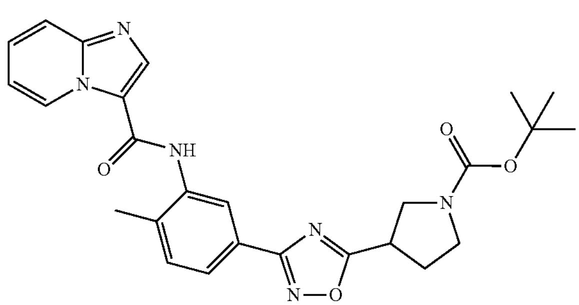 [SMILES: Cc1ccc(-c2noc(C3CCN(C(=O)OC(C)(C)C)C3)n2)cc1NC(=O)c1cnc2ccccn12] | MS m/z 489.22 (M + 1)+. | 0.912 |

TABLE 2-continued

| Cmpd No. | Structure | Physical Data | c-kit (Mo7e) μM |
|---|---|---|---|
| F269 | 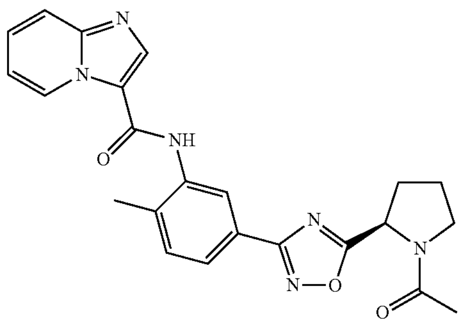 [SMILES: CC(=O)N1CCC[C@@H]1c1nc(-c2ccc(C)c(NC(=O)c3cnc4ccccn34)c2)no1] | MS m/z 431.17 (M + 1)+. | 1.012 |
| F270 | 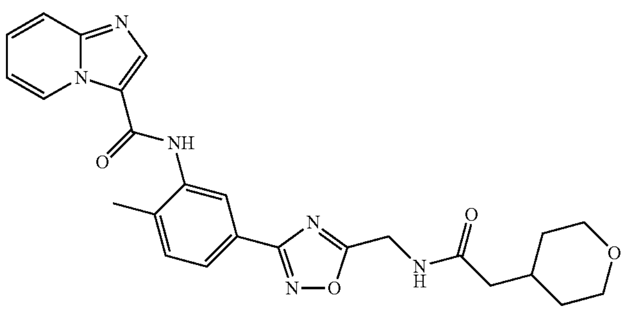 [SMILES: Cc1ccc(-c2noc(CNC(=O)CC3CCOCC3)n2)cc1NC(=O)c1cnc2ccccn12] | MS m/z 475.2 (M + 1)+. | 1.038 |
| F271 | 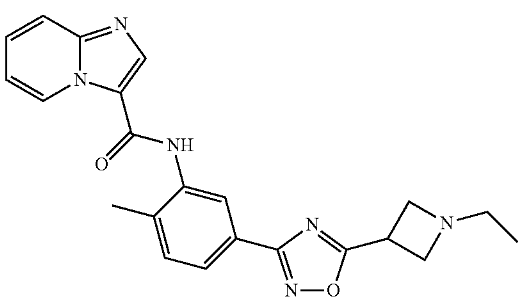 [SMILES: CCN1CC(c2nc(-c3ccc(C)c(NC(=O)c4cnc5ccccn45)c3)no2)C1] | MS m/z 403.18 (M + 1)+. | 1.12 |
| F272 | 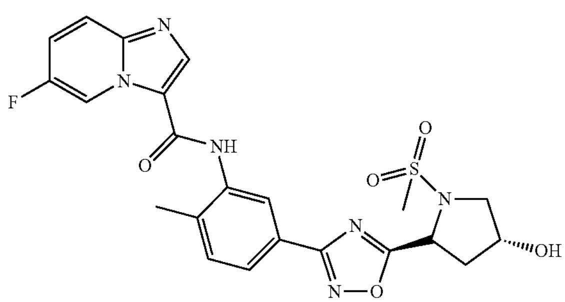 | MS m/z 501.13 (M + 1)+. | 1.139 |
| F273 | 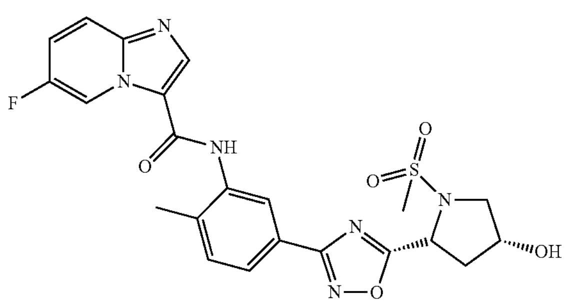 | MS m/z 501.13 (M + 1)+. | 1.168 |

TABLE 2-continued

| Cmpd No. | Structure | Physical Data | c-kit (Mo7e) μM |
|---|---|---|---|
| F274 | 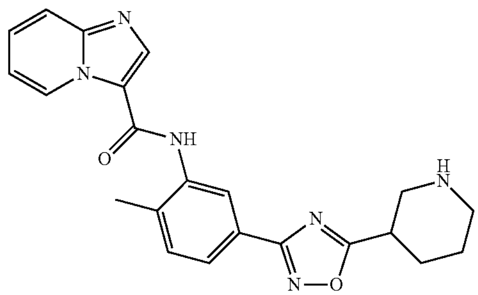 [SMILES: Cc1ccc(-c2noc(C3CCCNC3)n2)cc1NC(=O)c1cnc2ccccn12] | MS m/z 403.18 (M + 1)⁺. | 1.204 |
| F275 | 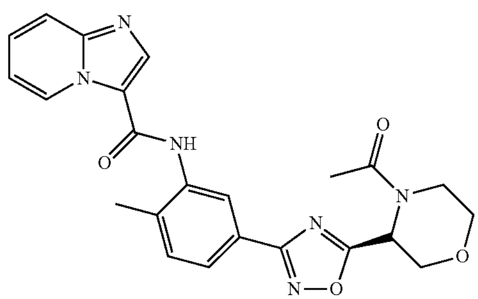 | MS m/z 447.18 (M + 1)⁺. | 1.233 |
| F276 | 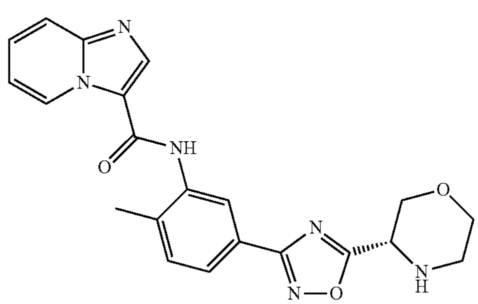 [SMILES: Cc1ccc(-c2noc([C@@H]3COCCN3)n2)cc1NC(=O)c1cnc2ccccn12] | MS m/z 405.17 (M + 1)⁺. | 1.243 |
| F277 | 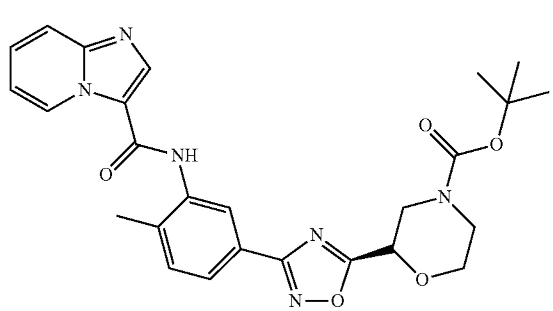 | MS m/z 505.21 (M + 1)⁺. | 1.247 |

TABLE 2-continued

| Cmpd No. | Structure | Physical Data | c-kit (Mo7e) μM |
|---|---|---|---|
| F278 | 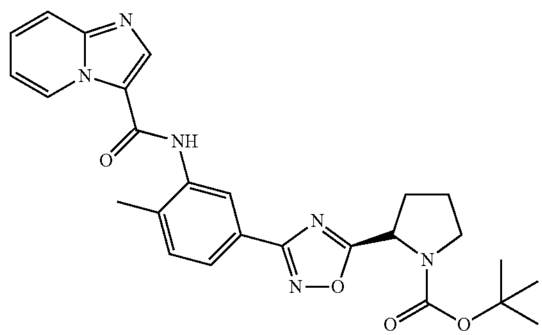 | MS m/z 489.22 (M + 1)+. | 1.278 |
| F279 | 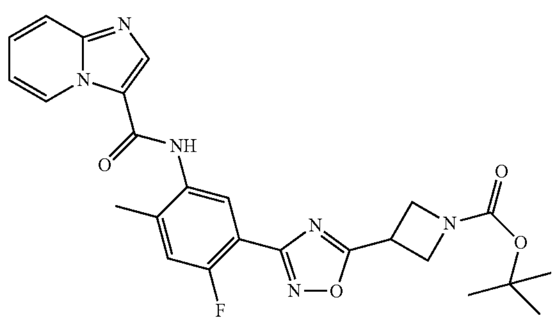 [SMILES: Cc1cc(F)c(-c2noc(C3CN(C(=O)OC(C)(C)C)C3)n2)cc1NC(=O)c1cnc2ccccn12] | MS m/z 493.19 (M + 1)+. | 1.284 |
| F280 | 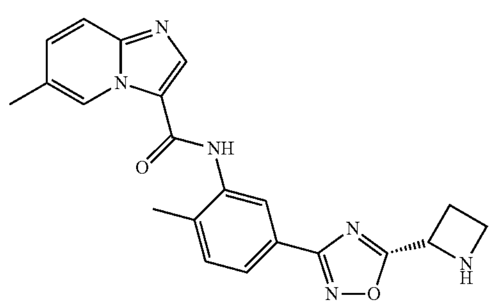 | MS m/z 389.15 (M + 1)+. | 1.309 |
| F281 | 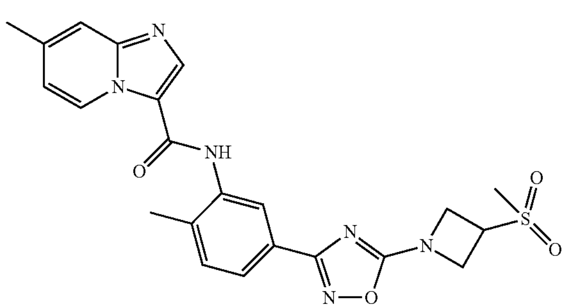 [SMILES: Cc1ccn2c(C(=O)Nc3cc(-c4noc(N5CC(S(C)(=O)=O)C5)n4)ccc3C)cnc2c1] | MS m/z 467.15 (M + 1)+. | 1.373 |

TABLE 2-continued

| Cmpd No. | Structure | Physical Data | c-kit (Mo7e) μM |
|---|---|---|---|
| F282 | 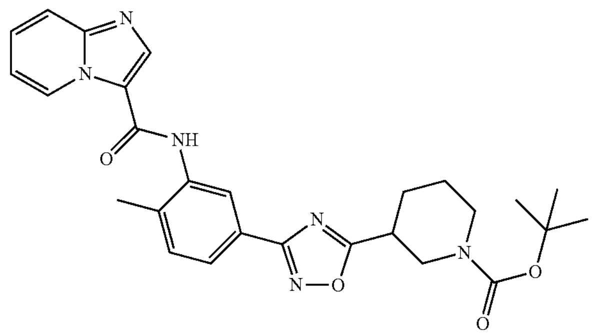 [SMILES: Cc1ccc(-c2noc(C3CCCN(C(=O)OC(C)(C)C)C3)n2)cc1NC(=O)c1cnc2ccccn12] | MS m/z 503.24 (M + 1)+. | 1.6* |
| F283 | 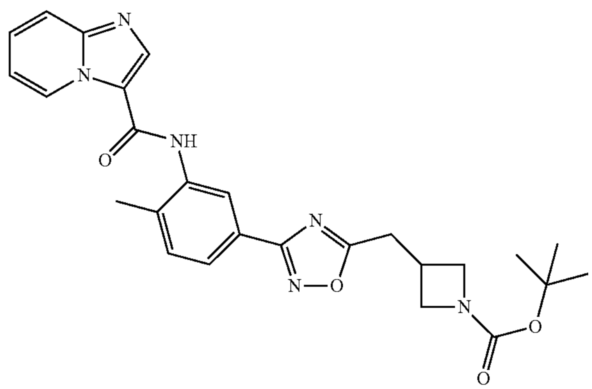 [SMILES: Cc1ccc(-c2noc(CC3CN(C(=O)OC(C)(C)C)C3)n2)cc1NC(=O)c1cnc2ccccn12] | MS m/z 489.22 (M + 1)+. | 1.633 |
| F284 | 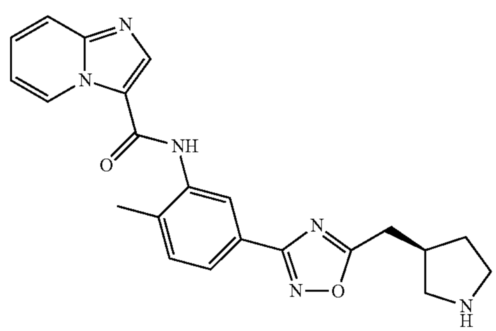 [SMILES: Cc1ccc(-c2noc(C[C@H]3CCNC3)n2)cc1NC(=O)c1cnc2ccccn12] | MS m/z 403.18 (M + 1)+. | 1.649 |
| F285 | 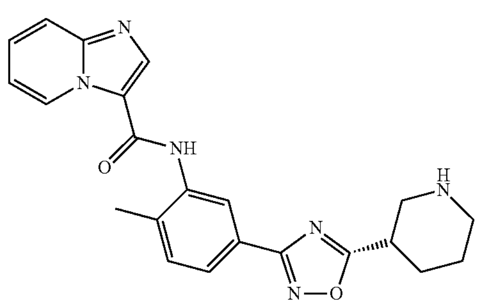 | MS m/z 403.18 (M + 1)+. | 1.673 |

TABLE 2-continued

| Cmpd No. | Structure | Physical Data | c-kit (Mo7e) μM |
|---|---|---|---|
| F286 | 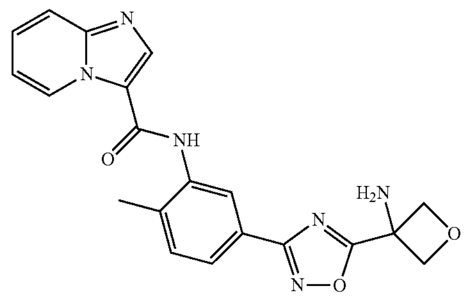 [SMILES: Cc1ccc(-c2noc(C3(N)COC3)n2)cc1NC(=O)c1cnc2ccccn12] | MS m/z 391.14 (M + 1)+. | 1.681 |
| F287 | 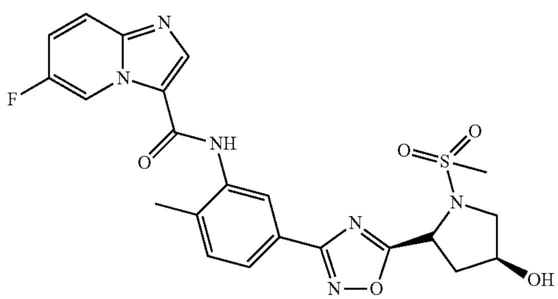 | MS m/z 501.13 (M + 1)+. | 1.681 |
| F288 | 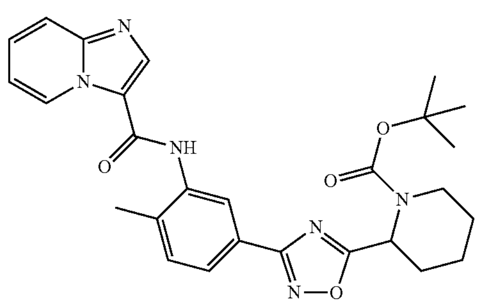 [SMILES: Cc1ccc(-c2noc(C3CCCCN3C(=O)OC(C)(C)C)n2)cc1NC(=O)c1cnc2ccccn12] | MS m/z 503.24 (M + 1)+. | 1.78* |
| F289 | 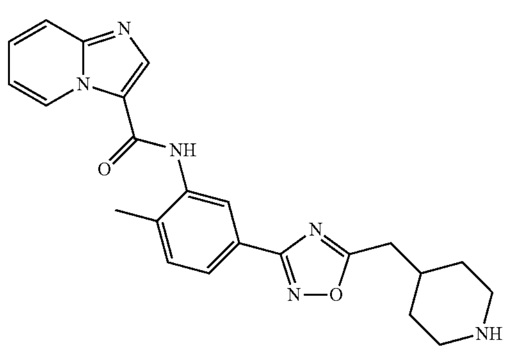 [SMILES: Cc1ccc(-c2noc(CC3CCNCC3)n2)cc1NC(=O)c1cnc2ccccn12] | MS m/z 417.19 (M + 1)+. | 1.884 |

TABLE 2-continued

| Cmpd No. | Structure | Physical Data | c-kit (Mo7e) μM |
|---|---|---|---|
| F290 | 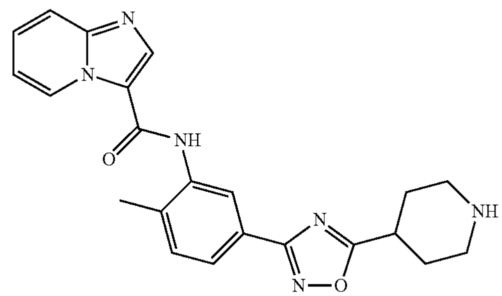 [SMILES: Cc1ccc(-c2noc(C3CCNCC3)n2)cc1NC(=O)c1cnc2ccccn12] | MS m/z 403.19 (M + 1)+. | 1.887 |
| F291 | 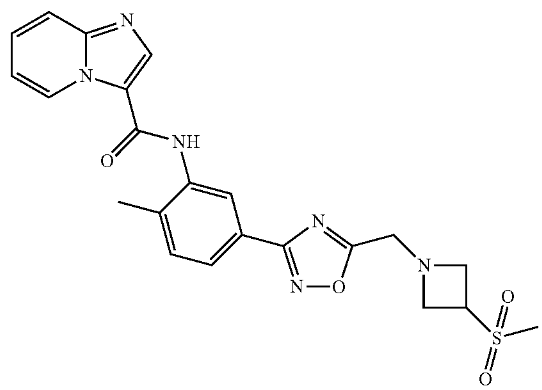 [SMILES: Cc1ccc(-c2noc(CN3CC(S(C)(=O)=O)C3)n2)cc1NC(=O)c1cnc2ccccn12] | MS m/z 467.15 (M + 1)+. | 1.921 |
| F292 | 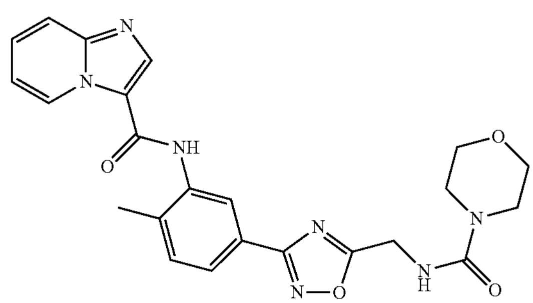 [SMILES: Cc1ccc(-c2noc(CNC(=O)N3CCOCC3)n2)cc1NC(=O)c1cnc2ccccn12] | MS m/z 462.18 (M + 1)+. | 1.934 |
| F293 | 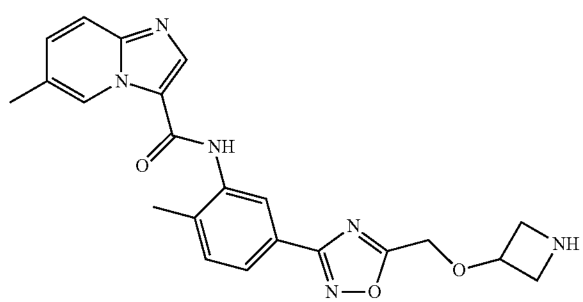 [SMILES: Cc1ccc2ncc(C(=O)Nc3cc(-c4noc(COC5CNC5)n4)ccc3C)n2c1] | MS m/z 419.17 (M + 1)+. | 2.153 |
| F294 | 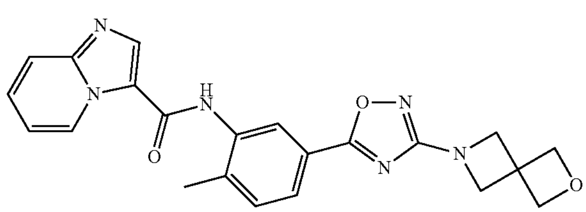 [SMILES: Cc1ccc(-c2nc(N3CC4(COC4)C3)no2)cc1NC(=O)c1cnc2ccccn12] | MS m/z 417.17 (M + 1)+. | 2.201 |

TABLE 2-continued
| Cmpd No. | Structure | Physical Data | c-kit (Mo7e) μM |
|---|---|---|---|
| F295 | 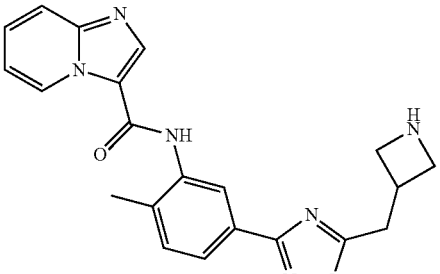 | MS m/z 389.17 (M + 1)+. | 2.203 |
| F296 | 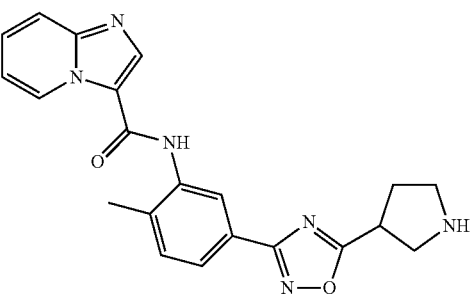 [SMILES: Cc1ccc(-c2noc(C3CCNC3)n2)cc1NC(=O)c1cnc2ccccn12] | MS m/z 389.17 (M + 1)+. | 2.443 |
| F297 | 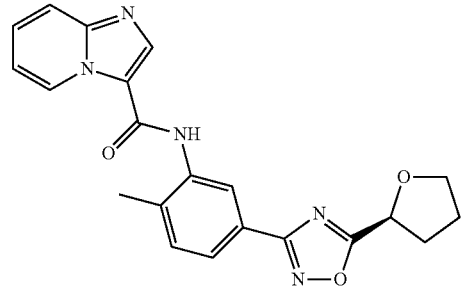 [SMILES: Cc1ccc(-c2noc([C@@H]3CCCO3)n2)cc1NC(=O)c1cnc2ccccn12] | MS m/z 390.15 (M + 1)+. | 2.79 |
| F298 | 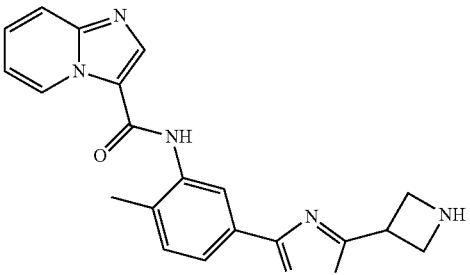 | MS m/z 375.16 (M + 1)+. | 2.857 |
| F299 | 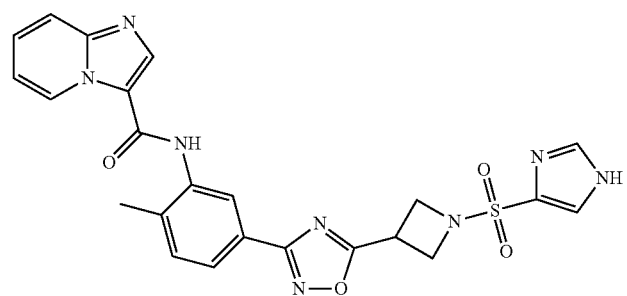 [SMILES: Cc1ccc(-c2noc(C3CN(S(=O)(=O)c4c[nH]cn4)C3)n2)cc1NC(=O)c1cnc2ccccn12] | MS m/z 505.14 (M + 1)+. | 3.52 |

TABLE 2-continued

| Cmpd No. | Structure | Physical Data | c-kit (Mo7e) μM |
|---|---|---|---|
| F300 | 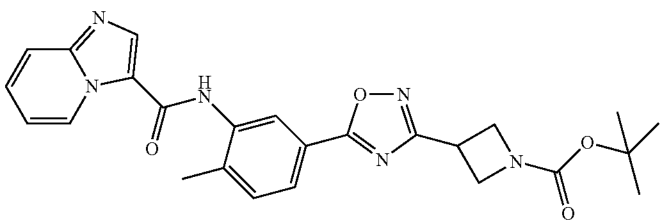 [SMILES: Cc1ccc(-c2nc(C3CN(C(=O)OC(C)(C)C)C3)no2)cc1NC(=O)c1cnc2ccccn12] | MS m/z 475.2 (M + 1)+. | 3.56 |
| F301 | 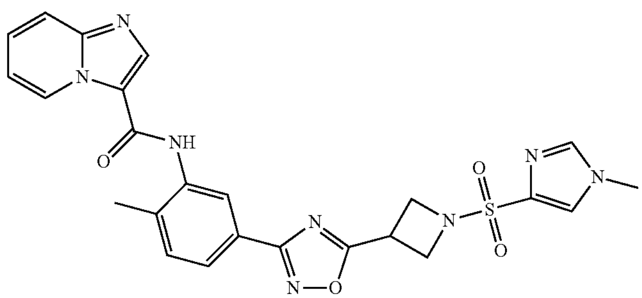 [SMILES: Cc1ccc(-c2noc(C3CN(S(=O)(=O)c4cn(C)cn4)C3)n2)cc1NC(=O)c1cnc2ccccn12] | MS m/z 519.16 (M + 1)+. | 3.97 |
| F302 | 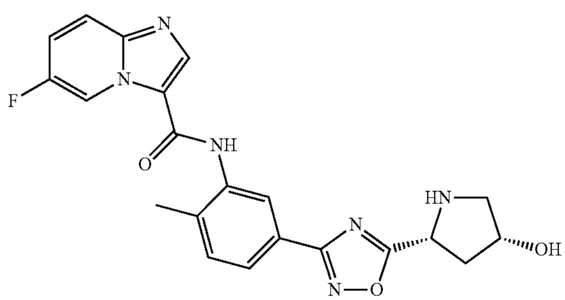 [SMILES: Cc1ccc(-c2noc([C@H]3C[C@@H](O)CN3)n2)cc1NC(=O)c1cnc2ccc(F)cn12] | MS m/z 423.15 (M + 1)+. | 4.33 |
| F303 | 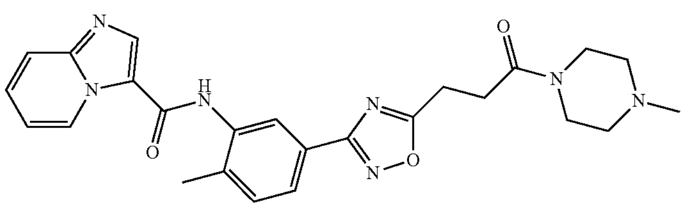 [SMILES: Cc1ccc(-c2noc(CCC(=O)N3CCN(C)CC3)n2)cc1NC(=O)c1cnc2ccccn12] | MS m/z 474.21 (M + 1)+. | 4.64 |
| F304 | 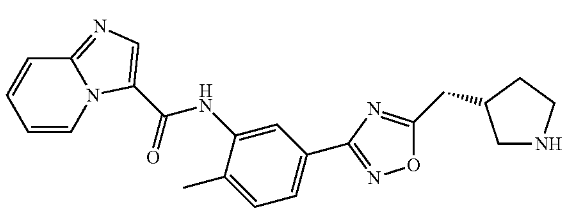 | MS m/z 403.18 (M + 1)+. | 5.23 |
| F305 | 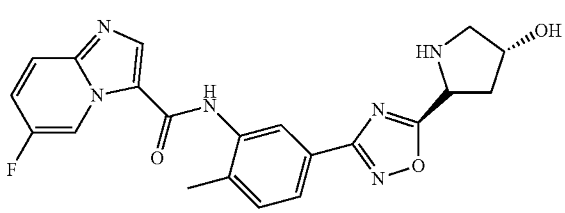 | MS m/z 423.15 (M + 1)+. | 8.08 |

TABLE 2-continued

| Cmpd No. | Structure | Physical Data | c-kit (Mo7e) μM |
|---|---|---|---|
| F306 | 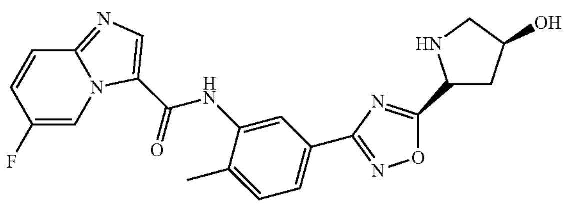 | MS m/z 423.15 (M + 1)+. | 8.37 |
| F307 | 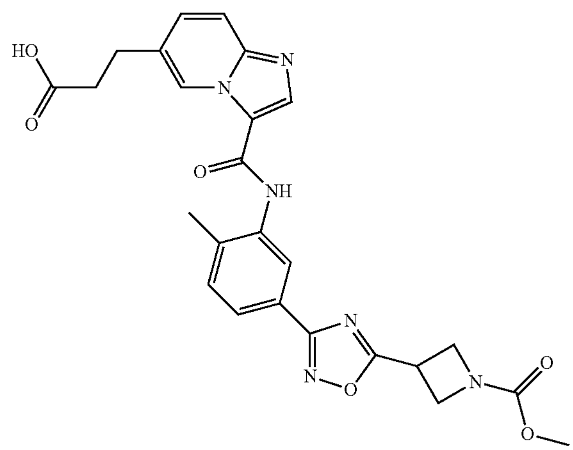 [SMILES: COC(=O)N1CC(c2nc(-c3ccc(C)c(NC(=O)c4cnc5ccc(CCC(=O)O)cn45)c3)no2)C1] | MS m/z 505.17 (M + 1)+. | >10 |
| F308 | 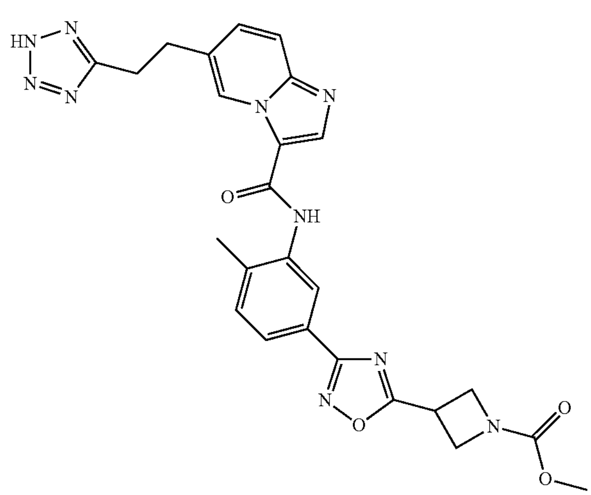 [SMILES: COC(=O)N1CC(c2nc(-c3ccc(C)c(NC(=O)c4cnc5ccc(CCc6nn[nH]n6)cn45)c3)no2)C1] | MS m/z 529.21 (M + 1)+. | >10 |

TABLE 2-continued

| Cmpd No. | Structure | Physical Data | c-kit (Mo7e) μM |
|---|---|---|---|
| F309 | 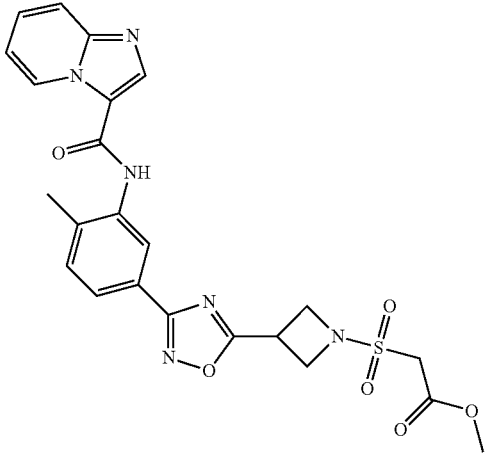 [SMILES: COC(=O)CS(=O)(=O)N1CC(c2nc(-c3ccc(C)c(NC(=O)c4cnc5ccccn45)c3)no2)C1] | MS m/z 511.14 (M + 1)+. | >10 |
| F310 | 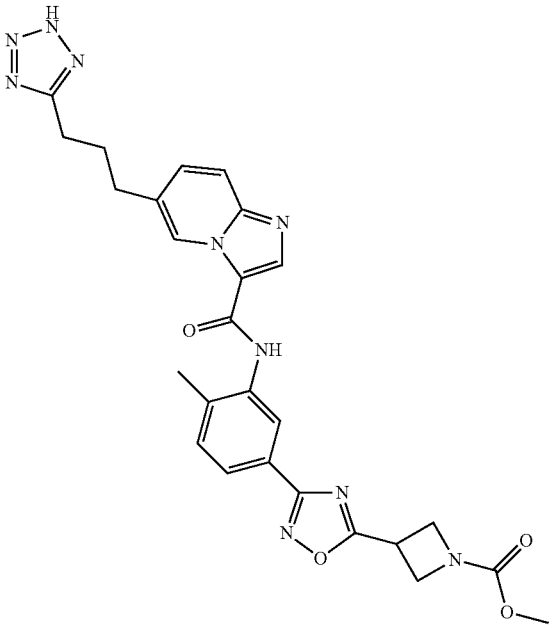 [SMILES: COC(=O)N1CC(c2nc(-c3ccc(C)c(NC(=O)c4cnc5ccc(CCCc6nn[nH]n6)cn45)c3)no2)C1] | MS m/z 543.21 (M + 1)+. | >10 |

*20% FBS instead of 1% FBS

Assays

Compounds of Formula (I) and Formula (II) provided herein were assayed to measure their capacity to inhibit c-kit and PDGFR kinases using the appropriate assay described below: c-Kit inhibition was evaluated using the Mo7e cell proliferation assay, and PDGFR inhibition was evaluated using the Rat A10 cell proliferation assay and the Human TG/HA-VSMC cell proliferation assay.

Mo7e Cell Proliferation Assay

The compounds of Table 1 and Table 2 were tested for inhibition of SCF dependent proliferation using human Mo7e cells which endogenously express c-kit in a 384 well format. Three-fold serially diluted test compounds ($C_{max}$=10 mM) were evaluated for their antiproliferative activity of Mo7e cells stimulated with human recombinant SCF. After 48 hours of incubation at 37° C., cell viability was measured by adding 25 uL of CellTiter Glo (Promega) to the cells and the luminescence was measured by a CLIPR CCD camera (Molecular Devices).

Rat A10 Cell Proliferation Assay

Rat A10 cells (ATCC) were resuspended in DMEM supplemented with 1% FBS or 20% FBS and 10 ng/mL recombinant rat PDGF-BB at 20,000 cells/mL. The cells were aliquoted into 384 well plates at 50 μL/well and incubated for 4 hours at 37° C. 0.5 μL of test compound 3-fold serially diluted in DMSO was added to each well. The plates were returned to the incubator for a further 68 hours. 25 μL of CellTiter-Glo (Promega) was added to each well and the plates were incubated on the bench for 15 minutes. Luminescence was then read using a CLIPR CCD camera (Molecular Devices).

Human TG/HA-VSMC Cell Proliferation Assay

Human TG/HA-VSMC cells (ATCC) were resuspended in DMEM supplemented with 1% FBS and 30 ng/mL recombinant human PDGF-BB at 60,000 cells/mL. The cells were aliquoted into 384 well plates at 50 μL/well and incubated for 4 hours at 37° C. 0.5 μL of test compound 3-fold serially diluted in DMSO was added to each well. The plates were returned to the incubator for a further 68 hours. 25 μL of CellTiter-Glo (Promega) was added to each well and the plates were incubated on the bench for 15 minutes. Luminescence was then read using a CLIPR CCD camera (Molecular Devices).

Certain Assay Results

Various compounds of Formula (I) and Formula (II) in free form or in pharmaceutically acceptable salt form, exhibit pharmacological properties, for example, as indicated by the tests described herein and presented in Table 1 and Table 2. The $IC_{50}$ value is given as that concentration of the test compound in question that provoke a response halfway between the baseline and maximum responses. Certain compounds of Formula (I) or Formula (II) having specific $IC_{50}$ for c-kit inhibition values of less than or equal to 100 nM are listed in Table 1, while certain compounds of Formula (I) or Formula (II) having specific $IC_{50}$ for c-kit inhibition values greater than 100 nM are listed in Table 2.

In other embodiments, compounds of Formula (I) or Formula (II) have $IC_{50}$ values for c-kit inhibition in the range from 1 nM to 1 μM. In other embodiments, compounds of Formula (I) or Formula (II) have $IC_{50}$ values for c-kit inhibition in the range from 1 nM to 500 nM. In other embodiments, compounds of Formula (I) or Formula (II) have $IC_{50}$ values for c-kit inhibition in the range from 1 nM to 200 nM. In other embodiments, compounds of Formula (I) or Formula (II) have $IC_{50}$ values for c-kit inhibition in the range from 1 nM to 100 nM. In other embodiments, compounds of Formula (I) or Formula (II) have $IC_{50}$ values for c-kit inhibition in the range from 1 nM to 50 nM. In other embodiments, compounds of Formula (I) or Formula (II) have $IC_{50}$ values for c-kit inhibition in the range from 1 nM to 25 nM. In other embodiments, compounds of Formula (I) or Formula (II) have $IC_{50}$ values for c-kit inhibition in the range from 1 nM to 10 nM. In other embodiments, compounds of Formula (I) or Formula (II) have $IC_{50}$ values for c-kit inhibition in the range from 1 nM to 5 nM. In other embodiments, compounds of Formula (I) or Formula (II) have $IC_{50}$ values for c-kit inhibition in the range from 1 nM to 2.5 nM.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A method for treating a disease or disorder where modulation of a kinase is implicated, wherein the method comprises administering to a system or subject in need of such treatment an effective amount of a compound of Formula (I) or Formula (II), or pharmaceutically acceptable salt thereof,

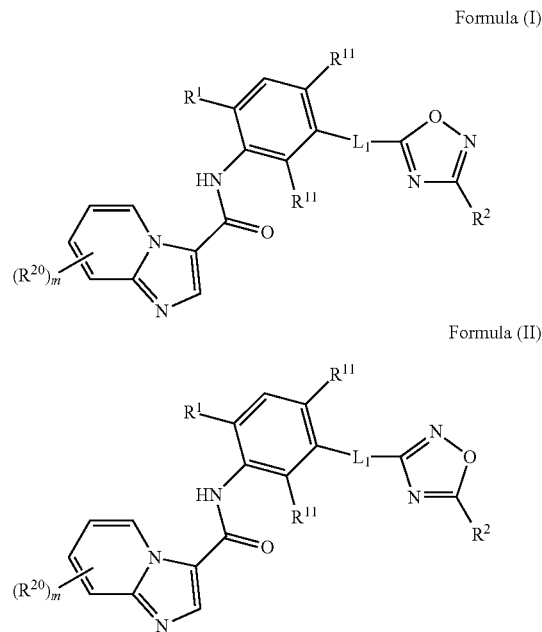

Formula (I)

Formula (II)

wherein:

m is 1 and $R^{20}$ is selected from H, halo, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9{}_2)_nOR^4$, —C(O)$R^4$, —$(CR^9{}_2)_nC(=O)OR^4$, $R^{10}$, —$(CR^9{}_2)_nR^{10}$, —$((CR^9{}_2)_nO)_rR^4$, —$(CR^9{}_2)_nO(CR^9{}_2)_nR^7$, —$(CR^9{}_2)_nC(=O)R^4$, —C(=O)N($R^4$)$_2$, —$OR^4$, and —$(CR^9{}_2)_n$CN;

or m is 4 and $R^{20}$ is deuterium;

$R^1$ is selected from $C_1$-$C_6$alkyl and halo;

each $R^{11}$ is independently selected from H, halo and $C_1$-$C_6$alkyl;

$L_1$ is a bond, —NH— or —C(O)NH—;

$L_2$ is —$(CR^9{}_2)_n$—, —$CHR^6$—, —$(CR^9{}_2)_nO$—, —NH—, —$(CR^9{}_2)_nC(=O)$—, —C(=O)O$(CR^9{}_2)_n$—, —$(CR^9{}_2)_nOC(=O)NR^4$—, —$(CR^9{}_2)_n$NR$^4$C(=O)$(CR^9{}_2)_n$—, —$(CR^9{}_2)_n$NR$^4$C(=O)—, or —$(CR^9{}_2)_n$NR$^4$C(=O)O—;

$R^2$ is $R^3$ or $L_2R^3$;

$R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —C(=O)$OR^4$, —C(=O)$R^4$, —C(=O)$R^7$, —C(=O)$OR^5$, —$(CR^9{}_2)_nOR^4$, —O$(CR^9{}_2)_nOR^4$, —C(=O)O$(CR^9{}_2)_nOR^4$, —N($R^4$)$_2$, —C(=O)NR$^4{}_2$, —NR$^4$C(=O)$OR^4$, —NR$^4$C(=O)$(CR^9{}_2)_nOR^4$, —NR$^4(CR^9{}_2)_nOR^4$, —NR$^4$S(=O)$_2R^4$, —N(C(=O)$OR^4$)$_2$, $R^8$, —$(CR^9{}_2)_n$$R^8$, deuterated $C_1$-$C_6$alkoxy, —S(=O)$_2R^4$, —S(=O)$_2R^7$, —S(=O)$_2R^8$, —S(=O)$_2N(R^4)_2$, —S(=O)$_2$NHC(=O)$OR^4$, —S(=O)$_2(CR^9{}_2)_nC(=O)OR^4$, S(=O)$_2(CR^9{}_2)_nOR^4$, a Spiro attached dioxolane, a spiro attached dioxolane which is substituted with $C_1$-$C_6$alkyl, a spiro attached dioxane, a spiro attached tetrahydrofuranly, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, —$OR^4$ and $R^8$;

each $R^4$ is independently selected from H and $C_1$-$C_6$alkyl;

$R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl;

each $R^6$ is independently selected from —$NR^4C(O)OR^4$, —$OR^4$ and —$(CR^9{}_2)_nOR^4$;

each $R^7$ is independently selected from $C_1$-$C_6$haloalkyl;

$R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —$(C(R^9)_2)_nOR^4$, —$(C(R^9)_2)_nR^5$, —$(C(R^9)_2)_nC(O)OR^4$, —$C(O)OR^4$ and —$S(O)_2R^4$;

each $R^9$ is independently selected from H and $C_1$-$C_6$alkyl;

$R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one, wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —$(C(R^9)_2)_nOR^4$, —$(C(R^9)_2)_nR^5$, —$(C(R^9)_2)_nC(O)OR^4$ and —$S(O)_2R^4$;

t is 1, 2 or 3, and each n is independently selected from 1, 2, 3 and 4;

wherein the kinase is selected from c-kit, PDGFRα and PDGFRβ, and wherein the disease is selected from asthma, allergic rhinitis, allergic sinusitis and Crohn's disease.

2. The method of claim 1, wherein the compound is a compound of Formula (Ia), Formula (IIa), Formula (Ib) or Formula (IIb):

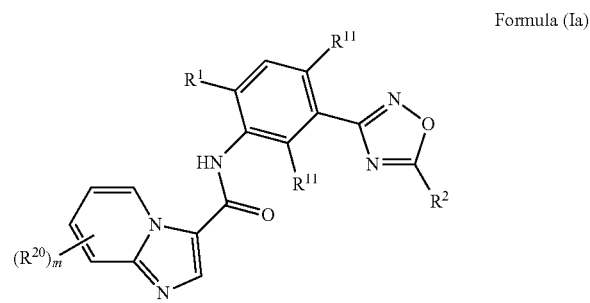

Formula (Ia)

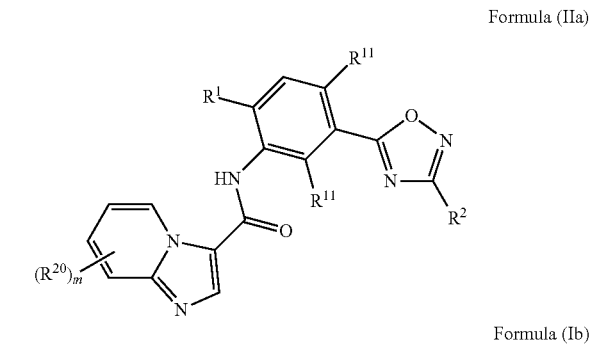

Formula (IIa)

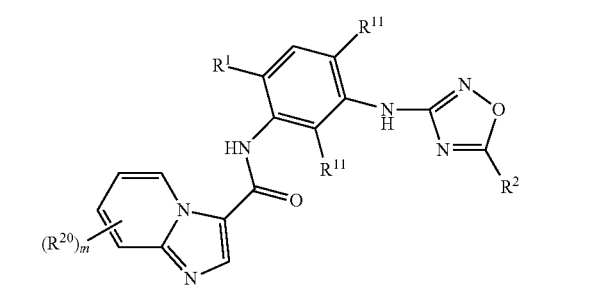

Formula (Ib)

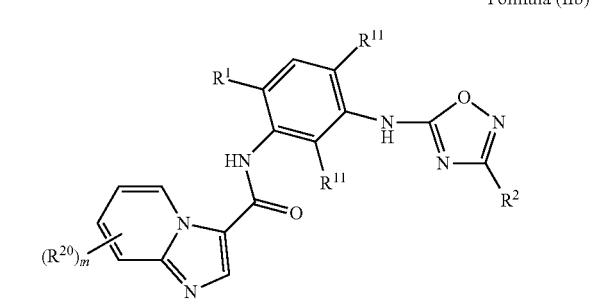

Formula (IIb)

wherein:
  m is 1 and $R^{20}$ is selected from H, halo, $C_1$-$C_6$alkyl, $C_1$-$C_6$haloalkyl, $C_1$-$C_6$haloalkoxy, deuterium, deuterated $C_1$-$C_6$alkyl, —CN, —$(CR^9{}_2)_nR^4$, —C(O)$R^4$, —$(CR^9{}_2)_nC(=O)OR^4$, $R^{10}$, —$(CR^9{}_2)_nR^{10}$, —$((CR^9{}_2)_nO)_tR^4$, —$(CR^9{}_2)_nO(CR^9{}_2)_nR^7$, —$(CR^9{}_2)_nC(=O)R^4$, —$C(=O)_N(R^4)_2$, —$OR^4$, and —$(CR^9{}_2)_nCN$;
  or m is 4 and $R^{20}$ is deuterium;
  $R^1$ is selected from $C_1$-$C_6$alkyl and halo;
  each $R^{11}$ is independently selected from H, halo and $C_1$-$C_6$alkyl;
  $L_2$ is —$(CR^9{}_2)_n$—, —$CHR^6$—, —$(CR^9{}_2)_nO$—, —NH—, —$(CR^9{}_2)_nC(=O)$—, —$C(=O)O(CR^9{}_2)_n$—, —$(CR^9{}_2)_nOC(=O)NR^4$—, —$(CR^9{}_2)_nNR^4C(=O)(CR^9{}_2)_n$—, —$(CR^9{}_2)_nNR^4C(=O)$—, or —$(CR^9{}_2)_nNR^4C(=O)O$—;
  $R^2$ is $R^3$ or $L_2R^3$;
  $R^3$ is selected from an unsubstituted 4-6 membered heterocycloalkyl with 1-2 heteroatoms independently selected from N, O and S, a piperidinone, a oxazolidin-2-one, pyrrolidinone, a pyrrolidin-2-one and a substituted 4-6 membered heterocycloalkyl with 1-2 heteroatoms independently selected from N, O and S, wherein the substituted 4-6 membered heterocycloalkyl of $R^3$ is substituted with 1-4 substituents independently selected from $C_1$-$C_6$alkyl halo, —CN, $C_1$-$C_6$haloalkyl, —$OR^4$, —$C(=O)OR^4$, —$C(=O)R^4$, —$C(=O)R^7$, —$C(=O)OR^5$, —$(CR^9{}_2)_nOR^4$, —$O(CR^9{}_2)_nOR^4$, —$C(=O)O(CR^9{}_2)_nOR^4$, —$N(R^4)_2$, —$C(=O)NR^4{}_2$, —$NR^4C(=O)OR^4$, —$NR^4C(=O)(CR^9{}_2)_nOR^4$, —$NR^4(CR^9{}_2)_nOR^4$, —$NR^4S(=O)_2R^4$, —$N(C(=O)OR^4)_2$, $R^8$, —$(CR^9{}_2)_n R^8$, deuterated $C_1$-$C_6$alkoxy, —$S(=O)_2R^4$, —$S(=O)_2R^7$, —$S(=O)_2R^8$, —$S(=O)_2N(R^4)_2$, —$S(=O)_2NHC(=O)R^4$, —$S(=O)_2(CR^9{}_2)_nC(=O)OR^4$, $S(=O)_2(CR^9{}_2)_nOR^4$, a spiro attached dioxolane, a spiro attached dioxolane which is substituted with $C_1$-$C_6$alkyl, a spiro attached dioxane, a spiro attached tetrahydrofuranyl, a spiro attached oxetane, a spiro attached cyclobutanone, a spiro attached cyclobutanol, a $C_1$ alkyl bridge, an unsubstituted 5-6 membered heterocycloalkyl with 1-2 heteroatoms independently selected from N, O and S and a 5-6 membered heterocycloalkyl with 1-2 heteroatoms independently selected from N, O and S substituted with 1-3 substituents independently selected from $C_1$-$C_6$alkyl, halo, $C_1$-$C_6$haloalkyl, $C_1$-$C_6$haloalkoxy, —$OR^4$ and $R^8$;
  each $R^4$ is independently selected from H and $C_1$-$C_6$alkyl;
  $R^5$ is an unsubstituted $C_3$-$C_8$cycloalkyl, an unsubstituted 5-6 membered heterocycloalkyl with 1-2 heteroatoms independently selected from N or O or a $C_3$-$C_8$cycloalkyl substituted with 1-3 substituents independently selected from $C_1$-$C_6$alkyl;
  each $R^6$ is independently selected from —$NR^4C(O)OR^4$, —$OR^4$ and —$(CR^9{}_2)_nOR^4$;
  each $R^7$ is independently selected from $C_1$-$C_6$haloalkyl;
  $R^8$ is selected from an unsubstituted phenyl, unsubstituted 5-6 membered heteroaryl with 1-3 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-3 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a tetrahydro-1H-oxazolo[3,4-a]pyrazin-3(5H)-one, a oxazolidin-2-one, pyrrolidinone and a pyrrolidin-2-one,
    wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl, —$(C(R^9)_2)_nOR^4$, —$(C(R^9)_2)_nR^5$, —$(C(R^9)_2)_nC(O)OR^4$, —$C(O)OR^4$ and —$S(O)_2R^4$;
  each $R^9$ is independently selected from H and $C_1$-$C_6$alkyl;
  $R^{10}$ is selected from an unsubstituted phenyl, unsubstituted 5-6 membered heteroaryl with 1-2 heteroatoms independently selected from N, O and S, an unsubstituted 5 membered heteroaryl with 1-4 heteroatoms selected from N, an unsubstituted 4-6 membered heterocycloalkyl with 1-2 heteroatoms independently selected from N, O and S, an unsubstituted $C_3$-$C_8$cycloalkyl, a substituted 5-6 membered heteroaryl with 1-2 heteroatoms independently selected from N, O and S, a substituted phenyl, a substituted 5 membered heteroaryl with 1-4 heteroatoms selected from N, a substituted 4-6 membered heterocycloalkyl with 1-2 heteroatoms independently selected from N, O and S, a substituted $C_3$-$C_8$cycloalkyl, a oxazolidin-2-one, pyrrolidinone and a pyrrolidin-2-one,
    wherein the substituted phenyl, the substituted 5-6 membered heteroaryl with 1-2 heteroatoms independently selected from N, O and S, the substituted 5 membered heteroaryl with 1-4 heteroatoms selected from N, substituted $C_3$-$C_8$cycloalkyl and substituted 4-6 membered heterocycloalkyl of $R^8$ are substituted with 1-3 substituents independently selected from $C_1$-$C_6$alkyl [Me], —$(C(R^9)_2)_nOR^4$, —$(C(R^9)_2)_nR^5$, —$(C(R^9)_2)_nC(O)OR^4$ and —$S(O)_2R^4$;
  t is 1, 2 or 3, and
  each n is independently selected from 1, 2, 3 and 4.

3. The method of claim 1, wherein $R^1$ is selected from —$CH_3$ and F.

4. The method of claim 3, wherein $R^1$ is —$CH_3$.

5. The method of claim 1, wherein each $R^{11}$ is independently selected from H, F and —$CH_3$.

6. The method of claim 5, wherein each $R^{11}$ is H.

7. The method of claim 1, wherein $R^3$ is selected from an unsubstituted 4-6 membered heterocycloalkyl with 1-2 heteroatoms independently selected from N and O, a piperidinone, a oxazolidin-2-one, pyrrolidinone, a pyrrolidin-2-one and a substituted 4-6 membered heterocycloalkyl with 1-2 heteroatoms independently selected from N and O,
  wherein the substituted 4-6 membered heterocycloalkyl of $R^3$ is substituted with 1-4 substituents independently selected from $C_1$-$C_6$alkyl, halo, —CN, $C_1$-$C_6$haloalkyl, —$OR^4$, —$C(=O)OR^4$, —$C(=O)R^4$, —$C(=O)R^7$, —$C(=O)OR^5$, —$(CR^9{}_2)_nOR^4$, —$C(=O)O(CR^9{}_2)_nOR^4$, —$C(=O)NR^4{}_2$, —$NR^4C(=O)OR^4$, —$NR^4C(=O)(CR^9{}_2)_nOR^4$, —$R^8$, —$(CR^9{}_2)_nR^8$, —$S(=O)_2R^4$, —$S(=O)_2R^7$, —$S(=O)_2R^8$, —$S(=O)_2N(R^4)_2$, —S(=O)$_2$NHC(=O)OR$^4$, —S(=O)$_2$(CR$^9_2$)$_n$OR$^4$, —S(=O)$_2$(CR$^9_2$)$_n$C(=O)OR$^4$ and a C$_1$ alkyl bridge.

8. The method of claim 7, wherein each R$^4$ is independently selected from H, methyl, ethyl, propyl, butyl, i-propyl and t-butyl.

9. The method of claim 7, wherein each R$^5$ is cyclopropyl, cyclopropyl substituted with a methyl or morpholinyl.

10. The method of claim 7, wherein each R$^7$ is independently selected from CH$_2$F, —CHF$_2$, —CH$_2$CHF$_2$, —CH$_2$CF$_3$ and —CF$_3$.

11. The method of claim 7, wherein each R$^9$ is independently selected from H, methyl and ethyl.

12. The method of claim 7, wherein R$^8$ is selected from an unsubstituted phenyl, unsubstituted 5-6 membered heteroaryl with 1-3 heteroatoms independently selected from N and O, an unsubstituted 5 membered heteroaryl with 1-4 heteroatoms selected from N, an unsubstituted 4-6 membered heterocycloalkyl with 1-2 heteroatoms independently selected from N and O, a substituted 5-6 membered heteroaryl with 1-3 heteroatoms independently selected from N and O, a substituted 5 membered heteroaryl with 1-4 heteroatoms selected from N, a substituted 4-6 membered heterocycloalkyl with 1-2 heteroatoms independently selected from N and O, and a tetrahydro-1H-oxazolo[3,4-a]pyrazin-3(5H)-one, wherein the substituted 5-6 membered heteroaryl with 1-3 heteroatoms independently selected from N and O, the substituted 5 membered heteroaryl with 1-4 heteroatoms selected from N and substituted 4-6 membered heterocycloalkyl of R$^8$ are substituted with 1-3 substituents independently selected from C$_1$-C$_6$alkyl and —C(=O)OR$^4$.

13. The method of claim 12, wherein R$^8$ is selected from pyridinyl, pyrazolyl tetrahydrofuranyl, tetrahydropyranyl, pyrrolidinyl, piperidinyl, pyrimidinyl and oxadiazolyl, each of which is unsubstituted or substituted with 1-2 substituents independently selected from CH$_3$ and C(=O)OC(CH$_3$)$_3$.

14. The method of claim 7, wherein R$^3$ is selected from azetidinyl, azetidin-1-yl, azetidin-2-yl, azetidin-3-yl, pyrrolidinyl, pyrrolidin-1-yl, pyrrolidin-2-yl, pyrrolidin-3-yl, piperidinyl, piperidin-1-yl, piperidin-2-yl, piperidin-3-yl, piperidin-4-yl, tetrahydropyranyl, tetrahydropyran-2-yl, tetrahydropyran-3-yl, tetrahydropyran-4-yl, tetrahydrofuranyl, tetrahydrofuran-2-yl, tetrahydrofuran-3-yl, oxetanyl, oxetan-2-yl, oxetan-3-yl, morpholinyl, morpholin-2-yl, morpholin-3-yl and morpholin-4-yl, each of which is unsubstituted or each of which is substituted with 1-4 substituents independently selected from —CH$_3$, —CH$_2$CH$_3$, F, —CF$_3$, —CN, —OH, —C(=O)CF$_3$, —OCH$_3$, —C(=O)OCH$_3$, —C(=O)CH$_3$, —C(=O)OCH$_2$CH$_2$OCH$_3$, —C=(O)OCH$_2$CH$_3$, —C(=O)OC(CH$_3$)$_3$, —CH$_2$OH, —CH$_2$OCH$_3$, —CH$_2$CH$_2$CH$_2$OCH$_3$, —NHC(=O)OC(CH$_3$)$_3$, —NHC(=O)OCH$_3$, —C(=O)N(CH$_3$)$_2$, —S(=O)$_2$CH$_3$, —S(=O)$_2$CH$_2$CH$_3$, —S(=O)$_2$CH$_2$CH$_2$CH$_3$, —S(=O)$_2$CH$_2$CH$_2$CH$_2$CH$_3$, —S(=O)$_2$CH(CH$_3$)$_2$, —S(=O)$_2$CH$_2$CH$_2$C(=O)OCH$_3$, —S(=O)$_2$CH$_2$CH$_2$OCH$_3$, —S(=O)$_2$CHF$_2$, —S(=O)$_2$NH$_2$, —S(=O)$_2$NHC(=O)OC(CH$_3$)$_3$, a C$_1$alkyl bridge, —C(=O)OR$^5$, —S(=O)$_2$R$^8$, —(CR$^9_2$)$_n$R$^8$ and R$^8$.

15. The method of claim 14, wherein:
R$^3$ is azetidinyl substituted with —C(=O)OCH$_3$.

16. The method of claim 14, wherein m is 1 and R$^{20}$ is selected from H, halo, C$_1$-C$_6$alkyl, C$_1$-C$_6$haloalkyl, deuterium, deuterated C$_1$-C$_6$alkyl, —CN, —(CR$^9_2$)$_n$OR$^4$, —C(O)R$^4$, —(CR$^9_2$)$_n$C(=O)OR$^4$, R$^{10}$, —(Cr$^9_2$)$_n$R$^{10}$, —(CR$^9_2$)$_n$O(CR$^9_2$)$_n$R$^7$, —(CR$^9_2$)$_n$C(=O)R$^4$, —OR$^4$, and —(CR$^9_2$)$_n$CN.

17. The method of claim 16, wherein m is 1 R$^{20}$ is selected from H, -D, —F, —CH$_3$, —CF$_3$, —CN, —CH$_2$CH$_2$CN, —CH$_2$CH$_2$CN, —OCH3, —CH$_2$CH$_2$C(=O)OC(CH$_3$)$_3$, —C(=O)CH$_3$, —CH$_2$CH$_2$C(=O)CH$_3$, —CD$_3$, —CH$_2$OH, —CH$_2$CH$_2$C(CH$_3$)$_2$OH, —CH$_2$C(CH$_3$)$_2$OH, —C(CH$_3$)$_2$OH, —CH$_2$OCH$_3$, —CH$_2$OCH$_2$CF$_3$, —CH$_2$OCH$_2$CHF$_2$, and —CH$_2$OCH$_2$CH$_2$F.

18. The method of claim 17, wherein m is 1 and R$^{20}$ is —CH$_3$.

19. The method of claim 17, wherein m is 1 and R$^{20}$ is H.

20. The method of claim 16, wherein:
R$^{10}$ is selected from morpholinyl, piperidinyl, piperidin-1-yl, piperidin-2-yl, piperidin-3-yl, piperidin-4-yl, piperazinyl, piperazin-1-yl, pyrazolyl, pyrazol-1-yl, pyrazol-3-yl, pyrazol-4-yl, triazolyl, 1H-1,2,3-triazol-4-yl, 4H-1,2,4-triazol-3-yl, 1H-1,2,4-triazol-5-yl, thiazolyl, thiazol-4-yl, thiazol-5-yl, imidazolyl, imidazol-1-yl, imidazol-2-yl, each of which is unsubstituted or each of which is substituted with 1-3 substituents independently selected from C$_1$-C$_6$alkyl, —(CR$^9_2$)$_n$OR$^4$, —(C(R$^9$)$_2$)$_n$C(O)OR$^4$, —(C(R$^9$)$_2$)$_n$R$^5$ and —S(=O)$_2$R$^4$,
or R$^{10}$ is selected from a oxazolidin-2-one and a pyrrolidin-2-one.

21. The method of claim 20, wherein:
R$^{10}$ is selected from morpholinyl, piperidinyl, piperidin-1-yl, piperidin-2-yl, piperidin-3-yl, piperidin-4-yl, piperazinyl, piperazin-1-yl, pyrazolyl, pyrazol-1-yl, pyrazol-3-yl, pyrazol-4-yl, triazolyl, 1H-1,2,3-triazol-4-yl, 4H-1,2,4-triazol-3-yl, 1H-1,2,4-triazol-5-yl, thiazolyl, thiazol-4-yl, thiazol-5-yl, imidazolyl, imidazol-1-yl, imidazol-2-yl, each of which is unsubstituted or each of which is substituted with 1-3 substituents independently selected from —CH$_3$, —CH$_2$CH$_2$OH, —CH$_2$C(O)OH, —CH$_2$CH$_2$OH, —CH$_2$C(CH$_3$)$_2$OH, —S(O)$_2$CH$_3$ and —CH$_2$CH$_2$—R$_5$.

22. The method of claim 15, wherein m is 4 and R$^{20}$ is deuterium.

23. The method of claim 1, wherein the compound is selected from:
N-{5-[3-(azetidin-1-yl)-1,2,4-oxadiazol-5-yl]-2-methylphenyl}imidazo[1,2-a]pyridine-3-carboxamide;
N-{5-[3-(3,3-difluoroazetidin-1-yl)-1,2,4-oxadiazol-5-yl]-2-methylphenyl}imidazo[1,2-a]pyridine-3-carboxamide;
N-(2-methyl-5-{3-[(1S,4S)-2-oxa-5-azabicyclo[2.2.1]heptan-5-yl]-1,2,4-oxadiazol-5-yl}phenyl)imidazo[1,2-a]pyridine-3-carboxamide;
N-{5-[3-(4,4-difluoropiperidin-1-yl)-1,2,4-oxadiazol-5-yl]-2-methylphenyl}imidazo[1,2-a]pyridine-3-carboxamide;
N-{5-[3-(4-fluoropiperidin-1-yl)-1,2,4-oxadiazol-5-yl]-2-methylphenyl}imidazo[1,2-a]pyridine-3-carboxamide;
N-(5-{5-[3-hydroxy-3-(trifluoromethyl)azetidin-1-yl]-1,2,4-oxadiazol-3-yl}-2-methylphenyl)-6-methylimidazo[1,2-a]pyridine-3-carboxamide;
N-{2-methyl-5-[5-(oxolan-3-yl)-1,2,4-oxadiazol-3-yl]phenyl}imidazo[1,2-a]pyridine-3-carboxamide;
N-{2-methyl-5-[5-(oxan-2-yl)-1,2,4-oxadiazol-3-yl]phenyl}imidazo[1,2-a]pyridine-3-carboxamide;
methyl 2-[3-(3-{imidazo[1,2-a]pyridine-3-amido}-4-methylphenyl)-1,2,4-oxadiazol-5-yl]piperidine-1-carboxylate;
N-{5-[5-(5,5-difluorooxan-2-yl)-1,2,4-oxadiazol-3-yl]-2-methylphenyl}imidazo[1,2-a]pyridine-3-carboxamide;
N-(5-{5-[(2S)-5,5-difluorooxan-2-yl]-1,2,4-oxadiazol-3-yl}-2-methylphenyl)imidazo[1,2-a]pyridine-3-carboxamide;

N-(5-{5-[(2R)-5,5-difluorooxan-2-yl]-1,2,4-oxadiazol-3-yl}-2-methylphenyl)imidazo[1,2-a]pyridine-3-carboxamide;

tert-butyl 3-[3-(3-{imidazo[1,2-a]pyridine-3-amido}-4-methylphenyl)-1,2,4-oxadiazol-5-yl]azetidine-1-carboxylate;

N-{5-[5-(1-methanesulfonylazetidin-3-yl)-1,2,4-oxadiazol-3-yl]-2-methylphenyl}imidazo[1,2-a]pyridine-3-carboxamide;

methyl 3-[3-(3-{imidazo[1,2-a]pyridine-3-amido}-4-methylphenyl)-1,2,4-oxadiazol-5-yl]azetidine-1-carboxylate;

N-(2-methyl-5-{5-[1-(propane-1-sulfonyl)azetidin-3-yl]-1,2,4-oxadiazol-3-yl}phenyl)imidazo[1,2-a]pyridine-3-carboxamide;

N-{2-methyl-5-[5-(oxan-4-ylmethyl)-1,2,4-oxadiazol-3-yl]phenyl}imidazo[1,2-a]pyridine-3-carboxamide;

N-{2-methyl-5-[5-(oxolan-2-ylmethyl)-1,2,4-oxadiazol-3-yl]phenyl}imidazo[1,2-a]pyridine-3-carboxamide;

N-(5-{5-[1-(ethanesulfonyl)azetidin-3-yl]-1,2,4-oxadiazol-3-yl}-2-methylphenyl)imidazo[1,2-a]pyridine-3-carboxamide;

N-(2-methyl-5-{5-[3-(morpholin-4-yl)propyl]-1,2,4-oxadiazol-3-yl}phenyl)imidazo[1,2-a]pyridine-3-carboxamide;

N-(5-{5-[(3,3-difluoroazetidin-1-yl)methyl]-1,2,4-oxadiazol-3-yl}-2-methylphenyl)imidazo[1,2-a]pyridine-3-carboxamide;

N-{2-methyl-5-[5-(morpholin-4-ylmethyl)-1,2,4-oxadiazol-3-yl]phenyl}imidazo[1,2-a]pyridine-3-carboxamide;

N-{2-methyl-5-[5-(1-sulfamoylazetidin-3-yl)-1,2,4-oxadiazol-3-yl]phenyl}imidazo[1,2-a]pyridine-3-carboxamide;

tert-butyl (2S)-2-[3-(3-{imidazo[1,2-a]pyridine-3-amido}-4-methylphenyl)-1,2,4-oxadiazol-5-yl]azetidine-1-carboxylate;

N-(5-{5-[(2S)-1-methanesulfonylazetidin-2-yl]-1,2,4-oxadiazol-3-yl}-2-methylphenyl)imidazo[1,2-a]pyridine-3-carboxamide;

methyl N-{3-[3-(3-{imidazo[1,2-a]pyridine-3-amido}-4-methylphenyl)-1,2,4-oxadiazol-5-yl]oxetan-3-yl}carbamate;

tert-butyl 3-[3-(4-fluoro-3-{imidazo[1,2-a]pyridine-3-amido}phenyl)-1,2,4-oxadiazol-5-yl]azetidine-1-carboxylate;

N-(5-{5-[1-(ethanesulfonyl)azetidin-3-yl]-1,2,4-oxadiazol-3-yl}-2-fluorophenyl)imidazo[1,2-a]pyridine-3-carboxamide;

N-(5-{5-[(3,3-difluoropyrrolidin-1-yl)methyl]-1,2,4-oxadiazol-3-yl}-2-methylphenyl)imidazo[1,2-a]pyridine-3-carboxamide;

N-(5-{5-[(4,4-difluoropiperidin-1-yl)methyl]-1,2,4-oxadiazol-3-yl}-2-methylphenyl)imidazo[1,2-a]pyridine-3-carboxamide;

N-(5-{5-[1-(butane-1-sulfonyl)azetidin-3-yl]-1,2,4-oxadiazol-3-yl}-2-methylphenyl)imidazo[1,2-a]pyridine-3-carboxamide;

N-(5-{5-[(2S)-4,4-difluoro-1-methanesulfonylpyrrolidin-2-yl]-1,2,4-oxadiazol-3-yl}-2-methylphenyl)imidazo[1,2-a]pyridine-3-carboxamide;

methyl 4-[3-(3-{imidazo[1,2-a]pyridine-3-amido}-4-methylphenyl)-1,2,4-oxadiazol-5-yl]piperidine-1-carboxylate;

N-{5-[5-(1-methanesulfonylpiperidin-4-yl)-1,2,4-oxadiazol-3-yl]-2-methylphenyl}imidazo[1,2-a]pyridine-3-carboxamide;

N-{5-[5-(4-methanesulfonylmorpholin-2-yl)-1,2,4-oxadiazol-3-yl]-2-methylphenyl}imidazo[1,2-a]pyridine-3-carboxamide;

N-(5-{5-[(2S)-1-methanesulfonylpyrrolidin-2-yl]-1,2,4-oxadiazol-3-yl}-2-methylphenyl)imidazo[1,2-a]pyridine-3-carboxamide;

N-(5-{5-[(2R)-4-methanesulfonylmorpholin-2-yl]-1,2,4-oxadiazol-3-yl}-2-methylphenyl)imidazo[1,2-a]pyridine-3-carboxamide;

N-[5-(5-{[(3S)-1-methanesulfonylpyrrolidin-3-yl]methyl}-1,2,4-oxadiazol-3-yl)-2-methylphenyl]imidazo[1,2-a]pyridine-3-carboxamide;

N-(5-{5-[(3R)-1-methanesulfonylpiperidin-3-yl]-1,2,4-oxadiazol-3-yl}-2-methylphenyl)imidazo[1,2-a]pyridine-3-carboxamide;

methyl (2S)-2-{[3-(3-{imidazo[1,2-a]pyridine-3-amido}-4-methylphenyl)-1,2,4-oxadiazol-5-yl]methyl}pyrrolidine-1-carboxylate;

N-[5-(5-{[(2S)-1-methanesulfonylpyrrolidin-2-yl]methyl}-1,2,4-oxadiazol-3-yl)-2-methylphenyl]imidazo[1,2-a]pyridine-3-carboxamide;

N-(2-methyl-5-{5-[(3,3,4,4-tetrafluoropyrrolidin-1-yl)methyl]-1,2,4-oxadiazol-3-yl}phenyl)imidazo[1,2-a]pyridine-3-carboxamide;

N-(5-{5-[1-(difluoromethane)sulfonylazetidin-3-yl]-1,2,4-oxadiazol-3-yl}-2-methylphenyl)imidazo[1,2-a]pyridine-3-carboxamide;

N-{2-methyl-5-[5-(oxan-2-ylmethyl)-1,2,4-oxadiazol-3-yl]phenyl}imidazo[1,2-a]pyridine-3-carboxamide;

N-(5-{5-[(3,3-difluoropyrrolidin-1-yl)methyl]-1,2,4-oxadiazol-3-yl}-2-fluorophenyl)imidazo[1,2-a]pyridine-3-carboxamide;

N-(5-{5-[(4,4-difluoropiperidin-1-yl)methyl]-1,2,4-oxadiazol-3-yl}-2-fluorophenyl)imidazo[1,2-a]pyridine-3-carboxamide;

N-(2-methyl-5-{5-[(2S)-1-(propane-2-sulfonyl)azetidin-2-yl]-1,2,4-oxadiazol-3-yl}phenyl)imidazo[1,2-a]pyridine-3-carboxamide;

methyl 3-[3-(4-methyl-3-{pyrazolo[1,5-a]pyridine-3-amido}phenyl)-1,2,4-oxadiazol-5-yl]azetidine-1-carboxylate;

N-{2-methyl-5-[5-(oxan-3-ylmethyl)-1,2,4-oxadiazol-3-yl]phenyl}imidazo[1,2-a]pyridine-3-carboxamide;

N-(5-{5-[(1S)-1-(3,3-difluoroazetidin-1-yl)ethyl]-1,2,4-oxadiazol-3-yl}-2-methylphenyl)imidazo[1,2-a]pyridine-3-carboxamide;

N-(5-{5-[(1S)-1-(3,3-difluoropyrrolidin-1-yl)ethyl]-1,2,4-oxadiazol-3-yl}-2-methylphenyl)imidazo[1,2-a]pyridine-3-carboxamide;

methyl 3-(3-{4-methyl-3-[6-(trifluoromethyl) imidazo[1,2-a]pyridine-3-amido]phenyl}-1,2,4-oxadiazol-5-yl)azetidine-1-carboxylate;

ethyl 3-[3-(3-{imidazo[1,2-a]pyridine-3-amido}-4-methylphenyl)-1,2,4-oxadiazol-5-yl]azetidine-1-carboxylate;

methyl 3-[3-(3-{7-fluoroimidazo[1,2-a]pyridine-3-amido}-4-methylphenyl)-1,2,4-oxadiazol-5-yl]azetidine-1-carboxylate;

methyl 3-[3-(3-{6-fluoroimidazo[1,2-a]pyridine-3-amido}-4-methylphenyl)-1,2,4-oxadiazol-5-yl]azetidine-1-carboxylate;

methyl 3-(3-{4-methyl-3-[7-(1-methyl-1H-pyrazol-3-yl)imidazo[1,2-a]pyridine-3-amido]phenyl}-1,2,4-oxadiazol-5-yl)azetidine-1-carboxylate;

methyl 3-(3-{4-methyl-3-[7-(trifluoromethyl)imidazo[1,2-a]pyridine-3-amido]phenyl}-1,2,4-oxadiazol-5-yl)azetidine-1-carboxylate;

N-{5-[5-(1-methanesulfonyl-3-methylazetidin-3-yl)-1,2,4-oxadiazol-3-yl]-2-methylphenyl}imidazo[1,2-a]pyridine-3-carboxamide;

methyl 3-(3-{3-[6-(3-cyanopropyl)imidazo[1,2-a]pyridine-3-amido]-4-methylphenyl}-1,2,4-oxadiazol-5-yl)azetidine-1-carboxylate;

methyl 3-[3-(3-{6-methoxyimidazo[1,2-a]pyridine-3-amido}-4-methylphenyl)-1,2,4-oxadiazol-5-yl]azetidine-1-carboxylate;

methyl 3-[3-(4-methyl-3-{7-methylimidazo[1,2-a]pyridine-3-amido}phenyl)-1,2,4-oxadiazol-5-yl]azetidine-1-carboxylate;

methyl 3-[3-(4-methyl-3-{6-methylimidazo[1,2-a]pyridine-3-amido}phenyl)-1,2,4-oxadiazol-5-yl]azetidine-1-carboxylate;

methyl 3-{3-[4-methyl-3-(7-{1-[2-(morpholin-4-yl)ethyl]-1H-pyrazol-4-yl}imidazo[1,2-a]pyridine-3-amido)phenyl]-1,2,4-oxadiazol-5-yl}azetidine-1-carboxylate;

methyl 3-(3-{3-[6-(2-cyanoethyl)imidazo[1,2-a]pyridine-3-amido]-4-methylphenyl}-1,2,4-oxadiazol-5-yl)azetidine-1-carboxylate;

methyl 3-(3-{4-methyl-3-[6-(3-oxobutyl)imidazo[1,2-a]pyridine-3-amido]phenyl}-1,2,4-oxadiazol-5-yl)azetidine-1-carboxylate;

methyl 3-[3-(4-methyl-3-{6-[2-(morpholin-4-yl)ethyl]imidazo[1,2-a]pyridine-3-amido}phenyl)-1,2,4-oxadiazol-5-yl]azetidine-1-carboxylate;

methyl 3-(3-{3-[6-(3-hydroxy-3-methylbutyl)imidazo[1,2-a]pyridine-3-amido]-4-methylphenyl}-1,2,4-oxadiazol-5-yl)azetidine-1-carboxylate;

methyl 3-(3-{4-methyl-3-[7-(1H-pyrazol-3-yl)imidazo[1,2-a]pyridine-3-amido]phenyl}-1,2,4-oxadiazol-5-yl)azetidine-1-carboxylate;

N-(2-methyl-5-{[5-(oxan-4-yl)-1,2,4-oxadiazol-3-yl]amino}phenyl)imidazo[1,2-a]pyridine-3-carboxamide;

N-(2-methyl-5-{[5-(oxan-2-yl)-1,2,4-oxadiazol-3-yl]amino}phenyl)imidazo[1,2-a]pyridine-3-carboxamide;

N-[2-methyl-5-({5-[(2R)-oxolan-2-yl]-1,2,4-oxadiazol-3-yl}amino)phenyl]imidazo[1,2-a]pyridine-3-carboxamide;

N-[2-methyl-5-({5-[(2S)-oxolan-2-yl]-1,2,4-oxadiazol-3-yl}amino)phenyl]imidazo[1,2-a]pyridine-3-carboxamide;

methyl 3-(3-{4-methyl-3-[7-(3-oxobutyl)imidazo[1,2-a]pyridine-3-amido]phenyl}-1,2,4-oxadiazol-5-yl)azetidine-1-carboxylate;

methyl 3-(3-{3-[7-(3-hydroxy-3-methylbutyl)imidazo[1,2-a]pyridine-3-amido]-4-methylphenyl}-1,2,4-oxadiazol-5-yl)azetidine-1-carboxylate;

N-{2-methyl-5-[3-(morpholin-4-yl)-1,2,4-oxadiazol-5-yl]phenyl}imidazo[1,2-a]pyridine-3-carboxamide;

methyl 3-[3-(4-methyl-3-{5,6,7,8-tetradeuteroimidazo[1,2-a]pyridine-3-amido}phenyl)-1,2,4-oxadiazol-5-yl]azetidine-1-carboxylate;

N-{5-[5-(azetidin-1-yl)-1,2,4-oxadiazol-3-yl]-2-methylphenyl}imidazo[1,2-a]pyridine-3-carboxamide;

N-{5-[5-(3,3-difluoroazetidin-1-yl)-1,2,4-oxadiazol-3-yl]-2-methylphenyl}imidazo[1,2-a]pyridine-3-carboxamide;

methyl 3-[3-(5-{imidazo[1,2-a]pyridine-3-amido}-2,4-dimethylphenyl)-1,2,4-oxadiazol-5-yl]azetidine-1-carboxylate;

methyl 3-[3-(4-methyl-3-{7-methylimidazo[1,2-a]pyridine-3-amido}phenyl)-1,2,4-oxadiazol-5-yl]azetidine-1-carboxylate;

7-fluoro-N-{2-methyl-5-[5-(oxan-4-ylamino)-1,2,4-oxadiazol-3-yl]phenyl}imidazo[1,2-a]pyridine-3-carboxamide;

6-methyl-N-{2-methyl-5-[5-(oxan-4-ylamino)-1,2,4-oxadiazol-3-yl]phenyl}imidazo[1,2-a]pyridine-3-carboxamide;

methyl 3-(3-{4-methyl-3-[6-(morpholin-4-yl)imidazo[1,2-a]pyridine-3-amido]phenyl}-1,2,4-oxadiazol-5-yl)azetidine-1-carboxylate;

methyl 3-[3-(4-methyl-3-{6-[(2,2,2-trifluoroethoxy)methyl]imidazo[1,2-a]pyridine-3-amido}phenyl)-1,2,4-oxadiazol-5-yl]azetidine-1-carboxylate;

N-(5-{5-[3-hydroxy-3-(trifluoromethyl)azetidin-1-yl]-1,2,4-oxadiazol-3-yl}-2-methylphenyl)-6-methylimidazo[1,2-a]pyridine-3-carboxamide;

N-{5-[5-(3,3-difluoroazetidin-1-yl)-1,2,4-oxadiazol-3-yl]-2-methylphenyl}-7-methylimidazo[1,2-a]pyridine-3-carboxamide;

N-{5-[5-(3,3-difluoroazetidin-1-yl)-1,2,4-oxadiazol-3-yl]-2-methylphenyl}-7-fluoroimidazo[1,2-a]pyridine-3-carboxamide;

N-{5-[5-(3-hydroxy-3-methylazetidin-1-yl)-1,2,4-oxadiazol-3-yl]-2-methylphenyl}-7-methylimidazo[1,2-a]pyridine-3-carboxamide;

N-{5-[5-(4,4-difluoropiperidin-1-yl)-1,2,4-oxadiazol-3-yl]-2-methylphenyl}-7-methylimidazo[1,2-a]pyridine-3-carboxamide;

N-{5-[5-(4-fluoropiperidin-1-yl)-1,2,4-oxadiazol-3-yl]-2-methylphenyl}-7-methylimidazo[1,2-a]pyridine-3-carboxamide;

7-methyl-N-{2-methyl-5-[5-(morpholin-4-yl)-1,2,4-oxadiazol-3-yl]phenyl}imidazo[1,2-a]pyridine-3-carboxamide;

N-{5-[5-(3,3-difluoropyrrolidin-1-yl)-1,2,4-oxadiazol-3-yl]-2-methylphenyl}-7-methylimidazo[1,2-a]pyridine-3-carboxamide;

7-methyl-N-(2-methyl-5-{5-[3-(trifluoromethyl)piperidin-1-yl]-1,2,4-oxadiazol-3-yl}phenyl)imidazo[1,2-a]pyridine-3-carboxamide;

N-(2-methyl-5-{3-[(1S,4S)-2-oxa-5-azabicyclo[2.2.1]heptan-5-yl]-1,2,4-oxadiazol-5-yl}phenyl)imidazo[1,2-a]pyridine-3-carboxamide;

methyl 3-[3-(3-{6-[(2,2-difluoroethoxy)methyl]imidazo[1,2-a]pyridine-3-amido}-4-methylphenyl)-1,2,4-oxadiazol-5-yl]azetidine-1-carboxylate;

methyl 3-[3-(3-{6-[(2-fluoroethoxy)methyl]imidazo[1,2-a]pyridine-3-amido}-4-methylphenyl)-1,2,4-oxadiazol-5-yl]azetidine-1-carboxylate;

methyl 3-[3-(3-{7-hydrogenioimidazo[1,2-a]pyridine-3-amido}-4-methylphenyl)-1,2,4-oxadiazol-5-yl]azetidine-1-carboxylate;

methyl 3-[3-(3-{6-hydrogenioimidazo[1,2-a]pyridine-3-amido}-4-methylphenyl)-1,2,4-oxadiazol-5-yl]azetidine-1-carboxylate, and N-(5-{5-[(3-cyanoazetidin-1-yl)methyl]-1,2,4-oxadiazol-3-yl}-2-methylphenyl)-6-(2,4-dimethyl-1,3-thiazol-5-yl)imidazo[1,2-a]pyridine-3-carboxamide.

24. The method of claim 1 wherein the compound is methyl 3-[3-(4-methyl-3-{5,6,7,8-tetradeuteroimidazo[1,2-a]pyridine-3-amido}phenyl)-1,2,4-oxadiazol-5-yl]azetidine-1-carboxylate.

* * * * *